US012653850B2

(12) United States Patent
June et al.

(10) Patent No.: US 12,653,850 B2
(45) Date of Patent: Jun. 16, 2026

(54) COMBINATION THERAPY USING A CHIMERIC ANTIGEN RECEPTOR

(71) Applicants: NOVARTIS AG, Basel (CH); THE TRUSTEES OF THE UNIVERSITY OF PENNSYLVANIA, Philadephia, PA (US)

(72) Inventors: Carl H. June, Merion Station, PA (US); Keisuke Watanabe, Wynnewood, PA (US); Sonia Guedan Carrio, Philadelphia, PA (US); Akseli Hemminki, Helsinki (FI); John Scholler, Narbeth, PA (US); Regina M. Young, Bryn Mawr, PA (US)

(73) Assignees: The Trustees of the University of Pennsylvania, Philadelphia, PA (US); Novartis AG, Basel (CH)

( * ) Notice: Subject to any disclaimer, the term of this patent is extended or adjusted under 35 U.S.C. 154(b) by 1093 days.

(21) Appl. No.: 16/965,880

(22) PCT Filed: Jan. 31, 2019

(86) PCT No.: PCT/US2019/016070

§ 371 (c)(1),
(2) Date: Jul. 29, 2020

(87) PCT Pub. No.: WO2019/152660

PCT Pub. Date: Aug. 8, 2019

(65) Prior Publication Data

US 2021/0038659 A1 Feb. 11, 2021

Related U.S. Application Data

(60) Provisional application No. 62/624,707, filed on Jan. 31, 2018.

(51) Int. Cl.

| | |
|---|---|
| ***A61K 35/76*** | (2015.01) |
| ***A61K 40/11*** | (2025.01) |
| ***A61K 40/31*** | (2025.01) |
| ***A61K 40/42*** | (2025.01) |
| ***C07K 14/525*** | (2006.01) |
| ***C07K 14/55*** | (2006.01) |
| ***C07K 14/705*** | (2006.01) |
| ***C12N 15/86*** | (2006.01) |

(52) U.S. Cl.

CPC .............. *A61K 35/76* (2013.01); *A61K 40/11* (2025.01); *A61K 40/31* (2025.01); *A61K 40/4232* (2025.01); *A61K 40/4234* (2025.01); *A61K 40/4255* (2025.01); *C07K 14/525* (2013.01); *C07K 14/55* (2013.01); *C07K 14/705* (2013.01); *C12N 15/86* (2013.01); *A61K 2239/31* (2023.05)

(58) Field of Classification Search

None

See application file for complete search history.

(56) References Cited

U.S. PATENT DOCUMENTS

2015/0232880 A1* 8/2015 Hemminki ............. C12N 15/86 435/320.1
2016/0311917 A1* 10/2016 Beatty ..................... A61P 15/00
2017/0209492 A1* 7/2017 June ................... A61K 39/0011

FOREIGN PATENT DOCUMENTS

WO 2012079000 A1 6/2012
WO WO-2013063419 A2 * 5/2013 ............. A61K 35/17
WO 2014153270 A1 9/2014
WO WO-2015090230 A1 * 6/2015 ........... A61K 31/436
WO 2015142675 A2 9/2015

OTHER PUBLICATIONS

Watanabe et al., JCI Insight 3(7): e99573 (Year: 2018).*
Morello et al., Cancer Discov 6(2): 133-146 (Year: 2016).*
Havunen et al., Molecular therapy oncolytics 4: 77-86 (Year: 2017).*
Rudikoff et al., Proc Natl Acad Sci USA 79: 1979 (Year: 1982).*
Piche-Nicholas et al MABS 10(1): 81-94 (Year: 2018).*
Zitvogel et al., Nature Reviews Cancer 16: 759-773 (Year: 2016).*
Lloyd et al. Protein Engineering, Design & Selection 22:159-168 (Year: 2009).*
Edwards et al., J Mol Biol. 334(1): 103-118 (Year: 2003).*
Poosarla et al., Biotechn. Bioeng. 114(6): 1331-1342 (Year: 2017).*
Beatty et al., Cancer Immunology Research 2(2): 112-217 (Year: 2014).*
[XPI]—Watanabe Keisuke et al., "Pancreatic cancer therapy with combined mesothelin-redirected chimeric antigen receptor T cells and cytokine-armed oncolytic adenoviruses.", JCI Insight Apr. 5, 2018, (Apr. 5, 2018), vol. 3, No. 7, ISSN 2379-3708, XP002790343.
Ajina Adam et al, "Prospects for combined use of oncolytic viruses and CAR T-cells.", Journal for Immunotherapy of Cancer Nov. 21, 2017, (Nov. 21, 2017), vol. 5, No. 1, ISSN 2051-1426, p. 90, XP002790342.
Andtbacka et al., "Talimogene Laherparepvec Improves Durable Response Rate in Patients with Advanced Melanoma", Journal of Clinical Oncology, vol. 33, No. 25, Sep. 1, 2015, 13 pages.
Balachandran et al., "Identification of unique neoantigen qualities in long term pancreatic cancer survivors", Nature, Nov. 23, 2017, 551(7681) 512-516.
Barrett, et al., "Regimen-Specific Effects of RNA-Modified Chimeric Antigen Receptor T Cells in Mice with Advanced Leukemia", Human Gene Therapy 24:717-727 (Aug. 2013).
Beatty et al., "Chireric antigen receptor-modified T cells for the treatment of solid tumors: Defining the challenges and next steps", Pharmacol Ther. Oct. 2016, 166, 30-39.

(Continued)

*Primary Examiner* — Phuong Huynh
(74) *Attorney, Agent, or Firm* — Saul Ewing LLP; Alireza Behrooz; Kathryn Doyle

(57) ABSTRACT

The invention provides compositions and methods for treating diseases such as cancer. The invention also relates to a method of administering a chimeric antigen receptor (CAR) therapy and an additional therapeutic agent, e.g., one or more cytokine molecules, e.g., a virus comprising a nucleic acid molecule encoding one or more cytokine molecules.

9 Claims, 52 Drawing Sheets

Specification includes a Sequence Listing.

(56) References Cited

OTHER PUBLICATIONS

Beatty et al., "Safety and antitumor activity of chimeric antigen receptor modified T cells in patients with chemotherapy refractory metastatic pancreatic cancer", Journal of Clinical Oncology 33, No. 15 Suppl, May 2015, 3007.
Brown et al., "Cancer Immunotherapy with Recombinant Poliovirus Induces IFN-Dominant Activation of Dendritic Cells and Tumor Antigen-Specific CTLs", Sci Transl Med. Sep. 20, 2017, 9(408).
Carpenito, et al., "Control of large, established tumor xenografts with genetically retargeted human T cells containing CD28 and CD137 domains", 2009, PNAS 106(9):3360-3365.
Grupp S. et al., "Chimeric Antigen Receptor-Modified T Cells for Acute Lymphoid Leukemia", N Eng J Med, (Apr. 18, 2013), vol. 368, No. 16, pp. 1509-1518, XP055169041.
Hassan et al, "Mesothelin targeted cancer immunotherapy", European Journal of Cancer, Elsevier, Amsterdam, NL, (Oct. 22, 2007), vol. 44, No. 1, doi: 10.1016/J.EJCA.2007.08.028, ISSN 0959-8049, pp. 46-53, XP022392314.
Havunen et al., "Oncolytic Adenoviruses Armed with Tumor Necrosis Factor Alpha and Interleukin-2 Enable Successful Adoptive Cell Therapy", Molecular Therapy: Oncolytics, vol. 4, Mar. 2017, 10 pages.
Hingorani et al., "Trp53R172H and KrasG12D cooperate to promote chromosomal instability and widely metastatic pancreatic ductal adenocarcinoma in mice", Cancer Cell, May 2005, vol. 7, 469-483.
Huh et al., "Prognostic Significance of Tumor-Infiltrating Lymphocytes for Patients with Coloretal Cancer", Arch Surg, 2012, 147(4), 366-371.
International Search Report and Written Opinion issued in App. No. PCT/US2019/016070, dated Apr. 30, 2019, 14 pages.
James E. Talmadge, "Immune cell infiltration of primary and metastatic lesions: Mechanisms and clinical impact", Semin Cancer Biol, 21(2):131-8 (2011) (Epub Dec. 9, 2010).
James et al., "Association between tumour infiltrating lymphocytes, histotype and clinical outcome in epithelial ovarian cancer", BMC Cancer, 2017, 17:657.
James N. Kochenderfer et al., "Chemotherapy-Refractory Diffuse Large B-Cell Lymphoma and Indolent B-Cell Malignancies Can Be Effectively Treated With Autologous T Cells Expressing an Anti-CD19 Chimeric Antigen Receptor", Journal of Clinical Oncology, (Feb. 20, 2015), vol. 33, No. 6, pp. 540-549, XP055552252.
Kanerva et al., "Enhanced Therapeutic Efficacy for Ovarian Cancer with a Serotype 3 Receptor-Targeted Oncolytic Adenovirus", Molecular Therapy, vol. 8, No. 3, Sep. 2003, 10 pages.
Keisuke Watanabe et al., "Oncolytic adenovirus armed with cytokines enhances CAR-T cell efficacy in pancreatic tumor model", Molecular Therapy, (May 2016), vol. 24, No. Supplement 1, pp. S205-S206, XP002790341.
Kho et al., "Application of xCELLigence RTCA Biosensor Technology for Revealing the Profile and Window of Drug Responsiveness in Real Time", Biosensors 2015, 5, 199-222.
Kim et al., "A Phase I Clinical Trial of Ad5/3-A24, a Novel Serotype-Chimeric, Infectivity-Enhanced, Conditionally-Replicative Adenovirus (CRAd), in Patients with Recurrent Ovarian Cancer", Gynecol Oncol, Sep. 2013, 130(3), 518-524.
Li et al., "The prognostic value of tumor-infiltrating T lymphocytes in ovarian cancer", Oncotarget, www.impactjournals.com/oncotarget, 2017, vol. 8, No. 9, 15621-15631.
Ichty et al., "Going viral with cancer immunotherapy", Nature Reviews, Cancer, vol. 14, Aug. 2014, 9 pages.
Liyanage et al., "Prevalence of Regulatory T Cells is Increased in Peripheral Blood and Tumor Microenvironment of Patients with Pancreas or Breast Adenocarcinoma", J Immunol, 2002, 169(5), 2756-2761.
Locke et al., "Phase 1 Results of ZUMA-1: A Multicenter Study of KTE-C19 Anti-CD19 Car T Cell Therapy in Refractory Aggressive Lymphoma", Molecular Therapy, vol. 25, No. 1, Jan. 2017, 11 pages.
Mantovani et al., "Tumor-Associated Macrophages as Treatment Targets in Oncology", Nat Rev Clin Oncol., Jul. 2017, 14(7), 399-416.
Michael C. Milone et al., "Chimeric Receptors Containing CD137 Signal Transduction Domains Mediate Enhanced Survival of T Cells and Increased Antileukemic Efficacy In Vivo", Molecular Therapy, (Aug. 1, 2009), vol. 17, No. 8, doi: 10.1038/mt.2009.83, ISSN 1525-0016, pp. 1453-1464, XP055052474.
Moon et al., "Multifactorial T-cell Hypofunction That is Reversible Can Limit the Efficacy of Chimeric Antigen Receptor-Transduced Human T cells in Solid Tumors", Clin Cancer Res, 20(16), 4262-73, 2014.
Morello et al., "Mesothelin-Targeted CARs: Driving T Cells to Solid Tumors", Cancer Discovery, US, (Oct. 26, 2015), doi:10.1158/2159-8290.CD-15-0583, ISSN 2159-8274, XP055239486.
Morello et al., "Mesothelin-Targeted CARs: Driving T cells to Solid Tumors", Cancer Discov, Feb. 2016, 6(2) 133-146.
Mukherjee et al., "MUC1-specific CTLs are non-functional within a pancreatic tumor microenvironment", Glycoconjugate Journal, 18, 931-942, 2001.
Nagarsheth et al., "Chemokines in the cancer microenvironment and their relevance in cancer immunotherapy", Nat Rev Immunol., Sep. 2017, 17(9), 559-572.
Nakasone et al., "Host-Derived MCP-1 and MIP-1a Regulate Protective Anti-Tumor Immunity to Localized and Metastatic B16 Melanoma", The American Journal of Pathology, vol. 180, No. 1, Jan. 2012.
Newick et al., "Chimeric antigen receptor T-cell therapy for solid tumors", Oncolytics, 2016, 3, 16006.
Nicholson et al., "Construction and Characterisation of a Function CD19 Specific Single Chain Fv Fragment for Immunotherapy of B Lineage Leukaemia and Lymphoma," Molecular Immunology 34(16-17): 1157-1165 (1997).
Nishio et al., "Armed Oncolytic Virus Enhances Immune Functions of Chimeric Antigen Receptor-Modified T Cells in Solid Tumors", Cancer Res, 74(18), 5195-205, 2014.
O'Rourke et al., "A single dose of peripherally infused EGFRvIII-directed CAR T cells mediates antigen loss and induces adaptive resistance in patients with recurrent glioblastoma", Sci Transl Med, Jul. 2017, 9(399), 30 pages.
Ranki et al., "Phase I study with ONCOS-102 for the treatment of solid tumors-an evaluation of clinical response and exploratory analyses of immune markers", Journal for ImmunoTherapy of Cancer, 2016, 4:17, 18 pages.
Rosewell Shaw et al., "Adenovirotherapy Delivering Cytokine and Checkpoint Inhibitor Augments CAR T Cells against Metastatic Head and Neck Cancer", Molecular Therapy, vol. 25, No. 11, Nov. 2017, 12 pages.
Ryan et al., "Pancreatic Adenocarcinoma", N Engl J Med, 2014, 371, 1039-1049.
Sadelain et al., "The Basic Principles of Chimeric Antigen Receptor Design" Cacner Discovery, vol. 3 No. 4 pp. 388-398 (Apr. 2013).
Siurala et al., "Adenoviral Delivery of Tumor Necrosis Factor-a and Interleukin-2 Enables Successful Adoptive Cell Therapy of Immunosuppressive Melanoma", Molecular Therapy, vol. 24, No. 8, Aug. 2016, 1435-1443.
Son et a., "Characteristics of chemokine signatures elicited by EGF and TNF in ovarian cancer cells", Journal of Inflammation, 2013, 10:25.
Stromnes et al., "T cells engineered against a native antigen can surmount immunologic and physical barriers to treat pancreatic ductal adenocarcinoma", Cancer Cell, Nov. 9, 2015, 28(5), 638-652.
Tahtinen et al., "Adenovirus Improves the Efficacy of Adoptive T-cell Therapy by Recruiting Immune Cells to and Promoting Their Activity at the Tumor", AACR, 2015, 12 pages.
Tahtinen et al., "Favorable Alteration of Tumor Microenvironment by Immunomodulatory Cytokines for Efficient T-cell Therapy in Solid Tumors", PLoS One 10(6), 2015, 20 pages.
Tanoue et al., "Armed oncolytic adenovirus expressing PD-L1 mini-body enhances anti-tumor effects of chimeric antigen receptor T-cells in solid tumors", Cancer Res,, 77(8):2040-2051 (2017).

(56) References Cited

OTHER PUBLICATIONS

Wachsmann et al., "Pancreatic Ductal Adenocarcinoma: A Review of Immunologic Aspects", J Investig Med, Apr. 2012, 60(4), 643-663.

Wang et al., "Desmoglein 2 is a receptor for adenovirus serotypes 3, 7, 11, and 14", Nat Med, Jan. 2011, 19(1), 96-104.

Watanabe et al., "Oncolytic Adenovirus Expressing Cytokines Enhances Anti-Tumor Efficacy of Mesothelin-Redirected CAR-T Cells", Blood, vol. 128, No. 22, (2016), p. 3360, Blood, URL: http://www.bloodjournal.org/content/128/22/3360, (Apr. 3, 2019), XP002790340.

Watanabe, et al., "Pancreatic Cancer Therapy With Combined Mesothelin-Redirected Chimeric Antigen Receptor T Cells and Cytokine-Armed Oncolytic Adenoviruses", JCI Insight 3 (7):pp. 1-17 (2018).

Wolf et al., "TNFa induces expression of the chemoattractant cytokine RANTES in cultured mouse mesangial cells", Kidney International, vol. 44, 1993, 795-804.

Yin et al., "Modulation of the Intratumoral Immune Landscape by Oncolytic Herpes Simplex Virus Virotherapy", 2017, Frontiers in Oncology, vol. 7, Article 136, 7 pages.

Zeng et al., "Prognostic and predictive value of tumor-infiltrating lymphocytes for clinical therapeutic research in patients with non-small cell lung cancer", Oncotarget, vol. 7, No. 12, 17 pages.

* cited by examiner

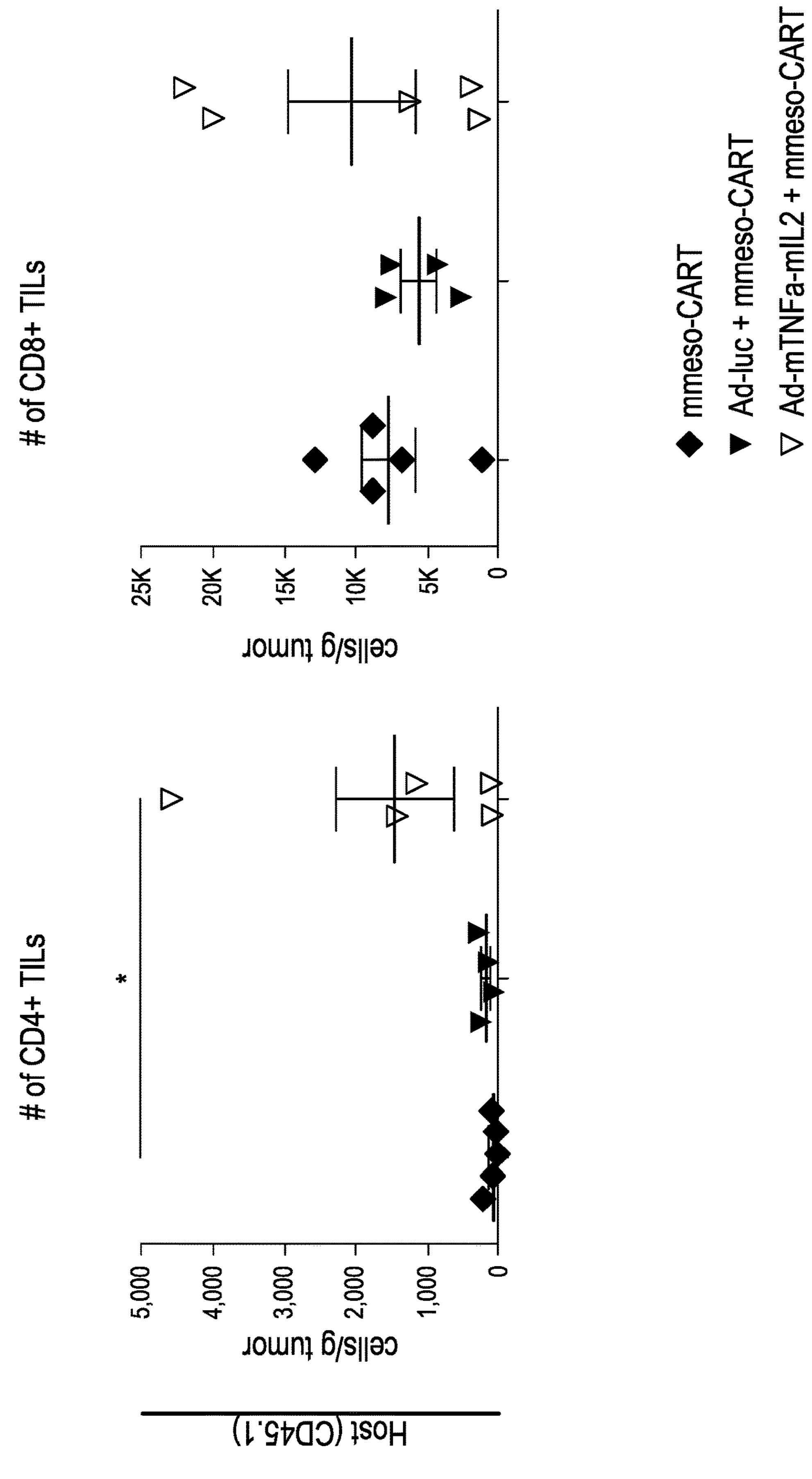
FIG. 6D (part 1)

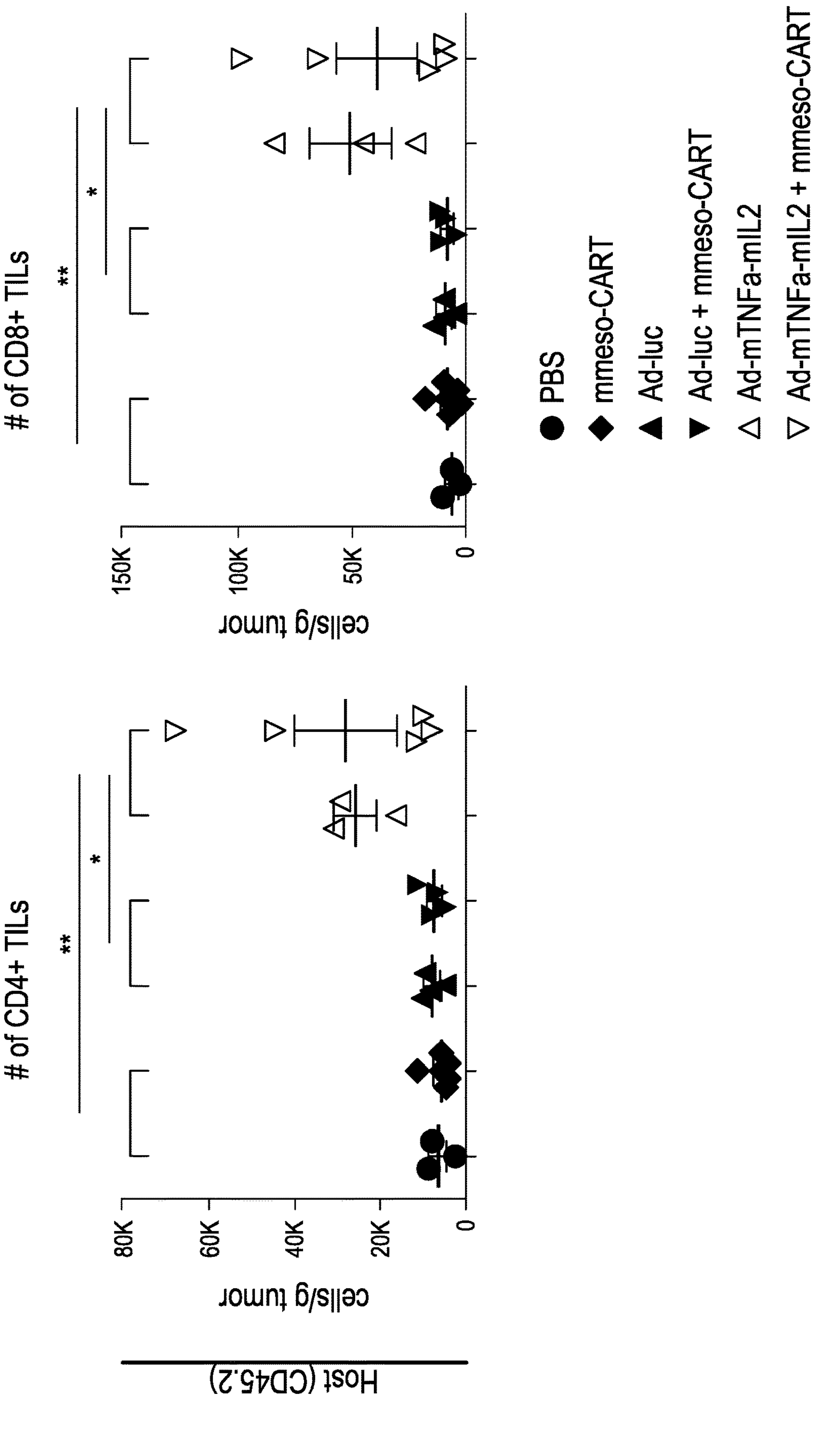
FIG. 6D (part 2)

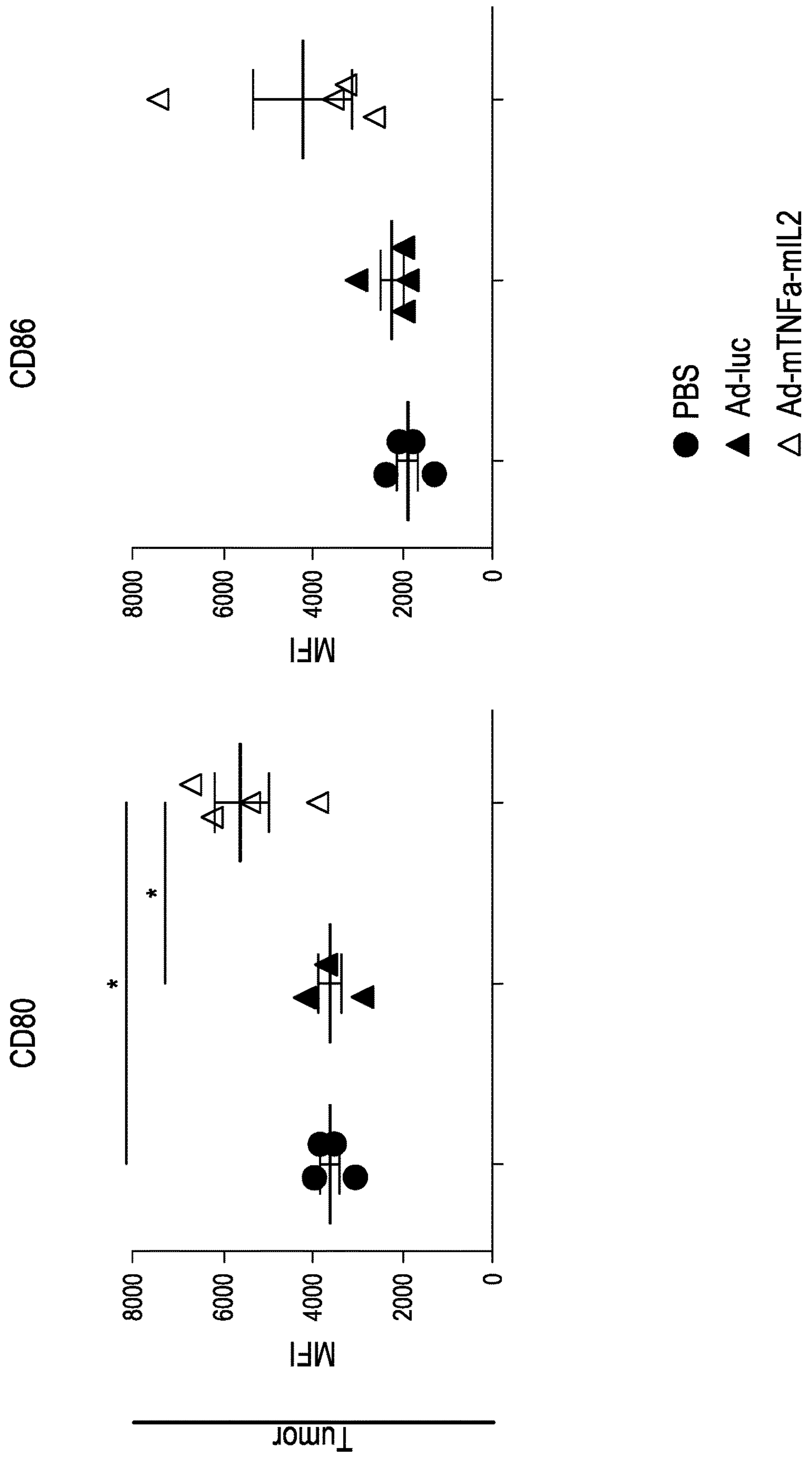
FIG. 6E (part 1)

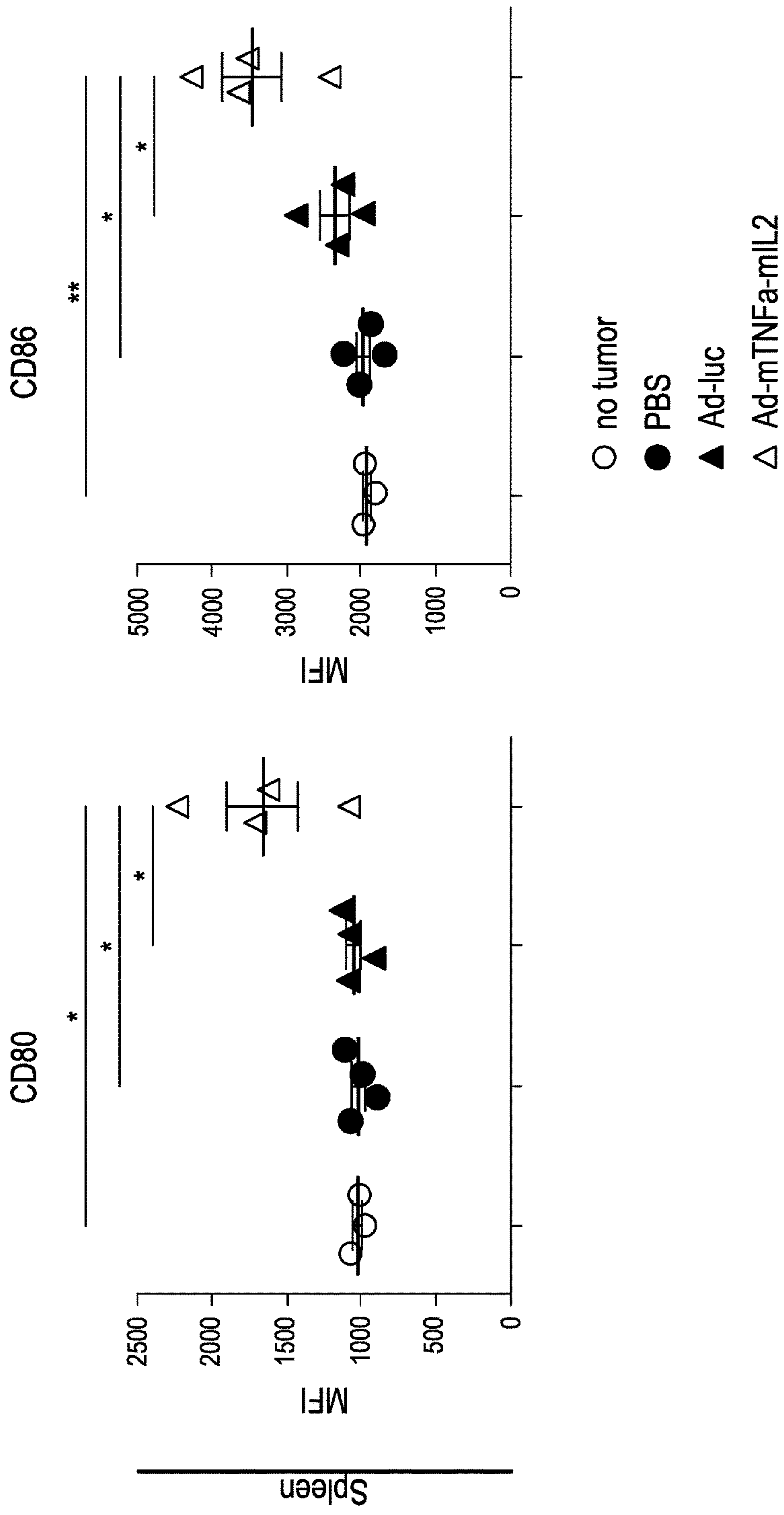
FIG. 6E (part 2)

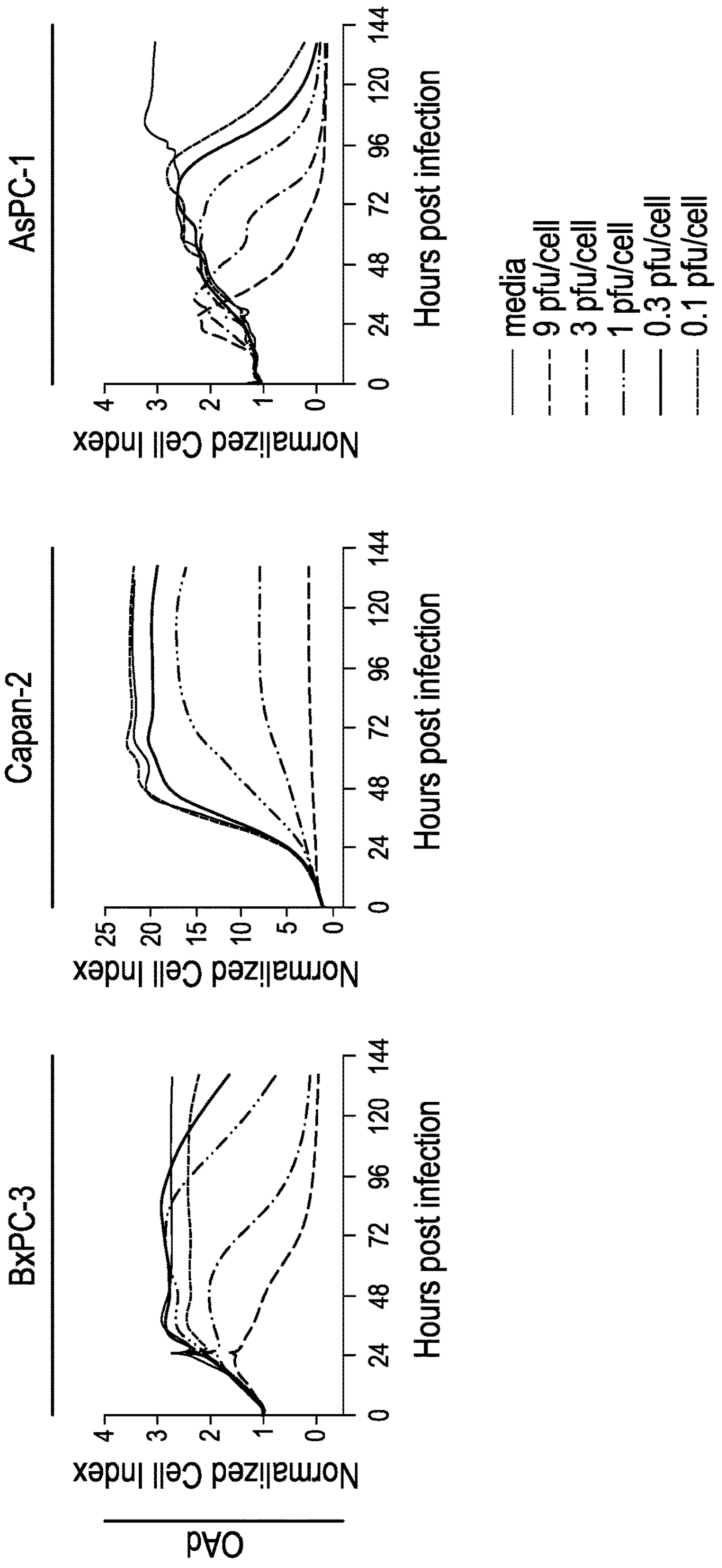
FIG. 7C (part 1)

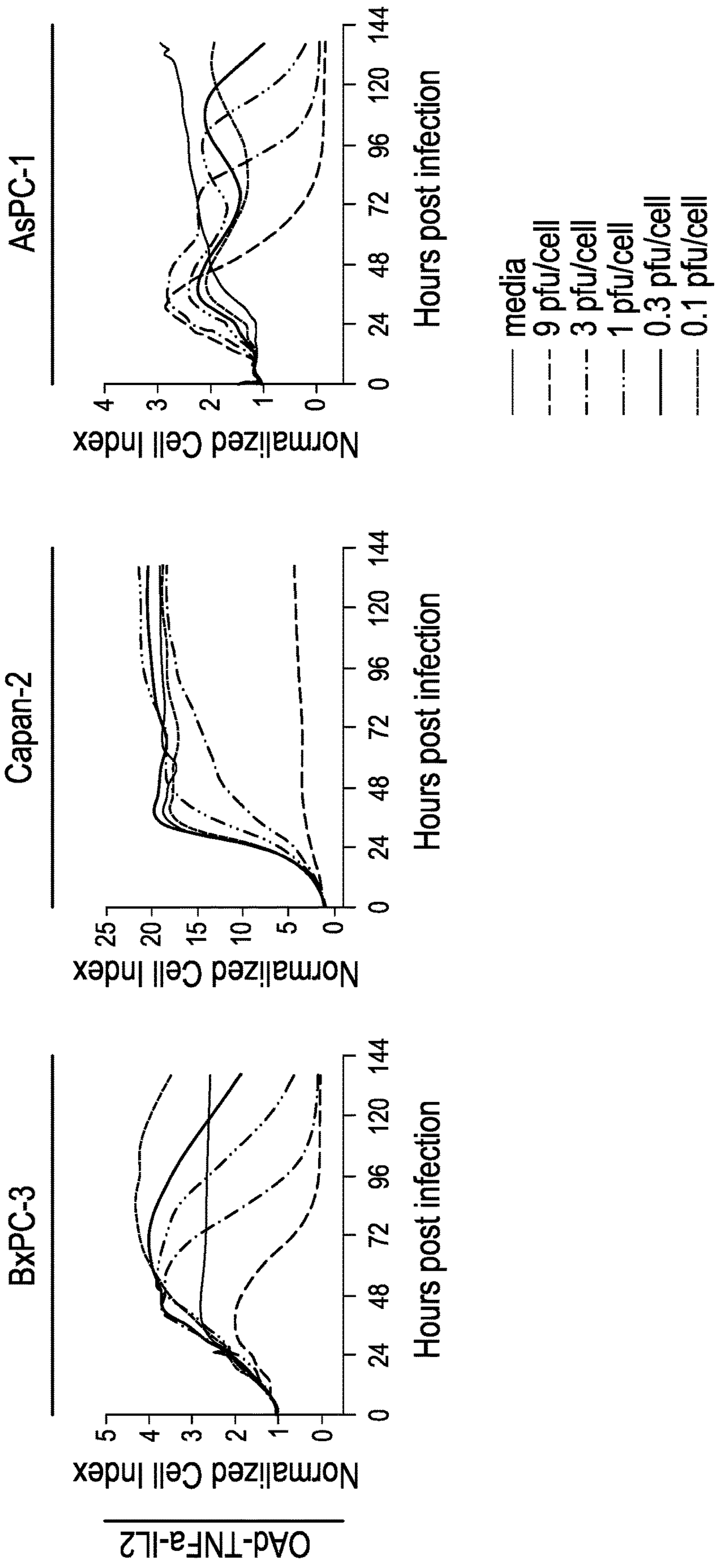
FIG. 7C (part 2)

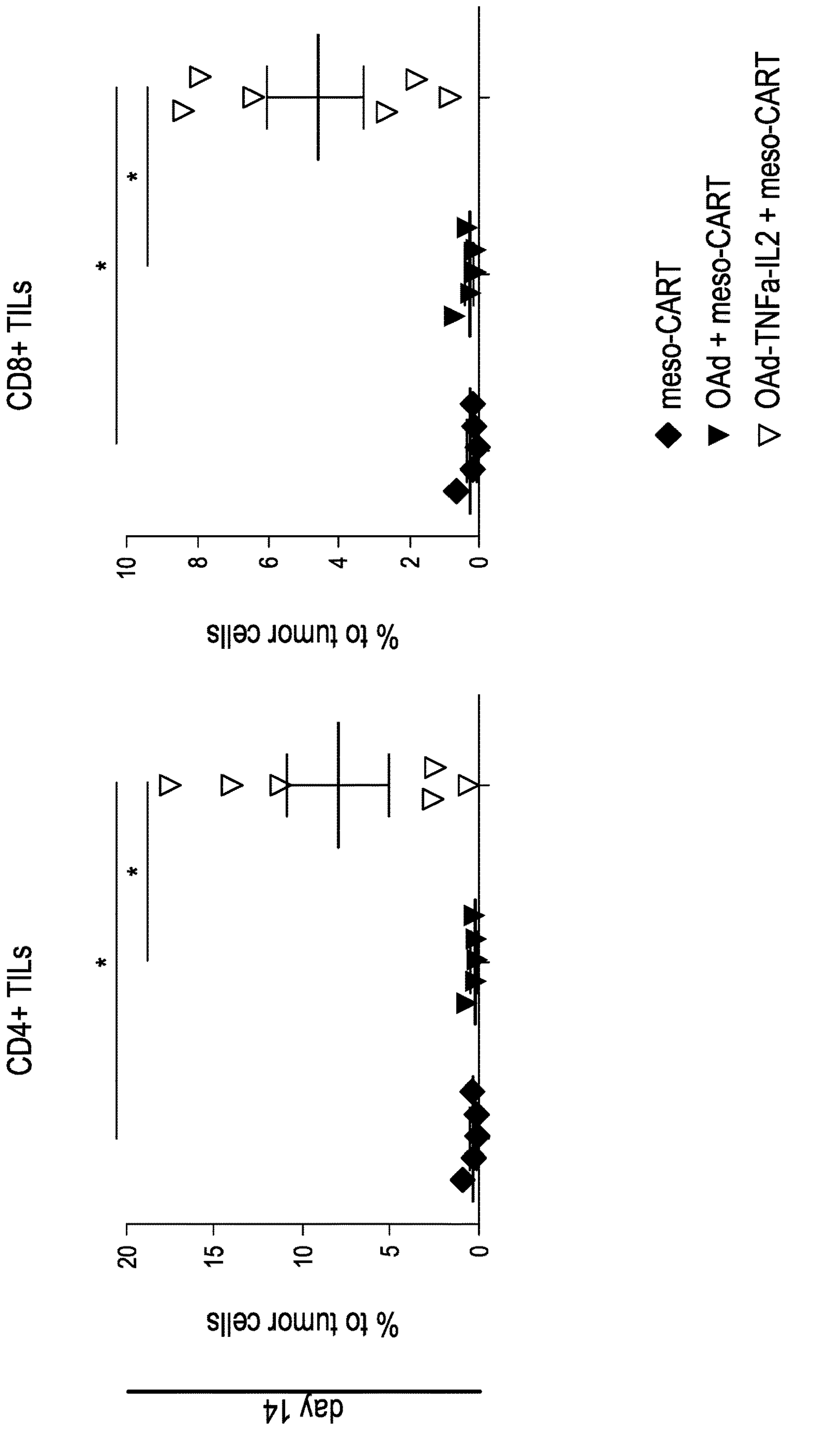
FIG. 9B (part 1)

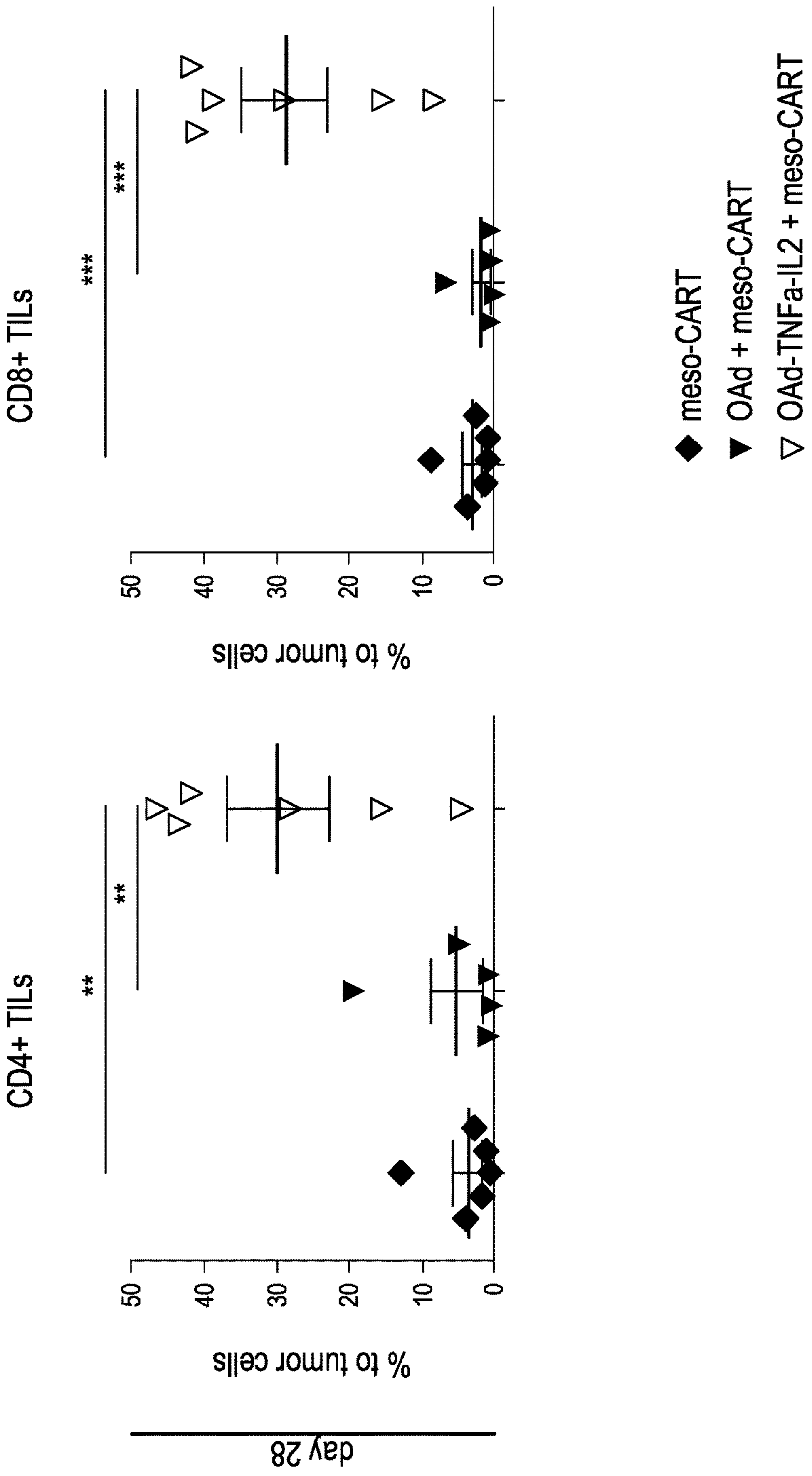
FIG. 9B (part 2)

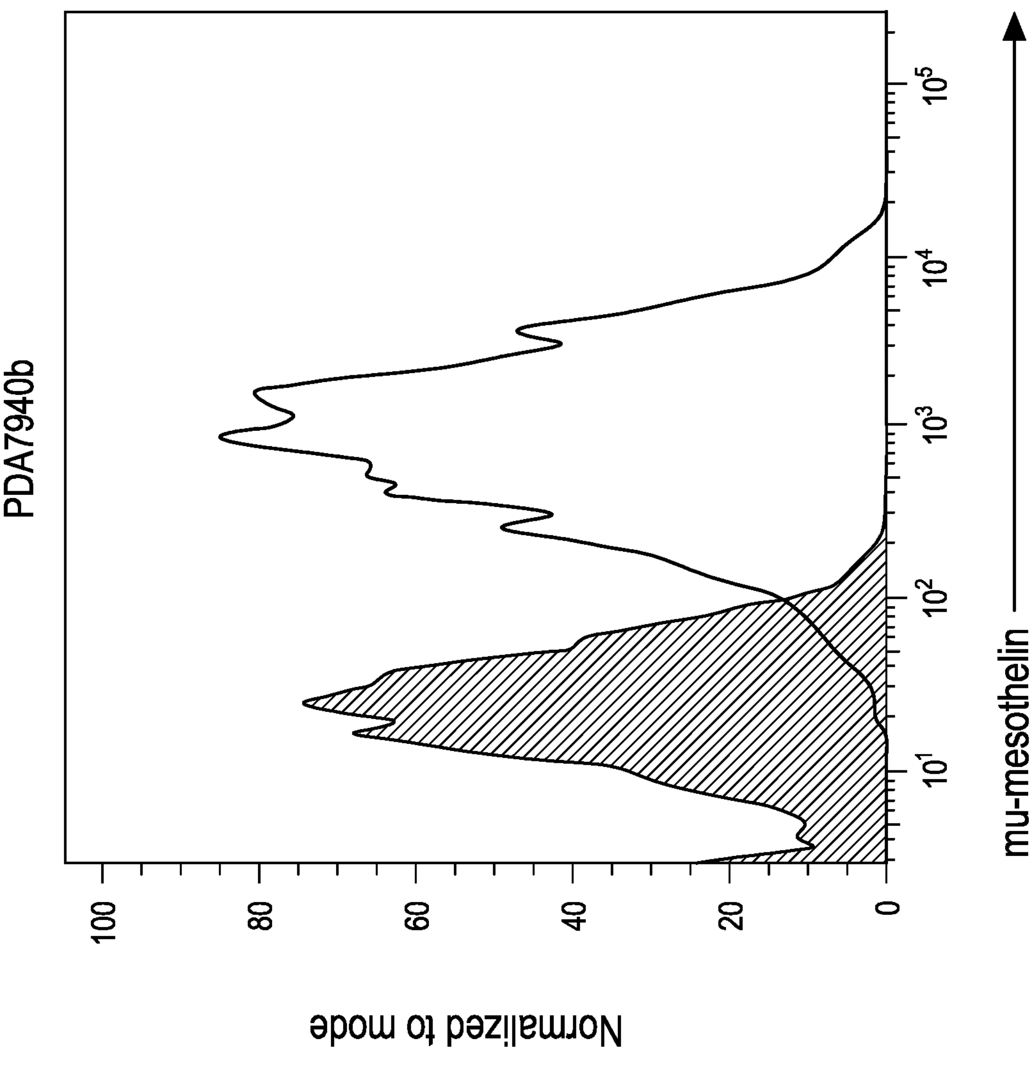
FIG. 10C (part 1)

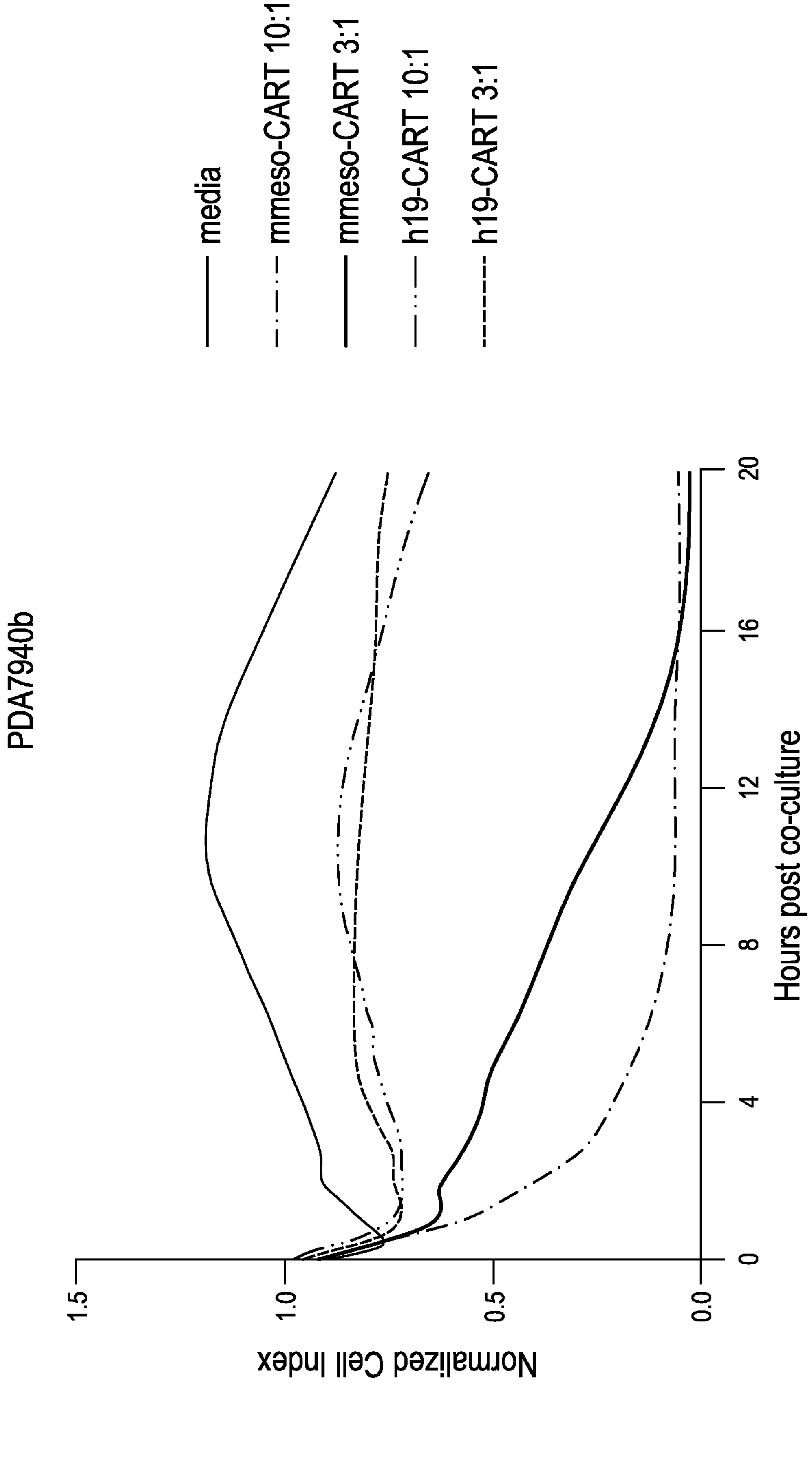
FIG. 10C (part 2)

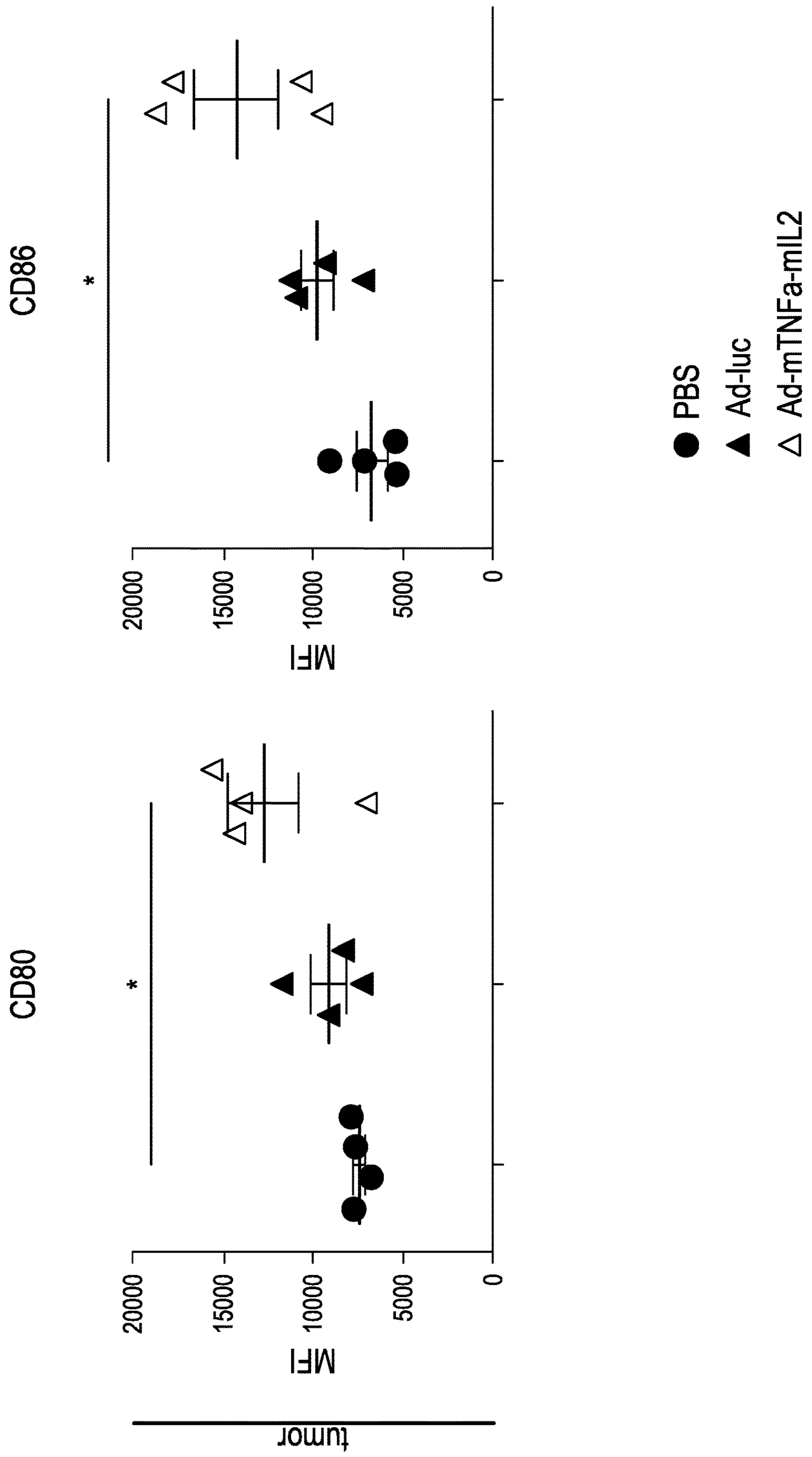
FIG. 10E (part 1)

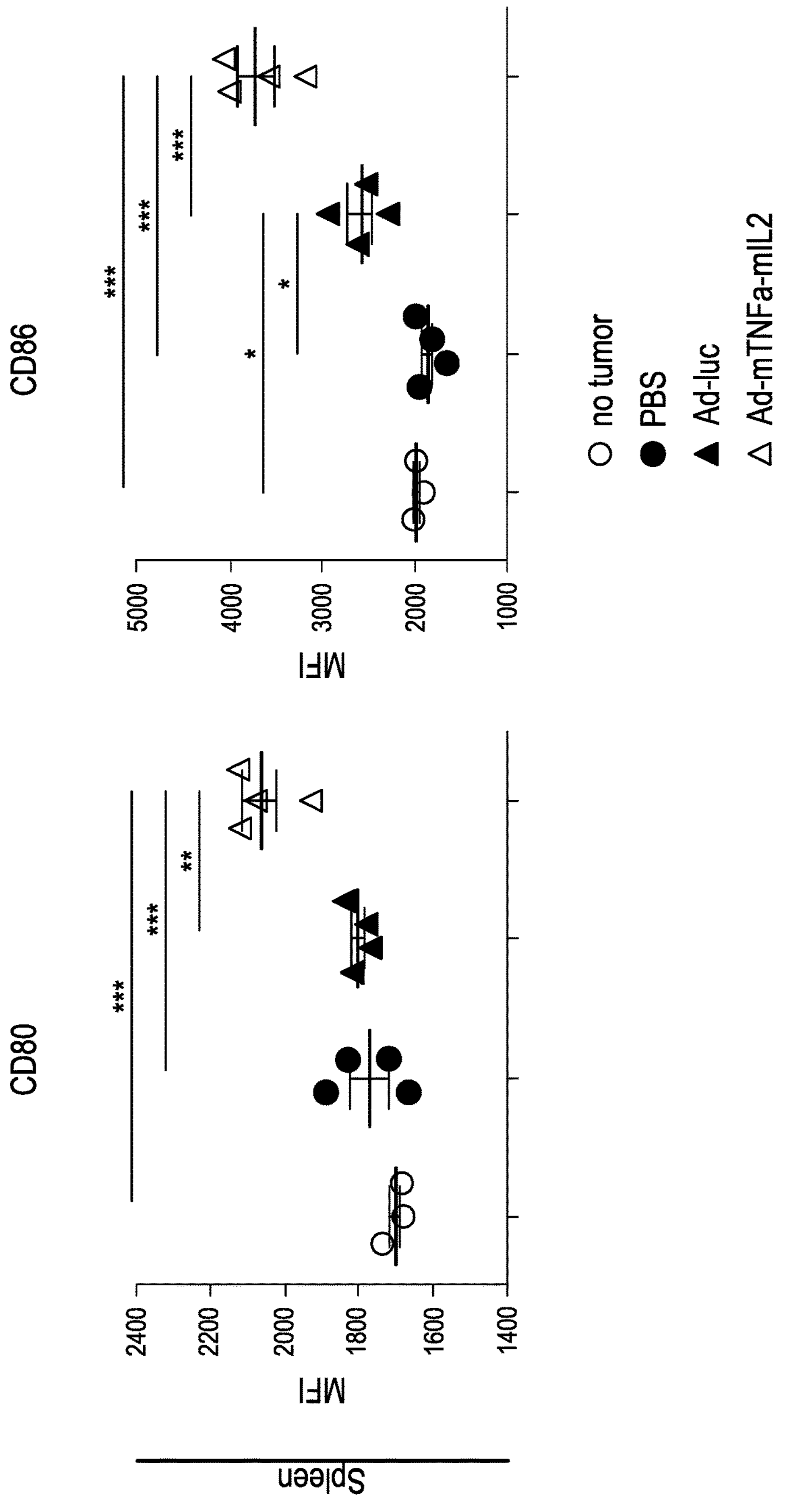
FIG. 10E (part 2)

COMBINATION THERAPY USING A CHIMERIC ANTIGEN RECEPTOR

CROSS-REFERENCE TO RELATED APPLICATIONS

This application is a 35 U.S.C. § 371 national phase application from, and claims priority to, International Application No. PCT/US2019/016070, filed Jan. 31, 2019, which claims priority to U.S. Provisional Application No. 62/624,707 filed Jan. 31, 2018, all of which applications are incorporated herein by reference in their entireties.

SEQUENCE LISTING

The instant application contains a Sequence Listing which has been submitted electronically in ASCII format and is hereby incorporated by reference in its entirety. Said ASCII copy, created on Jan. 31, 2019, is named N2067-7148WO_SL.txt and is 377,462 bytes in size.

FIELD OF THE INVENTION

The present invention relates generally to the use of cells, e.g., immune effector cells, engineered to express a Chimeric Antigen Receptor (CAR) in combination with one or more cytokine molecules, e.g., a virus, e.g., an oncolytic virus, e.g., an oncolytic adenovirus, comprising a nucleic acid molecule encoding one or more cytokine molecules, to treat a disease, e.g., cancer.

BACKGROUND OF THE INVENTION

Recent developments using chimeric antigen receptor (CAR) modified T cell (CART) therapy, which relies on redirecting T cells to a suitable cell-surface molecule on cancer cells, show promising results in harnessing the power of the immune system to treat cancers (see, e.g., Sadelain et al., Cancer Discovery 3:388-398 (2013)).

Given the ongoing need for improved strategies for targeting diseases such as cancer, new compositions and methods for improving CART therapies are highly desirable.

SUMMARY OF THE INVENTION

This disclosure features, at least in part, compositions and methods of treating disorders such as cancer using immune effector cells (e.g., T cells or NK cells) that express a chimeric antigen receptor (CAR) molecule, e.g., a CAR molecule that binds to a tumor antigen, e.g., an antigen expressed on the surface of a solid tumor or a hematological tumor. In one aspect, the invention features use of the CAR-expressing cell therapy in combination with one or more cytokine molecules (e.g., a TNFα molecule, an IL-2 molecule, and/or an IL-7 molecule). In one aspect, the invention features use of the CAR-expressing cell therapy in combination with a TNFα molecule and an IL-2 molecule. In one aspect, the invention features use of the CAR-expressing cell therapy in combination with a TNFα molecule and an IL-7 molecule. In one aspect, the invention features use of the CAR-expressing cell therapy in combination with an IL-7 molecule and an IL-2 molecule. In one aspect, the invention features use of the CAR-expressing cell therapy in combination with a TNFα molecule, an IL-2 molecule, and an IL-7 molecule. In one aspect, the invention features use of the CAR-expressing cell therapy in combination with a virus, e.g., an oncolytic virus, e.g., an oncolytic adenovirus, comprising a nucleic acid molecule encoding one or more cytokine molecules (e.g., a TNFα molecule, an IL-2 molecule, and/or an IL-7 molecule). In one aspect, the invention features use of the CAR-expressing cell therapy in combination with a virus, e.g., an oncolytic virus, e.g., an oncolytic adenovirus, comprising a nucleic acid molecule encoding a TNFα molecule and an IL-2 molecule. In one aspect, the invention features use of the CAR-expressing cell therapy in combination with a virus, e.g., an oncolytic virus, e.g., an oncolytic adenovirus, comprising a nucleic acid molecule encoding a TNFα molecule and an IL-7 molecule. In one aspect, the invention features use of the CAR-expressing cell therapy in combination with a virus, e.g., an oncolytic virus, e.g., an oncolytic adenovirus, comprising a nucleic acid molecule encoding an IL-7 molecule and an IL-2 molecule. In one aspect, the invention features use of the CAR-expressing cell therapy in combination with a virus, e.g., an oncolytic virus, e.g., an oncolytic adenovirus, comprising a nucleic acid molecule encoding a TNFα molecule, an IL-2 molecule, and an IL-7 molecule. In one aspect, the invention features use of the CAR-expressing cell therapy in combination with a first virus, e.g., an oncolytic virus, e.g., an oncolytic adenovirus, comprising a nucleic acid molecule encoding a TNFα molecule, and a second virus, e.g., an oncolytic virus, e.g., an oncolytic adenovirus, comprising a nucleic acid molecule encoding an IL-2 molecule. In one aspect, the invention features use of the CAR-expressing cell therapy in combination with a first virus, e.g., an oncolytic virus, e.g., an oncolytic adenovirus, comprising a nucleic acid molecule encoding a TNFα molecule, and a second virus, e.g., an oncolytic virus, e.g., an oncolytic adenovirus, comprising a nucleic acid molecule encoding an IL-7 molecule. In one aspect, the invention features use of the CAR-expressing cell therapy in combination with a first virus, e.g., an oncolytic virus, e.g., an oncolytic adenovirus, comprising a nucleic acid molecule encoding an IL-7 molecule, and a second virus, e.g., an oncolytic virus, e.g., an oncolytic adenovirus, comprising a nucleic acid molecule encoding an IL-2 molecule. In one embodiment, the virus, first virus, or second virus comprises an adenovirus vector, e.g., Ad5/3 vector.

In one aspect, disclosed herein is a method of treating a subject having a disease associated with expression of an antigen, e.g., a tumor antigen, e.g., a method of treating a subject having a cancer, comprising administering to the subject a cell (e.g., a population of cells) that expresses a chimeric antigen receptor (CAR) molecule that binds to the antigen ("CAR-expressing cell"), wherein the subject has received, is receiving, or is about to receive: (i) a virus comprising a nucleic acid molecule encoding a TNFα molecule and/or an IL-2 molecule; (ii) a first virus comprising a nucleic acid molecule encoding a TNFα molecule, and a second virus comprising a nucleic acid molecule encoding an IL-2 molecule; (iii) a virus comprising a nucleic acid molecule encoding an IL-7 molecule, optionally wherein the virus further comprises a nucleic acid molecule encoding a TNFα molecule and/or an IL-2 molecule; or (iv) a first virus comprising a nucleic acid molecule encoding an IL-7 molecule and a second virus comprising a nucleic acid molecule encoding a TNFα molecule and/or an IL-2 molecule.

In one embodiment, the antigen is chosen from CD19, CD20, CD22, BCMA, mesothelin, EGFRvIII, GD2, Tn antigen, sTn antigen, Tn-O-Glycopeptides, sTn-O-Glycopeptides, PSMA, CD97, TAG72, CD44v6, CEA, EPCAM, KIT, IL-13Ra2, leguman, GD3, CD171, IL-11Ra, PSCA, MAD-CT-1, MAD-CT-2, VEGFR2, LewisY, CD24, PDGFR-beta, SSEA-4, folate receptor alpha, ERBBs (e.g., ERBB2), Her2/neu, MUC1, EGFR, NCAM, Ephrin B2, CAIX, LMP2, sLe, HMWMAA, o-acetyl-GD2, folate receptor beta, TEM1/CD248, TEM7R, FAP, Legumain, HPV E6 or E7, ML-IAP, CLDN6, TSHR, GPRC5D, ALK, Polysialic acid, Fos-related antigen, neutrophil elastase, TRP-2, CYP1B1, sperm protein 17, beta human chorionic gonadotropin, AFP, thyroglobulin, PLAC1, globoH, RAGE1, MN-CA IX, human telomerase reverse transcriptase, intestinal carboxyl esterase, mut hsp 70-2, NA-17, NY-BR-1, UPK2, HAVCR1, ADRB3, PANX3, NY-ESO-1, GPR20, Ly6k, OR51E2, TARP, GFRα4, or a peptide of any of these antigens presented on MHC. In one embodiment, the antigen is mesothelin.

In one embodiment, the subject has received a virus comprising a nucleic acid molecule encoding a TNFα molecule and/or an IL-2 molecule. In one embodiment, the subject has received a first virus comprising a nucleic acid molecule encoding a TNFα molecule, and a second virus comprising a nucleic acid molecule encoding an IL-2 molecule. In one embodiment, the subject has received a virus comprising a nucleic acid molecule encoding an IL-7 molecule, optionally wherein the virus further comprises a nucleic acid molecule encoding a TNFα molecule and/or an IL-2 molecule. In one embodiment, the subject has received a first virus comprising a nucleic acid molecule encoding an IL-7 molecule and a second virus comprising a nucleic acid molecule encoding a TNFα molecule and/or an IL-2 molecule.

In one aspect, disclosed herein is a method of treating a subject having a disease associated with expression of an antigen, e.g., a tumor antigen, e.g., a method of treating a subject having a cancer, comprising administering to the subject: (i) a virus comprising a nucleic acid molecule encoding a TNFα molecule and/or an IL-2 molecule; (ii) a first virus comprising a nucleic acid molecule encoding a TNFα molecule, and a second virus comprising a nucleic acid molecule encoding an IL-2 molecule; (iii) a virus comprising a nucleic acid molecule encoding an IL-7 molecule, optionally wherein the virus further comprises a nucleic acid molecule encoding a TNFα molecule and/or an IL-2 molecule; or (iv) a first virus comprising a nucleic acid molecule encoding an IL-7 molecule and a second virus comprising a nucleic acid molecule encoding a TNFα molecule and/or an IL-2 molecule, wherein the subject has received, is receiving, or is about to receive a cell (e.g., a population of cells) that expresses a CAR molecule that binds to the antigen ("CAR-expressing cell").

In one embodiment, the antigen is chosen from CD19, CD20, CD22, BCMA, mesothelin, EGFRvIII, GD2, Tn antigen, sTn antigen, Tn-O-Glycopeptides, sTn-O-Glycopeptides, PSMA, CD97, TAG72, CD44v6, CEA, EPCAM, KIT, IL-13Ra2, leguman, GD3, CD171, IL-11Ra, PSCA, MAD-CT-1, MAD-CT-2, VEGFR2, LewisY, CD24, PDGFR-beta, SSEA-4, folate receptor alpha, ERBBs (e.g., ERBB2), Her2/neu, MUC1, EGFR, NCAM, Ephrin B2, CAIX, LMP2, sLe, HMWMAA, o-acetyl-GD2, folate receptor beta, TEM1/CD248, TEM7R, FAP, Legumain, HPV E6 or E7, ML-IAP, CLDN6, TSHR, GPRC5D, ALK, Polysialic acid, Fos-related antigen, neutrophil elastase, TRP-2, CYP1B1, sperm protein 17, beta human chorionic gonadotropin, AFP, thyroglobulin, PLAC1, globoH, RAGE1, MN-CA IX, human telomerase reverse transcriptase, intestinal carboxyl esterase, mut hsp 70-2, NA-17, NY-BR-1, UPK2, HAVCR1, ADRB3, PANX3, NY-ESO-1, GPR20, Ly6k, OR51E2, TARP, GFRα4, or a peptide of any of these antigens presented on MHC. In one embodiment, the antigen is mesothelin.

In one embodiment, the subject is about to receive the CAR-expressing cell.

In one aspect, disclosed herein is a method of treating a subject having a disease associated with expression of an antigen, e.g., a tumor antigen, e.g., a method of treating a subject having a cancer, comprising administering to the subject a first virus comprising a nucleic acid molecule encoding a TNFα molecule, wherein the subject has received, is receiving, or is about to receive: (i) a cell (e.g., a population of cells) that expresses a CAR molecule that binds to the antigen ("CAR-expressing cell"), and (ii) a second virus comprising a nucleic acid molecule encoding an IL-2 molecule or an IL-7 molecule. In one aspect, disclosed herein is a method of treating a subject having a disease associated with expression of an antigen, e.g., a tumor antigen, e.g., a method of treating a subject having a cancer, comprising administering to the subject a first virus comprising a nucleic acid molecule encoding an IL-2 molecule, wherein the subject has received, is receiving, or is about to receive: (i) a cell (e.g., a population of cells) that expresses a CAR molecule that binds to the antigen ("CAR-expressing cell"), and (ii) a second virus comprising a nucleic acid molecule encoding a TNFα molecule or an IL-7 molecule. In one aspect, disclosed herein is a method of treating a subject having a disease associated with expression of an antigen, e.g., a tumor antigen, e.g., a method of treating a subject having a cancer, comprising administering to the subject a first virus comprising a nucleic acid molecule encoding an IL-7 molecule, wherein the subject has received, is receiving, or is about to receive: (i) a cell (e.g., a population of cells) that expresses a CAR molecule that binds to the antigen ("CAR-expressing cell"), and (ii) a second virus comprising a nucleic acid molecule encoding a TNFα molecule or an IL-2 molecule.

In one embodiment, the antigen is chosen from CD19, CD20, CD22, BCMA, mesothelin, EGFRvIII, GD2, Tn antigen, sTn antigen, Tn-O-Glycopeptides, sTn-O-Glycopeptides, PSMA, CD97, TAG72, CD44v6, CEA, EPCAM, KIT, IL-13Ra2, leguman, GD3, CD171, IL-11Ra, PSCA, MAD-CT-1, MAD-CT-2, VEGFR2, LewisY, CD24, PDGFR-beta, SSEA-4, folate receptor alpha, ERBBs (e.g., ERBB2), Her2/neu, MUC1, EGFR, NCAM, Ephrin B2, CAIX, LMP2, sLe, HMWMAA, o-acetyl-GD2, folate receptor beta, TEM1/CD248, TEM7R, FAP, Legumain, HPV E6 or E7, ML-IAP, CLDN6, TSHR, GPRC5D, ALK, Polysialic acid, Fos-related antigen, neutrophil elastase, TRP-2, CYP1B1, sperm protein 17, beta human chorionic gonadotropin, AFP, thyroglobulin, PLAC1, globoH, RAGE1, MN-CA IX, human telomerase reverse transcriptase, intestinal carboxyl esterase, mut hsp 70-2, NA-17, NY-BR-1, UPK2, HAVCR1, ADRB3, PANX3, NY-ESO-1, GPR20, Ly6k, OR51E2, TARP, GFRα4, or a peptide of any of these antigens presented on MHC. In one embodiment, the antigen is mesothelin.

In one aspect, disclosed herein is a method of treating a subject having a cancer, wherein the cancer exhibits or is identified as exhibiting heterogeneous expression of an antigen, e.g., a tumor antigen, e.g., mesothelin, e.g., wherein less than 90%, 80%, 70%, 60%, or 50% of cells in the cancer express the antigen, comprising administering to the subject: a cell (e.g., a population of cells) that expresses a CAR molecule that binds to the antigen ("CAR-expressing cell"); and (i) a virus comprising a nucleic acid molecule encoding a TNFα molecule and/or an IL-2 molecule; (ii) a first virus comprising a nucleic acid molecule encoding a TNFα molecule, and a second virus comprising a nucleic acid molecule encoding an IL-2 molecule; (iii) a virus comprising a nucleic acid molecule encoding an IL-7 molecule, optionally wherein the virus further comprises a nucleic acid molecule encoding a TNFα molecule and/or an IL-2 molecule; or (iv) a first virus comprising a nucleic acid molecule encoding an IL-7 molecule and a second virus comprising a nucleic acid molecule encoding a TNFα molecule and/or an IL-2 molecule.

In one embodiment, the antigen is chosen from CD19, CD20, CD22, BCMA, mesothelin, EGFRvIII, GD2, Tn antigen, sTn antigen, Tn-O-Glycopeptides, sTn-O-Glycopeptides, PSMA, CD97, TAG72, CD44v6, CEA, EPCAM, KIT, IL-13Ra2, leguman, GD3, CD171, IL-11Ra, PSCA, MAD-CT-1, MAD-CT-2, VEGFR2, LewisY, CD24, PDGFR-beta, SSEA-4, folate receptor alpha, ERBBs (e.g., ERBB2), Her2/neu, MUC1, EGFR, NCAM, Ephrin B2, CAIX, LMP2, sLe, HMWMAA, o-acetyl-GD2, folate receptor beta, TEM1/CD248, TEM7R, FAP, Legumain, HPV E6 or E7, ML-IAP, CLDN6, TSHR, GPRC5D, ALK, Polysialic acid, Fos-related antigen, neutrophil elastase, TRP-2, CYP1B1, sperm protein 17, beta human chorionic gonadotropin, AFP, thyroglobulin, PLAC1, globoH, RAGE1, MN-CA IX, human telomerase reverse transcriptase, intestinal carboxyl esterase, mut hsp 70-2, NA-17, NY-BR-1, UPK2, HAVCR1, ADRB3, PANX3, NY-ESO-1, GPR20, Ly6k, OR51E2, TARP, GFRα4, or a peptide of any of these antigens presented on MHC. In one embodiment, the antigen is mesothelin.

In one aspect, disclosed herein is a method of treating a subject having a disease associated with expression of an antigen, e.g., a tumor antigen, e.g., a method of treating a subject having a cancer, comprising administering to the subject: a cell (e.g., a population of cells) that expresses a CAR molecule that binds to the antigen ("CAR-expressing cell"); and (i) a non-oncolytic virus comprising a nucleic acid molecule encoding a TNFα molecule and/or an IL-2 molecule; (ii) a first non-oncolytic virus comprising a nucleic acid molecule encoding a TNFα molecule, and a second non-oncolytic virus comprising a nucleic acid molecule encoding an IL-2 molecule; (iii) a non-oncolytic virus comprising a nucleic acid molecule encoding an IL-7 molecule, optionally wherein the non-oncolytic virus further comprises a nucleic acid molecule encoding a TNFα molecule and/or an IL-2 molecule; or (iv) a non-oncolytic first virus comprising a nucleic acid molecule encoding an IL-7 molecule and a second non-oncolytic virus comprising a nucleic acid molecule encoding a TNFα molecule and/or an IL-2 molecule.

In one embodiment, the antigen is chosen from CD19, CD20, CD22, BCMA, mesothelin, EGFRvIII, GD2, Tn antigen, sTn antigen, Tn-O-Glycopeptides, sTn-O-Glycopeptides, PSMA, CD97, TAG72, CD44v6, CEA, EPCAM, KIT, IL-13Ra2, leguman, GD3, CD171, IL-11Ra, PSCA, MAD-CT-1, MAD-CT-2, VEGFR2, LewisY, CD24, PDGFR-beta, SSEA-4, folate receptor alpha, ERBBs (e.g., ERBB2), Her2/neu, MUC1, EGFR, NCAM, Ephrin B2, CAIX, LMP2, sLe, HMWMAA, o-acetyl-GD2, folate receptor beta, TEM1/CD248, TEM7R, FAP, Legumain, HPV E6 or E7, ML-IAP, CLDN6, TSHR, GPRC5D, ALK, Polysialic acid, Fos-related antigen, neutrophil elastase, TRP-2, CYP1B1, sperm protein 17, beta human chorionic gonadotropin, AFP, thyroglobulin, PLAC1, globoH, RAGE1, MN-CA IX, human telomerase reverse transcriptase, intestinal carboxyl esterase, mut hsp 70-2, NA-17, NY-BR-1, UPK2, HAVCR1, ADRB3, PANX3, NY-ESO-1, GPR20, Ly6k, OR51E2, TARP, GFRα4, or a peptide of any of these antigens presented on MHC. In one embodiment, the antigen is mesothelin.

In one aspect, disclosed herein is a method of treating a subject having a disease associated with mesothelin expression, comprising administering to the subject: a cell (e.g., a population of cells) that expresses a chimeric antigen receptor (CAR) molecule that binds to mesothelin ("mesothelin CAR-expressing cell"), wherein the CAR molecule comprises a mesothelin binding domain comprising a heavy chain complementary determining region 1 (HC CDR1), a heavy chain complementary determining region 2 (HC CDR2), and a heavy chain complementary determining region 3 (HC CDR3) of any mesothelin heavy chain binding domain amino acid sequence listed in Table 2; and a light chain complementary determining region 1 (LC CDR1), a light chain complementary determining region 2 (LC CDR2), and a light chain complementary determining region 3 (LC CDR3) of any mesothelin light chain binding domain amino acid sequence listed in Table 2; and (i) a virus comprising a nucleic acid molecule encoding a TNFα molecule and/or an IL-2 molecule; (ii) a first virus comprising a nucleic acid molecule encoding a TNFα molecule, and a second virus comprising a nucleic acid molecule encoding an IL-2 molecule; (iii) a virus comprising a nucleic acid molecule encoding an IL-7 molecule, optionally wherein the virus further comprises a nucleic acid molecule encoding a TNFα molecule and/or an IL-2 molecule; or (iv) a first virus comprising a nucleic acid molecule encoding an IL-7 molecule and a second virus comprising a nucleic acid molecule encoding a TNFα molecule and/or an IL-2 molecule.

In one aspect, disclosed herein is a method of treating a subject having a disease associated with expression of an antigen, e.g., a tumor antigen, e.g., a method of treating a subject having a cancer, comprising administering to the subject: a cell (e.g., a population of cells) that expresses a chimeric antigen receptor (CAR) molecule that binds to the antigen ("CAR-expressing cell"); and (i) a virus comprising a nucleic acid molecule encoding a TNFα molecule and/or an IL-2 molecule; (ii) a first virus comprising a nucleic acid molecule encoding a TNFα molecule, and a second virus comprising a nucleic acid molecule encoding an IL-2 molecule; (iii) a virus comprising a nucleic acid molecule encoding an IL-7 molecule, optionally wherein the virus further comprises a nucleic acid molecule encoding a TNFα molecule and/or an IL-2 molecule; or (iv) a first virus comprising a nucleic acid molecule encoding an IL-7 molecule and a second virus comprising a nucleic acid molecule encoding a TNFα molecule and/or an IL-2 molecule.

In one aspect, disclosed herein is a method of providing an anti-cancer immune response in a subject having a cancer, comprising administering to the subject: a cell (e.g., a population of cells) that expresses a chimeric antigen receptor (CAR) molecule that binds to mesothelin ("mesothelin CAR-expressing cell"), wherein the CAR molecule comprises a mesothelin binding domain comprising a heavy chain complementary determining region 1 (HC CDR1), a heavy chain complementary determining region 2 (HC CDR2), and a heavy chain complementary determining region 3 (HC CDR3) of any mesothelin heavy chain binding domain amino acid sequence listed in Table 2; and a light chain complementary determining region 1 (LC CDR1), a light chain complementary determining region 2 (LC CDR2), and a light chain complementary determining region 3 (LC CDR3) of any mesothelin light chain binding domain amino acid sequence listed in Table 2; and (i) a virus comprising a nucleic acid molecule encoding a TNFα molecule and/or an IL-2 molecule; (ii) a first virus comprising a nucleic acid molecule encoding a TNFα molecule, and a second virus comprising a nucleic acid molecule encoding an IL-2 molecule; (iii) a virus comprising a nucleic acid molecule encoding an IL-7 molecule, optionally wherein the virus further comprises a nucleic acid molecule encoding a TNFα molecule and/or an IL-2 molecule; or (iv) a first virus comprising a nucleic acid molecule encoding an IL-7 molecule and a second virus comprising a nucleic acid molecule encoding a TNFα molecule and/or an IL-2 molecule.

In certain embodiments of the aforementioned aspects and embodiments, the virus (or the first virus and the second virus) are administered prior to the administration of the CAR-expressing cell (e.g., the mesothelin CAR-expressing cell), e.g., about 1, 2, 3, 4, or 5 days prior to the administration of the CAR-expressing cell (e.g., the mesothelin CAR-expressing cell).

In certain embodiments of the aforementioned aspects and embodiments, the virus (or the first virus and the second virus) are administered after the administration of the CAR-expressing cell (e.g., the mesothelin CAR-expressing cell), e.g., about 1, 2, 3, 4, or 5 days after the administration of the CAR-expressing cell (e.g., the mesothelin CAR-expressing cell).

In certain embodiments of the aforementioned aspects and embodiments, the first virus comprising the nucleic acid molecule encoding the TNFα molecule and the second virus comprising the nucleic acid molecule encoding the IL-2 molecule are administered simultaneously. In certain embodiments of the aforementioned aspects and embodiments, the first virus comprising the nucleic acid molecule encoding the TNFα molecule and the second virus comprising the nucleic acid molecule encoding the IL-7 molecule are administered simultaneously. In certain embodiments of the aforementioned aspects and embodiments, the first virus comprising the nucleic acid molecule encoding the IL-7 molecule and the second virus comprising the nucleic acid molecule encoding the IL-2 molecule are administered simultaneously.

In certain embodiments of the aforementioned aspects and embodiments, (i) the CAR-expressing cell (e.g., the mesothelin CAR-expressing cell), and (ii) the virus (or the first virus and the second virus) are administered for a first treatment interval, wherein the first treatment interval comprises a single dose of the CAR-expressing cell (e.g., the mesothelin CAR-expressing cell), and a single dose of the virus (or the first virus and the second virus).

In one embodiment, the first treatment interval is initiated upon administration of the single dose of the virus (or the first virus and the second virus) and completed upon administration of the single dose of the CAR-expressing cell (e.g., the mesothelin CAR-expressing cell).

In one embodiment, the single dose of the CAR-expressing cell (e.g., the mesothelin CAR-expressing cell) is administered, e.g., about 1, 2, 3, 4, or 5 days after the administration of the single dose of the virus (or the first virus and the second virus).

In one embodiment, the first treatment interval is repeated, e.g., one or more times, e.g., 1, 2, 3, 4, or 5 more times. In one embodiment, the first treatment interval is followed by one or more, e.g., 1, 2, 3, 4, or 5, subsequent treatment intervals. In one embodiment, the one or more subsequent treatment intervals are different from the first treatment interval.

In certain embodiments of the aforementioned aspects and embodiments, the virus (or the first virus and the second virus) is administered systemically or locally.

In one embodiment, the virus (or the first virus and the second virus) is administered locally. In one embodiment, the subject has a cancer and the virus (or the first virus and the second virus) is administered intratumorally.

In certain embodiments of the aforementioned aspects and embodiments, the CAR-expressing cell (e.g., the mesothelin CAR-expressing cell) is administered intravenously.

In certain embodiments of the aforementioned aspects and embodiments, the first virus and the second virus are the same virus. In certain embodiments of the aforementioned aspects and embodiments, the first virus and the second virus are different viruses. In one embodiment, the virus, the first virus, and/or the second virus are chosen from adenovirus, herpes simplex virus, retrovirus, parvovirus, vaccinia virus, sinbis virus, influenza virus, or RNA virus (e.g., reovirus, newcastle disease virus (NDV), measles virus, or vesicular stomatitis virus (VSV)). In one embodiment, the virus, the first virus, and/or the second virus are oncolytic virus, e.g., oncolytic adenovirus, oncolytic adeno-associated virus, oncolytic Herpes Simplex Virus (HSV), oncolytic parvovirus, oncolytic retrovirus, oncolytic lentivirus, oncolytic vaccinia virus, oncolytic Sinbis virus, oncolytic influenza virus, oncolytic reovirus, oncolytic Newcastle disease virus (NDV), oncolytic measles virus, oncolytic vesicular stomatitis virus (VSV), oncolytic poliovirus, oncolytic poxvirus, oncolytic Seneca Valley virus, oncolytic coxsackievirus, oncolytic enterovirus, oncolytic myxoma virus, or oncolytic maraba virus. In one embodiment, the virus, the first virus, and/or the second virus are oncolytic adenovirus. In one embodiment, the subject has cancer cells expressing desmoglein-2 (DSG-2). In one embodiment, the nucleic acid molecule encoding the TNFα molecule and/or the IL-2 molecule, the nucleic acid molecule encoding the TNFα molecule, and/or the nucleic acid molecule encoding the IL-2 molecule are disposed on an adenoviral vector. In one embodiment, the nucleic acid molecule encoding the TNFα molecule and/or the IL-7 molecule, the nucleic acid molecule encoding the TNFα molecule, and/or the nucleic acid molecule encoding the IL-7 molecule are disposed on an adenoviral vector. In one embodiment, the nucleic acid molecule encoding the IL-7 molecule and/or the IL-2 molecule, the nucleic acid molecule encoding the IL-7 molecule, and/or the nucleic acid molecule encoding the IL-2 molecule are disposed on an adenoviral vector. In one embodiment, the adenoviral vector is chosen from Ad5, Ad3 or Ad5/3. In one embodiment, the adenoviral vector is Ad5. In one embodiment, the adenoviral vector is Ad3. In one embodiment, the adenoviral vector is Ad5/3. In one embodiment, the adenoviral vector is Ad5/3 comprising an Ad5 nucleic acid backbone and Ad3 fiber knob or Ad5/3 chimeric fiber knob. In one embodiment, the nucleic acid molecule encoding the TNFα molecule and/or the IL-2 molecule, the nucleic acid molecule encoding the TNFα molecule, and/or the nucleic acid molecule encoding the IL-2 molecule are disposed on an oncolytic adenoviral vector. In one embodiment, the nucleic acid molecule encoding the TNFα molecule and/or the IL-7 molecule, the nucleic acid molecule encoding the TNFα molecule, and/or the nucleic acid molecule encoding the IL-7 molecule are disposed on an oncolytic adenoviral vector. In one embodiment, the nucleic acid molecule encoding the IL-7 molecule and/or the IL-2 molecule, the nucleic acid molecule encoding the IL-7 molecule, and/or the nucleic acid molecule encoding the IL-2 molecule are disposed on an oncolytic adenoviral vector. In some embodiments, (i) the oncolytic adenoviral vector comprises an Ad5 nucleic acid backbone comprising Ad5/3 chimeric fiber knob, (ii) the oncolytic adenoviral vector comprises E2F promoter, e.g., E2F1 promoter, (iii) the oncolytic adenoviral vector comprises a 24 bp deletion (D24) in the Rb binding constant region 2 of adenoviral E1, and/or (iv) the oncolytic adenoviral vector comprises a nucleic acid sequence deletion of viral gp19k and 6.7k reading frames. In some embodiments, the nucleic acid molecule encoding the TNFα molecule and/or the IL-2 molecule, the nucleic acid molecule encoding the TNFα molecule, and/or the nucleic acid molecule encoding the IL-2 molecule are in the place of the deleted gp19k/6.7k in the E3 region, e.g., resulting in replication-associated control of expression of the TNFα molecule and/or the IL-2 molecule under the viral E3 promoter. In some embodiments, the nucleic acid molecule encoding the TNFα molecule and/or the IL-7 molecule, the nucleic acid molecule encoding the TNFα molecule, and/or the nucleic acid molecule encoding the IL-7 molecule are in the place of the deleted gp19k/6.7k in the E3 region, e.g., resulting in replication-associated control of expression of the TNFα molecule and/or the IL-7 molecule under the viral E3 promoter. In some embodiments, the nucleic acid molecule encoding the IL-7 molecule and/or the IL-2 molecule, the nucleic acid molecule encoding the IL-7 molecule, and/or the nucleic acid molecule encoding the IL-2 molecule are in the place of the deleted gp19k/6.7k in the E3 region, e.g., resulting in replication-associated control of expression of the IL-7 molecule and/or the IL-2 molecule under the viral E3 promoter. In one embodiment, the nucleic acid molecule encoding the TNFα molecule and/or the IL-2 molecule, the nucleic acid molecule encoding the TNFα molecule, and/or the nucleic acid molecule encoding the IL-2 molecule are disposed on an Ad3 oncolytic adenoviral vector. In one embodiment, the nucleic acid molecule encoding the TNFα molecule and/or the IL-7 molecule, the nucleic acid molecule encoding the TNFα molecule, and/or the nucleic acid molecule encoding the IL-7 molecule are disposed on an Ad3 oncolytic adenoviral vector. In one embodiment, the nucleic acid molecule encoding the IL-7 molecule and/or the IL-2 molecule, the nucleic acid molecule encoding the IL-7 molecule, and/or the nucleic acid molecule encoding the IL-2 molecule are disposed on an Ad3 oncolytic adenoviral vector. In some embodiments, the Ad3 oncolytic adenoviral vector comprises: (i) a deletion in the E3 area, and (ii) a tumor specific promoter for expression of, e.g., the TNFα molecule and/or the IL-2 molecule, e.g., in the place of the deleted E3 area. In one embodiment, the nucleic acid molecule encoding the TNFα molecule and the nucleic acid molecule encoding the IL-2 molecule are encapsulated in a single viral particle. In one embodiment, the nucleic acid molecule encoding the TNFα molecule and the nucleic acid molecule encoding the IL-7 molecule are encapsulated in a single viral particle. In one embodiment, the nucleic acid molecule encoding the IL-7 molecule and the nucleic acid molecule encoding the IL-2 molecule are encapsulated in a single viral particle.

In one embodiment, the nucleic acid molecule encoding the TNFα molecule and/or the IL-2 molecule comprises a sequence encoding the TNFα molecule and a sequence encoding the IL-2 molecule, wherein the sequence encoding the TNFα molecule and the sequence encoding the IL-2 molecule are disposed on a single nucleic acid molecule, e.g., a single DNA molecule or a single mRNA molecule. In one embodiment, the nucleic acid molecule encoding the TNFα molecule and the nucleic acid molecule encoding the IL-2 molecule are disposed on a single nucleic acid molecule, e.g., a single DNA molecule or a single mRNA molecule. In one embodiment, the nucleic acid molecule encoding the TNFα molecule and/or the IL-2 molecule comprises a sequence encoding the TNFα molecule and a sequence encoding the IL-2 molecule, wherein the sequence encoding the TNFα molecule and the sequence encoding the IL-2 molecule are separated by a nucleic acid molecule encoding a self-cleavage site, e.g., a 2A site, or an internal ribosomal entry site. In one embodiment, the nucleic acid molecule encoding the TNFα molecule and the nucleic acid molecule encoding the IL-2 molecule are separated by a nucleic acid molecule encoding a self-cleavage site, e.g., a 2A site, or an internal ribosomal entry site. In one embodiment, the nucleic acid molecule encoding the TNFα molecule and/or the IL-2 molecule comprises a sequence encoding the TNFα molecule and a sequence encoding the IL-2 molecule, wherein the sequence encoding the TNFα molecule and the sequence encoding the IL-2 molecule are disposed on separate nucleic acid molecules. In one embodiment, the nucleic acid molecule encoding the TNFα molecule and the nucleic acid molecule encoding the IL-2 molecule are disposed on separate nucleic acid molecules.

In one embodiment, the nucleic acid molecule encoding the TNFα molecule and/or the IL-7 molecule comprises a sequence encoding the TNFα molecule and a sequence encoding the IL-7 molecule, wherein the sequence encoding the TNFα molecule and the sequence encoding the IL-7 molecule are disposed on a single nucleic acid molecule, e.g., a single DNA molecule or a single mRNA molecule. In one embodiment, the nucleic acid molecule encoding the TNFα molecule and the nucleic acid molecule encoding the IL-7 molecule are disposed on a single nucleic acid molecule, e.g., a single DNA molecule or a single mRNA molecule. In one embodiment, the nucleic acid molecule encoding the TNFα molecule and/or the IL-7 molecule comprises a sequence encoding the TNFα molecule and a sequence encoding the IL-7 molecule, wherein the sequence encoding the TNFα molecule and the sequence encoding the IL-7 molecule are separated by a nucleic acid molecule encoding a self-cleavage site, e.g., a 2A site, or an internal ribosomal entry site. In one embodiment, the nucleic acid molecule encoding the TNFα molecule and the nucleic acid molecule encoding the IL-7 molecule are separated by a nucleic acid molecule encoding a self-cleavage site, e.g., a 2A site, or an internal ribosomal entry site. In one embodiment, the nucleic acid molecule encoding the TNFα molecule and/or the IL-7 molecule comprises a sequence encoding the TNFα molecule and a sequence encoding the IL-7 molecule, wherein the sequence encoding the TNFα molecule and the sequence encoding the IL-7 molecule are disposed on separate nucleic acid molecules. In one embodiment, the nucleic acid molecule encoding the TNFα molecule and the nucleic acid molecule encoding the IL-7 molecule are disposed on separate nucleic acid molecules.

In one embodiment, the nucleic acid molecule encoding the IL-7 molecule and/or the IL-2 molecule comprises a sequence encoding the IL-7 molecule and a sequence encoding the IL-2 molecule, wherein the sequence encoding the IL-7 molecule and the sequence encoding the IL-2 molecule are disposed on a single nucleic acid molecule, e.g., a single DNA molecule or a single mRNA molecule. In one embodiment, the nucleic acid molecule encoding the IL-7 molecule and the nucleic acid molecule encoding the IL-2 molecule are disposed on a single nucleic acid molecule, e.g., a single DNA molecule or a single mRNA molecule. In one embodiment, the nucleic acid molecule encoding the IL-7 molecule and/or the IL-2 molecule comprises a sequence encoding the IL-7 molecule and a sequence encoding the IL-2 molecule, wherein the sequence encoding the IL-7 molecule and the sequence encoding the IL-2 molecule are separated by a nucleic acid molecule encoding a self-cleavage site, e.g., a 2A site, or an internal ribosomal entry site. In one embodiment, the nucleic acid molecule encoding the IL-7 molecule and the nucleic acid molecule encoding the IL-2 molecule are separated by a nucleic acid molecule encoding a self-cleavage site, e.g., a 2A site, or an internal ribosomal entry site. In one embodiment, the nucleic acid molecule encoding the IL-7 molecule and/or the IL-2 molecule comprises a sequence encoding the IL-7 molecule and a sequence encoding the IL-2 molecule, wherein the sequence encoding the IL-7 molecule and the sequence encoding the IL-2 molecule are disposed on separate nucleic acid molecules. In one embodiment, the nucleic acid molecule encoding the IL-7 molecule and the nucleic acid molecule encoding the IL-2 molecule are disposed on separate nucleic acid molecules.

In certain embodiments of the aforementioned aspects and embodiments, the antigen is mesothelin, wherein the CAR-expressing cell expresses a CAR that binds to mesothein ("mesothelin CAR-expressing cell")

In certain embodiments of the aforementioned aspects and embodiments, the virus comprising a nucleic acid molecule encoding the TNFα molecule and/or the IL-2 molecule, the first virus comprising the nucleic acid molecule encoding the TNFα molecule, and/or the second virus comprising the nucleic acid molecule encoding the IL-2 molecule, have one, two, or all of the following properties:

(i) mesothelin-expressing target cells, e.g., mesothelin-expressing tumor cells, e.g., BxPC-3 cells, infected with the virus, or the first and/or second virus, activates the mesothelin CAR-expressing cell, e.g., at a level at least about 20, 50, 100, 150, or 200% higher than, e.g., mesothelin-expressing target cells, e.g., mesothelin-expressing tumor cells, infected with an otherwise similar virus that does not comprise the nucleic acid molecule encoding the TNFα molecule or the IL-2 molecule, e.g., as measured by expression of an activation marker (e.g., CD69), e.g., as assessed using methods described in Example 1 with respect to FIG. 1B or 1C, (ii) mesothelin-expressing target cells, e.g., mesothelin-expressing tumor cells, e.g., BxPC-3 cells, infected with the virus, or the first and/or second virus, increases proliferation of the mesothelin CAR-expressing cell, e.g., at a level at least about 20, 50, 100, 150, or 200% higher than, e.g., mesothelin-expressing target cells, e.g., mesothelin-expressing tumor cells, infected with an otherwise similar virus that does not comprise the nucleic acid molecule encoding the TNFα molecule or the IL-2 molecule, e.g., as assessed using methods described in Example 1 with respect to FIG. 1D or 1E, or (iii) the lytic activity of the mesothelin CAR-expressing cell against mesothelin-expressing target cells, e.g., mesothelin-expressing tumor cells, e.g., BxPC-3 cells, infected with the virus, or the first and/or second virus, is increased by at least about 1, 2, 3, 4, or 5-fold, e.g., compared to the lytic activity of the mesothelin CAR-expressing cell against otherwise similar mesothelin-expressing target cells, e.g., mesothelin-expressing tumor cells, that are not infected with the virus, or the first and/or second virus, e.g., as assessed using methods described in Example 1 with respect to FIG. 1A.

In certain embodiments of the aforementioned aspects and embodiments, the administration of the mesothelin CAR-expressing cell and (a) the virus comprising a nucleic acid molecule encoding the TNFα molecule and/or the IL-2 molecule, or (b) the first virus comprising the nucleic acid molecule encoding the TNFα molecule, and the second virus comprising the nucleic acid molecule encoding the IL-2 molecule, results in one or more (2, 3, 4, 5, 6, 7, 8, 9, or all) of the following properties:

(i) administration of the mesothelin CAR-expressing cell and the virus (or the first and second viruses) in a subject having a cancer, e.g., a pancreatic cancer, produces a reduction in tumor load, e.g., a reduction of at least about 0.5, 1, 2, 5, 10, or 200-fold, e.g., about 15, 20, 25, 30, 35, 40, or 45 days after administration of the virus (or the first and second viruses), e.g., compared to administration of the mesothelin CAR-expressing cell without the virus (or without the first or second virus), or compared to administration of the mesothelin CAR-expressing cell and an otherwise similar virus that does not comprise the nucleic acid molecule encoding the TNFα molecule or the IL-2 molecule, e.g., as assessed using methods described in Example 1 with respect to FIG. 2B, 2C, 2D, or 6B.

(ii) administration of the mesothelin CAR-expressing cell and the virus (or the first and second viruses) in a subject having a cancer, e.g., a pancreatic cancer, increases survival of the subject, e.g., by at least about 2, 5, 10, 20, 50, or 100-fold, e.g., about 20, 40, 60, 80, or 100 days after administration of the virus (or the first and second viruses), e.g., compared to administration of the mesothelin CAR-expressing cell without the virus (or without the first or second virus), or compared to administration of the mesothelin CAR-expressing cell and an otherwise similar virus that does not comprise the nucleic acid molecule encoding the TNFα molecule or the IL-2 molecule, e.g., as assessed using methods described in Example 1 with respect to FIG. 2E, (iii) administration of the mesothelin CAR-expressing cell and the virus (or the first and second viruses) in a subject having a cancer, e.g., a pancreatic cancer, reduces tumor metastasis, e.g., tumor metastasis to the lung, by at least about 20, 40, 60, or 80%, e.g., about 20, 50, 100, or 150 days after administration of the virus (or the first and second viruses), e.g., compared to administration of the mesothelin CAR-expressing cell without the virus (or without the first or second virus), or compared to administration of the mesothelin CAR-expressing cell and an otherwise similar virus that does not comprise the nucleic acid molecule encoding the TNFα molecule or the IL-2 molecule, e.g., as assessed using methods described in Example 1 with respect to FIG. 2F, (iv) administration of the mesothelin CAR-expressing cell and the virus (or the first and second viruses) in a subject having a cancer, e.g., a pancreatic cancer, increases expression of a cytokine molecule, e.g., IFN-γ, by the mesothelin CAR-expressing cell, by at least about 1, 2, 3, or 4-fold, e.g., about 5, 10, 15, or 20 days after administration of the virus (or the first and second viruses), e.g., compared to administration of the mesothelin CAR-expressing cell without the virus (or without the first or second virus), or compared to administration of the mesothelin CAR-expressing cell and an otherwise similar virus that does not comprise the nucleic acid molecule encoding the TNFα molecule or the IL-2 molecule, e.g., as assessed using methods described in Example 1 with respect to FIG. 3E, (v) administration of the mesothelin CAR-expressing cell and the virus (or the first and second viruses) in a subject having a cancer, e.g., a pancreatic cancer, increases infiltration of the mesothelin CAR-expressing cell into a tumor, e.g., by at least about 5, 10, 25, 50, 75, 100, 125, 150, 175, or 200-fold, e.g., about 2, 4, 6, 8, 10, 12, 13, 14, 16, 18, 20, 30, 40, or 50 days after the administration of the virus (or the first and second viruses), e.g., compared to administration of the mesothelin CAR-expressing cell the virus (or without the first or second virus), or compared to administration of the mesothelin CAR-expressing cell and an otherwise similar virus that does not comprise the nucleic acid molecule encoding the TNFα molecule or the IL-2 molecule, e.g., as assessed using methods described in Example 1 with respect to FIG. 4A, 4B, or 6C, (vi) administration of the mesothelin CAR-expressing cell and the virus (or the first and second viruses) in a subject having a cancer, e.g., a pancreatic cancer, increases infiltration of endogenous T cells, e.g., CD4+ and/or CD8+ T cells, into a tumor, e.g., by at least about 1, 2, 5, 10, 20, 30, or 50-fold, e.g., about 15, 20, 25, 30, or 35 days after the administration of the virus (or the first and second viruses), e.g., compared to administration of the mesothelin CAR-expressing cell without the virus (or without the first or second virus), or compared to administration of the mesothelin CAR-expressing cell and an otherwise similar virus that does not comprise the nucleic acid molecule encoding the TNFα molecule or the IL-2 molecule, e.g., as assessed using methods described in Example 1 with respect to FIG. 3A, 3B, 9B, or 6D, (vii) administration of the mesothelin CAR-expressing cell and the virus (or the first and second viruses) in a subject having a cancer, e.g., a pancreatic cancer, activates tumor infiltrating lymphocytes (TILs), e.g., by at least about 20, 30, 40, or 50%, e.g., about 10, 20, 30, or 40 days after administration of the virus (or the first and second viruses), e.g., compared to administration of the mesothelin CAR-expressing cell without the virus (or without the first or second virus), or compared to administration of the mesothelin CAR-expressing cell and an otherwise similar virus that does not comprise the nucleic acid molecule encoding the TNFα molecule or the IL-2 molecule, e.g., as measured by expression of an activation marker, e.g., as measured by expression of CD69 and/or CD25, e.g., as assessed using methods described in Example 1 with respect to FIG. 3D or 9C, (viii) administration of the mesothelin CAR-expressing cell and the virus (or the first and second viruses) in a subject having a cancer, e.g., a pancreatic cancer, increases M1 polarization of macrophages, e.g., by at least about 20, 30, 40, or 50%, e.g., about 1, 2, 3, 5, or 10 days after administration of the virus (or the first and second viruses), e.g., compared to administration of the mesothelin CAR-expressing cell without the virus (or without the first or second virus), or compared to administration of the mesothelin CAR-expressing cell and an otherwise similar virus that does not comprise the nucleic acid molecule encoding the TNFα molecule or the IL-2 molecule, e.g., as measured by expression of CD80 and/or CD86 on macrophages, e.g., as assessed using methods described in Example 1 with respect to FIG. 6E, (ix) administration of the mesothelin CAR-expressing cell and the virus (or the first and second viruses) in a subject having a cancer, e.g., a pancreatic cancer, increases maturation of dendritic cells, e.g., maturation of CD11c+ dendritic cells, e.g., by at least about 20, 30, 40, or 50%, e.g., about 1, 2, 3, 5, or 10 days after administration of the virus (or the first and second viruses), e.g., compared to administration of the mesothelin CAR-expressing cell without the virus (or without the first or second virus), or compared to administration of the mesothelin CAR-expressing cell and an otherwise similar virus that does not comprise the nucleic acid molecule encoding the TNFα molecule or the IL-2 molecule, e.g., as measured by expression of CD80 and/or CD86 on dendritic cells, e.g., as assessed using methods described in Example 1 with respect to FIG. 10E, or (x) administration of the mesothelin CAR-expressing cell and the virus (or the first and second viruses) in a subject having a cancer, e.g., a pancreatic cancer, increases the level of a chemokine in the subject, e.g., an immune-cell attractive chemokine, e.g., a TNF-α inducible chemokine, e.g., one, two, or all of: monocyte chemoattractant protein-1 (MCP-1), C—X—C motif chemokine ligand 10 (CXCL-10) and RANTES, by at least about 5, 10, 25, 50, 75, 100, 125, 150, 175, or 200-fold, e.g., about 1, 2, 3, 5, or 10 days after administration of the virus (or the first and second viruses), e.g., compared to administration of the mesothelin CAR-expressing cell without the virus (or without the first or second virus), or compared to administration of the mesothelin CAR-expressing cell and an otherwise similar virus that does not comprise the nucleic acid molecule encoding the TNFα molecule or the IL-2 molecule, e.g., as assessed using methods described in Example 1 with respect to FIG. 6F or 10F.

In certain embodiments of the aforementioned aspects and embodiments, (a) the virus comprising a nucleic acid molecule encoding a TNFα molecule and/or an IL-2 molecule;

(b) the first virus comprising a nucleic acid molecule encoding a TNFα molecule, and the second virus comprising a nucleic acid molecule encoding an IL-2 molecule;

(c) the virus comprising a nucleic acid molecule encoding an IL-7 molecule, optionally wherein the virus further comprises a nucleic acid molecule encoding a TNFα molecule and/or an IL-2 molecule; or (d) the first virus comprising a nucleic acid molecule encoding an IL-7 molecule and the second virus comprising a nucleic acid molecule encoding a TNFα molecule and/or an IL-2 molecule, have one, two, or all of the following properties:

(i) mesothelin-expressing target cells, e.g., mesothelin-expressing tumor cells, e.g., BxPC-3 cells, infected with the virus, or the first and/or second virus, activates the mesothelin CAR-expressing cell, e.g., at a level at least about 20, 50, 100, 150, or 200% higher than, e.g., mesothelin-expressing target cells, e.g., mesothelin-expressing tumor cells, infected with an otherwise similar virus that does not comprise the nucleic acid molecule encoding the TNFα molecule, the IL-2 molecule, and/or the IL-7 molecule, e.g., as measured by expression of an activation marker (e.g., CD69), e.g., as assessed using methods described in Example 1 with respect to FIG. 1B or 1C, (ii) mesothelin-expressing target cells, e.g., mesothelin-expressing tumor cells, e.g., BxPC-3 cells, infected with the virus, or the first and/or second virus, increases proliferation of the mesothelin CAR-expressing cell, e.g., at a level at least about 20, 50, 100, 150, or 200% higher than, e.g., mesothelin-expressing target cells, e.g., mesothelin-expressing tumor cells, infected with an otherwise similar virus that does not comprise the nucleic acid molecule encoding the TNFα molecule, the IL-2 molecule, and/or the IL-7 molecule, e.g., as assessed using methods described in Example 1 with respect to FIG. 1D or 1E, or (iii) the lytic activity of the mesothelin CAR-expressing cell against mesothelin-expressing target cells, e.g., mesothelin-expressing tumor cells, e.g., BxPC-3 cells, infected with the virus, or the first and/or second virus, is increased by at least about 1, 2, 3, 4, or 5-fold, e.g., compared to the lytic activity of the mesothelin CAR-expressing cell against otherwise similar mesothelin-expressing target cells, e.g., mesothelin-expressing tumor cells, that are not infected with the virus, or the first and/or second virus, e.g., as assessed using methods described in Example 1 with respect to FIG. 1A.

In certain embodiments of the aforementioned aspects and embodiments, the administration of the mesothelin CAR-expressing cell and (a) the virus comprising a nucleic acid molecule encoding a TNFα molecule and/or an IL-2 molecule;

(b) the first virus comprising a nucleic acid molecule encoding a TNFα molecule, and the second virus comprising a nucleic acid molecule encoding an IL-2 molecule;

(c) the virus comprising a nucleic acid molecule encoding an IL-7 molecule, optionally wherein the virus further comprises a nucleic acid molecule encoding a TNFα molecule and/or an IL-2 molecule; or (d) the first virus comprising a nucleic acid molecule encoding an IL-7 molecule and the second virus comprising a nucleic acid molecule encoding a TNFα molecule and/or an IL-2 molecule, results in one or more (2, 3, 4, 5, 6, 7, 8, 9, or all) of the following properties:

(i) administration of the mesothelin CAR-expressing cell and the virus (or the first and second viruses) in a subject having a cancer, e.g., a pancreatic cancer, produces a reduction in tumor load, e.g., a reduction of at least about 0.5, 1, 2, 5, 10, or 200-fold, e.g., about 15, 20, 25, 30, 35, 40, or 45 days after administration of the virus (or the first and second viruses), e.g., compared to administration of the mesothelin CAR-expressing cell without the virus (or without the first or second virus), or compared to administration of the mesothelin CAR-expressing cell and an otherwise similar virus that does not comprise the nucleic acid molecule encoding the TNFα molecule, the IL-2 molecule, and/or the IL-7 molecule, e.g., as assessed using methods described in Example 1 with respect to FIG. 2B, 2C, 2D, or 6B.

(ii) administration of the mesothelin CAR-expressing cell and the virus (or the first and second viruses) in a subject having a cancer, e.g., a pancreatic cancer, increases survival of the subject, e.g., by at least about 2, 5, 10, 20, 50, or 100-fold, e.g., about 20, 40, 60, 80, or 100 days after administration of the virus (or the first and second viruses), e.g., compared to administration of the mesothelin CAR-expressing cell without the virus (or without the first or second virus), or compared to administration of the mesothelin CAR-expressing cell and an otherwise similar virus that does not comprise the nucleic acid molecule encoding the TNFα molecule, the IL-2 molecule, and/or the IL-7 molecule, e.g., as assessed using methods described in Example 1 with respect to FIG. 2E, (iii) administration of the mesothelin CAR-expressing cell and the virus (or the first and second viruses) in a subject having a cancer, e.g., a pancreatic cancer, reduces tumor metastasis, e.g., tumor metastasis to the lung, by at least about 20, 40, 60, or 80%, e.g., about 20, 50, 100, or 150 days after administration of the virus (or the first and second viruses), e.g., compared to administration of the mesothelin CAR-expressing cell without the virus (or without the first or second virus), or compared to administration of the mesothelin CAR-expressing cell and an otherwise similar virus that does not comprise the nucleic acid molecule encoding the TNFα molecule, the IL-2 molecule, and/or the IL-7 molecule, e.g., as assessed using methods described in Example 1 with respect to FIG. 2F, (iv) administration of the mesothelin CAR-expressing cell and the virus (or the first and second viruses) in a subject having a cancer, e.g., a pancreatic cancer, increases expression of a cytokine molecule, e.g., IFN-γ, by the mesothelin CAR-expressing cell, by at least about 1, 2, 3, or 4-fold, e.g., about 5, 10, 15, or 20 days after administration of the virus (or the first and second viruses), e.g., compared to administration of the mesothelin CAR-expressing cell without the virus (or without the first or second virus), or compared to administration of the mesothelin CAR-expressing cell and an otherwise similar virus that does not comprise the nucleic acid molecule encoding the TNFα molecule, the IL-2 molecule, and/or the IL-7 molecule, e.g., as assessed using methods described in Example 1 with respect to FIG. 3E, (v) administration of the mesothelin CAR-expressing cell and the virus (or the first and second viruses) in a subject having a cancer, e.g., a pancreatic cancer, increases infiltration of the mesothelin CAR-expressing cell into a tumor, e.g., by at least about 5, 10, 25, 50, 75, 100, 125, 150, 175, or 200-fold, e.g., about 2, 4, 6, 8, 10, 12, 13, 14, 16, 18, 20, 30, 40, or 50 days after the administration of the virus (or the first and second viruses), e.g., compared to administration of the mesothelin CAR-expressing cell the virus (or without the first or second virus), or compared to administration of the mesothelin CAR-expressing cell and an otherwise similar virus that does not comprise the nucleic acid molecule encoding the TNFα molecule, the IL-2 molecule, and/or the IL-7 molecule, e.g., as assessed using methods described in Example 1 with respect to FIG. 4A, 4B, or 6C, (vi) administration of the mesothelin CAR-expressing cell and the virus (or the first and second viruses) in a subject having a cancer, e.g., a pancreatic cancer, increases infiltration of endogenous T cells, e.g., CD4+ and/or CD8+ T cells, into a tumor, e.g., by at least about 1, 2, 5, 10, 20, 30, or 50-fold, e.g., about 15, 20, 25, 30, or 35 days after the administration of the virus (or the first and second viruses), e.g., compared to administration of the mesothelin CAR-expressing cell without the virus (or without the first or second virus), or compared to administration of the mesothelin CAR-expressing cell and an otherwise similar virus that does not comprise the nucleic acid molecule encoding the TNFα molecule, the IL-2 molecule, and/or the IL-7 molecule, e.g., as assessed using methods described in Example 1 with respect to FIG. 3A, 3B, 9B, or 6D, (vii) administration of the mesothelin CAR-expressing cell and the virus (or the first and second viruses) in a subject having a cancer, e.g., a pancreatic cancer, activates tumor infiltrating lymphocytes (TILs), e.g., by at least about 20, 30, 40, or 50%, e.g., about 10, 20, 30, or 40 days after administration of the virus (or the first and second viruses), e.g., compared to administration of the mesothelin CAR-expressing cell without the virus (or without the first or second virus), or compared to administration of the mesothelin CAR-expressing cell and an otherwise similar virus that does not comprise the nucleic acid molecule encoding the TNFα molecule, the IL-2 molecule, and/or the IL-7 molecule, e.g., as measured by expression of an activation marker, e.g., as measured by expression of CD69 and/or CD25, e.g., as assessed using methods described in Example 1 with respect to FIG. 3D or 9C, (viii) administration of the mesothelin CAR-expressing cell and the virus (or the first and second viruses) in a subject having a cancer, e.g., a pancreatic cancer, increases M1 polarization of macrophages, e.g., by at least about 20, 30, 40, or 50%, e.g., about 1, 2, 3, 5, or 10 days after administration of the virus (or the first and second viruses), e.g., compared to administration of the mesothelin CAR-expressing cell without the virus (or without the first or second virus), or compared to administration of the mesothelin CAR-expressing cell and an otherwise similar virus that does not comprise the nucleic acid molecule encoding the TNFα molecule, the IL-2 molecule, and/or the IL-7 molecule, e.g., as measured by expression of CD80 and/or CD86 on macrophages, e.g., as assessed using methods described in Example 1 with respect to FIG. 6E, (ix) administration of the mesothelin CAR-expressing cell and the virus (or the first and second viruses) in a subject having a cancer, e.g., a pancreatic cancer, increases maturation of dendritic cells, e.g., maturation of CD11c+ dendritic cells, e.g., by at least about 20, 30, 40, or 50%, e.g., about 1, 2, 3, 5, or 10 days after administration of the virus (or the first and second viruses), e.g., compared to administration of the mesothelin CAR-expressing cell without the virus (or without the first or second virus), or compared to administration of the mesothelin CAR-expressing cell and an otherwise similar virus that does not comprise the nucleic acid molecule encoding the TNFα molecule, the IL-2 molecule, and/or the IL-7 molecule, e.g., as measured by expression of CD80 and/or CD86 on dendritic cells, e.g., as assessed using methods described in Example 1 with respect to FIG. 10E, or (x) administration of the mesothelin CAR-expressing cell and the virus (or the first and second viruses) in a subject having a cancer, e.g., a pancreatic cancer, increases the level of a chemokine in the subject, e.g., an immune-cell attractive chemokine, e.g., a TNF-α inducible chemokine, e.g., one, two, or all of: monocyte chemoattractant protein-1 (MCP-1), C—X—C motif chemokine ligand 10 (CXCL-10) and RANTES, by at least about 5, 10, 25, 50, 75, 100, 125, 150, 175, or 200-fold, e.g., about 1, 2, 3, 5, or 10 days after administration of the virus (or the first and second viruses), e.g., compared to administration of the mesothelin CAR-expressing cell without the virus (or without the first or second virus), or compared to administration of the mesothelin CAR-expressing cell and an otherwise similar virus that does not comprise the nucleic acid molecule encoding the TNFα molecule, the IL-2 molecule, and/or the IL-7 molecule, e.g., as assessed using methods described in Example 1 with respect to FIG. 6F or 10F.

In one embodiment, the CAR molecule comprises a mesothelin binding domain comprising a heavy chain complementary determining region 1 (HC CDR1), a heavy chain complementary determining region 2 (HC CDR2), and a heavy chain complementary determining region 3 (HC CDR3) of any mesothelin heavy chain binding domain amino acid sequence listed in Table 2; and a light chain complementary determining region 1 (LC CDR1), a light chain complementary determining region 2 (LC CDR2), and a light chain complementary determining region 3 (LC CDR3) of any mesothelin light chain binding domain amino acid sequence listed in Table 2.

In one embodiment, the mesothelin binding domain comprises a HC CDR1, a HC CDR2, and a HC CDR3 according to the HC CDR amino acid sequences in Table 4 (or a sequence at least about 85%, 90%, 95%, 99% or more identical thereto, and/or having one, two, three or more substitutions, insertions or deletions, e.g., conserved substitutions), and a LC CDR1, a LC CDR2, and a LC CDR3 according to the LC CDR amino acid sequences in Table 5 (or a sequence at least about 85%, 90%, 95%, 99% or more identical thereto, and/or having one, two, three or more substitutions, insertions or deletions, e.g., conserved substitutions).

In one embodiment, the mesothelin binding domain comprises:

(i) a heavy chain variable region (VH) of any mesothelin binding domain listed in Table 2 (or a sequence at least about 85%, 90%, 95%, 99% or more identical thereto, and/or having one, two, three or more substitutions, insertions or deletions, e.g., conserved substitutions), and/or (ii) a light chain variable region (VL) of any mesothelin binding domain listed in Table 2 (or a sequence at least about 85%, 90%, 95%, 99% or more identical thereto, and/or having one, two, three or more substitutions, insertions or deletions, e.g., conserved substitutions).

In one embodiment, the mesothelin binding domain comprises:

(i) an scFv of any mesothelin binding domain listed in Table 2 (or a sequence at least about 85%, 90%, 95%, 99% or more identical thereto, and/or having one, two, three or more substitutions, insertions or deletions, e.g., conserved substitutions), or (ii) an amino acid sequence chosen from: SEQ ID NO: 43, SEQ ID NO: 49, SEQ ID NO: 275, SEQ ID NO: 39, SEQ ID NO: 40, SEQ ID NO: 41, SEQ ID NO: 42, SEQ ID NO: 44, SEQ ID NO: 45, SEQ ID NO: 46, SEQ ID NO: 47, SEQ ID NO: 48, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, or SEQ ID NO: 62 (or a sequence at least about 85%, 90%, 95%, 99% or more identical thereto, and/or having one, two, three or more substitutions, insertions or deletions, e.g., conserved substitutions).

In one embodiment, the CAR molecule comprises:

(i) a CAR sequence listed in Table 2 with or without the signal peptide MALPVTALLLPLALLLHAARP (SEQ ID NO: 1) (or a sequence at least about 85%, 90%, 95%, 99% or more identical thereto, and/or having one, two, three or more substitutions, insertions or deletions, e.g., conserved substitutions), or (ii) an amino acid sequence chosen from: SEQ ID NO: 67; SEQ ID NO: 73, SEQ ID NO: 278, SEQ ID NO: 63, SEQ ID NO: 64, SEQ ID NO: 65, SEQ ID NO: 66, SEQ ID NO: 68, SEQ ID NO: 69, SEQ ID NO: 70, SEQ ID NO: 71, SEQ ID NO: 72, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, or SEQ ID NO: 86 with or without the signal peptide MALPVTALLLPLALLLHAARP (SEQ ID NO: 1) (or a sequence at least about 85%, 90%, 95%, 99% or more identical thereto, and/or having one, two, three or more substitutions, insertions or deletions, e.g., conserved substitutions).

In one embodiment, the CAR molecule comprises:

(i) HC CDR1, HC CDR2, and HC CDR3 of SEQ ID NOs: 138, 156, and 179, respectively; and LC CDR1, LC CDR2, and LC CDR3 of SEQ ID NOs: 203, 227, and 251, respectively, (ii) the amino acid sequence of SEQ ID NO: 43, or (iii) the amino acid sequence of SEQ ID NO: 67 with or without the signal peptide MALPVTALLLPLALLLHAARP (SEQ ID NO: 1).

In one embodiment, the CAR molecule comprises:

(i) HC CDR1, HC CDR2, and HC CDR3 of SEQ ID NOs: 144, 162, 185, respectively; and LC CDR1, LC CDR2, and LC CDR3 of SEQ ID NOs: 209, 233, and 257, respectively, (ii) the amino acid sequence of SEQ ID NO: 49, or (iii) the amino acid sequence of SEQ ID NO: 73 with or without the signal peptide MALPVTALLLPLALLLHAARP (SEQ ID NO: 1).

In one embodiment, the CAR molecule comprises a transmembrane domain, optionally wherein the transmembrane domain comprises a transmembrane domain from a protein chosen from the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137 or CD154, optionally wherein the transmembrane domain comprises the amino acid sequence of SEQ ID NO: 6 (or a sequence at least about 85%, 90%, 95%, 99% or more identical thereto, and/or having one, two, three or more substitutions, insertions or deletions, e.g., conserved substitutions).

In one embodiment, the CAR molecule comprises an antigen binding domain that binds to the antigen, optionally wherein the antigen binding domain is connected to the transmembrane domain by a hinge region, optionally wherein the hinge region comprises an amino acid sequence chosen from SEQ ID NO: 2, 3, or 4 (or a sequence at least about 85%, 90%, 95%, 99% or more identical thereto, and/or having one, two, three or more substitutions, insertions or deletions, e.g., conserved substitutions).

In one embodiment, the CAR molecule comprises a primary signaling domain, optionally wherein the primary signaling domain comprises a functional signaling domain derived from CD3 zeta, TCR zeta, FcR gamma, FcR beta, CD3 gamma, CD3 delta, CD3 epsilon, CD5, CD22, CD79a, CD79b, CD278 (ICOS), FcεRI, DAP10, DAP12, or CD66d, optionally wherein the CAR molecule comprises the amino acid sequence of SEQ ID NO: 9 or 10 (or a sequence at least about 85%, 90%, 95%, 99% or more identical thereto, and/or having one, two, three or more substitutions, insertions or deletions, e.g., conserved substitutions).

In one embodiment, the CAR molecule comprises a costimulatory signaling domain, optionally wherein the costimulatory signaling domain comprises a functional signaling domain derived from a MHC class I molecule, a TNF receptor protein, an Immunoglobulin-like protein, a cytokine receptor, an integrin, a signalling lymphocytic activation molecule (SLAM protein), an activating NK cell receptor, BTLA, a Toll ligand receptor, OX40, CD2, CD7, CD27, CD28, CD30, CD40, CDS, ICAM-1, 4-1BB (CD137), B7-H3, ICOS (CD278), GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, ITGB7, NKG2D, NKG2C, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMFI, CD150, IPO-3), BLAME (SLAMF8), SELPLG (CD162), LTBR, LAT, GADS, SLP-76, PAG/Cbp, CD19a, CD28-OX40, CD28-4-1BB, or a ligand that specifically binds with CD83, optionally wherein the CAR molecule comprises the amino acid sequence of SEQ ID NO: 7 (or a sequence at least about 85%, 90%, 95%, 99% or more identical thereto, and/or having one, two, three or more substitutions, insertions or deletions, e.g., conserved substitutions).

In one embodiment, the CAR molecule comprises a functional signaling domain derived from 4-1BB and a functional signaling domain derived from CD3 zeta. In one embodiment, the CAR molecule comprises the amino acid sequence of SEQ ID NO: 7 (or a sequence at least about 85%, 90%, 95%, 99% or more identical thereto, and/or having one, two, three or more substitutions, insertions or deletions, e.g., conserved substitutions) and the amino acid sequence of SEQ ID NO: 9 or 10 (or a sequence at least about 85%, 90%, 95%, 99% or more identical thereto, and/or having one, two, three or more substitutions, insertions or deletions, e.g., conserved substitutions), optionally wherein the CAR molecule comprises the amino acid sequence of SEQ ID NO: 7 and the amino acid sequence of SEQ ID NO: 9 or 10.

In one embodiment, the CAR-expressing cell (e.g., the mesothelin CAR-expressing cell) is a cell comprising a nucleic acid molecule encoding the CAR molecule, optionally wherein the nucleic acid molecule encoding the CAR molecule is an RNA molecule, e.g., an in vitro transcribed RNA molecule.

In one embodiment, the CAR-expressing cell (e.g., the mesothelin CAR-expressing cell) is a cell comprising a vector comprising a nucleic acid molecule encoding the CAR molecule, optionally wherein the vector is a lentiviral vector.

In one embodiment, the CAR-expressing cell (e.g., the mesothelin CAR-expressing cell) is a T cell (e.g., an autologous or allogeneic T cell) or an NK cell (e.g., an autologous or allogeneic NK cell).

In one embodiment, the subject has a cancer. In one embodiment, the subject has a solid tumor.

In one embodiment, the cancer is chosen from one or more of mesothelioma, malignant pleural mesothelioma, non-small cell lung cancer, small cell lung cancer, squamous cell lung cancer, large cell lung cancer, pancreatic cancer, pancreatic ductal adenocarcinoma, esophageal adenocarcinoma, breast cancer, glioblastoma, ovarian cancer, colorectal cancer, prostate cancer, cervical cancer, skin cancer, melanoma, renal cancer, liver cancer, brain cancer, thymoma, sarcoma, carcinoma, uterine cancer, kidney cancer, gastrointestinal cancer, urothelial cancer, pharynx cancer, head and neck cancer, rectal cancer, esophagus cancer, or bladder cancer, or a metastasis thereof.

In one embodiment, the cancer is chosen from chronic lymphocytic leukemia (CLL), mantle cell lymphoma (MCL), multiple myeloma, acute lymphoid leukemia (ALL), Hodgkin lymphoma, B-cell acute lymphoid leukemia (BALL), T-cell acute lymphoid leukemia (TALL), small lymphocytic leukemia (SLL), B cell prolymphocytic leukemia, blastic plasmacytoid dendritic cell neoplasm, Burkitt's lymphoma, diffuse large B cell lymphoma (DLBCL), DLBCL associated with chronic inflammation, chronic myeloid leukemia, myeloproliferative neoplasms, follicular lymphoma, pediatric follicular lymphoma, hairy cell leukemia, small cell- or a large cell-follicular lymphoma, malignant lymphoproliferative conditions, MALT lymphoma (extranodal marginal zone lymphoma of mucosa-associated lymphoid tissue), Marginal zone lymphoma, myelodysplasia, myelodysplastic syndrome, non-Hodgkin lymphoma, plasmablastic lymphoma, plasmacytoid dendritic cell neoplasm, Waldenstrom macroglobulinemia, splenic marginal zone lymphoma, splenic lymphoma/leukemia, splenic diffuse red pulp small B-cell lymphoma, hairy cell leukemia-variant, lymphoplasmacytic lymphoma, a heavy chain disease, plasma cell myeloma, solitary plasmocytoma of bone, extraosseous plasmocytoma, nodal marginal zone lymphoma, pediatric nodal marginal zone lymphoma, primary cutaneous follicle center lymphoma, lymphomatoid granulomatosis, primary mediastinal (thymic) large B-cell lymphoma, intravascular large B-cell lymphoma, ALK+ large B-cell lymphoma, large B-cell lymphoma arising in HHV8-associated multicentric Castleman disease, primary effusion lymphoma, B-cell lymphoma, acute myeloid leukemia (AML), or unclassifiable lymphoma.

In one embodiment, the cancer exhibits heterogeneous expression of the antigen, e.g., wherein less than 90%, 80%, 70%, 60%, or 50% of cells in the cancer express the antigen.

In one embodiment, the method further comprises administering an additional therapeutic agent, e.g., an anti-cancer agent.

In one embodiment, the subject is a mammal, e.g., a human. In one embodiment, the cell is a T cell or NK cell. In one embodiment, the cell is autologous to the subject. In one embodiment, the cell is allogeneic to the subject.

In one aspect, disclosed herein is a combination comprising:

(i) a cell (e.g., a population of cells) that expresses a chimeric antigen receptor (CAR) molecule that binds to mesothelin ("mesothelin CAR-expressing cell"), wherein the CAR molecule comprises a mesothelin binding domain comprising a heavy chain complementary determining region 1 (HC CDR1), a heavy chain complementary determining region 2 (HC CDR2), and a heavy chain complementary determining region 3 (HC CDR3) of any mesothelin heavy chain binding domain amino acid sequence listed in Table 2; and a light chain complementary determining region 1 (LC CDR1), a light chain complementary determining region 2 (LC CDR2), and a light chain complementary determining region 3 (LC CDR3) of any mesothelin light chain binding domain amino acid sequence listed in Table 2; and (ii) (a) a virus comprising a nucleic acid molecule encoding the TNFα molecule and/or the IL-2 molecule;

(b) a first virus comprising a nucleic acid molecule encoding the TNFα molecule, and a second virus comprising a nucleic acid molecule encoding the IL-2 molecule;

(c) a virus comprising a nucleic acid molecule encoding an IL-7 molecule, optionally wherein the virus further comprises a nucleic acid molecule encoding a TNFα molecule and/or an IL-2 molecule; or (d) a first virus comprising a nucleic acid molecule encoding an IL-7 molecule and a second virus comprising a nucleic acid molecule encoding a TNFα molecule and/or an IL-2 molecule for use in treating a disease associated with mesothelin expression, e.g., a cancer, in a subject.

In one aspect, disclosed herein is a composition (e.g., one or more compositions or dosage forms), comprising:

(i) a cell (e.g., a population of cells) that expresses a chimeric antigen receptor (CAR) molecule that binds to mesothelin ("mesothelin CAR-expressing cell"), wherein the CAR molecule comprises a mesothelin binding domain comprising a heavy chain complementary determining region 1 (HC CDR1), a heavy chain complementary determining region 2 (HC CDR2), and a heavy chain complementary determining region 3 (HC CDR3) of any mesothelin heavy chain binding domain amino acid sequence listed in Table 2; and a light chain complementary determining region 1 (LC CDR1), a light chain complementary determining region 2 (LC CDR2), and a light chain complementary determining region 3 (LC CDR3) of any mesothelin light chain binding domain amino acid sequence listed in Table 2; and (ii) (a) a virus comprising a nucleic acid molecule encoding the TNFα molecule and/or the IL-2 molecule;

(b) a first virus comprising a nucleic acid molecule encoding the TNFα molecule, and a second virus comprising a nucleic acid molecule encoding the IL-2 molecule;

(c) a virus comprising a nucleic acid molecule encoding an IL-7 molecule, optionally wherein the virus further comprises a nucleic acid molecule encoding a TNFα molecule and/or an IL-2 molecule; or (d) a first virus comprising a nucleic acid molecule encoding an IL-7 molecule and a second virus comprising a nucleic acid molecule encoding a TNFα molecule and/or an IL-2 molecule.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In addition, the materials, methods, and examples are illustrative only and not intended to be limiting. Headings, sub-headings or numbered or lettered elements, e.g., (a), (b), (i) etc, are presented merely for ease of reading. The use of headings or numbered or lettered elements in this document does not require the steps or elements be performed in alphabetical order or that the steps or elements are necessarily discrete from one another. Other features, objects, and advantages of the invention will be apparent from the description and drawings, and from the claims.

BRIEF DESCRIPTION OF THE DRAWINGS

FIG. 1A: Kinetics of pancreatic ductal adenocarcinoma (PDA) tumor cell lysis incubated with the combination of OAd-TNFα-IL2 with meso-CAR T cells measured by the real-time xCELLigence cell analyzer. Means of cell index from triplicate wells are shown. Data are representative of three experiments from three different donors. FIG. 1B: Up-regulation of CD69 on T cells upon stimulation with PDA cell lines pre-infected with OAds. Histograms show CD69 expression of T cells at day 3 post co-culture with control media alone (Unstimulated) or co-culture with the indicated tumor cell lines pre-infected with either control media (media), parental OAd (OAd) or OAd-TNFα-IL2 (OAd-TNFα-IL2). Data are representative of three experiments from three different donors. FIG. 1C: Fold increase of % CD69 positive T cells from pooled data. Fold increase of percent CD69 positive T cells by co-culturing with tumor cell lines pre-treated either with OAd or OAd-TNFα-IL2 relative to those by co-culturing with cell lines pre-treated with control media (set to one) are shown. Means and SEM of pooled data from three experiments are shown. *, $p<0.05$; ****, $p<0.0001$ by one-way ANOVA with Turkey's post-hoc test. FIG. 1D: T cell proliferation upon the stimulation with tumor cell lines pre-infected with OAds. Using the same co-culture method as FIGS. 1B and 1C, T cell expansion was determined at day 5 by flow cytometry (FCM) and counting beads. Means and SD from triplicate wells are shown. Data are representative of four experiments from three different donors. FIG. 1E: Relative fold expansion of T cells upon stimulation with tumor cell lines pre-infected with OAds. Fold expansion of T cells co-cultured with cell lines pre-treated with control media was set to one. Means and SEM of pooled data from four experiments are shown. *, $p<0.05$ by one-way ANOVA with Tukey's post-hoc test.

FIG. 2A: Experimental schematic. AsPC-1 tumor bearing mice were treated with either intratumoral injection of PBS, $0.95\times10^9$ virus particle (vp) parental OAd (OAd) or OAd-TNFα-IL2 followed by intravenous injection of either PBS, $1\times10^6$ meso-CAR T cells or human CD19-redirected CAR T cells (h19-CAR T cells) at day 3 after OAd injection. Tumor volumes were followed by caliper measurement. FIG. 2B: Tumor volumes by caliper measurements. Data are representative of two experiments from two different donors. Means and SEM are shown (n=7 or 8 each). *, $p<0.05$; ****, $p<0.0001$ by repeated measures two-ANOVA with Bonferroni correction. FIG. 2C: Water fall plots comparing baseline to the endpoint (day 41). Percent change from baseline to the endpoint is shown. Each bar represents an individual mouse. Data are from the experiment shown as FIG. 2B. FIG. 2D: Tumor volumes by caliper measurements. Data are representative of two experiments from two different donors. Means and SEM are shown (n=3 each for PBS group and n=5 each for the other groups). *, $p<0.05$ by two-way ANOVA with Bonferroni correction. FIG. 2E: Kaplan-Meier survival curve. Data are from the experiment shown as FIG. 2D. *, $p<0.05$; **, $p<0.01$ (vs. OAd-TNFα-IL2+meso-CAR T cell group) by Log-rank test. FIG. 2F: Combined OAd-TNFα-IL2 with meso-CAR T cells can prevent tumor metastasis. Representative lungs from OAd-mTNFα-IL2+meso-CAR T cell group, OAd group and OAd+meso-CAR T cell group are shown. The two lungs with multiple metastasis shown here are from mice treated with OAd alone or combined OAd and meso-CAR T cells which were euthanized at day 102 due to weight loss (Center and right panel). The lung without metastasis is representative from mice treated with combined OAd-TNFα-IL2 and meso-CAR T cells (Left panel).

FIG. 3A: Analysis of CD8+ cell infiltration to the tumor at day 28 by immunohistochemistry (IHC). A group of mice was sacrificed and tumors were analyzed by IHC for CD8 staining. Representative tumors from the indicated treatment groups are shown. Original magnification, 20×; scale bar, 100 μm. FIG. 3B: Quantification of TILs at day 28. The number of CD8+ TILs was quantified using Aperio ImageScope software. Number of CD8+ cells was normalized as percent CD8+ cells in total nucleated cells. Data are representative of two experiments from two different donors. ***, $p<0.001$ by one-way ANOVA with Tukey's post-hoc test. FIG. 3C: Correlation between intensity of CD8+ TILs and tumor volumes. Number of CD8+ T cells (% of total cells) quantified from IHC against tumor sizes at day 28 are plotted. Each dot represents an individual mouse; a linear regression line and Pearson correlation coefficient (R) are shown. *, $p<0.05$ (D) Expression of activation markers on TILs at day 28. T cell activation markers, CD95 and CD25 on CD8+ TILs were analyzed by FCM. Data are representative of two experiments from two different donors. *, $p<0.05$.

FIG. 3E: Cytokine profile of the bulk tumors at day 14. A group of mice was sacrificed at day 14. Pieces of tumors were homogenized and cytokines in the supernatant of the homogenate were analyzed by high-sensitivity LUMINEX assay. *, $p<0.05$; , $p<0.01$; *, $p<0.001$ by one-way ANOVA with Tukey's post-hoc test. FIG. 3F: Analysis of mesothelin expression by tumors by IHC at day 28. Mesothelin expression by tumor cells was analyzed by IHC (upper panels). Mesothelin positive area and staining intensity were analyzed with Aperio ImageScope software. Digital masks over the same fields as upper panels are shown in the lower panels. Original magnification, 20×; scale bar, 100 μm. FIG. 3G: Mesothelin expression by tumors is shown as percentage of mesothelin positive area. Three tumors (one from OAd-TNFα-IL2 group and two from OAd-TNFα-IL2+meso-CAR T cell group) are not plotted as they achieved histological complete remission with no evaluable intact tumor areas. FIG. 3H: Correlation between mesothelin expression and tumor sizes. Area of mesothelin positive (%) are plotted against tumor size at day 28. Each dot represents an individual mouse and linear regression lines are shown. *, $p<0.05$; **, $p<0.01$. For vertical scatter grams, each dot represents an individual mouse and bars represents mean and SEM (FIGS. 3B, 3C, 3D, 3E and 3G).

FIGS. 4A and 4B: Trafficking of meso-CAR T cells by bioluminescence imaging (BLI). Using the same treatment schedule as FIG. 2A, luciferase labeled meso-CAR T cells (CBR-meso-CAR T cells) were tracked by BLI. Luminescence from tumor area was analyzed (FIG. 4B). Means and SEM are shown (n=5 each). **, $p<0.0001$ (vs. OAd-TNFα-IL2+meso-CAR T cell group at any time points between day 13 and day 28) by two-way repeated measures ANOVA with Bonferroni correction. FIG. 4C: CD3+ T cell counts in peripheral blood (PB). T cell number was determined by Trucount analysis. Means and SEM are shown (n=5 each). *, $p<0.001$ (vs. OAd-TNFα-IL2+meso-CAR T cell group) by repeated measures two-way ANOVA.

FIGS. 5A and 5B: Tumor volumes by caliper measurements and water fall plots comparing baseline to day 57. Mice from the indicated two treatment groups were observed until day 57 and then sacrificed. Tumor volumes and water fall plots for the surviving mice (six of eight mice for meso-CAR T cell group and all of the seven mice for OAd-TNFα-IL2+meso-CAR T cell group) are shown. Each dot and bar represent an individual mouse, and mean and SEM are shown for (FIG. 5A). FIG. 5C: Mesothelin expression on tumors at day 57. Mesothelin expression of the representative tumor from OAd-TNFα-IL2+meso-CAR T cell group by immunohistochemistry (IHC) (upper panels) and digital masks (lower panels) on the same fields as upper panels are shown. The low power fields (LPF) show central necrosis and heterogeneity in mesothelin intensity (far left panels). Representative high-power fields (HPF) of mesothelin positive area (center panels) and mesothelin low-negative area (far right panels) from the tumor shown in the LPF. Original magnification, 20×; scale bar, 5 mm for LPF, 100 μm for HPF. FIG. 5D: Correlation between mesothelin expression and tumor size at day 57. Area of mesothelin positive area (%) against tumor volumes for individual mice are plotted. n.s., not significant. FIG. 5E: Correlation between density of CD3+ TILs and tumor volumes. Percent CD3+ cells to tumor cells (%) against tumor volumes are plotted. Each dot represents an individual mouse, and a linear regression line and Pearson correlation coefficient (R) are shown. *, $p<0.05$. FIG. 5F: Expression of Ki67 by tumor infiltrating lymphocytes (TILs). Ki67 expression by CD3+ TILs from surviving mice were analyzed by FCM. Columns are arranged in the order of tumor volumes at day 57 (left is the smallest and the right is the largest) and the tumor sizes are shown at the top of each column. FIG. 5G: Correlation between Ki67 expression by CD4+ and CD8+ TILs and tumor volumes. % Ki67 expression by CD4+ TILs or CD8+ TILs against tumor volumes are plotted. Each dot represents an individual mouse, and linear regression lines and Pearson correlation coefficient (R) are shown. *, $p<0.05$; **, $p<0.01$.

FIGS. 6A-6F: Combined mouse TNF-α and IL-2 delivered by adenoviruses with mouse mesothelin-redirected chimeric antigen receptor T cells (mmeso-CAR T cells) enables significant tumor suppression by enhancing both CAR-dependent and CAR-independent host immunity in a syngeneic pancreatic ductal adenocarcinoma (PDA)-engrafted immunocompetent mouse model. FIG. 6A: Experimental schematic. Established PDA7940b tumors were treated either with intratumoral injection of PBS, $1\times10^9$ virus particle of control adenovirus (Ad-luc) or 1:1 mixture of Ad-mTNFα and Ad-mIL2 (total $1\times10^9$vp) (Ad-mTNFα-mIL2) followed by intravenous injection of either PBS, $5\times10^6$ mmeso-CAR T cells or human CD19 redirected chimeric antigen receptor T cells (h19-CAR T cells) at day 1 after Ad injection. Mice were preconditioned with Intraperitoneal injection of 120 mg/kg cyclophosphamide (Ctx) at 24 hours before the first T cell injection. Adenovirus and CAR T cell injections were repeated four times weekly. Tumor volumes were monitored by caliper measurement. FIG. 6B: Tumor volumes by caliper measurements. Means and SEM are shown (n=5 or 6 each). Data are representative of two experiments. *, $p<0.05$ by repeated measurements two-way ANOVA. FIG. 6C: Trafficking of CAR T cells by bioluminescence (BLI). Luciferase labeled CAR T cells (CBR-CAR T cells) after the first single injection was tracked by BLI. Experiment was performed with the same schedule as FIG. 6A but T cell injection was performed just once. Luminescence from tumor area was analyzed. Means and SEM are shown (n=5 each). *, $p<0.05$; ***, $p<0.001$ (vs. Ad-mTNFα-mIL2+mmeso-CAR T cell group) by repeated measurements two-way ANOVA with Bonferroni correction. FIG. 6D: Recruitment of donor derived tumor infiltrating lymphocytes (TILs) and host TILs at day 12. Number of CD4+ and CD8+ TILs were analyzed by FCM. Origin of T cells were determined by staining of CD45.1 (Donor) and CD45.2 (Host). Y-axis label: K, ×1000. *, $p<0.05$; **, $p<0.01$ by one-way ANOVA with Tukey's post-hoc test. FIG. 6E: Phenotype of macrophages in tumors and spleens at day 1. CD80 and CD86 expression on tumor infiltrating macrophages and spleen macrophages was analyzed at 24 hours post intratumoral injection of either PBS, Ad-luc or Ad-mTNFα-mIL2 by FCM.*, $p<0.05$; **, $p<0.01$ by one-way ANOVA with Tukey's post-hoc test. FIG. 6F: Chemokine analysis of bulk tumors at day 1. A group of mice was sacrificed at day 1 post intratumoral injection of adenoviruses. Pieces of tumors were homogenized and chemokines in the supernatant of the homogenate were analyzed by LUMINEX assay. *, $p<0.05$; ***, $p<0.001$ by one-way ANOVA with Tukey's post-hoc test. For vertical scatter grams, each dot represents an individual mouse, and bars represent means and SEM. (FIGS. 6D, 6E and 6F).

FIGS. 7A-7D: Oncolytic adenovirus (OAd) delivers cytokine genes to pancreatic ductal adenocarcinoma (PDA) tumor cell lines and directly lyses target cells. FIG. 7A: Schematic representation of oncolytic adenovirus expressing TNF-α and IL-2 (Ad5/3-E2F-D24-TNFα-IRES-IL2 or OAd-TNFα-IL2 for short) and its parental virus (Ad5/3-D24 or OAd for short). LITR, left inverted terminal repeats; RITR, right inverted terminal repeats; 100K, adenovirus 100K assembly protein; IRES, internal ribosome entry site; IL-2, IL-2 transgene; TNF-α, TNF-α transgene. FIG. 7B: Time course analysis of cytokine production by pancreatic tumor cell lines infected with OAd-TNFα-IL2. Twenty thousand tumor cells were infected with 30 virus particle (vp)/cell of OAd-TNFα-IL2 (total 250 μl media) and culture supernatant was harvested at intervals from day 1 to day 7 after virus infection. Concentrations of TNF-α and IL-2 were analyzed by ELISA. Data are representative of two experiments. Means and SD from triplicate wells are shown. FIG. 7C: Kinetics of tumor cell lysis by oncolytic adenoviruses. Ten thousand PDA targets were infected either with OAd (upper panels) or OAd-TNFα-IL2 (lower panels) at the indicated titers. Cell index over six days was collected with xCELLigence real time cell analyzer. Means of values from triplicate wells are plotted. pfu, plaque forming unit. Data are representative from three experiments. FIG. 7D: Mesothelin expression by pancreatic cancer cell lines, BxPC-3, Capan-2 and AsPC-1 was analyzed by FCM.

FIGS. 9A-9D: Oncolytic adenovirus (OAd) expressing TNF-α and IL-2 (Ad5/3-E2F-D24-TNFα-IRES-IL2 (Ad5/3-OAd-TNFα-IL2)) induces robust T cell recruitment and infiltration to tumors and enhances T cell functions. Data are from the experiment shown in main FIGS. 3A-3H. FIG. 9A: Tumor volumes at day 14 and day 28. Tumor volumes by caliper measurements are shown. FIG. 9B: Number of CD4+ and CD8+ tumor infiltrating lymphocytes (TILs) at day 14 and day 28. TILs were analyzed by FCM at day 14 and day 28. Number of TILs was normalized to percent CD4+ or CD8+ cells in total nucleated cells. *, $p<0.05$; , $p<0.01$; *, $p<0.001$ by one-way ANOVA with Tukey's post-hoc test. FIG. 9C: Expression of activation markers on TILs at day 28. T cell activation markers, CD95 and CD25 on CD4+ TILs were analyzed by FCM. FIG. 9D: Cytokine levels in serum at day 14. Indicated human cytokines in mouse serum were analyzed by high-sensitivity LUMINEX assay. *, $p<0.05$; *, $p<0.001$ by one-way ANOVA with Tukey's post-hoc test. For all scatter grams (FIGS. 9A, 9B, 9C and 9**D), each dot represents an individual mouse, and bars represent means and SEM.

FIGS. 10A-10F: Development of new mouse mesothelin-redirected CAR T cells (mmeso-CAR T cells) and adenoviruses expressing mouse cytokines (Ad-mTNFα and Ad-mIL2) enabling assessment of the combination therapy of Ad-mTNFα-IL2 with CAR T cells in an immunocompetent setting. FIG. 10A: Schematic representation of mmeso-CAR expressed using standard gamma retrovirus technology. FIG. 10B: Surface expression of mmeso-CAR and control h19-CAR on mouse T cells. CAR expression by mouse splenic T cells was analyzed at day 5 after retroviral transduction to express CARs. Data are representative of at least four different T cell preparations. FIG. 10C: Kinetics of target cell killing by mmeso-CAR T cells and control human CD19-redirected CAR T cells (h19-CAR T cells) by xCELLigence real time cell analyzer. PDA7940b cells expressed high levels of mesothelin (FIG. 10C (part 1)). Five thousand PDA7940b cells were seeded in the e-plate. After 24 hours incubation, either control media, control h19-CAR T cells or mmeso-CAR T cells were added at the indicated E:T ratio. Cell index was recorded every 20 minutes (FIG. 10C (part 2)). Data are representative of at least four experiments from four different T cell preparations. Means of triplicate wells are shown. FIG. 10D: Cytokine production of PDA7940b cells infected with Ad-mTNFα-mIL2. Five thousand PDA7940b tumor cells were seeded to a 96 well plate and infected with Ad-mTNFα-mIL2 at the indicated concentrations (total 250 μl media). Supernatant was harvested at 72 hours after the infection and cytokine levels were analyzed by ELISA. Data are representative of two experiments. Means and SD of triplicate wells are shown. FIG. 10E: CD80 and CD86 expression by DC at day 1 post intratumoral adenovirus injection. CD80 and CD86 expression on DCs from tumors and spleen were analyzed by FCM. Data are from the experiment shown in FIG. 6E. *, $p<0.05$; , $p<0.01$; *, $p<0.001$ by one-way ANOVA with Tukey's post-hoc test. FIG. 10F: Chemokine (RANTES) analysis from tumors at day 1 port adenovirus injection. A group of mice was sacrificed at day 1 post intratumoral injection of adenoviruses. Pieces of tumors were homogenized and a chemokine, RANTES in the supernatant of the tumor homogenate were analyzed by LUMINEX assay. Data are from the experiment shown in FIG. 6F. For all scatter grams (FIGS. 10E and 10F), each dot represents an individual mouse, and mean and SEM are shown.

DESCRIPTION

Definitions

Figure 1A:
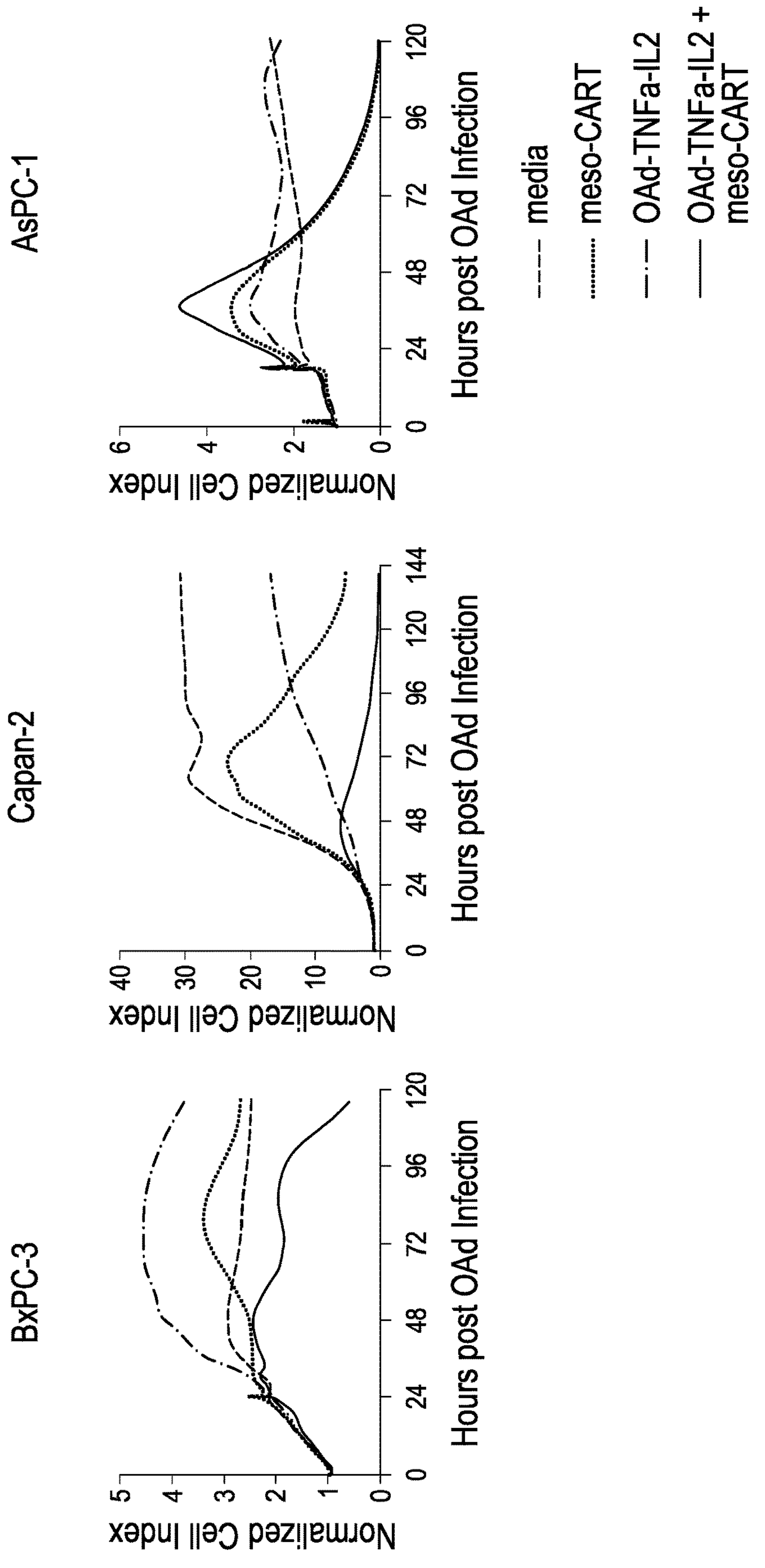
FIGS. 1A-1E: Oncolytic adenovirus (OAd) expressing TNF-α and IL-2 (Ad5/3-E2F-D24-TNFα-IRES-IL2 (Ad5/3-OAd-TNFα-IL2)) enhances activation, proliferation and lytic activity of mesothelin-redirected chimeric antigen receptor T cells (meso-CAR T cells).

Unless defined otherwise, all technical and scientific terms used herein have the same meaning as commonly understood by one of ordinary skill in the art to which the invention pertains.

The term "a" and "an" refers to one or to more than one (i.e., to at least one) of the grammatical object of the article. By way of example, "an element" means one element or more than one element.

The term "about" when referring to a measurable value such as an amount, a temporal duration, and the like, is meant to encompass variations of ±20% or in some instances ±10%, or in some instances ±5%, or in some instances ±1%, or in some instances ±0.1% from the specified value, as such variations are appropriate to perform the disclosed methods.

Administered "in combination", as used herein, means that two (or more) different treatments are delivered to the subject during the course of the subject's affliction with the disorder, e.g., the two or more treatments are delivered after the subject has been diagnosed with the disorder and before the disorder has been cured or eliminated or treatment has ceased for other reasons. In some embodiments, the delivery of one treatment is still occurring when the delivery of the second begins, so that there is overlap in terms of administration. This is sometimes referred to herein as "simultaneous" or "concurrent delivery". In other embodiments, the delivery of one treatment ends before the delivery of the other treatment begins. In some embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In some embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered.

The term "TNFα" or "TNFα molecule" refers to Tumor necrosis factor ligand superfamily member 2 (TNFSF2, also known as DIF, TNFA, TNLG1F, or TNF-alpha), a multifunctional cytokine that belongs to the tumor necrosis factor (TNF) superfamily. GenBank No. NP_000585.2 and SwissProt accession number P01375 provide exemplary human TNFα amino acid sequences. In some embodiments, TNFα or TNFα molecule is a naturally-existing TNFα or a functional variant or fragment thereof. In some embodiments, human TNFα has the following amino acid and nucleic acid sequences:

```
Tumor necrosis factor [Homo sapiens, NP_000585.2]
                                                                (SEQ ID NO: 611)
  1 MSTESMIRDV ELAEEALPKK TGGPQGSRRC LFLSLFSFLI VAGATTLFCL LHFGVIGPQR

 61 EEFPRDLSLI SPLAQAVRSS SRTPSDKPVA HVVANPQAEGQLQWLNRRAN ALLANGVELR

121 DNQLVVPSEG LYLIYSQVLF KGQGCPSTHV LLTHTISRIA VSYQTKVNLL SAIKSPCQRE
```

-continued

181 TPEGAEAKPW YEPIYLGGVF QLEKGDRLSA EINRPDYLDF AESGQVYFGI IAL

*Homo sapiens* tumor necrosis factor (TNF), mRNA [NM_000594.3]
(SEQ ID NO: 612)

1 cagacgctcc ctcagcaagg acagcagagg accagctaag agggagagaa gcaactacag 61 accccccctg aaaacaaccc tcagacgcca catcccctga caagctgcca ggcaggttct 121 cttcctctca catactgacc cacggctcca ccctctctcc cctggaaagg acaccatgag 181 cactgaaagc atgatccggg acgtggagct ggccgaggag gcgctcccca agaagacagg 241 ggggccccag ggctccaggc ggtgcttgtt cctcagcctc ttctccttcc tgatcgtggc 301 aggcgccacc acgctcttct gcctgctgca ctttggagtg atcggccccc agagggaaga 361 gttccccagg gacctctctc taatcagccc tctggcccag gcagtcagat catcttctcg 421 aaccccgagt gacaagcctg tagcccatgt tgtagcaaac cctcaagctg aggggcagct 481 ccagtggctg aaccgccggg ccaatgccct cctggccaat ggcgtggagc tgagagataa 541 ccagctggtg gtgccatcag agggcctgta cctcatctac tcccaggtcc tcttcaaggg 601 ccaaggctgc ccctccaccc atgtgctcct cacccacacc atcagccgca tcgccgtctc 661 ctaccagacc aaggtcaacc tcctctctgc catcaagagc ccctgccaga gggagacccc 721 agagggggct gaggccaagc cctggtatga gcccatctat ctgggagggg tcttccagct 781 ggagaagggt gaccgactca gcgctgagat caatcggccc gactatctcg actttgccga 841 gtctgggcag gtctactttg ggatcattgc cctgtgagga ggacgaacat ccaaccttcc 901 caaacgcctc ccctgcccca atccctttat taccccctcc ttcagacacc ctcaacctct 961 tctggctcaa aaagagaatt gggggcttag ggtcggaacc caagcttaga actttaagca 1021 acaagaccac cacttcgaaa cctgggattc aggaatgtgt ggcctgcaca gtgaagtgct 1081 ggcaaccact aagaattcaa actggggcct ccagaactca ctggggccta cagctttgat 1141 ccctgacatc tggaatctgg agaccaggga gcctttggtt ctggccagaa tgctgcagga 1201 cttgagaaga cctcacctag aaattgacac aagtggacct taggccttcc tctctccaga 1261 tgtttccaga cttccttgag acacggagcc cagccctccc catggagcca gctccctcta 1321 tttatgtttg cacttgtgat tatttattat ttatttatta tttatttatt tacagatgaa 1381 tgtatttatt tgggagaccg gggtatcctg ggggacccaa tgtaggagct gccttggctc 1441 agacatgttt tccgtgaaaa cggagctgaa caataggctg ttcccatgta gccccctggc 1501 ctctgtgcct tcttttgatt atgtttttta aaatatttat ctgattaagt tgtctaaaca 1561 atgctgattt ggtgaccaac tgtcactcat tgctgagcct ctgctcccca ggggagttgt 1621 gtctgtaatc gccctactat tcagtggcga gaaataaagt ttgcttagaa aagaaaaaaa 1681 aaaaaa The term “IL-2” or “IL-2 molecule” refers to interleukin-2 (also known as TCGF, or lymphokine), a secreted cytokine. GenBank No. NP_000577.2 and Swiss-Prot accession number P60568 provide exemplary human IL-2 amino acid sequences. In some embodiments, IL-2 or IL-2 molecule is a naturally-existing IL-2 or a functional variant or fragment thereof. In some embodiments, human IL-2 has the following amino acid and nucleic acid sequences:

Interleukin-2 precursor [*Homo sapiens*, NP_000577.2]
(SEQ ID NO: 613)

1 MYRMQLLSCI ALSLALVTNS APTSSSTKKT QLQLEHLLLD LQMILNGINN YKNPKLTRML

61 TFKFYMPKKA TELKHLQCLE EELKPLEEVL NLAQSKNFHL RPRDLISNIN VIVLELKGSE

121 TTFMCEYADE TATIVEFLNR WITFCQSIIS TLT

Homo sapiens interleukin 2 (IL2), mRNA [NM_000586.3]
(SEQ ID NO: 614)

1 agttccctat cactctcttt aatcactact cacagtaacc tcaactcctg ccacaatgta

-continued

```
 61 caggatgcaa ctcctgtctt gcattgcact aagtcttgca cttgtcacaa acagtgcacc

121 tacttcaagt tctacaaaga aaacacagct acaactggag catttactgc tggatttaca

181 gatgattttg aatggaatta ataattacaa gaatcccaaa ctcaccagga tgctcacatt

241 taagttttac atgcccaaga aggccacaga actgaaacat cttcagtgtc tagaagaaga

301 actcaaacct ctggaggaag tgctaaattt agctcaaagc aaaaactttc acttaagacc

361 cagggactta atcagcaata tcaacgtaat agttctggaa ctaaagggat ctgaaacaac

421 attcatgtgt gaatatgctg atgagacagc aaccattgta gaatttctga acagatggat

481 taccttttgt caaagcatca tctcaacact gacttgataa ttaagtgctt cccacttaaa

541 acatatcagg ccttctattt atttaaatat ttaaatttta tatttattgt tgaatgtatg

601 gtttgctacc tattgtaact attattctta atcttaaaac tataaatatg gatcttttat

661 gattcttttt gtaagcccta ggggctctaa aatggtttca cttatttatc ccaaaatatt

721 tattattatg ttgaatgtta aatatagtat ctatgtagat tggttagtaa aactatttaa

781 taaatttgat aaatataaaa aaaaaaaaaa aaaaaaaaaa aa
```

The term "IL-7" or "IL-7 molecule" refers to interleukin-7. GenBank No. NP_000871.1 and Swiss-Prot accession number P13232 provide exemplary human IL-7 amino acid sequences. In some embodiments, IL-7 or IL-7 molecule is a naturally-existing IL-7 or a functional variant or fragment thereof. In some embodiments, human IL-7 has the following amino acid and nucleic acid sequences:

Interleukin-7 isoform 1 precursor [*Homo sapiens*, NP_000871.1] (SEQ ID NO: 627)

```
  1 MFHVSFRYIF GLPPLILVLL PVASSDCDIE GKDGKQYESV LMVSIDQLLD SMKEIGSNCL

 61 NNEFNFFKRH ICDANKEGMF LFRAARKLRQ FLKMNSTGDF DLHLLKVSEG TTILLNCTGQ

121 VKGRKPAALG EAQPTKSLEE NKSLKEQKKL NDLCFLKRLL QEIKTCWNKI LMGTKEH
```

Homo sapiens interleukin 7 (IL7), transcript variant 1, mRNA [NM_000880.4] (SEQ ID NO: 628)

```
  1 acacttgtgg cttccgtgca cacattaaca actcatggtt ctagctccca gtcgccaagc

 61 gttgccaagg cgttgagaga tcatctggga agtcttttac ccagaattgc tttgattcag

121 gccagctggt tttcctgcg gtgattcgga aattcgcgaa ttcctctggt cctcatccag

181 gtgcgcggga agcaggtgcc caggagagag gggataatga agattccatg ctgatgatcc

241 caaagattga acctgcagac caagcgcaaa gtagaaactg aaagtacact gctggcggat

301 cctacggaag ttatggaaaa ggcaaagcgc agagccacgc cgtagtgtgt gccgcccccc

361 ttgggatgga tgaaactgca gtcgcggcgt gggtaagagg aaccagctgc agagatcacc

421 ctgcccaaca cagactcggc aactccgcgg aagaccaggg tcctgggagt gactatgggc

481 ggtgagagct tgctcctgct ccagttgcgg tcatcatgac tacgcccgcc tcccgcagac

541 catgttccat gtttctttta ggtatatctt tggacttcct cccctgatcc ttgttctgtt

601 gccagtagca tcatctgatt gtgatattga aggtaaagat ggcaaacaat atgagagtgt

661 tctaatggtc agcatcgatc aattattgga cagcatgaaa gaaattggta gcaattgcct

721 gaataatgaa tttaactttt ttaaaagaca tatctgtgat gctaataagg aaggtatgtt

781 tttattccgt gctgctcgca agttgaggca atttcttaaa atgaatagca ctggtgattt

841 tgatctccac ttattaaaag tttcagaagg cacaacaata ctgttgaact gcactggcca

901 ggttaaagga agaaaaccag ctgccctggg tgaagcccaa ccaacaaaga gtttggaaga
```

-continued

```
 961 aaataaatct ttaaaggaac agaaaaaact gaatgacttg tgtttcctaa agagactatt

1021 acaagagata aaaacttgtt ggaataaaat tttgatgggc actaaagaac actgaaaaat

1081 atggagtggc aatatagaaa cacgaacttt agctgcatcc tccaagaatc tatctgctta

1141 tgcagttttt cagagtggaa tgcttcctag aagttactga atgcaccatg gtcaaaacgg

1201 attagggcat ttgagaaatg catattgtat tactagaaga tgaatacaaa caatggaaac

1261 tgaatgctcc agtcaacaaa ctatttctta tatatgtgaa catttatcaa tcagtataat

1321 tctgtactga tttttgtaag acaatccatg taaggtatca gttgcaataa tacttctcaa

1381 acctgtttaa atatttcaag acattaaatc tatgaagtat ataatggttt caaagattca

1441 aaattgacat tgctttactg tcaaaataat tttatggctc actatgaatc tattatactg

1501 tattaagagt gaaaattgtc ttcttctgtg ctggagatgt tttagagtta acaatgatat

1561 atggataatg ccggtgagaa taagagagtc ataaacctta agtaagcaac agcataacaa

1621 ggtccaagat acctaaaaga gatttcaaga gatttaatta atcatgaatg tgtaacacag

1681 tgccttcaat aaatggtata gcaaatgttt tgacatgaaa aaaggacaat ttcaaaaaaa

1741 taaaataaaa taaaaataaa ttcacctagt ctaaggatgc taaaccttag tactgagtta

1801 cattgtcatt tatatagatt ataacttgtc taaataagtt tgcaatttgg gagatatatt

1861 tttaagataa taatatatgt ttacctttta attaatgaaa tatctgtatt taattttgac

1921 actatatctg tatataaaat attttcatac agcattacaa attgcttact ttggaataca

1981 tttctccttt gataaaataa atgagctatg tattaa
```

The compositions and methods of the present invention encompass polypeptides and nucleic acids having the sequences specified, or sequences substantially identical or similar thereto, e.g., sequences at least 85%, 90%, or 95% identical or higher to the sequence specified. In the context of an amino acid sequence, the term "substantially identical" is used herein to refer to a first amino acid sequence that contains a sufficient or minimum number of amino acid residues that are i) identical to, or ii) conservative substitutions of aligned amino acid residues in a second amino acid sequence such that the first and second amino acid sequences can have a common structural domain and/or common functional activity, for example, amino acid sequences that contain a common structural domain having at least about 85%, 90%. 91%, 92%, 93%, 94%, 95%, 96%, 97%, 98% or 99% identity to a reference sequence, e.g., a sequence provided herein.

In the context of a nucleotide sequence, the term "substantially identical" is used herein to refer to a first nucleic acid sequence that contains a sufficient or minimum number of nucleotides that are identical to aligned nucleotides in a second nucleic acid sequence such that the first and second nucleotide sequences encode a polypeptide having common functional activity, or encode a common structural polypeptide domain or a common functional polypeptide activity, for example, nucleotide sequences having at least about 85%, 90%, 91%, 92%, 93%, 94%, 95%, 96%, 97%, 98% or 99% identity to a reference sequence, e.g., a sequence provided herein.

The term "variant" refers to a polypeptide that has a substantially identical amino acid sequence to a reference amino acid sequence, or is encoded by a substantially identical nucleotide sequence. In some embodiments, the variant is a functional variant.

The term "functional variant" refers to a polypeptide that has a substantially identical amino acid sequence to a reference amino acid sequence, or is encoded by a substantially identical nucleotide sequence, and is capable of having one or more activities of the reference amino acid sequence.

The term "Chimeric Antigen Receptor" or alternatively a "CAR" refers to a recombinant polypeptide construct comprising at least an extracellular antigen binding domain, a transmembrane domain and a cytoplasmic signaling domain (also referred to herein as "an intracellular signaling domain") comprising a functional signaling domain derived from a stimulatory molecule as defined below. In some embodiments, the domains in the CAR polypeptide construct are in the same polypeptide chain, e.g., comprise a chimeric fusion protein. In some embodiments, the domains in the CAR polypeptide construct are not contiguous with each other, e.g., are in different polypeptide chains, e.g., as provided in an RCAR as described herein.

In one aspect, the cytoplasmic signaling domain comprises a primary signaling domain (e.g., a primary signaling domain of CD3-zeta). In one aspect, the cytoplasmic signaling domain further comprises one or more functional signaling domains derived from at least one costimulatory molecule as defined below. In one aspect, the costimulatory molecule is chosen from 41BB (i.e., CD137), CD27, ICOS, and/or CD28. In one aspect, the CAR comprises a chimeric fusion protein comprising an extracellular antigen recognition domain, a transmembrane domain and an intracellular signaling domain comprising a functional signaling domain derived from a stimulatory molecule. In one aspect, the CAR comprises a chimeric fusion protein comprising an extracellular antigen recognition domain, a transmembrane domain and an intracellular signaling domain comprising a functional signaling domain derived from a co-stimulatory molecule and a functional signaling domain derived from a stimulatory molecule. In one aspect, the CAR comprises a chimeric fusion protein comprising an extracellular antigen recognition domain, a transmembrane domain and an intracellular signaling domain comprising two functional signaling domains derived from one or more co-stimulatory molecule(s) and a functional signaling domain derived from a stimulatory molecule. In one aspect, the CAR comprises a chimeric fusion protein comprising an extracellular antigen recognition domain, a transmembrane domain and an intracellular signaling domain comprising at least two functional signaling domains derived from one or more co-stimulatory molecule(s) and a functional signaling domain derived from a stimulatory molecule. In one aspect the CAR comprises an optional leader sequence at the amino-terminus (N-ter) of the CAR fusion protein. In one aspect, the CAR further comprises a leader sequence at the N-terminus of the extracellular antigen recognition domain, wherein the leader sequence is optionally cleaved from the antigen recognition domain (e.g., an scFv) during cellular processing and localization of the CAR to the cellular membrane.

A CAR that comprises an antigen binding domain (e.g., an scFv, a single domain antibody, or TCR (e.g., a TCR alpha binding domain or TCR beta binding domain)) that targets a specific tumor marker X, wherein X can be a tumor marker as described herein, is also referred to as XCAR. For example, a CAR that comprises an antigen binding domain that targets CD19 is referred to as CD19CAR. The CAR can be expressed in any cell, e.g., an immune effector cell as described herein (e.g., a T cell or an NK cell).

The term "signaling domain" refers to the functional portion of a protein which acts by transmitting information within the cell to regulate cellular activity via defined signaling pathways by generating second messengers or functioning as effectors by responding to such messengers.

The term "antibody," as used herein, refers to a protein, or polypeptide sequence derived from an immunoglobulin molecule, which specifically binds with an antigen. Antibodies can be polyclonal or monoclonal, multiple or single chain, or intact immunoglobulins, and may be derived from natural sources or from recombinant sources. Antibodies can be tetramers of immunoglobulin molecules.

The term "antibody fragment" refers to at least one portion of an intact antibody, or recombinant variants thereof, and refers to the antigen binding domain, e.g., an antigenic determining variable region of an intact antibody, that is sufficient to confer recognition and specific binding of the antibody fragment to a target, such as an antigen. Examples of antibody fragments include, but are not limited to, Fab, Fab', F(ab')2, and Fv fragments, scFv antibody fragments, linear antibodies, single domain antibodies such as sdAb (either VL or VH), camelid VHH domains, and multi-specific molecules formed from antibody fragments such as a bivalent fragment comprising two or more, e.g., two, Fab fragments linked by a disulfide brudge at the hinge region, or two or more, e.g., two isolated CDR or other epitope binding fragments of an antibody linked. An antibody fragment can also be incorporated into single domain antibodies, maxibodies, minibodies, nanobodies, intrabodies, diabodies, triabodies, tetrabodies, v-NAR and bis-scFv (see, e.g., Hollinger and Hudson, Nature Biotechnology 23:1126-1136, 2005). Antibody fragments can also be grafted into scaffolds based on polypeptides such as a fibronectin type III (Fn3) (see U.S. Pat. No. 6,703,199, which describes fibronectin polypeptide minibodies).

The term "scFv" refers to a fusion protein comprising at least one antibody fragment comprising a variable region of a light chain and at least one antibody fragment comprising a variable region of a heavy chain, wherein the light and heavy chain variable regions are contiguously linked via a short flexible polypeptide linker, and capable of being expressed as a single chain polypeptide, and wherein the scFv retains the specificity of the intact antibody from which it is derived. Unless specified, as used herein an scFv may have the VL and VH variable regions in either order, e.g., with respect to the N-terminal and C-terminal ends of the polypeptide, the scFv may comprise VL-linker-VH or may comprise VH-linker-VL.

The terms "complementarity determining region" or "CDR," as used herein, refer to the sequences of amino acids within antibody variable regions which confer antigen specificity and binding affinity. For example, in general, there are three CDRs in each heavy chain variable region (e.g., HCDR1, HCDR2, and HCDR3) and three CDRs in each light chain variable region (LCDR1, LCDR2, and LCDR3). The precise amino acid sequence boundaries of a given CDR can be determined using any of a number of well-known schemes, including those described by Kabat et al. (1991), "Sequences of Proteins of Immunological Interest," 5th Ed. Public Health Service, National Institutes of Health, Bethesda, MD ("Kabat" numbering scheme), Al-Lazikani et al., (1997) JMB 273,927-948 ("Chothia" numbering scheme), or a combination thereof. Under the Kabat numbering scheme, in some embodiments, the CDR amino acid residues in the heavy chain variable domain (VH) are numbered 31-35 (HCDR1), 50-65 (HCDR2), and 95-102 (HCDR3); and the CDR amino acid residues in the light chain variable domain (VL) are numbered 24-34 (LCDR1), 50-56 (LCDR2), and 89-97 (LCDR3). Under the Chothia numbering scheme, in some embodiments, the CDR amino acids in the VH are numbered 26-32 (HCDR1), 52-56 (HCDR2), and 95-102 (HCDR3); and the CDR amino acid residues in the VL are numbered 26-32 (LCDR1), 50-52 (LCDR2), and 91-96 (LCDR3). In a combined Kabat and Chothia numbering scheme, in some embodiments, the CDRs correspond to the amino acid residues that are part of a Kabat CDR, a Chothia CDR, or both. For instance, in some embodiments, the CDRs correspond to amino acid residues 26-35 (HCDR1), 50-65 (HCDR2), and 95-102 (HCDR3) in a VH, e.g., a mammalian VH, e.g., a human VH; and amino acid residues 24-34 (LCDR1), 50-56 (LCDR2), and 89-97 (LCDR3) in a VL, e.g., a mammalian VL, e.g., a human VL.

The portion of the CAR composition of the invention comprising an antibody or antibody fragment thereof may exist in a variety of forms, for example, where the antigen binding domain is expressed as part of a polypeptide chain including, for example, a single domain antibody fragment (sdAb), a single chain antibody (scFv), or e.g., a humanized antibody (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, New York; Houston et al., 1988, Proc. Natl. Acad. Sci. USA 85:5879-5883; Bird et al., 1988, Science 242:423-426). In one aspect, the antigen binding domain of a CAR composition of the invention comprises an antibody fragment. In a further aspect, the CAR comprises an antibody fragment that comprises an scFv.

As used herein, the term "binding domain" or "antibody molecule" (also referred to herein as "anti-target binding domain") refers to a protein, e.g., an immunoglobulin chain or fragment thereof, comprising at least one immunoglobulin variable domain sequence. The term "binding domain" or "antibody molecule" encompasses antibodies and antibody fragments. In an embodiment, an antibody molecule is a multispecific antibody molecule, e.g., it comprises a plurality of immunoglobulin variable domain sequences, wherein a first immunoglobulin variable domain sequence of the plurality has binding specificity for a first epitope and a second immunoglobulin variable domain sequence of the plurality has binding specificity for a second epitope. In an embodiment, a multispecific antibody molecule is a bispecific antibody molecule. A bispecific antibody has specificity for no more than two antigens. A bispecific antibody molecule is characterized by a first immunoglobulin variable domain sequence which has binding specificity for a first epitope and a second immunoglobulin variable domain sequence that has binding specificity for a second epitope. The term "antibody heavy chain," refers to the larger of the two types of polypeptide chains present in antibody molecules in their naturally occurring conformations, and which normally determines the class to which the antibody belongs.

The term "antibody light chain," refers to the smaller of the two types of polypeptide chains present in antibody molecules in their naturally occurring conformations. Kappa (κ) and lambda (λ) light chains refer to the two major antibody light chain isotypes.

The term "recombinant antibody" refers to an antibody which is generated using recombinant DNA technology, such as, for example, an antibody expressed by a bacteriophage or yeast expression system. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using recombinant DNA or amino acid sequence technology which is available and well known in the art.

The term "antigen" or "Ag" refers to a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to encode polypeptides that elicit the desired immune response. Moreover, a skilled artisan will understand that an antigen need not be encoded by a "gene" at all. It is readily apparent that an antigen can be generated synthesized or can be derived from a biological sample, or might be macromolecule besides a polypeptide. Such a biological sample can include, but is not limited to a tissue sample, a tumor sample, a cell or a fluid with other biological components.

The term "anti-tumor effect" refers to a biological effect which can be manifested by various means, including but not limited to, e.g., a decrease in tumor volume, a decrease in the number of tumor cells, a decrease in the number of metastases, an increase in life expectancy, decrease in tumor cell proliferation, decrease in tumor cell survival, or amelioration of various physiological symptoms associated with the cancerous condition. An "anti-tumor effect" can also be manifested by the ability of the peptides, polynucleotides, cells and antibodies of the invention in prevention of the occurrence of tumor in the first place.

The term "anti-cancer effect" refers to a biological effect which can be manifested by various means, including but not limited to, e.g., a decrease in tumor volume, a decrease in the number of cancer cells, a decrease in the number of metastases, an increase in life expectancy, decrease in cancer cell proliferation, decrease in cancer cell survival, or amelioration of various physiological symptoms associated with the cancerous condition. An "anti-cancer effect" can also be manifested by the ability of the peptides, polynucleotides, cells and antibodies in prevention of the occurrence of cancer in the first place. The term "anti-tumor effect" refers to a biological effect which can be manifested by various means, including but not limited to, e.g., a decrease in tumor volume, a decrease in the number of tumor cells, a decrease in tumor cell proliferation, or a decrease in tumor cell survival. The term "autologous" refers to any material derived from the same individual to whom it is later to be re-introduced into the individual.

The term "allogeneic" refers to any material derived from a different animal of the same species as the individual to whom the material is introduced. Two or more individuals are said to be allogeneic to one another when the genes at one or more loci are not identical. In some aspects, allogeneic material from individuals of the same species may be sufficiently unlike genetically to interact antigenically.

The term "xenogeneic" refers to a graft derived from an animal of a different species.

The term "cancer" refers to a disease characterized by the rapid and uncontrolled growth of aberrant cells. Cancer cells can spread locally or through the bloodstream and lymphatic system to other parts of the body. Examples of various cancers are described herein and include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer and the like. Preferred cancers treated by the methods described herein include multiple myeloma, Hodgkin's lymphoma or non-Hodgkin's lymphoma.

The terms "tumor" and "cancer" are used interchangeably herein, e.g., both terms encompass solid and liquid, e.g., diffuse or circulating, tumors. As used herein, the term "cancer" or "tumor" includes premalignant, as well as malignant cancers and tumors.

"Derived from" as that term is used herein, indicates a relationship between a first and a second molecule. It generally refers to structural similarity between the first molecule and a second molecule and does not connotate or include a process or source limitation on a first molecule that is derived from a second molecule. For example, in the case of an intracellular signaling domain that is derived from a CD3zeta molecule, the intracellular signaling domain retains sufficient CD3zeta structure such that is has the required function, namely, the ability to generate a signal under the appropriate conditions. It does not connotate or include a limitation to a particular process of producing the intracellular signaling domain, e.g., it does not mean that, to provide the intracellular signaling domain, one must start with a CD3zeta sequence and delete unwanted sequence, or impose mutations, to arrive at the intracellular signaling domain.

The phrase "disease associated with expression of an antigen, e.g., a tumor antigen" includes, but is not limited to, a disease associated with a cell which expresses the antigen (e.g., wild-type or mutant antigen) or condition associated with a cell which expresses the antigen (e.g., wild-type or mutant antigen) including, e.g., proliferative diseases such as a cancer or malignancy or a precancerous condition such as a myelodysplasia, a myelodysplastic syndrome or a preleukemia; or a noncancer related indication associated with a cell which expresses the antigen (e.g., wild-type or mutant antigen). For the avoidance of doubt, a disease associated with expression of the antigen may include a condition associated with a cell which does not presently express the antigen, e.g., because expression of the antigen has been downregulated, e.g., due to treatment with a molecule targeting the antigen, but which at one time expressed the antigen. In some embodiments, the disease associated with expression of an antigen, e.g., a tumor antigen is a cancer (e.g., a solid cancer or a hematological cancer), a viral infection (e.g., HIV, a fungal infection, e.g., *C. neoformans*), an autoimmune disease (e.g. rheumatoid arthritis, system lupus erythematosus (SLE or lupus), pemphigus vulgaris, and Sjogren's syndrome; inflammatory bowel disease, ulcerative colitis; transplant-related allospecific immunity disorders related to mucosal immunity; and unwanted immune responses towards biologics (e.g., Factor VIII) where humoral immunity is important).

The phrase "disease associated with expression of mesothelin" includes, but is not limited to, a disease associated with expression of mesothelin or condition associated with cells which express mesothelin including, e.g., proliferative diseases such as a cancer or malignancy or a precancerous condition such as a mesothelial hyperplasia; or a noncancer related indication associated with cells which express mesothelin. Examples of various cancers that express mesothelin include but are not limited to, mesothelioma, lung cancer, ovarian cancer, pancreatic cancer, and the like.

The term "conservative sequence modifications" refers to amino acid modifications that do not significantly affect or alter the binding characteristics of the antibody or antibody fragment containing the amino acid sequence. Such conservative modifications include amino acid substitutions, additions and deletions. Modifications can be introduced into an antibody or antibody fragment of the invention by standard techniques known in the art, such as site-directed mutagenesis and PCR-mediated mutagenesis. Conservative substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within a CAR of the invention can be replaced with other amino acid residues from the same side chain family and the altered CAR can be tested using the functional assays described herein.

The term "stimulation," refers to a primary response induced by binding of a stimulatory molecule (e.g., a TCR/CD3 complex) with its cognate ligand thereby mediating a signal transduction event, such as, but not limited to, signal transduction via the TCR/CD3 complex. Stimulation can mediate altered expression of certain molecules, such as downregulation of TGF-β, and/or reorganization of cytoskeletal structures, and the like.

The term "stimulatory molecule," refers to a molecule expressed by a T cell that provides the primary cytoplasmic signaling sequence(s) that regulate primary activation of the TCR complex in a stimulatory way for at least some aspect of the T cell signaling pathway. In some embodiments, the ITAM-containing domain within the CAR recapitulates the signaling of the primary TCR independently of endogenous TCR complexes. In one aspect, the primary signal is initiated by, for instance, binding of a TCR/CD3 complex with an MHC molecule loaded with peptide, and which leads to mediation of a T cell response, including, but not limited to, proliferation, activation, differentiation, and the like. A primary cytoplasmic signaling sequence (also referred to as a "primary signaling domain") that acts in a stimulatory manner may contain a signaling motif which is known as immunoreceptor tyrosine-based activation motif or ITAM. Examples of an ITAM containing primary cytoplasmic signaling sequence that is of particular use in the invention includes, but is not limited to, those derived from TCR zeta, FcR gamma, FcR beta, CD3 gamma, CD3 delta, CD3 epsilon, CD5, CD22, CD79a, CD79b, CD278 (also known as "ICOS"), FcεRI and CD66d, DAP10 and DAP12. In a specific CAR of the invention, the intracellular signaling domain in any one or more CARS of the invention comprises an intracellular signaling sequence, e.g., a primary signaling sequence of CD3-zeta. The term "antigen presenting cell" or "APC" refers to an immune system cell such as an accessory cell (e.g., a B-cell, a dendritic cell, and the like) that displays a foreign antigen complexed with major histocompatibility complexes (MHC's) on its surface. T-cells may recognize these complexes using their T-cell receptors (TCRs). APCs process antigens and present them to T-cells.

An "intracellular signaling domain," as the term is used herein, refers to an intracellular portion of a molecule. In embodiments, the intracellular signal domain transduces the effector function signal and directs the cell to perform a specialized function. While the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The term intracellular signaling domain is thus meant to include any truncated portion of the intracellular signaling domain sufficient to transduce the effector function signal.

The intracellular signaling domain generates a signal that promotes an immune effector function of the CAR containing cell, e.g., a CART cell. Examples of immune effector function, e.g., in a CART cell, include cytolytic activity and helper activity, including the secretion of cytokines.

In an embodiment, the intracellular signaling domain can comprise a primary intracellular signaling domain. Exemplary primary intracellular signaling domains include those derived from the molecules responsible for primary stimulation, or antigen dependent simulation. In an embodiment, the intracellular signaling domain can comprise a costimulatory intracellular domain. Exemplary costimulatory intracellular signaling domains include those derived from molecules responsible for costimulatory signals, or antigen independent stimulation. For example, in the case of a CART, a primary intracellular signaling domain can comprise a cytoplasmic sequence of a T cell receptor, and a costimulatory intracellular signaling domain can comprise cytoplasmic sequence from co-receptor or costimulatory molecule.

A primary intracellular signaling domain can comprise a signaling motif which is known as an immunoreceptor tyrosine-based activation motif or ITAM. Examples of ITAM containing primary cytoplasmic signaling sequences include, but are not limited to, those derived from CD3 zeta, FcR gamma, FcR beta, CD3 gamma, CD3 delta, CD3 epsilon, CD5, CD22, CD79a, CD79b, CD278 (also known as "ICOS"), FcεRI, CD66d, DAP10 and DAP12.

The term "zeta" or alternatively "zeta chain", "CD3-zeta" or "TCR-zeta" refers to CD247. Swiss-Prot accession number P20963 provides exemplary human CD3 zeta amino acid sequences. A "zeta stimulatory domain" or alternatively a "CD3-zeta stimulatory domain" or a "TCR-zeta stimulatory domain" refers to a stimulatory domain of CD3-zeta or a variant thereof (e.g., a molecule having mutations, e.g., point mutations, fragments, insertions, or deletions). In one embodiment, the cytoplasmic domain of zeta comprises residues 52 through 164 of GenBank Acc. No. BAG36664.1 or a variant thereof (e.g., a molecule having mutations, e.g., point mutations, fragments, insertions, or deletions). In one embodiment, the "zeta stimulatory domain" or a "CD3-zeta stimulatory domain" is the sequence provided as SEQ ID NO: 9 or 10, or a variant thereof (e.g., a molecule having mutations, e.g., point mutations, fragments, insertions, or deletions).

The term "costimulatory molecule" refers to the cognate binding partner on a T cell that specifically binds with a costimulatory ligand, thereby mediating a costimulatory response by the T cell, such as, but not limited to, proliferation. Costimulatory molecules are cell surface molecules other than antigen receptors or their ligands that are required for an efficient immune response. Costimulatory molecules include, but are not limited to an MHC class I molecule, TNF receptor proteins, Immunoglobulin-like proteins, cytokine receptors, integrins, signaling lymphocytic activation molecules (SLAM proteins), activating NK cell receptors, BTLA, Toll ligand receptor, OX40, CD2, CD7, CD27, CD28, CD30, CD40, CDS, ICAM-1, LFA-1 (CD11a/CD18), 4-1BB (CD137), B7-H3, CDS, ICAM-1, ICOS (CD278), GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, NKG2C, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMFI, CD150, IPO-3), BLAME (SLAMF8), SELPLG (CD162), LTBR, LAT, GADS, SLP-76, PAG/Cbp, CD19a, CD28-OX40, CD28-4-1BB, and a ligand that specifically binds with CD83.

A costimulatory intracellular signaling domain refers to the intracellular portion of a costimulatory molecule.

The intracellular signaling domain can comprise the entire intracellular portion, or the entire native intracellular signaling domain, of the molecule from which it is derived, or a functional fragment thereof.

The term "4-1BB" refers to CD137 or Tumor necrosis factor receptor superfamily member 9. Swiss-Prot accession number P20963 provides exemplary human 4-1BB amino acid sequences. A "4-1BB costimulatory domain" refers to a costimulatory domain of 4-1BB, or a variant thereof (e.g., a molecule having mutations, e.g., point mutations, fragments, insertions, or deletions). In one embodiment, the "4-1BB costimulatory domain" is the sequence provided as SEQ ID NO: 7 or a variant thereof (e.g., a molecule having mutations, e.g., point mutations, fragments, insertions, or deletions).

"Immune effector cell," as that term is used herein, refers to a cell that is involved in an immune response, e.g., in the promotion of an immune effector response. Examples of immune effector cells include T cells, e.g., alpha/beta T cells and gamma/delta T cells, B cells, natural killer (NK) cells, natural killer T (NKT) cells, mast cells, and myeloic-derived phagocytes.

"Immune effector function or immune effector response," as that term is used herein, refers to function or response, e.g., of an immune effector cell, that enhances or promotes an immune attack of a target cell. E.g., an immune effector function or response refers a property of a T or NK cell that promotes killing or the inhibition of growth or proliferation, of a target cell. In the case of a T cell, primary stimulation and co-stimulation are examples of immune effector function or response.

The term "effector function" refers to a specialized function of a cell. Effector function of a T cell, for example, may be cytolytic activity or helper activity including the secretion of cytokines.

The term "encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (e.g., rRNA, tRNA and mRNA) or a defined sequence of amino acids and the biological properties resulting therefrom. Thus, a gene, cDNA, or RNA, encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or a RNA may also include introns to the extent that the nucleotide sequence encoding the protein may in some version contain an intron(s).

The term "effective amount" or "therapeutically effective amount" are used interchangeably herein, and refer to an amount of a compound, formulation, material, or composition, as described herein effective to achieve a particular biological result.

The term "endogenous" refers to any material from or produced inside an organism, cell, tissue or system.

The term "exogenous" refers to any material introduced from or produced outside an organism, cell, tissue or system.

The term "expression" refers to the transcription and/or translation of a particular nucleotide sequence. In some embodiments, expression comprises translation of an mRNA introduced into a cell.

The term "transfer vector" refers to a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "transfer vector" includes an autonomously replicating plasmid or a virus. The term should also be construed to further include non-plasmid and non-viral compounds which facilitate transfer of nucleic acid into cells, such as, for example, a polylysine compound, liposome, and the like. Examples of viral transfer vectors include, but are not limited to, adenoviral vectors, adeno-associated virus vectors, retroviral vectors, lentiviral vectors, and the like.

The term "expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, including cosmids, plasmids (e.g., naked or contained in liposomes) and viruses (e.g., lentiviruses, retroviruses, adenoviruses, and adeno-associated viruses) that incorporate the recombinant polynucleotide.

The term "lentivirus" refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses.

The term "lentiviral vector" refers to a vector derived from at least a portion of a lentivirus genome, including especially a self-inactivating lentiviral vector as provided in Milone et al., Mol. Ther. 17(8): 1453-1464 (2009). Other examples of lentivirus vectors that may be used in the clinic, include but are not limited to, e.g., the LENTIVECTOR® gene delivery technology from Oxford BioMedica, the LENTIMAX™ vector system from Lentigen and the like. Nonclinical types of lentiviral vectors are also available and would be known to one skilled in the art.

The term "homologous" or "identity" refers to the subunit sequence identity between two polymeric molecules, e.g., between two nucleic acid molecules, such as, two DNA molecules or two RNA molecules, or between two polypeptide molecules. When a subunit position in both of the two molecules is occupied by the same monomeric subunit; e.g., if a position in each of two DNA molecules is occupied by adenine, then they are homologous or identical at that position. The homology between two sequences is a direct function of the number of matching or homologous positions; e.g., if half (e.g., five positions in a polymer ten subunits in length) of the positions in two sequences are homologous, the two sequences are 50% homologous; if 90% of the positions (e.g., 9 of 10), are matched or homologous, the two sequences are 90% homologous.

"Humanized" forms of non-human (e.g., murine) antibodies are chimeric immunoglobulins, immunoglobulin chains or fragments thereof (such as Fv, Fab, Fab', F(ab')2 or other antigen-binding subsequences of antibodies) which contain minimal sequence derived from non-human immunoglobulin. For the most part, humanized antibodies and antibody fragments thereof are human immunoglobulins (recipient antibody or antibody fragment) in which residues from a complementary-determining region (CDR) of the recipient are replaced by residues from a CDR of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, a humanized antibody/antibody fragment can comprise residues which are found neither in the recipient antibody nor in the imported CDR or framework sequences. These modifications can further refine and optimize antibody or antibody fragment performance. In general, the humanized antibody or antibody fragment thereof will comprise substantially all of at least one, and typically two, variable domains, in which all or substantially all of the CDR regions correspond to those of a non-human immunoglobulin and all or a significant portion of the FR regions are those of a human immunoglobulin sequence. The humanized antibody or antibody fragment can also comprise at least a portion of an immunoglobulin constant region (Fc), typically that of a human immunoglobulin. For further details, see Jones et al., Nature, 321: 522-525, 1986; Reichmann et al., Nature, 332: 323-329, 1988; Presta, Curr. Op. Struct. Biol., 2: 593-596, 1992.

"Fully human" refers to an immunoglobulin, such as an antibody or antibody fragment, where the whole molecule is of human origin or consists of an amino acid sequence identical to a human form of the antibody or immunoglobulin.

The term "isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

The term "operably linked" or "transcriptional control" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Operably linked DNA sequences can be contiguous with each other and, e.g., where necessary to join two protein coding regions, are in the same reading frame.

The term "parenteral" administration of an immunogenic composition includes, e.g., subcutaneous (s.c.), intravenous (i.v.), intramuscular (i.m.), or intrasternal injection, intratumoral, or infusion techniques.

The term "nucleic acid," "nucleic acid molecule," "polynucleotide," or "polynucleotide molecule" refers to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. In some embodiments, a "nucleic acid," "nucleic acid molecule," "polynucleotide," or "polynucleotide molecule" comprise a nucleotide/nucleoside derivative or analog. Unless otherwise indicated, a particular nucleic acid sequence also implicitly encompasses conservatively modified variants thereof (e.g., degenerate codon substitutions, e.g., conservative substitutions), alleles, orthologs, SNPs, and complementary sequences as well as the sequence explicitly indicated. Specifically, degenerate codon substitutions, e.g., conservative substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); and Rossolini et al., Mol. Cell. Probes 8:91-98 (1994)).

The terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. A polypeptide includes a natural peptide, a recombinant peptide, or a combination thereof.

The term "promoter" refers to a DNA sequence recognized by the synthetic machinery of the cell, or introduced synthetic machinery, required to initiate the specific transcription of a polynucleotide sequence.

The term "promoter/regulatory sequence" refers to a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

The term "constitutive" promoter refers to a nucleotide sequence which, when operably linked with a polynucleotide which encodes or specifies a gene product, causes the gene product to be produced in a cell under most or all physiological conditions of the cell.

The term "inducible" promoter refers to a nucleotide sequence which, when operably linked with a polynucleotide which encodes or specifies a gene product, causes the gene product to be produced in a cell substantially only when an inducer which corresponds to the promoter is present in the cell.

The term "tissue-specific" promoter refers to a nucleotide sequence which, when operably linked with a polynucleotide encodes or specified by a gene, causes the gene product to be produced in a cell substantially only if the cell is a cell of the tissue type corresponding to the promoter.

The terms "cancer associated antigen" or "tumor antigen" interchangeably refers to a molecule (typically a protein, carbohydrate or lipid) that is expressed on the surface of a cancer cell, either entirely or as a fragment (e.g., MHC/peptide), and which is useful for the preferential targeting of a pharmacological agent to the cancer cell. In some embodiments, a tumor antigen is a marker expressed by both normal cells and cancer cells, e.g., a lineage marker, e.g., CD19 on B cells. In some embodiments, a tumor antigen is a cell surface molecule that is overexpressed in a cancer cell in comparison to a normal cell, for instance, 1-fold over expression, 2-fold overexpression, 3-fold overexpression or more in comparison to a normal cell. In some embodiments, a tumor antigen is a cell surface molecule that is inappropriately synthesized in the cancer cell, for instance, a molecule that contains deletions, additions or mutations in comparison to the molecule expressed on a normal cell. In some embodiments, a tumor antigen will be expressed exclusively on the cell surface of a cancer cell, entirely or as a fragment (e.g., MHC/peptide), and not synthesized or expressed on the surface of a normal cell. In some embodiments, the CARs of the present invention include CARs comprising an antigen binding domain (e.g., antibody or antibody fragment) that binds to a MHC presented peptide. Normally, peptides derived from endogenous proteins fill the pockets of Major histocompatibility complex (MHC) class I molecules, and are recognized by T cell receptors (TCRs) on CD8+ T lymphocytes. The MHC class I complexes are constitutively expressed by all nucleated cells. In cancer, virus-specific and/or tumor-specific peptide/MHC complexes represent a unique class of cell surface targets for immunotherapy. TCR-like antibodies targeting peptides derived from viral or tumor antigens in the context of human leukocyte antigen (HLA)-A1 or HLA-A2 have been described (see, e.g., Sastry et al., J Virol. 201185(5):1935-1942; Sergeeva et al., Blood, 2011 117(16):4262-4272; Verma et al., J Immunol 2010 184(4):2156-2165; Willemsen et al., Gene Ther 2001 8(21):1601-1608; Dao et al., Sci Transl Med 2013 5(176):176ra33; Tassev et al., Cancer Gene Ther 2012 19(2):84-100). For example, TCR-like antibody can be identified from screening a library, such as a human scFv phage displayed library.

The term "tumor-supporting antigen" or "cancer-supporting antigen" interchangeably refer to a molecule (typically a protein, carbohydrate or lipid) that is expressed on the surface of a cell that is, itself, not cancerous, but supports the cancer cells, e.g., by promoting their growth or survival e.g., resistance to immune cells. Exemplary cells of this type include stromal cells and myeloid-derived suppressor cells (MDSCs). The tumor-supporting antigen itself need not play a role in supporting the tumor cells so long as the antigen is present on a cell that supports cancer cells.

The term "flexible polypeptide linker" or "linker" as used in the context of an scFv refers to a peptide linker that consists of amino acids such as glycine and/or serine residues used alone or in combination, to link variable heavy and variable light chain regions together. In one embodiment, the flexible polypeptide linker is a Gly/Ser linker and comprises the amino acid sequence (Gly-Gly-Gly-Ser)n, where n is a positive integer equal to or greater than 1. For example, n=1, n=2, n=3. n=4, n=5 and n=6, n=7, n=8, n=9 and n=10 (SEQ ID NO: 606). In one embodiment, the flexible polypeptide linkers include, but are not limited to, (Gly4 Ser)4 (SEQ ID NO: 27) or (Gly4 Ser)3 (SEQ ID NO: 28). In another embodiment, the linkers include multiple repeats of (Gly2Ser), (GlySer) or (Gly3Ser) (SEQ ID NO: 29). Also included within the scope of the invention are linkers described in WO2012/138475, incorporated herein by reference.

As used herein, a 5' cap (also termed an RNA cap, an RNA 7-methylguanosine cap or an RNA m7G cap) is a modified guanine nucleotide that has been added to the "front" or 5' end of a eukaryotic messenger RNA shortly after the start of transcription. The 5' cap consists of a terminal group which is linked to the first transcribed nucleotide. Its presence is critical for recognition by the ribosome and protection from RNases. Cap addition is coupled to transcription, and occurs co-transcriptionally, such that each influences the other. Shortly after the start of transcription, the 5' end of the mRNA being synthesized is bound by a cap-synthesizing complex associated with RNA polymerase. This enzymatic complex catalyzes the chemical reactions that are required for mRNA capping. Synthesis proceeds as a multi-step biochemical reaction. The capping moiety can be modified to modulate functionality of mRNA such as its stability or efficiency of translation.

As used herein, "in vitro transcribed RNA" refers to RNA, preferably mRNA, that has been synthesized in vitro. Generally, the in vitro transcribed RNA is generated from an in vitro transcription vector. The in vitro transcription vector comprises a template that is used to generate the in vitro transcribed RNA.

As used herein, a "poly(A)" is a series of adenosines attached by polyadenylation to the mRNA. In the preferred embodiment of a construct for transient expression, the polyA is between 50 and 5000 (SEQ ID NO: 30), preferably greater than 64, more preferably greater than 100, most preferably greater than 300 or 400. poly(A) sequences can be modified chemically or enzymatically to modulate mRNA functionality such as localization, stability or efficiency of translation.

As used herein, "polyadenylation" refers to the covalent linkage of a polyadenylyl moiety, or its modified variant, to a messenger RNA molecule. In eukaryotic organisms, most messenger RNA (mRNA) molecules are polyadenylated at the 3' end. The 3' poly(A) tail is a long sequence of adenine nucleotides (often several hundred) added to the pre-mRNA through the action of an enzyme, polyadenylate polymerase. In higher eukaryotes, the poly(A) tail is added onto transcripts that contain a specific sequence, the polyadenylation signal. The poly(A) tail and the protein bound to it aid in protecting mRNA from degradation by exonucleases. Polyadenylation is also important for transcription termination, export of the mRNA from the nucleus, and translation. Polyadenylation occurs in the nucleus immediately after transcription of DNA into RNA, but additionally can also occur later in the cytoplasm. After transcription has been terminated, the mRNA chain is cleaved through the action of an endonuclease complex associated with RNA polymerase. The cleavage site is usually characterized by the presence of the base sequence AAUAAA near the cleavage site. After the mRNA has been cleaved, adenosine residues are added to the free 3' end at the cleavage site.

As used herein, "transient" refers to expression of a non-integrated transgene for a period of hours, days or weeks, wherein the period of time of expression is less than the period of time for expression of the gene if integrated into the genome or contained within a stable plasmid replicon in the host cell.

As used herein, the terms "treat", "treatment" and "treating" refer to the reduction or amelioration of the progression, severity and/or duration of a proliferative disorder, or the amelioration of one or more symptoms (preferably, one or more discernible symptoms) of a proliferative disorder resulting from the administration of one or more therapies (e.g., one or more therapeutic agents such as a CAR of the invention). In specific embodiments, the terms "treat", "treatment" and "treating" refer to the amelioration of at least one measurable physical parameter of a proliferative disorder, such as growth of a tumor, not necessarily discernible by the patient. In other embodiments the terms "treat", "treatment" and "treating"-refer to the inhibition of the progression of a proliferative disorder, either physically by, e.g., stabilization of a discernible symptom, physiologically by, e.g., stabilization of a physical parameter, or both. In other embodiments the terms "treat", "treatment" and "treating" refer to the reduction or stabilization of tumor size or cancerous cell count.

The term "signal transduction pathway" refers to the biochemical relationship between a variety of signal transduction molecules that play a role in the transmission of a signal from one portion of a cell to another portion of a cell. The phrase "cell surface receptor" includes molecules and complexes of molecules capable of receiving a signal and transmitting signal across the membrane of a cell.

The term "subject" is intended to include living organisms in which an immune response can be elicited (e.g., mammals, human).

The term, a "substantially purified" cell refers to a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cell that have been separated from the cells with which they are naturally associated in their natural state. In some aspects, the cells are cultured in vitro. In other aspects, the cells are not cultured in vitro.

The term "therapeutic" as used herein means a treatment. A therapeutic effect is obtained by reduction, suppression, remission, or eradication of a disease state.

The term "prophylaxis" as used herein means the prevention of or protective treatment for a disease or disease state.

In the context of the present invention, "tumor antigen" or "hyperproliferative disorder antigen" or "antigen associated with a hyperproliferative disorder" refers to antigens that are common to specific hyperproliferative disorders. In certain aspects, the hyperproliferative disorder antigens of the present invention are derived from, cancers including but not limited to primary or metastatic melanoma, thymoma, lymphoma, sarcoma, lung cancer, liver cancer, non-Hodgkin lymphoma, Hodgkin lymphoma, leukemias, uterine cancer, cervical cancer, bladder cancer, kidney cancer and adenocarcinomas such as breast cancer, prostate cancer (e.g., castrate-resistant or therapy-resistant prostate cancer, or metastatic prostate cancer), ovarian cancer, pancreatic cancer, and the like, or a plasma cell proliferative disorder, e.g., asymptomatic myeloma (smoldering multiple myeloma or indolent myeloma), monoclonal gammapathy of undetermined significance (MGUS), Waldenstrom's macroglobulinemia, plasmacytomas (e.g., plasma cell dyscrasia, solitary myeloma, solitary plasmacytoma, extramedullary plasmacytoma, and multiple plasmacytoma), systemic amyloid light chain amyloidosis, and POEMS syndrome (also known as Crow-Fukase syndrome, Takatsuki disease, and PEP syndrome).

The term "transfected" or "transformed" or "transduced" refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

The term "specifically binds," refers to an antibody, or a ligand, which recognizes and binds with a cognate binding partner (e.g., a stimulatory and/or costimulatory molecule present on a T cell) protein present in a sample, but which antibody or ligand does not substantially recognize or bind other molecules in the sample.

"Regulatable chimeric antigen receptor (RCAR)," as used herein, refers to a set of polypeptides, typically two in the simplest embodiments, which when in an immune effector cell, provides the cell with specificity for a target cell, typically a cancer cell, and with intracellular signal generation. In some embodiments, an RCAR comprises at least an extracellular antigen binding domain, a transmembrane domain and a cytoplasmic signaling domain (also referred to herein as "an intracellular signaling domain") comprising a functional signaling domain derived from a stimulatory molecule and/or costimulatory molecule as defined herein in the context of a CAR molecule. In some embodiments, the set of polypeptides in the RCAR are not contiguous with each other, e.g., are in different polypeptide chains. In some embodiments, the RCAR includes a dimerization switch that, upon the presence of a dimerization molecule, can couple the polypeptides to one another, e.g., can couple an antigen binding domain to an intracellular signaling domain. In some embodiments, the RCAR is expressed in a cell (e.g., an immune effector cell) as described herein, e.g., an RCAR-expressing cell (also referred to herein as "RCARX cell"). In an embodiment the RCARX cell is a T cell, and is referred to as a RCART cell. In an embodiment the RCARX cell is an NK cell, and is referred to as a RCARN cell. The RCAR can provide the RCAR-expressing cell with specificity for a target cell, typically a cancer cell, and with regulatable intracellular signal generation or proliferation, which can optimize an immune effector property of the RCAR-expressing cell. In embodiments, an RCAR cell relies at least in part, on an antigen binding domain to provide specificity to a target cell that comprises the antigen bound by the antigen binding domain.

"Membrane anchor" or "membrane tethering domain", as that term is used herein, refers to a polypeptide or moiety, e.g., a myristoyl group, sufficient to anchor an extracellular or intracellular domain to the plasma membrane.

"Switch domain," as that term is used herein, e.g., when referring to an RCAR, refers to an entity, typically a polypeptide-based entity, that, in the presence of a dimerization molecule, associates with another switch domain. The association results in a functional coupling of a first entity linked to, e.g., fused to, a first switch domain, and a second entity linked to, e.g., fused to, a second switch domain. A first and second switch domain are collectively referred to as a dimerization switch. In embodiments, the first and second switch domains are the same as one another, e.g., they are polypeptides having the same primary amino acid sequence, and are referred to collectively as a homodimerization switch. In embodiments, the first and second switch domains are different from one another, e.g., they are polypeptides having different primary amino acid sequences, and are referred to collectively as a heterodimerization switch. In embodiments, the switch is intracellular. In embodiments, the switch is extracellular. In embodiments, the switch domain is a polypeptide-based entity, e.g., FKBP or FRB-based, and the dimerization molecule is small molecule, e.g., a rapalogue. In embodiments, the switch domain is a polypeptide-based entity, e.g., an scFv that binds a myc peptide, and the dimerization molecule is a polypeptide, a fragment thereof, or a multimer of a polypeptide, e.g., a myc ligand or multimers of a myc ligand that bind to one or more myc scFvs. In embodiments, the switch domain is a polypeptide-based entity, e.g., myc receptor, and the dimerization molecule is an antibody or fragments thereof, e.g., myc antibody.

"Dimerization molecule," as that term is used herein, e.g., when referring to an RCAR, refers to a molecule that promotes the association of a first switch domain with a second switch domain. In embodiments, the dimerization molecule does not naturally occur in the subject, or does not occur in concentrations that would result in significant dimerization. In embodiments, the dimerization molecule is a small molecule, e.g., rapamycin or a rapalogue, e.g, RAD001.

The term "bioequivalent" refers to an amount of an agent other than the reference compound (e.g., RAD001), required to produce an effect equivalent to the effect produced by the reference dose or reference amount of the reference compound (e.g., RAD001). In an embodiment the effect is the level of mTOR inhibition, e.g., as measured by P70 S6 kinase inhibition, e.g., as evaluated in an in vivo or in vitro assay, e.g., as measured by an assay described herein, e.g., the Boulay assay, or measurement of phosphorylated S6 levels by western blot. In an embodiment, the effect is alteration of the ratio of PD-1 positive/PD-1 negative T cells, as measured by cell sorting. In an embodiment a bioequivalent amount or dose of an mTOR inhibitor is the amount or dose that achieves the same level of P70 S6 kinase inhibition as does the reference dose or reference amount of a reference compound. In an embodiment, a bioequivalent amount or dose of an mTOR inhibitor is the amount or dose that achieves the same level of alteration in the ratio of PD-1 positive/PD-1 negative T cells as does the reference dose or reference amount of a reference compound.

The term "low, immune enhancing, dose" when used in conjunction with an mTOR inhibitor, e.g., an allosteric mTOR inhibitor, e.g., RAD001 or rapamycin, or a catalytic mTOR inhibitor, refers to a dose of mTOR inhibitor that partially, but not fully, inhibits mTOR activity, e.g., as measured by the inhibition of P70 S6 kinase activity. Methods for evaluating mTOR activity, e.g., by inhibition of P70 S6 kinase, are discussed herein. The dose is insufficient to result in complete immune suppression but is sufficient to enhance the immune response. In an embodiment, the low, immune enhancing, dose of mTOR inhibitor results in a decrease in the number of PD-1 positive T cells and/or an increase in the number of PD-1 negative T cells, or an increase in the ratio of PD-1 negative T cells/PD-1 positive T cells. In an embodiment, the low, immune enhancing, dose of mTOR inhibitor results in an increase in the number of naive T cells. In an embodiment, the low, immune enhancing, dose of mTOR inhibitor results in one or more of the following:

- an increase in the expression of one or more of the following markers: CD62L$^{high}$ CD127$^{high}$, CD27$^{+}$, and BCL2, e.g., on memory T cells, e.g., memory T cell precursors;
- a decrease in the expression of KLRG1, e.g., on memory T cells, e.g., memory T cell precursors; and
- an increase in the number of memory T cell precursors, e.g., cells with any one or combination of the following characteristics: increased CD62L$^{high}$, increased CD127$^{high}$, increased CD27$^{+}$, decreased KLRG1, and increased BCL2;
- wherein any of the changes described above occurs, e.g., at least transiently, e.g., as compared to a non-treated subject.

"Refractory" as used herein refers to a disease, e.g., cancer, that does not respond to a treatment.

In embodiments, a refractory cancer can be resistant to a treatment before or at the beginning of the treatment. In other embodiments, the refractory cancer can become resistant during a treatment. A refractory cancer is also called a resistant cancer.

"Relapsed" or "relapse" as used herein refers to the return or reappearance of a disease (e.g., cancer) or the signs and symptoms of a disease such as cancer after a period of improvement or responsiveness, e.g., after prior treatment of a therapy, e.g., cancer therapy. The initial period of responsiveness may involve the level of cancer cells falling below a certain threshold, e.g., below 20%, 1%, 10%, 5%, 4%, 3%, 2%, or 1%. The reappearance may involve the level of cancer cells rising above a certain threshold, e.g., above 20%, 1%, 10%, 5%, 4%, 3%, 2%, or 1%. For example, e.g., in the context of B-ALL, the reappearance may involve, e.g., a reappearance of blasts in the blood, bone marrow (>5%), or any extramedullary site, after a complete response. A complete response, in this context, may involve <5% BM blast. More generally, in an embodiment, a response (e.g., complete response or partial response) can involve the absence of detectable MRD (minimal residual disease). In an embodiment, the initial period of responsiveness lasts at least 1, 2, 3, 4, 5, or 6 days; at least 1, 2, 3, or 4 weeks; at least 1, 2, 3, 4, 6, 8, 10, or 12 months; or at least 1, 2, 3, 4, or 5 years.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. As another example, a range such as 95-99% identity, includes something with 95%, 96%, 97%, 98%, or 99% identity, and includes subranges such as 96-99%, 96-98%, 96-97%, 97-99%, 97-98%, and 98-99% identity. This applies regardless of the breadth of the range.

A "gene editing system" as the term is used herein, refers to a system, e.g., one or more molecules, that direct and effect an alteration, e.g., a deletion, of one or more nucleic acids at or near a site of genomic DNA targeted by said system. Gene editing systems are known in the art, and are described more fully below.

Various aspects of the compositions and methods herein are described in further detail below. Additional definitions are set out throughout the specification.

DETAILED DESCRIPTION

Provided herein are compositions and methods for treating a disease such as cancer, by administering a cell comprising a chimeric antigen receptor (CAR) molecule, e.g., that targets a tumor antigen, in combination with a virus comprising a nucleic acid molecule encoding a TNFα molecule, an IL-2 molecule, and/or an IL-7 molecule. Exemplary components to generate a CAR and a CAR-expressing cell are disclosure herein. Exemplary viruses comprising a nucleic acid molecule encoding a TNFα molecule, an IL-2 molecule, and/or an IL-7 molecule are also described herein.

In embodiments, the combination therapy of a CAR-expressing cell (e.g., a mesothelin CAR-expressing cell) described herein and a virus comprising a nucleic acid molecule encoding a TNFα molecule, an IL-2 molecule, and/or an IL-7 molecule described herein results in one or more of the following: improved or increased anti-tumor activity of the CAR-expressing cell (e.g., the mesothelin CAR-expressing cell); increased proliferation or persistence of the CAR-expressing cell (e.g., the mesothelin CAR-expressing cell); improved or increased infiltration of the CAR-expressing cell (e.g., the mesothelin CAR-expressing cell); improved inhibition of tumor progression or metastasis; delay of tumor progression; inhibition or reduction in cancer cell proliferation; and/or reduction in tumor burden, e.g., tumor volume, or size.

As demonstrated in the examples provided herein, in some embodiments, administration of the virus comprising a nucleic acid molecule encoding a TNFα molecule, an IL-2 molecule, and/or an IL-7 molecule prior to administration of the CAR-expressing cell (e.g., the mesothelin CAR-expressing cell) results in increased therapeutic efficacy, e.g., increased inhibition of tumor progression and/or tumor growth, in some cancers, e.g., as compared to administration of the virus or the CAR-expressing cell (e.g., the mesothelin CAR-expressing cell) alone.

Virus Comprising a Nucleic Acid Molecule Encoding One or More Cytokine Molecules In one aspect, disclosed herein are methods using a virus comprising a nucleic acid molecule encoding one or more cytokine molecules.

In one embodiment, the one or more cytokine molecules are chosen from IFNα, IFNβ, IFNγ, complement C5a, IL-2, IL-7, TNFα, CD40L, IL12, IL-23, IL15, IL17, CCL1, CCL11, CCL12, CCL13, CCL14-1, CCL14-2, CCL14-3, CCL15-1, CCL15-2, CCL16, CCL17, CCL18, CCL19, CCL19, CCL2, CCL20, CCL21, CCL22, CCL23-1, CCL23-2, CCL24, CCL25-1, CCL25-2, CCL26, CCL27, CCL28, CCL3, CCL3L1, CCL4, CCL4L1, CCL5, CCL6, CCL7, CCL8, CCL9, CCR10, CCR2, CCR5, CCR6, CCR7, CCR8, CCRL1, CCRL2, CX3CL1, CX3CR, CXCL1, CXCL10, CXCL11, CXCL12, CXCL13, CXCL14, CXCL15, CXCL16, CXCL2, CXCL3, CXCL4, CXCL5, CXCL6, CXCL7, CXCL8, CXCL9, CXCL9, CXCR1, CXCR2, CXCR4, CXCR5, CXCR6, CXCR7, XCL2, or any combination thereof.

In one embodiment, the virus can be any virus suitable for treating a subject, e.g., a human.

In one embodiment, the virus is a virus, e.g., an oncolytic adenovirus, disclosed in US20150232880, herein incorporated by reference in its entirety. In one embodiment, the virus comprises a viral vector chosen from Ad5, Ad3 or Ad5/3 vector. In one embodiment, the vector is Ad5 vector. In one embodiment, the vector is Ad3 vector. In one embodiment, the vector is Ad5/3 vector. As used herein, the term "adenovirus serotype 5 (Ad5) nucleic acid backbone" refers to the genome of Ad5. "Ad3 nucleic acid backbone" refers to the genome of Ad3. "Ad5/3 vector" refers to a chimeric vector having parts of both Ad5 and Ad3 vectors. "Ad5/3 chimeric fiber knob" refers to a chimerism, wherein the knob part of the fiber is from Ad serotype 3, and the rest of the fiber is from Ad serotype 5. In one embodiment, the construct has the fiber knob from Ad3 while the remainder of the genome is from Ad5 (see FIGS. 17, 33 and 34 of US20150232880). The vectors may be modified in any way known in the art, e.g. by deleting, inserting, mutating or modifying any viral areas. The vectors are made tumor specific with regard to replication. In one embodiment, the adenoviral vector comprises modifications in E1, E3 and/or E4 such as insertion of tumor specific promoters (e.g., to drive E1), deletions of areas (e.g., the constant region 2 of E1 as used in "D24", E3/gp19k, E3/6.7k) and insertion of transgenes. In one embodiment, a tumor specific oncolytic adenovirus is generated by engineering a 24 base pair deletion (D24) affecting the constant region 2 (CR2) of E1. In one embodiment, an oncolytic adenovirus is generated by engineering a gp19k/6.7K deletion in E3 (a deletion of 965 base pairs from the adenoviral E3A region). In a resulting adenoviral construct, both gp19k and 6.7K genes are deleted (Kanerva A et al. 2005, Gene Therapy 12, 87-94). Furthermore, fiber knob areas of the vector can be modified. In one embodiment of the invention, the adenoviral vector is Ad5/3 comprising an Ad5 nucleic acid backbone and Ad3 fiber knob or Ad5/3 chimeric fiber knob.

In one embodiment, the virus is an oncolytic virus. Suitable oncolytic viruses are known in the art, e.g., those described in Kaufman, Nat Rev Drug Discov. 2015; 14(9): 642-662, which is incorporated by reference herein in its entirety. In some embodiments, the oncolytic virus specifically targets cancer cells, e.g., the oncolytic virus has no effect or a minimal effect on non-cancer cells. In some embodiments, the oncolytic virus selectively replicates in cancer cells. In embodiments, the oncolytic virus is capable of selectively replicating in and triggering the death of or slowing the growth of a cancer cell. An oncolytic virus includes but is not limited to an oncolytic adenovirus, oncolytic adeno-associated virus, oncolytic Herpes Simplex Virus (HSV), oncolytic parvovirus, oncolytic retrovirus, oncolytic lentivirus, oncolytic vaccinia virus, oncolytic Sinbis virus, oncolytic influenza virus, oncolytic reovirus, oncolytic Newcastle disease virus (NDV), oncolytic measles virus, oncolytic vesicular stomatitis virus (VSV), oncolytic poliovirus, oncolytic poxvirus, oncolytic Seneca Valley virus, oncolytic coxsackievirus, oncolytic enterovirus, oncolytic myxoma virus, or oncolytic maraba virus.

In some embodiments, the oncolytic virus is a recombinant oncolytic virus, such as those described in US2010/0178684, which is incorporated herein by reference in its entirety. In some embodiments, a recombinant oncolytic virus comprises a nucleic acid sequence (e.g., heterologous nucleic acid sequence) encoding an inhibitor of an immune or inflammatory response, e.g., as described in US2010/0178684, which is incorporated herein by reference in its entirety. In embodiments, the recombinant oncolytic virus, e.g., oncolytic NDV, comprises a pro-apoptotic protein (e.g., apoptin), a cytokine (e.g., GM-CSF, CSF, interferon-gamma, interleukin-2 (IL-2), tumor necrosis factor-alpha), an immunoglobulin (e.g., an antibody against ED-B firbonectin), tumor associated antigen, a bispecific adapter protein (e.g., bispecific antibody or antibody fragment directed against NDV HN protein and a T cell co-stimulatory receptor, such as CD3 or CD28; or fusion protein between human IL-2 and single chain antibody directed against NDV HN protein). See, e.g., Zamarin et al. Future Microbiol. 7.3(2012):347-67, incorporated herein by reference in its entirety. In some embodiments, the oncolytic virus is a chimeric oncolytic NDV described in U.S. Pat. No. 8,591,881 B2, US 2012/0122185 A1, or US 2014/0271677 A1, each of which is incorporated herein by reference in their entireties.

In some embodiments, the oncolytic virus comprises a conditionally replicative adenovirus (CRAd), which is designed to replicate exclusively in cancer cells. See, e.g., Alemany et al. Nature Biotechnol. 18(2000):723-27. In some embodiments, an oncolytic adenovirus comprises one described in Table 1 on page 725 of Alemany et al., incorporated herein by reference in its entirety.

Exemplary oncolytic viruses include but are not limited to the following:

Group B Oncolytic Adenovirus (ColoAd1) (PsiOxus Therapeutics Ltd.) (see, e.g., Clinical Trial Identifier: NCT02053220);

ONCOS-102 (previously called CGTG-102), which is an adenovirus comprising granulocyte-macrophage colony stimulating factor (GM-CSF) (Oncos Therapeutics) (see, e.g., Clinical Trial Identifier: NCT01598129);

VCN-01, which is a genetically modified oncolytic human adenovirus encoding human PH20 hyaluronidase (VCN Biosciences, S.L.) (see, e.g., Clinical Trial Identifiers: NCT02045602 and NCT02045589);

Conditionally Replicative Adenovirus ICOVIR-5, which is a virus derived from wild-type human adenovirus serotype 5 (Had5) that has been modified to selectively replicate in cancer cells with a deregulated retinoblastoma/E2F pathway (Institut Català d'Oncologia) (see, e.g., Clinical Trial Identifier: NCT01864759);

Celyvir, which comprises bone marrow-derived autologous mesenchymal stem cells (MSCs) infected with ICOVIRS, an oncolytic adenovirus (Hospital Infantil Universitario Nino Jesds, Madrid, Spain/Ramon Alemany) (see, e.g., Clinical Trial Identifier: NCT01844661);

CG0070, which is a conditionally replicating oncolytic serotype 5 adenovirus (Ad5) in which human E2F-1 promoter drives expression of the essential E1a viral genes, thereby restricting viral replication and cytotoxicity to Rb pathway-defective tumor cells (Cold Genesys, Inc.) (see, e.g., Clinical Trial Identifier: NCT02143804); or DNX-2401 (formerly named Delta-24-RGD), which is an adenovirus that has been engineered to replicate selectively in retinoblastoma (Rb)-pathway deficient cells and to infect cells that express certain RGD-binding integrins more efficiently (Clinica Universidad de Navarra, Universidad de Navarra/DNAtrix, Inc.) (see, e.g., Clinical Trial Identifier: NCT01956734).

In some embodiments, the oncolytic virus can express a detectable marker, e.g., a fluorescent molecule (e.g., fluorescein, Texas red, rhodamine, green fluorescent protein, and the like), an enzyme (e.g., horse radish peroxidase, alkaline phosphatase), a luminescent molecule (e.g., luciferase), a radioactive molecule (e.g., 3H, 125I, 35S, 14C, or 32P), or calorimetric labels such as colloidal gold or colored beads.

In some embodiments, a virus, e.g., an oncolytic virus, described herein is administering by injection, e.g., subcutaneous, intra-arterial, intravenous, intramuscular, intrathecal, or intraperitoneal injection. In some embodiments, an oncolytic virus described herein is administered intratumorally, transdermally, transmucosally, orally, intranasally, subcutaneously, intra-arterially, intravenously, intramuscularly, intrathecally, or intraperitoneally, or via pulmonary administration.

Additional viruses that are useful in this invention include, but are not limited to retroviruses, adenoviruses, adeno-associated viruses, herpes viruses, or lentiviruses.

Chimeric Antigen Receptor (CAR)

In one aspect, disclosed herein are methods using a cell (e.g., a population of cells) that expresses a CAR molecule. In one aspect, an exemplary CAR construct comprises an optional leader sequence (e.g., a leader sequence described herein), an antigen binding domain (e.g., an antigen binding domain described herein), a hinge (e.g., a hinge region described herein), a transmembrane domain (e.g., a transmembrane domain described herein), and an intracellular stimulatory domain (e.g., an intracellular stimulatory domain described herein). In one aspect, an exemplary CAR construct comprises an optional leader sequence (e.g., a leader sequence described herein), an extracellular antigen binding domain (e.g., an antigen binding domain described herein), a hinge (e.g., a hinge region described herein), a transmembrane domain (e.g., a transmembrane domain described herein), an intracellular costimulatory signaling domain (e.g., a costimulatory signaling domain described herein) and/or an intracellular primary signaling domain (e.g., a primary signaling domain described herein).

Sequences of non-limiting examples of various components that can be part of a CAR molecule described herein, are listed in Table 1, where "aa" stands for amino acids, and "na" stands for nucleic acids that encode the corresponding peptide.

TABLE 1

Sequences of various components of CAR (aa—amino acid sequence, na—nucleic acid sequence).

| SEQ ID NO | Description | Sequence |
|---|---|---|
| 11 | EF-1 promoter (na) | CGTGAGGCTCCGGTGCCCGTCAGTGGGCAGAGCGCACATCGCCCACAGTCC<br>CCGAGAAGTTGGGGGGAGGGGTCGGCAATTGAACCGGTGCCTAGAGAAGG<br>TGGCGCGGGGTAAACTGGGAAAGTGATGTCGTGTACTGGCTCCGCCTTTTTC<br>CCGAGGGTGGGGGAGAACCGTATATAAGTGCAGTAGTCGCCGTGAACGTTC<br>TTTTTCGCAACGGGTTTGCCGCCAGAACACAGGTAAGTGCCGTGTGTGGTTC<br>CCGCGGGCCTGGCCTCTTTACGGGTTATGGCCCTTGCGTGCCTTGAATTACT<br>TCCACCTGGCTGCAGTACGTGATTCTTGATCCCGAGCTTCGGGTTGGAAGTG<br>GGTGGGAGAGTTCGAGGCCTTGCGCTTAAGGAGCCCCTTCGCCTCGTGCTTG<br>AGTTGAGGCCTGGCCTGGGCGCTGGGGCCGCCGCGTGCGAATCTGGTGGCA<br>CCTTCGCGCCTGTCTCGCTGCTTTCGATAAGTCTCTAGCCATTTAAAATTTTT<br>GATGACCTGCTGCGACGCTTTTTTTCTGGCAAGATAGTCTTGTAAATGCGGG<br>CCAAGATCTGCACACTGGTATTTCGGTTTTTGGGGCCGCGGGCGGCGACGG<br>GGCCCGTGCGTCCCAGCGCACATGTTCGGCGAGGCGGGGCCTGCGAGCGCG<br>GCCACCGAGAATCGGACGGGGGTAGTCTCAAGCTGGCCGGCCTGCTCTGGT<br>GCCTGGCCTCGCGCCGCCGTGTATCGCCCCGCCCTGGGCGGCAAGGCTGGC<br>CCGGTCGGCACCAGTTGCGTGAGCGGAAAGATGGCCGCTTCCCGGCCCTGC<br>TGCAGGGAGCTCAAAATGGAGGACGCGGCGCTCGGGAGAGCGGGCGGGTG<br>AGTCACCCACACAAAGGAAAAGGGCCTTTCCGTCCTCAGCCGTCGCTTCATG<br>TGACTCCACGGAGTACCGGGCGCCGTCCAGGCACCTCGATTAGTTCTCGAGC<br>TTTTGGAGTACGTCGTCTTTAGGTTGGGGGGAGGGGTTTTATGCGATGGAGT<br>TTCCCCACACTGAGTGGGTGGAGACTGAAGTTAGGCCAGCTTGGCACTTGAT<br>GTAATTCTCCTTGGAATTTGCCCTTTTTGAGTTTGGATCTTGGTTCATTCTCA<br>AGCCTCAGACAGTGGTTCAAAGTTTTTTTCTTCCATTTCAGGTGTCGTGA |
| 1 | Leader (aa) | MALPVTALLLPLALLLHAARP |
| 12 | Leader (na) | ATGGCCCTGCCTGTGACAGCCCTGCTGCTGCCTCTGGCTCTGCTGCTGCATG<br>CCGCTAGACCC |
| 2 | CD8 hinge (aa) | TTTPAPRPPTPAPTIASQPLSLRPEACRPAAGGAVHTRGLDFACD |
| 13 | CD8 hinge (na) | ACCACGACGCCAGCGCCGCGACCACCAACACCGGCGCCCACCATCGCGTCG<br>CAGCCCCTGTCCCTGCGCCCAGAGGCGTGCCGGCCAGCGGCGGGGGGCGCA<br>GTGCACACGAGGGGGCTGGACTTCGCCTGTGAT |
| 3 | Ig4 hinge (aa) | ESKYGPPCPPCPAPEFLGGPSVFLFPPKPKDTLMISRTPEVTCVVVDVSQEDPEV<br>QFNWYVDGVEVHNAKTKPREEQFNSTYRVVSVLTVLHQDWLNGKEYKCKVS<br>NKGLPSSIEKTISKAKGQPREPQVYTLPPSQEEMTKNQVSLTCLVKGFYPSDIAV<br>EWESNGQPENNYKTTPPVLDSDGSFFLYSRLTVDKSRWQEGNVFSCSVMHEAL<br>HNHYTQKSLSLSLGKM |
| 14 | Ig4 hinge (na) | GAGAGCAAGTACGGCCCTCCCTGCCCCCCTTGCCCTGCCCCCGAGTTCCTGG<br>GCGGACCCAGCGTGTTCCTGTTCCCCCCCAAGCCCAAGGACACCCTGATGAT<br>CAGCCGGACCCCCGAGGTGACCTGTGTGGTGGTGGACGTGTCCCAGGAGGA<br>CCCCGAGGTCCAGTTCAACTGGTACGTGGACGGCGTGGAGGTGCACAACGC<br>CAAGACCAAGCCCCGGGAGGAGCAGTTCAATAGCACCTACCGGGTGGTGTC<br>CGTGCTGACCGTGCTGCACCAGGACTGGCTGAACGGCAAGGAATACAAGTG<br>TAAGGTGTCCAACAAGGGCCTGCCCAGCAGCATCGAGAAAACCATCAGCAA<br>GGCCAAGGGCCAGCCTCGGGAGCCCCAGGTGTACACCCTGCCCCCTAGCCA<br>AGAGGAGATGACCAAGAACCAGGTGTCCCTGACCTGCCTGGTGAAGGGCTT<br>CTACCCCAGCGACATCGCCGTGGAGTGGGAGAGCAACGGCCAGCCCGAGAA<br>CAACTACAAGACCACCCCCCCTGTGCTGGACAGCGACGGCAGCTTCTTCCTG<br>TACAGCCGGCTGACCGTGGACAAGAGCCGGTGGCAGGAGGGCAACGTCTTT<br>AGCTGCTCCGTGATGCACGAGGCCCTGCACAACCACTACACCCAGAAGAGC<br>CTGAGCCTGTCCCTGGGCAAGATG |
| 4 | IgD hinge (aa) | RWPESPKAQASSVPTAQPQAEGSLAKATTAPATTRNTGRGGEEKKKEKEKEEQ<br>EERETKTPECPSHTQPLGVYLLTPAVQDLWLRDKATFTCFVVGSDLKDAHLTW<br>EVAGKVPTGGVEEGLLERHSNGSQSQHSRLTLPRSLWNAGTSVTCTLNHPSLPP<br>QRLMALREPAAQAPVKLSLNLLASSDPPEAASWLLCEVSGFSPPNILLMWLEDQ<br>REVNTSGFAPARPPPQPGSTTFWAWSVLRVPAPPSPQPATYTCVVSHEDSRTLL<br>NASRSLEVSYVTDH |
| 15 | IgD hinge (na) | AGGTGGCCCGAAAGTCCCAAGGCCCAGGCATCTAGTGTTCCTACTGCACAG<br>CCCCAGGCAGAAGGCAGCCTAGCCAAAGCTACTACTGCACCTGCCACTACG<br>CGCAATACTGGCCGTGGCGGGGAGGAGAAGAAAAAGGAGAAAGAGAAAGA |

TABLE 1-continued

Sequences of various components of CAR (aa—amino acid sequence, na—nucleic acid sequence).

| SEQ ID NO | Description | Sequence |
|---|---|---|
| | | AGAACAGGAAGAGAGGGAGACCAAGACCCCTGAATGTCCATCCCATACCCA<br>GCCGCTGGGCGTCTATCTCTTGACTCCCGCAGTACAGGACTTGTGGCTTAGA<br>GATAAGGCCACCTTTACATGTTTCGTCGTGGGCTCTGACCTGAAGGATGCCC<br>ATTTGACTTGGGAGGTTGCCGGAAAGGTACCCACAGGGGGGGTTGAGGAAG<br>GGTTGCTGGAGCGCCATTCCAATGGCTCTCAGAGCCAGCACTCAAGACTCA<br>CCCTTCCGAGATCCCTGTGGAACGCCGGGACCTCTGTCACATGTACTCTAAA<br>TCATCCTAGCCTGCCCCCACAGCGTCTGATGGCCCTTAGAGAGCCAGCCGCC<br>CAGGCACCAGTTAAGCTTAGCCTGAATCTGCTCGCCAGTAGTGATCCCCCAG<br>AGGCCGCCAGCTGGCTCTTATGCGAAGTGTCCGGCTTTAGCCCGCCCAACAT<br>CTTGCTCATGTGGCTGGAGGACCAGCGAGAAGTGAACACCAGCGGCTTCGC<br>TCCAGCCCGGCCCCCACCCCAGCCGGGTTCTACCACATTCTGGGCCTGGAGT<br>GTCTTAAGGGTCCCAGCACCACCTAGCCCCCAGCCAGCCACATACACCTGTG<br>TTGTGTCCCATGAAGATAGCAGGACCCTGCTAAATGCTTCTAGGAGTCTGGA<br>GGTTTCCTACGTGACTGACCATT |
| 6 | CD8 Transmembrane (aa) | IYIWAPLAGTCGVLLLSLVITLYC |
| 17 | CD8 Transmembrane (na) | ATCTACATCTGGGCGCCCTTGGCCGGGACTTGTGGGGTCCTTCTCCTGTCAC<br>TGGTTATCACCCTTTACTGC |
| 7 | 4-1BB intracellular domain (aa) | KRGRKKLLYIFKQPFMRPVQTTQEEDGCSCRFPEEEEGGCEL |
| 18 | 4-1BB intracellular domain (na) | AAACGGGGCAGAAAGAAACTCCTGTATATATTCAAACAACCATTTATGAGA<br>CCAGTACAAACTACTCAAGAGGAAGATGGCTGTAGCTGCCGATTTCCAGAA<br>GAAGAAGAAGGAGGATGTGAACTG |
| 8 | CD27 (aa) | QRRKYRSNKGESPVEPAEPCRYSCPREEEGSTIPIQEDYRKPEPACSP |
| 19 | CD27 (na) | AGGAGTAAGAGGAGCAGGCTCCTGCACAGTGACTACATGAACATGACTCCC<br>CGCCGCCCCGGGCCCACCCGCAAGCATTACCAGCCCTATGCCCCACCACGC<br>GACTTCGCAGCCTATCGCTCC |
| 9 | CD3-zeta (aa) (Q/K mutant) | RVKFSRSADAPAYKQGQNQLYNELNLGRREEYDVLDKRRGRDPEMGGKPRRK<br>NPQEGLYNELQKDKMAEAYSEIGMKGERRRGKGHDGLYQGLSTATKDTYDAL<br>HMQALPPR |
| 20 | CD3-zeta (na) (Q/K mutant) | AGAGTGAAGTTCAGCAGGAGCGCAGACGCCCCCGCGTACAAGCAGGGCCA<br>GAACCAGCTCTATAACGAGCTCAATCTAGGACGAAGAGAGGAGTACGATGT<br>TTTGGACAAGAGACGTGGCCGGGACCCTGAGATGGGGGGAAAGCCGAGAA<br>GGAAGAACCCTCAGGAAGGCCTGTACAATGAACTGCAGAAAGATAAGATG<br>GCGGAGGCCTACAGTGAGATTGGGATGAAAGGCGAGCGCCGGAGGGGCAA<br>GGGGCACGATGGCCTTTACCAGGGTCTCAGTACAGCCACCAAGGACACCTA<br>CGACGCCCTTCACATGCAGGCCCTGCCCCCTCGC |
| 10 | CD3-zeta (aa) (NCBI Reference Sequence NM_000734.3) | RVKFSRSADAPAYQQGQNQLYNELNLGRREEYDVLDKRRGRDPEMGGKPRRK<br>NPQEGLYNELQKDKMAEAYSEIGMKGERRRGKGHDGLYQGLSTATKDTYDAL<br>HMQALPPR |
| 21 | CD3-zeta (na) (NCBI Reference Sequence NM_000734.3) | AGAGTGAAGTTCAGCAGGAGCGCAGACGCCCCCGCGTACCAGCAGGGCCA<br>GAACCAGCTCTATAACGAGCTCAATCTAGGACGAAGAGAGGAGTACGATGT<br>TTTGGACAAGAGACGTGGCCGGGACCCTGAGATGGGGGGAAAGCCGAGAA<br>GGAAGAACCCTCAGGAAGGCCTGTACAATGAACTGCAGAAAGATAAGATG<br>GCGGAGGCCTACAGTGAGATTGGGATGAAAGGCGAGCGCCGGAGGGGCAA<br>GGGGCACGATGGCCTTTACCAGGGTCTCAGTACAGCCACCAAGGACACCTA<br>CGACGCCCTTCACATGCAGGCCCTGCCCCCTCGC |
| 36 | CD28 Intracellular domain (amino acid sequence) | RSKRSRLLHSDYMNMTPRRPGPTRKHYQPYAPPRDFAAYRS |
| 37 | CD28 Intracellular domain (nucleotide sequence) | AGGAGTAAGAGGAGCAGGCTCCTGCACAGTGACTACATGAACATGACTCCC<br>CGCCGCCCCGGGCCCACCCGCAAGCATTACCAGCCCTATGCCCCACCACGC<br>GACTTCGCAGCCTATCGCTCC |

TABLE 1-continued

Sequences of various components of CAR (aa—amino acid sequence, na—nucleic acid sequence).

| SEQ ID NO | Description | Sequence |
|---|---|---|
| 38 | ICOS Intracellular domain (amino acid sequence) | T K K K Y S S S V H D P N G E Y M F M R A V N T A K K S R L T D V T L |
| 607 | ICOS Intracellular domain (nucleotide sequence) | ACAAAAAAGAAGTATTCATCCAGTGTGCACGACCCTAACGGTGAATACATG<br>TTCATGAGAGCAGTGAACACAGCCAAAAAATCCAGACTCACAGATGTGACC<br>CTA |
| 5 | GS hinge/ (linker aa) | GGGGSGGGGS |
| 16 | GS hinge/ linker (na) | GGTGGCGGAGGTTCTGGAGGTGGAGGTTCC |
| 608 | GS hinge/ linker (na) | GGTGGCGGAGGTTCTGGAGGTGGGGGTTCC |
| 25 | linker | GGGGS |
| 26 | linker | (Gly-Gly-Gly-Gly-Ser)n, where n = 1-6, e.g., GGGGSGGGGS GGGGSGGGGS<br>GGGGSGGGGS |
| 27 | linker | (Gly4 Ser)4 |
| 28 | linker | (Gly4 Ser)3 |
| 29 | linker | (Gly3Ser) |
| 609 | linker | (Gly-Gly-Gly-Ser)n where n is a positive integer equal to or greater than 1 |
| 606 | linker | (Gly-Gly-Gly-Ser)n, where n = 1-10, e.g., GGGSGGGSGG GSGGGSGGGS<br>GGGSGGGSGG GSGGGSGGGS |
| 610 | linker | GSTSGSGKPGSGEGSTKG |
| 30 | polyA | $(A)_{5000}$<br>This sequence may encompass 50-5000 adenines. |
| 31 | polyT | $(T)_{100}$ |
| 32 | polyT | $(T)_{5000}$<br>This sequence may encompass 50-5000 thymines. |
| 33 | polyA | $(A)_{5000}$<br>This sequence may encompass 100-5000 adenines. |
| 34 | polyA | $(A)_{400}$<br>This sequence may encompass 100-400 adenines. |
| 35 | polyA | $(A)_{2000}$<br>This sequence may encompass 50-2000 adenines. |
| 22 | PD1 CAR (aa) | pgwfldspdrpwnpptfspallvvtegdnatftcsfsntsesfylnwyrmspsnqtdklaafpedrsqpgqdcrfrvtqlp<br>ngrdfhmsvvrarrndsgtylcgaislapkaqikeslraelryterraevptahpspsprpagqfqtlvtttpaprpptpaptia<br>sqplslrpeacrpaaggavhtrgldfacdiyiwaplagtcgvlllslvitlyckrgrkkllyifkqpfmrpvqttqeedgcscrf<br>peeeeggcelrvkfsrsadapaykqgqnqlynelnlgrreeydvldkrrgrdpemggkprrknpqeglynelqkdkma<br>eayseigmkgerrrgkghdglyqglstatkdtydalhmqalppr |
| 23 | PD-1 CAR (na) (PD1 ECD underlined) | atggccctccctgtcactgccctgcttctccccctcgcactcctgctccacgccgctagaccacccggatggtttctggactctc<br>cggatcgcccgtggaatcccccaaccttctcaccggcactcttggttgtgactgagggcgataatgcgaccttcacgtgctcgt<br>tctccaacacctccgaatcattcgtgctgaactggtaccgcatgagcccgtcaaaccagaccgacaagctcgccgcgtttcg<br>gaagatcggtcgcaaccgggacaggattgtcggttccgcgtgactcaactgccgaatggcagagacttccacatgagcgtgg<br>tccgcgctaggcgaaacgactccgggacctacctgtgcggagccatctcgctggcgcctaaggcccaaatcaaagagagct<br>tgagggccgaactgagagtgaccgagcgcagagctgaggtgccaactgcacatccatccccatcgcctcggcctgcgggg<br>cagtttcagaccctggtcacgaccactccggcgccgcgcccaccgactccggccccaactatcgcgagccagcccctgtcg<br>ctgaggccggaagcatgccgccctgccgccggaggtgctgtgcatacccggggattggacttcgcatgcgacatctacattt<br>gggctcctctcgccggaacttgtggcgtgctccttctgtccctggtcatcaccctgtactgcaagcggggtcggaaaaagcttct<br>gtacattttcaagcagcccttcatgaggcccgtgcaaaccacccaggaggaggacggttgctcctgccggttccccgaagag<br>gaagaaggaggttgcgagctgcgcgtgaagttctcccggagcgccgacgcccccgcctataagcagggccagaaccagct |

TABLE 1-continued

Sequences of various components of CAR (aa—amino acid sequence, na—nucleic acid sequence).

| SEQ ID NO | Description | Sequence |
|---|---|---|
| | | gtacaacgaactgaacctgggacggcgggaagagtacgatgtgctggacaagcggcgcggccgggaccccgaaatggg cgggaagcctagaagaaagaaccctcaggaaggcctgtataacgagctgcagaaggacaagatggccgaggcctactccg aaattgggatgaagggagagcggcggaggggaaaggggcacgacggcctgtaccaaggactgtccaccgccaccaagg acacatacgatgccctgcacatgcaggcccttccccctcgc |
| 24 | PD-1 CAR (aa) with signal (PD1 ECD underlined) | Malpvtalllplalllhaarppgwfldspdrpwnpptfspallvvtegdnatftcsfsntsesfylnwyrmspsnqtdklaaf pedrsqpgqdcrfrvtqlpngrdfhmsvvrarrndsgtylcgaislapkaqikesllraelrvterraevptahpspsprpagq fqtlvtttpaprpptpaptiasqplslrpeacrpaaggavhtrgldfacdiyiwaplagtcgvlllslvitlyckrgrkkllyif kqpfmrpvqttqeedgcscrfpeeeeggcelrvkfsrsadapaykqgqnqlynelnlgrreeydvldkrrgrdpemggkprr knpqeglynelqkdkmaeayseigmkgerrrgkghdglyqglstatkdtydalhmqalppr |

CAR Antigen Binding Domain

In one aspect, the portion of the CAR comprising the antigen binding domain comprises an antigen binding domain that targets a tumor antigen, e.g., a tumor antigen described herein. In some embodiments, the antigen binding domain binds to: CD19; CD123; CD22; CD30; CD171; CS-1; C-type lectin-like molecule-1, CD33; epidermal growth factor receptor variant III (EGFRvIII); ganglioside G2 (GD2); ganglioside GD3; TNF receptor family member; B-cell maturation antigen (BCMA); Tn antigen ((Tn Ag) or (GaNAcα-Ser/Thr)); prostate-specific membrane antigen (PSMA); Receptor tyrosine kinase-like orphan receptor 1 (ROR1); Fms-Like Tyrosine Kinase 3 (FLT3); Tumor-associated glycoprotein 72 (TAG72); CD38; CD44v6; Carcinoembryonic antigen (CEA); Epithelial cell adhesion molecule (EPCAM); B7H3 (CD276); KIT (CD117); Interleukin-13 receptor subunit alpha-2; Mesothelin; Interleukin 11 receptor alpha (IL-11Ra); prostate stem cell antigen (PSCA); Protease Serine 21; vascular endothelial growth factor receptor 2 (VEGFR2); Lewis(Y) antigen; CD24; Platelet-derived growth factor receptor beta (PDGFR-beta); Stage-specific embryonic antigen-4 (SSEA-4); CD20; Folate receptor alpha; Receptor tyrosine-protein kinase ERBB2 (Her2/neu); Mucin 1, cell surface associated (MUC1); epidermal growth factor receptor (EGFR); neural cell adhesion molecule (NCAM); Prostase; prostatic acid phosphatase (PAP); elongation factor 2 mutated (ELF2M); Ephrin B2; fibroblast activation protein alpha (FAP); insulin-like growth factor 1 receptor (IGF-I receptor), carbonic anhydrase IX (CAIX); Proteasome (Prosome, Macropain) Subunit, Beta Type, 9 (LMP2); glycoprotein 100 (gp100); oncogene fusion protein consisting of breakpoint cluster region (BCR) and Abelson murine leukemia viral oncogene homolog 1 (Abl) (bcr-abl); tyrosinase; ephrin type-A receptor 2 (EphA2); Fucosyl GM1; sialyl Lewis adhesion molecule (sLe); ganglioside GM3; transglutaminase 5 (TGS5); high molecular weight-melanoma-associated antigen (HMWMAA); o-acetyl-GD2 ganglioside (OAcGD2); Folate receptor beta; tumor endothelial marker 1 (TEM1/CD248); tumor endothelial marker 7-related (TEM7R); claudin 6 (CLDN6); thyroid stimulating hormone receptor (TSHR); G protein-coupled receptor class C group 5, member D (GPRC5D); chromosome X open reading frame 61 (CXORF61); CD97; CD179a; anaplastic lymphoma kinase (ALK); Polysialic acid; placenta-specific 1 (PLAC1); hexasaccharide portion of globoH glycoceramide (GloboH); mammary gland differentiation antigen (NY-BR-1); uroplakin 2 (UPK2); Hepatitis A virus cellular receptor 1 (HAVCR1); adrenoceptor beta 3 (ADRB3); pannexin 3 (PANX3); G protein-coupled receptor 20 (GPR20); lymphocyte antigen 6 complex, locus K 9 (LY6K); Olfactory receptor 51E2 (OR51E2); TCR Gamma Alternate Reading Frame Protein (TARP); Wilms tumor protein (WTi); Cancer/testis antigen 1 (NY-ESO-1); Cancer/testis antigen 2 (LAGE-1a); Melanoma-associated antigen 1 (MAGE-A1); ETS translocation-variant gene 6, located on chromosome 12p (ETV6-AML); sperm protein 17 (SPA17); X Antigen Family, Member 1A (XAGE1); angiopoietin-binding cell surface receptor 2 (Tie 2); melanoma cancer testis antigen-1 (MAD-CT-1); melanoma cancer testis antigen-2 (MAD-CT-2); Fos-related antigen 1; tumor protein p53 (p53); p53 mutant; prostein; surviving; telomerase; prostate carcinoma tumor antigen-1, melanoma antigen recognized by T cells 1; Rat sarcoma (Ras) mutant; human Telomerase reverse transcriptase (hTERT); sarcoma translocation breakpoints; melanoma inhibitor of apoptosis (ML-IAP); ERG (transmembrane protease, serine 2 (TMPRSS2) ETS fusion gene); N-Acetyl glucosaminyl-transferase V (NA17); paired box protein Pax-3 (PAX3); Androgen receptor; Cyclin B1; v-myc avian myelocytomatosis viral oncogene neuroblastoma derived homolog (MYCN); Ras Homolog Family Member C (RhoC); Tyrosinase-related protein 2 (TRP-2); Cytochrome P450 1B1 (CYP1B1); CCCTC-Binding Factor (Zinc Finger Protein)-Like, Squamous Cell Carcinoma Antigen Recognized By T Cells 3 (SART3); Paired box protein Pax-5 (PAX5); proacrosin binding protein sp32 (OY-TES1); lymphocyte-specific protein tyrosine kinase (LCK); A kinase anchor protein 4 (AKAP-4); synovial sarcoma, X breakpoint 2 (SSX2); Receptor for Advanced Glycation Endproducts (RAGE-1); renal ubiquitous 1 (RU1); renal ubiquitous 2 (RU2); legumain; human papilloma virus E6 (HPV E6); human papilloma virus E7 (HPV E7); intestinal carboxyl esterase; heat shock protein 70-2 mutated (mut hsp70-2); CD79a; CD79b; CD72; Leukocyte-associated immunoglobulin-like receptor 1 (LAIR1); Fc fragment of IgA receptor (FCAR or CD89); Leukocyte immunoglobulin-like receptor subfamily A member 2 (LILRA2); CD300 molecule-like family member f (CD300LF); C-type lectin domain family 12 member A (CLECi2A); bone marrow stromal cell antigen 2 (BST2); EGF-like module-containing mucin-like hormone receptor-like 2 (EMR2); lymphocyte antigen 75 (LY75); Glypican-3 (GPC3); Fc receptor-like 5 (FCRL5); or immunoglobulin lambda-like polypeptide 1 (IGLL1).

The antigen binding domain can be any domain that binds to an antigen, including but not limited to a monoclonal antibody, a polyclonal antibody, a recombinant antibody, a human antibody, a humanized antibody, and a functional fragment thereof, including but not limited to a single-domain antibody such as a heavy chain variable domain (VH), a light chain variable domain (VL) and a variable domain (VHH) of camelid derived nanobody, and to an alternative scaffold known in the art to function as antigen binding domain, such as a recombinant fibronectin domain, a T cell receptor (TCR), or a fragment there of, e.g., single chain TCR, and the like. In some instances, it is beneficial for the antigen binding domain to be derived from the same species in which the CAR will ultimately be used in. For example, for use in humans, it may be beneficial for the antigen binding domain of the CAR to comprise human or humanized residues for the antigen binding domain of an antibody or antibody fragment.

CAR Transmembrane Domain

With respect to the transmembrane domain, in various embodiments, a CAR can be designed to comprise a transmembrane domain that is attached to the extracellular domain of the CAR. A transmembrane domain can include one or more additional amino acids adjacent to the transmembrane region, e.g., one or more amino acid associated with the extracellular region of the protein from which the transmembrane was derived (e.g., 1, 2, 3, 4, 5, 6, 7, 8, 9, 10 up to 15 amino acids of the extracellular region) and/or one or more additional amino acids associated with the intracellular region of the protein from which the transmembrane protein is derived (e.g., 1, 2, 3, 4, 5, 6, 7, 8, 9, 10 up to 15 amino acids of the intracellular region). In one aspect, the transmembrane domain is one that is associated with one of the other domains of the CAR is used, e.g., in one embodiment, the transmembrane domain may be from the same protein that the signaling domain, costimulatory domain or the hinge domain is derived from. In another aspect, the transmembrane domain is not derived from the same protein that any other domain of the CAR is derived from. In some instances, the transmembrane domain can be selected or modified by amino acid substitution to avoid binding of such domains to the transmembrane domains of the same or different surface membrane proteins, e.g., to minimize interactions with other members of the receptor complex. In one aspect, the transmembrane domain is capable of homodimerization with another CAR on the cell surface of a CAR-expressing cell. In a different aspect, the amino acid sequence of the transmembrane domain may be modified or substituted so as to minimize interactions with the binding domains of the native binding partner present in the same CAR-expressing cell.

The transmembrane domain may be derived either from a natural or from a recombinant source. Where the source is natural, the domain may be derived from any membrane-bound or transmembrane protein. In one aspect, the transmembrane domain is capable of signaling to the intracellular domain(s) whenever the CAR has bound to a target. A transmembrane domain of particular use in this invention may include at least the transmembrane domain(s) of, e.g., the alpha, beta or zeta chain of the T-cell receptor, CD28, CD3 epsilon, CD45, CD4, CD5, CD8 (e.g., CD8 alpha, CD8 beta), CD9, CD16, CD22, CD33, CD37, CD64, CD80, CD86, CD134, CD137, CD154. In some embodiments, a transmembrane domain may include at least the transmembrane region(s) of, e.g., KIRDS2, OX40, CD2, CD27, LFA-1 (CD11a, CD18), ICOS (CD278), 4-1BB (CD137), GITR, CD40, BAFFR, HVEM (LIGHTR), SLAMF7, NKp80 (KLRF1), NKp44, NKp30, NKp46, CD160, CD19, IL2R beta, IL2R gamma, IL7R a, ITGA1, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), SLAMF6 (NTB-A, Ly108), SLAM (SLAMFI, CD150, IPO-3), BLAME (SLAMF8), SELPLG (CD162), LTBR, PAG/Cbp, NKG2D, and NKG2C.

In some instances, the transmembrane domain can be attached to the extracellular region of the CAR, e.g., the antigen binding domain of the CAR, via a hinge, e.g., a hinge from a human protein. For example, in one embodiment, the hinge can be a human Ig (immunoglobulin) hinge (e.g., an IgG4 hinge, an IgD hinge), a GS linker (e.g., a GS linker described herein), a KIR2DS2 hinge or a CD8a hinge. In one embodiment, the hinge or spacer comprises (e.g., consists of) the amino acid sequence of SEQ ID NO:2. In one aspect, the transmembrane domain comprises (e.g., consists of) a transmembrane domain of SEQ ID NO: 6.

In one aspect, the hinge or spacer comprises an IgG4 hinge. For example, in one embodiment, the hinge or spacer comprises a hinge of the amino acid sequence SEQ ID NO:3.

In some embodiments, the hinge or spacer comprises a hinge encoded by a nucleotide sequence SEQ ID NO:14.

In one aspect, the hinge or spacer comprises an IgD hinge. For example, in one embodiment, the hinge or spacer comprises a hinge of the amino acid sequence SEQ ID NO:4.

In some embodiments, the hinge or spacer comprises a hinge encoded by a nucleotide sequence of SEQ ID NO:15.

In one aspect, the transmembrane domain may be recombinant, in which case it will comprise predominantly hydrophobic residues such as leucine and valine. In one aspect a triplet of phenylalanine, tryptophan and valine can be found at each end of a recombinant transmembrane domain.

Optionally, a short oligo- or polypeptide linker, between 2 and 10 amino acids in length may form the linkage between the transmembrane domain and the cytoplasmic signaling region of the CAR. A glycine-serine doublet provides a particularly suitable linker. For example, in one aspect, the linker comprises the amino acid sequence of GGGGSGGGGS (SEQ ID NO:5). In some embodiments, the linker is encoded by a nucleotide sequence of GGTGGCGGAGGTTCTGGAGGTGGAGGTTCC (SEQ ID NO:16).

In one aspect, the hinge or spacer comprises a KIR2DS2 hinge and portions thereof.

Cytoplasmic Domain

The cytoplasmic domain or region of the CAR includes an intracellular signaling domain. An intracellular signaling domain is generally responsible for activation of at least one of the normal effector functions of the immune cell in which the CAR has been introduced.

Examples of intracellular signaling domains for use in a CAR described herein include the cytoplasmic sequences of the T cell receptor (TCR) and co-receptors that act in concert to initiate signal transduction following antigen receptor engagement, as well as any derivative or variant of these sequences and any recombinant sequence that has the same functional capability.

It is known that signals generated through the TCR alone are insufficient for full activation of the T cell and that a secondary and/or costimulatory signal is also required. Thus, T cell activation can be said to be mediated by two distinct classes of cytoplasmic signaling sequences: those that initiate antigen-dependent primary activation through the TCR (primary intracellular signaling domains) and those that act in an antigen-independent manner to provide a secondary or costimulatory signal (secondary cytoplasmic domain, e.g., a costimulatory domain).

A primary signaling domain regulates primary activation of the TCR complex either in a stimulatory way, or in an inhibitory way. Primary intracellular signaling domains that act in a stimulatory manner may contain signaling motifs which are known as immunoreceptor tyrosine-based activation motifs or ITAMs.

Examples of ITAM containing primary intracellular signaling domains that are of particular use in the invention include those of TCR zeta, FcR gamma, FcR beta, CD3 gamma, CD3 delta, CD3 epsilon, CD5, CD22, CD79a, CD79b, CD278 (also known as "ICOS"), FcεRI, DAP10, DAP12, and CD66d. In one embodiment, a CAR of the invention comprises an intracellular signaling domain, e.g., a primary signaling domain of CD3-zeta, e.g., a CD3-zeta sequence described herein.

In one embodiment, a primary signaling domain comprises a modified ITAM domain, e.g., a mutated ITAM domain which has altered (e.g., increased or decreased) activity as compared to the native ITAM domain. In one embodiment, a primary signaling domain comprises a modified ITAM-containing primary intracellular signaling domain, e.g., an optimized and/or truncated ITAM-containing primary intracellular signaling domain. In an embodiment, a primary signaling domain comprises one, two, three, four or more ITAM motifs.

Costimulatory Signaling Domain

The intracellular signalling domain of the CAR can comprise the CD3-zeta signaling domain by itself or it can be combined with any other desired intracellular signaling domain(s) useful in the context of a CAR of the invention. For example, the intracellular signaling domain of the CAR can comprise a CD3 zeta chain portion and a costimulatory signaling domain. The costimulatory signaling domain refers to a portion of the CAR comprising the intracellular domain of a costimulatory molecule. In one embodiment, the intracellular domain is designed to comprise the signaling domain of CD3-zeta and the signaling domain of CD28. In one aspect, the intracellular domain is designed to comprise the signaling domain of CD3-zeta and the signaling domain of ICOS.

A costimulatory molecule can be a cell surface molecule other than an antigen receptor or its ligands that is required for an efficient response of lymphocytes to an antigen. Examples of such molecules include CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, and a ligand that specifically binds with CD83, and the like. For example, CD27 costimulation has been demonstrated to enhance expansion, effector function, and survival of human CART cells in vitro and augments human T cell persistence and antitumor activity in vivo (Song et al. Blood. 2012; 119(3):696-706). Further examples of such costimulatory molecules include CDS, ICAM-1, GITR, BAFFR, HVEM (LIGHTR), SLAMF7, NKp80 (KLRF1), NKp30, NKp44, NKp46, CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMFI, CD150, IPO-3), BLAME (SLAMF8), SELPLG (CD162), LTBR, LAT, GADS, SLP-76, NKG2D, NKG2C and PAG/Cbp.

The intracellular signaling sequences within the cytoplasmic portion of the CAR may be linked to each other in a random or specified order. Optionally, a short oligo- or polypeptide linker, for example, between 2 and 10 amino acids (e.g., 2, 3, 4, 5, 6, 7, 8, 9, or 10 amino acids) in length may form the linkage between intracellular signaling sequence. In one embodiment, a glycine-serine doublet can be used as a suitable linker. In one embodiment, a single amino acid, e.g., an alanine, a glycine, can be used as a suitable linker.

In one aspect, the intracellular signaling domain is designed to comprise two or more, e.g., 2, 3, 4, 5, or more, costimulatory signaling domains. In an embodiment, the two or more, e.g., 2, 3, 4, 5, or more, costimulatory signaling domains, are separated by a linker molecule, e.g., a linker molecule described herein. In one embodiment, the intracellular signaling domain comprises two costimulatory signaling domains. In some embodiments, the linker molecule is a glycine residue. In some embodiments, the linker is an alanine residue.

In one aspect, the intracellular signaling domain is designed to comprise the signaling domain of CD3-zeta and the signaling domain of CD28. In one aspect, the intracellular signaling domain is designed to comprise the signaling domain of CD3-zeta and the signaling domain of 4-1BB. In one aspect, the signaling domain of 4-1BB is a signaling domain of SEQ ID NO: 7. In one aspect, the signaling domain of CD3-zeta is a signaling domain of SEQ ID NO: 9.

In one aspect, the intracellular signaling domain is designed to comprise the signaling domain of CD3-zeta and the signaling domain of CD27. In one aspect, the signaling domain of CD27 comprises an amino acid sequence of SEQ ID NO: 8. In one aspect, the signalling domain of CD27 is encoded by a nucleic acid sequence of SEQ ID NO: 19.

In one aspect, the CAR-expressing cell described herein can further comprise a second CAR, e.g., a second CAR that includes a different antigen binding domain, e.g., to the same target or a different target (e.g., a target other than a cancer associated antigen described herein or a different cancer associated antigen described herein, e.g., CD19, CD33, CLL-1, CD34, FLT3, or folate receptor beta). In one embodiment, the second CAR includes an antigen binding domain to a target expressed the same cancer cell type as the cancer associated antigen. In one embodiment, the CAR-expressing cell comprises a first CAR that targets a first antigen and includes an intracellular signaling domain having a costimulatory signaling domain but not a primary signaling domain, and a second CAR that targets a second, different, antigen and includes an intracellular signaling domain having a primary signaling domain but not a costimulatory signaling domain. While not wishing to be bound by theory, placement of a costimulatory signaling domain, e.g., 4-1BB, CD28, ICOS, CD27 or OX-40, onto the first CAR, and the primary signaling domain, e.g., CD3 zeta, on the second CAR can limit the CAR activity to cells where both targets are expressed. In one embodiment, the CAR expressing cell comprises a first cancer associated antigen CAR that includes an antigen binding domain that binds a target antigen described herein, a transmembrane domain and a costimulatory domain and a second CAR that targets a different target antigen (e.g., an antigen expressed on that same cancer cell type as the first target antigen) and includes an antigen binding domain, a transmembrane domain and a primary signaling domain. In another embodiment, the CAR expressing cell comprises a first CAR that includes an antigen binding domain that binds a target antigen described herein, a transmembrane domain and a primary signaling domain and a second CAR that targets an antigen other than the first target antigen (e.g., an antigen expressed on the same cancer cell type as the first target antigen) and includes an antigen binding domain to the antigen, a transmembrane domain and a costimulatory signaling domain.

In another aspect, the disclosure features a population of CAR-expressing cells, e.g., CART cells. In some embodiments, the population of CAR-expressing cells comprises a mixture of cells expressing different CARs. For example, in one embodiment, the population of CART cells can include a first cell expressing a CAR having an antigen binding domain to a cancer associated antigen described herein, and a second cell expressing a CAR having a different antigen binding domain, e.g., an antigen binding domain to a different a cancer associated antigen described herein, e.g., an antigen binding domain to a cancer associated antigen described herein that differs from the cancer associate antigen bound by the antigen binding domain of the CAR expressed by the first cell. As another example, the population of CAR-expressing cells can include a first cell expressing a CAR that includes an antigen binding domain to a cancer associated antigen described herein, and a second cell expressing a CAR that includes an antigen binding domain to a target other than a cancer associate antigen as described herein. In one embodiment, the population of CAR-expressing cells includes, e.g., a first cell expressing a CAR that includes a primary intracellular signaling domain, and a second cell expressing a CAR that includes a secondary signaling domain.

In another aspect, the disclosure features a population of cells wherein at least one cell in the population expresses a CAR having an antigen binding domain to a cancer associated antigen described herein, and a second cell expressing another agent, e.g., an agent which enhances the activity of a CAR-expressing cell. For example, in one embodiment, the agent can be an agent which inhibits an inhibitory molecule. Inhibitory molecules, e.g., PD-1, can, in some embodiments, decrease the ability of a CAR-expressing cell to mount an immune effector response. Examples of inhibitory molecules include PD-1, PD-L1, CTLA4, TIM3, CEACAM (CEACAM-1, CEACAM-3, and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, and TGF (e.g., TGFbeta). In one embodiment, the agent which inhibits an inhibitory molecule comprises a first polypeptide, e.g., an inhibitory molecule, associated with a second polypeptide that provides a positive signal to the cell, e.g., an intracellular signaling domain described herein. In one embodiment, the agent comprises a first polypeptide, e.g., of an inhibitory molecule such as PD-1, PD-L1, CTLA4, TIM3, CEACAM (CEACAM-1, CEACAM-3, and/or CEACAM-5), LAG3, VISTA, BTLA, TIGIT, LAIR1, CD160, 2B4 and TGF beta, or a fragment of any of these, and a second polypeptide which is an intracellular signaling domain described herein (e.g., comprising a costimulatory domain (e.g., 41BB, CD27, OX40 or CD28, e.g., as described herein) and/or a primary signaling domain (e.g., a CD3 zeta signaling domain described herein). In one embodiment, the agent comprises a first polypeptide of PD-1 or a fragment thereof, and a second polypeptide of an intracellular signaling domain described herein (e.g., a CD28 signaling domain described herein and/or a CD3 zeta signaling domain described herein).

CD19 CAR

In some embodiments, the CAR-expressing cell described herein is a CD19 CAR-expressing cell (e.g., a cell expressing a CAR that binds to human CD19).

In one embodiment, the antigen binding domain of the CD19 CAR has the same or a similar binding specificity as the FMC63 scFv fragment described in Nicholson et al. Mol. Immun. 34 (16-17): 1157-1165 (1997). In one embodiment, the antigen binding domain of the CD19 CAR includes the scFv fragment described in Nicholson et al. *Mol. Immun.* 34 (16-17): 1157-1165 (1997).

In some embodiments, the CD19 CAR includes an antigen binding domain (e.g., a humanized antigen binding domain) according to Table 3 of WO2014/153270, incorporated herein by reference. WO2014/153270 also describes methods of assaying the binding and efficacy of various CAR constructs.

In one aspect, the parental murine scFv sequence is the CAR19 construct provided in PCT publication WO2012/079000 (incorporated herein by reference). In one embodiment, the anti-CD19 binding domain is a scFv described in WO2012/079000.

In one embodiment, the CAR molecule comprises the fusion polypeptide sequence provided as SEQ ID NO: 12 in PCT publication WO2012/079000, which provides an scFv fragment of murine origin that specifically binds to human CD19.

In one embodiment, the CD19 CAR comprises an amino acid sequence provided as SEQ ID NO: 12 in PCT publication WO2012/079000. In embodiment, the amino acid sequence is

```
                                   (SEQ ID NO: 624)
(MALPVTALLLPLALLLHAARP)diqmtqttsslsaslgdrvtiscrasqd
iskylnwyqqkpdgtvklliyhtsrlhsgvpsrfsgsgsgtdysltisnle
qediatyfcqqgntlpytfgggtkleitggggsggggsggggsevklqesg
pglvapsqslsvtctvsgvslpdygvswirqpprkglewlgviwgsettyy
nsalksrltiikdnsksqvflkmnslqtddtaiyycakhyyyggsyamdyw
gqgtsvtvsstapaprpptpaptiasqplslrpeacrpaaggavhtrgldf
acdiyiwaplagtcgvlllslvitlyckrgrkkllyifkqpfmrpvqttqe
edgcscrfpeeeeggcelrvkfsrsadapaykqgqnqlynelnlgrreeyd
vldkrrgrdpemggkprrknpqeglynelqkdkmaeayseigmkgerrrgk
ghdglyqglstatkdtydalhmqalppr,
```

or a sequence substantially homologous thereto. The optional sequence of the signal peptide is shown in capital letters and parenthesis.

In one embodiment, the amino acid sequence is:

```
                                   (SEQ ID NO: 625)
Diqmtqttsslsaslgdrvtiscrasqdiskylnwyqqkpdgtvklliyht
srlhsgvpsrfsgsgsgtdysltisnleqediatyfcqqgntlpytfgggt
kleitggggsggggsggggsevklqesgpglvapsqslsvtctvsgvslpd
ygvswirqpprkglewlgviwgsettyynsalksrltiikdnsksqvflkm
```

-continued

```
nslqtddtaiyycakhyyyggsyamdywgqgtsvtvssttpaprpptpap

tiasqplslrpeacrpaaggavhtrgldfacdiyiwaplagtcgvlllslv

itlyckrgrkkllyifkqpfmrpvqttqeedgcscrfpeeeeggcelrvkf

srsadapaykqgqnqlynelnlgrreeydvldkrrgrdpemggkprrknpq

eglynelqkdkmaeayseigmkgerrrgkghdglyqglstatkdtydalhm

qalppr,
```

or a sequence substantially homologous thereto.

In one embodiment, the CD19 CAR has the USAN designation TISAGENLECLEUCEL-T. In embodiments, CTL019 is made by a gene modification of T cells is mediated by stable insertion via transduction with a self-inactivating, replication deficient Lentiviral (LV) vector containing the CTL019 transgene under the control of the EF-1 alpha promoter. CTL019 can be a mixture of transgene positive and negative T cells that are delivered to the subject on the basis of percent transgene positive T cells.

In other embodiments, the CD19 CAR comprises an antigen binding domain (e.g., a humanized antigen binding domain) according to Table 3 of WO2014/153270, incorporated herein by reference.

Humanization of murine CD19 antibody is desired for the clinical setting, where the mouse-specific residues may induce a human-anti-mouse antigen (HAMA) response in patients who receive CART19 treatment, i.e., treatment with T cells transduced with the CAR19 construct. The production, characterization, and efficacy of humanized CD19 CAR sequences is described in International Application WO2014/153270 which is herein incorporated by reference in its entirety, including Examples 1-5 (p. 115-159).

Any known CD19 CAR, e.g., the CD19 antigen binding domain of any known CD19 CAR, in the art can be used in accordance with the present disclosure. For example, LG-740; CD19 CAR described in the U.S. Pat. Nos. 8,399,645; 7,446,190; Xu et al., Leuk Lymphoma. 2013 54(2): 255-260(2012); Cruz et al., Blood 122(17):2965-2973 (2013); Brentjens et al., Blood, 118(18):4817-4828 (2011); Kochenderfer et al., Blood 116(20):4099-102 (2010); Kochenderfer et al., Blood 122 (25):4129-39(2013); and 16th Annu Meet Am Soc Gen Cell Ther (ASGCT) (May 15-18, Salt Lake City) 2013, Abst 10.

Exemplary CD19 CARs include CD19 CARs described herein, e.g., in one or more tables described herein, or an anti-CD19 CAR described in Xu et al. Blood 123.24(2014): 3750-9; Kochenderfer et al. Blood 122.25(2013):4129-39, Cruz et al. Blood 122.17(2013):2965-73, NCT00586391, NCT01087294, NCT02456350, NCT00840853, NCT02659943, NCT02650999, NCT02640209, NCT01747486, NCT02546739, NCT02656147, NCT02772198, NCT00709033, NCT02081937, NCT00924326, NCT02735083, NCT02794246, NCT02746952, NCT01593696, NCT02134262, NCT01853631, NCT02443831, NCT02277522, NCT02348216, NCT02614066, NCT02030834, NCT02624258, NCT02625480, NCT02030847, NCT02644655, NCT02349698, NCT02813837, NCT02050347, NCT01683279, NCT02529813, NCT02537977, NCT02799550, NCT02672501, NCT02819583, NCT02028455, NCT01840566, NCT01318317, NCT01864889, NCT02706405, NCT01475058, NCT01430390, NCT02146924, NCT02051257, NCT02431988, NCT01815749, NCT02153580, NCT01865617, NCT02208362, NCT02685670, NCT02535364, NCT02631044, NCT02728882, NCT02735291, NCT01860937, NCT02822326, NCT02737085, NCT02465983, NCT02132624, NCT02782351, NCT01493453, NCT02652910, NCT02247609, NCT01029366, NCT01626495, NCT02721407, NCT01044069, NCT00422383, NCT01680991, NCT02794961, or NCT02456207, each of which is incorporated herein by reference in its entirety.

BCMA CAR

In some embodiments, the CAR-expressing cell described herein is a BCMA CAR-expressing cell (e.g., a cell expressing a CAR that binds to human BCMA). Exemplary BCMA CARs can include sequences disclosed in Table 1 or 16 of WO2016/014565, incorporated herein by reference. The BCMA CAR construct can include an optional leader sequence; an optional hinge domain, e.g., a CD8 hinge domain; a transmembrane domain, e.g., a CD8 transmembrane domain; an intracellular domain, e.g., a 4-1BB intracellular domain; and a functional signaling domain, e.g., a CD3 zeta domain. In certain embodiments, the domains are contiguous and in the same reading frame to form a single fusion protein. In other embodiments, the domain are in separate polypeptides, e.g., as in an RCAR molecule as described herein.

In some embodiments, the BCMA CAR molecule includes one or more CDRs, VH, VL, scFv, or full-length sequences of BCMA-1, BCMA-2, BCMA-3, BCMA-4, BCMA-5, BCMA-6, BCMA-7, BCMA-8, BCMA-9, BCMA-10, BCMA-11, BCMA-12, BCMA-13, BCMA-14, BCMA-15, 149362, 149363, 149364, 149365, 149366, 149367, 149368, 149369, BCMA_EBB-C1978-A4, BCMA_EBB-C1978-G1, BCMA_EBB-C1979-C1, BCMA_EBB-C1978-C7, BCMA_EBB-C1978-D10, BCMA_EBB-C1979-C12, BCMA_EBB-C1980-G4, BCMA_EBB-C1980-D2, BCMA_EBB-C1978-A10, BCMA_EBB-C1978-D4, BCMA_EBB-C1980-A2, BCMA_EBB-C1981-C3, BCMA_EBB-C1978-G4, A7D12.2, C11D5.3, C12A3.2, or C13F12.1 disclosed in WO2016/014565, or a sequence substantially (e.g., 95-99%) identical thereto.

Additional exemplary BCMA-targeting sequences that can be used in the anti-BCMA CAR constructs are disclosed in WO 2017/021450, WO 2017/011804, WO 2017/025038, WO 2016/090327, WO 2016/130598, WO 2016/210293, WO 2016/090320, WO 2016/014789, WO 2016/094304, WO 2016/154055, WO 2015/166073, WO 2015/188119, WO 2015/158671, U.S. Pat. Nos. 9,243,058, 8,920,776, 9,273,141, 7,083,785, 9,034,324, US 2007/0049735, US 2015/0284467, US 2015/0051266, US 2015/0344844, US 2016/0131655, US 2016/0297884, US 2016/0297885, US 2017/0051308, US 2017/0051252, US 2017/0051252, WO 2016/020332, WO 2016/087531, WO 2016/079177, WO 2015/172800, WO 2017/008169, U.S. Pat. No. 9,340,621, US 2013/0273055, US 2016/0176973, US 2015/0368351, US 2017/0051068, US 2016/0368988, and US 2015/0232557, herein incorporated by reference in their entirety. In some embodiments, additional exemplary BCMA CAR constructs are generated using the VH and VL sequences from PCT Publication WO2012/0163805 (the contents of which are hereby incorporated by reference in its entirety).

CD20 CAR

In some embodiments, the CAR-expressing cell described herein is a CD20 CAR-expressing cell (e.g., a cell expressing a CAR that binds to human CD20). In some embodiments, the CD20 CAR-expressing cell includes an antigen binding domain according to WO2016/164731 and PCT/

US2017/055627, incorporated herein by reference. Exemplary CD20-binding sequences or CD20 CAR sequences are disclosed in, e.g., Tables 1-5 of PCT/US2017/055627. In some embodiments, the CD20 CAR comprises a CDR, variable region, scFv, or full-length sequence of a CD20 CAR disclosed in PCT/US2017/055627 or WO2016/164731.

CD22 CAR

In some embodiments, the CAR-expressing cell described herein is a CD22 CAR-expressing cell (e.g., a cell expressing a CAR that binds to human CD22). In some embodiments, the CD22 CAR-expressing cell includes an antigen binding domain according to WO2016/164731 and PCT/US2017/055627, incorporated herein by reference. Exemplary CD22-binding sequences or CD22 CAR sequences are disclosed in, e.g., Tables 6A, 6B, 7A, 7B, 7C, 8A, 8B, 9A, 9B, 10A, and 10B of WO2016/164731 and Tables 6-10 of PCT/US2017/055627. In some embodiments, the CD22 CAR sequences comprise a CDR, variable region, scFv or full-length sequence of a CD22 CAR disclosed in PCT/US2017/055627 or WO2016/164731.

EGFR CAR

In some embodiments, the CAR-expressing cell described herein is an EGFR CAR-expressing cell (e.g., a cell expressing a CAR that binds to human EGFR). In some embodiments, the CAR-expressing cell described herein is an EGFRvIII CAR-expressing cell (e.g., a cell expressing a CAR that binds to human EGFRvIII). Exemplary EGFRvIII CARs can include sequences disclosed in WO2014/130657, e.g., Table 2 of WO2014/130657, incorporated herein by reference.

Exemplary EGFRvIII-binding sequences or EGFR CAR sequences may comprise a CDR, a variable region, an scFv, or a full-length CAR sequence of a EGFR CAR disclosed in WO2014/130657.

Mesothelin CAR

In some embodiments, the CAR-expressing cell described herein is a mesothelin CAR-expressing cell (e.g., a cell expressing a CAR that binds to human mesothelin). Exemplary mesothelin CARs can include sequences disclosed in WO2015090230 and WO2017112741, e.g., Tables 2, 3, 4, and 5 of WO2017112741, incorporated herein by reference.

Exemplary mesothelin CAR constructs disclosed herein comprise a scFv (e.g., a human scFv) as disclosed in Table 2 or 3 herein, optionally preceded with an optional leader sequence (e.g., SEQ ID NO:1 and SEQ ID NO:12 for exemplary leader amino acid and nucleotide sequences, respectively). The sequences of the scFv fragments (amino acid sequences of SEQ ID NOs: 39-62) are provided herein in Table 2. The mesothelin CAR construct can further include an optional hinge domain, e.g., a CD8 hinge domain (e.g., including the amino acid sequence of SEQ ID NO: 2 or encoded by a nucleic acid sequence of SEQ ID NO:13); a transmembrane domain, e.g., a CD8 transmembrane domain (e.g., including the amino acid sequence of SEQ ID NO: 6 or encoded by the nucleotide sequence of SEQ ID NO: 17); an intracellular domain, e.g., a 4-1BB intracellular domain (e.g., including the amino acid sequence of SEQ ID NO: 7 or encoded by the nucleotide sequence of SEQ ID NO: 18; and a functional signaling domain, e.g., a CD3 zeta domain (e.g., including amino acid sequence of SEQ ID NO: 9 or 10, or encoded by the nucleotide sequence of SEQ ID NO: 20 or 21). In certain embodiments, the domains are contiguous with and in the same reading frame to form a single fusion protein. In other embodiments, the domain are in separate polypeptides, e.g., as in an RCAR molecule as described herein.

In certain embodiments, the full length mesothelin CAR molecule includes the amino acid sequence of, or is encoded by the nucleotide sequence of, M1, M2, M3, M4, M5, M6, M7, M8, M9, M10, M11, M12, M13, M14, M15, M16, M17, M18, M19, M20, M21, M22, M23, M24, or ss1, provided in Table 2 or 3, or a sequence substantially identical (e.g., 95-99% identical thereto, or up to 20, 15, 10, 8, 6, 5, 4, 3, 2, or 1 amino acid changes) to any of the aforesaid sequences.

In certain embodiments, the mesothelin CAR molecule, or the mesothelin antigen binding domain, includes the scFv amino acid sequence of, or is encoded by the nucleotide sequence of, M1, M2, M3, M4, M5, M6, M7, M8, M9, M10, M11, M12, M13, M14, M15, M16, M17, M18, M19, M20, M21, M22, M23, M24, or ss1, provided in Table 2 or 3, or a sequence substantially identical (e.g., 95-99% identical thereto, or up to 20, 15, 10, 8, 6, 5, 4, 3, 2, or 1 amino acid changes) to any of the aforesaid sequences.

In certain embodiments, the mesothelin CAR molecule, or the mesothelin antigen binding domain, includes the heavy chain variable region and/or the light chain variable region of M1, M2, M3, M4, M5, M6, M7, M8, M9, M10, M11, M12, M13, M14, M15, M16, M17, M18, M19, M20, M21, M22, M23, M24, or ss1, provided in Table 2, or a sequence substantially identical (e.g., 95-99% identical, or up to 20, 15, 10, 8, 6, 5, 4, 3, 2, or 1 amino acid changes) to any of the aforesaid sequences.

In certain embodiments, the mesothelin CAR molecule, or the mesothelin antigen binding domain, includes one, two or three CDRs from the heavy chain variable region (e.g., HCDR1, HCDR2 and/or HCDR3) of M1, M2, M3, M4, M5, M6, M7, M8, M9, M10, M11, M12, M13, M14, M15, M16, M17, M18, M19, M20, M21, M22, M23, M24, or ss1, provided in Table 4; and/or one, two or three CDRs from the light chain variable region (e.g., LCDR1, LCDR2 and/or LCDR3) of M1, M2, M3, M4, M5, M6, M7, M8, M9, M10, M11, M12, M13, M14, M15, M16, M17, M18, M19, M20, M21, M22, M23, M24, or ss1, provided in Table 5; or a sequence substantially identical (e.g., 95-99% identical, or up to 5, 4, 3, 2, or 1 amino acid changes) to any of the aforesaid sequences.

The sequences of CDR sequences of the scFv domains are shown in Table 4 for the heavy chain variable domains and in Table 5 for the light chain variable domains.

The amino acid and nucleic acid sequences of the mesothelin scFv domains and mesothelin CAR molecules are provided in Table 2 (amino acid sequences) and Table 3 (nucleic acid sequences). In one embodiment, the mesothelin CAR molecule includes a leader sequence described herein, e.g., as underlined in the sequences provided in Table 2. In one embodiment, the mesothelin CAR molecule does not include A leader sequence.

TABLE 2

Amino Acid Sequences of Human scFvs and CARs (bold underline is the leader sequence and grey box is a linker sequence). In the case of the scFvs, the remaining amino acids are the heavy chain variable region and light chain variable regions, with each of the HC CDRs (HC CDR1, HC CDR2, HC CDR3) and LC CDRs (LC CDR1, LC CDR2, LCCDR3) underlined). In the case of the CARs, the further remaining amino acids are the remaining amino acids of the CARs.)

| SEQ ID NO:Description | Amino Acid Sequence |
|---|---|
| 39 M1 (ScFv domain) | QVQLQQSGAEVKKPGASVKVSCKASGYTFTGYYMHWVRQAPGQGLEWMGRINPNSGGTNY AQKFQGRVTMTRDTSISTAYMELSRLRSEDTAVYYCARGRYYGMDVWGQGTMVTVSSGGG GSGGGGSGGGGSGGGGSEIVLTQSPATLSLSPGERATISCRASQSVSSNFAWYQQRPGQA PRLLIYDASNRATGIPPRFSGSGSGTDFTLTISSLEPEDFAAYYCHQRSNWLYTFGQGTK VDIK |
| 63 M1 (full) >ZA53-27BC (M1 ZA53-27BC R001-A11 126161) | MALPVTALLLPLALLLHAARPQVQLQQSGAEVKKPGASVKVSCKASGYTFTGYYMHWVRQ APGQGLEWMGRINPNSGGTNYAQKFQGRVTMTRDTSISTAYMELSRLRSEDTAVYYCARG RYYGMDVWGQGTMVTVSSGGGGSGGGGSGGGGSGGGGSEIVLTQSPATLSLSPGERATIS CRASQSVSSNFAWYQQRPGQAPRLLIYDASNRATGIPPRFSGSGSGTDFTLTISSLEPED FAAYYCHQRSNWLYTFGQGTKVDIKTTTPAPRPPTPAPTIASQPLSLRPEACRPAAGGAV HTRGLDFACDIYIWAPLAGTCGVLLLSLVITLYCKRGRKKLLYIFKQPFMRPVQTTQEED GCSCRFPEEEEGGCELRVKFSRSADAPAYKQGQNQLYNELNLGRREEYDVLDKRRGRDPE MGGKPRRKNPQEGLYNELQKDKMAEAYSEIGMKGERRRGKGHDGLYQGLSTATKDTYDAL HMQALPPR |
| 40 M2 (ScFv domain) | QVQLVQSGAEVKKPGASVKVSCKASGYTFTGYYMHWVRQAPGQGLEWMGWINPNSGGTNY AQKFQGRVTMTRDTSISTAYMELSRLRSDDTAVYYCARDLRRTVVTPRAYYGMDVWGQGT TVTVSSGGGGSGGGGSGGGGSGGGGSDIQLTQSPSTLSASVGDRVTITCQASQDISNSLN WYQQKAGKAPKLLIYDASTLETGVPSRFSGSGSGTDFSETISSLQPEDIATYYCQQHDNL PLTFGQGTKVEIK |
| 64 M2 (full) >FA56-26RC (M2 FA56-26RC R001-A10 126162) | MALPVTALLLPLALLLHAARPQVQLVQSGAEVKKPGASVKVSCKASGYTFTGYYMHWVRQ APGQGLEWMGWINPNSGGTNYAQKFQGRVTMTRDTSISTAYMELSRLRSDDTAVYYCARD LRRTVVTPRAYYGMDVWGQGTTVTVSSGGGGSGGGGSGGGGSGGGGSDIQLTQSPSTLSA SVGDRVTITCQASQDISNSLNWYQQKAGKAPKLLIYDASTLETGVPSRFSGSGSGTDFSF TISSLQPEDIATYYCQQHDNLPLTFGQGTKVEIKTTTPAPRPPTPAPTIASQPLSLRPEA CRPAAGGAVHTRGLDFACDIYIWAPLAGTCGVLLLSLVITLYCKRGRKKLLYIFKQPFMR PVQTTQEEDGCSCRFPEEEEGGCELRVKFSRSADAPAYKQGQNQLYNELNLGRREEYDVL DKRRGRDPEMGGKPRRKNPQEGLYNELQKDKMAEAYSEIGMKGERRRGKGHDGLYQGLST ATKDTYDALHMQALPPR |
| 41 M3 (ScFv domain) | QVQLVQSGAEVKKPGAPVKVSCKASGYTFTGYYMHWVRQAPGQGLEWMGWINPNSGGTNY AQKFQGRVTMTRDTSISTAYMELSRLRSDDTAVYYCARGEWDGSYYYDYWGQGTLVTVSS GGGGSGGGGSGGGGSGGGGSDIVLTQTPSSLSASVGDRVTITCRASQSINTYLNWYQHKP GKAPKLLIYAASSLQSGVPSRFSGSGSGTDFTLTISSLQPEDFATYYCQQSFSPLTFGGG TKLEIK |
| 65 M3 >VA58-21LC (M3 VA58-21LC R001-A1 126163) | MALPVTALLLPLALLLHAARPQVQLVQSGAEVKKPGAPVKVSCKASGYTFTGYYMHWVRQ APGQGLEWMGWINPNSGGTNYAQKFQGRVTMTRDTSISTAYMELSRLRSDDTAVYYCARG EWDGSYYYDYWGQGTLVTVSSGGGGSGGGGSGGGGSGGGGSDIVLTQTPSSLSASVGDRV TITCRASQSINTYLNWYQHKPGKAPKLLIYAASSLQSGVPSRFSGSGSGTDFTLTISSLQ PEDFATYYCQQSFSPLTFGGGTKLEIKTTTPAPRPPTPAPTIASQPLSLRPEACRPAAGG AVHTRGLDFACDIYIWAPLAGTCGVLLLSLVITLYCKRGRKKLLYIFKQPFMRPVQTTQE EDGCSCRFPEEEEGGCELRVKFSRSADAPAYKQGQNQLYNELNLGRREEYDVLDKRRGRD PEMGGKPRRKNPQEGLYNELQKDKMAEAYSEIGMKGERRRGKGHDGLYQGLSTATKDTYD ALHMQALPPR |
| 42 M4 (ScFv domain) | QVQLVESGGGLVQPGGSLRLSCAASGFTFSSYWMHWVRQVPGKGLVWVSRINTDGSTTTY ADSVEGRFTISRDNAKNTLYLQMNSLRDDDTAVYYCVGGHWAVWGQGTTVTVSSGGGGSG GGGSGGGGSGGGGSDIQMTQSPSTLSASVGDRVTITCRASQSISDRLAWYQQKPGKAPKL LIYKASSLESGVPSRFSGSGSGTEFTLTISSLQPDDFAVYYCQQYGHLPMYTFGQGTKVE IK |
| 66 M4 >DP37-07IC (M4 DP37-07IC R001-C6 126164) | MALPVTALLLPLALLLHAARPQVQLVESGGGLVQPGGSLRLSCAASGFTFSSYWMHWVRQ VPGKGLVWVSRINTDGSTTTYADSVEGRFTISRDNAKNTLYLQMNSLRDDDTAVYYCVGG HWAVWGQGTTVTVSSGGGGSGGGGSGGGGSGGGGSDIQMTQSPSTLSASVGDRVTITCRA SQSISDRLAWYQQKPGKAPKLLIYKASSLESGVPSRFSGSGSGTEFTLTISSLQPDDFAV YYCQQYGHLPMYTFGQGTKVEIKTTTPAPRPPTPAPTIASQPLSLRPEACRPAAGGAVHT RGLDFACDIYIWAPLAGTCGVLLLSLVITLYCKRGRKKLLYIFKQPFMRPVQTTQEEDGC SCRFPEEEEGGCELRVKFSRSADAPAYKQGQNQLYNELNLGRREEYDVLDKRRGRDPEMG GKPRRKNPQEGLYNELQKDKMAEAYSEIGMKGERRRGKGHDGLYQGLSTATKDTYDALHM QALPPR |
| 43 M5 (ScFv domain) | QVQLVQSGAEVEKPGASVKVSCKASGYTFTDYYMHWVRQAPGQGLEWMGWINPNSGGTNY AQKFQGRVTMTRDTSISTAYMELSRLRSDDTAVYYCASGWDFDYWGQGTLVTVSSGGGGS GGGGSGGGGSGGGGSDIVMTQSPSSLSASVGDRVTITCRASQSIRYYLSWYQQKPGKAPK LLIYTASILQNGVPSRFSGSGSGTDFTLTISSLQPEDFATYYCLQTYTTPDFGPGTKVEI K |

TABLE 2-continued

Amino Acid Sequences of Human scFvs and CARs (bold underline is the leader sequence and grey box is a linker sequence). In the case of the scFvs, the remaining amino acids are the heavy chain variable region and light chain variable regions, with each of the HC CDRs (HC CDR1, HC CDR2, HC CDR3) and LC CDRs (LC CDR1, LC CDR2, LCCDR3) underlined). In the case of the CARs, the further remaining amino acids are the remaining amino acids of the CARs.)

| SEQ ID NO: | Description | Amino Acid Sequence |
|---|---|---|
| 67 | M5<br>>XP31-20LC<br>(M5<br>XP31-20LC<br>R001-B4<br>126165) | **MALPVTALLLPLALLLHAARP**QVQLVQSGAEVEKPGASVKVSCKASGYTFTDYYMHWVRQ<br>APGQGLEWMGWINPNSGGTNYAQKFQGRVTMTRDTSISTAYMELSRLRSDDTAVYYCASG<br>WDFDYWGQGTLVTVSSGGGGSGGGGSGGGGSGGGGSDIVMTQSPSSLSASVGDRVTITCR<br>ASQSIRYYLSWYQQKPGKAPKLLIYTASILQNGVPSRFSGSGSGTDFTLTISSLQPEDFA<br>TYYCLQTYTTPDFGPGTKVEIKTTTPAPRPPTPAPTIASQPLSLRPEACRPAAGGAVHTR<br>GLDFACDIYIWAPLAGTCGVLLLSLVITLYCKRGRKKLLYIFKQPFMRPVQTTQEEDGCS<br>CRFPEEEEGGCELRVKFSRSADAPAYKQGQNQLYNELNLGRREEYDVLDKRRGRDPEMGG<br>KPRRKNPQEGLYNELQKDKMAEAYSEIGMKGERRRGKGHDGLYQGLSTATKDTYDALHMQ<br>ALPPR |
| 44 | M6 (ScFv<br>domain) | QVQLVQSGAEVKKPGASVKVSCKASGYTFTSYYMHWVRQAPGQGLEWMGIINPSGGSTSY<br>AQKFQGRVTMTRDTSTSTVYMELSSLRSEDTAVYYCARYRLIAVAGDYYYYGMDVWGQGT<br>MVTVSSGGGGSGGGGSGGGGSGGGGSDIQMTQSPSSVSASVGDRVTITCRASQGVGRWLA<br>WYQQKPGTAPKLLIYAASTLQSGVPSRFSGSGSGTDFTLTINNLQPEDFATYYCQQANSF<br>PLTFGGGTRLEIK |
| 68 | M6<br>>FE10-06ID<br>(M6<br>46FE10-<br>06ID<br>R001-A4<br>126166) | **MALPVTALLLPLALLLHAARP**QVQLVQSGAEVKKPGASVKVSCKASGYTFTSYYMHWVRQ<br>APGQGLEWMGIINPSGGSTSYAQKFQGRVTMTRDTSTSTVYMELSSLRSEDTAVYYCARY<br>RLIAVAGDYYYYGMDVWGQGTMVTVSSGGGGSGGGGSGGGGSGGGGSDIQMTQSPSSVSA<br>SVGDRVTITCRASQGVGRWLAWYQQKPGTAPKLLIYAASTLQSGVPSRFSGSGSGTDFTL<br>TINNLQPEDFATYYCQQANSFPLTFGGGTRLEIKTTTPAPRPPTPAPTIASQPLSLRPEA<br>CRPAAGGAVHTRGLDFACDIYIWAPLAGTCGVLLLSLVITLYCKRGRKKLLYIFKQPFMR<br>PVQTTQEEDGCSCRFPEEEEGGCELRVKFSRSADAPAYKQGQNQLYNELNLGRREEYDVL<br>DKRRGRDPEMGGKPRRKNPQEGLYNELQKDKMAEAYSEIGMKGERRRGKGHDGLYQGLST<br>ATKDTYDALHMQALPPR |
| 45 | M7 (ScFv<br>domain) | QVQLVQSGGGVVQPGRSLRLSCAASGFTFSSYAMHWVRQAPGKGLEWVAVISYDGSNKYY<br>ADSVKGRFTISRDNSKNTLYLQMNSLRAEDTAVYYCARWKVSSSSPAFDYWGQGTLVTVS<br>SGGGGSGGGGSGGGGSGGGGSEIVLTQSPATLSLSPGERAILSCRASQSVYTKYLGWYQQ<br>KPGQAPRLLIYDASTRATGIPDRFSGSGSGTDFTLTINRLEPEDFAVYYCQHYGGSPLIT<br>FGQGTRLEIK |
| 69 | M7<br>>VE12-01CD<br>(M7<br>VE12-01CD<br>R001-A5<br>126167) | **MALPVTALLLPLALLLHAARP**QVQLVQSGGGVVQPGRSLRLSCAASGFTFSSYAMHWVRQ<br>APGKGLEWVAVISYDGSNKYYADSVKGRFTISRDNSKNTLYLQMNSLRAEDTAVYYCARW<br>KVSSSSPAFDYWGQGTLVTVSSGGGGSGGGGSGGGGSGGGGSEIVLTQSPATLSLSPGER<br>AILSCRASQSVYTKYLGWYQQKPGQAPRLLIYDASTRATGIPDRFSGSGSGTDFTLTINR<br>LEPEDFAVYYCQHYGGSPLITFGQGTRLEIKTTTPAPRPPTPAPTIASQPLSLRPEACRP<br>AAGGAVHTRGLDFACDIYIWAPLAGTCGVLLLSLVITLYCKRGRKKLLYIFKQPFMRPVQ<br>TTQEEDGCSCRFPEEEEGGCELRVKFSRSADAPAYKQGQNQLYNELNLGRREEYDVLDKR<br>RGRDPEMGGKPRRKNPQEGLYNELQKDKMAEAYSEIGMKGERRRGKGHDGLYQGLSTATK<br>DTYDALHMQALPPR |
| 46 | M8 (ScFv<br>domain) | QVQLQQSGAEVKKPGASVKVSCKTSGYPFTGYSLHWVRQAPGQGLEWMGWINPNSGGTNY<br>AQKFQGRVTMTRDTSISTAYMELSRLRSDDTAVYYCARDHYGGNSLFYWGQGTLVTVSSG<br>GGGSGGGGSGGGGSGGGGSDIQLTQSPSSISASVGDTVSITCRASQDSGTWLAWYQQKPG<br>KAPNLLMYDASTLEDGVPSRFSGSASGTEFTLTVNRLQPEDSATYYCQQYNSYPLTFGGG<br>TKVDIK |
| 70 | M8<br>>LE13-05XD<br>(M8<br>LE13-05XD<br>R001-E5<br>126168) | **MALPVTALLLPLALLLHAARP**QVQLQQSGAEVKKPGASVKVSCKTSGYPFTGYSLHWVRQ<br>APGQGLEWMGWINPNSGGTNYAQKFQGRVTMTRDTSISTAYMELSRLRSDDTAVYYCARD<br>HYGGNSLFYWGQGTLVTVSSGGGGSGGGGSGGGGSGGGGSDIQLTQSPSSISASVGDTVS<br>ITCRASQDSGTWLAWYQQKPGKAPNLLMYDASTLEDGVPSRFSGSASGTEFTLTVNRLQP<br>EDSATYYCQQYNSYPLTFGGGTKVDIKTTTPAPRPPTPAPTIASQPLSLRPEACRPAAGG<br>AVHTRGLDFACDIYIWAPLAGTCGVLLLSLVITLYCKRGRKKLLYIFKQPFMRPVQTTQE<br>EDGCSCRFPEEEEGGCELRVKFSRSADAPAYKQGQNQLYNELNLGRREEYDVLDKRRGRD<br>PEMGGKPRRKNPQEGLYNELQKDKMAEAYSEIGMKGERRRGKGHDGLYQGLSTATKDTYD<br>ALHMQALPPR |
| 47 | M9 (ScFv<br>domain) | QVQLVQSGAEVKKPGASVEVSCKASGYTFTSYYMHWVRQAPGQGLEWMGIINPSGGSTGY<br>AQKFQGRVTMTRDTSTSTVHMELSSLRSEDTAVYYCARGGYSSSSDAFDIWGQGTMVTVS<br>SGGGGSGGGGSGGGGSGGGGSDIQMTQSPPSLSASVGDRVTITCRASQDISSALAWYQQK<br>PGTPPKLLIYDASSLESGVPSRFSGSGSGTDFTLTISSLQPEDFATYYCQQFSSYPLTFG<br>GGTRLEIK |
| 71 | M9<br>>BE15-00SD<br>(M9<br>BE15-00SD<br>R001-A3<br>126169) | **MALPVTALLLPLALLLHAARP**QVQLVQSGAEVKKPGASVEVSCKASGYTFTSYYMHWVRQ<br>APGQGLEWMGIINPSGGSTGYAQKFQGRVTMTRDTSTSTVHMELSSLRSEDTAVYYCARG<br>GYSSSSDAFDIWGQGTMVTVSSGGGGSGGGGSGGGGSGGGGSDIQMTQSPPSLSASVGDR<br>VTITCRASQDISSALAWYQQKPGTPPKLLIYDASSLESGVPSRFSGSGSGTDFTLTISSL<br>QPEDFATYYCQQFSSYPLTFGGGTRLEIKTTTPAPRPPTPAPTIASQPLSLRPEACRPAA<br>GGAVHTRGLDFACDIYIWAPLAGTCGVLLLSLVITLYCKRGRKKLLYIFKQPFMRPVQTT |

TABLE 2-continued

Amino Acid Sequences of Human scFvs and CARs (bold underline is the leader sequence and grey box is a linker sequence). In the case of the scFvs, the remaining amino acids are the heavy chain variable region and light chain variable regions, with each of the HC CDRs (HC CDR1, HC CDR2, HC CDR3) and LC CDRs (LC CDR1, LC CDR2, LCCDR3) underlined). In the case of the CARs, the further remaining amino acids are the remaining amino acids of the CARs.)

| SEQ ID NO: | Description | Amino Acid Sequence |
|---|---|---|
| | | QEEDGCSCRFPEEEEGGCELRVKFSRSADAPAYKQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR |
| 48 | M10 (ScFv domain) | QVQLVQSGAEVKKPGASVKVSCKASGYTFTSYGISWVRQAPGQGLEWMGWISAYNGNTNYAQKLQGRVTMTTDTSTSTAYMELRSLRSDDTAVYYCARVAGGIYYYYGMDVWGQGTTITVSSGGGGSGGGGSGGGGSGGGGSDIVMTQTPDSLAVSLGERATISCKSSHSVLYNRNNKNYLAWYQQKPGQPPKLLFYWASTRKSGVPDRFSGSGSGTDFTLTISSLQPEDFATYFCQQTQTFPLTFGQGTRLEIN |
| 72 | M10 >RE16-05MD (M10 RE16-05MD R001-D10 126170) | **MALPVTALLLPLALLLHAARP**QVQLVQSGAEVKKPGASVKVSCKASGYTFTSYGISWVRQAPGQGLEWMGWISAYNGNTNYAQKLQGRVTMTTDTSTSTAYMELRSLRSDDTAVYYCARVAGGIYYYYGMDVWGQGTTITVSSGGGGSGGGGSGGGGSGGGGSDIVMTQTPDSLAVSLGERATISCKSSHSVLYNRNNKNYLAWYQQKPGQPPKLLFYWASTRKSGVPDRFSGSGSGTDFTLTISSLQPEDFATYFCQQTQTFPLTFGQGTRLEINTTTPAPRPPTPAPTIASQPLSLRPEACRPAAGGAVHTRGLDFACDIYIWAPLAGTCGVLLLSLVITLYCKRGRKKLLYIFKQPFMRPVQTTQEEDGCSCRFPEEEEGGCELRVKFSRSADAPAYKQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR |
| 49 | M11 (ScFv domain) | QVQLQQSGAEVKKPGASVKVSCKASGYTFTGYYMHWVRQAPGQGLEWMGWINPNSGGTNYAQNFQGRVTMTRDTSISTAYMELRRLRSDDTAVYYCASGWDFDYWGQGTLVTVSSGGGGSGGGGSGGGGSGGGGSDIRMTQSPSSLSASVGDRVTITCRASQSIRYYLSWYQQKPGKAPKLLIYTASILQNGVPSRFSGSGSGTDFTLTISSLQPEDFATYYCLQTYTTPDFGPGTKVEIK |
| 73 | M11 >NE10-19WD (M11 NE10-19WD R001-G2 126171) | **MALPVTALLLPLALLLHAARP**QVQLQQSGAEVKKPGASVKVSCKASGYTFTGYYMHWVRQAPGQGLEWMGWINPNSGGTNYAQNFQGRVTMTRDTSISTAYMELRRLRSDDTAVYYCASGWDFDYWGQGTLVTVSSGGGGSGGGGSGGGGSGGGGSDIRMTQSPSSLSASVGDRVTITCRASQSIRYYLSWYQQKPGKAPKLLIYTASILQNGVPSRFSGSGSGTDFTLTISSLQPEDFATYYCLQTYTTPDFGPGTKVEIKTTTPAPRPPTPAPTIASQPLSLRPEACRPAAGGAVHTRGLDFACDIYIWAPLAGTCGVLLLSLVITLYCKRGRKKLLYIFKQPFMRPVQTTQEEDGCSCRFPEEEEGGCELRVKFSRSADAPAYKQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR |
| 50 | M12 (ScFv domain) | QVQLVQSGAEVKKPGASVKVSCKASGYTFTGYYMHWVRQAPGQGLEWMGRINPNSGGTNYAQKFQGRVTMTTDTSTSTAYMELRSLRSDDTAVYYCARTTTSYAFDIWGQGTMVTVSSGGGGSGGGGSGGGGSGGGGSDIQLTQSPSTLSASVGDRVTITCRASQSISTWLAWYQQKPGKAPNLLIYKASTLESGVPSRFSGSGSGTEFTLTISSLQPDDFATYYCQQYNTYSPYTFGQGTKLEIK |
| 74 | M12 >DE12-14RD (M12 DE12-14RD R001-G9 126172) | **MALPVTALLLPLALLLHAARP**QVQLVQSGAEVKKPGASVKVSCKASGYTFTGYYMHWVRQAPGQGLEWMGRINPNSGGTNYAQKFQGRVTMTTDTSTSTAYMELRSLRSDDTAVYYCARTTTSYAFDIWGQGTMVTVSSGGGGSGGGGSGGGGSGGGGSDIQLTQSPSTLSASVGDRVTITCRASQSISTWLAWYQQKPGKAPNLLIYKASTLESGVPSRFSGSGSGTEFTLTISSLQPDDFATYYCQQYNTYSPYTFGQGTKLEIKTTTPAPRPPTPAPTIASQPLSLRPEACRPAAGGAVHTRGLDFACDIYIWAPLAGTCGVLLLSLVITLYCKRGRKKLLYIFKQPFMRPVQTTQEEDGCSCRFPEEEEGGCELRVKFSRSADAPAYKQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR |
| 51 | M13 (ScFv domain) | QVQLVQSGGGLVKPGGSLRLSCEASGFIFSDYYMGWIRQAPGKGLEWVSYIGRSGSSMYYADSVKGRFTFSRDNAKNSLYLQMNSLRAEDTAVYYCAASPVVAATEDFQHWGQGTLVTVSSGGGGSGGGGSGGGGSGGGGSDIVMTQTPATLSLSPGERATLSCRASQSVTSNYLAWYQQKPGQAPRLLLFGASTRATGIPDRFSGSGSGTDFTLTINRLEPEDFAMYYCQQYGSAPVTFGQGTKLEIK |
| 75 | M13 >TE13-19LD (M13 TE13-19LD R002-C3 126173) | **MALPVTALLLPLALLLHAARP**QVQLVQSGGGLVKPGGSLRLSCEASGFIFSDYYMGWIRQAPGKGLEWVSYIGRSGSSMYYADSVKGRFTFSRDNAKNSLYLQMNSLRAEDTAVYYCAASPVVAATEDFQHWGQGTLVTVSSGGGGSGGGGSGGGGSGGGGSDIVMTQTPATLSLSPGERATLSCRASQSVTSNYLAWYQQKPGQAPRLLLFGASTRATGIPDRFSGSGSGTDFTLTINRLEPEDFAMYYCQQYGSAPVTFGQGTKLEIKTTTPAPRPPTPAPTIASQPLSLRPEACRPAAGGAVHTRGLDFACDIYIWAPLAGTCGVLLLSLVITLYCKRGRKKLLYIFKQPFMRPVQTTQEEDGCSCRFPEEEEGGCELRVKFSRSADAPAYKQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR |
| 52 | M14 (ScFv domain) | QVQLVQSGAEVRAPGASVKISCKASGFTFRGYYIHWVRQAPGQGLEWMGIINPSGGSRAYAQKFQGRVTMTRDTSTSTVYMELSSLRSDDTAMYYCARTASCGGDCYYLDYWGQGTLVTV |

TABLE 2-continued

Amino Acid Sequences of Human scFvs and CARs (bold underline is the leader sequence and
grey box is a linker sequence). In the case of the scFvs, the remaining amino acids are the heavy chain
variable region and light chain variable regions, with each of the HC CDRs (HC CDR1, HC CDR2, HC
CDR3) and LC CDRs (LC CDR1, LC CDR2, LCCDR3) underlined). In the case of the CARs, the
further remaining amino acids are the remaining amino acids of the CARs.)

| SEQ ID NO:Description | Amino Acid Sequence |
| --- | --- |
|  | SSGGGGSGGGGSGGGGSGGGGSDIQMTQSPPTLSASVGDRVTITC**RASENVNIWLAWYQQ** **KPGKAPKLLIYK**SSSLASGVPSRFSGSGSGAEFTLTISSLQPDDFATYYCQQYQSYPLTF GGGTKVDIK |
| 76 M14 >BS83-95ID (M14 BS83-95ID R001-E8 126174) | **MALPVTALLLPLALLLHAARP**QVQLVQSGAEVRAPGASVKISCKASGFTFRGYYIHWVRQ APGQGLEWMGIINPSGGSRAYAQKFQGRVTMTRDTSTSTVYMELSSLRSDDTAMYYCART ASCGGDCYYLDYWGQGTLVTVSSGGGGSGGGGSGGGGSGGGGSDIQMTQSPPTLSASVGD RVTITCRASENVNIWLAWYQQKPGKAPKLLIYKSSSLASGVPSRFSGSGSGAEFTLTISS LQPDDFATYYCQQYQSYPLTFGGGTKVDIKTTTTPAPRPPTPAPTIASQPLSLRPEACRPA AGGAVHTRGLDFACDIYIWAPLAGTCGVLLLSLVITLYCKRGRKKLLYIFKQPFMRPVQT TQEEDGCSCRFPEEEEGGCELRVKFSRSADAPAYKQGQNQLYNELNLGRREEYDVLDKRR GRDPEMGGKPRRKNPQEGLYNELQKDKMAEAYSEIGMKGERRRGKGHDGLYQGLSTATKD TYDALHMQALPPR |
| 53 M15 (ScFv domain) | QVQLVQSGGGLVQPGRSLRLSCAASGFTFDDYAMHWVRQAPGKGLEWVSGISWNSGSIGY ADSVKGRFTISRDNAKNSLYLQMNSLRAEDTAVYYCAKDGSSSWSWGYFDYWGQGTLVTV SSGGGGSGGGGSGGGGSSELTQDPAVSVALGQTVRTTCQGDALRSYYASWYQQKPGQAP MLVIYGKNNRPSGIPDRFSGSDSGDTASLTITGAQAEDEADYYCNSRDSSGYPVFGTGTK VTVL |
| 77 M15 >HS86-94XD (M15 HS86-94XD NT 127553) | **MALPVTALLLPLALLLHAARP**QVQLVQSGGGLVQPGRSLRLSCAASGFTFDDYAMHWVRQ APGKGLEWVSGISWNSGSIGYADSVKGRFTISRDNAKNSLYLQMNSLRAEDTAVYYCAKD GSSSWSWGYFDYWGQGTLVTVSSGGGGSGGGGSGGGGSSSELTQDPAVSVALGQTVRTTC QGDALRSYYASWYQQKPGQAPMLVIYGKNNRPSGIPDRFSGSDSGDTASLTITGAQAEDE ADYYCNSRDSSGYPVFGTGTKVTVLTTTTPAPRPPTPAPTIASQPLSLRPEACRPAAGGAV HTRGLDFACDIYIWAPLAGTCGVLLLSLVITLYCKRGRKKLLYIFKQPFMRPVQTTQEED GCSCRFPEEEEGGCELRVKFSRSADAPAYKQGQNQLYNELNLGRREEYDVLDKRRGRDPE MGGKPRRKNPQEGLYNELQKDKMAEAYSEIGMKGERRRGKGHDGLYQGLSTATKDTYDAL HMQALPPR |
| 54 M16 (ScFv domain) | EVQLVESGGGLVQPGRSLRLSCAASGFTFDDYAMHWVRQAPGKGLEWVSGISWNSGSTGY ADSVKGRFTISRDNAKNSLYLQMNSLRAEDTALYYCAKDSSSWYGGGSAFDIWGQGTMVT VSSGGGGSGGGGSGGGGSSSELTQEPAVSVALGQTVRITCQGDSLRSYYASWYQQKPGQA PVLVIFGRSRRPSGIPDRFSGSSSGNTASLIITGAQAEDEADYYCNSRDNTANHYVFGTG TKLTVL |
| 78 M16 >XS87-99RD (M16 XS87-99RD NT 127554) | **MALPVTALLLPLALLLHAARP**EVQLVESGGGLVQPGRSLRLSCAASGFTFDDYAMHWVRQ APGKGLEWVSGISWNSGSTGYADSVKGRFTISRDNAKNSLYLQMNSLRAEDTALYYCAKD SSSWYGGGSAFDIWGQGTMVTVSSGGGGSGGGGSGGGGSSSELTQEPAVSVALGQTVRIT CQGDSLRSYYASWYQQKPGQAPVLVIFGRSRRPSGIPDRFSGSSSGNTASLIITGAQAED EADYYCNSRDNTANHYVFGTGTKLTVLTTTTPAPRPPTPAPTIASQPLSLRPEACRPAAGG AVHTRGLDFACDIYIWAPLAGTCGVLLLSLVITLYCKRGRKKLLYIFKQPFMRPVQTTQE EDGCSCRFPEEEEGGCELRVKFSRSADAPAYKQGQNQLYNELNLGRREEYDVLDKRRGRD PEMGGKPRRKNPQEGLYNELQKDKMAEAYSEIGMKGERRRGKGHDGLYQGLSTATKDTYD ALHMQALPPR |
| 55 M17 (ScFv domain) | EVQLVESGGGLVQPGRSLRLSCAASGFTFDDYAMHWVRQAPGKGLEWVSGISWNSGSTGY ADSVKGRFTISRDNAKNSLYLQMNSLRAEDTALYYCAKDSSSWYGGGSAFDIWGQGTMVT VSSGGGGSGGGGSGGGGSSSELTQDPAVSVALGQTVRITCQGDSLRSYYASWYQQKPGQA PVLVIYGKNNRPSGIPDRFSGSSSGNTASLTITGAQAEDEADYYCNSRGSSGNHYVFGTG TKVTVL |
| 79 M17 >NS89-94MD (M17 N589-94MD NT 127555) | **MALPVTALLLPLALLLHAARP**EVQLVESGGGLVQPGRSLRLSCAASGFTFDDYAMHWVRQ APGKGLEWVSGISWNSGSTGYADSVKGRFTISRDNAKNSLYLQMNSLRAEDTALYYCAKD SSSWYGGGSAFDIWGQGTMVTVSSGGGGSGGGGSGGGGSSSELTQDPAVSVALGQTVRIT CQGDSLRSYYASWYQQKPGQAPVLVIYGKNNRPSGIPDRFSGSSSGNTASLTITGAQAED EADYYCNSRGSSGNHYVFGTGTKVTVLTTTTPAPRPPTPAPTIASQPLSLRPEACRPAAGG AVHTRGLDFACDIYIWAPLAGTCGVLLLSLVITLYCKRGRKKLLYIFKQPFMRPVQTTQE EDGCSCRFPEEEEGGCELRVKFSRSADAPAYKQGQNQLYNELNLGRREEYDVLDKRRGRD PEMGGKPRRKNPQEGLYNELQKDKMAEAYSEIGMKGERRRGKGHDGLYQGLSTATKDTYD ALHMQALPPR |
| 56 M18 (ScFv domain) | QVQLVQSGGGLVQPGGSLRLSCAASGFTFSSYWMHWVRQAPGKGLVWVSRINSDGSSTSY ADSVKGRFTISRDNAKNTLYLQMNSLRAEDTAVYYCVRTGWVGSYYYYMDVWGKGTTVTV SSGGGGSGGGGSGGGGSGGGGSEIVLTQSPGTLSLSPGERATLSCRASQSVSSNYLAWYQ QKPGQPPRLLIYDVSTRATGIPARFSGGGSGTDFTLTISSLEPEDFAVYYCQQRSNWPPW TFGQGTKVEIK |
| 80 M18 >D590-09HD | **MALPVTALLLPLALLLHAARP**QVQLVQSGGGLVQPGGSLRLSCAASGFTFSSYWMHWVRQ APGKGLVWVSRINSDGSSTSYADSVKGRFTISRDNAKNTLYLQMNSLRAEDTAVYYCVRT |

TABLE 2-continued

Amino Acid Sequences of Human scFvs and CARs (bold underline is the leader sequence and grey box is a linker sequence). In the case of the scFvs, the remaining amino acids are the heavy chain variable region and light chain variable regions, with each of the HC CDRs (HC CDR1, HC CDR2, HC CDR3) and LC CDRs (LC CDR1, LC CDR2, LCCDR3) underlined). In the case of the CARs, the further remaining amino acids are the remaining amino acids of the CARs.)

| SEQ ID NO: | Description | Amino Acid Sequence |
|---|---|---|
| | (M18 D590-09HD R003-A05 127556) | GWVGSYYYYMDVWGKGTTVTVSSGGGGSGGGGSGGGGSGGGGSEIVLTQSPGTLSLSPGERATLSCRASQSVSSNYLAWYQQKPGQPPRLLIYDVSTRATGIPARFSGGGSGTDFTLTISSLEPEDFAVYYCQQRSNWPPWTFGQGTKVEIKTTTPAPRPPTPAPTIASQPLSLRPEACRPAAGGAVHTRGLDFACDIYIWAPLAGTCGVLLLSLVITLYCKRGRKKLLYIFKQPFMRPVQTTQEEDGCSCRFPEEEEGGCELRVKFSRSADAPAYKQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR |
| 57 | M19 (ScFv domain) | QVQLVQSGGGVVQPGRSLRLSCAASGFTFSSYGMHWVRQAPGKGLEWVAVISYDGSNKYYADSVKGRFTISRDNSKNTLYLQMNSLRAEDTAVYYCAKGYSRYYYYGMDVWGQGTTVTVSSGGGGSGGGGSGGGGSGGGGSEIVMTQSPATLSLSPGERAILSCRASQSVYTKYLGWYQQKPGQAPRLLIYDASTRATGIPDRFSGSGSGTDFTLTINRLEPEDFAVYYCQHYGGSPLITFGQGTKVDIK |
| 81 | M19 >TS92-04BD (M19 T592-04BD R003-C06 127557) | **MALPVTALLLPLALLLHAARP**QVQLVQSGGGVVQPGRSLRLSCAASGFTFSSYGMHWVRQAPGKGLEWVAVISYDGSNKYYADSVKGRFTISRDNSKNTLYLQMNSLRAEDTAVYYCAKGYSRYYYYGMDVWGQGTTVTVSSGGGGSGGGGSGGGGSGGGGSEIVMTQSPATLSLSPGERAILSCRASQSVYTKYLGWYQQKPGQAPRLLIYDASTRATGIPDRFSGSGSGTDFTLTINRLEPEDFAVYYCQHYGGSPLITFGQGTKVDIKTTTPAPRPPTPAPTIASQPLSLRPEACRPAAGGAVHTRGLDFACDIYIWAPLAGTCGVLLLSLVITLYCKRGRKKLLYIFKQPFMRPVQTTQEEDGCSCRFPEEEEGGCELRVKFSRSADAPAYKQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR |
| 58 | M20 (ScFv domain) | QVQLVQSGGGLVQPGGSLRLSCAASGFTFSSYAMSWVRQAPGKGLEWVSAISGSGGSTYYADSVKGRFTISRDNSKNTLYLQMNSLRAEDTAVYYCAKREAAAGHDWYFDLWGRGTLVTVSSGGGGSGGGGSGGGGSGGGGSDIRVTQSPSSLSASVGDRVTITCRASQSISSYLNWYQQKPGKAPKLLIYAASSLQSGVPSRFSGSGSGTDFTLTISSLQPEDFATYYCQQSYSIPLTFGQGTKVEIK |
| 82 | M20 (full) >JS93-08WD (M20 JS93-08WD R003-E07 127558) | **MALPVTALLLPLALLLHAARP**QVQLVQSGGGLVQPGGSLRLSCAASGFTFSSYAMSWVRQAPGKGLEWVSAISGSGGSTYYADSVKGRFTISRDNSKNTLYLQMNSLRAEDTAVYYCAKREAAAGHDWYFDLWGRGTLVTVSSGGGGSGGGGSGGGGSGGGGSDIRVTQSPSSLSASVGDRVTITCRASQSISSYLNWYQQKPGKAPKLLIYAASSLQSGVPSRFSGSGSGTDFTLTISSLQPEDFATYYCQQSYSIPLTFGQGTKVEIKTTTPAPRPPTPAPTIASQPLSLRPEACRPAAGGAVHTRGLDFACDIYIWAPLAGTCGVLLLSLVITLYCKRGRKKLLYIFKQPFMRPVQTTQEEDGCSCREPEEEEGGCELRVKFSRSADAPAYKQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR |
| 59 | M21 (ScFv domain) | QVQLVQSWAEVKKPGASVKVSCKASGYTFTSYYMHWVRQAPGQGLEWMGIINPSGGSTSYAQKFQGRVTMTRDTSTSTVYMELSNLRSEDTAVYYCARSPRVTTGYFDYWGQGTLVTVSSGGGGSGGGGSGGGGSGGGGSDIQLTQSPSTLSASVGDRVTITCRASQSISSWLAWYQQKPGKAPKLLIYKASSLESGVPSRFSGSGSGTEFTLTISSLQPDDFATYYCQQYSSYPLTFGGGTRLEIK |
| 83 | M21 (full CAR) | **MALPVTALLLPLALLLHAARP**QVQLVQSWAEVKKPGASVKVSCKASGYTFTSYYMHWVRQAPGQGLEWMGIINPSGGSTSYAQKFQGRVTMTRDTSTSTVYMELSNLRSEDTAVYYCARSPRVTTGYFDYWGQGTLVTVSSGGGGSGGGGSGGGGSGGGGSDIQLTQSPSTLSASVGDRVTITCRASQSISSWLAWYQQKPGKAPKLLIYKASSLESGVPSRFSGSGSGTEFTLTISSLQPDDFATYYCQQYSSYPLTFGGGTRLEIKTTTPAPRPPTPAPTIASQPLSLRPEACRPAAGGAVHTRGLDFACDIYIWAPLAGTCGVLLLSLVITLYCKRGRKKLLYIFKQPFMRPVQTTQEEDGCSCREPEEEEGGCELRVKFSRSADAPAYKQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR |
| 60 | M22 (ScFv domain) | QVQLVQSGAEVRRPGASVKISCRASGDTSTRHYIHWLRQAPGQGPEWMGVINPTTGPATGSPAYAQMLQGRVTMTRDTSTRTVYMELRSLRFEDTAVYYCARSVVGRSAPYYFDYWGQGTLVTVSSGGGGSGGGGSGGGGSGGGGSDIQMTQSPSSLSASVGDRVTITCRASQGISDYSAWYQQKPGKAPKLLIYAASTLQSGVPSRFSGSGSGTDFTLTISYLQSEDFATYYCQQYYSYPLTFGGGTKVDIK |
| 84 | M22 (full CAR) | **MALPVTALLLPLALLLHAARP**QVQLVQSGAEVRRPGASVKISCRASGDTSTRHYIHWLRQAPGQGPEWMGVINPTTGPATGSPAYAQMLQGRVTMTRDTSTRTVYMELRSLRFEDTAVYYCARSVVGRSAPYYFDYWGQGTLVTVSSGGGGSGGGGSGGGGSGGGGSDIQMTQSPSSLSASVGDRVTITCRASQGISDYSAWYQQKPGKAPKLLIYAASTLQSGVPSRFSGSGSGTDFTLTISYLQSEDFATYYCQQYYSYPLTFGGGTKVDIKTTTPAPRPPTPAPTIASQPLSLRPEACRPAAGGAVHTRGLDFACDIYIWAPLAGTCGVLLLSLVITLYCKRGRKKLLYIFKQPFMRPVQTTQEEDGCSCREPEEEEGGCELRVKFSRSADAPAYKQGQNQLYNELNLGRREEYDVLDKRRGRDPEMGGKPRRKNPQEGLYNELQKDKMAEAYSEIGMKGERRRGKGHDGLYQGLST |

TABLE 2-continued

Amino Acid Sequences of Human scFvs and CARs (bold underline is the leader sequence and grey box is a linker sequence). In the case of the scFvs, the remaining amino acids are the heavy chain variable region and light chain variable regions, with each of the HC CDRs (HC CDR1, HC CDR2, HC CDR3) and LC CDRs (LC CDR1, LC CDR2, LCCDR3) underlined). In the case of the CARs, the further remaining amino acids are the remaining amino acids of the CARs.)

| SEQ ID NO: | Description | Amino Acid Sequence |
|---|---|---|
| | | ATKDTYDALHMQALPPR |
| 61 | M23 (ScFv domain) | QVQLQQSGAEVKKPGASVKVSCKASGYTFTNYYMHWVRQAPGQGLEWMGIINPSGGYTTY<br>AQKFQGRLTMTRDTSTSTVYMELSSLRSEDTAVYYCARIRSCGGDCYYFDNWGQGTLVTV<br>SSGGGGSGGGGSGGGGSGGGGSDIQLTQSPSTLSASVGDRVTITCRASENVNIWLAWYQQ<br>KPGKAPKLLIYKSSSLASGVPSRFSGSGSGAEFTLTISSLQPDDFATYYCQQYQSYPLTF<br>GGGTKVDIK |
| 85 | M23 (full CAR) | **MALPVTALLLPLALLLHAARP**QVQLQQSGAEVKKPGASVKVSCKASGYTFTNYYMHWVRQ<br>APGQGLEWMGIINPSGGYTTYAQKFQGRLTMTRDTSTSTVYMELSSLRSEDTAVYYCARI<br>RSCGGDCYYFDNWGQGTLVTVSSGGGGSGGGGSGGGGSGGGGSDIQLTQSPSTLSASVGD<br>RVTITCRASENVNIWLAWYQQKPGKAPKLLIYKSSSLASGVPSRFSGSGSGAEFTLTISS<br>LQPDDFATYYCQQYQSYPLTEGGGTKVDIKTTTPAPRPPTPAPTIASQPLSLRPEACRPA<br>AGGAVHTRGLDFACDIYIWAPLAGTCGVLLLSLVITLYCKRGRKKLLYIFKQPFMRPVQT<br>TQEEDGCSCREPEEEEGGCELRVKFSRSADAPAYKQGQNQLYNELNLGRREEYDVLDKRR<br>GRDPEMGGKPRRKNPQEGLYNELQKDKMAEAYSEIGMKGERRRGKGHDGLYQGLSTATKD<br>TYDALHMQALPPR |
| 62 | M24 (ScFv domain) | QITLKESGPALVKPTQTLTLTCTFSGFSLSTAGVHVGWIRQPPGKALEWLALISWADDKR<br>YRPSLRSRLDITRVTSKDQVVLSMTNMQPEDTATYYCALQGFDGYEANWGPGTLVTVSSG<br>GGGSGGGGSGGGGSGGGGSDIVMTQSPSSLSASAGDRVTITCRASRGISSALAWYQQKPG<br>KPPKLLIYDASSLESGVPSRFSGSGSGTDFTLTIDSLEPEDFATYYCQQSYSTPWTFGQG<br>TKVDIK |
| 86 | M24 (full CAR) | **MALPVTALLLPLALLLHAARP**QITLKESGPALVKPTQTLTLTCTFSGFSLSTAGVHVGWI<br>RQPPGKALEWLALISWADDKRYRPSLRSRLDITRVTSKDQVVLSMTNMQPEDTATYYCAL<br>QGFDGYEANWGPGTLVTVSSGGGGSGGGGSGGGGSGGGGSDIVMTQSPSSLSASAGDRVT<br>ITCRASRGISSALAWYQQKPGKPPKLLIYDASSLESGVPSRFSGSGSGTDFTLTIDSLEP<br>EDFATYYCQQSYSTPWTFGQGTKVDIKTTTPAPRPPTPAPTIASQPLSLRPEACRPAAGG<br>AVHTRGLDFACDIYIWAPLAGTCGVLLLSLVITLYCKRGRKKLLYIFKQPFMRPVQTTQE<br>EDGCSCRFPEEEEGGCELRVKFSRSADAPAYKQGQNQLYNELNLGRREEYDVLDKRRGRD<br>PEMGGKPRRKNPQEGLYNELQKDKMAEAYSEIGMKGERRRGKGHDGLYQGLSTATKDTYD<br>ALHMQALPPR |
| 275 | Ss1 (scFv domain) | QVQLQQSGPELEKPGASVKISCKASGYSFTGYTMNWVKQSHGKSLEWIGLITPYNGASS<br>YNQKFRGKATLTVDKSSSTAYMDLLSLTSEDSAVYFCARGGYDGRGFDYWGQGTTVTVS<br>SGGGGSGGGGSGGGGSDIELTQSPAIMSASPGEKVTMTCSASSSVSYMHWYQQKSGTSP<br>KRWIYDTSKLASGVPGRFSGSGSGNSYSLTISSVEAEDDATYYCQQWSGYPLTFGAGTK<br>LEI |
| 278 | Ss1 (full CAR) | **MALPVTALLLPLALLLHAARP**QVQLQQSGPELEKPGASVKISCKASGYSFTGYTMNWVK<br>QSHGKSLEWIGLITPYNGASSYNQKFRGKATLTVDKSSSTAYMDLLSLTSEDSAVYFCA<br>RGGYDGRGFDYWGQGTTVTVSSGGGGSGGGGSGGGGSDIELTQSPAIMSASPGEKVTMT<br>CSASSSVSYMHWYQQKSGTSPKRWIYDTSKLASGVPGRFSGSGSGNSYSLTISSVEAED<br>DATYYCQQWSGYPLTFGAGTKLEITTTPAPRPPTPAPTIASQPLSLRPEACRPAAGGAV<br>HTRGLDFACDIYIWAPLAGTCGVLLLSLVITLYCKRGRKKLLYIFKQPFMRPVQTTQEE<br>DGCSCRFPEEEEGGCELRVKFSRSADAPA |

TABLE 3

Nucleic Acid Sequences encoding CAR molecules (the leader sequence is underlined)

| SEQ ID NO: | Desc. | Nucleic Acid Sequence |
|---|---|---|
| 87 | M1 (ScFv domain) >ZA5 3-27BC (M1) | CAAGTCCAACTGCAGCAGTCAGGAGCGGAAGTGAAGAAACCAGGAGCGTCAGTCAAAGTGTCGTGCAAGGCTAGCGGCTAC<br>ACCTTCACCGGCTACTACATGCACTGGGTTCGACAGGCTCCAGGGCAGGGTCTGGAGTGGATGGGCCGCATCAACCCGAAT<br>TCCGGTGGGACTAACTACGCCCAGAAGTTCCAGGGAAGAGTGACCATGACTAGGGACACGTCGATCAGCACTGCGTACATG<br>GAACTGAGCCGCCTGCGGTCCGAGGATACTGCCGTCTACTACTGCGCACGCGGAAGGTACTATGGAATGGACGTGTGGGGC<br>CAAGGGACTATGGTGACTGTGAGCTCGGGAGGGGGAGGCTCCGGTGGCGGGGGATCAGGAGGAGGAGGATCAGGGGGAGGA<br>GGTTCCGAAATTGTCCTCACCCAGAGCCCGGCAACCCTCTCACTTTCCCCGGGAGAGCGCGCAACCATCTCTTGCCGGGCT<br>AGCCAATCCGTGTCGTCCAATTTCGCCTGGTACCAGCAACGGCCGGGACAAGCCCCTAGACTCCTGATCTACGACGCCAGC<br>AACAGAGCGACTGGAATTCCTCCACGCTTTTCGGGATCAGGCTCCGGTACCGACTTCACCCTGACTATCTCGTCGCTCGAA<br>CCCGAGGATTTCGCCGCCTACTACTGTCATCAGCGGTCGAACTGGTTGTATACGTTTGGCCAGGGCACCAAGGTGGATATC<br>AAG |

TABLE 3-continued

Nucleic Acid Sequences encoding CAR molecules (the leader sequence is underlined)

| SEQ ID NO: | Desc. | Nucleic Acid Sequence |
|---|---|---|
| 111 | M1<br>(Full)<br>>ZA5<br>3-<br>27BC<br>(M1) | ATGGCCCTCCCTGTCACCGCCCTGCTGCTTCCGCTGGCTCTTCTGCTCCACGCCGCTCGGCCCCAAGTCCAACTGCAGCAG<br>TCAGGAGCGGAAGTGAAGAAACCAGGAGCGTCAGTCAAAGTGTCGTGCAAGGCTAGCGGCTACACCTTCACCGGCTACTA<br>CATGCACTGGGTTCGACAGGCTCCAGGGCAGGGTCTGGAGTGGATGGGCCGCATCAACCCGAATTCCGGTGGGACTAACT<br>ACGCCCAGAAGTTCCAGGGAAGAGTGACCATGACTAGGGACACGTCGATCAGCACTGCGTACATGGAACTGAGCCGCCTG<br>CGGTCCGAGGATACTGCCGTCTACTACTGCGCACGCGGAAGGTACTATGGAATGGACGTGTGGGGCCAAGGGACTATGGT<br>GACTGTGAGCTCGGGAGGGGGAGGCTCCGGTGGCGGGGGATCAGGAGGAGGAGGATCAGGGGGAGGAGGTTCCGAAATTG<br>TCCTCACCCAGAGCCCGGCAACCCTCTCACTTTCCCCGGGAGAGCGCGCAACCATCTCTTGCCGGGCTAGCCAATCCGTG<br>TCGTCCAATTTCGCCTGGTACCAGCAACGGCCGGGACAAGCCCCTAGACTCCTGATCTACGACGCCAGCAACAGAGCGAC<br>TGGAATTCCTCCACGCTTTTCGGGATCAGGCTCCGGTACCGACTTCACCCTGACTATCTCGTCGCTCGAACCCGAGGATT<br>TCGCCGCCTACTACTGTCATCAGCGGTCGAACTGGTTGTATACGTTTGGCCAGGGCACCAAGGTGGATATCAAGACCACT<br>ACCCCAGCACCGAGGCCACCCACCCCGGCTCCTACCATCGCCTCCCAGCCTCTGTCCCTGCGTCCGGAGGCATGTAGACC<br>CGCAGCTGGTGGGGCCGTGCATACCCGGGGTCTTGACTTCGCCTGCGATATCTACATTTGGGCCCCTCTGGCTGGTACTT<br>GCGGGGTCCTGCTGCTTTCACTCGTGATCACTCTTTACTGTAAGCGCGGTCGGAAGAAGCTGCTGTACATCTTTAAGCAA<br>CCCTTCATGAGGCCTGTGCAGACTACTCAAGAGGAGGACGGCTGTTCATGCCGGTTCCCAGAGGAGGAGGAAGGCGGCTG<br>CGAACTGCGCGTGAAATTCAGCCGCAGCGCAGATGCTCCAGCCTACAAGCAGGGGCAGAACCAGCTCTACAACGAACTCA<br>ATCTTGGTCGGAGAGAGGAGTACGACGTGCTGGACAAGCGGAGAGGACGGGACCCAGAAATGGGCGGGAAGCCGCGCAGA<br>AAGAATCCCCAAGAGGGCCTGTACAACGAGCTCCAAAAGGATAAGATGGCAGAAGCCTATAGCGAGATTGGTATGAAAGG<br>GGAACGCAGAAGAGGCAAAGGCCACGACGGACTGTACCAGGGACTCAGCACCGCCACCAAGGACACCTATGACGCTCTTC<br>ACATGCAGGCCCTGCCGCCTCGG |
| 88 | M2<br>(ScFv<br>domain)<br>>FA5<br>6-<br>26RC<br>(M2) | CAAGTCCAACTCGTCCAGTCAGGAGCAGAAGTCAAGAAACCAGGTGCTAGCGTGAAAGTGTCGTGCAAGGCGTCGGGATAC<br>ACTTTCACCGGATACTAC<br>ATGCACTGGGTCCGCCAGGCCCCCGGACAAGGACTGGAATGGATGGGCTGGATCAACCCGAATAGCGGGGGAACTAATTA<br>CGCCCAGAAGTTTCAGGGACGAGTGACCATGACCCGCGATACCTCTATCTCGACCGCCTACATGGAGCTCTCCAGACTGC<br>GCTCCGACGATACTGCAGTGTACTACTGCGCCCGGGACCTGAGGCGGACTGTGGTTACTCCTCGCGCCTATTATGGCATG<br>GACGTGTGGGGCCAAGGAACTACTGTGACTGTGAGCTCGGGAGGCGGTGGGTCAGGCGGAGGAGGGTCGGGCGGTGGTGG<br>CTCGGGAGGGGGAGGAAGCGACATTCAACTTACGCAGAGCCCGTCAACCCTGTCAGCGTCAGTGGGAGATCGGGTGACCA<br>TCACGTGTCAGGCCAGCCAGGATATCTCCAACTCGCTCAACTGGTACCAGCAAAAGGCGGGTAAAGCTCCGAAGCTGCTG<br>ATCTACGACGCTTCCACCCTCGAGACTGGAGTCCCATCCAGATTTTCCGGGTCAGGAAGCGGCACCGATTTCTCCTTCAC<br>CATTTCGTCCTTGCAACCGGAGGACATCGCAACCTACTACTGCCAGCAGCATGACAACTTGCCTCTGACGTTCGGGCAGG<br>GCACCAAGGTGGAAATCAAG |
| 112 | M2<br>(Full)<br>>FA5<br>6-<br>26RC<br>(M2) | ATGGCCCTCCCTGTCACCGCCCTGCTGCTTCCGCTGGCTCTTCTGCTCCACGCCGCTCGGCCCCAAGTCCAACTCGTCCAG<br>TCAGGAGCAGAAGTCAAGAAACCAGGTGCTAGCGTGAAAGTGTCGTGCAAGGCGTCGGGATACACTTTCACCGGATACTAC<br>ATGCACTGGGTCCGCCAGGCCCCCGGACAAGGACTGGAATGGATGGGCTGGATCAACCCGAATAGCGGGGGAACTAATTA<br>CGCCCAGAAGTTTCAGGGACGAGTGACCATGACCCGCGATACCTCTATCTCGACCGCCTACATGGAGCTCTCCAGACTGC<br>GCTCCGACGATACTGCAGTGTACTACTGCGCCCGGGACCTGAGGCGGACTGTGGTTACTCCTCGCGCCTATTATGGCATG<br>GACGTGTGGGGCCAAGGAACTACTGTGACTGTGAGCTCGGGAGGCGGTGGGTCAGGCGGAGGAGGGTCGGGCGGTGGTGG<br>CTCGGGAGGGGGAGGAAGCGACATTCAACTTACGCAGAGCCCGTCAACCCTGTCAGCGTCAGTGGGAGATCGGGTGACCA<br>TCACGTGTCAGGCCAGCCAGGATATCTCCAACTCGCTCAACTGGTACCAGCAAAAGGCGGGTAAAGCTCCGAAGCTGCTG<br>ATCTACGACGCTTCCACCCTCGAGACTGGAGTCCCATCCAGATTTTCCGGGTCAGGAAGCGGCACCGATTTCTCCTTCAC<br>CATTTCGTCCTTGCAACCGGAGGACATCGCAACCTACTACTGCCAGCAGCATGACAACTTGCCTCTGACGTTCGGGCAGG<br>GCACCAAGGTGGAAATCAAG**ACCACTACC**CCAGCACCGAGGCCACCCACCCCGGCTCCTACCATCGCCTCCCAGCCTCTG<br>TCCCTGCGTCCGGAGGCATGTAGACCCGCAGCTGGTGGGGCCGTGCATACCCGGGGTCTTGACTTCGCCTGCGATATCTA<br>CATTTGGGCCCCTCTGGCTGGTACTTGCGGGGTCCTGCTGCTTTCACTCGTGATCACTCTTTACTGTAAGCGCGGTCGGA<br>AGAAGCTGCTGTACATCTTTAAGCAACCCTTCATGAGGCCTGTGCAGACTACTCAAGAGGAGGACGGCTGTTCATGCCGG<br>TTCCCAGAGGAGGAGGAAGGCGGCTGCGAACTGCGCGTGAAATTCAGCCGCAGCGCAGATGCTCCAGCCTACAAGCAGGG<br>GCAGAACCAGCTCTACAACGAACTCAATCTTGGTCGGAGAGAGGAGTACGACGTGCTGGACAAGCGGAGAGGACGGGACC<br>CAGAAATGGGCGGGAAGCCGCGCAGAAAGAATCCCCAAGAGGGCCTGTACAACGAGCTCCAAAAGGATAAGATGGCAGAA<br>GCCTATAGCGAGATTGGTATGAAAGGGGAACGCAGAAGAGGCAAAGGCCACGACGGACTGTACCAGGGACTCAGCACCGC<br>CACCAAGGACACCTATGACGCTCTTCACATGCAGGCCCTGCCGCCTCGG |
| 89 | M3<br>(ScFv<br>domain)<br>>VA5<br>8-<br>21LC<br>(M3) | CAAGTCCAACTCGTCCAA<br>TCAGGAGCGGAAGTCAAAAAGCCCGGAGCTCCAGTGAAAGTGTCATGCAAGGCCTCCGGCTACACCTTCACCGGTTACTA<br>TATGCACTGGGTGCGGCAGGCCCCGGGCCAGGGGTTGGAATGGATGGGATGGATCAATCCAAACTCGGGTGGGACTAACT<br>ACGCCCAGAAGTTCCAAGGACGGGTGACCATGACTAGGGACACCTCGATCTCCACCGCATACATGGAGCTTAGCAGACTC<br>CGCTCCGACGATACCGCAGTCTACTATTGCGCGCGGGGAGAGTGGGACGGATCGTACTACTACGATTACTGGGGCCAGGG<br>AACTCTGGTGACTGTTTCCTCGGGTGGAGGAGGTTCAGGCGGAGGCGGCTCGGGCGGGGGAGGATCTGGAGGAGGAGGGT<br>CCGACATTGTGCTGACCCAAACTCCTTCGTCCCTGTCGGCCAGCGTGGGCGACCGCGTGACGATTACGTGCAGAGCTAGC<br>CAATCCATCAATACTTACCTCAACTGGTACCAGCATAAGCCGGGGAAAGCACCAAAGCTGCTGATCTACGCCGCCTCATC<br>CTTGCAGAGCGGTGTGCCTTCACGCTTTAGCGGATCGGGATCGGGAACGGATTTCACCCTGACTATCAGCTCCCTCCAGC<br>CGGAGGATTTTGCGACCTACTACTGTCAGCAGAGCTTCTCACCGCTGACTTTCGGCGGCGGGACCAAGCTGGAAATCAAG |
| 113 | M3<br>(Full)<br>>VA5<br>8-<br>21LC<br>(M3) | ATGGCCCTCCCTGTCACCGCCCTGCTGCTTCCGCTGGCTCTTCTGCTCCACGCCGCTCGGCCCCAAGTCCAACTCGTCCAA<br>TCAGGAGCGGAAGTCAAAAAGCCCGGAGCTCCAGTGAAAGTGTCATGCAAGGCCTCCGGCTACACCTTCACCGGTTACTA<br>TATGCACTGGGTGCGGCAGGCCCCGGGCCAGGGGTTGGAATGGATGGGATGGATCAATCCAAACTCGGGTGGGACTAACT<br>ACGCCCAGAAGTTCCAAGGACGGGTGACCATGACTAGGGACACCTCGATCTCCACCGCATACATGGAGCTTAGCAGACTC<br>CGCTCCGACGATACCGCAGTCTACTATTGCGCGCGGGGAGAGTGGGACGGATCGTACTACTACGATTACTGGGGCCAGGG<br>AACTCTGGTGACTGTTTCCTCGGGTGGAGGAGGTTCAGGCGGAGGCGGCTCGGGCGGGGGAGGATCTGGAGGAGGAGGGT<br>CCGACATTGTGCTGACCCAAACTCCTTCGTCCCTGTCGGCCAGCGTGGGCGACCGCGTGACGATTACGTGCAGAGCTAGC<br>CAATCCATCAATACTTACCTCAACTGGTACCAGCATAAGCCGGGGAAAGCACCAAAGCTGCTGATCTACGCCGCCTCATC<br>CTTGCAGAGCGGTGTGCCTTCACGCTTTAGCGGATCGGGATCGGGAACGGATTTCACCCTGACTATCAGCTCCCTCCAGC<br>CGGAGGATTTTGCGACCTACTACTGTCAGCAGAGCTTCTCACCGCTGACTTTCGGCGGCGGGACCAAGCTGGAAATCAAG<br>**ACCACTACC**CCAGCACCGAGGCCACCCACCCCGGCTCCTACCATCGCCTCCCAGCCTCTGTCCCTGCGTCCGGAGGCATG |

TABLE 3-continued

Nucleic Acid Sequences encoding CAR molecules (the leader sequence is underlined)

| SEQ ID NO: | Desc. | Nucleic Acid Sequence |
|---|---|---|
| | | TAGACCCGCAGCTGGTGGGGCCGTGCATACCCGGGGTCTTGACTTCGCCTGCGATATCTACATTTGGGCCCCTCTGGCTG<br>GTACTTGCGGGGTCCTGCTGCTTTCACTCGTGATCACTCTTTACTGTAAGCGCGGTCGGAAGAAGCTGCTGTACATCTTT<br>AAGCAACCCTTCATGAGGCCTGTGCAGACTACTCAAGAGGAGGACGGCTGTTCATGCCGGTTCCCAGAGGAGGAGGAAGG<br>CGGCTGCGAACTGCGCGTGAAATTCAGCCGCAGCGCAGATGCTCCAGCCTACAAGCAGGGGCAGAACCAGCTCTACAACG<br>AACTCAATCTTGGTCGGAGAGAGGAGTACGACGTGCTGGACAAGCGGAGAGGACGGGACCCAGAAATGGGCGGGAAGCCG<br>CGCAGAAAGAATCCCCAAGAGGGCCTGTACAACGAGCTCCAAAAGGATAAGATGGCAGAAGCCTATAGCGAGATTGGTAT<br>GAAAGGGGAACGCAGAAGAGGCAAAGGCCACGACGGACTGTACCAGGGACTCAGCACCGCCACCAAGGACACCTATGACG<br>CTCTTCACATGCAGGCCCTGCCGCCTCGG |
| 90 | M4<br>(ScFv<br>domain)<br>>DP3<br>7-<br>07IC<br>(M4) | CAAGTGCAACTCGTTGAA<br>TCAGGTGGAGGTTTGGTGCAACCCGGAGGATCTCTCAGACTGTCGTGTGCGGCGTCCGGGTTCACCTTTTCGTCCTACTG<br>GATGCACTGGGTGCGCCAGGTGCCGGGAAAAGGACTGGTGTGGGTGTCCAGAATCAACACCGACGGGTCAACGACTACCT<br>ACGCAGATAGCGTGGAAGGTCGGTTCACCATTTCGCGGGACAACGCTAAAAACACTCTGTACCTTCAGATGAATTCACTG<br>CGCGATGACGACACCGCAGTCTACTACTGCGTCGGTGGACACTGGGCGGTCTGGGGACAGGGAACTACGGTGACTGTGTC<br>CAGCGGCGGGGGAGGAAGCGGCGGAGGGGGGAGCGGAGGCGGAGGATCAGGAGGAGGCGGCTCCGATATCCAGATGACCC<br>AGTCGCCATCGACCCTCTCCGCTAGCGTGGGGGATAGGGTCACTATCACTTGCCGAGCCAGCCAATCCATTAGCGACCGG<br>CTTGCCTGGTACCAACAGAAACCTGGAAAGGCCCCGAAGCTGCTCATCTACAAGGCCTCGTCACTGGAGTCGGGAGTCCC<br>GTCCCGCTTTTCCGGCTCGGGCTCAGGCACCGAGTTCACTCTGACCATCTCGAGCCTGCAGCCGGACGATTTCGCCGTGT<br>ATTACTGCCAGCAATACGGACATCTCCCAATGTACACGTTCGGTCAGGGCACCAAGGTCGAAATCAAG |
| 114 | M4<br>>DP3<br>7-<br>07IC<br>(M4) | ATGGCCCTCCCTGTCACCGCCCTGCTGCTTCCGCTGGCTCTTCTGCTCCACGCCGCTCGGCCCCAAGTGCAACTCGTTGAA<br>TCAGGTGGAGGTTTGGTGCAACCCGGAGGATCTCTCAGACTGTCGTGTGCGGCGTCCGGGTTCACCTTTTCGTCCTACTG<br>GATGCACTGGGTGCGCCAGGTGCCGGGAAAAGGACTGGTGTGGGTGTCCAGAATCAACACCGACGGGTCAACGACTACCT<br>ACGCAGATAGCGTGGAAGGTCGGTTCACCATTTCGCGGGACAACGCTAAAAACACTCTGTACCTTCAGATGAATTCACTG<br>CGCGATGACGACACCGCAGTCTACTACTGCGTCGGTGGACACTGGGCGGTCTGGGGACAGGGAACTACGGTGACTGTGTC<br>CAGCGGCGGGGGAGGAAGCGGCGGAGGGGGGAGCGGAGGCGGAGGATCAGGAGGAGGCGGCTCCGATATCCAGATGACCC<br>AGTCGCCATCGACCCTCTCCGCTAGCGTGGGGGATAGGGTCACTATCACTTGCCGAGCCAGCCAATCCATTAGCGACCGG<br>CTTGCCTGGTACCAACAGAAACCTGGAAAGGCCCCGAAGCTGCTCATCTACAAGGCCTCGTCACTGGAGTCGGGAGTCCC<br>GTCCCGCTTTTCCGGCTCGGGCTCAGGCACCGAGTTCACTCTGACCATCTCGAGCCTGCAGCCGGACGATTTCGCCGTGT<br>ATTACTGCCAGCAATACGGACATCTCCCAATGTACACGTTCGGTCAGGGCACCAAGGTCGAAATCAAG**ACCACTACC**CCA<br>GCACCGAGGCCACCCACCCCGGCTCCTACCATCGCCTCCCAGCCTCTGTCCCTGCGTCCGGAGGCATGTAGACCCGCAGC<br>TGGTGGGGCCGTGCATACCCGGGGTCTTGACTTCGCCTGCGATATCTACATTTGGGCCCCTCTGGCTGGTACTTGCGGGG<br>TCCTGCTGCTTTCACTCGTGATCACTCTTTACTGTAAGCGCGGTCGGAAGAAGCTGCTGTACATCTTTAAGCAACCCTTC<br>ATGAGGCCTGTGCAGACTACTCAAGAGGAGGACGGCTGTTCATGCCGGTTCCCAGAGGAGGAGGAAGGCGGCTGCGAACT<br>GCGCGTGAAATTCAGCCGCAGCGCAGATGCTCCAGCCTACAAGCAGGGGCAGAACCAGCTCTACAACGAACTCAATCTTG<br>GTCGGAGAGAGGAGTACGACGTGCTGGACAAGCGGAGAGGACGGGACCCAGAAATGGGCGGGAAGCCGCGCAGAAAGAAT<br>CCCCAAGAGGGCCTGTACAACGAGCTCCAAAAGGATAAGATGGCAGAAGCCTATAGCGAGATTGGTATGAAAGGGGAACG<br>CAGAAGAGGCAAAGGCCACGACGGACTGTACCAGGGACTCAGCACCGCCACCAAGGACACCTATGACGCTCTTCACATGC<br>AGGCCCTGCCGCCTCGG |
| 91 | M5<br>(ScFv<br>domain)<br>>XP3<br>1-<br>20LC<br>(M5) | CAAGTCCAACTCGTTCAATCAGGCGCAGAAGTCGAAAAGCCCGGAGCATCAGTCAAAGTCTCTTGCAAGGCTTCCGGCTAC<br>ACCTTCACGGACTACTAC<br>ATGCACTGGGTGCGCCAGGCTCCAGGCCAGGGACTGGAGTGGATGGGATGGATCAACCCGAATTCCGGGGGAACTAACTA<br>CGCCCAGAAGTTTCAGGGCCGGGTGACTATGACTCGCGATACCTCGATCTCGACTGCGTACATGGAGCTCAGCCGCCTCC<br>GGTCGGACGATACCGCCGTGTACTATTGTGCGTCGGGATGGGACTTCGACTACTGGGGGCAGGGCACTCTGGTCACTGTG<br>TCAAGCGGAGGAGGTGGATCAGGTGGAGGTGGAAGCGGGGGAGGAGGTTCCGGCGGCGGAGGATCAGATATCGTGATGAC<br>GCAATCGCCTTCCTCGTTGTCCGCATCCGTGGGAGACAGGGTGACCATTACTTGCAGAGCGTCCCAGTCCATTCGGTACT<br>ACCTGTCGTGGTACCAGCAGAAGCCGGGGAAAGCCCCAAAACTGCTTATCTATACTGCCTCGATCCTCCAAAACGGCGTG<br>CCATCAAGATTCAGCGGTTCGGGCAGCGGGACCGACTTTACCCTGACTATCAGCAGCCTGCAGCCGGAAGATTTCGCCAC<br>GTACTACTGCCTGCAAACCTACACCACCCCGGACTTCGGACCTGGAACCAAGGTGGAGATCAAG |
| 115 | M5<br>(Full)<br>>XP3<br>1-<br>20LC<br>(M5) | ATGGCCCTCCCTGTCACCGCCCTGCTGCTTCCGCTGGCTCTTCTGCTCCACGCCGCTCGGCCCCAAGTCCAACTCGTTCAA<br>TCAGGCGCAGAAGTCGAAAAGCCCGGAGCATCAGTCAAAGTCTCTTGCAAGGCTTCCGGCTACACCTTCACGGACTACTAC<br>ATGCACTGGGTGCGCCAGGCTCCAGGCCAGGGACTGGAGTGGATGGGATGGATCAACCCGAATTCCGGGGGAACTAACTA<br>CGCCCAGAAGTTTCAGGGCCGGGTGACTATGACTCGCGATACCTCGATCTCGACTGCGTACATGGAGCTCAGCCGCCTCC<br>GGTCGGACGATACCGCCGTGTACTATTGTGCGTCGGGATGGGACTTCGACTACTGGGGGCAGGGCACTCTGGTCACTGTG<br>TCAAGCGGAGGAGGTGGATCAGGTGGAGGTGGAAGCGGGGGAGGAGGTTCCGGCGGCGGAGGATCAGATATCGTGATGAC<br>GCAATCGCCTTCCTCGTTGTCCGCATCCGTGGGAGACAGGGTGACCATTACTTGCAGAGCGTCCCAGTCCATTCGGTACT<br>ACCTGTCGTGGTACCAGCAGAAGCCGGGGAAAGCCCCAAAACTGCTTATCTATACTGCCTCGATCCTCCAAAACGGCGTG<br>CCATCAAGATTCAGCGGTTCGGGCAGCGGGACCGACTTTACCCTGACTATCAGCAGCCTGCAGCCGGAAGATTTCGCCAC<br>GTACTACTGCCTGCAAACCTACACCACCCCGGACTTCGGACCTGGAACCAAGGTGGAGATCAAG**ACCACTACC**CCAGCAC<br>CGAGGCCACCCACCCCGGCTCCTACCATCGCCTCCCAGCCTCTGTCCCTGCGTCCGGAGGCATGTAGACCCGCAGCTGGT<br>GGGGCCGTGCATACCCGGGGTCTTGACTTCGCCTGCGATATCTACATTTGGGCCCCTCTGGCTGGTACTTGCGGGGTCCT<br>GCTGCTTTCACTCGTGATCACTCTTTACTGTAAGCGCGGTCGGAAGAAGCTGCTGTACATCTTTAAGCAACCCTTCATGA<br>GGCCTGTGCAGACTACTCAAGAGGAGGACGGCTGTTCATGCCGGTTCCCAGAGGAGGAGGAAGGCGGCTGCGAACTGCGC<br>GTGAAATTCAGCCGCAGCGCAGATGCTCCAGCCTACAAGCAGGGGCAGAACCAGCTCTACAACGAACTCAATCTTGGTCG<br>GAGAGAGGAGTACGACGTGCTGGACAAGCGGAGAGGACGGGACCCAGAAATGGGCGGGAAGCCGCGCAGAAAGAATCCCC<br>AAGAGGGCCTGTACAACGAGCTCCAAAAGGATAAGATGGCAGAAGCCTATAGCGAGATTGGTATGAAAGGGGAACGCAGA<br>AGAGGCAAAGGCCACGACGGACTGTACCAGGGACTCAGCACCGCCACCAAGGACACCTATGACGCTCTTCACATGCAGGC<br>CCTGCCGCCTCGG |
| 92 | M6<br>(ScFv<br>domain) | CAAGTGCAACTCGTCCAGTCAGGTGCAGAAGTGAAGAAACCCGGAGCGTCAGTCAAAGTGTCATGCAAGGCGTCAGGCTAC<br>ACCTTCACCAGCTACTAC<br>ATGCACTGGGTGCGGCAGGCCCCAGGCCAAGGCTTGGAGTGGATGGGAATCATTAACCCGTCAGGAGGCTCCACCTCCTA |

TABLE 3-continued

| Nucleic Acid Sequences encoding CAR molecules (the leader sequence is underlined) | | |
|---|---|---|
| SEQ ID NO: | Desc. | Nucleic Acid Sequence |
| | >FE1 0- 06ID (M6) | CGCCCAGAAGTTTCAGGGAAGAGTGACGATGACTCGGGATACGTCGACCTCGACCGTGTACATGGAACTGAGCTCGCTGC<br>GCTCCGAGGACACTGCTGTGTACTACTGCGCACGGTACAGACTCATTGCCGTGGCAGGAGACTACTACTACTATGGCATG<br>GACGTCTGGGGGCAGGGCACTATGGTCACTGTGTCGTCCGGCGGAGGAGGCTCGGGTGGAGGAGGTAGCGGAGGAGGGGG<br>AAGCGGAGGGGGGGGCTCCGATATCCAGATGACTCAGTCGCCTTCCTCCGTGTCGGCCTCGGTTGGAGATCGCGTCACCA<br>TCACTTGTCGAGCTTCCCAAGGAGTCGGTAGGTGGCTGGCGTGGTACCAGCAAAAGCCGGGAACTGCCCCGAAGCTCCTG<br>ATCTACGCGGCTAGCACCCTGCAGTCGGGAGTGCCATCCCGCTTCAGCGGATCTGGGTCAGGTACCGACTTCACCCTTAC<br>GATCAACAATCTCCAGCCGGAGGACTTTGCCACCTATTACTGCCAACAGGCCAACAGCTTCCCTCTGACTTTCGGAGGGG<br>GCACTCGCCTGGAAATCAAG |
| 116 | M6 (Full) >FE1 0- 06ID (M6) | ATGGCCCTCCCTGTCACCGCCCTGCTGCTTCCGCTGGCTCTTCTGCTCCACGCCGCTCGGCCCCAAGTGCAACTCGTCCAG<br>TCAGGTGCAGAAGTGAAGAAACCCGGAGCGTCAGTCAAAGTGTCATGCAAGGCGTCAGGCTACACCTTCACCAGCTACTAC<br>ATGCACTGGGTGCGGCAGGCCCCAGGCCAAGGCTTGGAGTGGATGGGAATCATTAACCCGTCAGGAGGCTCCACCTCCTA<br>CGCCCAGAAGTTTCAGGGAAGAGTGACGATGACTCGGGATACGTCGACCTCGACCGTGTACATGGAACTGAGCTCGCTGC<br>GCTCCGAGGACACTGCTGTGTACTACTGCGCACGGTACAGACTCATTGCCGTGGCAGGAGACTACTACTACTATGGCATG<br>GACGTCTGGGGGCAGGGCACTATGGTCACTGTGTCGTCCGGCGGAGGAGGCTCGGGTGGAGGAGGTAGCGGAGGAGGGGG<br>AAGCGGAGGGGGGGGCTCCGATATCCAGATGACTCAGTCGCCTTCCTCCGTGTCGGCCTCGGTTGGAGATCGCGTCACCA<br>TCACTTGTCGAGCTTCCCAAGGAGTCGGTAGGTGGCTGGCGTGGTACCAGCAAAAGCCGGGAACTGCCCCGAAGCTCCTG<br>ATCTACGCGGCTAGCACCCTGCAGTCGGGAGTGCCATCCCGCTTCAGCGGATCTGGGTCAGGTACCGACTTCACCCTTAC<br>GATCAACAATCTCCAGCCGGAGGACTTTGCCACCTATTACTGCCAACAGGCCAACAGCTTCCCTCTGACTTTCGGAGGGG<br>GCACTCGCCTGGAAATCAAG**ACCACTACC**CCAGCACCGAGGCCACCCACCCCGGCTCCTACCATCGCCTCCCAGCCTCTG<br>TCCCTGCGTCCGGAGGCATGTAGACCCGCAGCTGGTGGGGCCGTGCATACCCGGGGTCTTGACTTCGCCTGCGATATCTA<br>CATTTGGGCCCCTCTGGCTGGTACTTGCGGGGTCCTGCTGCTTTCACTCGTGATCACTCTTTACTGTAAGCGCGGTCGGA<br>AGAAGCTGCTGTACATCTTTAAGCAACCCTTCATGAGGCCTGTGCAGACTACTCAAGAGGAGGACGGCTGTTCATGCCGG<br>TTCCCAGAGGAGGAGGAAGGCGGCTGCGAACTGCGCGTGAAATTCAGCCGCAGCGCAGATGCTCCAGCCTACAAGCAGGG<br>GCAGAACCAGCTCTACAACGAACTCAATCTTGGTCGGAGAGAGGAGTACGACGTGCTGGACAAGCGGAGAGGACGGGACC<br>CAGAAATGGGCGGGAAGCCGCGCAGAAAGAATCCCCAAGAGGGCCTGTACAACGAGCTCCAAAAGGATAAGATGGCAGAA<br>GCCTATAGCGAGATTGGTATGAAAGGGGAACGCAGAAGAGGCAAAGGCCACGACGGACTGTACCAGGGACTCAGCACCGC<br>CACCAAGGACACCTATGACGCTCTTCACATGCAGGCCCTGCCGCCTCGG |
| 93 | M7 (ScFv domain) >VE1 2- 01CD (M7) | CAAGTGCAATTGGTTCAA<br>TCAGGAGGAGGAGTGGTGCAACCTGGAAGATCTCTCAGACTGTCGTGTGCGGCATCGGGATTCACTTTCTCATCATACGC<br>AATGCACTGGGTCCGCCAGGCCCCGGGCAAAGGCTTGGAATGGGTGGCGGTCATTTCATACGACGGCTCGAACAAGTACT<br>ACGCTGACAGCGTGAAGGGACGCTTTACTATTTCCCGGGACAATTCGAAGAACACTCTGTACCTCCAGATGAACTCCCTT<br>AGGGCTGAGGACACCGCCGTCTACTACTGCGCACGCTGGAAAGTGTCGTCCAGCTCCCCAGCTTTTGACTACTGGGGACA<br>GGGAACCCTTGTGACCGTGTCGTCCGGTGGAGGGGGAAGCGGCGGAGGGGGATCAGGTGGCGGCGGATCGGGAGGCGGGG<br>GATcAGAAATcGTGcTGAcTcAGTccccGGccAcGcTGTcTcTcAGcccGGGAGAGAGAGcGATccTGTccTGccGcGcc<br>TCGCAGAGCGTGTACACTAAGTACCTGGGGTGGTACCAGCAGAAACCGGGTCAAGCGCCTCGGCTGCTGATCTACGATGC<br>CTCCACCCGGGCCACCGGAATCCCCGATCGGTTCTCCGGCAGCGGCTCGGGAACTGATTTCACGCTGACCATCAATCGCC<br>TGGAGCCGGAAGATTTCGCCGTCTATTACTGCCAGCATTACGGCGGGAGCCCACTCATCACCTTCGGTCAAGGAACCCGA<br>CTCGAAATCAAG |
| 117 | M7 (Full) >VE1 2- 01CD (M7) | ATGGCCCTCCCTGTCACCGCCCTGCTGCTTCCGCTGGCTCTTCTGCTCCACGCCGCTCGGCCCCAAGTGCAATTGGTTCAA<br>TCAGGAGGAGGAGTGGTGCAACCTGGAAGATCTCTCAGACTGTCGTGTGCGGCATCGGGATTCACTTTCTCATCATACGC<br>AATGCACTGGGTCCGCCAGGCCCCGGGCAAAGGCTTGGAATGGGTGGCGGTCATTTCATACGACGGCTCGAACAAGTACT<br>ACGCTGACAGCGTGAAGGGACGCTTTACTATTTCCCGGGACAATTCGAAGAACACTCTGTACCTCCAGATGAACTCCCTT<br>AGGGCTGAGGACACCGCCGTCTACTACTGCGCACGCTGGAAAGTGTCGTCCAGCTCCCCAGCTTTTGACTACTGGGGACA<br>GGGAACCCTTGTGACCGTGTCGTCCGGTGGAGGGGGAAGCGGCGGAGGGGGATCAGGTGGCGGCGGATCGGGAGGCGGGG<br>GATCAGAAATCGTGCTGACTCAGTCCCCGGCCACGCTGTCTCTCAGCCCGGGAGAGAGAGCGATCCTGTCCTGCCGCGCC<br>TCGCAGAGCGTGTACACTAAGTACCTGGGGTGGTACCAGCAGAAACCGGGTCAAGCGCCTCGGCTGCTGATCTACGATGC<br>CTCCACCCGGGCCACCGGAATCCCCGATCGGTTCTCCGGCAGCGGCTCGGGAACTGATTTCACGCTGACCATCAATCGCC<br>TGGAGCCGGAAGATTTCGCCGTCTATTACTGCCAGCATTACGGCGGGAGCCCACTCATCACCTTCGGTCAAGGAACCCGA<br>CTCGAAATCAAG**ACCACTACC**CCAGCACCGAGGCCACCCACCCCGGCTCCTACCATCGCCTCCCAGCCTCTGTCCCTGCG<br>TCCGGAGGCATGTAGACCCGCAGCTGGTGGGGCCGTGCATACCCGGGGTCTTGACTTCGCCTGCGATATCTACATTTGGG<br>CCCCTCTGGCTGGTACTTGCGGGGTCCTGCTGCTTTCACTCGTGATCACTCTTTACTGTAAGCGCGGTCGGAAGAAGCTG<br>CTGTACATCTTTAAGCAACCCTTCATGAGGCCTGTGCAGACTACTCAAGAGGAGGACGGCTGTTCATGCCGGTTCCCAGA<br>GGAGGAGGAAGGCGGCTGCGAACTGCGCGTGAAATTCAGCCGCAGCGCAGATGCTCCAGCCTACAAGCAGGGGCAGAACC<br>AGCTCTACAACGAACTCAATCTTGGTCGGAGAGAGGAGTACGACGTGCTGGACAAGCGGAGAGGACGGGACCCAGAAATG<br>GGCGGGAAGCCGCGCAGAAAGAATCCCCAAGAGGGCCTGTACAACGAGCTCCAAAAGGATAAGATGGCAGAAGCCTATAG<br>CGAGATTGGTATGAAAGGGGAACGCAGAAGAGGCAAAGGCCACGACGGACTGTACCAGGGACTCAGCACCGCCACCAAGG<br>ACACCTATGACGCTCTTCACATGCAGGCCCTGCCGCCTCGG |
| 94 | M8 (ScFv domain) >LE1 3- 05XD (M8) | CAAGTCCAACTCCAGCAG<br>TCAGGTGCAGAAGTCAAAAAGCCAGGAGCATCCGTGAAGGTTTCGTGCAAGACTTCCGGCTACCCTTTTACCGGGTACTC<br>CCTCCATTGGGTGAGACAAGCACCGGGCCAGGGACTGGAGTGGATGGGATGGATCAACCCAAATTCGGGCGGCACCAACT<br>ATGCGCAGAAGTTCCAGGGACGGGTGACCATGACTCGCGACACTTCGATCTCCACTGCCTACATGGAGCTGTCCCGCTTG<br>AGATCTGACGACACGGCCGTCTACTACTGCGCCCGGGATCACTACGGAGGTAATTCGCTGTTCTACTGGGGGCAGGGAAC<br>CCTTGTGACTGTGTCCTCGGGTGGTGGAGGGTCAGGAGGCGGAGGCTCAGGGGGAGGAGGTAGCGGAGGAGGCGGATCAG<br>ACATCCAACTGACCCAGTCACCATCCTCCATCTCGGCTAGCGTCGGAGACACCGTGTCGATTACTTGTAGGGCCTCCCAA<br>GACTCAGGGACGTGGCTGGCGTGGTATCAGCAAAAACCGGGCAAAGCTCCGAACCTGTTGATGTACGACGCCAGCACCCT<br>CGAAGATGGAGTGCCTAGCCGCTTCAGCGGAAGCGCCTCGGGCACTGAATTCACGCTGACTGTGAATCGGCTCCAGCCGG<br>AGGATTCGGCGACCTACTACTGCCAGCAGTACAACAGCTACCCCCTGACCTTTGGAGGCGGGACCAAGGTGGATATCAAG |
| 118 | M8 (Full) | ATGGCCCTCCCTGTCACCGCCCTGCTGCTTCCGCTGGCTCTTCTGCTCCACGCCGCTCGGCCCCAAGTCCAACTCCAGCAG<br>TCAGGTGCAGAAGTCAAAAAGCCAGGAGCATCCGTGAAGGTTTCGTGCAAGACTTCCGGCTACCCTTTTACCGGGTACTC |

TABLE 3-continued

Nucleic Acid Sequences encoding CAR molecules (the leader sequence is underlined)

| SEQ ID NO: | Desc. | Nucleic Acid Sequence |
|---|---|---|
| | >LE1<br>3-<br>05XD<br>(M8) | CCTCCATTGGGTGAGACAAGCACCGGGCCAGGGACTGGAGTGGATGGGATGGATCAACCCAAATTCGGGCGGCACCAACT<br>ATGCGCAGAAGTTCCAGGGACGGGTGACCATGACTCGCGACACTTCGATCTCCACTGCCTACATGGAGCTGTCCCGCTTG<br>AGATCTGACGACACGGCCGTCTACTACTGCGCCCGGGATCACTACGGAGGTAATTCGCTGTTCTACTGGGGGCAGGGAAC<br>CCTTGTGACTGTGTCCTCGGGTGGTGGAGGGTCAGGAGGCGGAGGCTCAGGGGGAGGAGGTAGCGGAGGAGGCGGATCAG<br>ACATCCAACTGACCCAGTCACCATCCTCCATCTCGGCTAGCGTCGGAGACACCGTGTCGATTACTTGTAGGGCCTCCCAA<br>GACTCAGGGACGTGGCTGGCGTGGTATCAGCAAAAACCGGGCAAAGCTCCGAACCTGTTGATGTACGACGCCAGCACCCT<br>CGAAGATGGAGTGCCTAGCCGCTTCAGCGGAAGCGCCTCGGGCACTGAATTCACGCTGACTGTGAATCGGCTCCAGCCGG<br>AGGATTCGGCGACCTACTACTGCCAGCAGTACAACAGCTACCCCCTGACCTTTGGAGGCGGGACCAAGGTGGATATCAAG<br>**ACCACTACC**CCAGCACCGAGGCCACCCACCCCGGCTCCTACCATCGCCTCCCAGCCTCTGTCCCTGCGTCCGGAGGCATG<br>TAGACCCGCAGCTGGTGGGGCCGTGCATACCCGGGGTCTTGACTTCGCCTGCGATATCTACATTTGGGCCCCTCTGGCTG<br>GTACTTGCGGGGTCCTGCTGCTTTCACTCGTGATCACTCTTTACTGTAAGCGCGGTCGGAAGAAGCTGCTGTACATCTTT<br>AAGCAACCCTTCATGAGGCCTGTGCAGACTACTCAAGAGGAGGACGGCTGTTCATGCCGGTTCCCAGAGGAGGAGGAAGG<br>CGGCTGCGAACTGCGCGTGAAATTCAGCCGCAGCGCAGATGCTCCAGCCTACAAGCAGGGGCAGAACCAGCTCTACAACG<br>AACTCAATCTTGGTCGGAGAGAGGAGTACGACGTGCTGGACAAGCGGAGAGGACGGGACCCAGAAATGGGCGGGAAGCCG<br>CGCAGAAAGAATCCCCAAGAGGGCCTGTACAACGAGCTCCAAAAGGATAAGATGGCAGAAGCCTATAGCGAGATTGGTAT<br>GAAAGGGGAACGCAGAAGAGGCAAAGGCCACGACGGACTGTACCAGGGACTCAGCACCGCCACCAAGGACACCTATGACG<br>CTCTTCACATGCAGGCCCTGCCGCCTCGG |
| 95 | M9<br>(ScFv<br>domain)<br>>BE1<br>5-<br>00SD<br>(M9) | CAAGTGCAACTCGTCCAG<br>TCAGGTGCAGAAGTGAAGAAACCAGGAGCGTCCGTCGAAGTGTCGTGTAAGGCGTCCGGCTACACTTTCACCTCGTACTA<br>CATGCACTGGGTGCGGCAGGCCCCGGGACAAGGCCTCGAATGGATGGGAATCATCAACCCGAGCGGAGGCTCGACTGGTT<br>ACGCCCAGAAGTTCCAGGGAAGGGTGACGATGACCCGCGATACCTCGACTTCGACCGTTCATATGGAGCTCTCGTCCCTG<br>CGGAGCGAGGACACTGCTGTCTACTATTGCGCGCGGGGAGGATACTCTAGCTCCTCCGATGCATTTGACATTTGGGGCCA<br>GGGAACTATGGTGACCGTGTCATCAGGCGGAGGTGGATCAGGAGGAGGAGGGTCGGGAGGGGGAGGCAGCGGCGGGGGTG<br>GGTCGGACATTCAGATGACGCAGTCCCCTCCTAGCCTGAGCGCCTCGGTGGGTGACAGAGTGACCATCACTTGCAGAGCC<br>TCGCAAGACATCTCCTCCGCATTGGCTTGGTACCAGCAAAAGCCGGGCACTCCGCCGAAACTGCTCATCTACGATGCCTC<br>CTCACTGGAGTCAGGAGTCCCATCTCGCTTCTCGGGGTCAGGAAGCGGCACCGATTTTACCCTTACCATCTCCAGCCTGC<br>AGCCCGAGGACTTCGCCACGTACTACTGCCAACAGTTCAGCTCCTACCCACTGACCTTCGGGGGCGGAACTCGCCTGGAA<br>ATCAAG |
| 119 | M9<br>(Full)<br>>BE1<br>5-<br>00SD<br>(M9) | ATGGCCCTCCCTGTCACCGCCCTGCTGCTTCCGCTGGCTCTTCTGCTCCACGCCGCTCGGCCCCAAGTGCAACTCGTCCAG<br>TCAGGTGCAGAAGTGAAGAAACCAGGAGCGTCCGTCGAAGTGTCGTGTAAGGCGTCCGGCTACACTTTCACCTCGTACTA<br>CATGCACTGGGTGCGGCAGGCCCCGGGACAAGGCCTCGAATGGATGGGAATCATCAACCCGAGCGGAGGCTCGACTGGTT<br>ACGCCCAGAAGTTCCAGGGAAGGGTGACGATGACCCGCGATACCTCGACTTCGACCGTTCATATGGAGCTCTCGTCCCTG<br>CGGAGCGAGGACACTGCTGTCTACTATTGCGCGCGGGGAGGATACTCTAGCTCCTCCGATGCATTTGACATTTGGGGCCA<br>GGGAACTATGGTGACCGTGTCATCAGGCGGAGGTGGATCAGGAGGAGGAGGGTCGGGAGGGGGAGGCAGCGGCGGGGGTG<br>GGTCGGACATTCAGATGACGCAGTCCCCTCCTAGCCTGAGCGCCTCGGTGGGTGACAGAGTGACCATCACTTGCAGAGCC<br>TCGCAAGACATCTCCTCCGCATTGGCTTGGTACCAGCAAAAGCCGGGCACTCCGCCGAAACTGCTCATCTACGATGCCTC<br>CTCACTGGAGTCAGGAGTCCCATCTCGCTTCTCGGGGTCAGGAAGCGGCACCGATTTTACCCTTACCATCTCCAGCCTGC<br>AGCCCGAGGACTTCGCCACGTACTACTGCCAACAGTTCAGCTCCTACCCACTGACCTTCGGGGGCGGAACTCGCCTGGAA<br>ATCAAG**ACCACTACC**CCAGCACCGAGGCCACCCACCCCGGCTCCTACCATCGCCTCCCAGCCTCTGTCCCTGCGTCCGGA<br>GGCATGTAGACCCGCAGCTGGTGGGGCCGTGCATACCCGGGGTCTTGACTTCGCCTGCGATATCTACATTTGGGCCCCTCT<br>GGCTGGTACTTGCGGGGTCCTGCTGCTTTCACTCGTGATCACTCTTTACTGTAAGCGCGGTCGGAAGAAGCTGCTGTAC<br>ATCTTTAAGCAACCCTTCATGAGGCCTGTGCAGACTACTCAAGAGGAGGACGGCTGTTCATGCCGGTTCCCAGAGGAGGA<br>GGAAGGCGGCTGCGAACTGCGCGTGAAATTCAGCCGCAGCGCAGATGCTCCAGCCTACAAGCAGGGGCAGAACCAGCTCT<br>ACAACGAACTCAATCTTGGTCGGAGAGAGGAGTACGACGTGCTGGACAAGCGGAGAGGACGGGACCCAGAAATGGGCGGG<br>AAGCCGCGCAGAAAGAATCCCCAAGAGGGCCTGTACAACGAGCTCCAAAAGGATAAGATGGCAGAAGCCTATAGCGAGAT<br>TGGTATGAAAGGGGAACGCAGAAGAGGCAAAGGCCACGACGGACTGTACCAGGGACTCAGCACCGCCACCAAGGACACCT<br>ATGACGCTCTTCACATGCAGGCCCTGCCGCCTCGG |
| 96 | M10<br>(ScFv<br>domain)<br>>RE1<br>6-<br>05MD<br>(M10) | CAAGTGCAACTCGTCCAGAGCGGAGCAGAAGTCAAGAAGCCAGGAGCGTCAGTGAAAGTGTCATGCAAGGCCAGCGGCTAT<br>ACCTTTACTTCGTATGGG<br>ATCTCCTGGGTGCGGCAGGCACCGGGCCAAGGACTGGAGTGGATGGGATGGATCTCAGCCTACAACGGTAACACCAACTA<br>CGCCCAGAAGCTGCAAGGACGCGTGACCATGACTACTGATACGAGCACCTCCACTGCCTACATGGAATTGCGGTCCCTTC<br>GGTCGGACGATACTGCTGTGTACTACTGCGCAAGAGTCGCCGGAGGGATCTACTACTACTACGGCATGGACGTCTGGGGA<br>CAGGGAACCACCATTACGGTGTCGAGCGGAGGGGGAGGCTCGGGGGGAGGAGGAAGCGGAGGTGGCGGCTCCGGGGGCGG<br>CGGATCGGACATTGTGATGACCCAGACTCCTGACTCCCTGGCTGTTTCGTTGGGAGAGCGCGCGACTATCTCGTGTAAGT<br>CCAGCCACTCAGTCCTGTACAATCGCAATAACAAGAACTACCTCGCGTGGTACCAGCAAAAACCGGGTCAGCCGCCTAAA<br>CTCCTGTTCTACTGGGCCTCCACCAGAAAGAGCGGGGTGCCAGATCGATTCTCTGGATCAGGATCAGGTACCGACTTTAC<br>GCTGACCATCTCGTCCCTGCAGCCGGAGGATTTCGCGACTTACTTCTGCCAGCAGACTCAGACTTTCCCCCTCACCTTCG<br>GTCAAGGCACCAGGCTGGAAATCAAT |
| 120 | M10<br>(Full)<br>>RE1<br>6-<br>05MD<br>(M10) | ATGGCCCTCCCTGTCACCGCCCTGCTGCTTCCGCTGGCTCTTCTGCTCCACGCCGCTCGGCCCCAAGTGCAACTCGTCCAG<br>AGCGGAGCAGAAGTCAAGAAGCCAGGAGCGTCAGTGAAAGTGTCATGCAAGGCCAGCGGCTATACCTTTACTTCGTATGGG<br>ATCTCCTGGGTGCGGCAGGCACCGGGCCAAGGACTGGAGTGGATGGGATGGATCTCAGCCTACAACGGTAACACCAACTA<br>CGCCCAGAAGCTGCAAGGACGCGTGACCATGACTACTGATACGAGCACCTCCACTGCCTACATGGAATTGCGGTCCCTTC<br>GGTCGGACGATACTGCTGTGTACTACTGCGCAAGAGTCGCCGGAGGGATCTACTACTACTACGGCATGGACGTCTGGGGA<br>CAGGGAACCACCATTACGGTGTCGAGCGGAGGGGGAGGCTCGGGGGGAGGAGGAAGCGGAGGTGGCGGCTCCGGGGGCGG<br>CGGATCGGACATTGTGATGACCCAGACTCCTGACTCCCTGGCTGTTTCGTTGGGAGAGCGCGCGACTATCTCGTGTAAGT<br>CCAGCCACTCAGTCCTGTACAATCGCAATAACAAGAACTACCTCGCGTGGTACCAGCAAAAACCGGGTCAGCCGCCTAAA<br>CTCCTGTTCTACTGGGCCTCCACCAGAAAGAGCGGGGTGCCAGATCGATTCTCTGGATCAGGATCAGGTACCGACTTTAC<br>GCTGACCATCTCGTCCCTGCAGCCGGAGGATTTCGCGACTTACTTCTGCCAGCAGACTCAGACTTTCCCCCTCACCTTCG<br>GTCAAGGCACCAGGCTGGAAATCAAT**ACCACTACC**CCAGCACCGAGGCCACCCACCCCGGCTCCTACCATCGCCTCCCAG<br>CCTCTGTCCCTGCGTCCGGAGGCATGTAGACCCGCAGCTGGTGGGGCCGTGCATACCCGGGGTCTTGACTTCGCCTGCGA |

TABLE 3-continued

Nucleic Acid Sequences encoding CAR molecules (the leader sequence is underlined)

| SEQ ID NO: | Desc. | Nucleic Acid Sequence |
|---|---|---|
| | | TATCTACATTTGGGCCCCTCTGGCTGGTACTTGCGGGGTCCTGCTGCTTTCACTCGTGATCACTCTTTACTGTAAGCGCG<br>GTCGGAAGAAGCTGCTGTACATCTTTAAGCAACCCTTCATGAGGCCTGTGCAGACTACTCAAGAGGAGGACGGCTGTTCA<br>TGCCGGTTCCCAGAGGAGGAGGAAGGCGGCTGCGAACTGCGCGTGAAATTCAGCCGCAGCGCAGATGCTCCAGCCTACAA<br>GCAGGGGCAGAACCAGCTCTACAACGAACTCAATCTTGGTCGGAGAGAGGAGTACGACGTGCTGGACAAGCGGAGAGGAC<br>GGGACCCAGAAATGGGCGGGAAGCCGCGCAGAAAGAATCCCCAAGAGGGCCTGTACAACGAGCTCCAAAAGGATAAGATG<br>GCAGAAGCCTATAGCGAGATTGGTATGAAAGGGGAACGCAGAAGAGGCAAAGGCCACGACGGACTGTACCAGGGACTCAG<br>CACCGCCACCAAGGACACCTATGACGCTCTTCACATGCAGGCCCTGCCGCCTCGG |
| 97 | M11 (ScFv domain) >NE1 0-19WD (M11) | CAAGTCCAATTGCAGCAGAGCGGAGCAGAAGTGAAGAAGCCAGGAGCGTCAGTCAAAGTGTCGTGTAAGGCGTCAGGATAC<br>ACCTTCACGGGATACTAC<br>ATGCACTGGGTGCGCCAGGCCCCGGGCCAAGGACTCGAGTGGATGGGCTGGATCAACCCTAACTCTGGAGGCACCAACTA<br>CGCCCAGAATTTCCAAGGCAGAGTGACCATGACCCGGGACACCTCCATCTCGACTGCCTATATGGAACTGCGGCGGCTGC<br>GCTCGGACGATACTGCTGTGTATTACTGCGCCAGCGGCTGGGACTTTGACTACTGGGGACAGGGTACTCTGGTGACTGTT<br>TCCTCGGGAGGAGGCGGATCGGGTGGAGGAGGTAGCGGGGGAGGGGGGTCGGGAGGCGGAGGCAGCGATATTCGCATGAC<br>TCAATCGCCGTCCTCCCTGAGCGCTAGCGTGGGAGATCGAGTCACCATCACTTGCAGAGCGTCACAGTCGATTCGCTACT<br>ACCTGTCCTGGTACCAGCAGAAACCGGGAAAGGCACCAAAGCTTCTGATCTACACGGCCTCCATCCTGCAAAATGGTGTC<br>CCATCAAGGTTCTCCGGGTCAGGGAGCGGCACTGACTTCACTCTCACCATCTCCTCACTCCAGCCCGAGGACTTTGCAAC<br>CTACTACTGCCTCCAGACGTACACCACCCCGGATTTCGGTCCTGGAACCAAGGTGGAAATCAAA |
| 121 | M11 (Full) >NE1 0-19WD (M11) | ATGGCCCTCCCTGTCACCGCCCTGCTGCTTCCGCTGGCTCTTCTGCTCCACGCCGCTCGGCCCCAAGTCCAATTGCAGCAG<br>AGCGGAGCAGAAGTGAAGAAGCCAGGAGCGTCAGTCAAAGTGTCGTGTAAGGCGTCAGGATACACCTTCACGGGATACTAC<br>ATGCACTGGGTGCGCCAGGCCCCGGGCCAAGGACTCGAGTGGATGGGCTGGATCAACCCTAACTCTGGAGGCACCAACTA<br>CGCCCAGAATTTCCAAGGCAGAGTGACCATGACCCGGGACACCTCCATCTCGACTGCCTATATGGAACTGCGGCGGCTGC<br>GCTCGGACGATACTGCTGTGTATTACTGCGCCAGCGGCTGGGACTTTGACTACTGGGGACAGGGTACTCTGGTGACTGTT<br>TCCTCGGGAGGAGGCGGATCGGGTGGAGGAGGTAGCGGGGGAGGGGGGTCGGGAGGCGGAGGCAGCGATATTCGCATGAC<br>TCAATCGCCGTCCTCCCTGAGCGCTAGCGTGGGAGATCGAGTCACCATCACTTGCAGAGCGTCACAGTCGATTCGCTACT<br>ACCTGTCCTGGTACCAGCAGAAACCGGGAAAGGCACCAAAGCTTCTGATCTACACGGCCTCCATCCTGCAAAATGGTGTC<br>CCATCAAGGTTCTCCGGGTCAGGGAGCGGCACTGACTTCACTCTCACCATCTCCTCACTCCAGCCCGAGGACTTTGCAAC<br>CTACTACTGCCTCCAGACGTACACCACCCCGGATTTCGGTCCTGGAACCAAGGTGGAAATCAAA**ACCACTACC**CCAGCAC<br>CGAGGCCACCCACCCCGGCTCCTACCATCGCCTCCCAGCCTCTGTCCCTGCGTCCGGAGGCATGTAGACCCGCAGCTGGT<br>GGGGCCGTGCATACCCGGGGTCTTGACTTCGCCTGCGATATCTACATTTGGGCCCCTCTGGCTGGTACTTGCGGGGTCCT<br>GCTGCTTTCACTCGTGATCACTCTTTACTGTAAGCGCGGTCGGAAGAAGCTGCTGTACATCTTTAAGCAACCCTTCATGA<br>GGCCTGTGCAGACTACTCAAGAGGAGGACGGCTGTTCATGCCGGTTCCCAGAGGAGGAGGAAGGCGGCTGCGAACTGCGC<br>GTGAAATTCAGCCGCAGCGCAGATGCTCCAGCCTACAAGCAGGGGCAGAACCAGCTCTACAACGAACTCAATCTTGGTCG<br>GAGAGAGGAGTACGACGTGCTGGACAAGCGGAGAGGACGGGACCCAGAAATGGGCGGGAAGCCGCGCAGAAAGAATCCCC<br>AAGAGGGCCTGTACAACGAGCTCCAAAAGGATAAGATGGCAGAAGCCTATAGCGAGATTGGTATGAAAGGGGAACGCAGA<br>AGAGGCAAAGGCCACGACGGACTGTACCAGGGACTCAGCACCGCCACCAAGGACACCTATGACGCTCTTCACATGCAGGC<br>CCTGCCGCCTCGG |
| 98 | M12 (ScFv domain) >DE1 2-14RD (M12) | CAAGTCCAACTCGTCCAA<br>AGCGGAGCAGAAGTCAAAAAGCCAGGAGCGTCGGTGAAAGTGTCTTGCAAAGCCAGCGGCTACACCTTCACGGGTTACTA<br>CATGCACTGGGTGCGCCAGGCGCCGGGCCAGGGGCTGGAGTGGATGGGCCGGATTAACCCTAACAGCGGGGGAACTAATT<br>ACGCTCAGAAGTTCCAGGGTAGAGTCACCATGACTACGGACACTTCCACTTCCACCGCCTATATGGAACTGCGCTCCCTC<br>CGCTCAGATGATACTGCCGTGTATTACTGCGCGCGGACTACCACGTCATACGCATTTGACATCTGGGGCCAGGGAACTAT<br>GGTGACCGTGAGCTCGGGCGGAGGCGGTTCAGGGGGAGGAGGAAGCGGAGGAGGAGGATCGGGAGGAGGTGGCTCCGATA<br>TCCAGCTGACTCAGTCCCCGAGCACCCTGTCGGCGTCGGTGGGGGACAGGGTTACCATCACCTGTAGAGCTTCCCAATCC<br>ATTTCGACTTGGCTGGCCTGGTACCAGCAAAAGCCGGGAAAGGCCCCTAATTTGCTTATCTACAAGGCATCGACCCTCGA<br>AAGCGGTGTGCCCTCCCGGTTTTCGGGATCAGGATCAGGGACCGAGTTCACCCTGACCATCTCATCCCTCCAGCCGGACG<br>ACTTCGCCACTTACTACTGCCAGCAGTACAACACCTACTCGCCATACACTTTCGGCCAAGGCACCAAGCTGGAGATCAAG |
| 122 | M12 (Full) >DE1 2-14RD (M12) | ATGGCCCTCCCTGTCACCGCCCTGCTGCTTCCGCTGGCTCTTCTGCTCCACGCCGCTCGGCCCCAAGTCCAACTCGTCCAA<br>AGCGGAGCAGAAGTCAAAAAGCCAGGAGCGTCGGTGAAAGTGTCTTGCAAAGCCAGCGGCTACACCTTCACGGGTTACTA<br>CATGCACTGGGTGCGCCAGGCGCCGGGCCAGGGGCTGGAGTGGATGGGCCGGATTAACCCTAACAGCGGGGGAACTAATT<br>ACGCTCAGAAGTTCCAGGGTAGAGTCACCATGACTACGGACACTTCCACTTCCACCGCCTATATGGAACTGCGCTCCCTC<br>CGCTCAGATGATACTGCCGTGTATTACTGCGCGCGGACTACCACGTCATACGCATTTGACATCTGGGGCCAGGGAACTAT<br>GGTGACCGTGAGCTCGGGCGGAGGCGGTTCAGGGGGAGGAGGAAGCGGAGGAGGAGGATCGGGAGGAGGTGGCTCCGATA<br>TCCAGCTGACTCAGTCCCCGAGCACCCTGTCGGCGTCGGTGGGGGACAGGGTTACCATCACCTGTAGAGCTTCCCAATCC<br>ATTTCGACTTGGCTGGCCTGGTACCAGCAAAAGCCGGGAAAGGCCCCTAATTTGCTTATCTACAAGGCATCGACCCTCGA<br>AAGCGGTGTGCCCTCCCGGTTTTCGGGATCAGGATCAGGGACCGAGTTCACCCTGACCATCTCATCCCTCCAGCCGGACG<br>ACTTCGCCACTTACTACTGCCAGCAGTACAACACCTACTCGCCATACACTTTCGGCCAAGGCACCAAGCTGGAGATCAAG<br>**ACCACTACC**CCAGCACCGAGGCCACCCACCCCGGCTCCTACCATCGCCTCCCAGCCTCTGTCCCTGCGTCCGGAGGCATG<br>TAGACCCGCAGCTGGTGGGGCCGTGCATACCCGGGGTCTTGACTTCGCCTGCGATATCTACATTTGGGCCCCTCTGGCTG<br>GTACTTGCGGGGTCCTGCTGCTTTCACTCGTGATCACTCTTTACTGTAAGCGCGGTCGGAAGAAGCTGCTGTACATCTTT<br>AAGCAACCCTTCATGAGGCCTGTGCAGACTACTCAAGAGGAGGACGGCTGTTCATGCCGGTTCCCAGAGGAGGAGGAAGG<br>CGGCTGCGAACTGCGCGTGAAATTCAGCCGCAGCGCAGATGCTCCAGCCTACAAGCAGGGGCAGAACCAGCTCTACAACG<br>AACTCAATCTTGGTCGGAGAGAGGAGTACGACGTGCTGGACAAGCGGAGAGGACGGGACCCAGAAATGGGCGGGAAGCCG<br>CGCAGAAAGAATCCCCAAGAGGGCCTGTACAACGAGCTCCAAAAGGATAAGATGGCAGAAGCCTATAGCGAGATTGGTAT<br>GAAAGGGGAACGCAGAAGAGGCAAAGGCCACGACGGACTGTACCAGGGACTCAGCACCGCCACCAAGGACACCTATGACG<br>CTCTTCACATGCAGGCCCTGCCGCCTCGG |
| 99 | M13 (ScFv domain) >TE1 | CAAGTTCAACTCGTGCAATCAGGTGGAGGACTCGTCAAACCCGGAGGATCATTGAGACTGTCATGCGAAGCGAGCGGTTTT<br>ATCTTCTCCGATTACTAT<br>ATGGGATGGATTCGGCAGGCCCCGGGAAAGGGACTCGAATGGGTGTCATACATCGGAAGGTCAGGCTCGTCCATGTACTA<br>CGCAGACTCGGTGAAAGGCAGATTCACCTTTAGCCGGGACAACGCCAAGAATTCCCTCTACTTGCAGATGAACAGCCTGC |

TABLE 3-continued

Nucleic Acid Sequences encoding CAR molecules (the leader sequence is underlined)

| SEQ ID NO: | Desc. | Nucleic Acid Sequence |
|---|---|---|
| | 3- | GAGCCGAGGATACTGCTGTCTACTACTGTGCCGCGTCGCCGGTGGTGGCAGCTACTGAAGATTTCCAGCACTGGGGACAG |
| | 19LD | GGAACTCTGGTCACGGTGTCGAGCGGTGGGGGCGGAAGCGGAGGCGGAGGATCGGGCGGCGGAGGTTCGGGGGGGGGAGG |
| | (M13) | GTCTGACATCGTGATGACCCAAACCCCAGCCACCCTGAGCCTCTCCCCTGGAGAGCGCGCGACTCTTTCGTGCCGCGCTT |
| | | CCCAGTCAGTGACCAGCAATTACTTGGCTTGGTACCAACAGAAGCCGGGACAGGCGCCACGGCTGCTGCTTTTTGGTGCC |
| | | AGCACTCGCGCCACCGGAATCCCGGATCGCTTCTCGGGCTCAGGGTCCGGGACGGACTTCACCCTGACTATCAACCGGCT |
| | | GGAACCTGAGGACTTCGCGATGTACTACTGCCAGCAGTACGGCTCCGCACCAGTCACTTTCGGACAAGGCACCAAGCTGG |
| | | AGATCAAG |
| 123 | M13 | ATGGCCCTCCCTGTCACCGCCCTGCTGCTTCCGCTGGCTCTTCTGCTCCACGCCGCTCGGCCCCAAGTTCAACTCGTGCAA |
| | (Full) | TCAGGTGGAGGACTCGTCAAACCCGGAGGATCATTGAGACTGTCATGCGAAGCGAGCGGTTTTATCTTCTCCGATTACTAT |
| | >TE1 | ATGGGATGGATTCGGCAGGCCCCGGGAAAGGGACTCGAATGGGTGTCATACATCGGAAGGTCAGGCTCGTCCATGTACTA |
| | 3- | CGCAGACTCGGTGAAAGGCAGATTCACCTTTAGCCGGGACAACGCCAAGAATTCCCTCTACTTGCAGATGAACAGCCTGC |
| | 19LD | GAGCCGAGGATACTGCTGTCTACTACTGTGCCGCGTCGCCGGTGGTGGCAGCTACTGAAGATTTCCAGCACTGGGGACAG |
| | (M13) | GGAACTCTGGTCACGGTGTCGAGCGGTGGGGGCGGAAGCGGAGGCGGAGGATCGGGCGGCGGAGGTTCGGGGGGGGGAGG |
| | | GTCTGACATCGTGATGACCCAAACCCCAGCCACCCTGAGCCTCTCCCCTGGAGAGCGCGCGACTCTTTCGTGCCGCGCTT |
| | | CCCAGTCAGTGACCAGCAATTACTTGGCTTGGTACCAACAGAAGCCGGGACAGGCGCCACGGCTGCTGCTTTTTGGTGCC |
| | | AGCACTCGCGCCACCGGAATCCCGGATCGCTTCTCGGGCTCAGGGTCCGGGACGGACTTCACCCTGACTATCAACCGGCT |
| | | GGAACCTGAGGACTTCGCGATGTACTACTGCCAGCAGTACGGCTCCGCACCAGTCACTTTCGGACAAGGCACCAAGCTGG |
| | | AGATCAAG**ACCACTACC**CCAGCACCGAGGCCACCCACCCCGGCTCCTACCATCGCCTCCCAGCCTCTGTCCCTGCGTCCG |
| | | GAGGCATGTAGACCCGCAGCTGGTGGGGCCGTGCATACCCGGGGTCTTGACTTCGCCTGCGATATCTACATTTGGGCCCC |
| | | TCTGGCTGGTACTTGCGGGGTCCTGCTGCTTTCACTCGTGATCACTCTTTACTGTAAGCGCGGTCGGAAGAAGCTGCTGT |
| | | ACATCTTTAAGCAACCCTTCATGAGGCCTGTGCAGACTACTCAAGAGGAGGACGGCTGTTCATGCCGGTTCCCAGAGGAG |
| | | GAGGAAGGCGGCTGCGAACTGCGCGTGAAATTCAGCCGCAGCGCAGATGCTCCAGCCTACAAGCAGGGGCAGAACCAGCT |
| | | CTACAACGAACTCAATCTTGGTCGGAGAGAGGAGTACGACGTGCTGGACAAGCGGAGAGGACGGGACCCAGAAATGGGCG |
| | | GGAAGCCGCGCAGAAAGAATCCCCAAGAGGGCCTGTACAACGAGCTCCAAAAGGATAAGATGGCAGAAGCCTATAGCGAG |
| | | ATTGGTATGAAAGGGGAACGCAGAAGAGGCAAAGGCCACGACGGACTGTACCAGGGACTCAGCACCGCCACCAAGGACAC |
| | | CTATGACGCTCTTCACATGCAGGCCCTGCCGCCTCGG |
| 100 | M14 | CAAGTCCAACTCGTCCAGTCGGGAGCAGAAGTTAGAGCACCAGGAGCGTCAGTGAAAATCTCATGCAAGGCCTCGGGCTTC |
| | (ScFv | ACGTTCCGCGGATACTAC |
| | domain) | ATCCACTGGGTGCGCCAAGCCCCGGGTCAGGGATTGGAGTGGATGGGAATCATTAACCCATCAGGAGGGAGCCGGGCTTA |
| | >BS8 | CGCGCAGAAGTTCCAGGGACGCGTCACTATGACCCGAGATACTTCCACCTCGACTGTGTACATGGAACTCTCGTCCCTGA |
| | 3- | GGTCCGACGACACTGCGATGTATTACTGTGCTCGGACTGCCAGCTGCGGTGGGGACTGTTACTACCTCGATTACTGGGGC |
| | 95ID | CAGGGAACTCTGGTGACCGTGTCCAGCGGAGGTGGCGGGTCAGGGGGTGGCGGAAGCGGAGGCGGCGGTTCAGGCGGAGG |
| | (M14) | AGGCTCGGACATCCAAATGACGCAATCGCCGCCTACCCTGAGCGCTTCCGTGGGAGATCGGGTGACCATTACTTGCAGAG |
| | | CATCCGAGAACGTCAATATCTGGCTGGCCTGGTACCAACAGAAGCCGGGGAAGGCCCCTAAACTGCTGATCTACAAGTCG |
| | | AGCAGCCTTGCCTCTGGAGTGCCCTCCCGCTTCTCGGGCTCGGGATCAGGAGCGGAATTCACCCTCACCATCTCCTCCCT |
| | | GCAGCCAGATGACTTTGCCACCTACTACTGCCAGCAGTACCAGAGCTATCCGTTGACCTTTGGGGGAGGCACTAAAGTGG |
| | | ACATCAAG |
| 124 | M14 | ATGGCCCTCCCTGTCACCGCCCTGCTGCTTCCGCTGGCTCTTCTGCTCCACGCCGCTCGGCCCCAAGTCCAACTCGTCCAG |
| | (Full) | TCGGGAGCAGAAGTTAGAGCACCAGGAGCGTCAGTGAAAATCTCATGCAAGGCCTCGGGCTTCACGTTCCGCGGATACTAC |
| | >BS8 | ATCCACTGGGTGCGCCAAGCCCCGGGTCAGGGATTGGAGTGGATGGGAATCATTAACCCATCAGGAGGGAGCCGGGCTTA |
| | 3- | CGCGCAGAAGTTCCAGGGACGCGTCACTATGACCCGAGATACTTCCACCTCGACTGTGTACATGGAACTCTCGTCCCTGA |
| | 95ID | GGTCCGACGACACTGCGATGTATTACTGTGCTCGGACTGCCAGCTGCGGTGGGGACTGTTACTACCTCGATTACTGGGGC |
| | (M14) | CAGGGAACTCTGGTGACCGTGTCCAGCGGAGGTGGCGGGTCAGGGGGTGGCGGAAGCGGAGGCGGCGGTTCAGGCGGAGG |
| | | AGGCTCGGACATCCAAATGACGCAATCGCCGCCTACCCTGAGCGCTTCCGTGGGAGATCGGGTGACCATTACTTGCAGAG |
| | | CATCCGAGAACGTCAATATCTGGCTGGCCTGGTACCAACAGAAGCCGGGGAAGGCCCCTAAACTGCTGATCTACAAGTCG |
| | | AGCAGCCTTGCCTCTGGAGTGCCCTCCCGCTTCTCGGGCTCGGGATCAGGAGCGGAATTCACCCTCACCATCTCCTCCCT |
| | | GCAGCCAGATGACTTTGCCACCTACTACTGCCAGCAGTACCAGAGCTATCCGTTGACCTTTGGGGGAGGCACTAAAGTGG |
| | | ACATCAAG**ACCACTACC**CCAGCACCGAGGCCACCCACCCCGGCTCCTACCATCGCCTCCCAGCCTCTGTCCCTGCGTCCG |
| | | GAGGCATGTAGACCCGCAGCTGGTGGGGCCGTGCATACCCGGGGTCTTGACTTCGCCTGCGATATCTACATTTGGGCCCC |
| | | TCTGGCTGGTACTTGCGGGGTCCTGCTGCTTTCACTCGTGATCACTCTTTACTGTAAGCGCGGTCGGAAGAAGCTGCTGT |
| | | ACATCTTTAAGCAACCCTTCATGAGGCCTGTGCAGACTACTCAAGAGGAGGACGGCTGTTCATGCCGGTTCCCAGAGGAG |
| | | GAGGAAGGCGGCTGCGAACTGCGCGTGAAATTCAGCCGCAGCGCAGATGCTCCAGCCTACAAGCAGGGGCAGAACCAGCT |
| | | CTACAACGAACTCAATCTTGGTCGGAGAGAGGAGTACGACGTGCTGGACAAGCGGAGAGGACGGGACCCAGAAATGGGCG |
| | | GGAAGCCGCGCAGAAAGAATCCCCAAGAGGGCCTGTACAACGAGCTCCAAAAGGATAAGATGGCAGAAGCCTATAGCGAG |
| | | ATTGGTATGAAAGGGGAACGCAGAAGAGGCAAAGGCCACGACGGACTGTACCAGGGACTCAGCACCGCCACCAAGGACAC |
| | | CTATGACGCTCTTCACATGCAGGCCCTGCCGCCTCGG |
| 101 | M15 | CAAGTTCAACTCGTTCAA |
| | (ScFv | TCAGGTGGAGGACTCGTGCAACCAGGAAGATCACTCAGACTCAGCTGCGCCGCGTCGGGATTCACTTTCGATGACTACGC |
| | domain) | AATGCACTGGGTGCGGCAGGCCCCGGGCAAAGGACTGGAATGGGTGAGCGGAATTAGCTGGAACTCGGGGTCCATCGGGT |
| | >HS8 | ACGCCGACTCGGTGAAGGGACGCTTTACGATCTCCCGGGACAATGCCAAGAACTCCCTGTATTTGCAGATGAACTCCTTG |
| | 6- | AGGGCTGAGGACACCGCCGTGTACTACTGCGCTAAAGATGGATCATCGTCCTGGTCCTGGGGATACTTCGATTACTGGGG |
| | 94XD | CCAGGGCACTCTGGTGACCGTGTCGTCAGGCGGTGGAGGGTCGGGCGGAGGAGGTAGCGGAGGCGGAGGGAGCAGCTCTG |
| | (M15) | AACTGACCCAAGACCCGGCGGTGTCGGTCGCCCTTGGTCAGACTGTGCGGACTACCTGTCAGGGGGACGCGCTGCGCTCG |
| | | TACTACGCTTCATGGTACCAGCAGAAGCCCGGACAGGCACCTATGCTGGTCATCTACGGAAAGAATAACCGCCCATCGG |
| | | CATCCCGGATCGCTTCTCGGGTTCGGACAGCGGCGACACCGCATCCCTGACGATCACTGGAGCGCAGGCCGAGGATGAAG |
| | | CCGACTACTACTGCAATTCCCGAGATTCAAGCGGCTACCCTGTGTTTGGGACCGGAACTAAGGTCACCGTCCTG |
| 125 | M15 | ATGGCCCTCCCTGTCACCGCCCTGCTGCTTCCGCTGGCTCTTCTGCTCCACGCCGCTCGGCCCCAAGTTCAACTCGTTCAA |
| | (Full) | TCAGGTGGAGGACTCGTGCAACCAGGAAGATCACTCAGACTCAGCTGCGCCGCGTCGGGATTCACTTTCGATGACTACGC |
| | >HS8 | AATGCACTGGGTGCGGCAGGCCCCGGGCAAAGGACTGGAATGGGTGAGCGGAATTAGCTGGAACTCGGGGTCCATCGGGT |

TABLE 3-continued

| Nucleic Acid Sequences encoding CAR molecules (the leader sequence is underlined) | | |
|---|---|---|
| SEQ ID NO: | Desc. | Nucleic Acid Sequence |
| | 6-<br>94XD<br>(M15) | ACGCCGACTCGGTGAAGGGACGCTTTACGATCTCCCGGGACAATGCCAAGAACTCCCTGTATTTGCAGATGAACTCCTTG<br>AGGGCTGAGGACACCGCCGTGTACTACTGCGCTAAAGATGGATCATCGTCCTGGTCCTGGGGATACTTCGATTACTGGGG<br>CCAGGGCACTCTGGTGACCGTGTCGTCAGGCGGTGGAGGGTCGGGCGGAGGAGGTAGCGGAGGCGGAGGGAGCAGCTCTG<br>AACTGACCCAAGACCCGGCGGTGTCGGTCGCCCTTGGTCAGACTGTGCGGACTACCTGTCAGGGGGACGCGCTGCGCTCG<br>TACTACGCTTCATGGTACCAGCAGAAGCCCGGACAGGCACCTATGCTGGTCATCTACGGAAAGAATAACCGCCCATCCGG<br>CATCCCGGATCGCTTCTCGGGTTCGGACAGCGGCGACACCGCATCCCTGACGATCACTGGAGCGCAGGCCGAGGATGAAG<br>CCGACTACTACTGCAATTCCCGAGATTCAAGCGGCTACCCTGTGTTTGGGACCGGAACTAAGGTCACCGTCCTGACCACT<br>ACCCCAGCACCGAGGCCACCCACCCCGGCTCCTACCATCGCCTCCCAGCCTCTGTCCCTGCGTCCGGAGGCATGTAGACC<br>CGCAGCTGGTGGGGCCGTGCATACCCGGGGTCTTGACTTCGCCTGCGATATCTACATTTGGGCCCCTCTGGCTGGTACTT<br>GCGGGGTCCTGCTGCTTTCACTCGTGATCACTCTTTACTGTAAGCGCGGTCGGAAGAAGCTGCTGTACATCTTTAAGCAA<br>CCCTTCATGAGGCCTGTGCAGACTACTCAAGAGGAGGACGGCTGTTCATGCCGGTTCCCAGAGGAGGAGGAAGGCGGCTG<br>CGAACTGCGCGTGAAATTCAGCCGCAGCGCAGATGCTCCAGCCTACAAGCAGGGGCAGAACCAGCTCTACAACGAACTCA<br>ATCTTGGTCGGAGAGAGGAGTACGACGTGCTGGACAAGCGGAGAGGACGGGACCCAGAAATGGGCGGGAAGCCGCGCAGA<br>AAGAATCCCCAAGAGGGCCTGTACAACGAGCTCCAAAAGGATAAGATGGCAGAAGCCTATAGCGAGATTGGTATGAAAGG<br>GGAACGCAGAAGAGGCAAAGGCCACGACGGACTGTACCAGGGACTCAGCACCGCCACCAAGGACACCTATGACGCTCTTC<br>ACATGCAGGCCCTGCCGCCTCGG |
| 102 | M16<br>(ScFv<br>domain)<br>>XS8<br>7-<br>99RD<br>(M16) | GAAGTGCAACTCGTGGAA<br>TCTGGTGGAGGACTTGTGCAACCTGGAAGATCGTTGAGACTCTCATGTGCTGCCTCCGGGTTCACCTTTGACGACTACGC<br>CATGCACTGGGTGCGCCAGGCACCAGGAAAGGGTCTGGAGTGGGTTTCGGGTATCTCGTGGAACTCCGGGAGCACTGGCT<br>ACGCTGATTCGGTGAAAGGCCGGTTTACCATCTCCCGAGACAATGCGAAGAATTCCCTCTATCTGCAGATGAACAGCCTC<br>CGGGCCGAGGATACTGCCCTGTACTACTGCGCCAAGGATAGCTCATCATGGTACGGAGGTGGATCGGCTTTCGATATCTG<br>GGGCCAGGGCACGATGGTCACCGTGTCCTCGGGGGGCGGAGGCTCCGGGGGAGGAGGTAGCGGAGGAGGAGGATCGAGCT<br>CAGAGTTGACTCAAGAACCCGCAGTGTCCGTGGCACTGGGCCAAACCGTCAGGATCACTTGCCAGGGAGACAGCCTGAGG<br>TCGTACTACGCGTCCTGGTACCAGCAGAAGCCGGGACAGGCCCCGGTCCTGGTCATTTTCGGACGCTCAAGACGCCCATC<br>GGGCATCCCGGACCGGTTCAGCGGAAGCTCCTCGGGAAACACCGCGTCACTTATCATTACCGGCGCACAGGCTGAGGACG<br>AAGCGGATTACTACTGCAACTCCCGCGACAATACTGCCAACCATTACGTGTTCGGGACCGGAACGAAACTGACTGTCCTG |
| 126 | M16<br>(Full)<br>>XS8<br>7-<br>99RD<br>(M16) | ATGGCCCTCCCTGTCACCGCCCTGCTGCTTCCGCTGGCTCTTCTGCTCCACGCCGCTCGGCCCGAAGTGCAACTCGTGGAA<br>TCTGGTGGAGGACTTGTGCAACCTGGAAGATCGTTGAGACTCTCATGTGCTGCCTCCGGGTTCACCTTTGACGACTACGC<br>CATGCACTGGGTGCGCCAGGCACCAGGAAAGGGTCTGGAGTGGGTTTCGGGTATCTCGTGGAACTCCGGGAGCACTGGCT<br>ACGCTGATTCGGTGAAAGGCCGGTTTACCATCTCCCGAGACAATGCGAAGAATTCCCTCTATCTGCAGATGAACAGCCTC<br>CGGGCCGAGGATACTGCCCTGTACTACTGCGCCAAGGATAGCTCATCATGGTACGGAGGTGGATCGGCTTTCGATATCTG<br>GGGCCAGGGCACGATGGTCACCGTGTCCTCGGGGGGCGGAGGCTCCGGGGGAGGAGGTAGCGGAGGAGGAGGATCGAGCT<br>CAGAGTTGACTCAAGAACCCGCAGTGTCCGTGGCACTGGGCCAAACCGTCAGGATCACTTGCCAGGGAGACAGCCTGAGG<br>TCGTACTACGCGTCCTGGTACCAGCAGAAGCCGGGACAGGCCCCGGTCCTGGTCATTTTCGGACGCTCAAGACGCCCATC<br>GGGCATCCCGGACCGGTTCAGCGGAAGCTCCTCGGGAAACACCGCGTCACTTATCATTACCGGCGCACAGGCTGAGGACG<br>AAGCGGATTACTACTGCAACTCCCGCGACAATACTGCCAACCATTACGTGTTCGGGACCGGAACGAAACTGACTGTCCTG<br>**ACCACTACC**CCAGCACCGAGGCCACCCACCCCGGCTCCTACCATCGCCTCCCAGCCTCTGTCCCTGCGTCCGGAGGCATG<br>TAGACCCGCAGCTGGTGGGGCCGTGCATACCCGGGGTCTTGACTTCGCCTGCGATATCTACATTTGGGCCCCTCTGGCTG<br>GTACTTGCGGGGTCCTGCTGCTTTCACTCGTGATCACTCTTTACTGTAAGCGCGGTCGGAAGAAGCTGCTGTACATCTTT<br>AAGCAACCCTTCATGAGGCCTGTGCAGACTACTCAAGAGGAGGACGGCTGTTCATGCCGGTTCCCAGAGGAGGAGGAAGG<br>CGGCTGCGAACTGCGCGTGAAATTCAGCCGCAGCGCAGATGCTCCAGCCTACAAGCAGGGGCAGAACCAGCTCTACAACG<br>AACTCAATCTTGGTCGGAGAGAGGAGTACGACGTGCTGGACAAGCGGAGAGGACGGGACCCAGAAATGGGCGGGAAGCCG<br>CGCAGAAAGAATCCCCAAGAGGGCCTGTACAACGAGCTCCAAAAGGATAAGATGGCAGAAGCCTATAGCGAGATTGGTAT<br>GAAAGGGGAACGCAGAAGAGGCAAAGGCCACGACGGACTGTACCAGGGACTCAGCACCGCCACCAAGGACACCTATGACG<br>CTCTTCACATGCAGGCCCTGCCGCCTCGG |
| 103 | M17<br>(ScFv<br>domain)<br>>NS8<br>9-<br>94MD<br>(M17) | GAAGTTCAATTGGTGGAA<br>TCTGGAGGAGGACTTGTGCAACCCGGTAGATCTCTGAGACTGTCCTGTGCGGCATCGGGATTCACCTTCGACGACTACGC<br>TATGCACTGGGTGAGACAAGCCCCTGGAAAAGGACTGGAGTGGGTGTCAGGCATCTCCTGGAATAGCGGGTCCACTGGAT<br>ACGCCGATTCGGTCAAGGGTCGCTTCACCATTTCCCGGGACAATGCCAAGAACTCCCTGTACCTTCAAATGAACTCCCTC<br>CGGGCCGAGGATACCGCCCTCTACTACTGCGCCAAAGACAGCTCGTCATGGTATGGCGGAGGGTCGGCATTTGACATCTG<br>GGGACAGGGAACTATGGTGACTGTGTCATCAGGAGGCGGCGGAAGCGGCGGCGGCGGGTCCGGCGGAGGAGGGTCGTCCA<br>GCGAACTCACCCAAGATCCAGCAGTGAGCGTCGCGCTGGGCCAGACCGTCAGGATCACGTGCCAGGGAGATTCACTGCGC<br>TCATACTACGCGTCCTGGTACCAGCAGAAGCCGGGGCAGGCCCCGGTCCTCGTGATCTACGGAAAGAACAACCGCCCGTC<br>GGGTATCCCAGACCGCTTTTCGGGTAGCTCCAGCGGAAATACGGCTAGCCTGACCATCACTGGAGCACAGGCTGAGGATG<br>AAGCGGACTACTACTGCAATTCGCGGGGCTCATCGGGGAACCATTACGTGTTCGGAACTGGTACCAAGGTGACTGTCCTG |
| 127 | M17<br>(Full)<br>>NS8<br>9-<br>94MD<br>(M17) | ATGGCCCTCCCTGTCACCGCCCTGCTGCTTCCGCTGGCTCTTCTGCTCCACGCCGCTCGGCCCGAAGTTCAATTGGTGGAA<br>TCTGGAGGAGGACTTGTGCAACCCGGTAGATCTCTGAGACTGTCCTGTGCGGCATCGGGATTCACCTTCGACGACTACGC<br>TATGCACTGGGTGAGACAAGCCCCTGGAAAAGGACTGGAGTGGGTGTCAGGCATCTCCTGGAATAGCGGGTCCACTGGAT<br>ACGCCGATTCGGTCAAGGGTCGCTTCACCATTTCCCGGGACAATGCCAAGAACTCCCTGTACCTTCAAATGAACTCCCTC<br>CGGGCCGAGGATACCGCCCTCTACTACTGCGCCAAAGACAGCTCGTCATGGTATGGCGGAGGGTCGGCATTTGACATCTG<br>GGGACAGGGAACTATGGTGACTGTGTCATCAGGAGGCGGCGGAAGCGGCGGCGGCGGGTCCGGCGGAGGAGGGTCGTCCA<br>GCGAACTCACCCAAGATCCAGCAGTGAGCGTCGCGCTGGGCCAGACCGTCAGGATCACGTGCCAGGGAGATTCACTGCGC<br>TCATACTACGCGTCCTGGTACCAGCAGAAGCCGGGGCAGGCCCCGGTCCTCGTGATCTACGGAAAGAACAACCGCCCGTC<br>GGGTATCCCAGACCGCTTTTCGGGTAGCTCCAGCGGAAATACGGCTAGCCTGACCATCACTGGAGCACAGGCTGAGGATG<br>AAGCGGACTACTACTGCAATTCGCGGGGCTCATCGGGGAACCATTACGTGTTCGGAACTGGTACCAAGGTGACTGTCCTG<br>**ACCACTACC**CCAGCACCGAGGCCACCCACCCCGGCTCCTACCATCGCCTCCCAGCCTCTGTCCCTGCGTCCGGAGGCATG<br>TAGACCCGCAGCTGGTGGGGCCGTGCATACCCGGGGTCTTGACTTCGCCTGCGATATCTACATTTGGGCCCCTCTGGCTG<br>GTACTTGCGGGGTCCTGCTGCTTTCACTCGTGATCACTCTTTACTGTAAGCGCGGTCGGAAGAAGCTGCTGTACATCTTT<br>AAGCAACCCTTCATGAGGCCTGTGCAGACTACTCAAGAGGAGGACGGCTGTTCATGCCGGTTCCCAGAGGAGGAGGAAGG<br>CGGCTGCGAACTGCGCGTGAAATTCAGCCGCAGCGCAGATGCTCCAGCCTACAAGCAGGGGCAGAACCAGCTCTACAACG |

TABLE 3-continued

Nucleic Acid Sequences encoding CAR molecules (the leader sequence is underlined)

| SEQ ID NO: | Desc. | Nucleic Acid Sequence |
|---|---|---|
| | | AACTCAATCTTGGTCGGAGAGAGGAGTACGACGTGCTGGACAAGCGGAGAGGACGGGACCCAGAAATGGGCGGGAAGCCG<br>CGCAGAAAGAATCCCCAAGAGGGCCTGTACAACGAGCTCCAAAAGGATAAGATGGCAGAAGCCTATAGCGAGATTGGTAT<br>GAAAGGGGAACGCAGAAGAGGCAAAGGCCACGACGGACTGTACCAGGGACTCAGCACCGCCACCAAGGACACCTATGACG<br>CTCTTCACATGCAGGCCCTGCCGCCTCGG |
| 104 | M18 (ScFv domain) >DS9 0-09HD (M18) | CAAGTGCAGCTCGTTCAATCAGGCGGAGGACTCGTTCAACCAGGAGGATCATTGCGACTCTCATGTGCGGCCTCTGGATTC<br>ACGTTTAGCTCATATTGG<br>ATGCACTGGGTGCGGCAGGCGCCGGGGAAAGGTCTGGTGTGGGTCAGCCGCATCAACTCAGACGGCTCCTCGACTTCGTA<br>CGCCGACTCCGTGAAGGGACGCTTTACCATTTCCCGCGACAACGCCAAGAATACCCTTTACCTTCAGATGAACTCCCTCC<br>GCGCTGAGGATACCGCCGTGTACTACTGCGTGAGGACTGGCTGGGTCGGCAGCTACTACTACTACATGGACGTGTGGGGC<br>AAAGGAACTACTGTCACCGTGTCAAGCGGCGGTGGAGGTTCCGGCGGGGGAGGATCGGGGGGGGGCGGATCGGGTGGCGG<br>AGGATCGGAGATCGTGTTGACCCAGTCGCCGGGAACCCTGTCGCTGTCGCCTGGGGAGAGAGCAACTCTGTCCTGCCGGG<br>CTTCCCAGTCGGTGTCGAGCAATTACCTGGCATGGTACCAACAGAAGCCGGGACAGCCGCCACGCCTGCTGATCTATGAC<br>GTGTCAACTCGGGCAACTGGAATCCCTGCGCGGTTCAGCGGCGGAGGGAGCGGTACCGATTTCACCCTGACTATTTCCTC<br>CCTCGAACCAGAAGATTTCGCCGTCTACTACTGCCAGCAGAGAAGCAACTGGCCGCCCTGGACGTTCGGACAAGGAACCA<br>AGGTCGAAATCAAG |
| 128 | M18 (Full) >DS9 0-09HD (M18) | ATGGCCCTCCCTGTCACCGCCCTGCTGCTTCCGCTGGCTCTTCTGCTCCACGCCGCTCGGCCCCAAGTGCAGCTCGTTCAA<br>TCAGGCGGAGGACTCGTTCAACCAGGAGGATCATTGCGACTCTCATGTGCGGCCTCTGGATTCACGTTTAGCTCATATTGG<br>ATGCACTGGGTGCGGCAGGCGCCGGGGAAAGGTCTGGTGTGGGTCAGCCGCATCAACTCAGACGGCTCCTCGACTTCGTA<br>CGCCGACTCCGTGAAGGGACGCTTTACCATTTCCCGCGACAACGCCAAGAATACCCTTTACCTTCAGATGAACTCCCTCC<br>GCGCTGAGGATACCGCCGTGTACTACTGCGTGAGGACTGGCTGGGTCGGCAGCTACTACTACTACATGGACGTGTGGGGC<br>AAAGGAACTACTGTCACCGTGTCAAGCGGCGGTGGAGGTTCCGGCGGGGGAGGATCGGGGGGGGGCGGATCGGGTGGCGG<br>AGGATCGGAGATCGTGTTGACCCAGTCGCCGGGAACCCTGTCGCTGTCGCCTGGGGAGAGAGCAACTCTGTCCTGCCGGG<br>CTTCCCAGTCGGTGTCGAGCAATTACCTGGCATGGTACCAACAGAAGCCGGGACAGCCGCCACGCCTGCTGATCTATGAC<br>GTGTCAACTCGGGCAACTGGAATCCCTGCGCGGTTCAGCGGCGGAGGGAGCGGTACCGATTTCACCCTGACTATTTCCTC<br>CCTCGAACCAGAAGATTTCGCCGTCTACTACTGCCAGCAGAGAAGCAACTGGCCGCCCTGGACGTTCGGACAAGGAACCA<br>AGGTCGAAATCAAG**ACCACTACC**CCAGCACCGAGGCCACCCACCCCGGCTCCTACCATCGCCTCCCAGCCTCTGTCCCTG<br>CGTCCGGAGGCATGTAGACCCGCAGCTGGTGGGGCCGTGCATACCCGGGGTCTTGACTTCGCCTGCGATATCTACATTTG<br>GGCCCCTCTGGCTGGTACTTGCGGGGTCCTGCTGCTTTCACTCGTGATCACTCTTTACTGTAAGCGCGGTCGGAAGAAGC<br>TGCTGTACATCTTTAAGCAACCCTTCATGAGGCCTGTGCAGACTACTCAAGAGGAGGACGGCTGTTCATGCCGGTTCCCA<br>GAGGAGGAGGAAGGCGGCTGCGAACTGCGCGTGAAATTCAGCCGCAGCGCAGATGCTCCAGCCTACAAGCAGGGGCAGAA<br>CCAGCTCTACAACGAACTCAATCTTGGTCGGAGAGAGGAGTACGACGTGCTGGACAAGCGGAGAGGACGGGACCCAGAAA<br>TGGGCGGGAAGCCGCGCAGAAAGAATCCCCAAGAGGGCCTGTACAACGAGCTCCAAAAGGATAAGATGGCAGAAGCCTAT<br>AGCGAGATTGGTATGAAAGGGGAACGCAGAAGAGGCAAAGGCCACGACGGACTGTACCAGGGACTCAGCACCGCCACCAA<br>GGACACCTATGACGCTCTTCACATGCAGGCCCTGCCGCCTCGG |
| 105 | M19 (ScFv domain) >TS9 2-04BD (M19) | CAAGTGCAATTGGTTCAA<br>TCAGGAGGAGGAGTCGTGCAGCCCGGAAGATCGTTGAGACTGTCATGTGCCGCGAGCGGCTTTACTTTCTCAAGCTACGG<br>AATGCATTGGGTGCGACAGGCTCCGGGAAAAGGACTGGAATGGGTCGCAGTGATCTCATACGACGGCTCGAACAAGTACT<br>ACGCCGACTCCGTCAAGGGTCGGTTCACGATTTCGCGCGATAATTCCAAGAACACTCTGTACCTCCAAATGAACAGCCTC<br>CGGGCAGAGGACACCGCCGTCTACTACTGCGCTAAGGGATACTCGCGCTACTACTACTATGGAATGGATGTGTGGGGCCA<br>GGGAACTACCGTGACGGTGTCGTCCGGCGGCGGTGGGTCGGGCGGAGGCGGATCAGGTGGAGGTGGAAGCGGAGGAGGAG<br>GGAGCGAAATCGTCATGACTCAGTCCCCTGCTACCCTTTCTCTGTCGCCGGGAGAAAGAGCCATCCTGAGCTGCCGGGCC<br>TCCCAGAGCGTGTACACCAAATACCTGGGATGGTACCAGCAGAAGCCGGGGCAGGCACCAAGGCTCCTGATCTACGATGC<br>GTCCACCCGCGCGACTGGTATCCCAGACCGCTTTTCCGGCTCGGGGTCAGGGACTGACTTCACCCTTACTATCAATCGGC<br>TCGAGCCTGAGGATTTCGCCGTGTATTACTGCCAGCACTACGGAGGGTCCCCGCTGATTACCTTCGGCCAAGGCACCAAA<br>GTGGACATCAAG |
| 129 | M19 (Full) >TS9 2-04BD (M19) | ATGGCCCTCCCTGTCACCGCCCTGCTGCTTCCGCTGGCTCTTCTGCTCCACGCCGCTCGGCCCCAAGTGCAATTGGTTCAA<br>TCAGGAGGAGGAGTCGTGCAGCCCGGAAGATCGTTGAGACTGTCATGTGCCGCGAGCGGCTTTACTTTCTCAAGCTACGG<br>AATGCATTGGGTGCGACAGGCTCCGGGAAAAGGACTGGAATGGGTCGCAGTGATCTCATACGACGGCTCGAACAAGTACT<br>ACGCCGACTCCGTCAAGGGTCGGTTCACGATTTCGCGCGATAATTCCAAGAACACTCTGTACCTCCAAATGAACAGCCTC<br>CGGGCAGAGGACACCGCCGTCTACTACTGCGCTAAGGGATACTCGCGCTACTACTACTATGGAATGGATGTGTGGGGCCA<br>GGGAACTACCGTGACGGTGTCGTCCGGCGGCGGTGGGTCGGGCGGAGGCGGATCAGGTGGAGGTGGAAGCGGAGGAGGAG<br>GGAGCGAAATCGTCATGACTCAGTCCCCTGCTACCCTTTCTCTGTCGCCGGGAGAAAGAGCCATCCTGAGCTGCCGGGCC<br>TCCCAGAGCGTGTACACCAAATACCTGGGATGGTACCAGCAGAAGCCGGGGCAGGCACCAAGGCTCCTGATCTACGATGC<br>GTCCACCCGCGCGACTGGTATCCCAGACCGCTTTTCCGGCTCGGGGTCAGGGACTGACTTCACCCTTACTATCAATCGGC<br>TCGAGCCTGAGGATTTCGCCGTGTATTACTGCCAGCACTACGGAGGGTCCCCGCTGATTACCTTCGGCCAAGGCACCAAA<br>GTGGACATCAAG**ACCACTACC**CCAGCACCGAGGCCACCCACCCCGGCTCCTACCATCGCCTCCCAGCCTCTGTCCCTGCG<br>TCCGGAGGCATGTAGACCCGCAGCTGGTGGGGCCGTGCATACCCGGGGTCTTGACTTCGCCTGCGATATCTACATTTGGG<br>CCCCTCTGGCTGGTACTTGCGGGGTCCTGCTGCTTTCACTCGTGATCACTCTTTACTGTAAGCGCGGTCGGAAGAAGCTG<br>CTGTACATCTTTAAGCAACCCTTCATGAGGCCTGTGCAGACTACTCAAGAGGAGGACGGCTGTTCATGCCGGTTCCCAGA<br>GGAGGAGGAAGGCGGCTGCGAACTGCGCGTGAAATTCAGCCGCAGCGCAGATGCTCCAGCCTACAAGCAGGGGCAGAACC<br>AGCTCTACAACGAACTCAATCTTGGTCGGAGAGAGGAGTACGACGTGCTGGACAAGCGGAGAGGACGGGACCCAGAAATG<br>GGCGGGAAGCCGCGCAGAAAGAATCCCCAAGAGGGCCTGTACAACGAGCTCCAAAAGGATAAGATGGCAGAAGCCTATAG<br>CGAGATTGGTATGAAAGGGGAACGCAGAAGAGGCAAAGGCCACGACGGACTGTACCAGGGACTCAGCACCGCCACCAAGG<br>ACACCTATGACGCTCTTCACATGCAGGCCCTGCCGCCTCGG |
| 106 | M20 (ScFv domain) >JS9 3- | CAAGTGCAACTTGTTCAATCAGGAGGAGGACTCGTTCAACCCGGAGGATCACTGCGACTCTCATGTGCAGCGTCGGGGTTC<br>ACCTTCTCCAGCTACGCA<br>ATGTCCTGGGTGCGCCAAGCCCCTGGAAAAGGCCTGGAGTGGGTGTCGGCCATCTCTGGGAGCGGGGGATCAACTTACTA<br>CGCTGACTCCGTCAAGGGCCGCTTTACCATCTCCCGGGACAACAGCAAGAACACTCTCTATCTCCAGATGAACTCGCTGA<br>GAGCCGAAGATACCGCTGTCTACTACTGCGCGAAGAGAGAAGCTGCCGCAGGGCACGATTGGTACTTCGACTTGTGGGGC |

TABLE 3-continued

Nucleic Acid Sequences encoding CAR molecules (the leader sequence is underlined)

| SEQ ID NO: | Desc. | Nucleic Acid Sequence |
|---|---|---|
| | 08WD (M20) | AGGGGCACCCTTGTGACCGTGTCCTCCGGTGGAGGCGGATCAGGAGGTGGGGGATCGGGTGGAGGAGGAAGCGGAGGCGG<br>cGGTTcGGAcATTcGcGTcAcccAGTcAccGAGcTcccTcAGcGcATcGGTGGGcGAccGGGTcAcTATcAcTTGccGGG<br>CGTCCCAGTCGATCTCATCGTATCTGAATTGGTACCAGCAGAAACCGGGAAAGGCGCCGAAGCTGTTGATCTACGCTGCC<br>AGCTCCCTGCAGTCGGGTGTGCCATCACGCTTTTCCGGCTCGGGATCGGGAACCGATTTCACTCTGACGATCTCTAGCCT<br>GCAGCCAGAAGATTTCGCCACTTACTACTGCCAGCAGTCCTACAGCATCCCTCTGACTTTCGGACAAGGGACGAAAGTGG<br>AGATTAAG |
| 130 | M20 (Full) >JS9 3- 08WD (M20) | ATGGCCCTCCCTGTCACCGCCCTGCTGCTTCCGCTGGCTCTTCTGCTCCACGCCGCTCGGCCCCAAGTGCAACTTGTTCAA<br>TCAGGAGGAGGACTCGTTCAACCCGGAGGATCACTGCGACTCTCATGTGCAGCGTCGGGGTTCACCTTCTCCAGCTACGCA<br>ATGTCCTGGGTGCGCCAAGCCCCTGGAAAAGGCCTGGAGTGGGTGTCGGCCATCTCTGGGAGCGGGGGATCAACTTACTA<br>CGCTGACTCCGTCAAGGGCCGCTTTACCATCTCCCGGGACAACAGCAAGAACACTCTCTATCTCCAGATGAACTCGCTGA<br>GAGCCGAAGATACCGCTGTCTACTACTGCGCGAAGAGAGAAGCTGCCGCAGGGCACGATTGGTACTTCGACTTGTGGGGC<br>AGGGGCACCCTTGTGACCGTGTCCTCCGGTGGAGGCGGATCAGGAGGTGGGGGATCGGGTGGAGGAGGAAGCGGAGGCGG<br>CGGTTCGGACATTCGCGTCACCCAGTCACCGAGCTCCCTCAGCGCATCGGTGGGCGACCGGGTCACTATCACTTGCCGGG<br>CGTCCCAGTCGATCTCATCGTATCTGAATTGGTACCAGCAGAAACCGGGAAAGGCGCCGAAGCTGTTGATCTACGCTGCC<br>AGCTCCCTGCAGTCGGGTGTGCCATCACGCTTTTCCGGCTCGGGATCGGGAACCGATTTCACTCTGACGATCTCTAGCCT<br>GCAGCCAGAAGATTTCGCCACTTACTACTGCCAGCAGTCCTACAGCATCCCTCTGACTTTCGGACAAGGGACGAAAGTGG<br>AGATTAAG**ACCACTACC**CCAGCACCGAGGCCACCCACCCCGGCTCCTACCATCGCCTCCCAGCCTCTGTCCCTGCGTCCG<br>GAGGCATGTAGACCCGCAGCTGGTGGGGCCGTGCATACCCGGGGTCTTGACTTCGCCTGCGATATCTACATTTGGGCCCC<br>TCTGGCTGGTACTTGCGGGGTCCTGCTGCTTTCACTCGTGATCACTCTTTACTGTAAGCGCGGTCGGAAGAAGCTGCTGT<br>ACATCTTTAAGCAACCCTTCATGAGGCCTGTGCAGACTACTCAAGAGGAGGACGGCTGTTCATGCCGGTTCCCAGAGGAG<br>GAGGAAGGCGGCTGCGAACTGCGCGTGAAATTCAGCCGCAGCGCAGATGCTCCAGCCTACAAGCAGGGGCAGAACCAGCT<br>CTACAACGAACTCAATCTTGGTCGGAGAGAGGAGTACGACGTGCTGGACAAGCGGAGAGGACGGGACCCAGAAATGGGCG<br>GGAAGCCGCGCAGAAAGAATCCCCAAGAGGGCCTGTACAACGAGCTCCAAAAGGATAAGATGGCAGAAGCCTATAGCGAG<br>ATTGGTATGAAAGGGGAACGCAGAAGAGGCAAAGGCCACGACGGACTGTACCAGGGACTCAGCACCGCCACCAAGGACAC<br>CTATGACGCTCTTCACATGCAGGCCCTGCCGCCTCGG |
| 107 | M21 (ScFv domain) >ZS9 5- 03QD (M21) | CAAGTCCAACTCGTTCAGTCATGGGCAGAAGTCAAGAAACCCGGTGCAAGCGTCAAAGTGTCGTGTAAGGCCTCCGGCTAC<br>ACTTTCACTTCCTACTAC<br>ATGCACTGGGTGCGCCAAGCCCCGGGACAGGGCCTTGAATGGATGGGCATCATCAACCCATCAGGAGGTTCCACGAGCTA<br>CGCGCAGAAGTTCCAGGGGAGAGTGACGATGACTAGAGATACCTCCACGAGCACCGTCTACATGGAGCTGTCGAATCTGC<br>GGTCAGAGGACACTGCTGTGTATTACTGCGCGCGCTCCCCGCGGGTGACCACTGGCTACTTTGACTACTGGGGACAAGGG<br>ACCCTGGTGACCGTCAGCTCGGGAGGCGGAGGATCGGGAGGTGGAGGGTCCGGTGGAGGCGGCTCTGGAGGAGGCGGGTC<br>GGAcATTcAATTGAcccAGAGcccAtccAcccTcTcAcccrcGGTGGGGGATAGGGTGAcTATcAcTTGccGGGccTccc<br>AGTCAATTTCCAGCTGGCTGGCTTGGTACCAGCAAAAGCCTGGAAAGGCACCGAAGCTCCTGATCTACAAGGCCTCATCT<br>CTGGAATCAGGAGTGCCTTCGCGCTTCAGCGGAAGCGGCTCGGGAACTGAGTTTACCCTGACCATCTCGAGCCTGCAGCC<br>AGATGACTTCGCGACCTATTACTGCCAGCAGTACTCGTCCTACCCGTTGACTTTCGGAGGAGGTACCCGCCTCGAAATCA<br>AA |
| 131 | M21 (Full) >ZS9 5- 03QD (M21) | ATGGCCCTCCCTGTCACCGCCCTGCTGCTTCCGCTGGCTCTTCTGCTCCACGCCGCTCGGCCCCAAGTCCAACTCGTTCAG<br>TCATGGGCAGAAGTCAAGAAACCCGGTGCAAGCGTCAAAGTGTCGTGTAAGGCCTCCGGCTACACTTTCACTTCCTACTAC<br>ATGCACTGGGTGCGCCAAGCCCCGGGACAGGGCCTTGAATGGATGGGCATCATCAACCCATCAGGAGGTTCCACGAGCTA<br>CGCGCAGAAGTTCCAGGGGAGAGTGACGATGACTAGAGATACCTCCACGAGCACCGTCTACATGGAGCTGTCGAATCTGC<br>GGTCAGAGGACACTGCTGTGTATTACTGCGCGCGCTCCCCGCGGGTGACCACTGGCTACTTTGACTACTGGGGACAAGGG<br>ACCCTGGTGACCGTCAGCTCGGGAGGCGGAGGATCGGGAGGTGGAGGGTCCGGTGGAGGCGGCTCTGGAGGAGGCGGGTC<br>GGACATTCAATTGACCCAGAGCCCATCCACCCTCTCAGCCTCGGTGGGGGATAGGGTGACTATCACTTGCCGGGCCTCCC<br>AGTCAATTTCCAGCTGGCTGGCTTGGTACCAGCAAAAGCCTGGAAAGGCACCGAAGCTCCTGATCTACAAGGCCTCATCT<br>CTGGAATCAGGAGTGCCTTCGCGCTTCAGCGGAAGCGGCTCGGGAACTGAGTTTACCCTGACCATCTCGAGCCTGCAGCC<br>AGATGACTTCGCGACCTATTACTGCCAGCAGTACTCGTCCTACCCGTTGACTTTCGGAGGAGGTACCCGCCTCGAAATCA<br>AA**ACCACTACC**CCAGCACCGAGGCCACCCACCCCGGCTCCTACCATCGCCTCCCAGCCTCTGTCCCTGCGTCCGGAGGCA<br>TGTAGACCCGCAGCTGGTGGGGCCGTGCATACCCGGGGTCTTGACTTCGCCTGCGATATCTACATTTGGGCCCCTCTGGC<br>TGGTACTTGCGGGGTCCTGCTGCTTTCACTCGTGATCACTCTTTACTGTAAGCGCGGTCGGAAGAAGCTGCTGTACATCT<br>TTAAGCAACCCTTCATGAGGCCTGTGCAGACTACTCAAGAGGAGGACGGCTGTTCATGCCGGTTCCCAGAGGAGGAGGAA<br>GGCGGCTGCGAACTGCGCGTGAAATTCAGCCGCAGCGCAGATGCTCCAGCCTACAAGCAGGGGCAGAACCAGCTCTACAA<br>CGAACTCAATCTTGGTCGGAGAGAGGAGTACGACGTGCTGGACAAGCGGAGAGGACGGGACCCAGAAATGGGCGGGAAGC<br>CGCGCAGAAAGAATCCCCAAGAGGGCCTGTACAACGAGCTCCAAAAGGATAAGATGGCAGAAGCCTATAGCGAGATTGGT<br>ATGAAAGGGGAACGCAGAAGAGGCAAAGGCCACGACGGACTGTACCAGGGACTCAGCACCGCCACCAAGGACACCTATGA<br>CGCTCTTCACATGCAGGCCCTGCCGCCTCGG |
| 108 | M22 (ScFv domain) >PS9 6- 08LD (M22) | CAAGTCCAACTCGTCCAGTCCGGTGCAGAAGTCAGAAGGCCAGGAGCAAGCGTGAAGATCTCGTGTAGAGCGTCAGGAGAC<br>ACCAGCACTCGCCATTAC<br>ATCCACTGGCTGCGCCAGGCTCCGGGCCAAGGGCCGGAGTGGATGGGTGTGATCAACCCGACTACGGGACCGGCTACCGG<br>AAGCCCTGCGTACGCACAGATGCTGCAGGGACGGGTGACTATGACCCGCGATACTAGCACTAGGACCGTGTACATGGAAC<br>TCCGCTCGTTGCGGTTCGAAGATACCGCCGTCTACTACTGCGCCCGGTCCGTGGTGGGCCGAAGCGCCCCTTACTACTTC<br>GATTACTGGGGACAGGGCACTCTGGTGACCGTTAGCTCCGGTGGGGGAGGCTCGGGTGGAGGCGGATCGGGAGGAGGAGG<br>CAGCGGTGGAGGGGGATCGGACATTCAGATGACCCAGTCACCCTCCTCCCTCTCAGCCTCGGTCGGGGACCGGGTGACCA<br>TTACGTGCAGAGCCTCACAAGGGATCTCGGACTACTCCGCCTGGTACCAGCAGAAACCGGGAAAAGCGCCAAAGCTCCTG<br>ATCTACGCCGCGAGCACCCTGCAATCAGGAGTGCCATCGCGCTTTTCTGGATCGGGCTCAGGGACTGACTTCACGCTGAC<br>TATCTCCTACCTTCAGTCCGAGGATTTCGCTACCTACTACTGCCAACAGTATTACTCCTATCCCCTGACCTTTGGCGGAG<br>GCACTAAGGTGGACATCAAG |
| 132 | M22 (Full) >PS9 | ATGGCCCTCCCTGTCACCGCCCTGCTGCTTCCGCTGGCTCTTCTGCTCCACGCCGCTCGGCCCCAAGTCCAACTCGTCCAG<br>TCCGGTGCAGAAGTCAGAAGGCCAGGAGCAAGCGTGAAGATCTCGTGTAGAGCGTCAGGAGACACCAGCACTCGCCATTAC<br>ATCCACTGGCTGCGCCAGGCTCCGGGCCAAGGGCCGGAGTGGATGGGTGTGATCAACCCGACTACGGGACCGGCTACCGG |

TABLE 3-continued

Nucleic Acid Sequences encoding CAR molecules (the leader sequence is underlined)

| SEQ ID NO: | Desc. | Nucleic Acid Sequence |
|---|---|---|
| | 6-08LD (M22) | AAGCCCTGCGTACGCACAGATGCTGCAGGGACGGGTGACTATGACCCGCGATACTAGCACTAGGACCGTGTACATGGAAC<br>TCCGCTCGTTGCGGTTCGAAGATACCGCCGTCTACTACTGCGCCCGGTCCGTGGTGGGCCGAAGCGCCCCTTACTACTTC<br>GATTACTGGGGACAGGGCACTCTGGTGACCGTTAGCTCCGGTGGGGGAGGCTCGGGTGGAGGCGGATCGGGAGGAGGAGG<br>CAGCGGTGGAGGGGGATCGGACATTCAGATGACCCAGTCACCCTCCTCCCTCTCAGCCTCGGTCGGGGACCGGGTGACCA<br>TTACGTGCAGAGCCTCACAAGGGATCTCGGACTACTCCGCCTGGTACCAGCAGAAACCGGGAAAAGCGCCAAAGCTCCTG<br>ATCTACGCCGCGAGCACCCTGCAATCAGGAGTGCCATCGCGCTTTTCTGGATCGGGCTCAGGGACTGACTTCACGCTGAC<br>TATCTCCTACCTTCAGTCCGAGGATTTCGCTACCTACTACTGCCAACAGTATTACTCCTATCCCCTGACCTTTGGCGGAG<br>GCACTAAGGTGGACATCAAG**ACCACTACC**CCAGCACCGAGGCCACCCACCCCGGCTCCTACCATCGCCTCCCAGCCTCTG<br>TCCCTGCGTCCGGAGGCATGTAGACCCGCAGCTGGTGGGGCCGTGCATACCCGGGGTCTTGACTTCGCCTGCGATATCTA<br>CATTTGGGCCCCTCTGGCTGGTACTTGCGGGGTCCTGCTGCTTTCACTCGTGATCACTCTTTACTGTAAGCGCGGTCGGA<br>AGAAGCTGCTGTACATCTTTAAGCAACCCTTCATGAGGCCTGTGCAGACTACTCAAGAGGAGGACGGCTGTTCATGCCGG<br>TTCCCAGAGGAGGAGGAAGGCGGCTGCGAACTGCGCGTGAAATTCAGCCGCAGCGCAGATGCTCCAGCCTACAAGCAGGG<br>GCAGAACCAGCTCTACAACGAACTCAATCTTGGTCGGAGAGAGGAGTACGACGTGCTGGACAAGCGGAGAGGACGGGACC<br>CAGAAATGGGCGGGAAGCCGCGCAGAAAGAATCCCCAAGAGGGCCTGTACAACGAGCTCCAAAAGGATAAGATGGCAGAA<br>GCCTATAGCGAGATTGGTATGAAAGGGGAACGCAGAAGAGGCAAAGGCCACGACGGACTGTACCAGGGACTCAGCACCGC<br>CACCAAGGACACCTATGACGCTCTTCACATGCAGGCCCTGCCGCCTCGG |
| 109 | M23 (ScFv domain) >XH6 6-84HE (M23) | CAAGTCCAACTCCAGCAATCGGGAGCAGAAGTCAAGAAACCAGGCGCATCGGTGAAAGTGTCGTGTAAGGCGTCAGGGTAC<br>ACCTTCACCAACTACTAT<br>ATGCACTGGGTGCGCCAGGCTCCAGGCCAGGGGTTGGAGTGGATGGGGATCATCAATCCGTCAGGTGGCTACACCACTTA<br>CGCTCAGAAGTTCCAGGGACGCCTCACTATGACTCGCGATACTAGCACCTCCACGGTGTACATGGAACTGTCATCGCTGA<br>GGTCCGAAGATACCGCCGTCTACTACTGCGCACGGATCAGATCCTGCGGAGGAGATTGTTACTACTTTGACAACTGGGGA<br>CAGGGCACCCTTGTTACTGTGTCATCGGGAGGAGGGGGAAGCGGAGGAGGTGGATCAGGCGGCGGTGGCAGCGGGGGCGG<br>AGGATCGGACATTCAGCTGACTCAGTCCCCCTCCACTTTGTCGGCCAGCGTGGGAGACAGAGTGACCATCACTTGCCGGG<br>CGTCCGAGAACGTCAATATCTGGCTGGCCTGGTACCAGCAAAAGCCTGGAAAAGCCCCGAAGCTGCTCATCTATAAGTCA<br>TCCAGCCTGGCGTCTGGTGTGCCGTCGCGGTTCTCCGGCAGCGGGAGCGGAGCCGAGTTCACTCTCACCATTTCGAGCCT<br>TCAACCGGACGATTTCGCCACCTACTACTGCCAGCAGTACCAATCCTACCCTCTGACGTTTGGAGGTGGAACCAAGGTGG<br>ACATCAAG |
| 133 | M23 (Full) >XH6 6-84HE (M23) | ATGGCCCTCCCTGTCACCGCCCTGCTGCTTCCGCTGGCTCTTCTGCTCCACGCCGCTCGGCCCCAAGTCCAACTCCAGCAA<br>TCGGGAGCAGAAGTCAAGAAACCAGGCGCATCGGTGAAAGTGTCGTGTAAGGCGTCAGGGTACACCTTCACCAACTACTAT<br>ATGCACTGGGTGCGCCAGGCTCCAGGCCAGGGGTTGGAGTGGATGGGGATCATCAATCCGTCAGGTGGCTACACCACTTA<br>CGCTCAGAAGTTCCAGGGACGCCTCACTATGACTCGCGATACTAGCACCTCCACGGTGTACATGGAACTGTCATCGCTGA<br>GGTCCGAAGATACCGCCGTCTACTACTGCGCACGGATCAGATCCTGCGGAGGAGATTGTTACTACTTTGACAACTGGGGA<br>CAGGGCACCCTTGTTACTGTGTCATCGGGAGGAGGGGGAAGCGGAGGAGGTGGATCAGGCGGCGGTGGCAGCGGGGGCGG<br>AGGATCGGACATTCAGCTGACTCAGTCCCCCTCCACTTTGTCGGCCAGCGTGGGAGACAGAGTGACCATCACTTGCCGGG<br>CGTCCGAGAACGTCAATATCTGGCTGGCCTGGTACCAGCAAAAGCCTGGAAAAGCCCCGAAGCTGCTCATCTATAAGTCA<br>TCCAGCCTGGCGTCTGGTGTGCCGTCGCGGTTCTCCGGCAGCGGGAGCGGAGCCGAGTTCACTCTCACCATTTCGAGCCT<br>TCAACCGGACGATTTCGCCACCTACTACTGCCAGCAGTACCAATCCTACCCTCTGACGTTTGGAGGTGGAACCAAGGTGG<br>ACATCAAG**ACCACTACC**CCAGCACCGAGGCCACCCACCCCGGCTCCTACCATCGCCTCCCAGCCTCTGTCCCTGCGTCCG<br>GAGGCATGTAGACCCGCAGCTGGTGGGGCCGTGCATACCCGGGGTCTTGACTTCGCCTGCGATATCTACATTTGGGCCCC<br>TCTGGCTGGTACTTGCGGGGTCCTGCTGCTTTCACTCGTGATCACTCTTTACTGTAAGCGCGGTCGGAAGAAGCTGCTGT<br>ACATCTTTAAGCAACCCTTCATGAGGCCTGTGCAGACTACTCAAGAGGAGGACGGCTGTTCATGCCGGTTCCCAGAGGAG<br>GAGGAAGGCGGCTGCGAACTGCGCGTGAAATTCAGCCGCAGCGCAGATGCTCCAGCCTACAAGCAGGGGCAGAACCAGCT<br>CTACAACGAACTCAATCTTGGTCGGAGAGAGGAGTACGACGTGCTGGACAAGCGGAGAGGACGGGACCCAGAAATGGGCG<br>GGAAGCCGCGCAGAAAGAATCCCCAAGAGGGCCTGTACAACGAGCTCCAAAAGGATAAGATGGCAGAAGCCTATAGCGAG<br>ATTGGTATGAAAGGGGAACGCAGAAGAGGCAAAGGCCACGACGGACTGTACCAGGGACTCAGCACCGCCACCAAGGACAC<br>CTATGACGCTCTTCACATGCAGGCCCTGCCGCCTCGG |
| 110 | M24 (ScFv domain) >NH6 7-89CE (M24) | CAAATCACTCTGAAAGAA<br>TCTGGACCGGCCCTGGTTAAGCCGACTCAAACGCTCACCCTTACTTGCACCTTCAGCGGATTCTCACTCAGCACTGCTGG<br>TGTGCACGTCGGATGGATTAGACAGCCGCCTGGAAAGGCCCTGGAATGGCTCGCCCTCATCTCCTGGGCCGATGACAAGA<br>GATACAGGCCCTCGCTTCGATCCCGGTTGGACATTACCCGGGTGACCTCGAAAGATCAGGTGGTGCTCTCAATGACCAAT<br>ATGCAGCCGGAGGACACCGCTACGTACTACTGCGCACTGCAAGGATTTGACGGCTACGAGGCTAACTGGGGACCAGGTAC<br>TCTGGTCACCGTGAGCTCCGGCGGGGGAGGATCAGGCGGGGGGGGGTCAGGAGGCGGAGGCTCCGGTGGAGGAGGATCGG<br>ATATCGTCATGACCCAGTCCCCAAGCTCGCTGAGCGCGTCAGCGGGCGACCGCGTGACTATCACTTGCCGGGCCAGCCGC<br>GGCATCTCCTCCGCACTGGCGTGGTACCAGCAGAAGCCTGGAAAACCGCCAAAGCTCCTGATCTATGATGCCTCCAGCCT<br>GGAGTCAGGTGTCCCCAGCCGCTTCTCGGGTTCGGGCTCGGGAACCGACTTCACTTTGACCATCGACTCGCTGGAACCGG<br>AAGATTTCGCAACCTACTACTGTCAGCAGTCCTACTCGACCCCTTGGACTTTTGGACAAGGGACGAAGGTGGACATCAAG |
| 134 | M24 (Full) >NH6 7-89CE (M24) | ATGGCCCTCCCTGTCACCGCCCTGCTGCTTCCGCTGGCTCTTCTGCTCCACGCCGCTCGGCCCCAAATCACTCTGAAAGAA<br>TCTGGACCGGCCCTGGTTAAGCCGACTCAAACGCTCACCCTTACTTGCACCTTCAGCGGATTCTCACTCAGCACTGCTGG<br>TGTGCACGTCGGATGGATTAGACAGCCGCCTGGAAAGGCCCTGGAATGGCTCGCCCTCATCTCCTGGGCCGATGACAAGA<br>GATACAGGCCCTCGCTTCGATCCCGGTTGGACATTACCCGGGTGACCTCGAAAGATCAGGTGGTGCTCTCAATGACCAAT<br>ATGCAGCCGGAGGACACCGCTACGTACTACTGCGCACTGCAAGGATTTGACGGCTACGAGGCTAACTGGGGACCAGGTAC<br>TCTGGTCACCGTGAGCTCCGGCGGGGGAGGATCAGGCGGGGGGGGGTCAGGAGGCGGAGGCTCCGGTGGAGGAGGATCGG<br>ATATCGTCATGACCCAGTCCCCAAGCTCGCTGAGCGCGTCAGCGGGCGACCGCGTGACTATCACTTGCCGGGCCAGCCGC<br>GGCATCTCCTCCGCACTGGCGTGGTACCAGCAGAAGCCTGGAAAACCGCCAAAGCTCCTGATCTATGATGCCTCCAGCCT<br>GGAGTCAGGTGTCCCCAGCCGCTTCTCGGGTTCGGGCTCGGGAACCGACTTCACTTTGACCATCGACTCGCTGGAACCGG<br>AAGATTTCGCAACCTACTACTGTCAGCAGTCCTACTCGACCCCTTGGACTTTTGGACAAGGGACGAAGGTGGACATCAAG<br>**ACCACTACC**CCAGCACCGAGGCCACCCACCCCGGCTCCTACCATCGCCTCCCAGCCTCTGTCCCTGCGTCCGGAGGCATG<br>TAGACCCGCAGCTGGTGGGGCCGTGCATACCCGGGGTCTTGACTTCGCCTGCGATATCTACATTTGGGCCCCTCTGGCTG<br>GTACTTGCGGGGTCCTGCTGCTTTCACTCGTGATCACTCTTTACTGTAAGCGCGGTCGGAAGAAGCTGCTGTACATCTTT<br>AAGCAACCCTTCATGAGGCCTGTGCAGACTACTCAAGAGGAGGACGGCTGTTCATGCCGGTTCCCAGAGGAGGAGGAAGG |

TABLE 3-continued

| SEQ ID NO: | Desc. | Nucleic Acid Sequence |
|---|---|---|
| | | CGGCTGCGAACTGCGCGTGAAATTCAGCCGCAGCGCAGATGCTCCAGCCTACAAGCAGGGGCAGAACCAGCTCTACAACG<br>AACTCAATCTTGGTCGGAGAGAGGAGTACGACGTGCTGGACAAGCGGAGAGGACGGGACCCAGAAATGGGCGGGAAGCCG<br>CGCAGAAAGAATCCCCAAGAGGGCCTGTACAACGAGCTCCAAAAGGATAAGATGGCAGAAGCCTATAGCGAGATTGGTAT<br>GAAAGGGGAACGCAGAAGAGGCAAAGGCCACGACGGACTGTACCAGGGACTCAGCACCGCCACCAAGGACACCTATGACG<br>CTCTTCACATGCAGGCCCTGCCGCCTCGG |
| 279 | Ss1 (scFv domain) | CAAGTCCAGCTCCAGCAGTCGGGCCCAGAGTTGGAGAAGCCTGGGGCGAGCGTGAAGAT<br>CTCATGCAAAGCCTCAGGCTACTCCTTTACTGGATACACGATGAATTGGGTGAAACAGT<br>CGCATGGAAAGTCACTGGAATGGATCGGTCTGATTACGCCCTACAACGGCGCCTCCAGC<br>TACAACCAGAAGTTCAGGGGAAAGGCGACCCTTACTGTCGACAAGTCGTCAAGCACCGC<br>CTACATGGACCTCCTGTCCCTGACCTCCGAAGATAGCGCGGTCTACTTTTGTGCACGCG<br>GAGGTTACGATGGACGGGGATTCGACTACTGGGGCCAGGGAACCACTGTCACCGTGTCG<br>AGCGGAGGCGGAGGGAGCGGAGGAGGAGGCAGCGGAGGTGGAGGGTCGGATATCGAACT<br>CACTCAGTCCCCAGCAATCATGTCCGCTTCACCGGGAGAAAAGGTGACCATGACTTGCT<br>CGGCCTCCTCGTCCGTGTCATACATGCACTGGTACCAACAAAAATCGGGGACCTCCCCT<br>AAGAGATGGATCTACGATACCAGCAAACTGGCTTCAGGCGTGCCGGGACGCTTCTCGGG<br>TTCGGGGAGCGGAAATTCGTATTCGTTGACCATTTCGTCCGTGGAAGCCGAGGACGACG<br>CAACTTATTACTGCCAACAGTGGTCAGGCTACCCGCTCACTTTCGGAGCCGGCACTAAG<br>CTGGAGATC |
| 280 | Ss1 (full) | ATGGCCCTCCCTGTCACCGCCCTGCTGCTTCCGCTGGCTCTTCTGCTCCACGCCGCTCG<br>GCCCCAAGTCCAGCTCCAGCAGTCGGGCCCAGAGTTGGAGAAGCCTGGGGCGAGCGTGA<br>AGATCTCATGCAAAGCCTCAGGCTACTCCTTTACTGGATACACGATGAATTGGGTGAAA<br>CAGTCGCATGGAAAGTCACTGGAATGGATCGGTCTGATTACGCCCTACAACGGCGCCTC<br>CAGCTACAACCAGAAGTTCAGGGGAAAGGCGACCCTTACTGTCGACAAGTCGTCAAGCA<br>CCGCCTACATGGACCTCCTGTCCCTGACCTCCGAAGATAGCGCGGTCTACTTTTGTGCA<br>CGCGGAGGTTACGATGGACGGGGATTCGACTACTGGGGCCAGGGAACCACTGTCACCGT<br>GTCGAGCGGAGGCGGAGGGAGCGGAGGAGGAGGCAGCGGAGGTGGAGGGTCGGATATCG<br>AACTCACTCAGTCCCCAGCAATCATGTCCGCTTCACCGGGAGAAAAGGTGACCATGACT<br>TGCTCGGCCTCCTCGTCCGTGTCATACATGCACTGGTACCAACAAAAATCGGGGACCTC<br>CCCTAAGAGATGGATCTACGATACCAGCAAACTGGCTTCAGGCGTGCCGGGACGCTTCT<br>CGGGTTCGGGGAGCGGAAATTCGTATTCGTTGACCATTTCGTCCGTGGAAGCCGAGGAC<br>GACGCAACTTATTACTGCCAACAGTGGTCAGGCTACCCGCTCACTTTCGGAGCCGGCAC<br>TAAGCTGGAGATCACCACTACCCCAGCACCGAGGCCACCCACCCCGGCTCCTACCATCG<br>CCTCCCAGCCTCTGTCCCTGCGTCCGGAGGCATGTAGACCCGCAGCTGGTGGGGCCGTG<br>CATACCCGGGGTCTTGACTTCGCCTGCGATATCTACATTTGGGCCCCTCTGGCTGGTAC<br>TTGCGGGGTCCTGCTGCTTTCACTCGTGATCACTCTTTACTGTAAGCGCGGTCGGAAGA<br>AGCTGCTGTACATCTTTAAGCAACCCTTCATGAGGCCTGTGCAGACTACTCAAGAGGAG<br>GACGGCTGTTCATGCCGGTTCCCAGAGGAGGAGGAAGGCGGCTGCGAACTGCGCGTGAA<br>ATTCAGCCGCAGCGCAGATGCTCCAGCC |

Nucleic Acid Sequences encoding CAR molecules (the leader sequence is underlined)

TABLE 4

Amino acid sequences for the heavy chain (HC) CDR1, CDR2, and CDR3 regions of human anti-mesothelin scFvs

| Descrip. | HC-CDR1 | SEQ ID NO: | HC-CDR2 | SEQ ID NO: | HC-CDR3 | SEQ ID NO: |
|---|---|---|---|---|---|---|
| M1 | GYTFTGYYMH | 136 | RINPNSGGTNYAQKFQG | 155 | GRYYGMDV | 175 |
| M2 | GYTFTGYYMH | 136 | WINPNSGGTNYAQKFQG | 156 | DLRRTVVTPRAYYGMDV | 176 |
| M3 | GYTFTGYYMH | 136 | WINPNSGGTNYAQKFQG | 156 | GEWDGSYYYDY | 177 |
| M4 | GFTFSSYWMH | 137 | RINTDGSTTTYADSVEG | 157 | GHWAV | 178 |
| M5 | GYTFTDYYMH | 138 | WINPNSGGTNYAQKFQG | 156 | GWDFDY | 179 |
| M6 | GYTFTSYYMH | 139 | IINPSGGSTSYAQKFQ | 158 | YRLIAVAGDYYYYGMDV | 180 |
| M7 | GFTFSSYAMH | 140 | VISYDGSNKYYADSVKG | 274 | WKVSSSSPAFDY | 181 |
| M8 | GYPFTGYSLH | 141 | WINPNSGGTNYAQKFQG | 159 | DHYGGNSLFY | 182 |
| M9 | GYTFTSYYMH | 142 | IINPSGGSTGYAQKFQG | 160 | GGYSSSSDAFDI | 183 |
| M10 | GYTFTSYGIS | 143 | WISAYNGNTNYAQKLQ | 161 | VAGGIYYYYGMDV | 184 |
| M11 | GYTFTGYYMH | 144 | WINPNSGGTNYAQNFQG | 162 | GWDFDY | 185 |

TABLE 4-continued

Amino acid sequences for the heavy chain (HC) CDR1, CDR2, and CDR3 regions of human anti-mesothelin scFvs

| Descrip. | HC-CDR1 | SEQ ID NO: | HC-CDR2 | SEQ ID NO: | HC-CDR3 | SEQ ID NO: |
|---|---|---|---|---|---|---|
| M12 | GYTFTGYYMH | 144 | RINPNSGGTNYAQKFQG | 163 | TTTSYAFDI | 186 |
| M13 | GFTFSDYYMG | 145 | YIGRSGSSMYYADSVKG | 164 | SPVVAATEDFQH | 187 |
| M14 | GFTFRGYYIH | 146 | IINPSGGSRAYAQKFQG | 165 | TASCGGDCYYLDY | 188 |
| M15 | GFTFDDYAMH | 147 | GISWNSGSIGYADSVK | 166 | DGSSSWSWGYFDY | 189 |
| M16 | GFTFDDYAMH | 147 | GISWNSGSTGYADSVKG | 167 | DSSSWYGGGSAFDI | 190 |
| M17 | GFTFDDYAMH | 147 | GISWNSGSTGYADSVKG | 167 | DSSSWYGGGSAFDI | 191 |
| M18 | GFTFSSYWMH | 148 | RINSDGSSTSYADSVKG | 168 | TGWVGSYYYYMDV | 192 |
| M19 | GFTFSSYGMH | 149 | VISYDGSNKYYADSVKG | 169 | GYSRYYYYGMDV | 193 |
| M20 | GFTFSSYAMS | 150 | AISGSGGSTYYADSVKG | 170 | REAAAGHDWYFDL | 194 |
| M21 | GYTFTSYYMH | 151 | IINPSGGSTSYAQKFQG | 171 | SPRVTTGYFDY | 195 |
| M22 | GDTSTRHYIH | 152 | VINPTTGPATGSPAYAQML QG | 172 | SVVGRSAPYYFDY | 196 |
| M23 | GYTFTNYYMH | 153 | IINPSGGYTTYAQKFQG | 173 | IRSCGGDCYYFDN | 197 |
| M24 | GFSLSTAGVHV G | 154 | LISWADDKRYRPSLRS | 174 | QGFDGYEAN | 198 |
| Ss1 | GYSFTGYTMN | 281 | LITPYNGASSYNQKFRG | 282 | GGYDGRGFDY | 283 |

TABLE 5

Amino acid sequences for the light chain (LC) CDR1, CDR2, and CDR3 regions of human anti-mesothelin scFvs

| Description | LC-CDR1 | SEQ ID NO: | LC-CDR2 | SEQ ID NO: | LC-CDR3 | SEQ ID NO: |
|---|---|---|---|---|---|---|
| M1 | RASQSVSSNFA | 199 | DASNRAT | 223 | HQRSNWLYT | 247 |
| M2 | QASQDISNSLN | 200 | DASTLET | 224 | QQHDNLPLT | 248 |
| M3 | RASQSINTYLN | 201 | AASSLQS | 225 | QQSFSPLT | 249 |
| M4 | RASQSISDRLA | 202 | KASSLES | 226 | QQYGHLPMYT | 250 |
| M5 | RASQSIRYYLS | 203 | TASILQN | 227 | LQTYTTPD | 251 |
| M6 | RASQGVGRWLA | 204 | AASTLQS | 228 | QQANSFPLT | 252 |
| M7 | RASQSVYTKYLG | 205 | DASTRAT | 229 | QHYGGSPLIT | 253 |
| M8 | RASQDSGTWLA | 206 | DASTLED | 230 | QQYNSYPLT | 254 |
| M9 | RASQDISSALA | 207 | DASSLES | 231 | QQFSSYPLT | 255 |
| M10 | KSSHSVLYNRNNKNYLA | 208 | WASTRKS | 232 | QQTQTFPLT | 256 |
| M11 | RASQSIRYYLS | 209 | TASILQN | 233 | LQTYTTPD | 257 |
| M12 | RASQSISTWLA | 210 | KASTLES | 234 | QQYNTYSPYT | 258 |
| M13 | RASQSVTSNYLA | 211 | GASTRAT | 235 | QQYGSAPVT | 259 |
| M14 | RASENVNIWLA | 212 | KSSSLAS | 236 | QQYQSYPLT | 260 |
| M15 | QGDALRSYYAS | 213 | GKNNRPS | 237 | NSRDSSGYPV | 261 |

TABLE 5-continued

Amino acid sequences for the light chain (LC) CDR1, CDR2, and CDR3 regions of human anti-mesothelin scFvs

| Description | LC-CDR1 | SEQ ID NO: | LC-CDR2 | SEQ ID NO: | LC-CDR3 | SEQ ID NO: |
|---|---|---|---|---|---|---|
| M16 | QGDSLRSYYAS | 214 | GRSRRPS | 238 | NSRDNTANHYV | 262 |
| M17 | QGDSLRSYYAS | 215 | GKNNRPS | 239 | NSRGSSGNHYV | 263 |
| M18 | RASQSVSSNYLA | 216 | DVSTRAT | 240 | QQRSNWPPWT | 264 |
| M19 | RASQSVYTKYLG | 217 | DASTRAT | 241 | QHYGGSPLIT | 265 |
| M20 | RASQSISSYLN | 218 | AASSLQS | 242 | QQSYSIPLT | 266 |
| M21 | RASQSISSWLA | 219 | KASSLES | 243 | QQYSSYPLT | 267 |
| M22 | RASQGISDYS | 220 | AASTLQS | 244 | QQYYSYPLT | 268 |
| M23 | RASENVNIWLA | 221 | KSSSLAS | 245 | QQYQSYPLT | 269 |
| M24 | RASRGISSALA | 222 | DASSLES | 246 | QQSYSTPWT | 270 |
| Ss1 | SASSSVSYMH | 284 | DTSKLAS | 285 | QQWSGYPLT | 286 |

Bispecific CARs

In an embodiment a multispecific antibody molecule is a bispecific antibody molecule. A bispecific antibody has specificity for no more than two antigens. A bispecific antibody molecule is characterized by a first immunoglobulin variable domain sequence which has binding specificity for a first epitope and a second immunoglobulin variable domain sequence that has binding specificity for a second epitope. In an embodiment the first and second epitopes are on the same antigen, e.g., the same protein (or subunit of a multimeric protein). In an embodiment the first and second epitopes overlap. In an embodiment the first and second epitopes do not overlap. In an embodiment the first and second epitopes are on different antigens, e.g., different proteins (or different subunits of a multimeric protein). In an embodiment a bispecific antibody molecule comprises a heavy chain variable domain sequence and a light chain variable domain sequence which have binding specificity for a first epitope and a heavy chain variable domain sequence and a light chain variable domain sequence which have binding specificity for a second epitope. In an embodiment a bispecific antibody molecule comprises a half antibody having binding specificity for a first epitope and a half antibody having binding specificity for a second epitope. In an embodiment a bispecific antibody molecule comprises a half antibody, or fragment thereof, having binding specificity for a first epitope and a half antibody, or fragment thereof, having binding specificity for a second epitope. In an embodiment a bispecific antibody molecule comprises a scFv, or fragment thereof, have binding specificity for a first epitope and a scFv, or fragment thereof, have binding specificity for a second epitope.

In certain embodiments, the antibody molecule is a multispecific (e.g., a bispecific or a trispecific) antibody molecule. Protocols for generating bispecific or heterodimeric antibody molecules are known in the art; including but not limited to, for example, the "knob in a hole" approach described in, e.g., U.S. Pat. No. 5,731,168; the electrostatic steering Fc pairing as described in, e.g., WO 09/089004, WO 06/106905 and WO 2010/129304; Strand Exchange Engineered Domains (SEED) heterodimer formation as described in, e.g., WO 07/110205; Fab arm exchange as described in, e.g., WO 08/119353, WO 2011/131746, and WO 2013/060867; double antibody conjugate, e.g., by antibody cross-linking to generate a bi-specific structure using a heterobifunctional reagent having an amine-reactive group and a sulfhydryl reactive group as described in, e.g., U.S. Pat. No. 4,433,059; bispecific antibody determinants generated by recombining half antibodies (heavy-light chain pairs or Fabs) from different antibodies through cycle of reduction and oxidation of disulfide bonds between the two heavy chains, as described in, e.g., U.S. Pat. No. 4,444,878; trifunctional antibodies, e.g., three Fab' fragments cross-linked through sulfhdryl reactive groups, as described in, e.g., U.S. Pat. No. 5,273,743; biosynthetic binding proteins, e.g., pair of scFvs cross-linked through C-terminal tails preferably through disulfide or amine-reactive chemical cross-linking, as described in, e.g., U.S. Pat. No. 5,534,254; bifunctional antibodies, e.g., Fab fragments with different binding specificities dimerized through leucine zippers (e.g., c-fos and c-jun) that have replaced the constant domain, as described in, e.g., U.S. Pat. No. 5,582,996; bispecific and oligospecific mono- and oligovalent receptors, e.g., VH-CH1 regions of two antibodies (two Fab fragments) linked through a polypeptide spacer between the CH1 region of one antibody and the VH region of the other antibody typically with associated light chains, as described in, e.g., U.S. Pat. No. 5,591,828; bispecific DNA-antibody conjugates, e.g., crosslinking of antibodies or Fab fragments through a double stranded piece of DNA, as described in, e.g., U.S. Pat. No. 5,635,602; bispecific fusion proteins, e.g., an expression construct containing two scFvs with a hydrophilic helical peptide linker between them and a full constant region, as described in, e.g., U.S. Pat. No. 5,637,481; multivalent and multispecific binding proteins, e.g., dimer of polypeptides having first domain with binding region of Ig heavy chain variable region, and second domain with binding region of Ig light chain variable region, generally termed diabodies (higher order structures are also encompassed creating for bispecifc, trispecific, or tetraspecific molecules, as described in, e.g., U.S. Pat. No. 5,837,242; minibody constructs with linked VL and VH chains further connected with peptide spacers to an antibody hinge region and CH3 region, which can be dimerized to form bispecific/multivalent molecules, as described in, e.g., U.S. Pat. No. 5,837,821; VH and VL domains linked with a short peptide linker (e.g., 5 or 10 amino acids) or no linker at all in either orientation, which can form dimers to form bispecific diabodies; trimers and tetramers, as described in, e.g., U.S. Pat. No. 5,844,094; String of VH domains (or VL domains in family members) connected by peptide linkages with crosslinkable groups at the C-terminus further associated with VL domains to form a series of FVs (or scFvs), as described in, e.g., U.S. Pat. No. 5,864,019; and single chain binding polypeptides with both a VH and a VL domain linked through a peptide linker are combined into multivalent structures through non-covalent or chemical crosslinking to form, e.g., homobivalent, heterobivalent, trivalent, and tetravalent structures using both scFV or diabody type format, as described in, e.g., U.S. Pat. No. 5,869,620. Additional exemplary multispecific and bispecific molecules and methods of making the same are found, for example, in U.S. Pat. Nos. 5,910,573, 5,932,448, 5,959,083, 5,989,830, 6,005,079, 6,239,259, 6,294,353, 6,333,396, 6,476,198, 6,511,663, 6,670,453, 6,743,896, 6,809,185, 6,833,441, 7,129,330, 7,183,076, 7,521,056, 7,527,787, 7,534,866, 7,612,181, US2002004587A1, US2002076406A1, US2002103345A1, US2003207346A1, US2003211078A1, US2004219643A1, US2004220388A1, US2004242847A1, US2005003403A1, US2005004352A1, US2005069552A1, US2005079170A1, US2005100543A1, US2005136049A1, US2005136051A1, US2005163782A1, US2005266425A1, US2006083747A1, US2006120960A1, US2006204493A1, US2006263367A1, US2007004909A1, US2007087381A1, US2007128150A1, US2007141049A1, US2007154901A1, US2007274985A1, US2008050370A1, US2008069820A1, US2008152645A1, US2008171855A1, US2008241884A1, US2008254512A1, US2008260738A1, US2009130106A1, US2009148905A1, US2009155275A1, US2009162359A1, US2009162360A1, US2009175851A1, US2009175867A1, US2009232811A1, US2009234105A1, US2009263392A1, US2009274649A1, EP346087A2, WO0006605A2, WO02072635A2, WO04081051A1, WO06020258A2, WO2007044887A2, WO2007095338A2, WO2007137760A2, WO2008119353A1, WO2009021754A2, WO2009068630A1, WO9103493A1, WO9323537A1, WO9409131A1, WO9412625A2, WO9509917A1, WO9637621A2, WO9964460A1. The contents of the above-referenced applications are incorporated herein by reference in their entireties.

Within each antibody or antibody fragment (e.g., scFv) of a bispecific antibody molecule, the VH can be upstream or downstream of the VL. In some embodiments, the upstream antibody or antibody fragment (e.g., scFv) is arranged with its VH ($VH_1$) upstream of its VL ($VL_1$) and the downstream antibody or antibody fragment (e.g., scFv) is arranged with its VL ($VL_2$) upstream of its VH ($VH_2$), such that the overall bispecific antibody molecule has the arrangement $VH_1$-$VL_1$-$VL_2$-$VH_2$.

In other embodiments, the upstream antibody or antibody fragment (e.g., scFv) is arranged with its VL ($VL_1$) upstream of its VH ($VH_1$) and the downstream antibody or antibody fragment (e.g., scFv) is arranged with its VH ($VH_2$) upstream of its VL ($VL_2$), such that the overall bispecific antibody molecule has the arrangement $VL_1$-$VH_1$-$VH_2$-$VL_2$. Optionally, a linker is disposed between the two antibodies or antibody fragments (e.g., scFvs), e.g., between $VL_1$ and $VL_2$ if the construct is arranged as $VH_1$-$VL_1$-$VL_2$-$VH_2$, or between $VH_1$ and $VH_2$ if the construct is arranged as VL-$VH_1$-$VH_2$-$VL_2$. The linker may be a linker as described herein, e.g., a ($Gly_4$-Ser)n linker, wherein n is 1, 2, 3, 4, 5, or 6, preferably 4 (SEQ ID NO: 26). In general, the linker between the two scFvs should be long enough to avoid mispairing between the domains of the two scFvs. Optionally, a linker is disposed between the VL and VH of the first scFv. Optionally, a linker is disposed between the VL and VH of the second scFv. In constructs that have multiple linkers, any two or more of the linkers can be the same or different. Accordingly, in some embodiments, a bispecific CAR comprises VLs, VHs, and optionally one or more linkers in an arrangement as described herein.

In one aspect, the bispecific antibody molecule is characterized by a first immunoglobulin variable domain sequence, e.g., a scFv, which has binding specificity for mesothelin, e.g., comprises a scFv as described herein, e.g., as described in Table 2 or 3, or comprises the light chain CDRs and/or heavy chain CDRs from a mesothelin scFv described herein, and a second immunoglobulin variable domain sequence that has binding specificity for a second epitope on a different antigen. In some aspects the second immunoglobulin variable domain sequence has binding specificity for an antigen other than mesothelin, e.g., an antigen expressed by a cancer or tumor cell. In some aspects, the second immunoglobulin variable domain sequence has binding specificity for an antigen selected from a target other than mesothelin on stroma cells, e.g., FAP; a target other than mesothelin on prostate cancer cells, e.g., androgen receptor, OR51E2, PSMA, PSCA, PDGRF-β, TARP, GloboH, MAD-CT-1, or MAD-CT-2; a target other than mesothelin on ovararian cancer cells, e.g., Tn, PRSS21, CD171, Lewis Y, folate receptor α, claudin6, GloboH, or sperm protein 17, e.g., a target other than mesothelin on lung cancer cells, e.g., VEGF, HER3, IGF-1R, EGFR, DLL4, or Trop-2.

Chimeric TCR

In one aspect, the mesothelin antibodies and antibody fragments of the present invention (for example, those disclosed in Tables 2 or 3) can be grafted to one or more constant domain of a T cell receptor ("TCR") chain, for example, a TCR alpha or TCR beta chain, to create an chimeric TCR that binds specificity to mesothelin. Without being bound by theory, it is believed that chimeric TCRs will signal through the TCR complex upon antigen binding. For example, a mesothelin scFv as disclosed herein, can be grafted to the constant domain, e.g., at least a portion of the extracellular constant domain, the transmembrane domain and the cytoplasmic domain, of a TCR chain, for example, the TCR alpha chain and/or the TCR beta chain. As another example, a mesothelin antibody fragment, for example a VL domain as described herein, can be grafted to the constant domain of a TCR alpha chain, and a mesothelin antibody fragment, for example a VH domain as described herein, can be grafted to the constant domain of a TCR beta chain (or alternatively, a VL domain may be grafted to the constant domain of the TCR beta chain and a VH domain may be grafted to a TCR alpha chain). As another example, the CDRs of a mesothelin antibody or antibody fragment, e.g., the CDRs of a mesothelin antibody or antibody fragment as described in Tables 4 or 5 may be grafted into a TCR alpha and/or beta chain to create a chimeric TCR that binds specifically to mesothelin. For example, the LCDRs disclosed herein may be grafted into the variable domain of a TCR alpha chain and the HCDRs disclosed herein may be grafted to the variable domain of a TCR beta chain, or vice versa. Such chimeric TCRs may be produced by methods known in the art (For example, Willemsen R A et al, Gene Therapy 2000; 7: 1369-1377; Zhang T et al, Cancer Gene Ther 2004; 11: 487-496; Aggen et al, Gene Ther. 2012 April; 19(4):365-74).

Natural Killer Cell Receptor (NKR) CARs

In an embodiment, the CAR molecule described herein comprises one or more components of a natural killer cell receptor (NKR), thereby forming an NKR-CAR. The NKR component can be a transmembrane domain, a hinge domain, or a cytoplasmic domain from any of the following natural killer cell receptors: killer cell immunoglobulin-like receptor (KIR), e.g., KIR2DL1, KIR2DL2/L3, KIR2DL4, KIR2DL5A, KIR2DL5B, KIR2DS1, KIR2DS2, KIR2DS3, KIR2DS4, DIR2DS5, KIR3DL1/S1, KIR3DL2, KIR3DL3, KIR2DP1, and KIR3DP1; natural cytotoxicity receptor (NCR), e.g., NKp30, NKp44, NKp46; signaling lymphocyte activation molecule (SLAM) family of immune cell receptors, e.g., CD48, CD229, 2B4, CD84, NTB-A, CRACC, BLAME, and CD2F-10; Fc receptor (FcR), e.g., CD16, and CD64; and Ly49 receptors, e.g., LY49A, LY49C. The NKR-CAR molecules described herein may interact with an adaptor molecule or intracellular signaling domain, e.g., DAP12. Exemplary configurations and sequences of CAR molecules comprising NKR components are described in International Publication No. WO2014/145252, the contents of which are hereby incorporated by reference.

Split CAR

In some embodiments, the CAR-expressing cell described herein, uses a split CAR. The split CAR approach is described in more detail in publications WO2014/055442 and WO2014/055657, incorporated herein by reference. Briefly, a split CAR system comprises a cell expressing a first CAR having a first antigen binding domain and a costimulatory domain (e.g., 41BB), and the cell also expresses a second CAR having a second antigen binding domain and an intracellular signaling domain (e.g., CD3 zeta). When the cell encounters the first antigen, the costimulatory domain is activated, and the cell proliferates. When the cell encounters the second antigen, the intracellular signaling domain is activated and cell-killing activity begins. Thus, the CAR-expressing cell is only fully activated in the presence of both antigens. In embodiments the first antigen binding domain recognizes the tumor antigen or B cell antigen described herein, e.g., comprises an antigen binding domain described herein, and the second antigen binding domain recognizes a second antigen, e.g., a second tumor antigen or a second B cell antigen described herein.

Co-Expression of CAR with Other Molecules or Agents

Co-Expression of a Second CAR

In one aspect, the CAR-expressing cell described herein can further comprise a second CAR, e.g., a second CAR that includes a different antigen binding domain, e.g., to the same target (mesothelin) or a different target (e.g., a target other than mesothelin on stroma cells, e.g., FAP; a target other than mesothelin on prostate cancer cells, e.g., androgen receptor, OR51E2, PSMA, PSCA, PDGRF-0, TARP, GloboH, MAD-CT-1, or MAD-CT-2; a target other than mesothelin on ovararian cancer cells, e.g., Tn, PRSS21, CD171, Lewis Y, folate receptor α, claudin6, GloboH, or sperm protein 17, e.g., a target other than mesothelin on lung cancer cells, e.g., VEGF, HER3, IGF-1R, EGFR, DLL4, or Trop-2). In one embodiment, the CAR-expressing cell comprises a first CAR that targets a first antigen and includes an intracellular signaling domain having a costimulatory signaling domain but not a primary signaling domain, and a second CAR that targets a second, different, antigen and includes an intracellular signaling domain having a primary signaling domain but not a costimulatory signaling domain. Placement of a costimulatory signaling domain, e.g., 4-1BB, CD28, CD27, OX-40 or ICOS, onto the first CAR, and the primary signaling domain, e.g., CD3 zeta, on the second CAR can limit the CAR activity to cells where both targets are expressed. In one embodiment, the CAR expressing cell comprises a first mesothelin CAR that includes a mesothelin binding domain, a transmembrane domain and a costimulatory domain and a second CAR that targets an antigen other than mesothelin (e.g., a target other than mesothelin on stroma cells, e.g., FAP; a target other than mesothelin on prostate cancer cells, e.g., androgen receptor, OR51E2, PSMA, PSCA, PDGRF-0, TARP, GloboH, MAD-CT-1, or MAD-CT-2; a target other than mesothelin on ovararian cancer cells, e.g., Tn, PRSS21, CD171, Lewis Y, folate receptor α, claudin6, GloboH, or sperm protein 17, e.g., a target other than mesothelin on lung cancer cells, e.g., VEGF, HER3, IGF-1R, EGFR, DLL4, or Trop-2) and includes an antigen binding domain, a transmembrane domain and a primary signaling domain. In another embodiment, the CAR expressing cell comprises a first mesothelin CAR that includes a mesothelin binding domain, a transmembrane domain and a primary signaling domain and a second CAR that targets an antigen other than mesothelin (e.g., a target other than mesothelin on stroma cells, e.g., FAP; a target other than mesothelin on prostate cancer cells, e.g., androgen receptor, OR51E2, PSMA, PSCA, PDGRF-0, TARP, GloboH, MAD-CT-1, or MAD-CT-2; a target other than mesothelin on ovararian cancer cells, e.g., Tn, PRSS21, CD171, Lewis Y, folate receptor α, claudin6, GloboH, or sperm protein 17, e.g., a target other than mesothelin on lung cancer cells, e.g., VEGF, HER3, IGF-1R, EGFR, DLL4, or Trop-2) and includes an antigen binding domain to the antigen, a transmembrane domain and a costimulatory signaling domain.

In one embodiment, the CAR-expressing cell comprises a mesothelin CAR described herein and an inhibitory CAR. In one embodiment, the inhibitory CAR comprises an antigen binding domain that binds an antigen found on normal cells but not cancer cells, e.g., normal cells that also express mesothelin. In one embodiment, the inhibitory CAR comprises the antigen binding domain, a transmembrane domain and an intracellular domain of an inhibitory molecule. For example, the intracellular domain of the inhibitory CAR can be an intracellular domain of PD1, PD-L1, CTLA4, TIM3, LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, or TGFR beta.

In one embodiment, when the CAR-expressing cell comprises two or more different CARs, the antigen binding domains of the different CARs can be such that the antigen binding domains do not interact with one another. For example, a cell expressing a first and second CAR can have an antigen binding domain of the first CAR, e.g., as a fragment, e.g., an scFv, that does not form an association with the antigen binding domain of the second CAR, e.g., the antigen binding domain of the second CAR is a VHH.

In some embodiments, the antigen binding domain comprises a single domain antigen binding (SDAB) molecules include molecules whose complementary determining regions are part of a single domain polypeptide. Examples include, but are not limited to, heavy chain variable domains, binding molecules naturally devoid of light chains, single domains derived from conventional 4-chain antibodies, engineered domains and single domain scaffolds other than those derived from antibodies. SDAB molecules may be any of the art, or any future single domain molecules.

SDAB molecules may be derived from any species including, but not limited to mouse, human, camel, llama, lamprey, fish, shark, goat, rabbit, and bovine. This term also includes naturally occurring single domain antibody molecules from species other than Camelidae and sharks.

In one aspect, an SDAB molecule can be derived from a variable region of the immunoglobulin found in fish, such as, for example, that which is derived from the immunoglobulin isotype known as Novel Antigen Receptor (NAR) found in the serum of shark. Methods of producing single domain molecules derived from a variable region of NAR ("IgNARs") are described in WO 03/014161 and Streltsov (2005) Protein Sci. 14:2901-2909.

According to another aspect, an SDAB molecule is a naturally occurring single domain antigen binding molecule known as heavy chain devoid of light chains. Such single domain molecules are disclosed in WO 9404678 and Hamers-Casterman, C. et al. (1993) Nature 363:446-448, for example. For clarity reasons, this variable domain derived from a heavy chain molecule naturally devoid of light chain is known herein as a VHH or nanobody to distinguish it from the conventional VH of four chain immunoglobulins. Such a VHH molecule can be derived from Camelidae species, for example in camel, llama, dromedary, alpaca and guanaco. Other species besides Camelidae may produce heavy chain molecules naturally devoid of light chain; such VHHs are within the scope of the invention.

The SDAB molecules can be recombinant, CDR-grafted, humanized, camelized, de-immunized and/or in vitro generated (e.g., selected by phage display).

It has also been discovered, that cells having a plurality of chimeric membrane embedded receptors comprising an antigen binding domain that interactions between the antigen binding domain of the receptors can be undesirable, e.g., because it inhibits the ability of one or more of the antigen binding domains to bind its cognate antigen. Accordingly, disclosed herein are cells having a first and a second non-naturally occurring chimeric membrane embedded receptor comprising antigen binding domains that minimize such interactions. Also disclosed herein are nucleic acids encoding a first and a second non-naturally occurring chimeric membrane embedded receptor comprising an antigen binding domains that minimize such interactions, as well as methods of making and using such cells and nucleic acids. In an embodiment the antigen binding domain of one of the first and the second non-naturally occurring chimeric membrane embedded receptor, comprises an scFv, and the other comprises a single VH domain, e.g., a camelid, shark, or lamprey single VH domain, or a single VH domain derived from a human or mouse sequence.

In some embodiments, the claimed invention comprises a first and second CAR, wherein the antigen binding domain of one of the first and the second CAR does not comprise a variable light domain and a variable heavy domain. In some embodiments, the antigen binding domain of one of the first and the second CAR is an scFv, and the other is not an scFv. In some embodiments, the antigen binding domain of one of the first and the second CAR comprises a single VH domain, e.g., a camelid, shark, or lamprey single VH domain, or a single VH domain derived from a human or mouse sequence. In some embodiments, the antigen binding domain of one of the first and the second CAR comprises a nanobody. In some embodiments, the antigen binding domain of one of the first and the second CAR comprises a camelid VHH domain.

In some embodiments, the antigen binding domain of one of the first and the second CAR comprises an scFv, and the other comprises a single VH domain, e.g., a camelid, shark, or lamprey single VH domain, or a single VH domain derived from a human or mouse sequence. In some embodiments, the antigen binding domain of one of the first and the second CAR comprises an scFv, and the other comprises a nanobody. In some embodiments, the antigen binding domain of one of the first and the second CAR comprises an scFv, and the other comprises a camelid VHH domain.

In some embodiments, when present on the surface of a cell, binding of the antigen binding domain of the first CAR to its cognate antigen is not substantially reduced by the presence of the second CAR. In some embodiments, binding of the antigen binding domain of the first CAR to its cognate antigen in the presence of the second CAR is 85%, 90%, 95%, 96%, 97%, 98% or 99% of binding of the antigen binding domain of the first CAR to its cognate antigen in the absence of the second CAR.

In some embodiments, when present on the surface of a cell, the antigen binding domains of the first and the second CAR, associate with one another less than if both were scFv antigen binding domains. In some embodiments, the antigen binding domains of the first and the second CAR, associate with one another 85%, 90%, 95%, 96%, 97%, 98% or 99% less than if both were scFv antigen binding domains.

Co-Expression of an Agent that Enhances CAR Activity

In another aspect, the CAR-expressing cell described herein can further express another agent, e.g., an agent that enhances the activity or fitness of a CAR-expressing cell.

For example, in one embodiment, the agent can be an agent which inhibits a molecule that modulates or regulates, e.g., inhibits, T cell function. In some embodiments, the molecule that modulates or regulates T cell function is an inhibitory molecule. Inhibitory molecules, e.g., PD1, can, in some embodiments, decrease the ability of a CAR-expressing cell to mount an immune effector response. Examples of inhibitory molecules include PD1, PD-L1, CTLA4, TIM3, LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, or TGFR beta.

In embodiments, an agent, e.g., an inhibitory nucleic acid, e.g., a dsRNA, e.g., an siRNA or shRNA; or e.g., an inhibitory protein or system, e.g., a clustered regularly interspaced short palindromic repeats (CRISPR), a transcription-activator like effector nuclease (TALEN), or a zinc finger endonuclease (ZFN), e.g., as described herein, can be used to inhibit expression of a molecule that modulates or regulates, e.g., inhibits, T-cell function in the CAR-expressing cell. In an embodiment the agent is an shRNA, e.g., an shRNA described herein. In an embodiment, the agent that modulates or regulates, e.g., inhibits, T-cell function is inhibited within a CAR-expressing cell. For example, a dsRNA molecule that inhibits expression of a molecule that modulates or regulates, e.g., inhibits, T-cell function is linked to the nucleic acid that encodes a component, e.g., all of the components, of the CAR.

In one embodiment, the agent which inhibits an inhibitory molecule comprises a first polypeptide, e.g., an inhibitory molecule, associated with a second polypeptide that provides a positive signal to the cell, e.g., an intracellular signaling domain described herein. In one embodiment, the agent comprises a first polypeptide, e.g., of an inhibitory molecule such as PD1, PD-L1, CTLA4, TIM3, LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, or TGFR beta, or a fragment of any of these (e.g., at least a portion of an extracellular domain of any of these), and a second polypeptide which is an intracellular signaling domain described herein (e.g., comprising a costimulatory domain (e.g., 41BB, CD27 or CD28, e.g., as described herein) and/or a primary signaling domain (e.g., a CD3 zeta signaling domain described herein). In one embodiment, the agent comprises a first polypeptide of PD1 or a fragment thereof (e.g., at least a portion of an extracellular domain of PD1), and a second polypeptide of an intracellular signaling domain described herein (e.g., a CD28 signaling domain described herein and/or a CD3 zeta signaling domain described herein). PD1 is an inhibitory member of the CD28 family of receptors that also includes CD28, CTLA-4, ICOS, and BTLA. PD-1 is expressed on activated B cells, T cells and myeloid cells (Agata et al. 1996 Int. Immunol 8:765-75). Two ligands for PD1, PD-L1 and PD-L2 have been shown to downregulate T cell activation upon binding to PD1 (Freeman et a. 2000 J Exp Med 192:1027-34; Latchman et al. 2001 Nat Immunol 2:261-8; Carter et al. 2002 Eur J Immunol 32:634-43). PD-L1 is abundant in human cancers (Dong et al. 2003 J Mol Med 81:281-7; Blank et al. 2005 Cancer Immunol. Immunother 54:307-314; Konishi et al. 2004 Clin Cancer Res 10:5094). Immune suppression can be reversed by inhibiting the local interaction of PD1 with PD-L1.

In one embodiment, the agent comprises the extracellular domain (ECD) of an inhibitory molecule, e.g., Programmed Death 1 (PD1), can be fused to a transmembrane domain and intracellular signaling domains such as 41BB and CD3 zeta (also referred to herein as a PD1 CAR). In one embodiment, the PD1 CAR, when used in combinations with a mesothelin CAR described herein, improves the persistence of the T cell. In one embodiment, the CAR is a PD1 CAR comprising the extracellular domain of PD1 indicated as underlined in SEQ ID NO: 24 and a signal sequence at amino acids 1-21 of SEQ ID NO:24. In one embodiment, the PD1 CAR comprises the amino acid sequence of SEQ ID NO:24.

In one embodiment, the PD1 CAR without the N-terminal signal sequence comprises the amino acid sequence provided of SEQ ID NO:22.

In one embodiment, the agent comprises a nucleic acid sequence encoding the PD1 CAR with the N-terminal signal sequence, e.g., the PD1 CAR described herein. In one embodiment, the nucleic acid sequence for the PD1 CAR is shown in Table 1, with the PD1 ECD underlined in SEQ ID NO: 23.

In another example, in one embodiment, the agent which enhances the activity of a CAR-expressing cell can be a costimulatory molecule or costimulatory molecule ligand. Examples of costimulatory molecules include MHC class I molecule, BTLA and a Toll ligand receptor, as well as OX40, CD27, CD28, CDS, ICAM-1, LFA-1 (CD11a/CD18), ICOS (CD278), and 4-1BB (CD137). Further examples of such costimulatory molecules include CDS, ICAM-1, GITR, BAFFR, HVEM (LIGHTR), SLAMF7, NKp80 (KLRF1), NKp44, NKp30, NKp46, CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, NKG2C, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMFI, CD150, IPO-3), BLAME (SLAMF8), SELPLG (CD162), LTBR, LAT, GADS, SLP-76, PAG/Cbp, CD19a, CD28-OX40, CD28-4-1BB, and a ligand that specifically binds with CD83., e.g., as described herein. Examples of costimulatory molecule ligands include CD80, CD86, CD40L, ICOSL, CD70, OX40L, 4-1BBL, GITRL, and LIGHT. In embodiments, the costimulatory molecule ligand is a ligand for a costimulatory molecule different from the costimulatory molecule domain of the CAR. In embodiments, the costimulatory molecule ligand is a ligand for a costimulatory molecule that is the same as the costimulatory molecule domain of the CAR. In an embodiment, the costimulatory molecule ligand is 4-1BBL. In an embodiment, the costimulatory ligand is CD80 or CD86. In an embodiment, the costimulatory molecule ligand is CD70. In embodiments, a CAR-expressing immune effector cell described herein can be further engineered to express one or more additional costimulatory molecules or costimulatory molecule ligands.

Co-Expression of CAR with a Chemokine Receptor

In embodiments, the CAR-expressing cell described herein, e.g., mesothelin CAR-expressing cell, further comprises a chemokine receptor molecule. Transgenic expression of chemokine receptors CCR2b or CXCR2 in T cells enhances trafficking to CCL2- or CXCL1-secreting solid tumors including melanoma and neuroblastoma (Craddock et al., *J Immunother.* 2010 October; 33(8):780-8 and Kershaw et al., *Hum Gene Ther.* 2002 Nov. 1; 13(16):1971-80). Thus, without wishing to be bound by theory, it is believed that chemokine receptors expressed in CAR-expressing cells that recognize chemokines secreted by tumors, e.g., solid tumors, can improve homing of the CAR-expressing cell to the tumor, facilitate the infiltration of the CAR-expressing cell to the tumor, and enhances antitumor efficacy of the CAR-expressing cell. The chemokine receptor molecule can comprise a naturally occurring or recombinant chemokine receptor or a chemokine-binding fragment thereof. A chemokine receptor molecule suitable for expression in a CAR-expressing cell (e.g., CAR-Tx) described herein include a CXC chemokine receptor (e.g., CXCR1, CXCR2, CXCR3, CXCR4, CXCR5, CXCR6, or CXCR7), a CC chemokine receptor (e.g., CCR1, CCR2, CCR3, CCR4, CCR5, CCR6, CCR7, CCR8, CCR9, CCR10, or CCR11), a CX3C chemokine receptor (e.g., CX3CR1), a XC chemokine receptor (e.g., XCR1), or a chemokine-binding fragment thereof. In one embodiment, the chemokine receptor molecule to be expressed with a CAR described herein is selected based on the chemokine(s) secreted by the tumor. In one embodiment, the CAR-expressing cell described herein further comprises, e.g., expresses, a CCR2b receptor or a CXCR2 receptor. In an embodiment, the CAR described herein and the chemokine receptor molecule are on the same vector or are on two different vectors. In embodiments where the CAR described herein and the chemokine receptor molecule are on the same vector, the CAR and the chemokine receptor molecule are each under control of two different promoters or are under the control of the same promoter.

RNA Transfection

Disclosed herein are methods for producing an in vitro transcribed RNA CAR. The present invention also includes a CAR encoding RNA construct that can be directly transfected into a cell. A method for generating mRNA for use in transfection can involve in vitro transcription (IVT) of a template with specially designed primers, followed by polyA addition, to produce a construct containing 3' and 5' untranslated sequence ("UTR"), a 5' cap and/or Internal Ribosome Entry Site (IRES), the nucleic acid to be expressed, and a polyA tail, typically 50-2000 bases in length (SEQ ID NO: 35). RNA so produced can efficiently transfect different kinds of cells. In one aspect, the template includes sequences for the CAR.

In one aspect the CAR is encoded by a messenger RNA (mRNA). In one aspect the mRNA encoding the CAR is introduced into an immune effector cell, e.g., a T cell or a NK cell, for production of a CAR-expressing cell (e.g., CART cell or CAR-expressing NK cell).

In one embodiment, the in vitro transcribed RNA CAR can be introduced to a cell as a form of transient transfection. The RNA is produced by in vitro transcription using a polymerase chain reaction (PCR)-generated template. DNA of interest from any source can be directly converted by PCR into a template for in vitro mRNA synthesis using appropriate primers and RNA polymerase. The source of the DNA can be, for example, genomic DNA, plasmid DNA, phage DNA, cDNA, synthetic DNA sequence or any other appropriate source of DNA. The desired temple for in vitro transcription is a CAR of the present invention. For example, the template for the RNA CAR comprises an extracellular region comprising a single chain variable domain of an anti-tumor antibody; a hinge region, a transmembrane domain (e.g., a transmembrane domain of CD8a); and a cytoplasmic region that includes an intracellular signaling domain, e.g., comprising the signaling domain of CD3-zeta and the signaling domain of 4-1BB.

In one embodiment, the DNA to be used for PCR contains an open reading frame. The DNA can be from a naturally occurring DNA sequence from the genome of an organism. In one embodiment, the nucleic acid can include some or all of the 5' and/or 3' untranslated regions (UTRs). The nucleic acid can include exons and introns. In one embodiment, the DNA to be used for PCR is a human nucleic acid sequence. In another embodiment, the DNA to be used for PCR is a human nucleic acid sequence including the 5' and 3' UTRs. The DNA can alternatively be an artificial DNA sequence that is not normally expressed in a naturally occurring organism. An exemplary artificial DNA sequence is one that contains portions of genes that are ligated together to form an open reading frame that encodes a fusion protein. The portions of DNA that are ligated together can be from a single organism or from more than one organism.

PCR is used to generate a template for in vitro transcription of mRNA which is used for transfection. Methods for performing PCR are well known in the art. Primers for use in PCR are designed to have regions that are substantially complementary to regions of the DNA to be used as a template for the PCR. "Substantially complementary," as used herein, refers to sequences of nucleotides where a majority or all of the bases in the primer sequence are complementary, or one or more bases are non-complementary, or mismatched. Substantially complementary sequences are able to anneal or hybridize with the intended DNA target under annealing conditions used for PCR. The primers can be designed to be substantially complementary to any portion of the DNA template. For example, the primers can be designed to amplify the portion of a nucleic acid that is normally transcribed in cells (the open reading frame), including 5' and 3' UTRs. The primers can also be designed to amplify a portion of a nucleic acid that encodes a particular domain of interest. In one embodiment, the primers are designed to amplify the coding region of a human cDNA, including all or portions of the 5' and 3' UTRs. Primers useful for PCR can be generated by synthetic methods that are well known in the art. "Forward primers" are primers that contain a region of nucleotides that are substantially complementary to nucleotides on the DNA template that are upstream of the DNA sequence that is to be amplified. "Upstream" is used herein to refer to a location 5, to the DNA sequence to be amplified relative to the coding strand. "Reverse primers" are primers that contain a region of nucleotides that are substantially complementary to a double-stranded DNA template that are downstream of the DNA sequence that is to be amplified. "Downstream" is used herein to refer to a location 3' to the DNA sequence to be amplified relative to the coding strand.

Any DNA polymerase useful for PCR can be used in the methods disclosed herein. The reagents and polymerase are commercially available from a number of sources.

Chemical structures with the ability to promote stability and/or translation efficiency may also be used. The RNA preferably has 5' and 3' UTRs. In one embodiment, the 5' UTR is between one and 3000 nucleotides in length. The length of 5' and 3' UTR sequences to be added to the coding region can be altered by different methods, including, but not limited to, designing primers for PCR that anneal to different regions of the UTRs. Using this approach, one of ordinary skill in the art can modify the 5' and 3' UTR lengths required to achieve optimal translation efficiency following transfection of the transcribed RNA.

The 5' and 3' UTRs can be the naturally occurring, endogenous 5' and 3' UTRs for the nucleic acid of interest. Alternatively, UTR sequences that are not endogenous to the nucleic acid of interest can be added by incorporating the UTR sequences into the forward and reverse primers or by any other modifications of the template. The use of UTR sequences that are not endogenous to the nucleic acid of interest can be useful for modifying the stability and/or translation efficiency of the RNA. For example, it is known that AU-rich elements in 3' UTR sequences can decrease the stability of mRNA. Therefore, 3' UTRs can be selected or designed to increase the stability of the transcribed RNA based on properties of UTRs that are well known in the art.

In one embodiment, the 5' UTR can contain the Kozak sequence of the endogenous nucleic acid. Alternatively, when a 5' UTR that is not endogenous to the nucleic acid of interest is being added by PCR as described above, a consensus Kozak sequence can be redesigned by adding the 5' UTR sequence. Kozak sequences can increase the efficiency of translation of some RNA transcripts, but does not appear to be required for all RNAs to enable efficient translation. The requirement for Kozak sequences for many mRNAs is known in the art. In other embodiments the 5' UTR can be 5'UTR of an RNA virus whose RNA genome is stable in cells. In other embodiments various nucleotide analogues can be used in the 3' or 5' UTR to impede exonuclease degradation of the mRNA.

To enable synthesis of RNA from a DNA template without the need for gene cloning, a promoter of transcription should be attached to the DNA template upstream of the sequence to be transcribed. When a sequence that functions as a promoter for an RNA polymerase is added to the 5' end of the forward primer, the RNA polymerase promoter becomes incorporated into the PCR product upstream of the open reading frame that is to be transcribed. In one preferred embodiment, the promoter is a T7 polymerase promoter, as described elsewhere herein. Other useful promoters include, but are not limited to, T3 and SP6 RNA polymerase promoters. Consensus nucleotide sequences for T7, T3 and SP6 promoters are known in the art.

In a preferred embodiment, the mRNA has both a cap on the 5' end and a 3' poly(A) tail which determine ribosome binding, initiation of translation and stability mRNA in the cell. On a circular DNA template, for instance, plasmid DNA, RNA polymerase produces a long concatameric product which is not suitable for expression in eukaryotic cells. The transcription of plasmid DNA linearized at the end of the 3' UTR results in normal sized mRNA which is not effective in eukaryotic transfection even if it is polyadenylated after transcription.

On a linear DNA template, phage T7 RNA polymerase can extend the 3' end of the transcript beyond the last base of the template (Schenborn and Mierendorf, Nuc Acids Res., 13:6223-36 (1985); Nacheva and Berzal-Herranz, Eur. J. Biochem., 270:1485-65 (2003).

The conventional method of integration of polyA/T stretches into a DNA template is molecular cloning. However polyA/T sequence integrated into plasmid DNA can cause plasmid instability, which is why plasmid DNA templates obtained from bacterial cells are often highly contaminated with deletions and other aberrations. This makes cloning procedures not only laborious and time consuming but often not reliable. That is why a method which allows construction of DNA templates with polyA/T 3' stretch without cloning highly desirable.

The polyA/T segment of the transcriptional DNA template can be produced during PCR by using a reverse primer containing a polyT tail, such as 100T tail (SEQ ID NO: 31) (size can be 50-5000 T (SEQ ID NO: 32)), or after PCR by any other method, including, but not limited to, DNA ligation or in vitro recombination. Poly(A) tails also provide stability to RNAs and reduce their degradation. Generally, the length of a poly(A) tail positively correlates with the stability of the transcribed RNA. In one embodiment, the poly(A) tail is between 100 and 5000 adenosines (SEQ ID NO: 33).

Poly(A) tails of RNAs can be further extended following in vitro transcription with the use of a poly(A) polymerase, such as *E. coli* polyA polymerase (E-PAP). In one embodiment, increasing the length of a poly(A) tail from 100 nucleotides to between 300 and 400 nucleotides (SEQ ID NO: 34) results in about a two-fold increase in the translation efficiency of the RNA. Additionally, the attachment of different chemical groups to the 3' end can increase mRNA stability. Such attachment can contain modified/artificial nucleotides, aptamers and other compounds. For example, ATP analogs can be incorporated into the poly(A) tail using poly(A) polymerase. ATP analogs can further increase the stability of the RNA.

5' caps on also provide stability to RNA molecules. In a preferred embodiment, RNAs produced by the methods disclosed herein include a 5' cap. The 5' cap is provided using techniques known in the art and described herein (Cougot, et al., Trends in Biochem. Sci., 29:436-444 (2001); Stepinski, et al., RNA, 7:1468-95 (2001); Elango, et al., Biochim. Biophys. Res. Commun., 330:958-966 (2005)).

The RNAs produced by the methods disclosed herein can also contain an internal ribosome entry site (IRES) sequence. The IRES sequence may be any viral, chromosomal or artificially designed sequence which initiates cap-independent ribosome binding to mRNA and facilitates the initiation of translation. Any solutes suitable for cell electroporation, which can contain factors facilitating cellular permeability and viability such as sugars, peptides, lipids, proteins, antioxidants, and surfactants can be included.

RNA can be introduced into target cells using any of a number of different methods, for instance, commercially available methods which include, but are not limited to, electroporation (Amaxa Nucleofector-II (Amaxa Biosystems, Cologne, Germany)), (ECM 830 (BTX) (Harvard Instruments, Boston, Mass.) or the Gene Pulser II (BioRad, Denver, Colo.), Multiporator (Eppendort, Hamburg Germany), cationic liposome mediated transfection using lipofection, polymer encapsulation, peptide mediated transfection, or biolistic particle delivery systems such as "gene guns" (see, for example, Nishikawa, et al. Hum Gene Ther., 12(8):861-70 (2001).

Non-Viral Delivery Methods

In some aspects, non-viral methods can be used to deliver a nucleic acid encoding a CAR described herein into a cell or tissue or a subject.

In some embodiments, the non-viral method includes the use of a transposon (also called a transposable element). In some embodiments, a transposon is a piece of DNA that can insert itself at a location in a genome, for example, a piece of DNA that is capable of self-replicating and inserting its copy into a genome, or a piece of DNA that can be spliced out of a longer nucleic acid and inserted into another place in a genome. For example, a transposon comprises a DNA sequence made up of inverted repeats flanking genes for transposition.

Exemplary methods of nucleic acid delivery using a transposon include a Sleeping Beauty transposon system (SBTS) and a piggyBac (PB) transposon system. See, e.g., Aronovich et al. Hum. Mol. Genet. 20.R1(2011):R14-20; Singh et al. Cancer Res. 15(2008):2961-2971; Huang et al. Mol. Ther. 16(2008):580-589; Grabundzija et al. Mol. Ther. 18(2010):1200-1209; Kebriaei et al. Blood. 122.21(2013): 166; Williams. Molecular Therapy 16.9(2008):1515-16; Bell et al. Nat. Protoc. 2.12(2007):3153-65; and Ding et al. Cell. 122.3(2005):473-83, all of which are incorporated herein by reference.

The SBTS includes two components: 1) a transposon containing a transgene and 2) a source of transposase enzyme. The transposase can transpose the transposon from a carrier plasmid (or other donor DNA) to a target DNA, such as a host cell chromosome/genome. For example, the transposase binds to the carrier plasmid/donor DNA, cuts the transposon (including transgene(s)) out of the plasmid, and inserts it into the genome of the host cell. See, e.g., Aronovich et al. supra.

Exemplary transposons include a pT2-based transposon. See, e.g., Grabundzija et al. Nucleic Acids Res. 41.3(2013): 1829-47; and Singh et al. Cancer Res. 68.8(2008): 2961-2971, all of which are incorporated herein by reference. Exemplary transposases include a Tc1/mariner-type transposase, e.g., the SB10 transposase or the SB11 transposase (a hyperactive transposase which can be expressed, e.g., from a cytomegalovirus promoter). See, e.g., Aronovich et al.; Kebriaei et al.; and Grabundzija et al., all of which are incorporated herein by reference.

Use of the SBTS permits efficient integration and expression of a transgene, e.g., a nucleic acid encoding a CAR described herein. Provided herein are methods of generating a cell, e.g., T cell or NK cell, that stably expresses a CAR described herein, e.g., using a transposon system such as SBTS.

In accordance with methods described herein, in some embodiments, one or more nucleic acids, e.g., plasmids, containing the SBTS components are delivered to a cell (e.g., T or NK cell). For example, the nucleic acid(s) are delivered by standard methods of nucleic acid (e.g., plasmid DNA) delivery, e.g., methods described herein, e.g., electroporation, transfection, or lipofection. In some embodiments, the nucleic acid contains a transposon comprising a transgene, e.g., a nucleic acid encoding a CAR described herein. In some embodiments, the nucleic acid contains a transposon comprising a transgene (e.g., a nucleic acid encoding a CAR described herein) as well as a nucleic acid sequence encoding a transposase enzyme. In other embodiments, a system with two nucleic acids is provided, e.g., a dual-plasmid system, e.g., where a first plasmid contains a transposon comprising a transgene, and a second plasmid contains a nucleic acid sequence encoding a transposase enzyme. For example, the first and the second nucleic acids are co-delivered into a host cell.

In some embodiments, cells, e.g., T or NK cells, are generated that express a CAR described herein by using a combination of gene insertion using the SBTS and genetic editing using a nuclease (e.g., Zinc finger nucleases (ZFNs), Transcription Activator-Like Effector Nucleases (TALENs), the CRISPR/Cas system, or engineered meganuclease re-engineered homing endonucleases).

In some embodiments, use of a non-viral method of delivery permits reprogramming of cells, e.g., T or NK cells, and direct infusion of the cells into a subject. Advantages of non-viral vectors include but are not limited to the ease and relatively low cost of producing sufficient amounts required to meet a patient population, stability during storage, and lack of immunogenicity.

Nucleic Acid Constructs Encoding a CAR

The present invention also provides nucleic acid molecules encoding one or more CAR constructs described herein. In one aspect, the nucleic acid molecule is provided as a messenger RNA transcript. In one aspect, the nucleic acid molecule is provided as a DNA construct.

Accordingly, in one aspect, the invention pertains to an isolated nucleic acid molecule encoding a chimeric antigen receptor (CAR), wherein the CAR comprises an antigen binding domain, a transmembrane domain, and an intracellular signaling domain comprising a stimulatory domain, e.g., a costimulatory signaling domain and/or a primary signaling domain, e.g., zeta chain.

The nucleic acid sequences coding for the desired molecules can be obtained using recombinant methods known in the art, such as, for example by screening libraries from cells expressing the gene, by deriving the gene from a vector known to include the same, or by isolating directly from cells and tissues containing the same, using standard techniques. Alternatively, the gene of interest can be produced synthetically, rather than cloned.

Vectors

The present invention also provides vectors in which a DNA of the present invention is inserted. Vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity. A retroviral vector may also be, e.g., a gammaretroviral vector. A gammaretroviral vector may include, e.g., a promoter, a packaging signal (ψ), a primer binding site (PBS), one or more (e.g., two) long terminal repeats (LTR), and a transgene of interest, e.g., a gene encoding a CAR. A gammaretroviral vector may lack viral structural gens such as gag, pol, and env. Exemplary gammaretroviral vectors include Murine Leukemia Virus (MLV), Spleen-Focus Forming Virus (SFFV), and Myeloproliferative Sarcoma Virus (MPSV), and vectors derived therefrom. Other gammaretroviral vectors are described, e.g., in Tobias Maetzig et al., "Gammaretroviral Vectors: Biology, Technology and Application" Viruses. 2011 June; 3(6): 677-713.

In another embodiment, the vector comprising the nucleic acid encoding the desired CAR of the invention is an adenoviral vector (A5/35). In another embodiment, the expression of nucleic acids encoding CARs can be accomplished using of transposons such as sleeping beauty, CRISPR, CAS9, and zinc finger nucleases. See below June et al. 2009*Nature Reviews Immunology* 9.10: 704-716, is incorporated herein by reference.

In brief summary, the expression of natural or synthetic nucleic acids encoding CARs is typically achieved by operably linking a nucleic acid encoding the CAR polypeptide or portions thereof to a promoter, and incorporating the construct into an expression vector. The vectors can be suitable for replication and integration eukaryotes. Typical cloning vectors contain transcription and translation terminators, initiation sequences, and promoters useful for regulation of the expression of the desired nucleic acid sequence.

The expression constructs of the present invention may also be used for nucleic acid immunization and gene therapy, using standard gene delivery protocols. Methods for gene delivery are known in the art. See, e.g., U.S. Pat. Nos. 5,399,346, 5,580,859, 5,589,466, incorporated by reference herein in their entireties. In another embodiment, the invention provides a gene therapy vector.

The nucleic acid can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the expression vector may be provided to a cell in the form of a viral vector. Viral vector technology is well known in the art and is described, for example, in Sambrook et al., 2012, MOLECULAR CLONING: A LABORATORY MANUAL, volumes 1-4, Cold Spring Harbor Press, NY), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some embodiments, adenovirus vectors are used. A number of adenovirus vectors are known in the art. In one embodiment, lentivirus vectors are used.

Additional promoter elements, e.g., enhancers, regulate the frequency of transcriptional initiation. Typically, these are located in the region 30-110 bp upstream of the start site, although a number of promoters have been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

An example of a promoter that is capable of expressing a CAR transgene in a mammalian T cell is the EF1a promoter. The native EF1a promoter drives expression of the alpha subunit of the elongation factor-1 complex, which is responsible for the enzymatic delivery of aminoacyl tRNAs to the ribosome. The EF1a promoter has been extensively used in mammalian expression plasmids and has been shown to be effective in driving CAR expression from transgenes cloned into a lentiviral vector. See, e.g., Milone et al., Mol. Ther. 17(8): 1453-1464 (2009).

Another example of a promoter is the immediate early cytomegalovirus (CMV) promoter sequence. This promoter sequence is a strong constitutive promoter sequence capable of driving high levels of expression of any polynucleotide sequence operatively linked thereto. However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the elongation factor-1α promoter, the hemoglobin promoter, and the creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

Another example of a promoter is the phosphoglycerate kinase (PGK) promoter. In embodiments, a truncated PGK promoter (e.g., a PGK promoter with one or more, e.g., 1, 2, 5, 10, 100, 200, 300, or 400, nucleotide deletions when compared to the wild-type PGK promoter sequence) may be desired. The nucleotide sequences of exemplary PGK promoters are provided below.

```
WT PGK Promoter
                                    (SEQ ID NO: 615)
ACCCCTCTCTCCAGCCACTAAGCCAGTTGCTCCCTCGGCTGACGGCTGCA

CGCGAGGCCTCCGAACGTCTTACGCCTTGTGGCGCGCCCGTCCTTGTCCC

GGGTGTGATGGCGGGGTGTGGGGCGGAGGGCGTGGCGGGGAAGGGCCGGC

GACGAGAGCCGCGCGGGACGACTCGTCGGCGATAACCGGTGTCGGGTAGC

GCCAGCCGCGCGACGGTAACGAGGGACCGCGACAGGCAGACGCTCCCATG

ATCACTCTGCACGCCGAAGGCAAATAGTGCAGGCCGTGCGGCGCTTGGCG

TTCCTTGGAAGGGCTGAATCCCCGCCTCGTCCTTCGCAGCGGCCCCCCGG

GTGTTCCCATCGCCGCTTCTAGGCCCACTGCGACGCTTGCCTGCACTTCT

TACACGCTCTGGGTCCCAGCCGCGGCGACGCAAAGGGCCTTGGTGCGGGT

CTCGTCGGCGCAGGGACGCGTTTGGGTCCCGACGGAACCTTTTCCGCGTT

GGGGTTGGGGCACCATAAGCT
```

Exemplary Truncated PGK Promoters:

```
PGK100:
                                    (SEQ ID NO: 616)
ACCCCTCTCTCCAGCCACTAAGCCAGTTGCTCCCTCGGCTGACGGCTGCA

CGCGAGGCCTCCGAACGTCTTACGCCTTGTGGCGCGCCCGTCCTTGTCCC

GGGTGTGATGGCGGGGTG

PGK200:
                                    (SEQ ID NO: 617)
ACCCCTCTCTCCAGCCACTAAGCCAGTTGCTCCCTCGGCTGACGGCTGCA

CGCGAGGCCTCCGAACGTCTTACGCCTTGTGGCGCGCCCGTCCTTGTCCC

GGGTGTGATGGCGGGGTGTGGGGCGGAGGGCGTGGCGGGGAAGGGCCGGC

GACGAGAGCCGCGCGGGACGACTCGTCGGCGATAACCGGTGTCGGGTAGC

GCCAGCCGCGCGACGGTAACG

PGK300:
                                    (SEQ ID NO: 618)
ACCCCTCTCTCCAGCCACTAAGCCAGTTGCTCCCTCGGCTGACGGCTGCA

CGCGAGGCCTCCGAACGTCTTACGCCTTGTGGCGCGCCCGTCCTTGTCCC

GGGTGTGATGGCGGGGTGTGGGGCGGAGGGCGTGGCGGGGAAGGGCCGGC

GACGAGAGCCGCGCGGGACGACTCGTCGGCGATAACCGGTGTCGGGTAGC

GCCAGCCGCGCGACGGTAACGAGGGACCGCGACAGGCAGACGCTCCCATG

ATCACTCTGCACGCCGAAGGCAAATAGTGCAGGCCGTGCGGCGCTTGGCG

TTCCTTGGAAGGGCTGAATCCCCG

PGK400:
                                    (SEQ ID NO: 619)
ACCCCTCTCTCCAGCCACTAAGCCAGTTGCTCCCTCGGCTGACGGCTGCA

CGCGAGGCCTCCGAACGTCTTACGCCTTGTGGCGCGCCCGTCCTTGTCCC

GGGTGTGATGGCGGGGTGTGGGGCGGAGGGCGTGGCGGGGAAGGGCCGGC

GACGAGAGCCGCGCGGGACGACTCGTCGGCGATAACCGGTGTCGGGTAGC

GCCAGCCGCGCGACGGTAACGAGGGACCGCGACAGGCAGACGCTCCCATG

ATCACTCTGCACGCCGAAGGCAAATAGTGCAGGCCGTGCGGCGCTTGGCG

TTCCTTGGAAGGGCTGAATCCCCGCCTCGTCCTTCGCAGCGGCCCCCCGG

GTGTTCCCATCGCCGCTTCTAGGCCCACTGCGACGCTTGCCTGCACTTCT

TACACGCTCTGGGTCCCAGCCG
```

A vector may also include, e.g., a signal sequence to facilitate secretion, a polyadenylation signal and transcription terminator (e.g., from Bovine Growth Hormone (BGH) gene), an element allowing episomal replication and replication in prokaryotes (e.g. SV40 origin and ColE1 or others known in the art) and/or elements to allow selection (e.g., ampicillin resistance gene and/or zeocin marker).

In order to assess the expression of a CAR polypeptide or portions thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

In one embodiment, the vector can further comprise a nucleic acid encoding a second CAR. In one embodiment, the second CAR includes an antigen binding domain to a target expressed on acute myeloid leukemia cells, such as, e.g., CD123, CD34, CLL-1, folate receptor beta, or FLT3; or a target expressed on a B cell, e.g., CD10, CD19, CD20, CD22, CD34, CD123, FLT-3, ROR1, CD79b, CD179b, or CD79a. In one embodiment, the vector comprises a nucleic acid sequence encoding a first CAR that specifically binds a first antigen and includes an intracellular signaling domain having a costimulatory signaling domain but not a primary signaling domain, and a nucleic acid encoding a second CAR that specifically binds a second, different, antigen and includes an intracellular signaling domain having a primary signaling domain but not a costimulatory signaling domain.

In one embodiment, the vector comprises a nucleic acid encoding a CAR described herein and a nucleic acid encoding an inhibitory CAR. In one embodiment, the inhibitory CAR comprises an antigen binding domain that binds an antigen found on normal cells but not cancer cells. In one embodiment, the inhibitory CAR comprises the antigen binding domain, a transmembrane domain and an intracellular domain of an inhibitory molecule. For example, the intracellular domain of the inhibitory CAR can be an intracellular domain of PD1, PD-L1, PD-L2, CTLA4, TIM3, CEACAM (e.g., CEACAM-1, CEACAM-3 and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, and TGFR beta.

In embodiments, the vector may comprise two or more nucleic acid sequences encoding a CAR, e.g., a CAR described herein and a second CAR, e.g., an inhibitory CAR or a CAR that specifically binds to a different antigen. In such embodiments, the two or more nucleic acid sequences encoding the CAR are encoded by a single nucleic molecule in the same frame and as a single polypeptide chain. In this aspect, the two or more CARs, can, e.g., be separated by one or more peptide cleavage sites. (e.g., an auto-cleavage site or a substrate for an intracellular protease). Examples of peptide cleavage sites include the following, wherein the GSG residues are optional:

```
T2A:
                                        (SEQ ID NO: 620)
(GSG)E G R G S L L T C G D V E E N P G P
P2A:
                                        (SEQ ID NO: 621)
(GSG)A T N F S L L K Q A G D V E E N P G P
E2A:
                                        (SEQ ID NO: 622)
(GSG)Q C T N Y A L L K L A G D V E S N P G P
F2A:
                                        (SEQ ID NO: 623)
(GSG)V K Q T L N F D L L K L A G D V E S N P G P
```

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al., 2012, MOLECULAR CLONING: A LABORATORY MANUAL, volumes 1-4, Cold Spring Harbor Press, NY). A preferred method for the introduction of a polynucleotide into a host cell is calcium phosphate transfection Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle). Other methods of state-of-the-art targeted delivery of nucleic acids are available, such as delivery of polynucleotides with targeted nanoparticles or other suitable submicron sized delivery system.

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, MO; dicetyl phosphate ("DCP") can be obtained from K & K Laboratories (Plainview, NY); cholesterol ("Choi") can be obtained from Calbiochem-Behring; dimyristyl phosphatidylglycerol ("DMPG") and other lipids may be obtained from Avanti Polar Lipids, Inc. (Birmingham, AL). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Regardless of the method used to introduce exogenous nucleic acids into a host cell or otherwise expose a cell to the inhibitor of the present invention, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

The present invention further provides a vector comprising a CAR encoding nucleic acid molecule. In one aspect, a CAR vector can be directly transduced into a cell, e.g., a T cell or NK cell. In one aspect, the vector is a cloning or expression vector, e.g., a vector including, but not limited to, one or more plasmids (e.g., expression plasmids, cloning vectors, minicircles, minivectors, double minute chromosomes), retroviral and lentiviral vector constructs. In one aspect, the vector is capable of expressing the CAR construct in mammalian T cells or NK cells. In one aspect, the mammalian T cell is a human T cell. In one aspect, the mammalian NK cell is a human NK cell.

Sources of Cells

Prior to expansion and genetic modification, a source of cells, e.g., immune effector cells (e.g., T cells or NK cells), is obtained from a subject. The term "subject" is intended to include living organisms in which an immune response can be elicited (e.g., mammals). Examples of subjects include humans, dogs, cats, mice, rats, and transgenic species thereof. T cells can be obtained from a number of sources, including peripheral blood mononuclear cells, bone marrow, lymph node tissue, cord blood, thymus tissue, tissue from a site of infection, ascites, pleural effusion, spleen tissue, and tumors.

In certain aspects of the present invention, any number of immune effector cell (e.g., T cell or NK cell) lines available in the art, may be used. In certain aspects of the present invention, T cells can be obtained from a unit of blood collected from a subject using any number of techniques known to the skilled artisan, such as Ficoll™ separation. In one preferred aspect, cells from the circulating blood of an individual are obtained by apheresis. The apheresis product typically contains lymphocytes, including T cells, monocytes, granulocytes, B cells, other nucleated white blood cells, red blood cells, and platelets. In one aspect, the cells collected by apheresis may be washed to remove the plasma fraction and to place the cells in an appropriate buffer or media for subsequent processing steps. In one aspect of the invention, the cells are washed with phosphate buffered saline (PBS). In an alternative aspect, the wash solution lacks calcium and may lack magnesium or may lack many if not all divalent cations.

Initial activation steps in the absence of calcium can lead to magnified activation. As those of ordinary skill in the art would readily appreciate a washing step may be accomplished by methods known to those in the art, such as by using a semi-automated "flow-through" centrifuge (for example, the Cobe 2991 cell processor, the Baxter CytoMate, or the Haemonetics Cell Saver 5) according to the manufacturer's instructions. After washing, the cells may be resuspended in a variety of biocompatible buffers, such as, for example, Ca-free, Mg-free PBS, PlasmaLyte A, or other saline solution with or without buffer. Alternatively, the undesirable components of the apheresis sample may be removed and the cells directly resuspended in culture media.

It is recognized that the methods of the application can utilize culture media conditions comprising 5% or less, for example 2%, human AB serum, and employ known culture media conditions and compositions, for example those described in Smith et al., "Ex vivo expansion of human T cells for adoptive immunotherapy using the novel Xeno-free CTS Immune Cell Serum Replacement" *Clinical & Translational Immunology* (2015) 4, e31; doi:10.1038/cti.2014.31.

In one aspect, T cells are isolated from peripheral blood lymphocytes by lysing the red blood cells and depleting the monocytes, for example, by centrifugation through a PERCOLL™ gradient or by counterflow centrifugal elutriation. A specific subpopulation of T cells, such as CD3+, CD4+, CD8+, CD45RA+, and/or CD45RO+ T cells, can be further isolated by positive or negative selection techniques. For example, in one aspect, T cells are isolated by incubation with anti-CD3/anti-CD28 (e.g., 3×28)-conjugated beads, such as DYNABEADS® M-450 CD3/CD28 T, for a time period sufficient for positive selection of the desired T cells. In one aspect, the time period is about 30 minutes. In a further aspect, the time period ranges from 30 minutes to 36 hours or longer and all integer values there between. In a further aspect, the time period is at least 1, 2, 3, 4, 5, or 6 hours. In yet another preferred aspect, the time period is 10 to 24 hours. In one aspect, the incubation time period is 24 hours. Longer incubation times may be used to isolate T cells in any situation where there are few T cells as compared to other cell types, such in isolating tumor infiltrating lymphocytes (TIL) from tumor tissue or from immunocompromised individuals. Further, use of longer incubation times can increase the efficiency of capture of CD8+ T cells. Thus, by simply shortening or lengthening the time T cells are allowed to bind to the CD3/CD28 beads and/or by increasing or decreasing the ratio of beads to T cells (as described further herein), subpopulations of T cells can be preferentially selected for or against at culture initiation or at other time points during the process. Additionally, by increasing or decreasing the ratio of anti-CD3 and/or anti-CD28 antibodies on the beads or other surface, subpopulations of T cells can be preferentially selected for or against at culture initiation or at other desired time points. The skilled artisan would recognize that multiple rounds of selection can also be used in the context of this invention. In certain aspects, it may be desirable to perform the selection procedure and use the "unselected" cells in the activation and expansion process. "Unselected" cells can also be subjected to further rounds of selection.

Enrichment of a T cell population by negative selection can be accomplished with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD11b, CD16, HLA-DR, and CD8. In certain aspects, it may be desirable to enrich for or positively select for regulatory T cells which typically express CD4+, CD25+, CD62Lhi, GITR+, and FoxP3+. In certain aspects, it may be desirable to enrich for cells that are CD127low. Alternatively, in certain aspects, T regulatory cells are depleted by anti-C25 conjugated beads or other similar method of selection.

The methods described herein can include, e.g., selection of a specific subpopulation of immune effector cells, e.g., T cells, that are a T regulatory cell-depleted population, CD25+ depleted cells, using, e.g., a negative selection technique, e.g., described herein. Preferably, the population of T regulatory depleted cells contains less than 30%, 25%, 20%, 15%, 10%, 5%, 4%, 3%, 2%, 1% of CD25+ cells.

In one embodiment, T regulatory cells, e.g., CD25+ T cells, are removed from the population using an anti-CD25 antibody, or fragment thereof, or a CD25-binding ligand, IL-2. In one embodiment, the anti-CD25 antibody, or fragment thereof, or CD25-binding ligand is conjugated to a substrate, e.g., a bead, or is otherwise coated on a substrate, e.g., a bead. In one embodiment, the anti-CD25 antibody, or fragment thereof, is conjugated to a substrate as described herein.

In one embodiment, the T regulatory cells, e.g., CD25+ T cells, are removed from the population using CD25 depletion reagent from Miltenyi™. In one embodiment, the ratio of cells to CD25 depletion reagent is 1e7 cells to 20 uL, or 1e7 cells to 15 uL, or 1e7 cells to 10 uL, or 1e7 cells to 5 uL, or 1e7 cells to 2.5 uL, or 1e7 cells to 1.25 uL. In one embodiment, e.g., for T regulatory cells, e.g., CD25+ depletion, greater than 500 million cells/ml is used. In a further aspect, a concentration of cells of 600, 700, 800, or 900 million cells/ml is used.

In one embodiment, the population of immune effector cells to be depleted includes about $6\times10^9$ CD25+ T cells. In other aspects, the population of immune effector cells to be depleted include about $1\times10^9$ to $1\times10^{10}$ CD25+ T cell, and any integer value in between. In one embodiment, the resulting population T regulatory depleted cells has $2\times10^9$ T regulatory cells, e.g., CD25+ cells, or less (e.g., $1\times10^9$, $5\times10^8$, $1\times10^8$, $5\times10^7$, $1\times10^7$, or less CD25+ cells).

In one embodiment, the T regulatory cells, e.g., CD25+ cells, are removed from the population using the CliniMAC system with a depletion tubing set, such as, e.g., tubing 162-01. In one embodiment, the CliniMAC system is run on a depletion setting such as, e.g., DEPLETION2.1.

Without wishing to be bound by a particular theory, decreasing the level of negative regulators of immune cells (e.g., decreasing the number of unwanted immune cells, e.g., $T_{REG}$ cells), in a subject prior to apheresis or during manufacturing of a CAR-expressing cell product can reduce the risk of subject relapse. For example, methods of depleting $T_{REG}$ cells are known in the art. Methods of decreasing $T_{REG}$ cells include, but are not limited to, cyclophosphamide, anti-GITR antibody (an anti-GITR antibody described herein), CD25-depletion, and combinations thereof.

In some embodiments, the manufacturing methods comprise reducing the number of (e.g., depleting) $T_{REG}$ cells prior to manufacturing of the CAR-expressing cell. For example, manufacturing methods comprise contacting the sample, e.g., the apheresis sample, with an anti-GITR antibody and/or an anti-CD25 antibody (or fragment thereof, or a CD25-binding ligand), e.g., to deplete $T_{REG}$ cells prior to manufacturing of the CAR-expressing cell (e.g., T cell, NK cell) product.

In an embodiment, a subject is pre-treated with one or more therapies that reduce $T_{REG}$ cells prior to collection of cells for CAR-expressing cell product manufacturing, thereby reducing the risk of subject relapse to CAR-expressing cell treatment. In an embodiment, methods of decreasing $T_{REG}$ cells include, but are not limited to, administration to the subject of one or more of cyclophosphamide, anti-GITR antibody, CD25-depletion, or a combination thereof. Administration of one or more of cyclophosphamide, anti-GITR antibody, CD25-depletion, or a combination thereof, can occur before, during or after an infusion of the CAR-expressing cell product.

In an embodiment, a subject is pre-treated with cyclophosphamide prior to collection of cells for CAR-expressing cell product manufacturing, thereby reducing the risk of subject relapse to CAR-expressing cell treatment. In an embodiment, a subject is pre-treated with an anti-GITR antibody prior to collection of cells for CAR-expressing cell product manufacturing, thereby reducing the risk of subject relapse to CAR-expressing cell treatment.

In one embodiment, the population of cells to be removed are neither the regulatory T cells or tumor cells, but cells that otherwise negatively affect the expansion and/or function of CART cells, e.g. cells expressing CD14, CD11b, CD33, CD15, or other markers expressed by potentially immune suppressive cells. In one embodiment, such cells are envisioned to be removed concurrently with regulatory T cells and/or tumor cells, or following said depletion, or in another order.

The methods described herein can include more than one selection step, e.g., more than one depletion step. Enrichment of a T cell population by negative selection can be accomplished, e.g., with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail can include antibodies to CD14, CD20, CD11b, CD16, HLA-DR, and CD8.

The methods described herein can further include removing cells from the population which express a tumor antigen, e.g., a tumor antigen that does not comprise CD25, e.g., CD19, CD30, CD38, CD123, CD20, CD14 or CD11b, to thereby provide a population of T regulatory depleted, e.g., CD25+ depleted, and tumor antigen depleted cells that are suitable for expression of a CAR, e.g., a CAR described herein. In one embodiment, tumor antigen expressing cells are removed simultaneously with the T regulatory, e.g., CD25+ cells. For example, an anti-CD25 antibody, or fragment thereof, and an anti-tumor antigen antibody, or fragment thereof, can be attached to the same substrate, e.g., bead, which can be used to remove the cells or an anti-CD25 antibody, or fragment thereof, or the anti-tumor antigen antibody, or fragment thereof, can be attached to separate beads, a mixture of which can be used to remove the cells. In other embodiments, the removal of T regulatory cells, e.g., CD25+ cells, and the removal of the tumor antigen expressing cells is sequential, and can occur, e.g., in either order.

Also provided are methods that include removing cells from the population which express a check point inhibitor, e.g., a check point inhibitor described herein, e.g., one or more of PD1+ cells, LAG3+ cells, and TIM3+ cells, to thereby provide a population of T regulatory depleted, e.g., CD25+ depleted cells, and check point inhibitor depleted cells, e.g., PD1+, LAG3+ and/or TIM3+ depleted cells. Exemplary check point inhibitors include PD1, PD-L1, PD-L2, CTLA4, TIM3, CEACAM (e.g., CEACAM-1, CEACAM-3 and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, and TGFR beta. In embodiments, the checkpoint inhibitor is PD1 or PD-L1. In one embodiment, check point inhibitor expressing cells are removed simultaneously with the T regulatory, e.g., CD25+ cells. For example, an anti-CD25 antibody, or fragment thereof, and an anti-check point inhibitor antibody, or fragment thereof, can be attached to the same bead which can be used to remove the cells, or an anti-CD25 antibody, or fragment thereof, and the anti-check point inhibitor antibody, or fragment there, can be attached to separate beads, a mixture of which can be used to remove the cells. In other embodiments, the removal of T regulatory cells, e.g., CD25+ cells, and the removal of the check point inhibitor expressing cells is sequential, and can occur, e.g., in either order.

In one embodiment, a T cell population can be selected that expresses one or more of IFN-γ, TNFα, IL-17A, IL-7, IL-2, IL-3, IL-4, GM-CSF, IL-10, IL-13, granzyme B, and perforin, or other appropriate molecules, e.g., other cytokines. Methods for screening for cell expression can be determined, e.g., by the methods described in PCT Publication No.: WO 2013/126712.

For isolation of a desired population of cells by positive or negative selection, the concentration of cells and surface (e.g., particles such as beads) can be varied. In certain aspects, it may be desirable to significantly decrease the volume in which beads and cells are mixed together (e.g., increase the concentration of cells), to ensure maximum contact of cells and beads. For example, in one aspect, a concentration of 2 billion cells/ml is used. In one aspect, a concentration of 1 billion cells/ml is used. In a further aspect, greater than 100 million cells/ml is used. In a further aspect, a concentration of cells of 10, 15, 20, 25, 30, 35, 40, 45, or 50 million cells/ml is used. In yet one aspect, a concentration of cells from 75, 80, 85, 90, 95, or 100 million cells/ml is used. In further aspects, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells, or from samples where there are many tumor cells present (e.g., leukemic blood, tumor tissue, etc.). Such populations of cells may have therapeutic value and would be desirable to obtain. For example, using high concentration of cells allows more efficient selection of CD8+ T cells that normally have weaker CD28 expression.

In a related aspect, it may be desirable to use lower concentrations of cells. By significantly diluting the mixture of T cells and surface (e.g., particles such as beads), interactions between the particles and cells is minimized. This selects for cells that express high amounts of desired antigens to be bound to the particles. For example, CD4+ T cells express higher levels of CD28 and are more efficiently captured than CD8+ T cells in dilute concentrations. In one aspect, the concentration of cells used is 5×10e6/ml. In other aspects, the concentration used can be from about $1\times10^5$/ml to $1\times10^6$/ml, and any integer value in between.

In other aspects, the cells may be incubated on a rotator for varying lengths of time at varying speeds at either 2-10° C. or at room temperature.

T cells for stimulation can also be frozen after a washing step. Wishing not to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, one method involves using PBS containing 20% DMSO and 8% human serum albumin, or culture media containing 10% Dextran 40 and 5% Dextrose, 20% Human Serum Albumin and 7.5% DMSO, or 31.25% Plasmalyte-A, 31.25% Dextrose 5%, 0.45% NaCl, 10% Dextran 40 and 5% Dextrose, 20% Human Serum Albumin, and 7.5% DMSO or other suitable cell freezing media containing for example, Hespan and PlasmaLyte A, the cells then are frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

In certain aspects, cryopreserved cells are thawed and washed as described herein and allowed to rest for one hour at room temperature prior to activation using the methods of the present invention.

Also contemplated in the context of the invention is the collection of blood samples or apheresis product from a subject at a time period prior to when the expanded cells as described herein might be needed. As such, the source of the cells to be expanded can be collected at any time point necessary, and desired cells, such as immune effector cells, e.g., T cells or NK cells, isolated and frozen for later use in cell therapy, e.g., T cell therapy, for any number of diseases or conditions that would benefit from cell therapy, e.g., T cell therapy, such as those described herein. In one aspect a blood sample or an apheresis is taken from a generally healthy subject. In certain aspects, a blood sample or an apheresis is taken from a generally healthy subject who is at risk of developing a disease, but who has not yet developed a disease, and the cells of interest are isolated and frozen for later use. In certain aspects, the immune effector cells (e.g., T cells or NK cells) may be expanded, frozen, and used at a later time. In certain aspects, samples are collected from a patient shortly after diagnosis of a particular disease as described herein but prior to any treatments. In a further aspect, the cells are isolated from a blood sample or an apheresis from a subject prior to any number of relevant treatment modalities, including but not limited to treatment with agents such as natalizumab, efalizumab, antiviral agents, chemotherapy, radiation, immunosuppressive agents, such as cyclosporin, azathioprine, methotrexate, mycophenolate, and FK506, antibodies, or other immunoablative agents such as CAMPATH, anti-CD3 antibodies, cytoxan, fludarabine, cyclosporin, FK506, rapamycin, mycophenolic acid, steroids, FR901228, and irradiation.

In a further aspect of the present invention, T cells are obtained from a patient directly following treatment that leaves the subject with functional T cells. In this regard, it has been observed that following certain cancer treatments, in particular treatments with drugs that damage the immune system, shortly after treatment during the period when patients would normally be recovering from the treatment, the quality of T cells obtained may be optimal or improved for their ability to expand ex vivo. Likewise, following ex vivo manipulation using the methods described herein, these cells may be in a preferred state for enhanced engraftment and in vivo expansion. Thus, it is contemplated within the context of the present invention to collect blood cells, including T cells, dendritic cells, or other cells of the hematopoietic lineage, during this recovery phase. Further, in certain aspects, mobilization (for example, mobilization with GM-CSF) and conditioning regimens can be used to create a condition in a subject wherein repopulation, recirculation, regeneration, and/or expansion of particular cell types is favored, especially during a defined window of time following therapy. Illustrative cell types include T cells, B cells, dendritic cells, and other cells of the immune system.

In one embodiment, the immune effector cells expressing a CAR molecule, e.g., a CAR molecule described herein, are obtained from a subject that has received a low, immune enhancing dose of an mTOR inhibitor. In an embodiment, the population of immune effector cells, e.g., T cells, to be engineered to express a CAR, are harvested after a sufficient time, or after sufficient dosing of the low, immune enhancing, dose of an mTOR inhibitor, such that the level of PD1 negative immune effector cells, e.g., T cells, or the ratio of PD1 negative immune effector cells, e.g., T cells/PD1 positive immune effector cells, e.g., T cells, in the subject or harvested from the subject has been, at least transiently, increased.

In other embodiments, population of immune effector cells, e.g., T cells, which have, or will be engineered to express a CAR, can be treated ex vivo by contact with an amount of an mTOR inhibitor that increases the number of PD1 negative immune effector cells, e.g., T cells or increases the ratio of PD1 negative immune effector cells, e.g., T cells/PD1 positive immune effector cells, e.g., T cells.

In one embodiment, a T cell population is diaglycerol kinase (DGK)-deficient. DGK-deficient cells include cells that do not express DGK RNA or protein, or have reduced or inhibited DGK activity. DGK-deficient cells can be generated by genetic approaches, e.g., administering RNA-interfering agents, e.g., siRNA, shRNA, miRNA, to reduce or prevent DGK expression. Alternatively, DGK-deficient cells can be generated by treatment with DGK inhibitors described herein.

In one embodiment, a T cell population is Ikaros-deficient. Ikaros-deficient cells include cells that do not express Ikaros RNA or protein, or have reduced or inhibited Ikaros activity, Ikaros-deficient cells can be generated by genetic approaches, e.g., administering RNA-interfering agents, e.g., siRNA, shRNA, miRNA, to reduce or prevent Ikaros expression. Alternatively, Ikaros-deficient cells can be generated by treatment with Ikaros inhibitors, e.g., lenalidomide.

In embodiments, a T cell population is DGK-deficient and Ikaros-deficient, e.g., does not express DGK and Ikaros, or has reduced or inhibited DGK and Ikaros activity. Such DGK and Ikaros-deficient cells can be generated by any of the methods described herein.

In an embodiment, the NK cells are obtained from the subject. In another embodiment, the NK cells are an NK cell line, e.g., NK-92 cell line (Conkwest).

Modifications of CAR Cells, Including Allogeneic CAR Cells

In embodiments described herein, the immune effector cell can be an allogeneic immune effector cell, e.g., T cell or NK cell. For example, the cell can be an allogeneic T cell, e.g., an allogeneic T cell lacking expression of a functional T cell receptor (TCR) and/or human leukocyte antigen (HLA), e.g., HLA class I and/or HLA class II, and/or beta-2 microglobulin ($\beta_2$m). Compositions of allogeneic CAR and methods thereof have been described in, e.g., pages 227-237 of WO 2016/014565, incorporated herein by reference in its entirety.

In some embodiments, a cell, e.g., a T cell or a NK cell, is modified to reduce the expression of a TCR, and/or HLA, and/or $\beta_2$m, and/or an inhibitory molecule described herein (e.g., PD1, PD-L1, PD-L2, CTLA4, TIM3, CEACAM (e.g., CEACAM-1, CEACAM-3 and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, and TGFR beta), using, e.g., a method described herein, e.g., siRNA, shRNA, clustered regularly interspaced short palindromic repeats (CRISPR) transcription-activator like effector nuclease (TALEN), or zinc finger endonuclease (ZFN).

In some embodiments, a cell, e.g., a T cell or a NK cell is engineered to express a telomerase subunit, e.g., the catalytic subunit of telomerase, e.g., TERT, e.g., hTERT. In one embodiment, such modification improves persistence of the cell in a patient.

Activation and Expansion of T Cells

T cells may be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005.

Generally, the T cells of the invention may be expanded by contact with a surface having attached thereto an agent that stimulates a CD3/TCR complex associated signal and a ligand that stimulates a costimulatory molecule on the surface of the T cells. In particular, T cell populations may be stimulated as described herein, such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. To stimulate proliferation of either CD4+ T cells or CD8+ T cells, an anti-CD3 antibody and an anti-CD28 antibody can be used. Examples of an anti-CD28 antibody include 9.3, B-T3, XR-CD28 (Diaclone, Besangon, France) can be used as can other methods commonly known in the art (Berg et al., Transplant Proc. 30(8):3975-3977, 1998; Haanen et al., J. Exp. Med. 190(9):13191328, 1999; Garland et al., J. Immunol Meth. 227(1-2):53-63, 1999).

In certain aspects, the primary stimulatory signal and the costimulatory signal for the T cell may be provided by different protocols. For example, the agents providing each signal may be in solution or coupled to a surface. When coupled to a surface, the agents may be coupled to the same surface (i.e., in "cis" formation) or to separate surfaces (i.e., in "trans" formation). Alternatively, one agent may be coupled to a surface and the other agent in solution. In one aspect, the agent providing the costimulatory signal is bound to a cell surface and the agent providing the primary activation signal is in solution or coupled to a surface. In certain aspects, both agents can be in solution. In one aspect, the agents may be in soluble form, and then cross-linked to a surface, such as a cell expressing Fc receptors or an antibody or other binding agent which will bind to the agents. In this regard, see for example, U.S. Patent Application Publication Nos. 20040101519 and 20060034810 for artificial antigen presenting cells (aAPCs) that are contemplated for use in activating and expanding T cells in the present invention.

In one aspect, the two agents are immobilized on beads, either on the same bead, i.e., "cis," or to separate beads, i.e., "trans." By way of example, the agent providing the primary activation signal is an anti-CD3 antibody or an antigen-binding fragment thereof and the agent providing the costimulatory signal is an anti-CD28 antibody or antigen-binding fragment thereof; and both agents are co-immobilized to the same bead in equivalent molecular amounts. In one aspect, a 1:1 ratio of each antibody bound to the beads for CD4+ T cell expansion and T cell growth is used. In certain aspects of the present invention, a ratio of anti CD3:CD28 antibodies bound to the beads is used such that an increase in T cell expansion is observed as compared to the expansion observed using a ratio of 1:1. In one particular aspect an increase of from about 1 to about 3 fold is observed as compared to the expansion observed using a ratio of 1:1. In one aspect, the ratio of CD3:CD28 antibody bound to the beads ranges from 100:1 to 1:100 and all integer values there between. In one aspect of the present invention, more anti-CD28 antibody is bound to the particles than anti-CD3 antibody, i.e., the ratio of CD3:CD28 is less than one. In certain aspects of the invention, the ratio of anti CD28 antibody to anti CD3 antibody bound to the beads is greater than 2:1. In one particular aspect, a 1:100 CD3:CD28 ratio of antibody bound to beads is used. In one aspect, a 1:75 CD3:CD28 ratio of antibody bound to beads is used. In a further aspect, a 1:50 CD3:CD28 ratio of antibody bound to beads is used. In one aspect, a 1:30 CD3:CD28 ratio of antibody bound to beads is used. In one preferred aspect, a 1:10 CD3:CD28 ratio of antibody bound to beads is used. In one aspect, a 1:3 CD3:CD28 ratio of antibody bound to the beads is used. In yet one aspect, a 3:1 CD3:CD28 ratio of antibody bound to the beads is used.

Ratios of particles to cells from 1:500 to 500:1 and any integer values in between may be used to stimulate T cells or other target cells. As those of ordinary skill in the art can readily appreciate, the ratio of particles to cells may depend on particle size relative to the target cell. For example, small sized beads could only bind a few cells, while larger beads could bind many. In certain aspects the ratio of cells to particles ranges from 1:100 to 100:1 and any integer values in-between and in further aspects the ratio comprises 1:9 to 9:1 and any integer values in between, can also be used to stimulate T cells. The ratio of anti-CD3- and anti-CD28-coupled particles to T cells that result in T cell stimulation can vary as noted above, however certain preferred values include 1:100, 1:50, 1:40, 1:30, 1:20, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, and 15:1 with one preferred ratio being at least 1:1 particles per T cell. In one aspect, a ratio of particles to cells of 1:1 or less is used. In one particular aspect, a preferred particle:cell ratio is 1:5. In further aspects, the ratio of particles to cells can be varied depending on the day of stimulation. For example, in one aspect, the ratio of particles to cells is from 1:1 to 10:1 on the first day and additional particles are added to the cells every day or every other day thereafter for up to 10 days, at final ratios of from 1:1 to 1:10 (based on cell counts on the day of addition). In one particular aspect, the ratio of particles to cells is 1:1 on the first day of stimulation and adjusted to 1:5 on the third and fifth days of stimulation. In one aspect, particles are added on a daily or every other day basis to a final ratio of 1:1 on the first day, and 1:5 on the third and fifth days of stimulation. In one aspect, the ratio of particles to cells is 2:1 on the first day of stimulation and adjusted to 1:10 on the third and fifth days of stimulation. In one aspect, particles are added on a daily or every other day basis to a final ratio of 1:1 on the first day, and 1:10 on the third and fifth days of stimulation. One of skill in the art will appreciate that a variety of other ratios may be suitable for use in the present invention. In particular, ratios will vary depending on particle size and on cell size and type. In one aspect, the most typical ratios for use are in the neighborhood of 1:1, 2:1 and 3:1 on the first day.

In further aspects of the present invention, the cells, such as T cells, are combined with agent-coated beads, the beads and the cells are subsequently separated, and then the cells are cultured. In an alternative aspect, prior to culture, the agent-coated beads and cells are not separated but are cultured together. In a further aspect, the beads and cells are first concentrated by application of a force, such as a magnetic force, resulting in increased ligation of cell surface markers, thereby inducing cell stimulation.

By way of example, cell surface proteins may be ligated by allowing paramagnetic beads to which anti-CD3 and anti-CD28 are attached (3×28 beads) to contact the T cells. In one aspect the cells (for example, $10^4$ to $10^9$ T cells) and beads (for example, DYNABEADS® M-450 CD3/CD28 T paramagnetic beads at a ratio of 1:1) are combined in a buffer, for example PBS (without divalent cations such as, calcium and magnesium). Again, those of ordinary skill in the art can readily appreciate any cell concentration may be used. For example, the target cell may be very rare in the sample and comprise only 0.01% of the sample or the entire sample (i.e., 100%) may comprise the target cell of interest. Accordingly, any cell number is within the context of the present invention. In certain aspects, it may be desirable to significantly decrease the volume in which particles and cells are mixed together (i.e., increase the concentration of cells), to ensure maximum contact of cells and particles. For example, in one aspect, a concentration of about 10 billion cells/ml, 9 billion/ml, 8 billion/ml, 7 billion/ml, 6 billion/ml, 5 billion/ml, or 2 billion cells/ml is used. In one aspect, greater than 100 million cells/ml is used. In a further aspect, a concentration of cells of 10, 15, 20, 25, 30, 35, 40, 45, or 50 million cells/ml is used. In yet one aspect, a concentration of cells from 75, 80, 85, 90, 95, or 100 million cells/ml is used. In further aspects, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells. Such populations of cells may have therapeutic value and would be desirable to obtain in certain aspects. For example, using high concentration of cells allows more efficient selection of CD8+ T cells that normally have weaker CD28 expression.

In one embodiment, cells transduced with a nucleic acid encoding a CAR, e.g., a CAR described herein, are expanded, e.g., by a method described herein. In one embodiment, the cells are expanded in culture for a period of several hours (e.g., about 2, 3, 4, 5, 6, 7, 8, 9, 10, 15, 18, 21 hours) to about 14 days (e.g., 1, 2, 3, 4, 5, 6, 7, 8, 9, 10, 11, 12, 13 or 14 days). In one embodiment, the cells are expanded for a period of 4 to 9 days. In one embodiment, the cells are expanded for a period of 8 days or less, e.g., 7, 6 or 5 days. In one embodiment, the cells, e.g., a CAR cell described herein, are expanded in culture for 5 days, and the resulting cells are more potent than the same cells expanded in culture for 9 days under the same culture conditions. Potency can be defined, e.g., by various T cell functions, e.g. proliferation, target cell killing, cytokine production, activation, migration, or combinations thereof. In one embodiment, the cells, e.g., a CAR cell described herein, expanded for 5 days show at least a one, two, three or four fold increase in cells doublings upon antigen stimulation as compared to the same cells expanded in culture for 9 days under the same culture conditions. In one embodiment, the cells, e.g., the cells expressing a CAR described herein, are expanded in culture for 5 days, and the resulting cells exhibit higher proinflammatory cytokine production, e.g., IFN-γ and/or GM-CSF levels, as compared to the same cells expanded in culture for 9 days under the same culture conditions. In one embodiment, the cells, e.g., a CAR cell described herein, expanded for 5 days show at least a one, two, three, four, five, ten fold or more increase in pg/ml of proinflammatory cytokine production, e.g., IFN-γ and/or GM-CSF levels, as compared to the same cells expanded in culture for 9 days under the same culture conditions.

In one aspect of the present invention, the mixture may be cultured for several hours (about 3 hours) to about 14 days or any hourly integer value in between. In one aspect, the mixture may be cultured for 21 days. In one aspect of the invention the beads and the T cells are cultured together for about eight days. In one aspect, the beads and T cells are cultured together for 2-3 days. Several cycles of stimulation may also be desired such that culture time of T cells can be 60 days or more. Conditions appropriate for T cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-γ, IL-4, IL-7, GM-CSF, IL-10, IL-12, IL-15, TGFβ, and TNF-α or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, α-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$).

In one embodiment, the cells are expanded in an appropriate media (e.g., media described herein) that includes one or more interleukin that result in at least a 200-fold (e.g., 200-fold, 250-fold, 300-fold, 350-fold) increase in cells over a 14 day expansion period, e.g., as measured by a method described herein such as flow cytometry. In one embodiment, the cells are expanded in the presence of IL-15 and/or IL-7 (e.g., IL-15 and IL-7).

In embodiments, methods described herein, e.g., CAR-expressing cell manufacturing methods, comprise removing T regulatory cells, e.g., CD25+ T cells, from a cell population, e.g., using an anti-CD25 antibody, or fragment thereof, or a CD25-binding ligand, IL-2. Methods of removing T regulatory cells, e.g., CD25+ T cells, from a cell population are described herein. In embodiments, the methods, e.g., manufacturing methods, further comprise contacting a cell population (e.g., a cell population in which T regulatory cells, such as CD25+ T cells, have been depleted; or a cell population that has previously contacted an anti-CD25 antibody, fragment thereof, or CD25-binding ligand) with IL-15 and/or IL-7. For example, the cell population (e.g., that has previously contacted an anti-CD25 antibody, fragment thereof, or CD25-binding ligand) is expanded in the presence of IL-15 and/or IL-7.

In some embodiments a CAR-expressing cell described herein is contacted with a composition comprising a interleukin-15 (IL-15) polypeptide, a interleukin-15 receptor alpha (IL-15Ra) polypeptide, or a combination of both a IL-15 polypeptide and a IL-15Ra polypeptide e.g., hetIL-15, during the manufacturing of the CAR-expressing cell, e.g., ex vivo. In embodiments, a CAR-expressing cell described herein is contacted with a composition comprising a IL-15 polypeptide during the manufacturing of the CAR-expressing cell, e.g., ex vivo. In embodiments, a CAR-expressing cell described herein is contacted with a composition comprising a combination of both a IL-15 polypeptide and a IL-15 Ra polypeptide during the manufacturing of the CAR-expressing cell, e.g., ex vivo. In embodiments, a CAR-expressing cell described herein is contacted with a composition comprising hetIL-15 during the manufacturing of the CAR-expressing cell, e.g., ex vivo.

In one embodiment the CAR-expressing cell described herein is contacted with a composition comprising hetIL-15 during ex vivo expansion. In an embodiment, the CAR-expressing cell described herein is contacted with a composition comprising an IL-15 polypeptide during ex vivo expansion. In an embodiment, the CAR-expressing cell described herein is contacted with a composition comprising both an IL-15 polypeptide and an IL-15Ra polypeptide during ex vivo expansion. In one embodiment the contacting results in the survival and proliferation of a lymphocyte subpopulation, e.g., CD8+ T cells.

T cells that have been exposed to varied stimulation times may exhibit different characteristics. For example, typical blood or apheresed peripheral blood mononuclear cell products have a helper T cell population (TH, CD4+) that is greater than the cytotoxic or suppressor T cell population. Ex vivo expansion of T cells by stimulating CD3 and CD28 receptors produces a population of T cells that prior to about days 8-9 consists predominately of TH cells, while after about days 8-9, the population of T cells comprises an increasingly greater population of TC cells. Accordingly, depending on the purpose of treatment, infusing a subject with a T cell population comprising predominately of TH cells may be advantageous. Similarly, if an antigen-specific subset of TC cells has been isolated it may be beneficial to expand this subset to a greater degree.

Further, in addition to CD4 and CD8 markers, other phenotypic markers vary significantly, but in large part, reproducibly during the course of the cell expansion process. Thus, such reproducibility enables the ability to tailor an activated T cell product for specific purposes.

Once a CAR is constructed, various assays can be used to evaluate the activity of the molecule, such as but not limited to, the ability to expand T cells following antigen stimulation, sustain T cell expansion in the absence of re-stimulation, and anti-cancer activities in appropriate in vitro and animal models. Assays to evaluate the effects of a CAR are described in further detail below Western blot analysis of CAR expression in primary T cells can be used to detect the presence of monomers and dimers. See, e.g., Milone et al., Molecular Therapy 17(8): 1453-1464 (2009). Very briefly, T cells (1:1 mixture of $CD4^+$ and $CD8^+$ T cells) expressing the CARs are expanded in vitro for more than 10 days followed by lysis and SDS-PAGE under reducing conditions. CARs containing the full length TCR-ζ cytoplasmic domain and the endogenous TCR-ζ chain are detected by western blotting using an antibody to the TCR-ζ chain. The same T cell subsets are used for SDS-PAGE analysis under non-reducing conditions to permit evaluation of covalent dimer formation.

In vitro expansion of $CAR^+$ T cells following antigen stimulation can be measured by flow cytometry. For example, a mixture of $CD4^+$ and $CD8^+$ T cells are stimulated with αCD3/αCD28 aAPCs followed by transduction with lentiviral vectors expressing GFP under the control of the promoters to be analyzed. Exemplary promoters include the CMV IE gene, EF-1α, ubiquitin C, or phosphoglycerokinase (PGK) promoters. GFP fluorescence is evaluated on day 6 of culture in the $CD4^+$ and/or $CD8^+$ T cell subsets by flow cytometry. See, e.g., Milone et al., Molecular Therapy 17(8): 1453-1464 (2009). Alternatively, a mixture of $CD4^+$ and $CD8^+$ T cells are stimulated with αCD3/αCD28 coated magnetic beads on day 0, and transduced with CAR on day 1 using a bicistronic lentiviral vector expressing CAR along with eGFP using a 2A ribosomal skipping sequence. Cultures are re-stimulated with antigen-expressing cells, such as multiple myeloma cell lines or K562 expressing the antigen, following washing. Exogenous IL-2 is added to the cultures every other day at 100 IU/ml. $GFP^+$ T cells are enumerated by flow cytometry using bead-based counting. See, e.g., Milone et al., Molecular Therapy 17(8): 1453-1464 (2009).

Sustained $CAR^+$ T cell expansion in the absence of re-stimulation can also be measured. See, e.g., Milone et al., Molecular Therapy 17(8): 1453-1464 (2009). Briefly, mean T cell volume (fl) is measured on day 8 of culture using a Coulter Multisizer III particle counter, a Nexcelom Cellometer Vision or Millipore Scepter, following stimulation with αCD3/αCD28 coated magnetic beads on day 0, and transduction with the indicated CAR on day 1.

Animal models can also be used to measure a CART activity. For example, xenograft model using human antigen-specific $CAR^+$ T cells to treat a primary human multiple myeloma in immunodeficient mice can be used. See, e.g., Milone et al., Molecular Therapy 17(8): 1453-1464 (2009). Very briefly, after establishment of MM, mice are randomized as to treatment groups. Different numbers of CART cells can be injected into immunodeficient mice bearing MM. Animals are assessed for disease progression and tumor burden at weekly intervals. Survival curves for the groups are compared using the log-rank test. In addition, absolute peripheral blood $CD4^+$ and $CD8^+$ T cell counts 4 weeks following T cell injection in the immunodeficient mice can also be analyzed. Mice are injected with multiple myeloma cells and 3 weeks later are injected with T cells engineered to express CAR, e.g., by a bicistronic lentiviral vector that encodes the CAR linked to eGFP. T cells are normalized to 45-50% input $GFP^+$ T cells by mixing with mock-transduced cells prior to injection, and confirmed by flow cytometry. Animals are assessed for leukemia at 1-week intervals. Survival curves for the $CAR^+$ T cell groups are compared using the log-rank test.

Assessment of cell proliferation and cytokine production has been previously described, e.g., at Milone et al., Molecular Therapy 17(8): 1453-1464 (2009). Briefly, assessment of CAR-mediated proliferation is performed in microtiter plates by mixing washed T cells with K562 cells expressing the antigen or other antigen-expressing myeloma cells are irradiated with gamma-radiation prior to use. Anti-CD3 (clone OKT3) and anti-CD28 (clone 9.3) monoclonal antibodies are added to cultures with KT32-BBL cells to serve as a positive control for stimulating T-cell proliferation since these signals support long-term $CD8^+$ T cell expansion ex vivo. T cells are enumerated in cultures using CountBright™ fluorescent beads (Invitrogen, Carlsbad, CA) and flow cytometry as described by the manufacturer. $CAR^+$ T cells are identified by GFP expression using T cells that are engineered with eGFP-2A linked CAR-expressing lentiviral vectors. For $CAR^+$ T cells not expressing GFP, the $CAR^+$ T cells are detected with biotinylated recombinant antigen protein and a secondary avidin-PE conjugate. $CD4^+$ and $CD8^+$ expression on T cells are also simultaneously detected with specific monoclonal antibodies (BD Biosciences). Cytokine measurements are performed on supernatants collected 24 hours following re-stimulation using the human TH1/TH2 cytokine cytometric bead array kit (BD Biosciences, San Diego, CA) according the manufacturer's instructions. Fluorescence is assessed using a FACScalibur flow cytometer, and data is analyzed according to the manufacturer's instructions.

Cytotoxicity can be assessed by a standard 51Cr-release assay. See, e.g., Milone et al., Molecular Therapy 17(8): 1453-1464 (2009). Briefly, target cells (e.g., K562 lines expressing the antigen and primary multiple myeloma cells) are loaded with 51Cr (as NaCrO4, New England Nuclear, Boston, MA) at 37° C. for 2 hours with frequent agitation, washed twice in complete RPMI and plated into microtiter plates. Effector T cells are mixed with target cells in the wells in complete RPMI at varying ratios of effector cell: target cell (E:T). Additional wells containing media only (spontaneous release, SR) or a 1% solution of triton-X 100 detergent (total release, TR) are also prepared. After 4 hours of incubation at 37° C., supernatant from each well is harvested. Released 51Cr is then measured using a gamma particle counter (Packard Instrument Co., Waltham, MA). Each condition is performed in at least triplicate, and the percentage of lysis is calculated using the formula: % Lysis=(ER−SR)/(TR−SR), where ER represents the average 51Cr released for each experimental condition. Alternatively, cytotoxicity can also be assessed using a Bright-Glo™ Luciferase Assay.

Imaging technologies can be used to evaluate specific trafficking and proliferation of CARs in tumor-bearing animal models. Such assays have been described, for example, in Barrett et al., Human Gene Therapy 22:1575-1586 (2011). Briefly, NOD/SCID/$\gamma c^{-/-}$ (NSG) mice or other immunodeficient are injected IV with multiple myeloma cells followed 7 days later with CART cells 4 hour after electroporation with the CAR constructs. The T cells are stably transfected with a lentiviral construct to express firefly luciferase, and mice are imaged for bioluminescence. Alternatively, therapeutic efficacy and specificity of a single injection of $CAR^+$ T cells in a multiple myeloma xenograft model can be measured as the following: NSG mice are injected with multiple myeloma cells transduced to stably express firefly luciferase, followed by a single tail-vein injection of T cells electroporated with CAR construct days later. Animals are imaged at various time points post injection. For example, photon-density heat maps of firefly luciferasepositive tumors in representative mice at day 5 (2 days before treatment) and day 8 (24 hr post $CAR^+$ PBLs) can be generated.

Alternatively, or in combination to the methods disclosed herein, methods and compositions for one or more of: detection and/or quantification of CAR-expressing cells (e.g., in vitro or in vivo (e.g., clinical monitoring)); immune cell expansion and/or activation; and/or CAR-specific selection, that involve the use of a CAR ligand, are disclosed. In one exemplary embodiment, the CAR ligand is an antibody that binds to the CAR molecule, e.g., binds to the extracellular antigen binding domain of CAR (e.g., an antibody that binds to the antigen binding domain, e.g., an anti-idiotypic antibody; or an antibody that binds to a constant region of the extracellular binding domain). In other embodiments, the CAR ligand is a CAR antigen molecule (e.g., a CAR antigen molecule as described herein).

In one aspect, a method for detecting and/or quantifying CAR-expressing cells is disclosed. For example, the CAR ligand can be used to detect and/or quantify CAR-expressing cells in vitro or in vivo (e.g., clinical monitoring of CAR-expressing cells in a patient, or dosing a patient). The method includes:

providing the CAR ligand (optionally, a labelled CAR ligand, e.g., a CAR ligand that includes a tag, a bead, a radioactive or fluorescent label);

- acquiring the CAR-expressing cell (e.g., acquiring a sample containing CAR-expressing cells, such as a manufacturing sample or a clinical sample);
- contacting the CAR-expressing cell with the CAR ligand under conditions where binding occurs, thereby detecting the level (e.g., amount) of the CAR-expressing cells present. Binding of the CAR-expressing cell with the CAR ligand can be detected using standard techniques such as FACS, ELISA and the like.

In another aspect, a method of expanding and/or activating cells (e.g., immune effector cells) is disclosed. The method includes:

- providing a CAR-expressing cell (e.g., a first CAR-expressing cell or a transiently expressing CAR cell);
- contacting said CAR-expressing cell with a CAR ligand, e.g., a CAR ligand as described herein), under conditions where immune cell expansion and/or proliferation occurs, thereby producing the activated and/or expanded cell population.

In certain embodiments, the CAR ligand is present on (e.g., is immobilized or attached to a substrate, e.g., a non-naturally occurring substrate). In some embodiments, the substrate is a non-cellular substrate. The non-cellular substrate can be a solid support chosen from, e.g., a plate (e.g., a microtiter plate), a membrane (e.g., a nitrocellulose membrane), a matrix, a chip or a bead. In embodiments, the CAR ligand is present in the substrate (e.g., on the substrate surface). The CAR ligand can be immobilized, attached, or associated covalently or non-covalently (e.g., cross-linked) to the substrate. In one embodiment, the CAR ligand is attached (e.g., covalently attached) to a bead. In the aforesaid embodiments, the immune cell population can be expanded in vitro or ex vivo. The method can further include culturing the population of immune cells in the presence of the ligand of the CAR molecule, e.g., using any of the methods described herein.

In other embodiments, the method of expanding and/or activating the cells further comprises addition of a second stimulatory molecule, e.g., CD28. For example, the CAR ligand and the second stimulatory molecule can be immobilized to a substrate, e.g., one or more beads, thereby providing increased cell expansion and/or activation.

In yet another aspect, a method for selecting or enriching for a CAR expressing cell is provided. The method includes contacting the CAR expressing cell with a CAR ligand as described herein; and selecting the cell on the basis of binding of the CAR ligand.

In yet other embodiments, a method for depleting, reducing and/or killing a CAR expressing cell is provided. The method includes contacting the CAR expressing cell with a CAR ligand as described herein; and targeting the cell on the basis of binding of the CAR ligand, thereby reducing the number, and/or killing, the CAR-expressing cell. In one embodiment, the CAR ligand is coupled to a toxic agent (e.g., a toxin or a cell ablative drug). In another embodiment, the anti-idiotypic antibody can cause effector cell activity, e.g., ADCC or ADC activities.

Exemplary anti-CAR antibodies that can be used in the methods disclosed herein are described, e.g., in WO 2014/190273 and by Jena et al., "Chimeric Antigen Receptor (CAR)-Specific Monoclonal Antibody to Detect CD19-Specific T cells in Clinical Trials", PLOS Mar. 2013 8:3 e57838, the contents of which are incorporated by reference. In one embodiment, the anti-idiotypic antibody molecule recognizes an anti-CD19 antibody molecule, e.g., an anti-CD19 scFv. For instance, the anti-idiotypic antibody molecule can compete for binding with the CD19-specific CAR mAb clone no. 136.20.1 described in Jena et al., PLOS Mar. 2013 8:3 e57838; may have the same CDRs (e.g., one or more of, e.g., all of, VH CDR1, VH CDR2, CH CDR3, VL CDR1, VL CDR2, and VL CDR3, using the Kabat definition, the Chothia definition, or a combination of the Kabat and Chothia definitions) as the CD19-specific CAR mAb clone no. 136.20.1; may have one or more (e.g., 2) variable regions as the CD19-specific CAR mAb clone no. 136.20.1, or may comprise the CD19-specific CAR mAb clone no. 136.20.1. In some embodiments, the anti-idiotypic antibody was made according to a method described in Jena et al. In another embodiment, the anti-idiotypic antibody molecule is an anti-idiotypic antibody molecule described in WO 2014/190273. In some embodiments, the anti-idiotypic antibody molecule has the same CDRs (e.g., one or more of, e.g., all of, VH CDR1, VH CDR2, CH CDR3, VL CDR1, VL CDR2, and VL CDR3) as an antibody molecule of WO 2014/190273 such as 136.20.1; may have one or more (e.g., 2) variable regions of an antibody molecule of WO 2014/190273, or may comprise an antibody molecule of WO 2014/190273 such as 136.20.1. In other embodiments, the anti-CAR antibody binds to a constant region of the extracellular binding domain of the CAR molecule, e.g., as described in WO 2014/190273. In some embodiments, the anti-CAR antibody binds to a constant region of the extracellular binding domain of the CAR molecule, e.g., a heavy chain constant region (e.g., a CH2-CH3 hinge region) or light chain constant region. For instance, in some embodiments the anti-CAR antibody competes for binding with the 2D3 monoclonal antibody described in WO 2014/190273, has the same CDRs (e.g., one or more of, e.g., all of, VH CDR1, VH CDR2, CH CDR3, VL CDR1, VL CDR2, and VL CDR3) as 2D3, or has one or more (e.g., 2) variable regions of 2D3, or comprises 2D3 as described in WO 2014/190273.

In some aspects and embodiments, the compositions and methods herein are optimized for a specific subset of T cells, e.g., as described in U.S. Ser. No. 62/031,699 filed Jul. 31, 2014, the contents of which are incorporated herein by reference in their entirety. In some embodiments, the optimized subsets of T cells display an enhanced persistence compared to a control T cell, e.g., a T cell of a different type (e.g., $CD8^+$ or $CD4^+$) expressing the same construct.

In some embodiments, a $CD4^+$ T cell comprises a CAR described herein, which CAR comprises an intracellular signaling domain suitable for (e.g., optimized for, e.g., leading to enhanced persistence in) a $CD4^+$ T cell, e.g., an ICOS domain. In some embodiments, a $CD8^+$ T cell comprises a CAR described herein, which CAR comprises an intracellular signaling domain suitable for (e.g., optimized for, e.g., leading to enhanced persistence of) a $CD8^+$ T cell, e.g., a 4-1BB domain, a CD28 domain, or another costimulatory domain other than an ICOS domain.

In an aspect, described herein is a method of treating a subject, e.g., a subject having cancer. The method includes administering to said subject, an effective amount of:

1) a $CD4^+$ T cell comprising a CAR (the $CAR^{CD4+}$) comprising:
   - an antigen binding domain, e.g., an antigen binding domain described herein;
   - a transmembrane domain; and
   - an intracellular signaling domain, e.g., a first costimulatory domain, e.g., an ICOS domain; and
2) a $CD8^+$ T cell comprising a CAR (the $CAR^{CD8+}$) comprising:
   - an antigen binding domain, e.g., an antigen binding domain described herein;
   - a transmembrane domain; and
   - an intracellular signaling domain, e.g., a second costimulatory domain, e.g., a 4-1BB domain, a CD28 domain, or another costimulatory domain other than an ICOS domain;
   - wherein the $CAR^{CD4+}$ and the $CAR^{CD8+}$ differ from one another.

Optionally, the method further includes administering:

3) a second $CD8^+$ T cell comprising a CAR (the second $CAR^{CD8+}$) comprising:
   - an antigen binding domain, e.g., an antigen binding domain described herein;
   - a transmembrane domain; and
     - an intracellular signaling domain, wherein the second $CAR^{CD8+}$ comprises an intracellular signaling domain, e.g., a costimulatory signaling domain, not present on the $CAR^{CD8+}$ and, optionally, does not comprise an ICOS signaling domain.

Other assays, including those that are known in the art can also be used to evaluate the CAR constructs of the invention.

Therapeutic Application

Methods Using Biomarkers for Evaluating CAR-Effectiveness, Subject Suitability, or Sample Suitability In another aspect, the invention features a method of evaluating or monitoring the effectiveness of a CAR-expressing cell therapy in a subject (e.g., a subject having a cancer). The method includes acquiring a value of effectiveness to the CAR therapy, subject suitability, or sample suitability, wherein said value is indicative of the effectiveness or suitability of the CAR-expressing cell therapy.

In some embodiments of any of the methods disclosed herein, the subject is evaluated prior to receiving, during, or after receiving, the CAR-expressing cell therapy.

In some embodiments of any of the methods disclosed herein, a responder (e.g., a complete responder) has, or is identified as having, a greater level or activity of one, two, or more (all) of GZMK, PPF1BP2, or naïve T cells as compared to a non-responder.

In some embodiments of any of the methods disclosed herein, a non-responder has, or is identified as having, a greater level or activity of one, two, three, four, five, six, seven, or more (e.g., all) of IL22, IL-2RA, IL-21, IRF8, IL8, CCL17, CCL22, effector T cells, or regulatory T cells, as compared to a responder.

In an embodiment, a relapser is a patient having, or who is identified as having, an increased level of expression of one or more of (e.g., 2, 3, 4, or all of) the following genes, compared to non relapsers: MIR199A1, MIR1203, uc021ovp, ITM2C, and HLA-DQB1 and/or a decreased levels of expression of one or more of (e.g., 2, 3, 4, 5, 6, 7, 8, 9, 10, 11, or all of) the following genes, compared to non relapsers: PPIAL4D, TTTY10, TXLNG2P, MIR4650-1, KDM5D, USP9Y, PRKY, RPS4Y2, RPS4Y1, NCRNA00185, SULT1E1, and EIF1AY.

In some embodiments of any of the methods disclosed herein, a non-responder has, or is identified as having, a greater percentage of an immune cell exhaustion marker, e.g., one, two or more immune checkpoint inhibitors (e.g., PD-1, PD-L1, TIM-3 and/or LAG-3). In one embodiment, a non-responder has, or is identified as having, a greater percentage of PD-1, PD-L1, or LAG-3 expressing immune effector cells (e.g., $CD4^+$ T cells and/or $CD8^+$ T cells) (e.g., CAR-expressing CD4+ cells and/or $CD8^+$ T cells) compared to the percentage of PD-1 or LAG-3 expressing immune effector cells from a responder.

In one embodiment, a non-responder has, or is identified as having, a greater percentage of immune cells having an exhausted phenotype, e.g., immune cells that co-express at least two exhaustion markers, e.g., co-expresses PD-1, PD-L1 and/or TIM-3. In other embodiments, a non-responder has, or is identified as having, a greater percentage of immune cells having an exhausted phenotype, e.g., immune cells that co-express at least two exhaustion markers, e.g., co-expresses PD-1 and LAG-3.

In some embodiments of any of the methods disclosed herein, a non-responder has, or is identified as having, a greater percentage of PD-1/PD-L1+/LAG-3+ cells in the CAR-expressing cell population compared to a responder (e.g., a complete responder) to the CAR-expressing cell therapy.

In some embodiments of any of the methods disclosed herein, a partial responder has, or is identified as having, a higher percentages of PD-1/PD-L1+/LAG-3+ cells, than a responder, in the CAR-expressing cell population.

In some embodiments of any of the methods disclosed herein, a non-responder has, or is identified as having, an exhausted phenotype of PD1/PD-L1+ CAR+ and co-expression of LAG3 in the CAR-expressing cell population.

In some embodiments of any of the methods disclosed herein, a non-responder has, or is identified as having, a greater percentage of PD-1/PD-L1+/TIM-3+ cells in the CAR-expressing cell population compared to the responder (e.g., a complete responder).

In some embodiments of any of the methods disclosed herein, a partial responders has, or is identified as having, a higher percentage of PD-1/PD-L1+/TIM-3+ cells, than responders, in the CAR-expressing cell population.

In some embodiments of any of the methods disclosed herein, the presence of CD8+CD27+CD45RO− T cells in an apheresis sample is a positive predictor of the subject response to a CAR-expressing cell therapy.

In some embodiments of any of the methods disclosed herein, a high percentage of PD1+ CAR+ and LAG3+ or TIM3+ T cells in an apheresis sample is a poor prognostic predictor of the subject response to a CAR-expressing cell therapy.

In some embodiments of any of the methods disclosed herein, the responder (e.g., the complete or partial responder) has one, two, three or more (or all) of the following profile:

(i) has a greater number of CD27+ immune effector cells compared to a reference value, e.g., a non-responder number of CD27+ immune effector cells;

(ii) (i) has a greater number of $CD8^+$ T cells compared to a reference value, e.g., a non-responder number of $CD8^+$ T cells;

(iii) has a lower number of immune cells expressing one or more checkpoint inhibitors, e.g., a checkpoint inhibitor chosen from PD-1, PD-L1, LAG-3, TIM-3, or KLRG-1, or a combination, compared to a reference value, e.g., a non-responder number of cells expressing one or more checkpoint inhibitors; or (iv) has a greater number of one, two, three, four or more (all) of resting $T_{EFF}$ ells, resting $T_{REG}$ cells, naïve CD4 cells, unstimulated memory cells or early memory T cells, or a combination thereof, compared to a reference value, e.g., a non-responder number of resting $T_{EFF}$ ells, resting $T_{REG}$ cells, naïve CD4 cells, unstimulated memory cells or early memory T cells.

In some embodiments of any of the methods disclosed herein, the cytokine level or activity of (vi) is chosen from one, two, three, four, five, six, seven, eight, or more (or all) of cytokine CCL20/MIP3a, IL17A, IL6, GM-CSF, IFN-γ, IL10, IL13, IL2, IL21, IL4, IL, IL9 or TNFα, or a combination thereof. The cytokine can be chosen from one, two, three, four or more (all) of IL-17a, CCL20, IL2, IL6, or TNFα. In one embodiment, an increased level or activity of a cytokine is chosen from one or both of IL-17a and CCL20, is indicative of increased responsiveness or decreased relapse.

In embodiments, the responder, a non-responder, a relapser or a non-relapser identified by the methods herein can be further evaluated according to clinical criteria. For example, a complete responder has, or is identified as, a subject having a disease, e.g., a cancer, who exhibits a complete response, e.g., a complete remission, to a treatment. A complete response may be identified, e.g., using the NCCN Guidelines®, or Cheson et al, J Clin Oncol 17:1244 (1999) and Cheson et al., "Revised Response Criteria for Malignant Lymphoma", J Clin Oncol 25:579-586 (2007) (both of which are incorporated by reference herein in their entireties), as described herein. A partial responder has, or is identified as, a subject having a disease, e.g., a cancer, who exhibits a partial response, e.g., a partial remission, to a treatment. A partial response may be identified, e.g., using the NCCN Guidelines®, or Cheson criteria as described herein. A non-responder has, or is identified as, a subject having a disease, e.g., a cancer, who does not exhibit a response to a treatment, e.g., the patient has stable disease or progressive disease. A non-responder may be identified, e.g., using the NCCN Guidelines®, or Cheson criteria as described herein.

Alternatively, or in combination with the methods disclosed herein, responsive to said value, performing one, two, three four or more of:

- administering e.g., to a responder or a non-relapser, a CAR-expressing cell therapy;
- administered an altered dosing of a CAR-expressing cell therapy;
- altering the schedule or time course of a CAR-expressing cell therapy;
- administering, e.g., to a non-responder or a partial responder, an additional agent in combination with a CAR-expressing cell therapy, e.g., a checkpoint inhibitor, e.g., a checkpoint inhibitor described herein;
- administering to a non-responder or partial responder a therapy that increases the number of younger T cells in the subject prior to treatment with a CAR-expressing cell therapy;
- modifying a manufacturing process of a CAR-expressing cell therapy, e.g., enriching for younger T cells prior to introducing a nucleic acid encoding a CAR, or increasing the transduction efficiency, e.g., for a subject identified as a non-responder or a partial responder;
- administering an alternative therapy, e.g., for a non-responder or partial responder or relapser; or
- if the subject is, or is identified as, a non-responder or a relapser, decreasing the $T_{REG}$ cell population and/or $T_{REG}$ gene signature, e.g., by one or more of CD25 depletion, administration of cyclophosphamide, anti-GITR antibody, or a combination thereof.

In certain embodiments, the subject is pre-treated with an anti-GITR antibody. In certain embodiment, the subject is treated with an anti-GITR antibody prior to infusion or re-infusion.

Combination Therapies

A CAR-expressing cell described herein may be used in combination with other known agents and therapies. Administered "in combination", as used herein, means that two (or more) different treatments are delivered to the subject during the course of the subject's affliction with the disorder, e.g., the two or more treatments are delivered after the subject has been diagnosed with the disorder and before the disorder has been cured or eliminated or treatment has ceased for other reasons. In some embodiments, the delivery of one treatment is still occurring when the delivery of the second begins, so that there is overlap in terms of administration. This is sometimes referred to herein as "simultaneous" or "concurrent delivery". In other embodiments, the delivery of one treatment ends before the delivery of the other treatment begins. In some embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In some embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered.

A CAR-expressing cell described herein and the at least one additional therapeutic agent can be administered simultaneously, in the same or in separate compositions, or sequentially. For sequential administration, the CAR-expressing cell described herein can be administered first, and the additional agent can be administered second, or the order of administration can be reversed.

The CAR therapy and/or other therapeutic agents, procedures or modalities can be administered during periods of active disorder, or during a period of remission or less active disease. The CAR therapy can be administered before the other treatment, concurrently with the treatment, post-treatment, or during remission of the disorder.

When administered in combination, the CAR therapy and the additional agent (e.g., second or third agent), or all, can be administered in an amount or dose that is higher, lower or the same than the amount or dosage of each agent used individually, e.g., as a monotherapy. In certain embodiments, the administered amount or dosage of the CAR therapy, the additional agent (e.g., second or third agent), or all, is lower (e.g., at least 20%, at least 30%, at least 40%, or at least 50%) than the amount or dosage of each agent used individually, e.g., as a monotherapy. In other embodiments, the amount or dosage of the CAR therapy, the additional agent (e.g., second or third agent), or all, that results in a desired effect (e.g., treatment of cancer) is lower (e.g., at least 20%, at least 30%, at least 40%, or at least 50% lower) than the amount or dosage of each agent used individually, e.g., as a monotherapy, required to achieve the same therapeutic effect.

In some embodiments, the invention discloses a combination therapy including a CAR-expressing cell therapy described herein, a virus comprising a nucleic acid molecule encoding a TNFα molecule, an IL-2 molecule, and/or an IL-7 molecule, and an additional therapeutic agent.

PD-1 Inhibitor

In some embodiments, the additional therapeutic agent is a PD-1 inhibitor. In some embodiments, the PD-1 inhibitor is chosen from PDR001 (Novartis), Nivolumab (Bristol-Myers Squibb), Pembrolizumab (Merck & Co), Pidilizumab (CureTech), MEDI0680 (Medimmune), REGN2810 (Regeneron), TSR-042 (Tesaro), PF-06801591 (Pfizer), BGB-A317 (Beigene), BGB-108 (Beigene), INCSHRI210 (Incyte), or AMP-224 (Amplimmune).

In one embodiment, the PD-1 inhibitor is an anti-PD-1 antibody molecule. In one embodiment, the PD-1 inhibitor is an anti-PD-1 antibody molecule as described in US 2015/0210769, published on Jul. 30, 2015, entitled "Antibody Molecules to PD-1 and Uses Thereof," incorporated by reference in its entirety. In one embodiment, the anti-PD-1 antibody molecule comprises the CDRs, variable regions, heavy chains and/or light chains of BAP49-Clone-E or BAP049-Clone-B disclosed in US 2015/0210769. The antibody molecules described herein can be made by vectors, host cells, and methods described in US 2015/0210769, incorporated by reference in its entirety.

In one embodiment, the anti-PD-1 antibody molecule is Nivolumab (Bristol-Myers Squibb), also known as MDX-1106, MDX-1106-04, ONO-4538, BMS-936558, or OPDIVO®. Nivolumab (clone 5C4) and other anti-PD-1 antibodies are disclosed in U.S. Pat. No. 8,008,449 and WO 2006/121168, incorporated by reference in their entirety. In one embodiment, the anti-PD-1 antibody molecule is Pembrolizumab (Merck & Co), also known as Lambrolizumab, MK-3475, MK03475, SCH-900475, or KEYTRUDA. Pembrolizumab and other anti-PD-1 antibodies are disclosed in Hamid, O. et al. (2013) *New England Journal of Medicine* 369 (2): 134-44, U.S. Pat. No. 8,354,509, and WO 2009/114335, incorporated by reference in their entirety. In one embodiment, the anti-PD-1 antibody molecule is Pidilizumab (CureTech), also known as CT-011. Pidilizumab and other anti-PD-1 antibodies are disclosed in Rosenblatt, J. et al. (2011) *J Immunotherapy* 34(5): 409-18, U.S. Pat. Nos. 7,695,715, 7,332,582, and U.S. Pat. No. 8,686,119, incorporated by reference in their entirety. In one embodiment, the anti-PD-1 antibody molecule is MEDI0680 (Medimmune), also known as AMP-514. MEDI0680 and other anti-PD-1 antibodies are disclosed in U.S. Pat. No. 9,205,148 and WO 2012/145493, incorporated by reference in their entirety. In one embodiment, the anti-PD-1 antibody molecule is REGN2810 (Regeneron). In one embodiment, the anti-PD-1 antibody molecule is PF-06801591 (Pfizer). In one embodiment, the anti-PD-1 antibody molecule is BGB-A317 or BGB-108 (Beigene). In one embodiment, the anti-PD-1 antibody molecule is INCSHRI210 (Incyte), also known as INCSHR01210 or SHR-1210. In one embodiment, the anti-PD-1 antibody molecule is TSR-042 (Tesaro), also known as ANB011.

Further known anti-PD-1 antibody molecules include those described, e.g., in WO 2015/112800, WO 2016/092419, WO 2015/085847, WO 2014/179664, WO 2014/194302, WO 2014/209804, WO 2015/200119, U.S. Pat. Nos. 8,735,553, 7,488,802, 8,927,697, 8,993,731, and 9,102,727, incorporated by reference in their entirety.

In one embodiment, the PD-1 inhibitor is a peptide that inhibits the PD-1 signaling pathway, e.g., as described in U.S. Pat. No. 8,907,053, incorporated by reference in its entirety. In one embodiment, the PD-1 inhibitor is an immunoadhesin (e.g., an immunoadhesin comprising an extracellular or PD-1 binding portion of PD-L1 or PD-L2 fused to a constant region (e.g., an Fc region of an immunoglobulin sequence). In one embodiment, the PD-1 inhibitor is AMP-224 (B7-DCIg (Amplimmune), e.g., disclosed in WO 2010/027827 and WO 2011/066342, incorporated by reference in their entirety).

PD-L1 Inhibitors

In some embodiments, the additional therapeutic agent is a PD-L1 inhibitor. In some embodiments, the PD-L1 inhibitor is chosen from FAZ053 (Novartis), Atezolizumab (Genentech/Roche), Avelumab (Merck Serono and Pfizer), Durvalumab (Medlmmune/AstraZeneca), or BMS-936559 (Bristol-Myers Squibb).

In one embodiment, the PD-L1 inhibitor is an anti-PD-L1 antibody molecule. In one embodiment, the PD-L1 inhibitor is an anti-PD-L1 antibody molecule as disclosed in US 2016/0108123, published on Apr. 21, 2016, entitled "Antibody Molecules to PD-L1 and Uses Thereof," incorporated by reference in its entirety. In one embodiment, the anti-PD-L1 antibody molecule comprises the CDRs, variable regions, heavy chains and/or light chains of BAP058-Clone 0 or BAP058-Clone N disclosed in US 2016/0108123.

In one embodiment, the anti-PD-L1 antibody molecule is Atezolizumab (Genentech/Roche), also known as MPDL3280A, RG7446, RO5541267, YW243.55.570, or TECENTRIQ™ Atezolizumab and other anti-PD-L1 antibodies are disclosed in U.S. Pat. No. 8,217,149, incorporated by reference in its entirety. In one embodiment, the anti-PD-L1 antibody molecule is Avelumab (Merck Serono and Pfizer), also known as MSB0010718C. Avelumab and other anti-PD-L1 antibodies are disclosed in WO 2013/079174, incorporated by reference in its entirety. In one embodiment, the anti-PD-L1 antibody molecule is Durvalumab (Medlmmune/AstraZeneca), also known as MED14736. Durvalumab and other anti-PD-L1 antibodies are disclosed in U.S. Pat. No. 8,779,108, incorporated by reference in its entirety. In one embodiment, the anti-PD-L1 antibody molecule is BMS-936559 (Bristol-Myers Squibb), also known as MDX-1105 or 12A4. BMS-936559 and other anti-PD-L1 antibodies are disclosed in U.S. Pat. No. 7,943,743 and WO 2015/081158, incorporated by reference in their entirety.

Further known anti-PD-L1 antibodies include those described, e.g., in WO 2015/181342, WO 2014/100079, WO 2016/000619, WO 2014/022758, WO 2014/055897, WO 2015/061668, WO 2013/079174, WO 2012/145493, WO 2015/112805, WO 2015/109124, WO 2015/195163, U.S. Pat. Nos. 8,168,179, 8,552,154, 8,460,927, and 9,175,082, incorporated by reference in their entirety.

LAG-3 Inhibitors

In some embodiments, the additional therapeutic agent is a LAG-3 inhibitor. In some embodiments, the LAG-3 inhibitor is chosen from LAG525 (Novartis), BMS-986016 (Bristol-Myers Squibb), or TSR-033 (Tesaro).

In one embodiment, the LAG-3 inhibitor is an anti-LAG-3 antibody molecule. In one embodiment, the LAG-3 inhibitor is an anti-LAG-3 antibody molecule as disclosed in US 2015/0259420, published on Sep. 17, 2015, entitled "Antibody Molecules to LAG-3 and Uses Thereof," incorporated by reference in its entirety. In one embodiment, the anti-LAG-3 antibody molecule comprises the CDRs, variable regions, heavy chains and/or light chains of BAP050-Clone I or BAP050-Clone J disclosed in US 2015/0259420.

In one embodiment, the anti-LAG-3 antibody molecule is BMS-986016 (Bristol-Myers Squibb), also known as BMS986016. BMS-986016 and other anti-LAG-3 antibodies are disclosed in WO 2015/116539 and U.S. Pat. No. 9,505,839, incorporated by reference in their entirety. In one embodiment, the anti-LAG-3 antibody molecule is TSR-033 (Tesaro). In one embodiment, the anti-LAG-3 antibody molecule is IMP731 or GSK2831781 (GSK and Prima BioMed). IMP731 and other anti-LAG-3 antibodies are disclosed in WO 2008/132601 and U.S. Pat. No. 9,244,059, incorporated by reference in their entirety. In one embodiment, the anti-LAG-3 antibody molecule is IMP761 (Prima BioMed).

Further known anti-LAG-3 antibodies include those described, e.g., in WO 2008/132601, WO 2010/019570, WO 2014/140180, WO 2015/116539, WO 2015/200119, WO 2016/028672, U.S. Pat. Nos. 9,244,059, 9,505,839, incorporated by reference in their entirety.

In one embodiment, the anti-LAG-3 inhibitor is a soluble LAG-3 protein, e.g., IMP321 (Prima BioMed), e.g., as disclosed in WO 2009/044273, incorporated by reference in its entirety.

TIM-3 Inhibitors

In some embodiments, the additional therapeutic agent is a TIM-3 inhibitor. In some embodiments, the TIM-3 inhibitor is MGB453 (Novartis) or TSR-022 (Tesaro).

In one embodiment, the TIM-3 inhibitor is an anti-TIM-3 antibody molecule. In one embodiment, the TIM-3 inhibitor is an anti-TIM-3 antibody molecule as disclosed in US 2015/0218274, published on Aug. 6, 2015, entitled "Antibody Molecules to TIM-3 and Uses Thereof," incorporated by reference in its entirety. In one embodiment, the anti-TIM-3 antibody molecule comprises the CDRs, variable regions, heavy chains and/or light chains of ABTIM3-hum11 or ABTIM3-hum03 disclosed in US 2015/0218274.

In one embodiment, the anti-TIM-3 antibody molecule is TSR-022 (AnaptysBio/Tesaro). In one embodiment, the anti-TIM-3 antibody molecule comprises one or more of the CDR sequences (or collectively all of the CDR sequences), the heavy chain or light chain variable region sequence, or the heavy chain or light chain sequence of APE5137 or APE5121. APE5137, APE5121, and other anti-TIM-3 antibodies are disclosed in WO 2016/161270, incorporated by reference in its entirety. In one embodiment, the anti-TIM-3 antibody molecule is the antibody clone F38-2E2.

Further known anti-TIM-3 antibodies include those described, e.g., in WO 2016/111947, WO 2016/071448, WO 2016/144803, U.S. Pat. Nos. 8,552,156, 8,841,418, and 9,163,087, incorporated by reference in their entirety.

Chemotherapeutic Agents

In some embodiments, the additional therapeutic agent is a chemotherapeutic agent. Exemplary chemotherapeutic agents include an anthracycline (e.g., doxorubicin (e.g., liposomal doxorubicin)), a vinca alkaloid (e.g., vinblastine, vincristine, vindesine, vinorelbine), an alkylating agent (e.g., cyclophosphamide, decarbazine, melphalan, ifosfamide, temozolomide), an immune cell antibody (e.g., alemtuzamab, gemtuzumab, rituximab, tositumomab), an antimetabolite (including, e.g., folic acid antagonists, pyrimidine analogs, purine analogs and adenosine deaminase inhibitors (e.g., fludarabine)), an mTOR inhibitor, a TNFR glucocorticoid induced TNFR related protein (GITR) agonist, a proteasome inhibitor (e.g., aclacinomycin A, gliotoxin or bortezomib), an immunomodulator such as thalidomide or a thalidomide derivative (e.g., lenalidomide).

General Chemotherapeutic agents considered for use in combination therapies include anastrozole (Arimidex®), bicalutamide (Casodex®), bleomycin sulfate (Blenoxane®), busulfan (Myleran®), busulfan injection (Busulfex®), capecitabine (Xeloda®), N4-pentoxycarbonyl-5-deoxy-5-fluorocytidine, carboplatin (Paraplatin®), carmustine (BiCNU®), chlorambucil (Leukeran®), cisplatin (Platinol®), cladribine (Leustatin®), cyclophosphamide (Cytoxan® or Neosar®), cytarabine, cytosine arabinoside (Cytosar-U®), cytarabine liposome injection (DepoCyt®), dacarbazine (DTIC-Dome®), dactinomycin (Actinomycin D, Cosmegan), daunorubicin hydrochloride (Cerubidine®), daunorubicin citrate liposome injection (DaunoXome®), dexamethasone, docetaxel (Taxotere®), doxorubicin hydrochloride (Adriamycin®, Rubex®), etoposide (Vepesid®), fludarabine phosphate (Fludara®), 5-fluorouracil (Adrucil®, Efudex®), flutamide (Eulexin®), tezacitibine, Gemcitabine (difluorodeoxycitidine), hydroxyurea (Hydrea®), Idarubicin (Idamycin®), ifosfamide (IFEX®), irinotecan (Camptosar®), L-asparaginase (ELSPAR®), leucovorin calcium, melphalan (Alkeran®), 6-mercaptopurine (Purinethol®), methotrexate (Folex®), mitoxantrone (Novantrone®), mylotarg, paclitaxel (Taxol®), phoenix (Yttrium90/MX-DTPA), pentostatin, polifeprosan 20 with carmustine implant (Gliadel®), tamoxifen citrate (Nolvadex®), teniposide (Vumon®), 6-thioguanine, thiotepa, tirapazamine (Tirazone®), topotecan hydrochloride for injection (Hycamptin®), vinblastine (Velban®), vincristine (Oncovin®), and vinorelbine (Navelbine®).

Exemplary alkylating agents include, without limitation, nitrogen mustards, ethylenimine derivatives, alkyl sulfonates, nitrosoureas and triazenes): uracil mustard (Aminouracil Mustard®, Chlorethaminacil®, Demethyldopan®, Desmethyldopan®, Haemanthamine®, Nordopan®, Uracil nitrogen Mustard®, Uracillost®, Uracilmostaza®, Uramustin®, Uramustine®), chlormethine (Mustargen®), cyclophosphamide (Cytoxan®, Neosar®, Clafen®, Endoxan®, Procytox®, Revimmune™), ifosfamide (Mitoxana®), melphalan (Alkeran®), Chlorambucil (Leukeran®), pipobroman (Amedel®, Vercyte®), triethylenemelamine (Hemel®, Hexalen®, Hexastat®), triethylenethiophosphoramine, Temozolomide (Temodar®), thiotepa (Thioplex®), busulfan (Busilvex®, Myleran®), carmustine (BiCNU®), lomustine (CeeNU®), streptozocin (Zanosar®), and Dacarbazine (DTIC-Dome®). Additional exemplary alkylating agents include, without limitation, Oxaliplatin (Eloxatin®); Temozolomide (Temodar® and Temodal®); Dactinomycin (also known as actinomycin-D, Cosmegen®); Melphalan (also known as L-PAM, L-sarcolysin, and phenylalanine mustard, Alkeran®); Altretamine (also known as hexamethylmelamine (HMM), Hexalen®); Carmustine (BiCNU®); Bendamustine (Treanda®); Busulfan (Busulfex® and Myleran®); Carboplatin (Paraplatin®); Lomustine (also known as CCNU, CeeNU®); Cisplatin (also known as CDDP, Platinol® and Platinol®-AQ); Chlorambucil (Leukeran®); Cyclophosphamide (Cytoxan® and Neosar®); Dacarbazine (also known as DTIC, DIC and imidazole carboxamide, DTIC-Dome®); Altretamine (also known as hexamethylmelamine (HMM), Hexalen®); Ifosfamide (Ifex®); Prednumustine; Procarbazine (Matulane®); Mechlorethamine (also known as nitrogen mustard, mustine and mechloroethamine hydrochloride, Mustargen®); Streptozocin (Zanosar®); Thiotepa (also known as thiophosphoamide, TESPA and TSPA, Thioplex®); Cyclophosphamide (Endoxan®, Cytoxan®, Neosar®, Procytox®, Revimmune®); and Bendamustine HCl (Treanda®).

Exemplary mTOR inhibitors include, e.g., temsirolimus; ridaforolimus (formally known as deferolimus, (1R,2R,4S)-4-[(2R)-2 [(1R,9S,12S,15R,16E,18R,19R,21R, 23S,24E, 26E,28Z,30S,32S,35R)-1,18-dihydroxy-19,30-dimethoxy-15,17,21,23, 29,35-hexamethyl-2,3,10,14,20-pentaoxo-11, 36-dioxa-4-azatricyclo[30.3.1.$0^{4,9}$] hexatriaconta-16,24,26, 28-tetraen-12-yl]propyl]-2-methoxycyclohexyl dimethylphosphinate, also known as AP23573 and MK8669, and described in PCT Publication No. WO 03/064383); everolimus (Afinitor® or RAD001); rapamycin (AY22989, Sirolimus®); simapimod (CAS 164301-51-3); emsirolimus, (5-{2,4-Bis[(3S)-3-methylmorpholin-4-yl] pyrido[2,3-d]pyrimidin-7-yl}-2-methoxyphenyl)methanol (AZD8055); 2-Amino-8-[trans-4-(2-hydroxyethoxy)cyclohexyl]-6-(6-methoxy-3-pyridinyl)-4-methyl-pyrido[2,3-d] pyrimidin-7(8H)-one (PF04691502, CAS 1013101-36-4); and $N^2$-[1,4-dioxo-4-[[4-(4-oxo-8-phenyl-4H-1-benzopyran-2-yl)morpholinium-4-yl]methoxy]butyl]-L-arginylglycyl-L-α-aspartylL-serine-(SEQ ID NO: 626), inner salt (SF1126, CAS 936487-67-1), and XL765.

Exemplary immunomodulators include, e.g., afutuzumab (available from Roche®); pegfilgrastim (Neulasta®); lenalidomide (CC-5013, Revlimid®); thalidomide (Thalomid®), actimid (CC4047); and IRX-2 (mixture of human cytokines including interleukin 1, interleukin 2, and interferon γ, CAS 951209-71-5, available from IRX Therapeutics).

Exemplary anthracyclines include, e.g., doxorubicin (Adriamycin® and Rubex®); bleomycin (Lenoxane®); daunorubicin (dauorubicin hydrochloride, daunomycin, and rubidomycin hydrochloride, Cerubidine®); daunorubicin liposomal (daunorubicin citrate liposome, DaunoXome®); mitoxantrone (DHAD, Novantrone®); epirubicin (Ellence™); idarubicin (Idamycin®, Idamycin PFS®); mitomycin C (Mutamycin®); geldanamycin; herbimycin; ravidomycin; and desacetylravidomycin.

Exemplary vinca alkaloids include, e.g., vinorelbine tartrate (Navelbine®), Vincristine (Oncovin®), and Vindesine (Eldisine®)); vinblastine (also known as vinblastine sulfate, vincaleukoblastine and VLB, Alkaban-AQ® and Velban®); and vinorelbine (Navelbine®).

Exemplary proteosome inhibitors include bortezomib (Velcade®); carfilzomib (PX-171-007, (S)-4-Methyl-N—((S)-1-(((S)-4-methyl-1-((R)-2-methyloxiran-2-yl)-1-oxopentan-2-yl)amino)-1-oxo-3-phenylpropan-2-yl)-2-((S)-2-(2-morpholinoacetamido)-4-phenylbutanamido)-pentanamide); marizomib (NPI-0052); ixazomib citrate (MLN-9708); delanzomib (CEP-18770); and O-Methyl-N-[(2-methyl-5-thiazolyl)carbonyl]-L-seryl-O-methyl-N-[(1S)-2-[(2R)-2-methyl-2-oxiranyl]-2-oxo-1-(phenylmethyl)ethyl]-L-serinamide (ONX-0912).

Biopolymer Delivery Methods

In some embodiments, one or more CAR-expressing cells as disclosed herein can be administered or delivered to the subject via a biopolymer scaffold, e.g., a biopolymer implant. Biopolymer scaffolds can support or enhance the delivery, expansion, and/or dispersion of the CAR-expressing cells described herein. A biopolymer scaffold comprises a biocompatible (e.g., does not substantially induce an inflammatory or immune response) and/or a biodegradable polymer that can be naturally occurring or synthetic.

Examples of suitable biopolymers include, but are not limited to, agar, agarose, alginate, alginate/calcium phosphate cement (CPC), beta-galactosidase (β-GAL), (1,2,3,4, 6-pentaacetyl a-D-galactose), cellulose, chitin, chitosan, collagen, elastin, gelatin, hyaluronic acid collagen, hydroxyapatite, poly(3-hydroxybutyrate-co-3-hydroxyhexanoate) (PHBHHx), poly(lactide), poly(caprolactone) (PCL), poly(lactide-co-glycolide) (PLG), polyethylene oxide (PEO), poly(lactic-co-glycolic acid) (PLGA), polypropylene oxide (PPO), polyvinyl alcohol) (PVA), silk, soy protein, and soy protein isolate, alone or in combination with any other polymer composition, in any concentration and in any ratio. The biopolymer can be augmented or modified with adhesion- or migration-promoting molecules, e.g., collagen-mimetic peptides that bind to the collagen receptor of lymphocytes, and/or stimulatory molecules to enhance the delivery, expansion, or function, e.g., anti-cancer activity, of the cells to be delivered. The biopolymer scaffold can be an injectable, e.g., a gel or a semi-solid, or a solid composition.

In some embodiments, CAR-expressing cells described herein are seeded onto the biopolymer scaffold prior to delivery to the subject. In embodiments, the biopolymer scaffold further comprises one or more additional therapeutic agents described herein (e.g., another CAR-expressing cell, an antibody, or a small molecule) or agents that enhance the activity of a CAR-expressing cell, e.g., incorporated or conjugated to the biopolymers of the scaffold. In embodiments, the biopolymer scaffold is injected, e.g., intratumorally, or surgically implanted at the tumor or within a proximity of the tumor sufficient to mediate an anti-tumor effect. Additional examples of biopolymer compositions and methods for their delivery are described in Stephan et al., *Nature Biotechnology,* 2015, 33:97-101; and WO2014/110591.

Pharmaceutical Compositions and Treatments

Pharmaceutical compositions of the present invention may comprise a CAR-expressing cell, e.g., a plurality of CAR-expressing cells, as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are in one aspect formulated for intravenous administration.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

In one embodiment, the pharmaceutical composition is substantially free of, e.g., there are no detectable levels of a contaminant, e.g., selected from the group consisting of endotoxin, *mycoplasma*, replication competent lentivirus (RCL), p24, VSV-G nucleic acid, HIV gag, residual anti-CD3/anti-CD28 coated beads, mouse antibodies, pooled human serum, bovine serum albumin, bovine serum, culture media components, vector packaging cell or plasmid components, a bacterium and a fungus. In one embodiment, the bacterium is at least one selected from the group consisting of *Alcaligenes faecalis, Candida albicans, Escherichia coli, Haemophilus influenza, Neisseria meningitides, Pseudomonas aeruginosa, Staphylococcus aureus, Streptococcus pneumonia*, and *Streptococcus pyogenes* group A.

When "an immunologically effective amount," "an anti-tumor effective amount," "a tumor-inhibiting effective amount," or "therapeutic amount" is indicated, the precise amount of the compositions of the present invention to be administered can be determined by a physician with consideration of individual differences in age, weight, tumor size, extent of infection or metastasis, and condition of the patient (subject). It can generally be stated that a pharmaceutical composition comprising the T cells described herein may be administered at a dosage of 10 to 10 cells/kg body weight, in some instances $10^5$ to $10^6$ cells/kg body weight, including all integer values within those ranges. T cell compositions may also be administered multiple times at these dosages. The cells can be administered by using infusion techniques that are commonly known in immunotherapy (see, e.g., Rosenberg et al., New Eng. J. of Med. 319:1676, 1988).

In certain aspects, it may be desired to administer activated T cells to a subject and then subsequently redraw blood (or have an apheresis performed), activate T cells therefrom according to the present invention, and reinfuse the patient with these activated and expanded T cells. This process can be carried out multiple times every few weeks. In certain aspects, T cells can be activated from blood draws of from 10 cc to 400 cc. In certain aspects, T cells are activated from blood draws of 20 cc, 30 cc, 40 cc, 50 cc, 60 cc, 70 cc, 80 cc, 90 cc, or 100 cc.

The administration of the subject compositions may be carried out in any convenient manner, including by aerosol inhalation, injection, ingestion, transfusion, implantation or transplantation. The compositions described herein may be administered to a patient trans arterially, subcutaneously, intradermally, intratumorally, intranodally, intramedullary, intramuscularly, by intravenous (i.v.) injection, or intraperitoneally. In one aspect, the T cell compositions of the present invention are administered to a patient by intradermal or subcutaneous injection. In one aspect, the CAR-expressing cell (e.g., T cell or NK cell) compositions of the present invention are administered by i.v. injection. The compositions of CAR-expressing cells (e.g., T cells or NK cells) may be injected directly into a tumor, lymph node, or site of infection.

In a particular exemplary aspect, subjects may undergo leukapheresis, wherein leukocytes are collected, enriched, or depleted ex vivo to select and/or isolate the cells of interest, e.g., immune effector cells (e.g., T cells or NK cells). These immune effector cell (e.g., T cell or NK cell) isolates may be expanded by methods known in the art and treated such that one or more CAR constructs of the invention may be introduced, thereby creating a CAR-expressing cell (e.g., CAR T cell or CAR-expressing NK cell) of the invention. Subjects in need thereof may subsequently undergo standard treatment with high dose chemotherapy followed by peripheral blood stem cell transplantation. In certain aspects, following or concurrent with the transplant, subjects receive an infusion of the expanded CAR-expressing cells (e.g., CAR T cells or NK cells) of the present invention. In an additional aspect, expanded cells are administered before or following surgery.

In embodiments, lymphodepletion is performed on a subject, e.g., prior to administering one or more cells that express a CAR described herein. In embodiments, the lymphodepletion comprises administering one or more of melphalan, cytoxan, cyclophosphamide, and fludarabine.

The dosage of the above treatments to be administered to a patient will vary with the precise nature of the condition being treated and the recipient of the treatment. The scaling of dosages for human administration can be performed according to art-accepted practices. The dose for CAMPATH, for example, will generally be in the range 1 to about 100 mg for an adult patient, usually administered daily for a period between 1 and 30 days. The preferred daily dose is 1 to 10 mg per day although in some instances larger doses of up to 40 mg per day may be used (described in U.S. Pat. No. 6,120,766).

In one embodiment, the CAR is introduced into immune effector cells (e.g., T cells or NK cells), e.g., using in vitro transcription, and the subject (e.g., human) receives an initial administration of CAR immune effector cells (e.g., T cells or NK cells) of the invention, and one or more subsequent administrations of the CAR immune effector cells (e.g., T cells or NK cells) of the invention, wherein the one or more subsequent administrations are administered less than 15 days, e.g., 14, 13, 12, 11, 10, 9, 8, 7, 6, 5, 4, 3, or 2 days after the previous administration. In one embodiment, more than one administration of the CAR immune effector cells (e.g., T cells or NK cells) of the invention are administered to the subject (e.g., human) per week, e.g., 2, 3, or 4 administrations of the CAR immune effector cells (e.g., T cells or NK cells) of the invention are administered per week. In one embodiment, the subject (e.g., human subject) receives more than one administration of the CAR immune effector cells (e.g., T cells or NK cells) per week (e.g., 2, 3 or 4 administrations per week) (also referred to herein as a cycle), followed by a week of no CAR immune effector cells (e.g., T cells or NK cells) administrations, and then one or more additional administration of the CAR immune effector cells (e.g., T cells or NK cells) (e.g., more than one administration of the CAR immune effector cells (e.g., T cells or NK cells) per week) is administered to the subject. In another embodiment, the subject (e.g., human subject) receives more than one cycle of CAR immune effector cells (e.g., T cells or NK cells), and the time between each cycle is less than 10, 9, 8, 7, 6, 5, 4, or 3 days. In one embodiment, the CAR immune effector cells (e.g., T cells or NK cells) are administered every other day for 3 administrations per week. In one embodiment, the CAR immune effector cells (e.g., T cells or NK cells) of the invention are administered for at least two, three, four, five, six, seven, eight or more weeks.

In one aspect, CAR-expressing cells (e.g., CARTs or CAR-expressing NK cells) are generated using lentiviral viral vectors, such as lentivirus. CAR-expressing cells (e.g., CARTs or CAR-expressing NK cells) generated that way will have stable CAR expression.

In one aspect, CAR-expressing cells, e.g., CARTs, are generated using a viral vector such as a gammaretroviral vector, e.g., a gammaretroviral vector described herein. CARTs generated using these vectors can have stable CAR expression.

In one aspect, CAR-expressing cells (e.g., CARTs or CAR-expressing NK cells) transiently express CAR vectors for 4, 5, 6, 7, 8, 9, 10, 11, 12, 13, 14, 15 days after transduction. Transient expression of CARs can be effected by RNA CAR vector delivery. In one aspect, the CAR RNA is transduced into the cell, e.g., T cell or NK cell, by electroporation.

A potential issue that can arise in patients being treated using transiently expressing CAR-expressing cells (e.g., CARTs or CAR-expressing NK cells) (particularly with murine scFv bearing CAR-expressing cells (e.g., CARTs or CAR-expressing NK cells)) is anaphylaxis after multiple treatments.

Without being bound by this theory, it is believed that such an anaphylactic response might be caused by a patient developing humoral anti-CAR response, i.e., anti-CAR antibodies having an anti-IgE isotype. It is thought that a patient's antibody producing cells undergo a class switch from IgG isotype (that does not cause anaphylaxis) to IgE isotype when there is a ten to fourteen day break in exposure to antigen.

If a patient is at high risk of generating an anti-CAR antibody response during the course of transient CAR therapy (such as those generated by RNA transductions), CAR-expressing cell (e.g., CART or CAR-expressing NK cell) infusion breaks should not last more than ten to fourteen days.

EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compositions of the present invention and practice the claimed methods. The following working examples specifically point out various aspects of the present invention, and are not to be construed as limiting in any way the remainder of the disclosure.

Example 1: Treatment of Pancreatic Cancer with Combined Mesothelin-Redirected Chimeric Antigen Receptor T Cells and Cytokine-Armed Oncolytic Adenoviruses

Abstract

Pancreatic ductal adenocarcinoma (PDA) is characterized by its highly immunosuppressive tumor microenvironment (TME) that limits T cell infiltration and induces T cell hypofunction. Mesothelin-redirected chimeric antigen receptor T cell (meso-CAR T cell) therapy has shown feasibility and some efficacy in clinical trials but antitumor efficacy remains modest. This study tested the hypothesis that combined meso-CAR T cells with an oncolytic adenovirus expressing TNF-α and IL-2 (Ad5/3-E2F-D24-TNFα-IRES-IL2 or OAd-TNFα-IL2 for short) would improve efficacy. OAd-TNFα-IL2 enhanced the anti-tumor efficacy of meso-CAR T cells in immunodeficient mice engrafted with human PDA and efficacy was associated with robustly increased tumor infiltrating lymphocytes (TILs), enhancing and prolonging CAR T cell function. Importantly, the combined therapy prevented metastasis, indicating a systemic effect of the intratumorally injected OAd-TNFα-IL2 and meso-CAR T cells. This study also evaluated this approach in a syngeneic mouse tumor model by combining adenovirus expressing murine TNF-α and IL-2 (Ad-mTNFα-mIL2) and mouse CAR T cells. This approach induced significant tumor regression in mice engrafted with highly aggressive and immunosuppressive PDA tumors. In contrast, multiple dosing of CAR T cells failed to suppress tumor growth. Ad-mTNFα-mIL2 increased both CAR T cell and host T cell infiltration to the tumor and altered host tumor immune status with M1 polarization of macrophages and increased dendritic cell maturation. These findings indicate that combining cytokine-armed oncolytic adenovirus to enhance the efficacy of CAR T cell therapy is a promising approach to overcome the immunosuppressive TME by inducing both CAR-dependent and CAR-independent host immunity for the treatment of PDA.

Introduction

CAR T cell therapy has shown significant efficacy in patients with CD19-positive acute lymphoblastic leukemia (Grupp S A, et al. The New England journal of medicine. 2013; 368(16):1509-18) and lymphoma (Kochenderfer J N, et al. J Clin Oncol. 2015; 33(6):540-9; Locke F L, et al. 2017; 25(1):285-95). However, CAR T cell efficacy remains disappointing in the setting of solid tumors (Beatty G L, and O'Hara M. Chimeric antigen receptor-modified T cells for the treatment of solid tumors: Defining the challenges and next steps. Pharmacol Ther. 2016; Newick K, Moon E, and Albelda S M. Mol Ther Oncolytics. 2016; 3:16006). There are several factors that can potentially limit the efficacy of CAR T cell therapy in solid tumors and particularly, in pancreatic cancer. First, in solid tumors there are no ideal CAR targets like CD19: most tumor associated antigens are not uniformly expressed in all tumor cells, which can likely lead to tumor escape (O'Rourke D M, et al. Science translational medicine. 2017; 9(399)). Moreover, in pancreatic cancer the TME is particularly immunosuppressive, inhibiting T cell infiltration and functions (Liyanage U K, et al. J Immunol. 2002; 169(5):2756-61; Mukherjee P, et al. Glycoconj J. 2001; 18(11-12):931-42; Moon E K, et al. Clin Cancer Res. 2014; 20(16):4262-73). Therefore, developing strategies to address tumor immunosuppression and heterogeneity would represent a vertical advance in the field.

Mesothelin is a promising target for CAR T cell therapy as it is overexpressed in the majority of pancreatic cancers, mesotheliomas, ovarian cancers, and some lung cancers and it is not expressed on T cells (Hassan R, and Ho M. Eur J Cancer. 2008; 44(1):46-53; Morello A, Sadelain M, and Adusumilli P S. Cancer discovery. 2016; 6(2):133-46). In previous work, meso-CAR T cells were shown to be effective in mesothelioma xenograft models (Carpenito C, et al. Proc Natl Acad Sci USA. 2009; 106(9):3360-5). A phase I clinical trial using T cells engineered to express an anti-mesothelin CAR showed stable disease in two out of six patients (NCT01897415) (Beatty G L, et al. Journal of Clinical Oncology. 2015; 33(15_suppl):3007-), however there is a clear unmet medical need to improve responses in PDA and in patients with other solid tumors.

Oncolytic viruses represent highly promising agents for the treatment of solid tumors, and an oncolytic herpes virus expressing GM-CSF was approved by the US FDA for the therapy of advanced melanoma based on therapeutic benefit demonstrated in a clinical study (Andtbacka R H, et al. J Clin Oncol. 2015; 33(25):2780-8). Oncolytic adenoviruses (OAds) can be programmed to specifically target, replicate in and kill cancer cells while sparing normal cells. The release of virus progeny results in an exponential increase of the virus inoculum, which can cause direct tumor debulking while providing danger signals necessary to awaken the immune system (Lichty B D, et al. Nature reviews Cancer. 2014; 14(8):559-67). Importantly, OAds can be genetically modified to express therapeutic transgenes selectively in the TME (Siurala M, et al. Molecular therapy: the journal of the American Society of Gene Therapy. 2016; 24(8):1435-43; Nishio N, et al. Cancer Res. 2014; 74(18):5195-205; Tanoue K, et al. Cancer Res. 2017; 77(8):2040-51; Rosewell Shaw A, et al. Molecular therapy: the journal of the American Society of Gene Therapy. 2017). The feasibility and safety of OAds in human patients have been demonstrated in clinical trials (Kim K H, et al. Gynecol Oncol. 2013; 130(3):518-24; Ranki T, et al. Journal for immunotherapy of cancer. 2016; 4:17).

Another possible strategy to modulate the TME in favor of adoptive T cell therapy is the local administration of recombinant cytokines. In this regard, it was previously demonstrated that local tumor delivery of tumor necrosis factor-alpha (TNF-α) and Interleukin-2 (IL-2) can enhance the anti-tumor efficacy of adoptively transferred OT-I cells (Tahtinen S, et al. PLoS One. 2015; 10(6):e0131242). These two cytokines were selected from a panel of cytokines that are used in clinical oncology in the US and Europe. When combined, TNF-α and IL-2 provide non-overlapping synergistic effects. TNF-α appears to be responsible for immunological danger signaling and T-cell trafficking, while IL-2 activates and propagates T-cells locally (Siurala M, et al. Molecular therapy: the journal of the American Society of Gene Therapy. 2016; 24(8):1435-43).

Here OAd was engineered to express TNF-α and IL-2 within the TME and tested in combination with CAR T cells targeting mesothelin. It was tested if OAds expressing cytokines could improve the efficacy of CAR T cell therapy by: (i) enhancing and sustaining T cell function and trafficking to the tumor microenvironment, (ii) overcoming tumor heterogeneity in antigen expression, and (iii) reducing tumor immunosuppression.

Results

Combined OAd-TNFα-IL2 and Meso-CAR T Cells Efficiently Lyse Target Tumor Cells

Figure 7A:
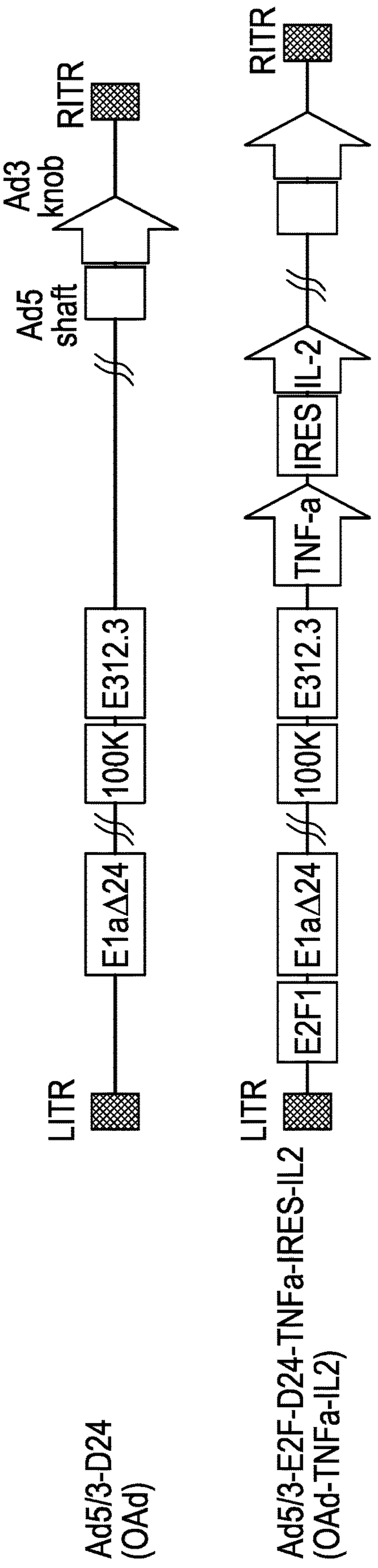
Figure 7B:
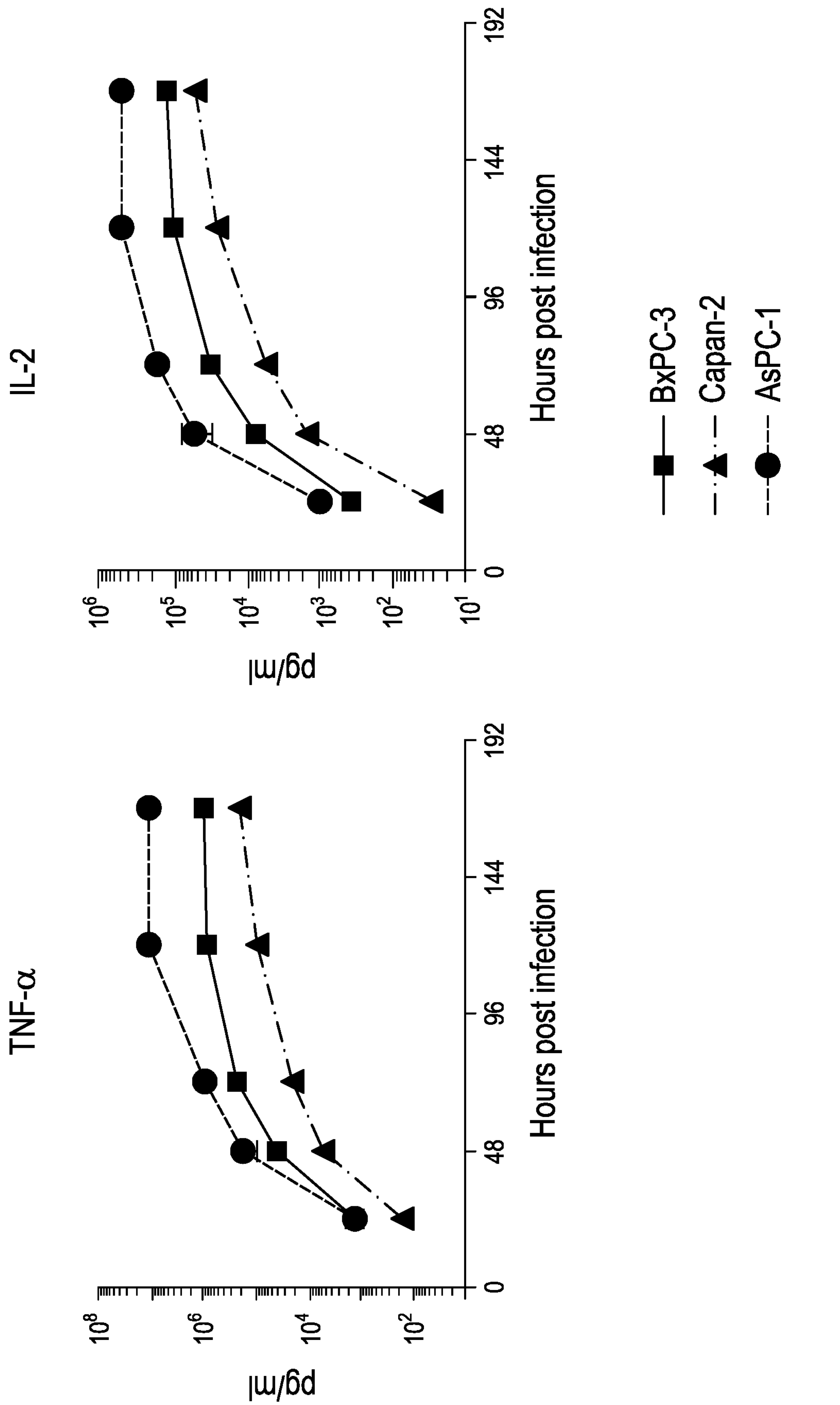

OAds were modified to express TNF-α and IL-2 (OAd-TNFα-IL2) (Havunen R, et al. Mol Ther Oncolytics. 2017; 4:77-86) (FIG. 7A). Cytokine production and cell lysis induced by infection of PDA tumor lines were tested first. Pancreatic tumor cell lines infected with OAd-TNFα-IL2 secreted large amounts of cytokines and tumor cell lysis was induced in dose-dependent manner (FIGS. 7B and 7C). Incorporation of cytokine transgenes did not enhance the lytic activity of OAds but rather modestly decreased the lytic activity in vitro (FIG. 7C). This was not surprising as the additional payload possibly decreases the efficiency of virus replication.

Figure 7D:
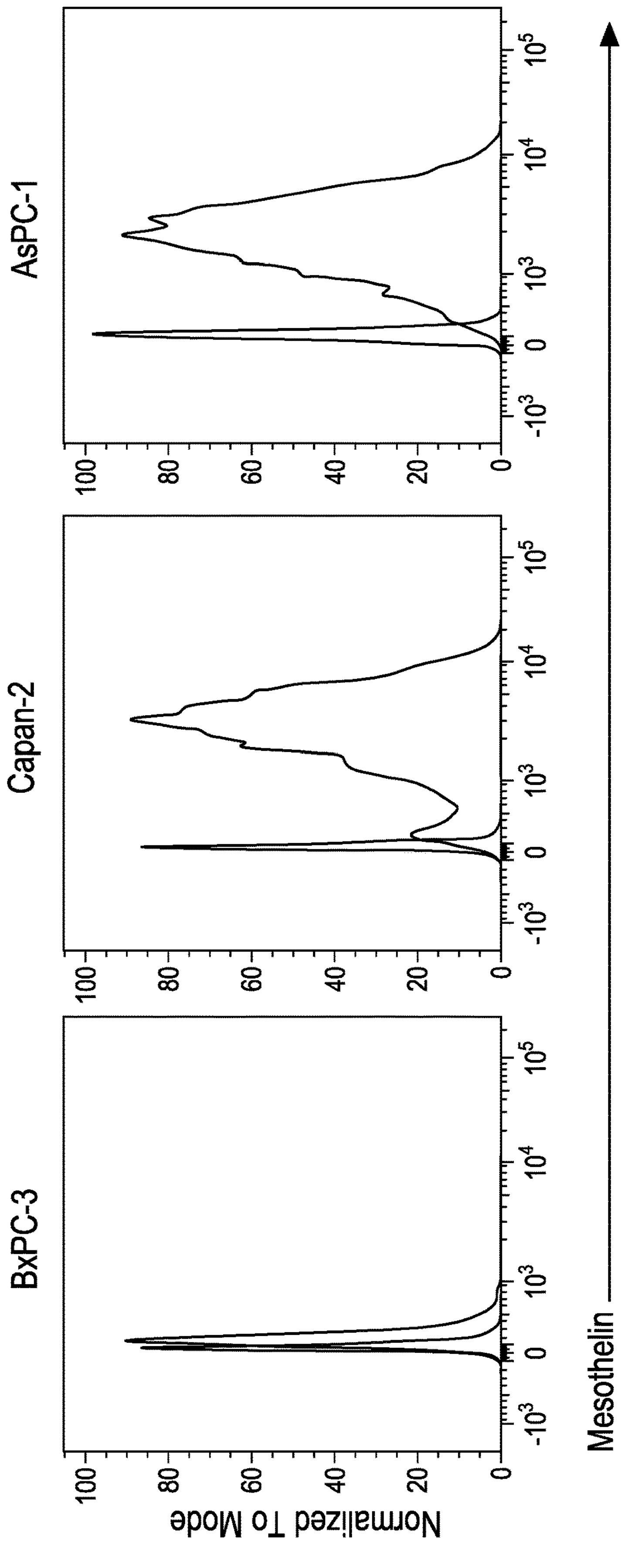
Figure 8:
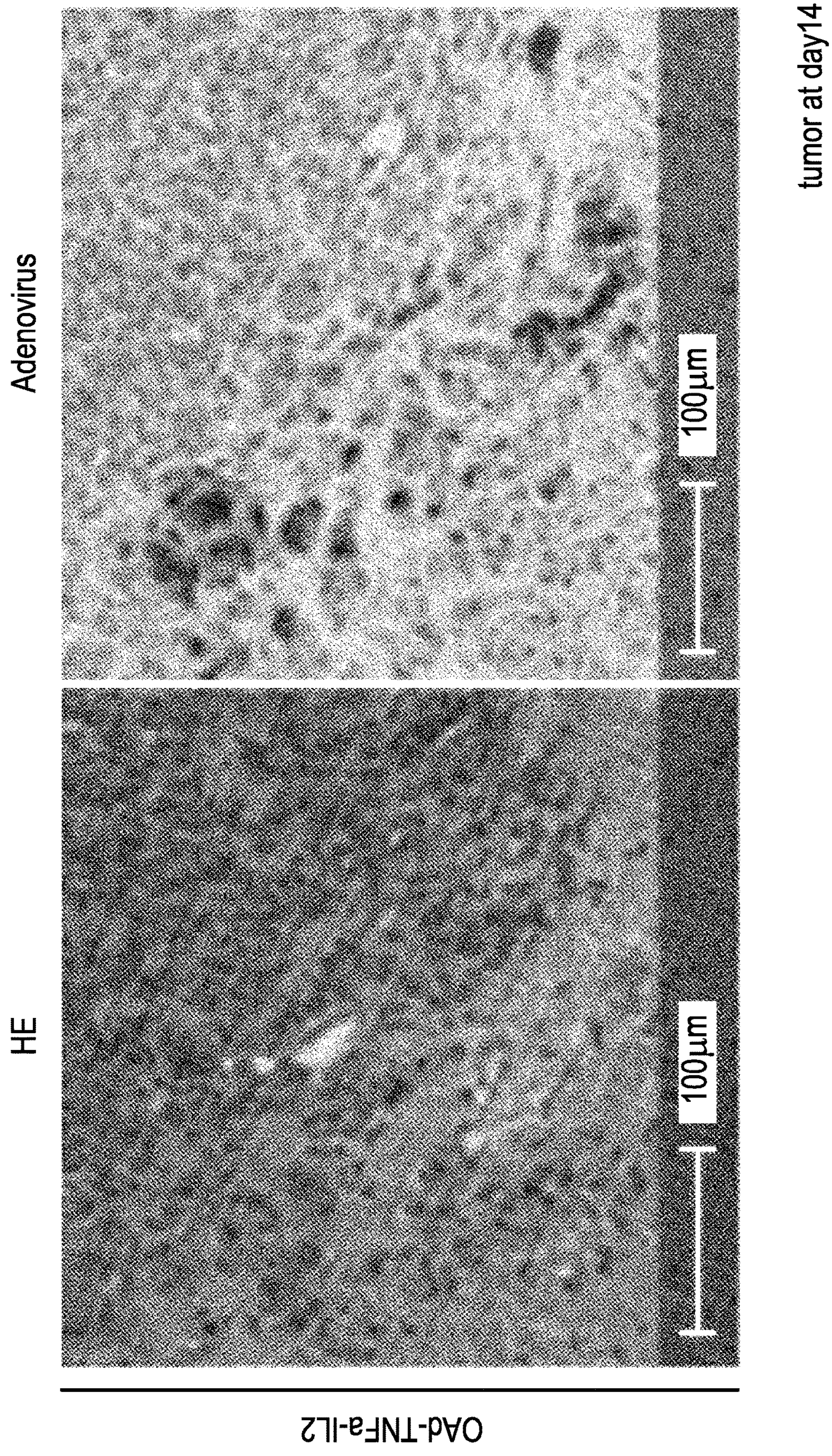
FIG. 8: Adenovirus infects AsPC-1 tumors and induces necrosis. Adenovirus staining on tumors at day 14 after the injection of Oncolytic adenovirus (OAd) expressing TNF-α and IL-2 (Ad5/3-E2F-D24-TNFα-IRES-IL2 (Ad5/3-OAd-TNFα-IL2)) in an AsPC-1 xenograft NSG mouse model. A representative tumor treated with intratumoral injection of OAd-TNFα-IL2 using the same schedules and procedures as described in FIG. 2A is shown. Adenovirus positive cells are typically observed between intact tumor area and necrotic tumor area, which indicated that adenoviruses were gradually expanding while inducing tumor necrosis.

Subsequently, it was tested whether OAd-TNFα-IL2 enhances the lytic activity of meso-CAR T cells using real time cell analysis. Target cell lines BxPC-3, Capan-2, AsPC-1 expressing various levels of mesothelin were tested; mesothelin was highly positive in Capan-2, medium positive in AsPC-1 but dim in BxPC-3 (FIG. 7D). BxPC-3 cells expressed very low levels of mesothelin and were resistant to meso-CAR T cells; meso-CAR T cell alone suppressed BxPC-3 cell growth transiently but the cells eventually started growing again. However, when OAd-TNFα-IL2 was combined, meso-CAR T cells efficiently lysed all three target tumor cells (FIG. 1A). Meso-CAR T cells suppressed Capan-2 tumor cells slowly. The combined OAd-TNFα-IL2 with meso-CAR T cells induced substantially more rapid lysis of Capan-2 cells (FIG. 1A). Meso-CAR T cells lysed AsPC-1 cells rapidly and there was no additional benefit of OAd-TNFα-IL2 combination therapy in this in vitro assay (FIG. 1A).

OAd-TNFα-IL2 Activates T Cells and Induces T Cell Proliferation

Figure 1B:
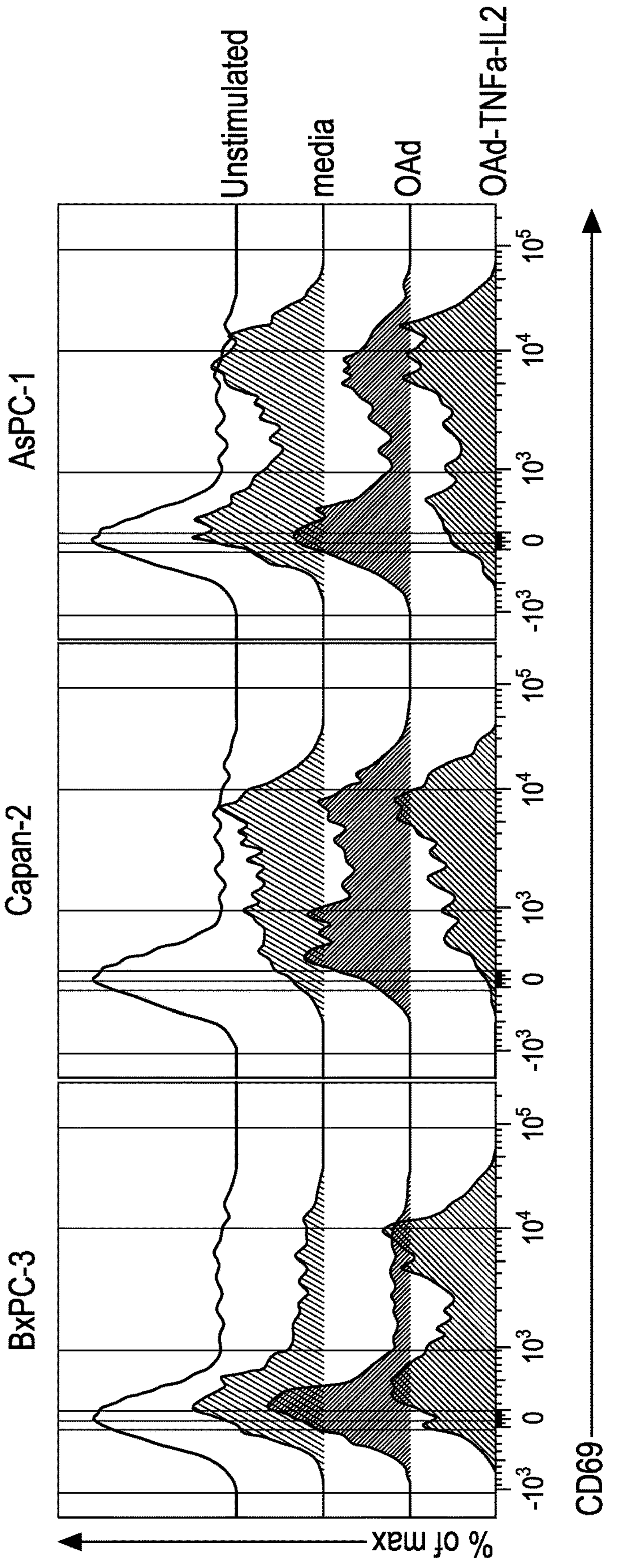
Figure 1C:
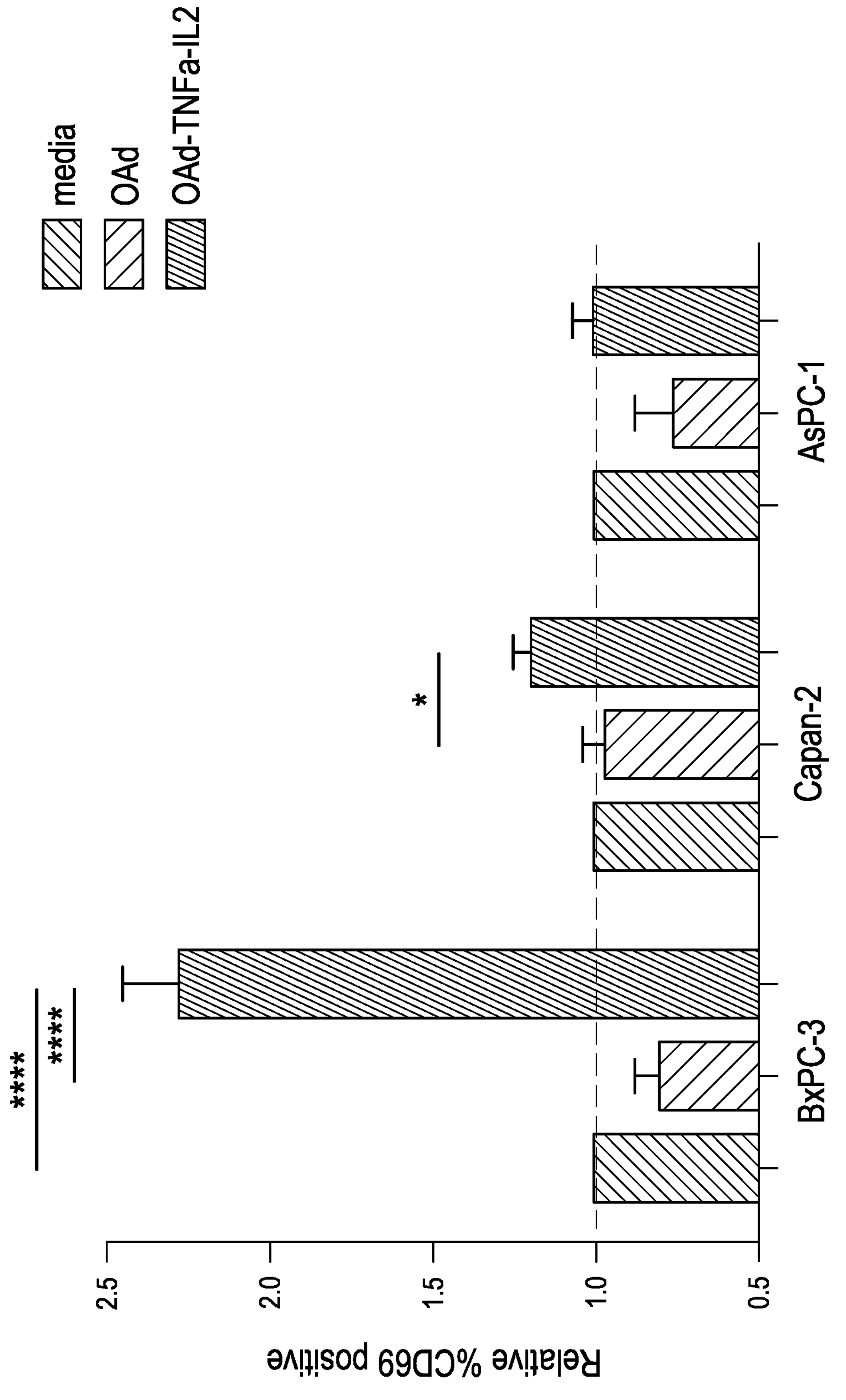
Figure 1D:
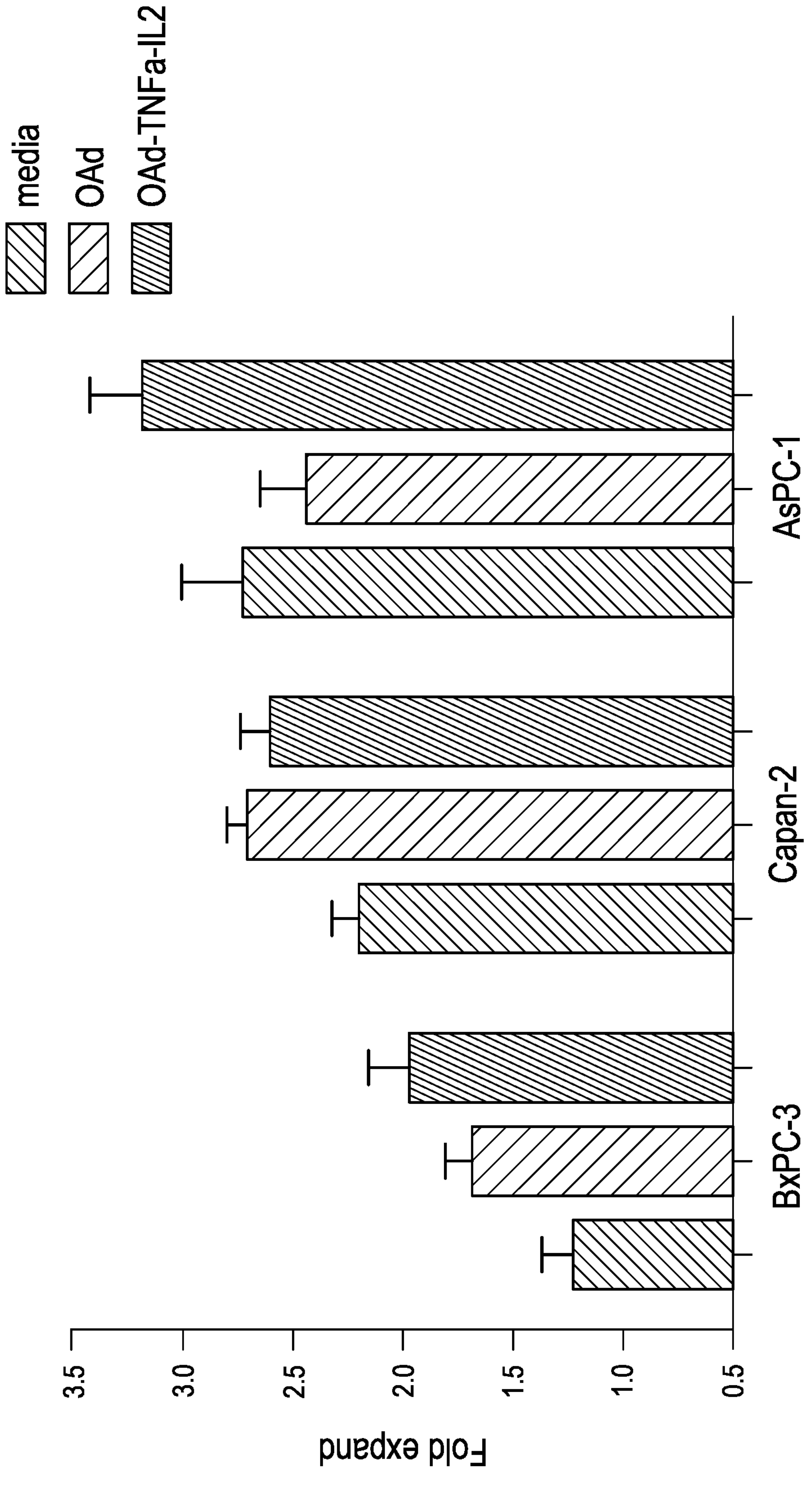
Figure 1E:
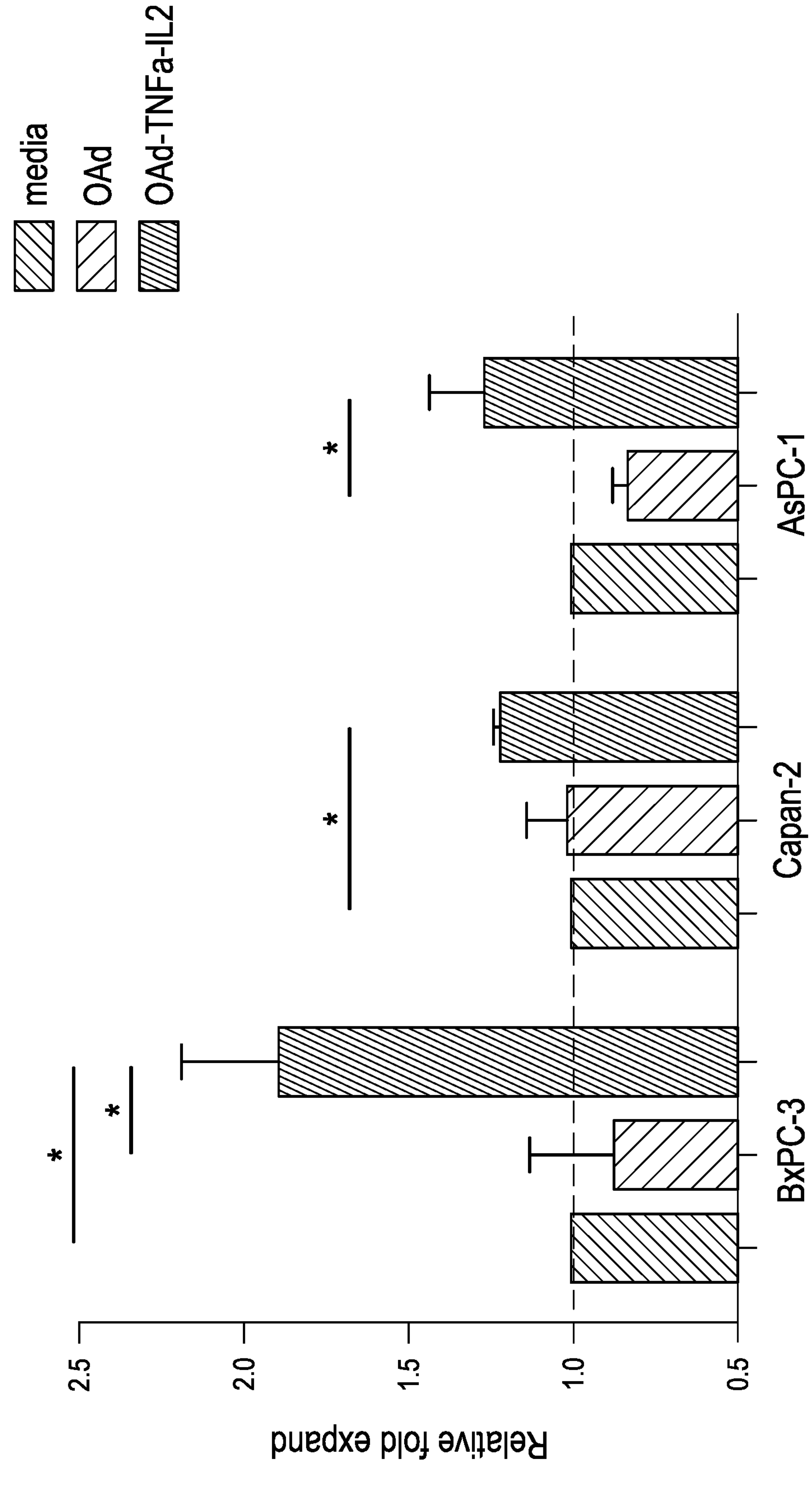

To test how OAd-TNFα-IL2 enhances the killing activity of meso-CAR T cells, T cell proliferation and upregulation of early T cell activation marker CD69 upon co-incubation with OAd pre-infected tumor cell lines were analyzed. Consistent with the enhanced killing activity (FIG. 1A), CD69 upregulation was poorest when stimulated by BxPC-3 cells, while moderate with Capan-2 cells and the highest with AsPC-1 cells in the absence of OAd-TNFα-IL2 (FIGS. 1B and 1C). However, OAd-TNFα-IL2 induced enhanced CAR T cell responses, especially when the CAR T cells were stimulated with BxPC-3 cells. Similar to CD69 up-regulation, OAd-TNFα-IL2 pre-infection significantly improved CAR T cell proliferation when cultured with the PDA tumor cells (FIGS. 1D and 1E). Thus, OAd-TNFα-IL2 increased target cell killing by meso-CAR T cells presumably by enhancing the function of meso-CAR T cells. Importantly, the most significant enhancement of T cell responses was observed when mesothelin low expressing and meso-CAR T resistant BxPC-3 cells were targeted, suggesting that OAd-TNFα-IL2 can be used to augment CAR T-mediated killing, particularly when target antigen expression is limiting.

Combination of OAd-TNFα-IL2 with Meso-CAR T Cells Causes Tumor Regression in an AsPC-1 Tumor Xenograft NSG Mouse Model.

Figure 2A:
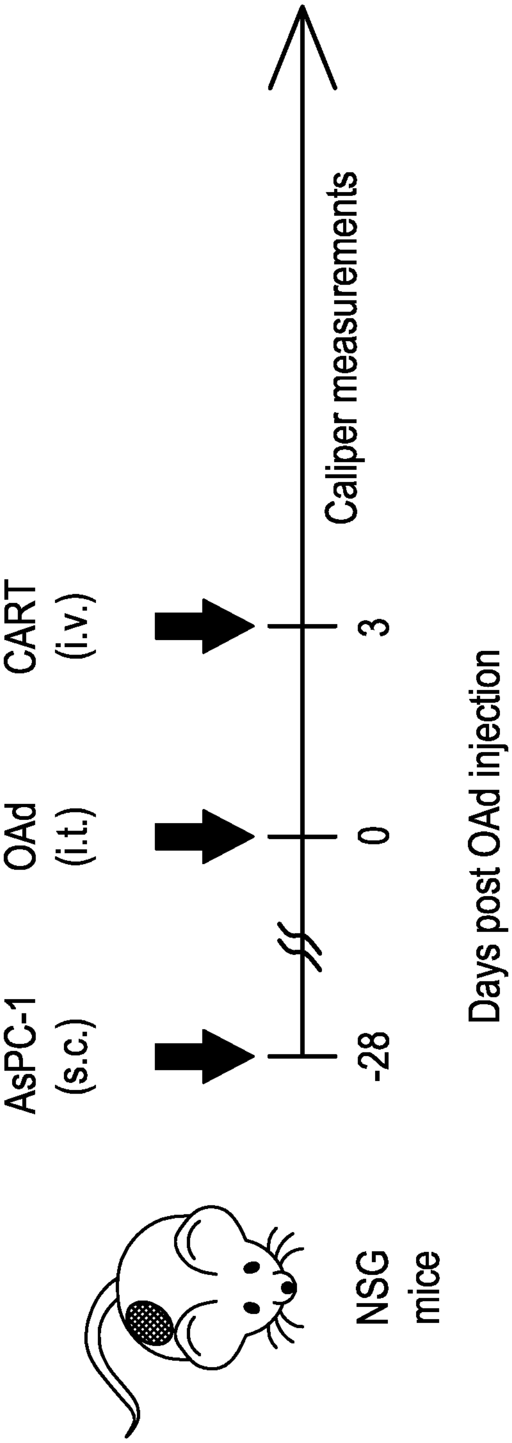
FIGS. 2A-2F: Oncolytic adenovirus (OAd) expressing TNF-α and IL-2 (Ad5/3-E2F-D24-TNFα-IRES-IL2 (Ad5/3-OAd-TNFα-IL2)) enhances anti-tumor efficacy of mesothelin-redirected chimeric antigen receptor T cells (meso-CAR T cells) and improves survival in the pancreatic ductal adenocarcinoma (PDA) xenograft model.
Figure 2B:
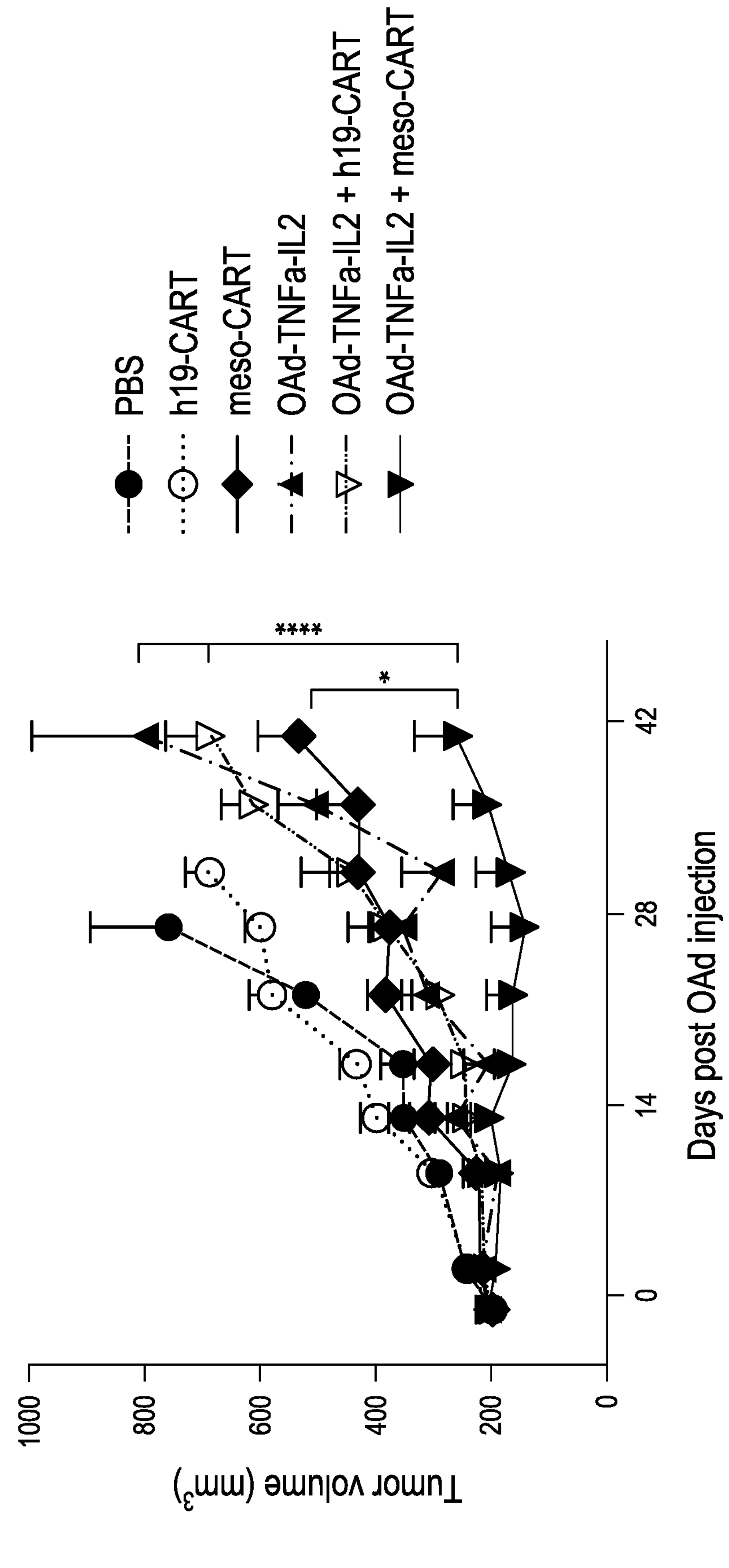
Figure 2C:
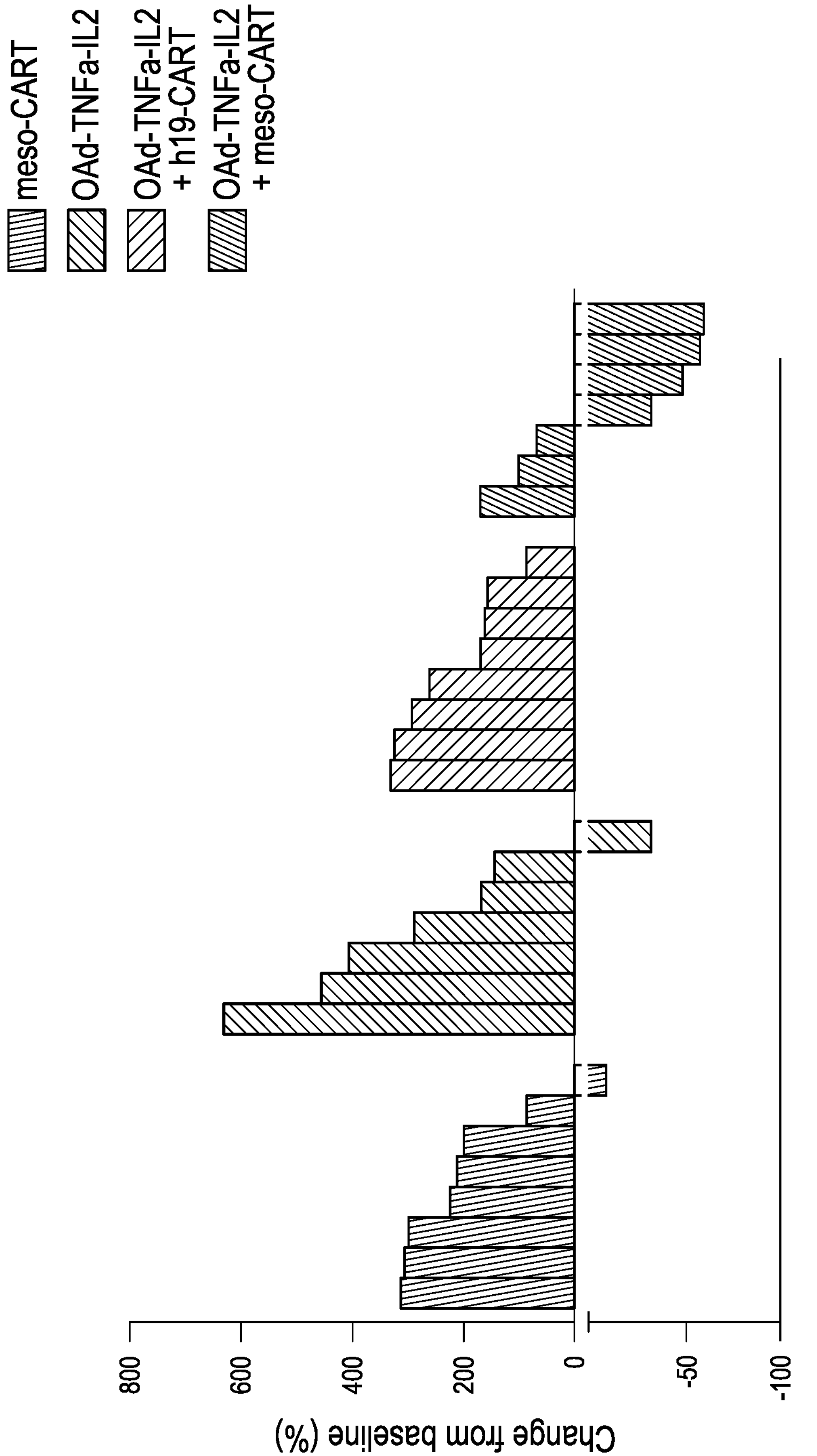
Figure 2D:
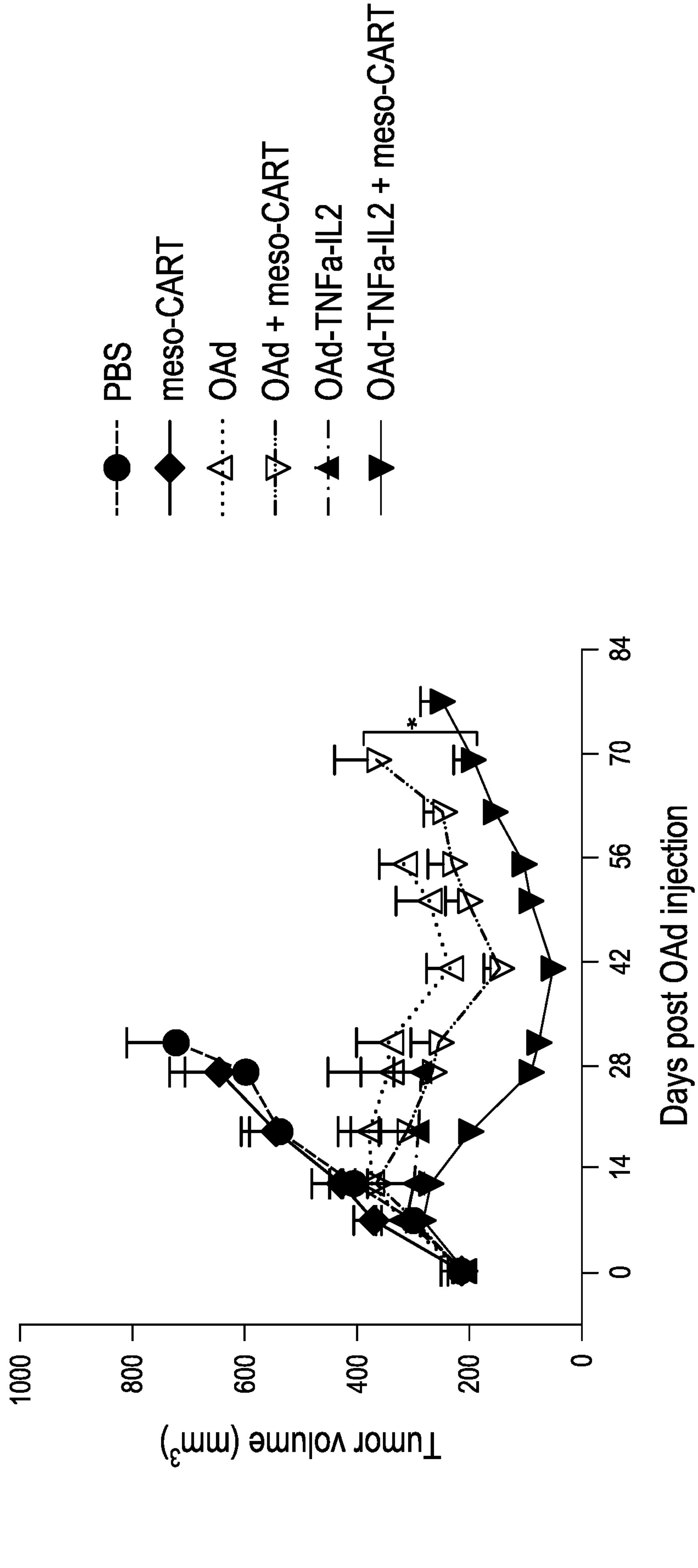
Figure 2E:
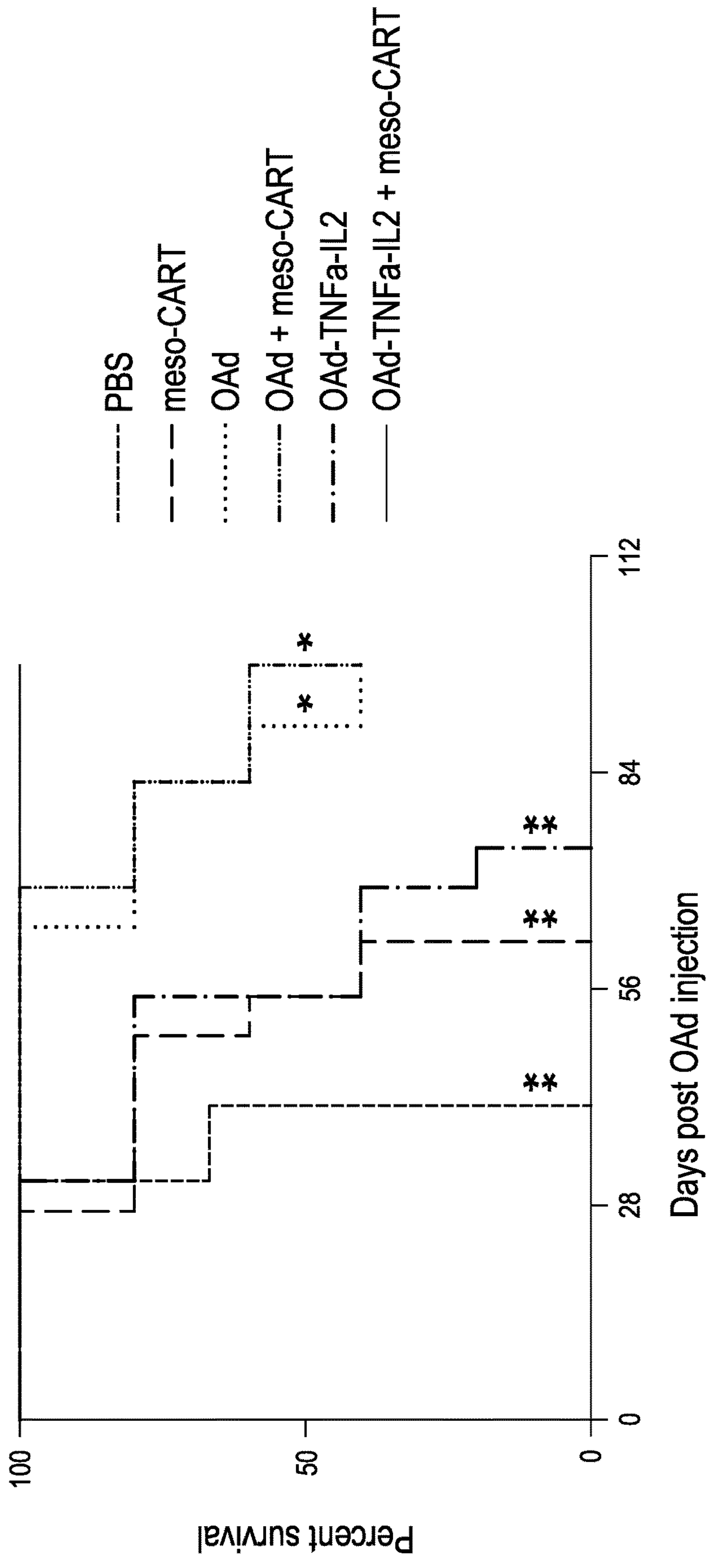

To evaluate whether OAd-TNFα-IL2 improves the anti-tumor efficacy of meso-CAR T cells, combined OAd with CAR T cell therapy was tested in an AsPC-1 xenograft NSG mouse model (FIG. 2A). Meso-CAR T monotherapy suppressed tumor growth moderately and OAd-TNFα-IL2 monotherapy failed to suppress tumor growth although infection was confirmed in tumor IHC (FIG. 7D). On the other hand, combined OAd-TNFα-IL2 with meso-CAR T cells efficiently suppressed tumor growth and achieved higher rate of tumor regressions at the endpoint (FIGS. 2B and 2C). To determine the benefit of cytokine transgenes, the parental OAd and OAd-TNFα-IL2 in combination with meso-CAR T cells were compared in the same mouse model as FIG. 2B. OAd and OAd-TNFα-IL2 monotherapy similarly reduced tumor growth and mice injected with OAd had modestly improved survival compared to OAd-TNFα-IL2 monotherapy (FIGS. 2D and 2E), which may be because baseline killing activity of parental OAd is higher than that of OAd-TNFα-IL2 (FIG. 7C). However, importantly, only OAd-TNFα-IL2 enhanced the tumor regression by meso-CAR T cells and improved survival while parental OAd failed to induce additional efficacy of meso-CAR T cells. These results suggested that the encoded cytokines have clear benefit to enhance the in vivo antitumor efficacy of CAR T cells, enabling the regression of established PDA tumors that fail to respond to CAR T cell monotherapy.

Figure 2F:
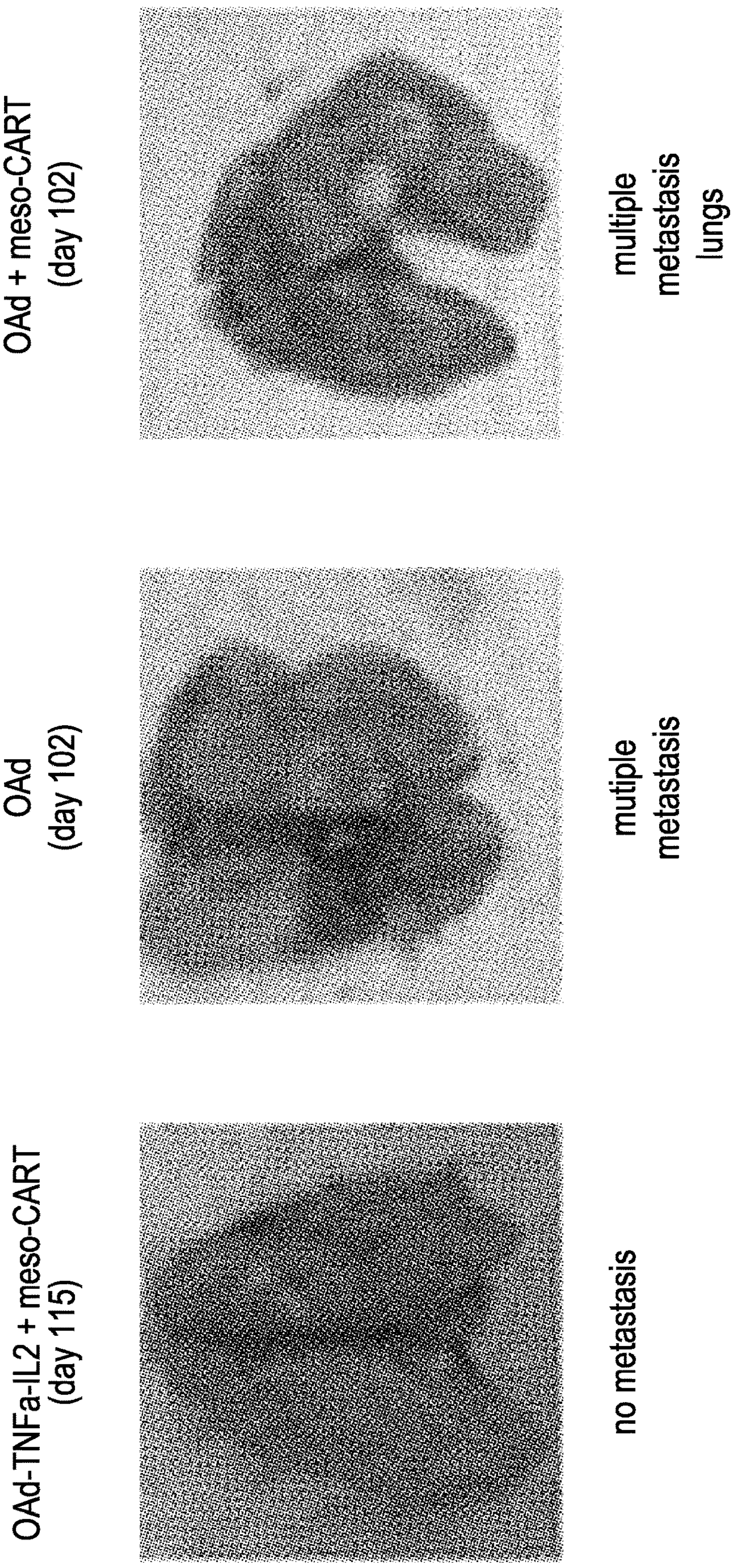

Furthermore, mice treated with OAd, OAd-TNFα-IL2 or even the combination of parental OAd and meso-CAR T developed tumor metastasis to the lungs even if primary tumors were controlled (FIG. 2F). However, no mice treated with combined OAd-TNFα-IL2 and meso-CAR T died of tumor metastasis. These results suggest that locally activated meso-CAR T cells in tumor site by OAd-TNFα-IL2 have the potential to target tumors systemically or to prevent PDA cells from egressing from tumors.

OAd-TNFα-IL2 Increases Tumor Infiltrating T Cells

Figure 3A:
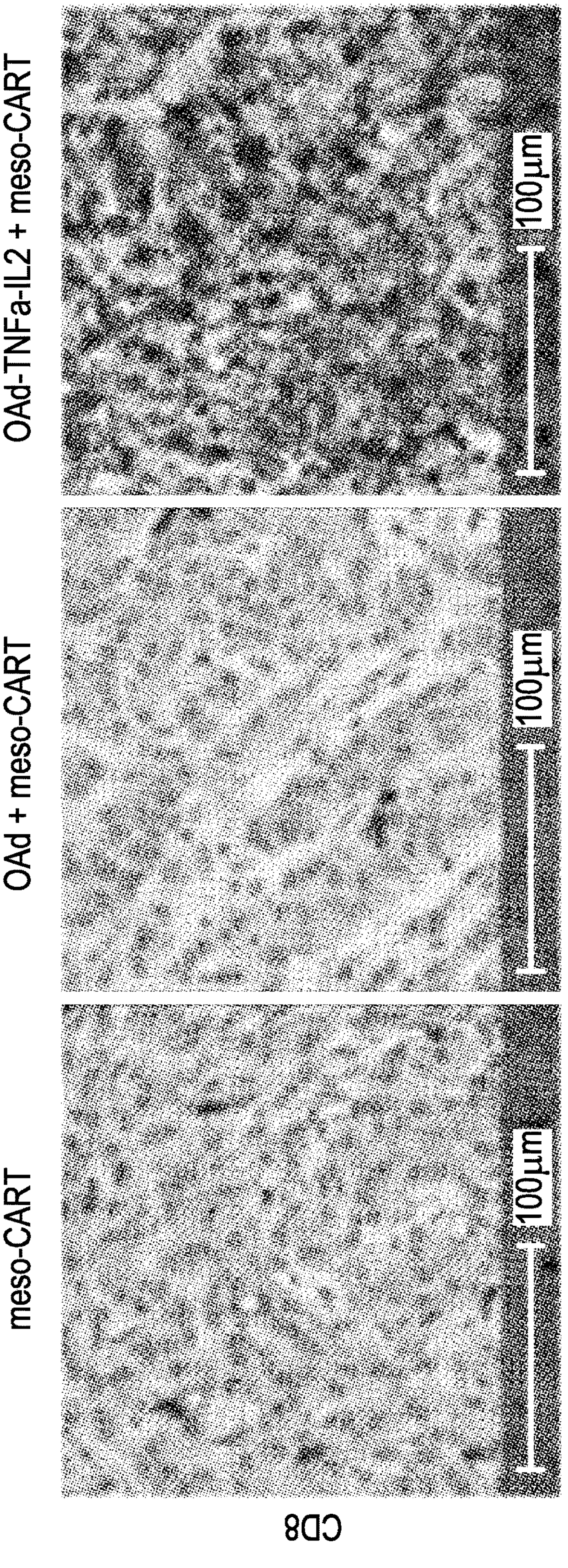
FIGS. 3A-3H: Oncolytic adenovirus (OAd) expressing TNF-α and IL-2 (Ad5/3-E2F-D24-TNFα-IRES-IL2 (Ad5/3-OAd-TNFα-IL2)) induces robust T cell infiltration of tumors and enhances T cell functions.
Figure 3B:
Figure 3C:
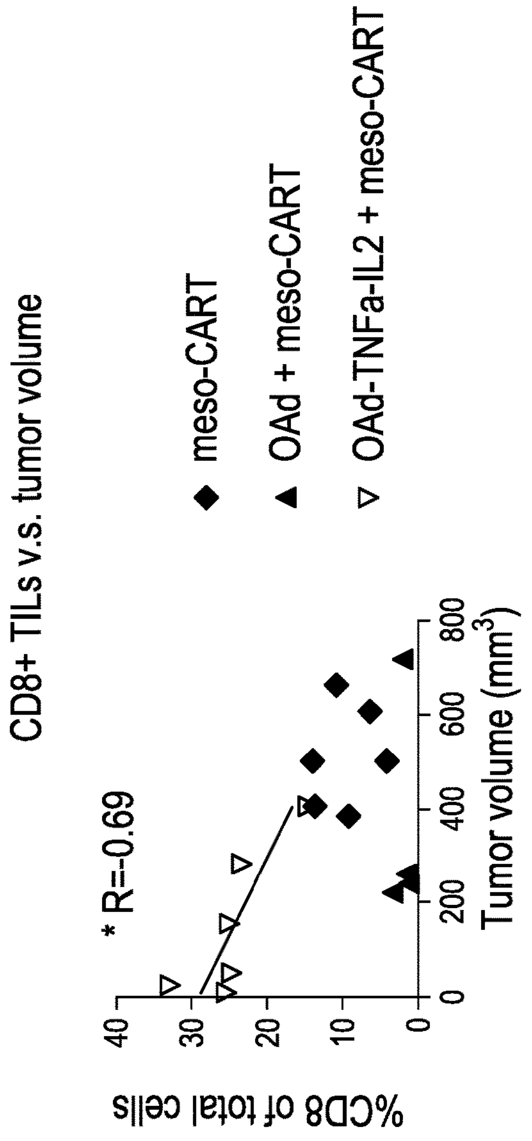
Figure 9A:
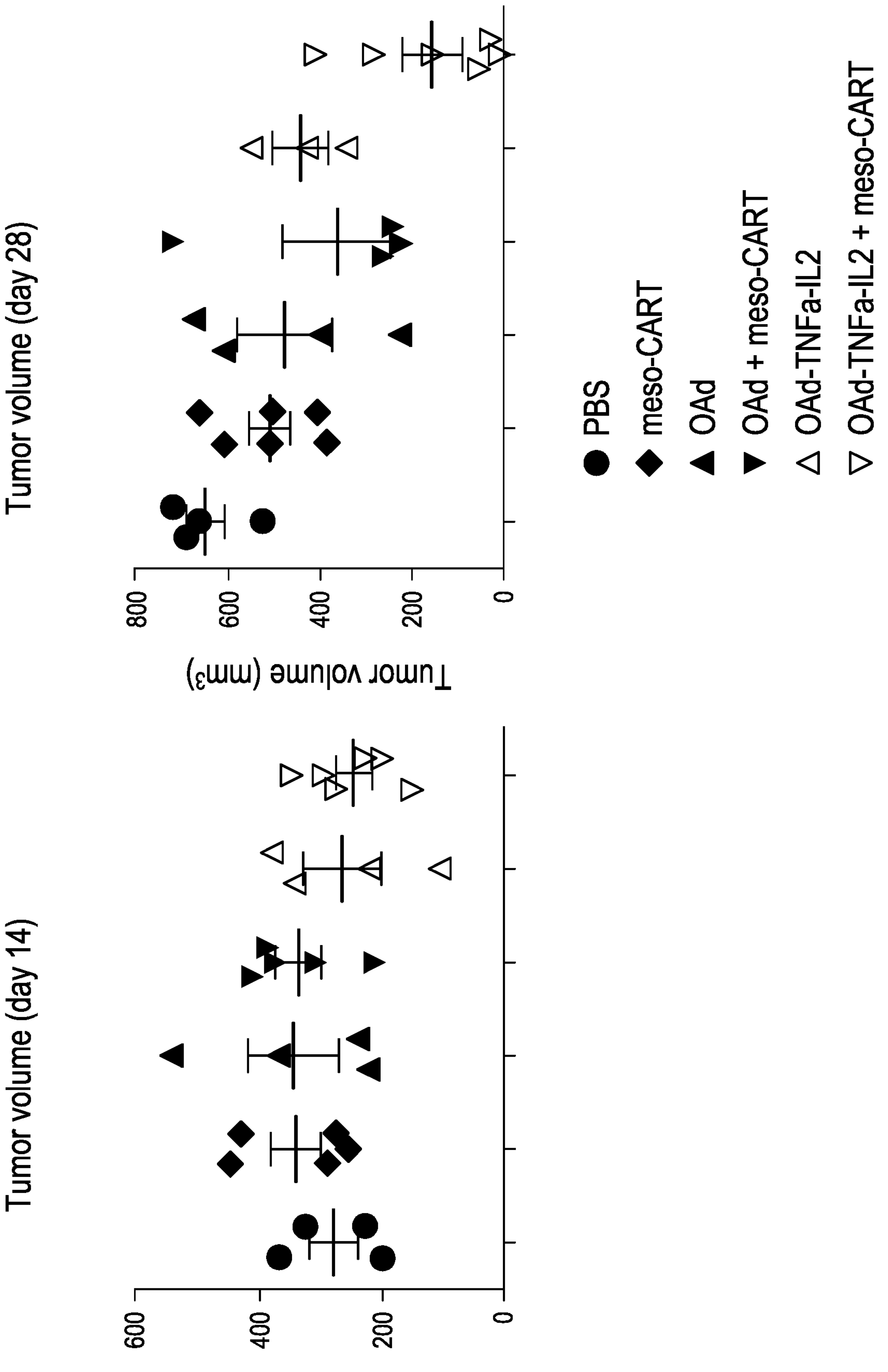

The magnitude of T cell infiltration has a strong impact on the natural history of many types of cancer (Talmadge J E. Semin Cancer Biol. 2011; 21(2):131-8). To determine how parental OAd and OAd-TNFα-IL2 affect tumor infiltrating T cells (TILs), NSG animals were treated as in FIG. 2A, and groups of mice were sacrificed at days 14 and 28 for analysis of TILs and tumors. Consistent with the experiment in FIG. 2A, tumors treated with the combination of OAd-TNFα-IL2 and meso-CAR T tend to be smaller in volume on day 28 (FIG. 9A). In histopathological and FCM analysis, tumors treated with the combination of OAd-TNFα-IL2 with meso-CAR T were infiltrated with significantly more CD4 and CD8 positive T cells compared to those treated with meso-CAR T monotherapy or in combination with the parental OAd (FIGS. 3A and 3B and FIG. 9B). The number of $CD8^+$ TILs in IHC was inversely correlated with tumor volume in mice treated with OAd-TNFα-IL2 and meso-CAR T but did not correlate in any other treatment group (FIG. 3C).

OAd-TNFα-IL2 Activates TILs and Induces Responses of T Cells to the Tumor

Figure 3D:
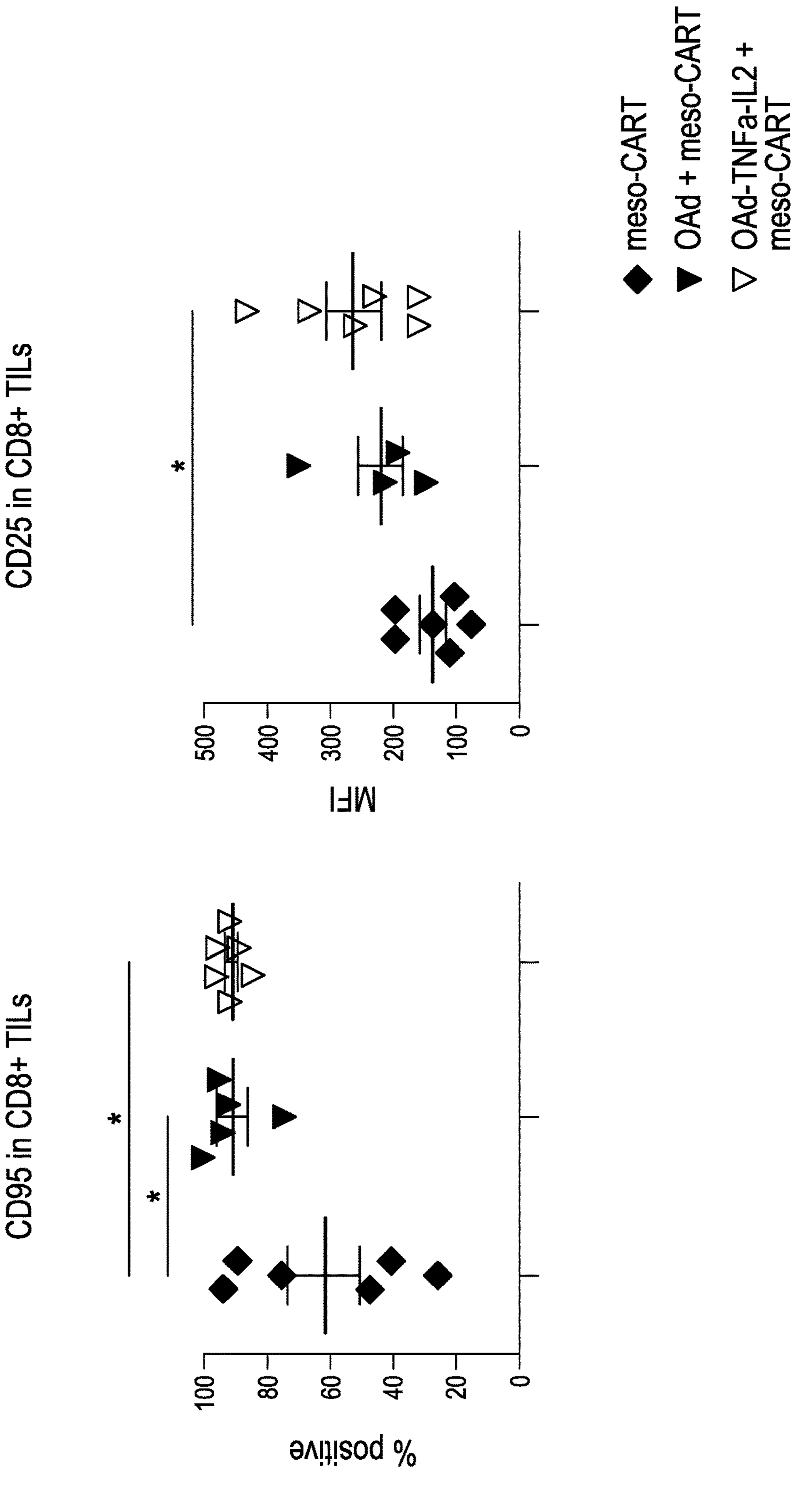
Figure 9C:
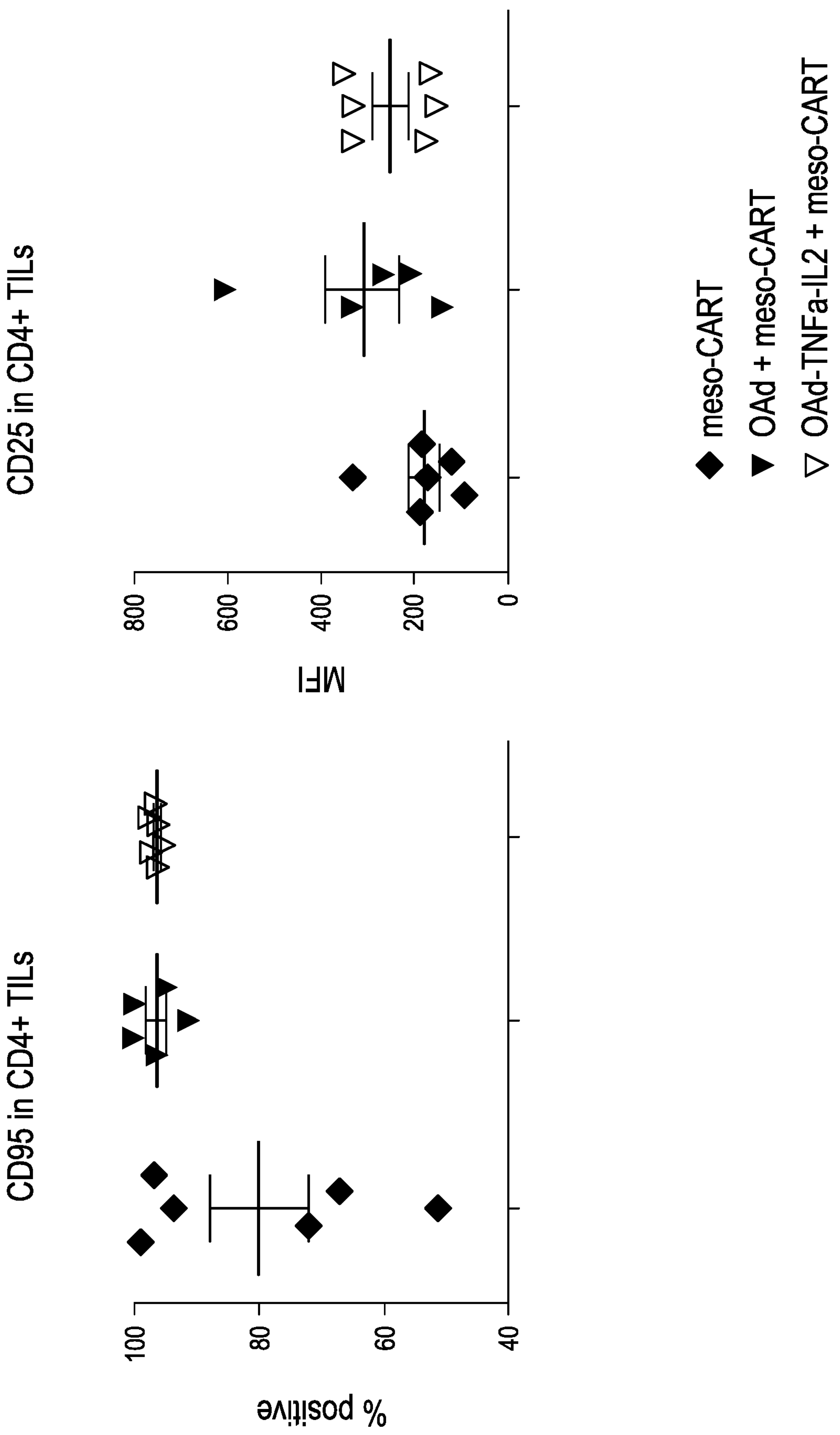

The function of TILs also has a strong impact on the outcome of cancer treatments (Talmadge J E. Semin Cancer Biol. 2011; 21(2):131-8). Expression of activation markers by TILs was analyzed at day 28. $CD8^+$ TILs in tumors treated with meso-CAR T in combination with OAd-TNFα-IL2 as well as parental OAd expressed higher activation markers CD95 and CD25 compared to meso-CAR T monotherapy (FIG. 3D) with the same trend in CD4+ TILs (FIG. 9C), which indicates that OAd and OAd-TNFα-IL2 activated TILs.

Figure 3E:
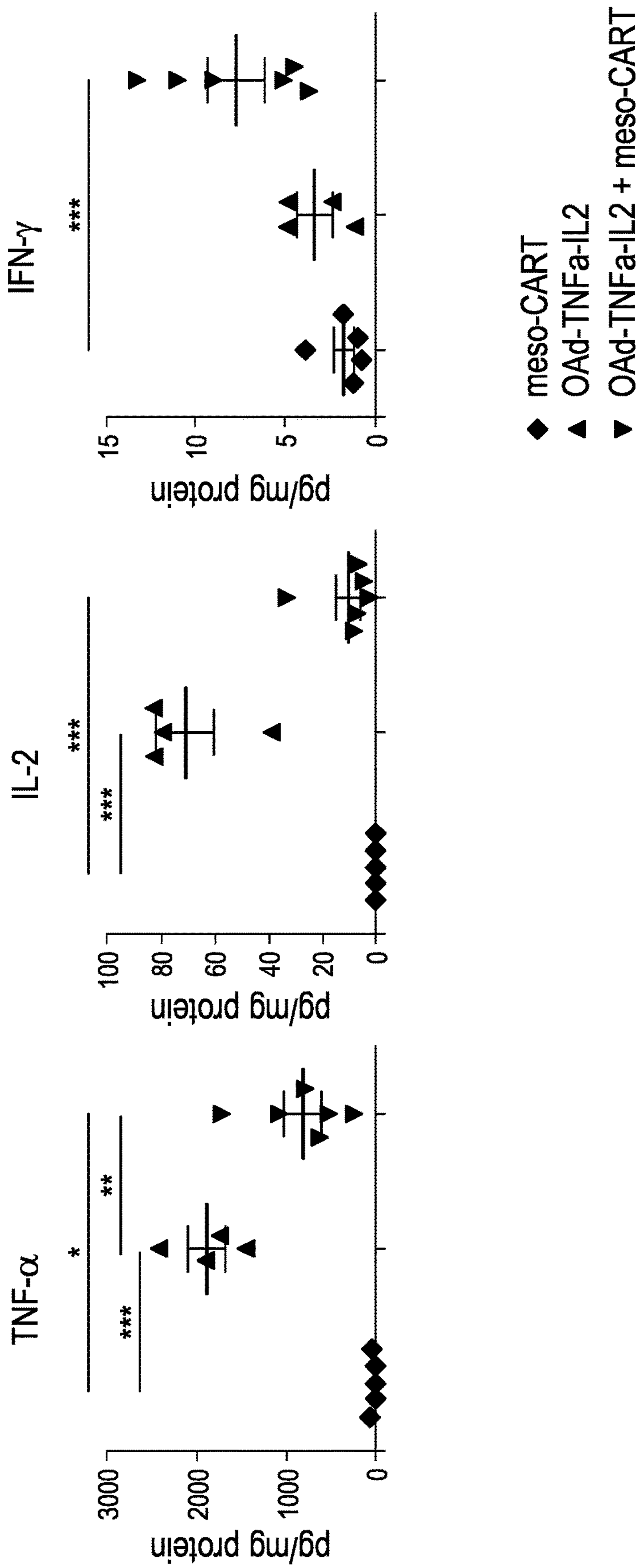
Figure 9D:
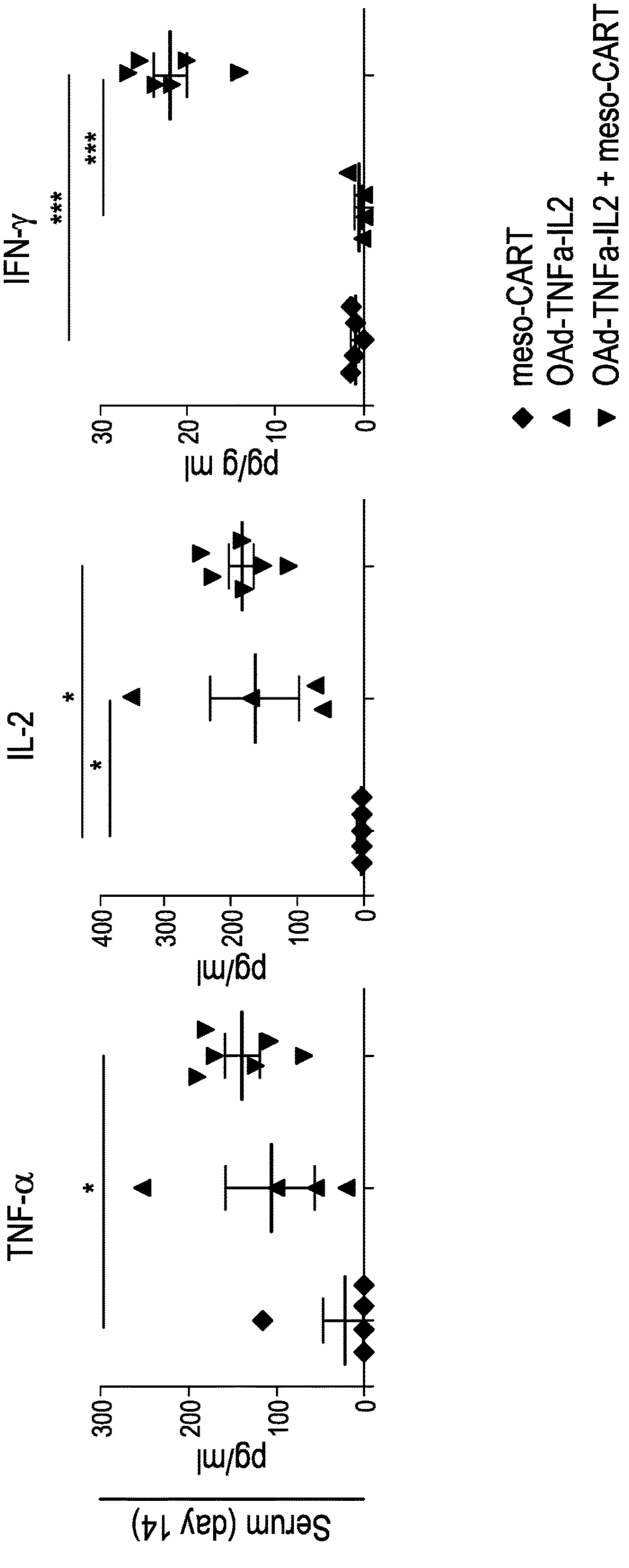

Subsequently, the cytokine profile of bulk tumors was analyzed for two purposes. The first was to assess whether OAd-TNFα-IL2 successfully delivered cytokine genes to the tumor and made tumor cells produce the corresponding cytokines, and the second was to assess whether T cells in the tumors are functional and responding to the tumors. As a note, TNF-α and IL-2 are potentially derived either from tumors infected with OAd-TNFα-IL-2, meso-CAR T cells or both, while human IFN-γ is expected to be produced only by meso-CAR T cells in this mouse model. As expected, TNF-α and IL-2 were detectable from tumors treated with OAd-TNFα-IL2 monotherapy, which indicates vector-mediated secretion of cytokine genes expressed in the PDA tumor cells (FIG. 3E). The levels of all cytokines (TNF-α, IL-2 and IFN-γ) were very low or undetectable in tumors treated with meso-CAR T monotherapy (FIG. 3E), which indicated that T cells in the tumors were hypofunctional and/or that the absolute number of CAR T cells responding to the tumor cells was low. On the other hand, higher levels of all three cytokines were detected from tumors treated with the combination of OAd-TNFα-IL2 with meso-CAR T cells than meso-CAR T cell monotherapy (FIG. 3E). The same trend was confirmed in serum, indicating that systemic levels of cytokines were produced by this procedure (FIG. 9D). While it was impossible to separate the relative contribution of CAR T cell derived IL-2 and TNF-α from OAd delivered IL-2 and TNF-α, the systemic levels of IFN-γ which should be derived only from T cells, indicated that the CAR T cell function was enhanced.

Combined OAd-TNFα-IL2 with Meso-CAR T Cells Induces Decreased Mesothelin Intensity, which is Associated with Anti-Tumor Efficacy.

Figure 3F:
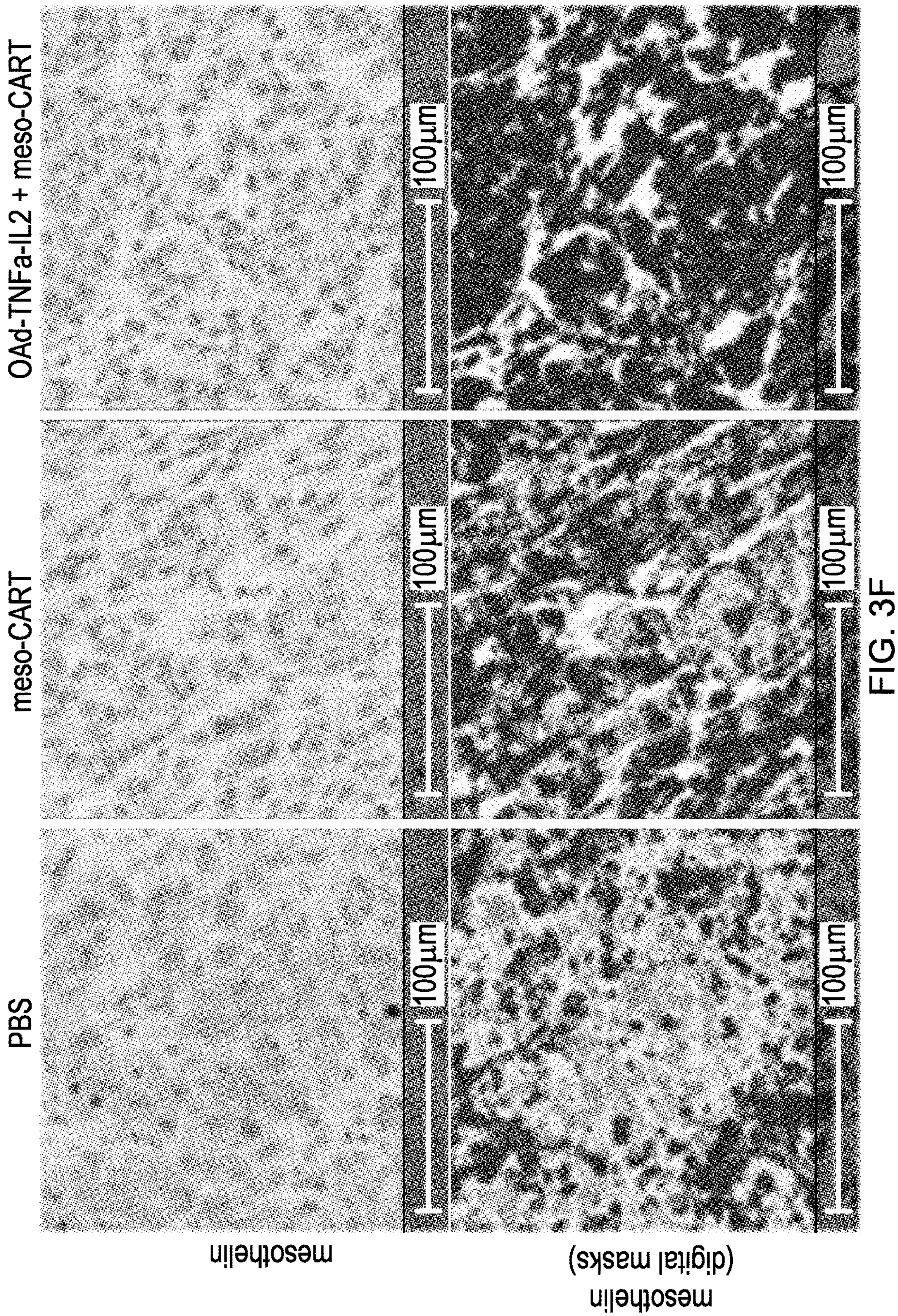
Figure 3G:
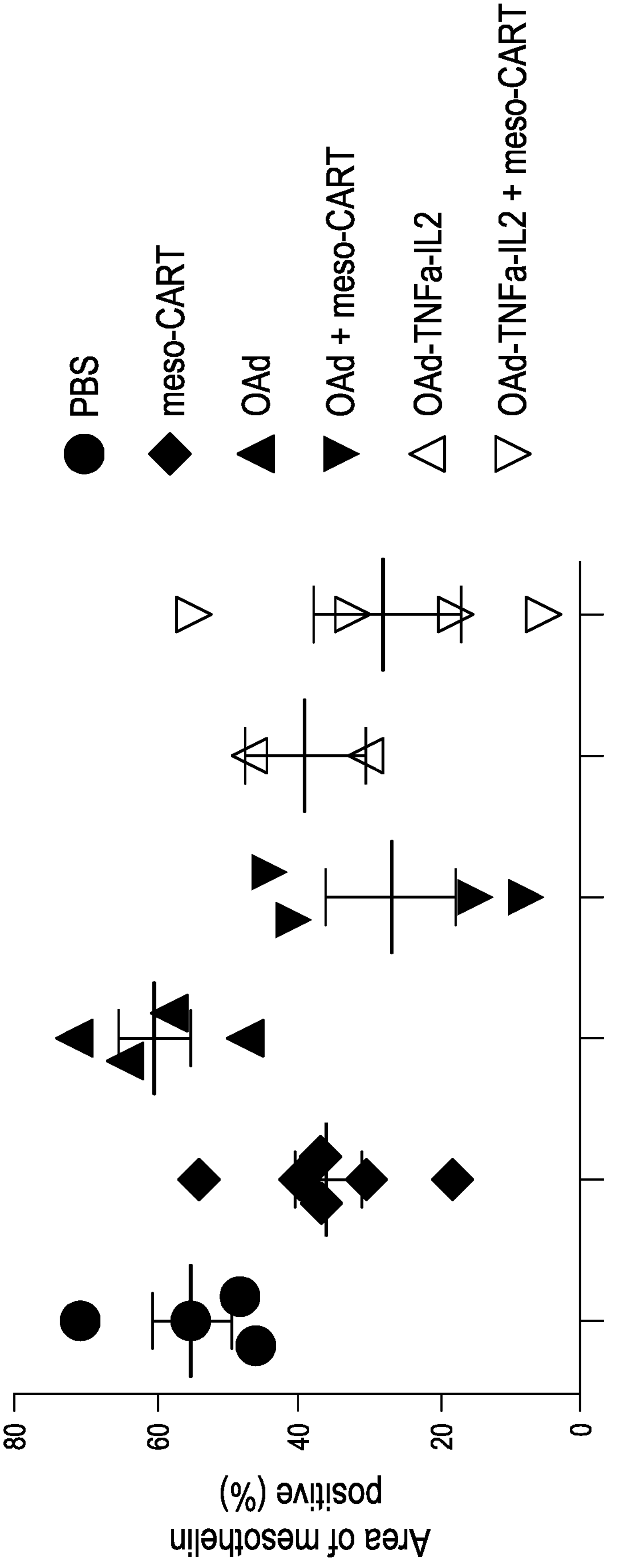
Figure 3H:
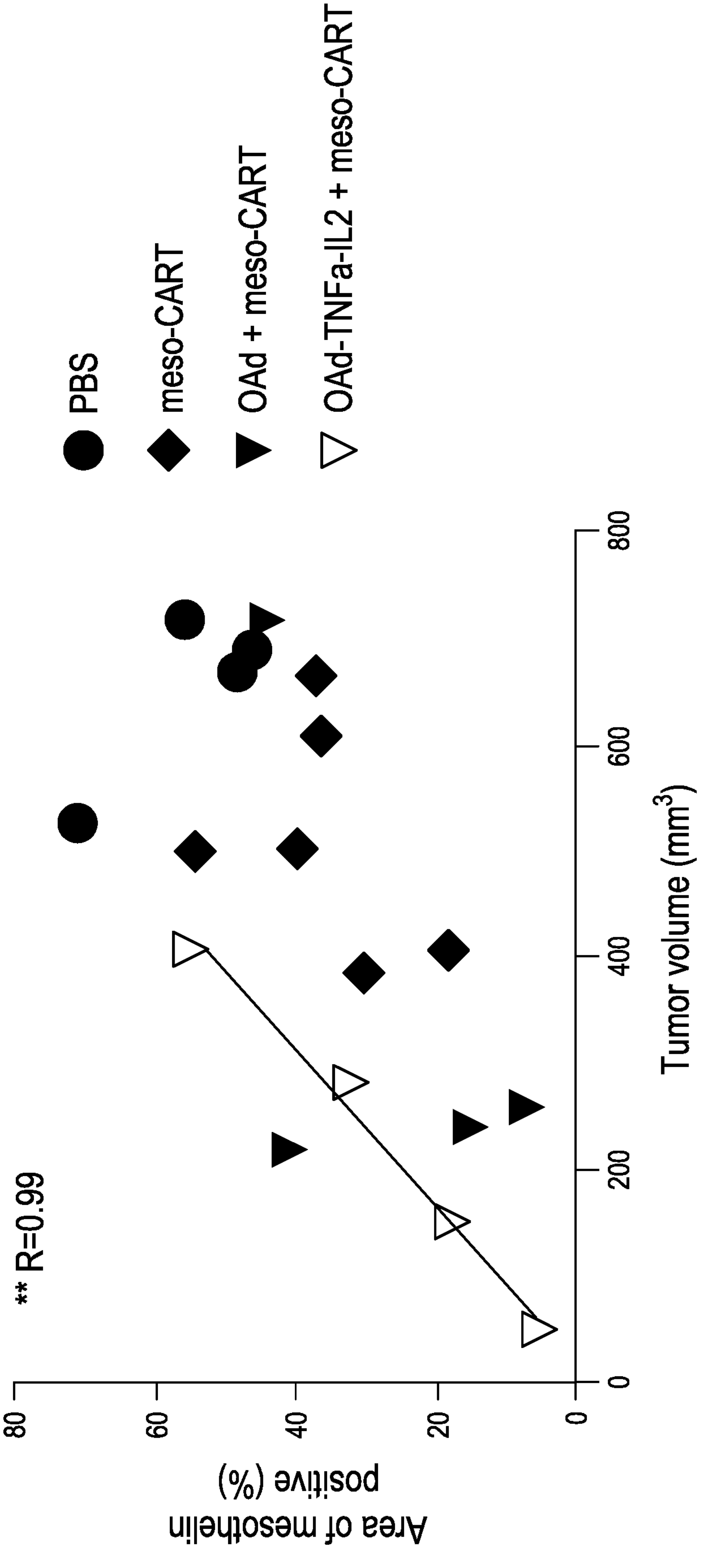

Target antigen decrease by adoptive cell therapies is an indicator of enhanced on-target effect after adoptive transfer with TCR modified T cells (Stromnes I M, et al. Cancer cell. 2015; 28(5):638-52). To address how combining OAd-TNFα-IL2 with meso-CAR T cells affects target antigen expression, mesothelin levels on tumors were quantified. Meso-CAR T cells alone or in combination therapy induced decreases in mesothelin intensity within tumors at day 28, which is consistent with selection for tumor cell variants expressing lower levels of mesothelin (FIGS. 3F and 3G). Meso-CAR T cells induced the most significant decrease in mesothelin expression when combined with OAd-TNFα-IL2, and the mesothelin decrease correlated with anti-tumor efficacy (FIG. 3H). These results suggested that OAd-TNFα-IL2 enhanced on-target tumor lytic activity of meso-CAR T cells, which is associated with improved tumor regression.

Figure 4A:
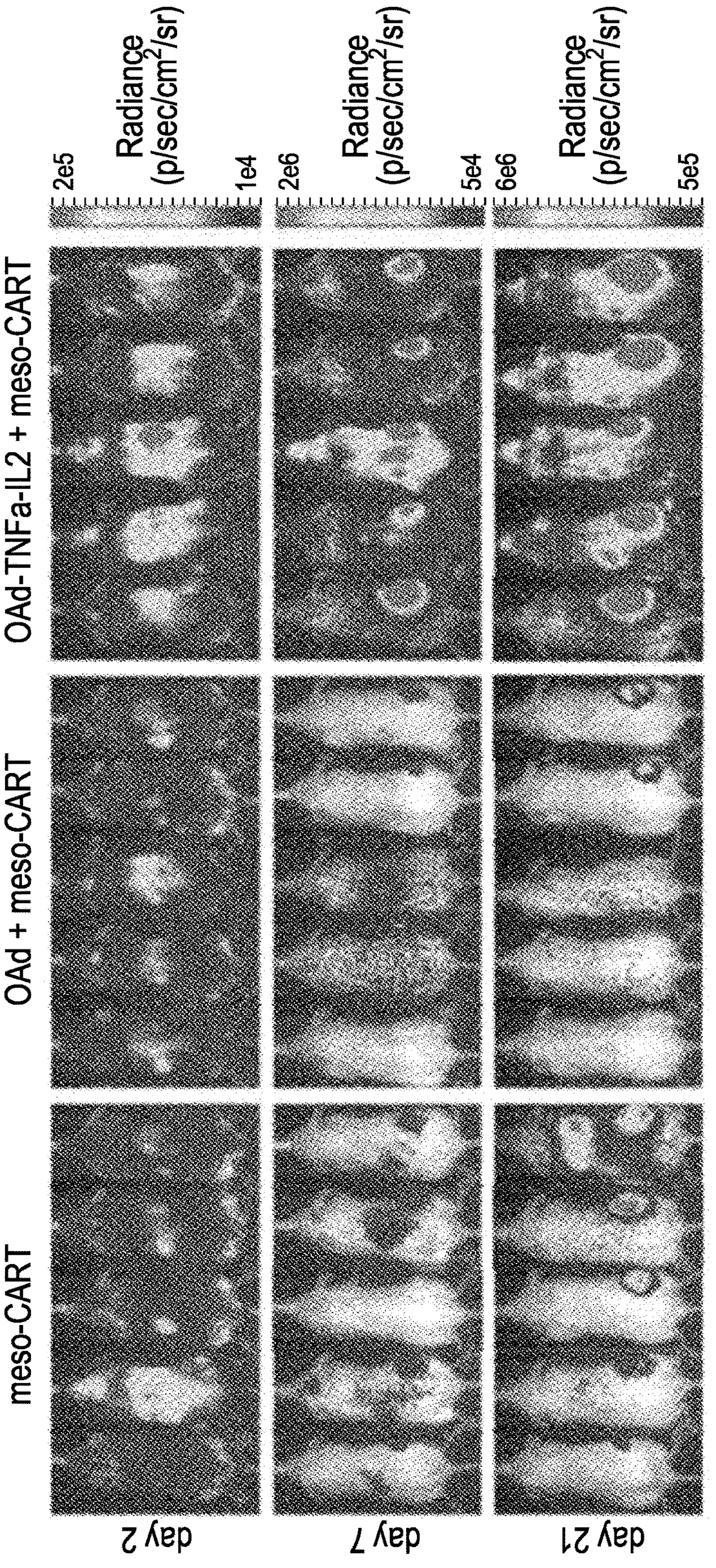
FIGS. 4A-4C: Oncolytic adenovirus (OAd) expressing TNF-α and IL-2 (Ad5/3-E2F-D24-TNFα-IRES-IL2 (Ad5/3-OAd-TNFα-IL2)) induces robust and persistent mesothelin-redirected chimeric antigen receptor T cell (meso-CAR T cell) accumulation in the tumor and improves T cell engraftment.
Figure 4B:
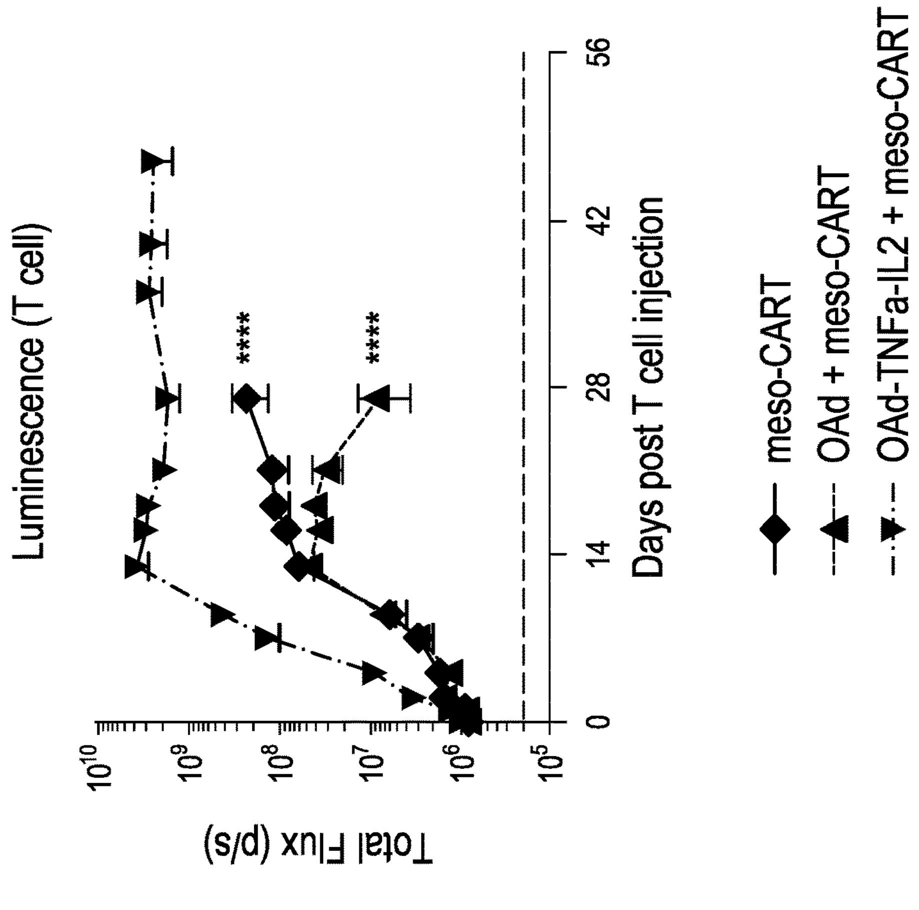
Figure 4C:
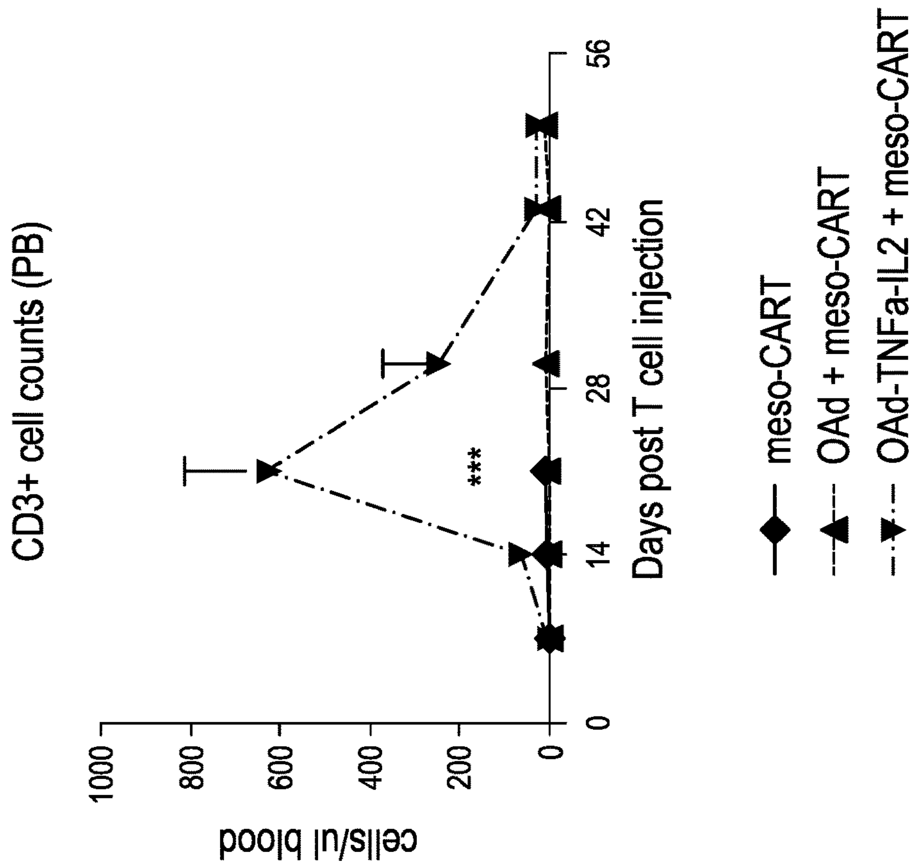

OAd-TNFα-IL2 Induces Robust and Sustained Meso-CAR T Cell Accumulation to Tumors As flow cytometry and histological analysis at days 14 and 28 indicated that Ad-TNFα-IL2 increases CAR T cell recruitment (FIGS. 3A and 3B and FIG. 9B), T cell trafficking assays were performed to determine the precise kinetics of meso-CAR T cell distribution. As early as day 2 after the injection, meso-CAR T cells in combination with OAd-TNFα-IL2 started to show higher accumulation to the tumor site and reached a two-log higher accumulation compared with parental OAd at day 13 (FIGS. 4A and B). OAd-TNFα-IL2 also enhanced T cell engraftment in peripheral blood with the peak at day 21 (FIG. 4C). Interestingly, meso-CAR T cell expansion was transient in peripheral blood (PB) (FIG. 4C), while meso-CAR T cells persisted at the tumor site with sustained high-level accumulation for at least 50 days (FIGS. 4A and 4B). These results indicate that the enhanced proliferation of CAR T cells by OAd-TNFα-IL-2 is due to recognition of tumor associated mesothelin rather than xenogeneic antigens and GVHD.

Figure 5A:
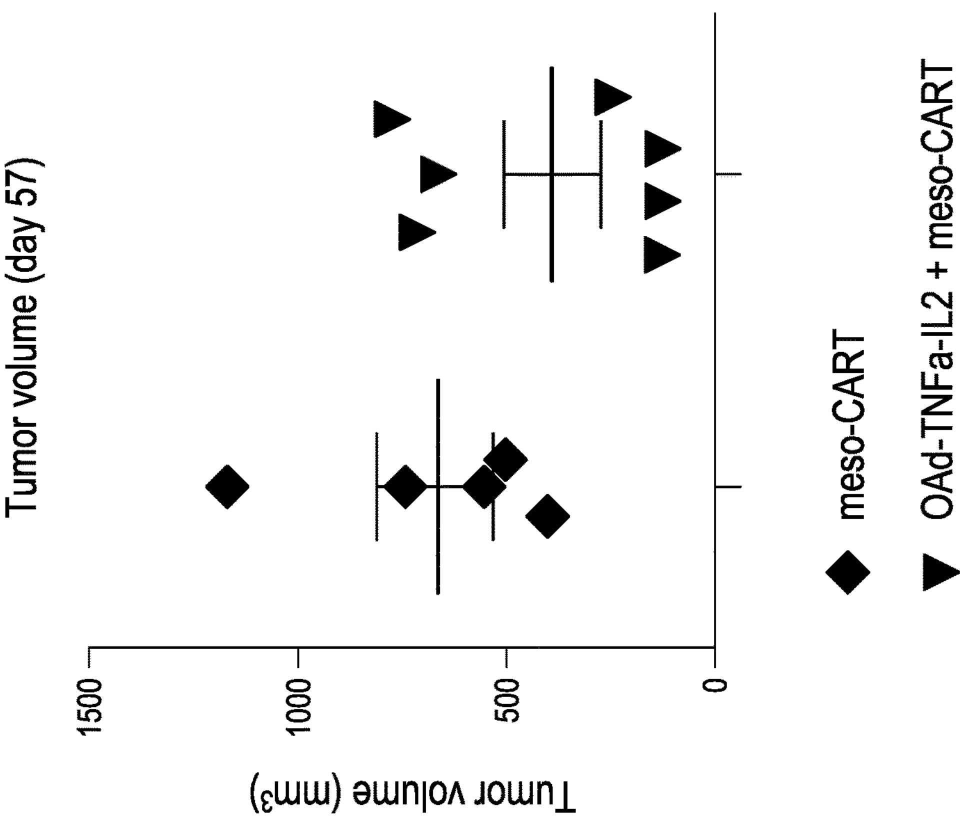
FIGS. 5A-5G: Intensity of functional T cell infiltration is associated with sustained tumor regression after mesothelin-redirected chimeric antigen receptor T cells (meso-CAR T cells) and oncolytic adenovirus expressing TNF-α and IL-2, Ad5/3-E2F-D24-TNFα-IRES-IL2 (Ad5/3-OAd-TNFα-IL2) treatment in an AsPC-1 tumor xenograft immunodeficient mouse model.
Figure 5B:
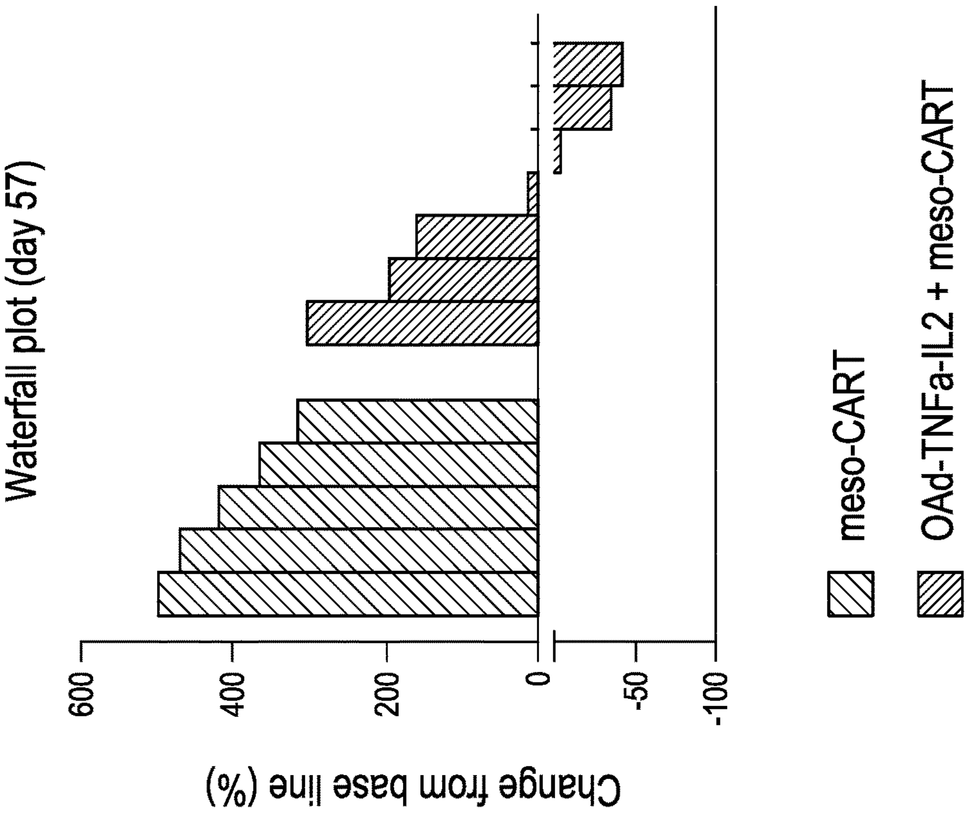
Figure 5C:
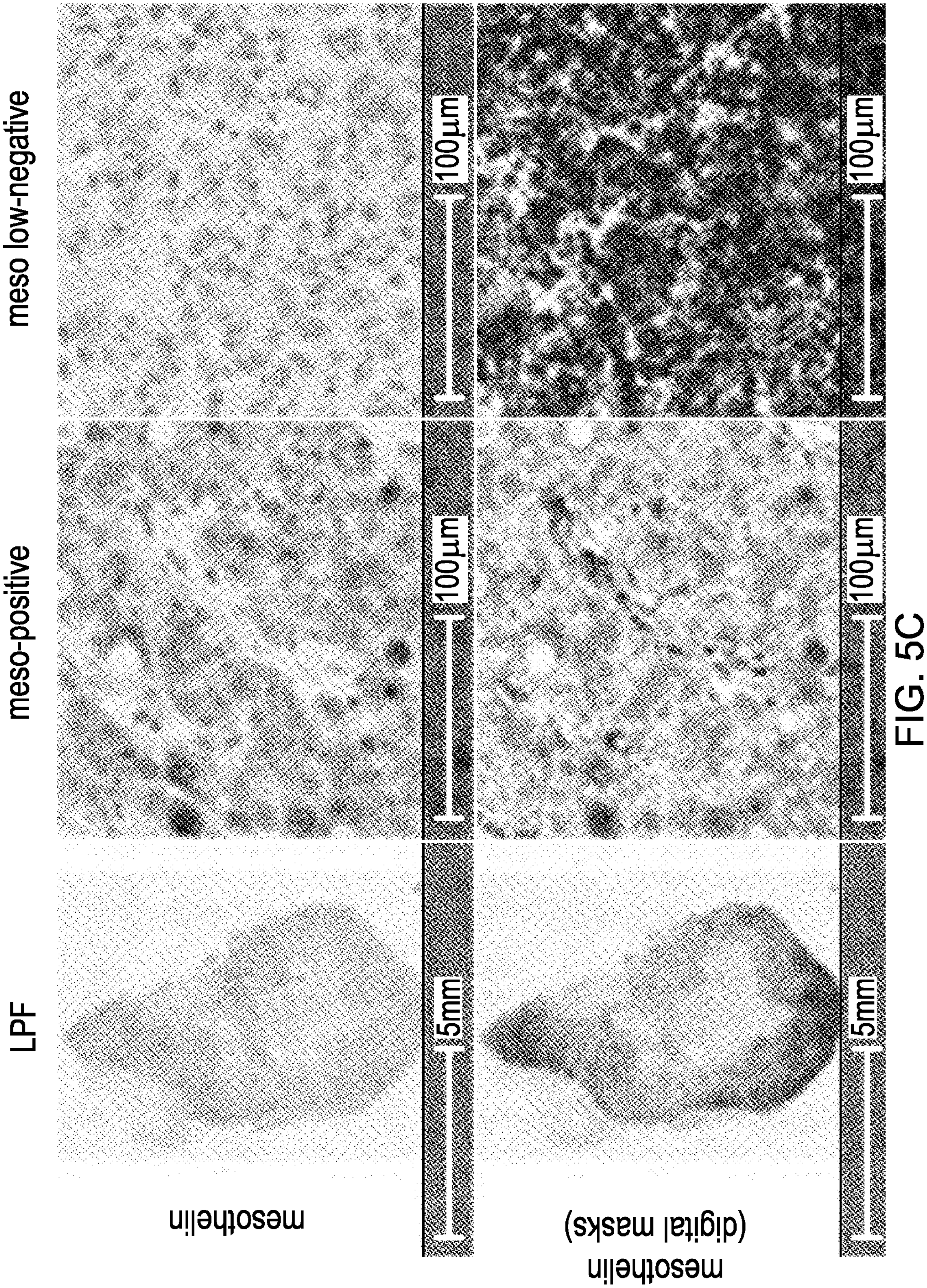
Figure 5E:
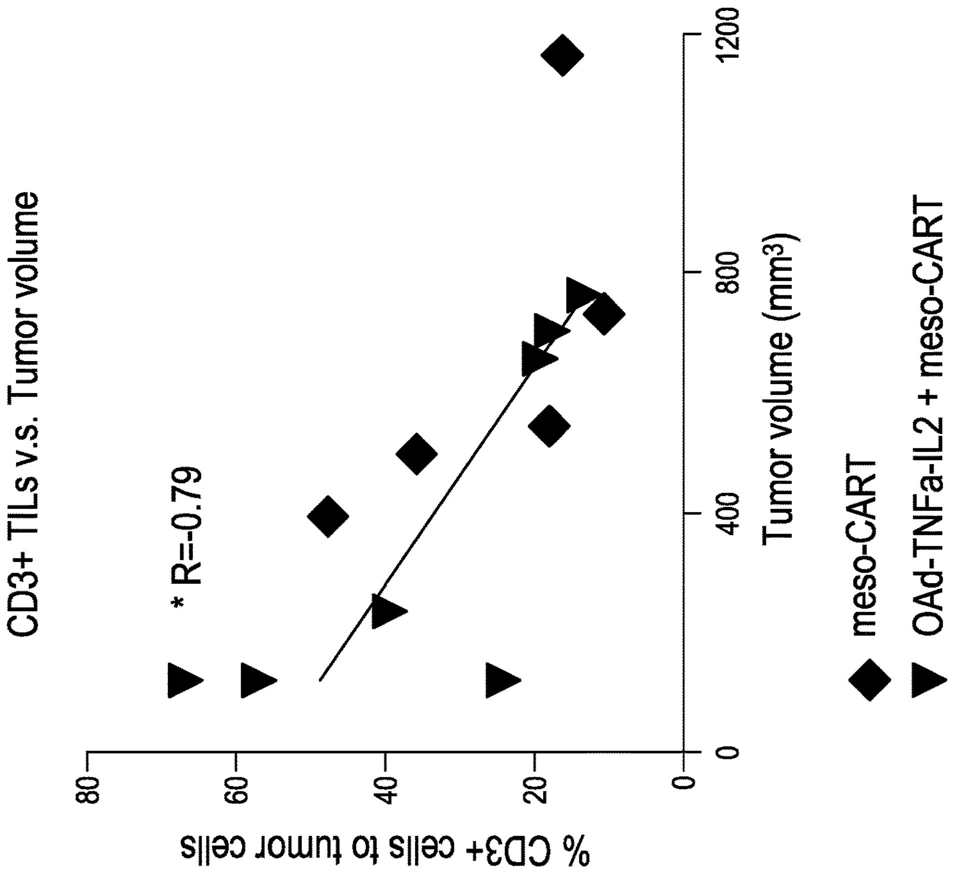
Figure 5D:
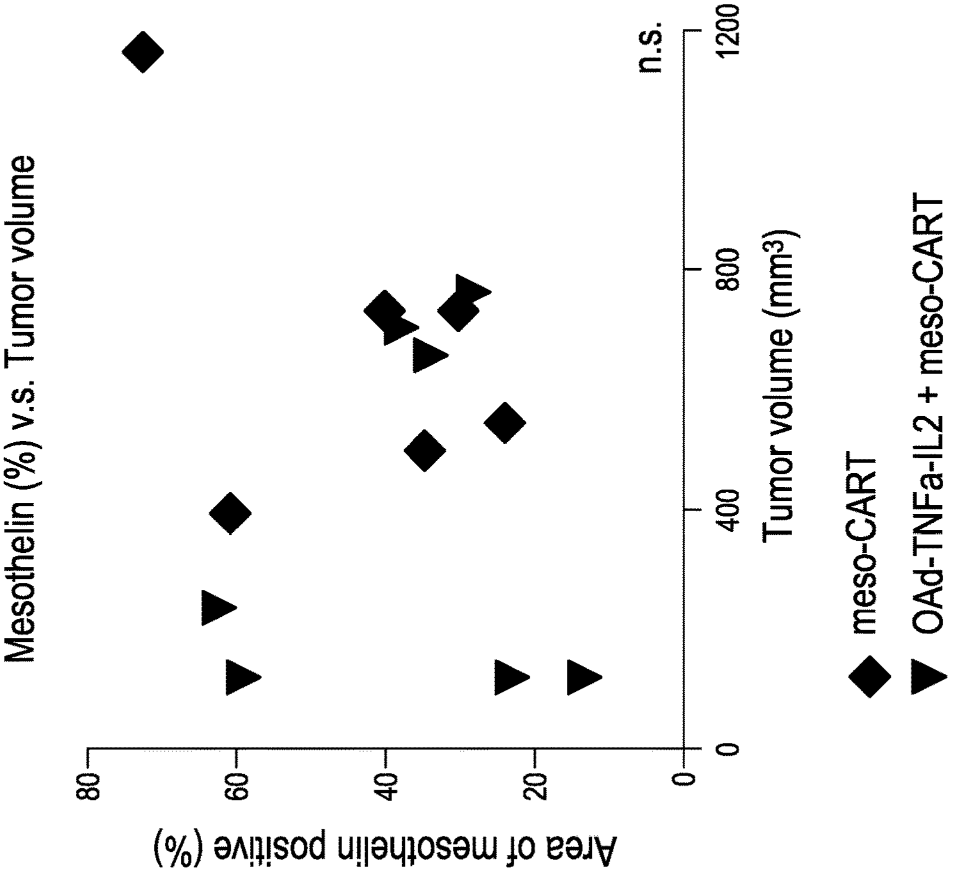
Figure 5F:
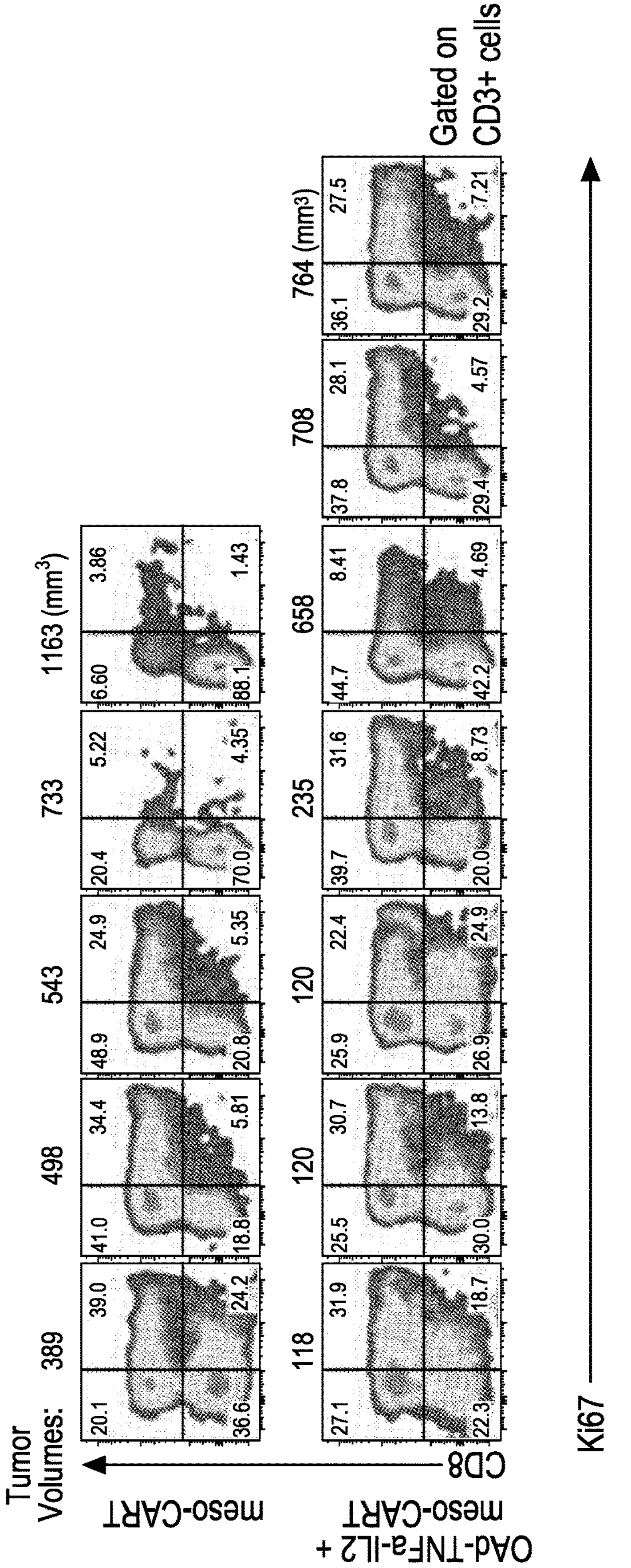
Figure 5G:
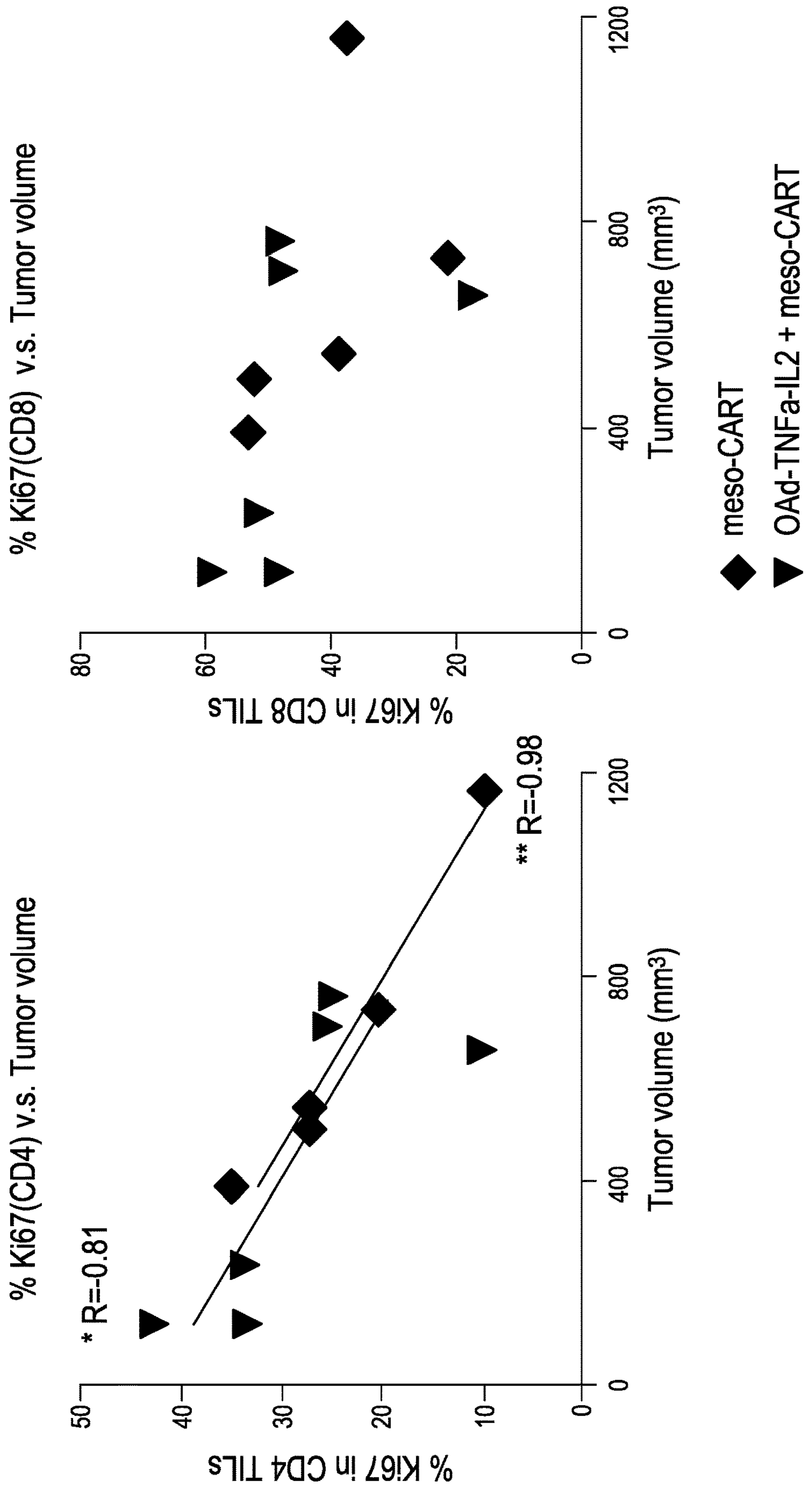

T Cell Factors Dominate the Causes of Tumor Resistance Rather than Target Antigen Loss in Meso-CAR T Therapies Target antigen loss and T cell hypofunction or insufficient tumor infiltration are major causes of tumor relapse for adoptive cell therapies (O'Rourke D M, et al. Science translational medicine. 2017; 9(399)). To explore the causes of tumor resistance, tumors and TILs were analyzed late after treatment. The mice treated with meso-CAR T monotherapy and mice treated with combined OAd-TNFα-IL2 with meso-CAR T cells were sacrificed on day 57 in the experiment shown in FIGS. 2B and 2C. Five out of seven mice from meso-CAR T group and all mice out of seven mice from OAd-TNFα-IL2+meso-CAR T cell group were surviving at day 57. Four tumors from the OAd-TNFα-IL2+meso-CAR T cell group had sustained regression, while three other tumors showed regrowth (FIGS. 5A and 5B). The tumors retained mesothelin expression, but the distribution was heterogenous with areas of negative or low expression (FIG. 5C). However, the residual mesothelin intensity did not correlate with tumor regression on day 57 (FIG. 5D), unlike on day 28 (FIG. 3H). On the other hand, the density of CD3+ TILs still clearly correlated with anti-tumor efficacy at this later time point (FIG. 5E). By flow cytometry, both $CD4^+$ and CD8+ CAR T cells were recovered from the tumors (FIG. 5F). The fraction of CD4+ TILs expressing Ki67+ was inversely correlated with tumor volume (FIG. 5G). These results indicate that loss of mesothelin expression and CAR T cell hypofunction may both contribute to tumor recurrence and it is likely that loss of function or induction of exhaustion may be a major factor explaining delayed tumor progression in this model.

Figure 10A:
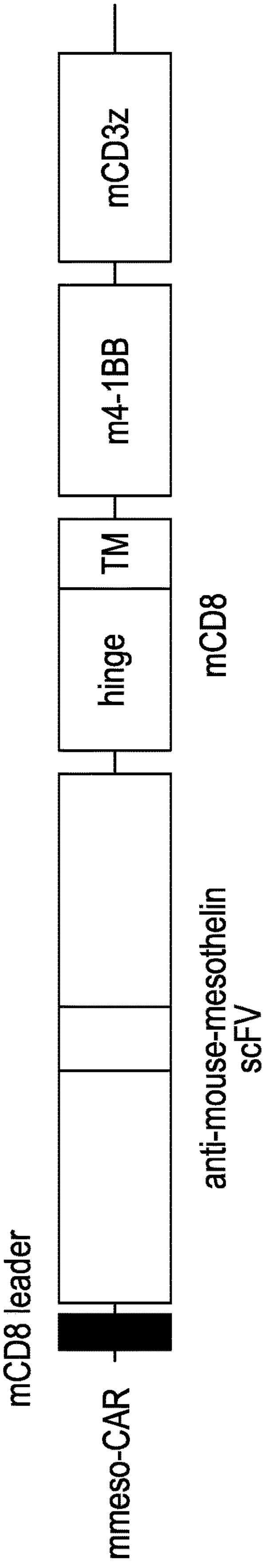
Figure 10B:
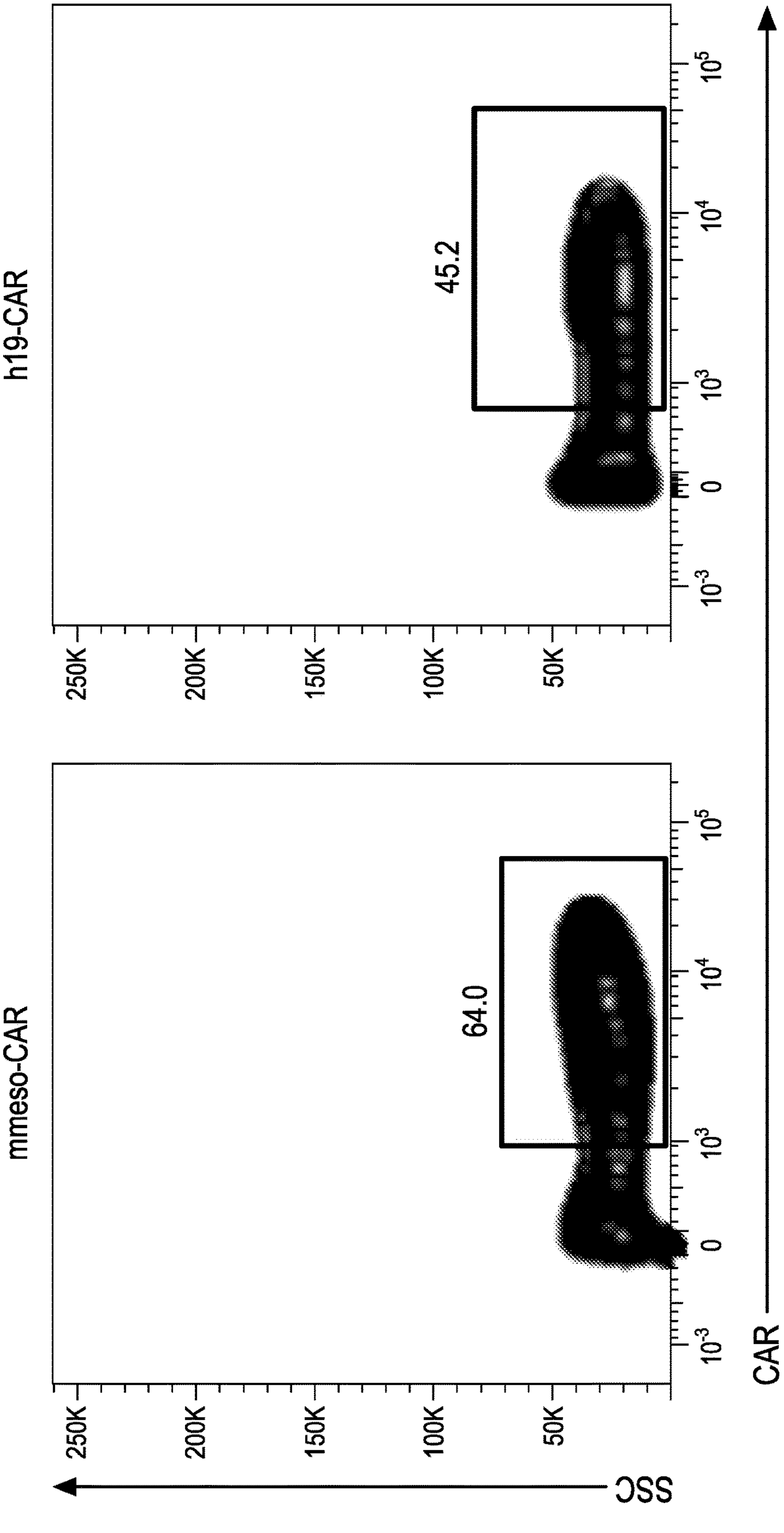

Syngeneic Immunocompetent Mouse PDA Model to Test Combination Therapy with CAR T Cells and Adenovirus Expressing Cytokines Human xenograft NSG mouse models are useful tools to define the anti-tumor efficacy of new treatments. However, they lack a functional immune system and do not faithfully reproduce the human TME (Shultz L D, Ishikawa F, and Greiner D L. Nature reviews Immunology. 2007; 7(2):118-30), which prevents evaluation of mechanisms of OAd therapy other than direct enhancement of CAR T cells. Therefore, engineered mouse T cells were established expressing an anti-mouse mesothelin CAR with mouse 4-1BB and murine CD3-(signaling domains (mmeso-CAR T) (FIGS. 10A and 10B). In vitro the mmeso-CAR T cells effectively lysed PDA7940b cells derived from the genetically engineered KrasLSL.G12D/+p53R172H/+ mouse model, while control h19-CAR T cells did not (FIG. 10C).

Established Mouse Pancreatic Tumors are Resistant to Mouse-Meso-CAR T Cells but Combining Ad-mTNFα-mIL2 Enables Tumor Regression.

Figure 6A:
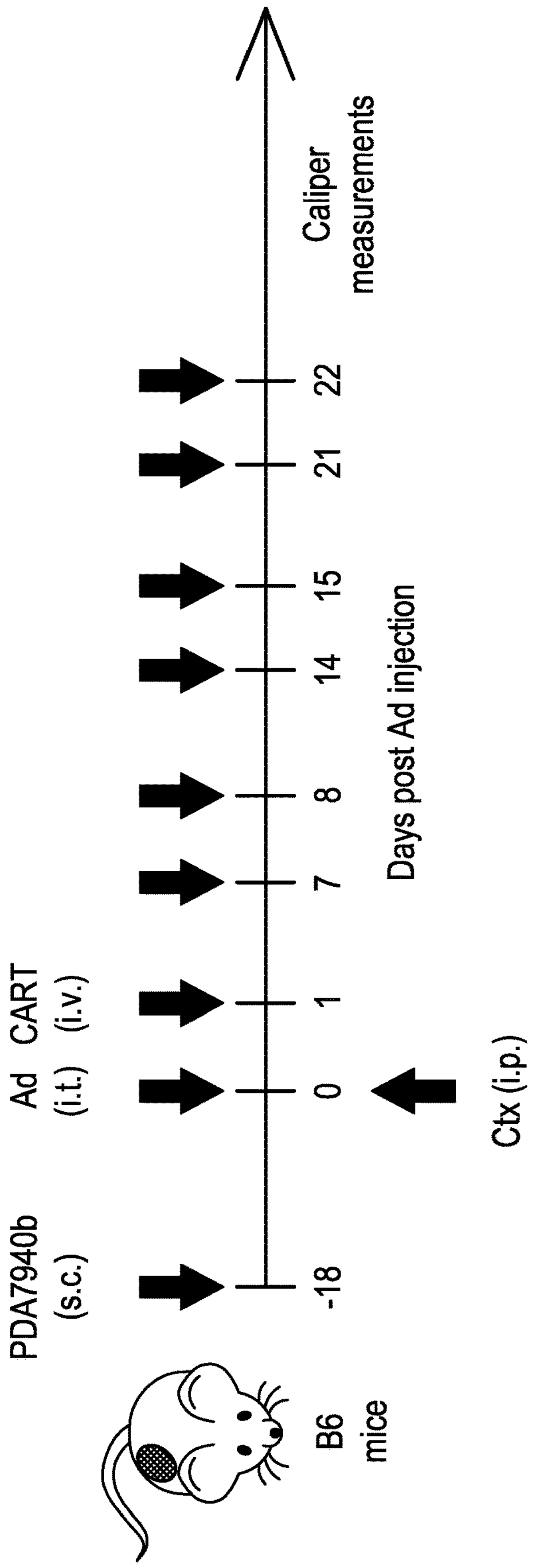
Figure 6B:
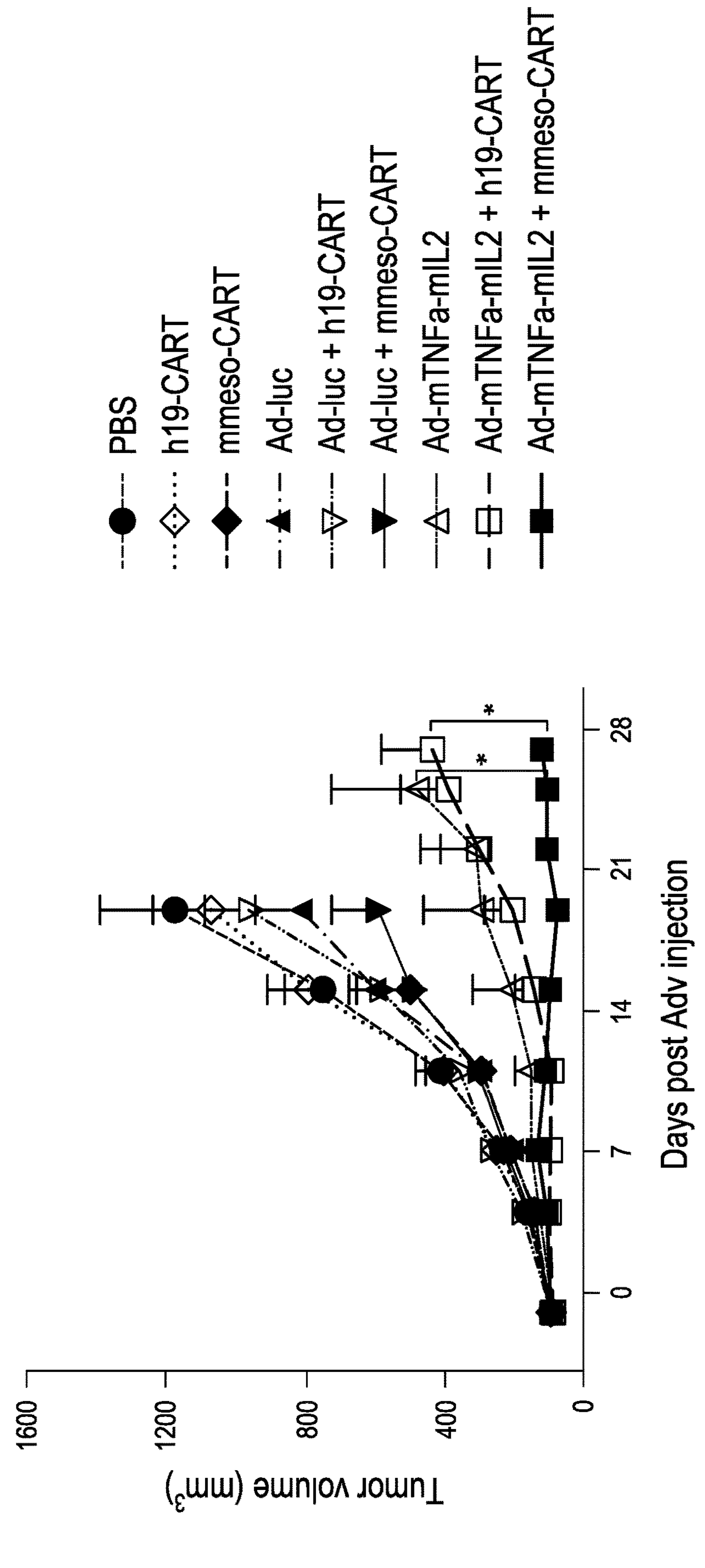
Figure 10D:
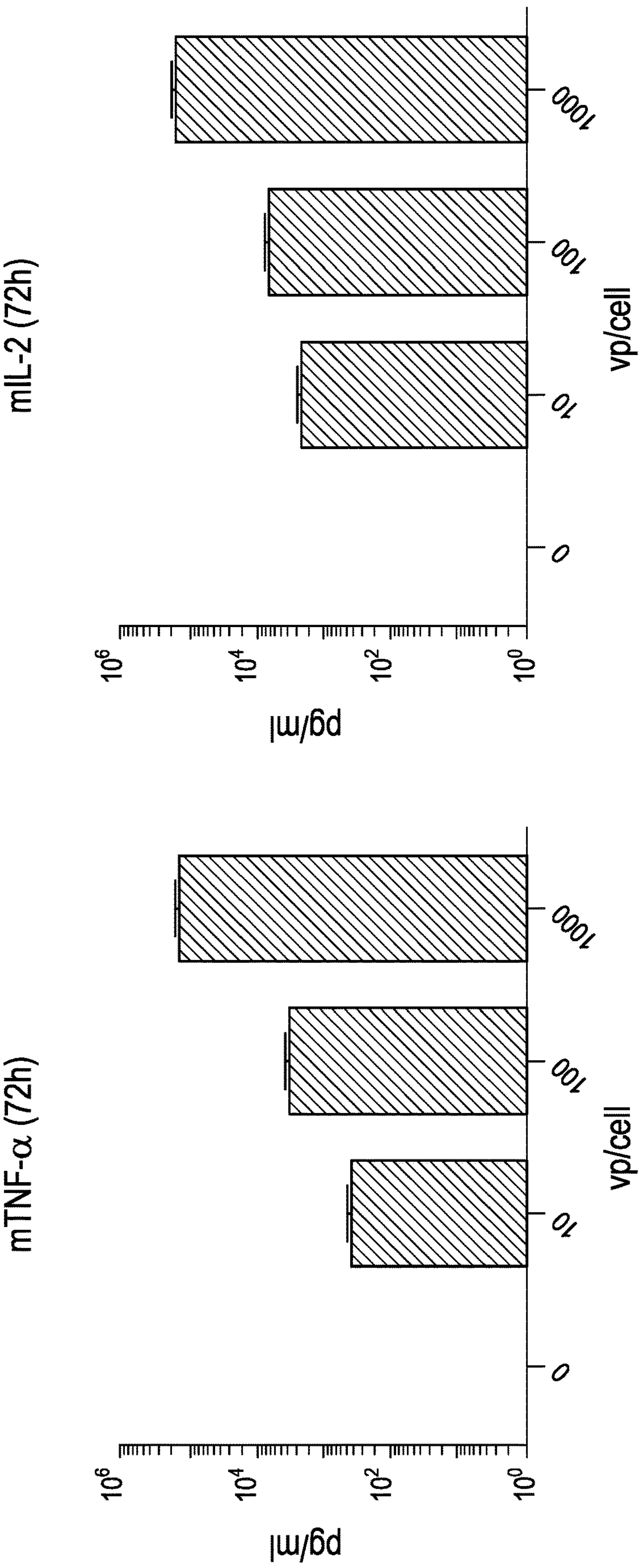

The anti-tumor efficacy of mmeso-CAR T cells was tested in combination with an adenovirus expressing murine TNF-α and murine IL-2 in immunocompetent mice engrafted with syngeneic PDA7940b tumor (FIG. 6A). Non-replicative serotype 5 adenovirus coding for murine TNF-α (Ad-mTNFα) and murine IL-2 (Ad-mIL2) with CMV promoters was used to deliver cytokine genes to mouse tumors, recognizing that murine cells are non-permissive for human adenoviral replication (Siurala M, et al. Molecular therapy: the journal of the American Society of Gene Therapy. 2016; 24(8):1435-43). These viruses could infect PDA7940 cells and induce cytokine production in a dose-dependent manner in vitro (FIG. 10D). Established PDA7940b tumors were highly aggressive and even multiple weekly dosing of mmeso-CAR T cell infusions failed to suppress tumor growth. In contrast, combined Ad-mTNFα-mIL2 (one to one ratio mixture of Ad-mTNFα and Ad-mIL2) with mmeso-CAR T cells had robust antitumor efficacy even though control Ad-luc did not significantly enhance the anti-tumor efficacy of mmeso-CAR T cells (FIG. 6B). Interestingly, Ad-mTNFα-mIL2 monotherapy or in combination with control h19-CAR T also showed partial antitumor efficacy, highlighting the importance of therapeutic transgenes in an immunocompetent setting which likely activate endogenous adaptive and innate antitumor activity.

Figure 6C:
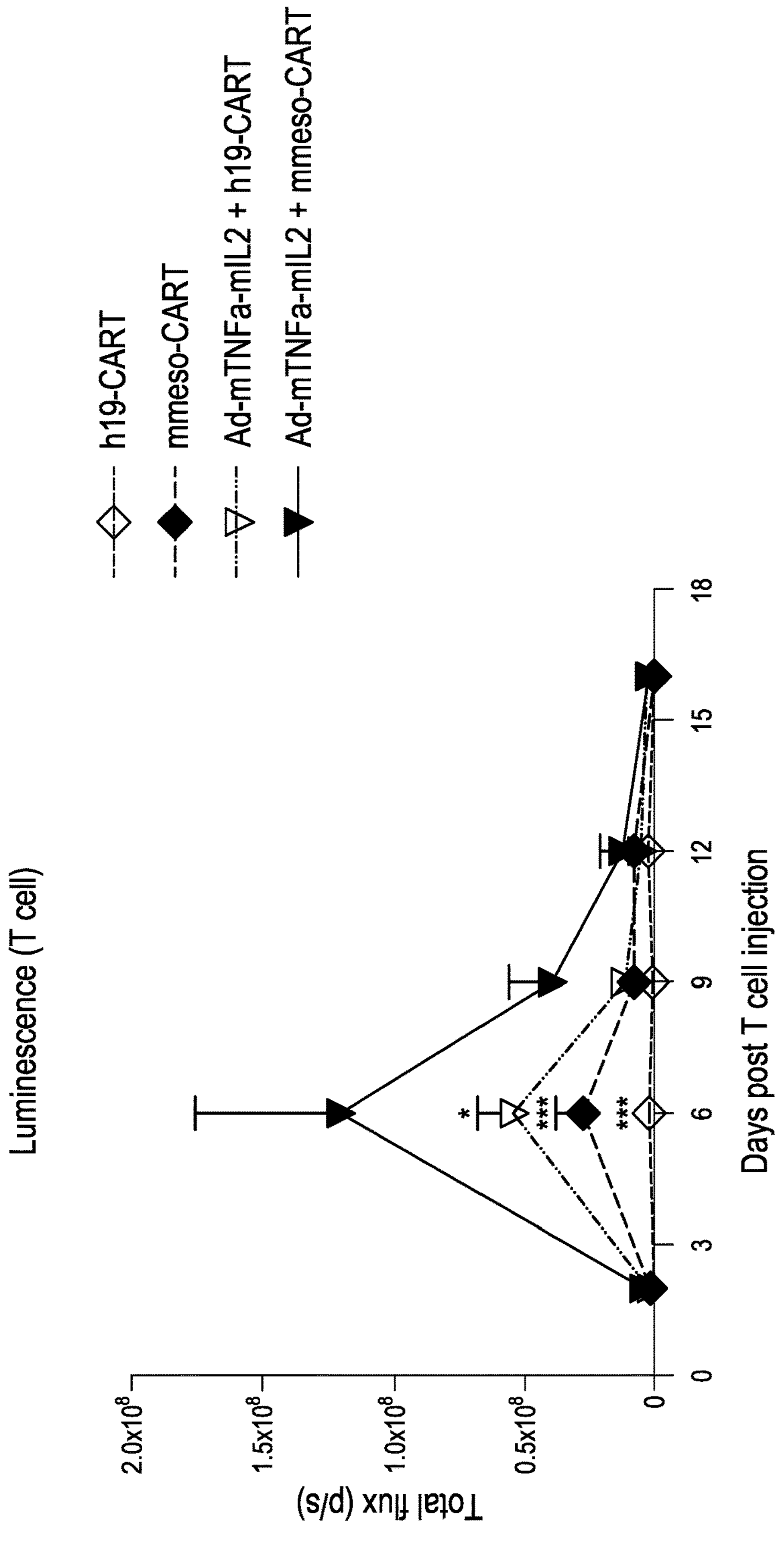

Ad-mTNFα-mIL2 Recruits Both Adoptively Transferred Meso-CAR T Cells and Host T Cells to PDA Tumors It has been reported that mouse PDA tumors are "cold tumors" with low level T cell infiltration which is associated with poor responses to immunotherapies (Hingorani S R, et al. Cancer cell. 2005; 7(5):469-83). To determine whether Ad-mTNFα-mIL2 could improve T cell infiltration into the tumor bed, CAR T cells were tracked after the first injection by BLI using CBR labeled CAR T cells. Meso-CAR T cells alone showed transient low-level engraftment. In contrast, Ad-mTNFα-IL2 induced robustly higher meso-CAR T accumulation that peaked on day 6 after injection (FIG. 6C). Ad-mTNFα-mIL2 also induced low level h19-CAR T cell accumulation although h19-CAR T cell alone did not accumulate in the tumor (FIG. 6C). TILs were also analyzed at day 12 by FCM using the same experimental schedule (FIG. 6A). Tumors were poorly infiltrated with adoptively transferred T cells and host T cells after mmeso-CAR T cell monotherapy. In contrast, Ad-mTNFα-mIL2 induced significantly higher donor and host $CD4^+$ and $CD8^+$ T cell infiltration in the tumor (FIG. 6D).

Ad-mTNFα-mIL2 Alters Host Immune Status and Induces M1 Polarization of Macrophages and DC Maturation It has been reported that KPC tumors faithfully reproduce the highly immunosuppressive phenotype of human PDA (Hingorani S R, et al. Cancer cell. 2005; 7(5):469-83). The above results suggested that mIL-2 and mTNF-α delivered by adenoviruses enhanced the antitumor effect of adoptively transferred mmeso-CAR T cells that may be additionally augmented by CAR-independent host immunity. M1 macrophages are critical components involved in innate antitumor immunity (Mantovani A, et al. Nature reviews Clinical oncology. 2017; 14(7):399-416). To assess how Ad-mTNFα-mIL2 alters host immune suppression, the phenotypes of macrophages and dendritic cells (DCs) were analyzed. Ad-mTNFα-mIL2 clearly induced upregulation of CD80 and CD86 expression from F4/80+ macrophages both in tumors and spleens on day 1 after intratumoral injection (FIG. 6E), which is consistent with M1 polarization. In contrast, injection of control Ad-luc did not induce upregulation of CD80 and CD86. Moreover Ad-TNFα-mIL2 also induced CD11c+DC maturation assessed by CD80 and CD86 upregulation both in tumors and spleen (FIG. 10E).

Ad-mTNFα-mIL2 Creates TME with High Immune Cell Attractive Chemokines.

Figure 6F:
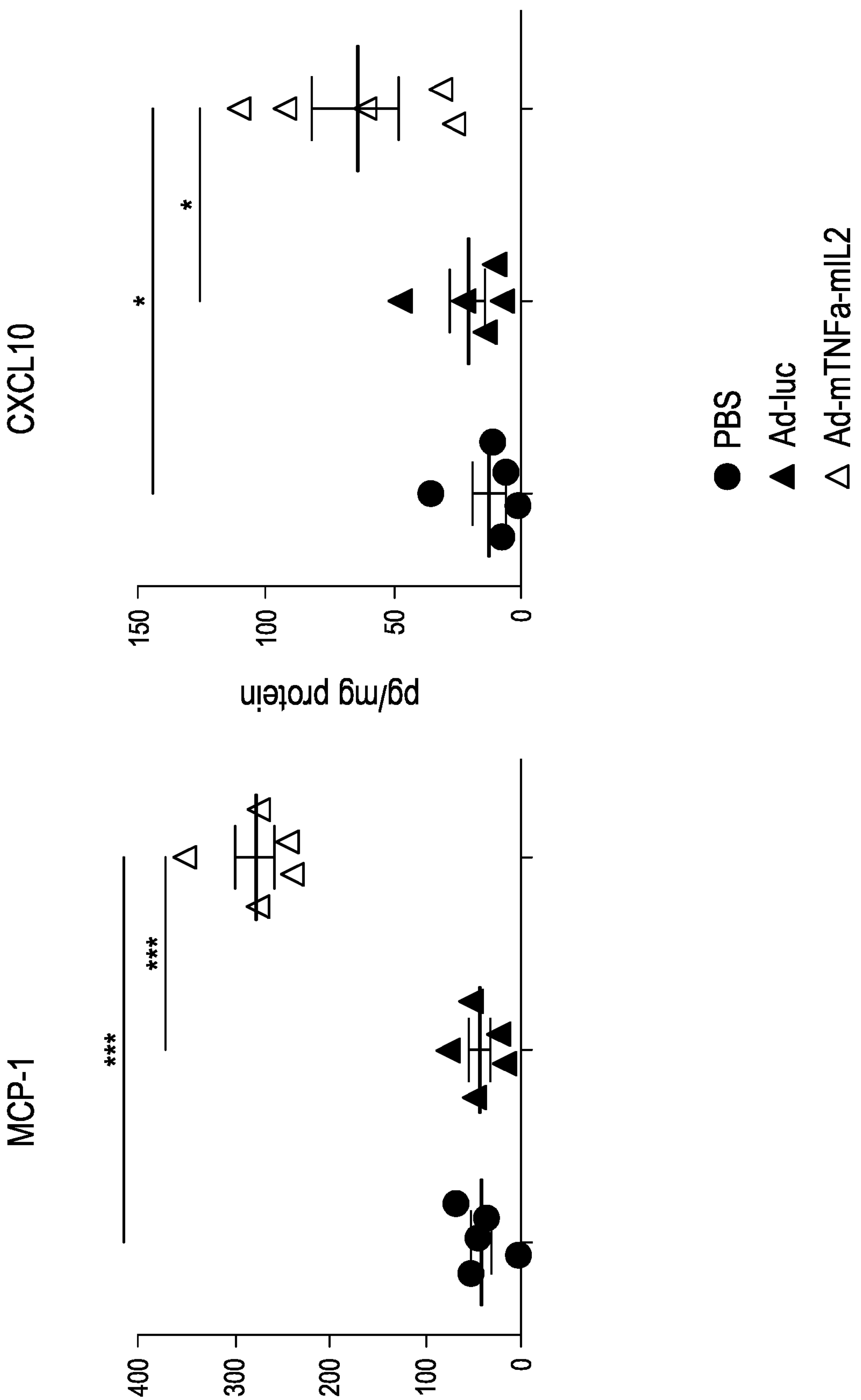
Figure 10F:
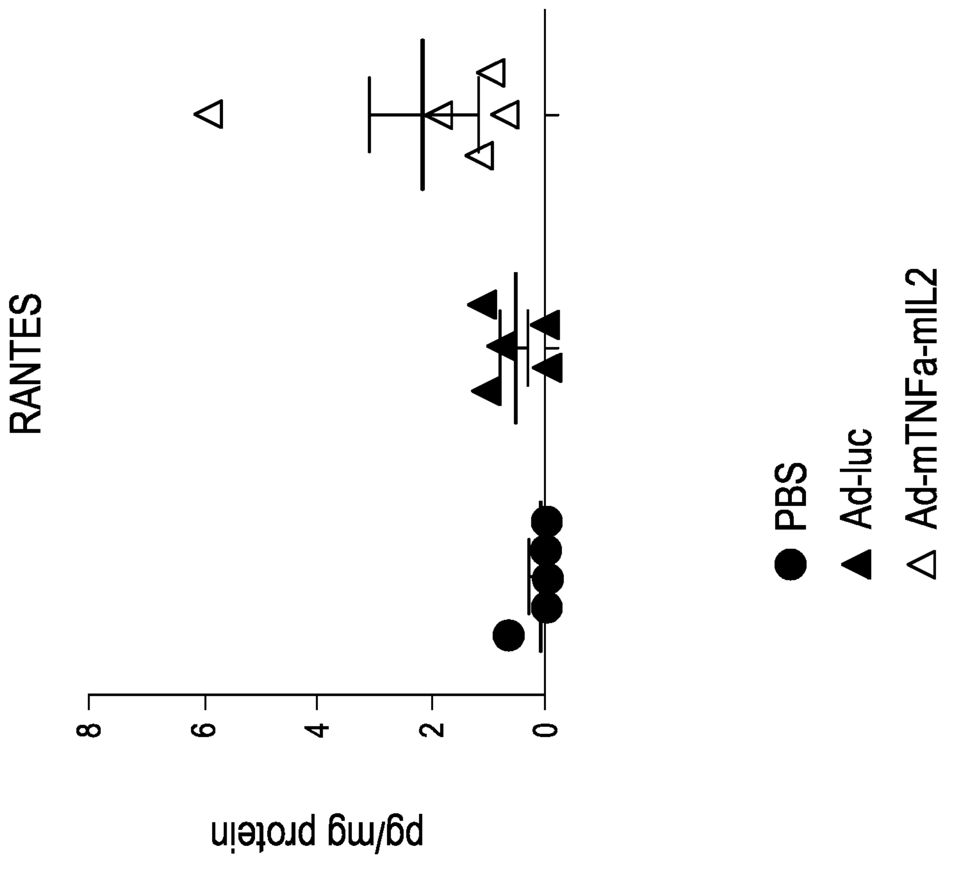

Chemokines are secondary pro-inflammatory mediators that are induced by primary pro-inflammatory mediators such as interleukins or tumor necrosis factors and have critical roles for recruitment of immune cells (Nagarsheth N, Wicha M S, and Zou W. Nature reviews Immunology. 2017; 17(9):559-72). The alteration of chemokine expression in tumors was investigated at day 1 after adenovirus injection. Ad-mTNFα-mIL2 but not Ad-luc clearly increased immune-cell attractive chemokines; monocyte chemoattractant protein-1 (MCP-1), C—X—C motif chemokine ligand 10 (CXCL-10) and RANTES (FIG. 6F and FIG. 10F), which are reported as TNF-α inducible chemokines and function to attract immune cells including T cells, NK cells, macrophages and DCs (Nakasone Y, et al. The American journal of pathology. 2012; 180(1):365-74; Narumi S, et al. Cytokine. 2000; 12(7):1007-16; Wolf G, et al. Kidney international. 1993; 44(4):795-804). These results suggested that in addition to direct efficacy of mTNF-α and mIL-2 delivered by adenoviruses, secondarily-induced chemokines also contribute to recruit adoptively transferred CAR T cells and host immune cells to the tumors.

Taken together, these results suggest that Ad-mTNFα-mIL2 has the potential to enhance the efficacy of mmeso-CAR T therapy by altering the host immune status to a more proinflammatory anti-tumor state and by inducing both CAR-dependent and CAR-independent immune reactions against pancreatic cancer.

Discussion

The central issues for adoptive cell therapies against solid tumors are poor T cell infiltration, hypofunction of T cells in the tumors and tumor heterogeneity (Beatty G L, and O'Hara M. Chimeric antigen receptor-modified T cells for the treatment of solid tumors: Defining the challenges and next steps. Pharmacol Ther. 2016; Newick K, Moon E, and Albelda S M. Mol Ther Oncolytics. 2016; 3:16006; O'Rourke D M, et al. Science translational medicine. 2017; 9(399)). PDA is characterized by a strongly immunosuppressive TME, which can limit the efficacy of adoptively transferred T cells (Liyanage U K, et al. J Immunol. 2002; 169(5):2756-61; Mukherjee P, et al. Glycoconj J. 2001; 18(11-12):931-42; Moon E K, et al. Clin Cancer Res. 2014; 20(16):4262-73). The goals of the present study were to establish effective therapy against PDA by combining two promising immunotherapeutic approaches, OAd expressing cytokines and CAR T cells and to reveal the mechanisms of synergy and resistance to this combination therapy in PDA in syngeneic and xenogeneic experiments. This work confirms and extends work by Nishio and colleagues, who found that OAd armed with RANTES and IL-15 augmented apoptosis in tumor cells exposed to CAR-T cells, while the intratumoral release of both RANTES and IL-15 attracted CAR-T cells and promoted their local survival, respectively, and increasing the overall survival of neuroblastoma bearing mice (Tanoue K, et al. Cancer Res. 2017; 77(8):2040-51).

It has been reported that PDA typically has few TILs whereas the lymphocytic populations are predominantly found in the stroma surrounding the tumor mass (Wachsmann M B, Journal of investigative medicine: the official publication of the American Federation for Clinical Research. 2012; 60(4):643-63), and recent studies suggest that the T cells in long term survivors with pancreatic cancer target neoantigens (Balachandran V P, et al. Nature. 2017; 551(7681):512-6). The presence of high number of TILs and extensive infiltration are major indicators of favorable patient prognosis and positive therapeutic responses in treating several solid tumors, including colorectal cancer (Huh J W, Lee J H, and Kim H R. Archives of surgery (Chicago, Ill.: 1960). 2012; 147(4):366-72), lung cancer (Zeng D Q, et al. Oncotarget. 2016; 7(12):13765-81), and ovarian carcinomas (James F R, et al. BMC cancer. 2017; 17(1):657; Li J, et al. Oncotarget. 2017; 8(9):15621-31). Although it is not clear yet whether the intensity of CAR TILs directly correlates with its efficacy or patient outcome in solid tumors, it is reasonable to assume that augmentation of CAR-TILs will enhance antitumor efficacy. It was demonstrated here that OAd-TNFα-IL2 induced robust CAR T cell infiltration, which was clearly associated with enhanced antitumor efficacy. TNF-α is reported to induce T cell attractive chemokines (Son D S, et al. Journal of inflammation (London, England). 2013; 10(1):25) and IL-2 itself has ability to induce proliferation and chemotaxis of T cells (Robbins R A, et al. J Lab Clin Med. 1986; 108(4):340-5). Moreover, in the context of local delivery with adenovirus, TNF-α appears to mediate potent immunological danger signaling and trafficking of a T-cells, while IL-2 can sustain activity of T cells and NK cells (Siurala M, et al. Molecular therapy: the journal of the American Society of Gene Therapy. 2016; 24(8):1435-43). Taken together the main mechanism of the combination cytokine-armed OAd plus CAR T cell therapy was associated with robustly enhanced and sustained T cell function in the tumor.

The mechanisms of the combination therapy were further investigated by focusing on target antigen expression. O'Rourke et al. reported from the first in human study of epidermal growth factor receptor variant III (EGFRvIII) redirected CAR T cell therapy against glioblastoma (GBM) that most of patients had specific loss or decrease of EGFRvIII expression in tumors resected after CAR T cell infusion (O'Rourke D M, et al. Science translational medicine. 2017; 9(399)). This finding supports the idea that additional therapies to enhance epitope spreading such as this approach to combine OAds with CAR T may be needed to prevent antigen escape. It was found here that mesothelin intensity in the TME was a predictor of response early after treatment but not late at the time of tumor recurrence, where T cell factors such as the intensity of T cell infiltration and enhanced T cell function was an important factor. A unique advantage of the combined OAd and CAR T cell therapy is that OAds recognize and infect tumor cells using different antigens from the ones that CAR T cells typically recognize. The 5/3 chimeric OAds that were used herein recognize desmoglein-2 (DSG-2) (Wang H, et al. Nat Med. 2011; 17(1):96-104), whereas CAR T cells recognize mesothelin. It is likely that OAds can target and suppress mesothelin low or negative tumor cells. Indeed, it was observed that OAd-TNFα-IL2 not only enhanced function of meso-CAR T cells but also directly suppressed tumor growth independently of meso-CAR T cells. From these observations, meso-CAR T cells and OAd-TNFα-IL2 are an attractive combination to improve the treatment of PDA by overcoming T cell hypofunction and tumor heterogeneity in target antigen expression.

Whether OAd-TNFα-IL2 could enhance the efficacy of meso-CAR T cells was investigated in an AsPC-1 tumor xenograft NSG mouse model. Even though parental OAd combined with meso-CAR T or parental OAd monotherapy could suppress primary tumors to some extent, these mice typically died of tumor metastasis even in cases where primary tumors were being controlled. On the other hand, mice treated with combined OAd-TNFα-IL2 and meso-CAR T cells did not develop tumor metastasis. These results suggested that locally activated meso-CAR T cells at the primary tumor site exerted systemic immunosurveillance to prevent tumor progression. This is an important aspect of this combination therapy, as patients frequently die from tumor metastasis in PDA (Ryan D P, Hong T S, and Bardeesy N. The New England journal of medicine. 2014; 371(11):1039-49).

Regarding the immunocompetent model, although replication deficient adenoviruses do not directly lyse infected tumor cells, Ad-mTNFα-mIL2 rapidly and aggressively reduced tumor growth after virus injection. These results indicate that host innate immunity such as macrophages, DCs and NK cells contributed to tumor control. It was observed that Ad-mTNFα-mIL2 induced infiltration of non-CAR host T cells in addition to adoptively transferred donor CAR T cells. Ad-mTNFα-mIL2 modulated the tumor immunosuppression by promoting M1 polarization of macrophages and maturation of DCs. As it was previously found that OAd therapy can prime T cells that recognize additional tumor antigens via T cell receptors (TCR-T cells) in the ovalbumin expressing B16 melanoma mouse model (TKhtinen S, et al. Cancer Immunol Res. 2015; 3(8):915-25), this reprogramming of the TME is expected to prime TCR-T cells that recognize tumor neoantigens by epitope spreading. Thus, the immunocompetent mouse model revealed that adenovirus could enhance the efficacy of CAR T cell therapy not only by directly enhancing CAR T cell functions but also by inducing CAR-independent immunity of host cells perhaps by eliciting neoantigen responses to overcome tumor heterogeneity and tumor escape caused by target antigen loss.

One limitation of this study is that it used established PDA tumor lines and primary PDA tumor xenografts have not been tested. In addition, NSG mice do not have a complete immune system and human xenograft models do not reproduce the human TME (Shultz L D, et al. Nature reviews Immunology. 2007; 7(2):118-30). Recent studies indicated that the main impact of oncolytic polio and herpes virus therapy is its immune modulating effects (Brown M C, et al. Science translational medicine. 2017; 9(408); Yin J, et al. Frontiers in oncology. 2017; 7:136). The lack of an intact immune system in NSG mice may overlook these important immunological aspects of OAd therapy. Therefore, this combination therapy was tested in a fully immunocompetent setting. Our newly established mouse mesothelin redirected CAR T cells enabled testing the mmeso-CAR T cell therapies in a fully immunocompetent setting. This is the first report demonstrating that mouse CAR T cells targeting native syngeneic mouse tumor antigens in solid tumors augment the antitumor efficacy of adenoviral delivery of cytokine transgenes. Even in the highly immunosuppressive PDA TME, Ad-mTNFα-mIL2 successfully enhanced the antitumor efficacy with mmeso-CAR T cells.

In summary, this study describes a novel combination therapy of oncolytic adenovirus expressing TNF-α and IL-2 with meso-CAR T cells in the treatment of PDA. Meso-CAR T cells failed to work effectively in PDA tumors as monotherapy, but combining of OAds expressing TNF-α and IL-2 enabled effective meso-CAR T cell therapy by modulating the immunosuppressive TME and inducing CAR-dependent and CAR-independent host immunities. In addition to the preclinical data reported here, the safety profiles of the same platform of OAds used in these experiments have already been evaluated as monotherapies in several clinical trials (Kim K H, et al. Gynecol Oncol. 2013; 130(3):518-24; Ranki T, et al. Journal for immunotherapy of cancer. 2016; 4:17), and provide a compelling rationale for CAR T cell combination therapy targeting PDA.

Methods

Generation of Mesothelin-Redirected Human CAR T Cells

Anti-mesothelin CAR containing the CD3-(signaling domain and the 4-1BB co-stimulatory domain were generated as previously described (Carpenito C, et al. Proc Natl Acad Sci USA. 2009; 106(9):3360-5). T cells from normal donors were transduced with lentivirus to express anti-mesothelin CAR.

Generation of Mouse Mesothelin-Redirected Mouse CAR T Cells

Mmeso-CAR was constructed by fusing anti-mesothelin scFv to a mouse CD3-(signaling domain and a mouse 4-1BB co-stimulatory domain. The CAR was cloned into MSGV vector and packaged in the Plat E cell line to obtain the retrovirus. For the T cell transduction, spleens were harvested from CD45.1 donor mice and T cells were purified with mouse T cell selection beads (Stemcell Technologies Vancouver, Canada). Purified mouse T cells were activated with anti-mouse CD3 and CD28 antibody coated beads (Dynabeads, ThermoFisher, Waltham, MA) at a 2:1 ratio of bead:cell and then transduced with retroviral vector MSGV for CAR expression on the recombinant human fibronectin (Retronectin, Takara Bio USA, Mountain View, CA) coated plates at day 3 post beads stimulation. Recombinant mouse IL-2 (50 U/ml) was supplemented at day 1 and then complemented as fresh media containing 50 U/ml IL-2 every day. Mouse T cells were harvested and subjected to the in vivo experiments at day 5.

Cell Lines

BxPC-3, Capan-2 and AsPC-1 cell lines were obtained from the American Type Culture Collection (ATCC) and authenticated by the University of Arizona Genetics Core. PDA7940b cell line which was established from KrasLSL.G12D/+p53R172H/+(KPC) mouse pancreatic tumor model (Hingorani S R, et al. Cancer cell. 2005; 7(5):469-83) was kindly provided by Dr. Gregory Beatty, the University of Pennsylvania. All cell lines were tested for the presence of mycoplasma contamination (MycoAlert Mycoplasma Detection Kit, Lonza). BxPC-3 and AsPC-1 were maintained in culture with DMEM/F12 (1:1) (Gibco, LifeTechnologies, Grand Island, NY) supplemented with 20% FBS (Seradigm, Providence, UT) and 50 U/ml penicillin/streptomycin (Gibco, LifeTechnologies). Capan-2 and PDA7940b were maintained in culture with DMEM (Gibco, LifeTechnologies) supplemented with 10% FBS and 50 U/ml penicillin/streptomycin.

Adenovirus Construction

The oncolytic adenovirus that has a 24-base pair deletion in constant region 2 of the E1A gene and chimeric serotype 5 shaft and serotype 3 knob (Ad5/3-D24 (OAd) was constructed and produced as has been described previously (Kanerva A, et al. Molecular therapy: the journal of the American Society of Gene Therapy. 2003; 8(3):449-58). Parental OAd was modified by adding a tumor specific E2F1 promoter driving an E1 gene deleted at the retinoblastoma protein binding site (Δ24) and further modified by encoding TNF-α and IL-2 genes to deliver cytokine genes to target tumor cells (Ad5/3-E2F-D24-TNFα-IRES-IL2 or OAd-TNFα-IL2 for short) (Havunen R, et al. Mol Ther Oncolytics. 2017; 4:77-86) (FIG. 7A). Replication-incompetent adenovirus serotype 5 expressing luciferase (Ad-luc) and adenovirus serotype 5 expressing murine TNF-α and murine IL-2 with the cytomegalovirus (CMV) promoter (Ad-mTNFα and Ad-mIL2, respectively) were constructed as described previously (Siurala M, et al. Molecular therapy: the journal of the American Society of Gene Therapy. 2016; 24(8):1435-43; TKhtinen S, et al. Cancer Immunol Res. 2015; 3(8):915-25).

Killing Assay Using xCELLigence Real Time Cell Analyzer (RTCA) and In Vitro Co-Culture Assay Kinetic analysis of tumor cell lysis was performed using xCELLigence real time cell analyzer (ACEA Biosciences, San Diego, CA) as previously described (Kho D, et al. Biosensors (Basel). 2015; 5(2):199-222). Ten thousand tumor cells were seeded to the e-plate. After 24-hour culture, tumor cells were infected with 30 virus particle (vp)/cell OAd-TNFα-IL2 or control media. After another 24-hour culture, T cells or control media were added. Cell index was recorded every 20 minutes. For coculture assay, tumor cells were seeded in 48-well plates and infected either with control media or 30 virus particle vp/cell of OAd or OAd-TNFα-IL2. After 24 hours, either meso-CAR T cells or control media were added at the 1:1 of effector:target ratio. The expression of an activation marker CD69 on T cells was analyzed at 72 hours. Total T cell number was determined at day 5 by flow cytometry (FCM) using CountBright fluorescent beads (Invitrogen).

Study Approval

The University of Pennsylvania Institutional Animal Care and Use Committee approved all animal experiments and all animal procedures were performed in animal facility at the University of Pennsylvania in accordance with Federal and Institutional Animal Care and Use Committee requirements.

Mouse Experiments

NOD-SCID-γ-chain−/− (NSG) and C57BL/6 (B6) (CD45.1 donor and CD45.2 recipient) mice were purchased from Jackson Laboratories. For the human pancreatic tumor xenograft model, NSG mice were subcutaneously injected with $2\times10^6$ AsPC-1 cells in total 100 μl PBS with 50% Matrigel (Corning, Corning, NY) into the right flanks. When the mean of tumor volumes reached 200 $mm^3$, mice were treated with either intratumoral injection of PBS, $0.95\times10^9$ vp OAd or $3\times10^9$ vp OAd-TNFα-IL2 in 50 μl PBS followed by intravenous injection of either PBS, $1\times10^6$ meso-CAR T cells or control h19-CAR T cells at day 3 after OAd injection ($0.95\times10^9$ vp of OAd is equivalent to $3\times10^9$ vp of OAd-TNFα-IL2 in the plaque formation unit). For the syngeneic mouse PDA tumor engrafted model, B6 mice were subcutaneously injected with $5\times10^5$ PDA7940b cells in 100 μl PBS in the right flanks. Established PDA7940b tumors were treated either with intratumoral injection of PBS, $1\times10^9$ virus particle of control adenovirus (Ad-luc) or 1:1 mixture of Ad-mTNFα and Ad-mIL2 (total $1\times10^9$vp) followed by intravenous injection of either PBS, $5\times10^6$ mmeso-CAR T cells or human CD19 redirected chimeric antigen receptor mouse T cells (h19-CAR T cells) at day 1 after Ad injection. Mice were preconditioned with intraperitoneal injection of 120 mg/kg cyclophosphamide (Ctx) at 24 hours before the first T cell injection. Adenovirus and CAR T cell injections were repeated four times weekly. Tumor volumes were monitored by caliper measurement.

Tumor and Peripheral Blood Analysis

Tumor dimensions were measured with calipers and the volumes were calculated; volume=length×width$^2$/2. Peripheral blood (PB) was obtained by retro-orbital bleeding or cardiac puncture and cell numbers of each subsets (CD3, CD4, CD8) were quantified using TruCount tubes (BD Biosciences, San Jose, CA). All experiments were performed in a blind, randomized fashion.

Tumor Processing for FCM

AsPC-1 tumors were mechanically diced and then pushed through a 70 μm strainer twice using a syringe plunger and washed with RPMI. PDA7940b tumors were mechanically diced and dissociated by incubating in RPMI media with 100U/ml Collagenase I (Gibco, Life technologies) and 100 U/ml Collagenase IV (Gibco, Life technologies) at 37° C. for 30 minutes. Dissociated cells were passed through a 70 μm cell strainer twice and washed with RPMI media. Cells were then used for FCM analysis.

Tumor Homogenate Preparation for Cytokine Assay

Tumor pieces were homogenized with 300 μl ice-cold PBS supplemented with protease inhibitor cocktail (Sigma-Aldrich, St. Louis, MO) in Lysing Matrix D 2 ml tubes (MP Biomedicals, Solon, OH) using FastPrep™ FP120 (Thermo Savant, Woburn, MA). Tumor homogenate was centrifuged and supernatant was analyzed by high sensitivity LUMINEX assay per manufacturer's instructions (Merck Millipore, Burlington, MA).

Immunohistochemistry and Quantification of the Staining

Immunohistochemistry (IHC) was performed on paraformaldehyde fixed and paraffin embedded samples. Tumors were cut on a microtome and stained according to the standard protocols. For adenovirus detection, sections were incubated overnight at 4° C. with rabbit anti-adenovirus type 2/5 E1A antibody (polyclonal, sc-430, Santa Cruz Biotechnology, Dallas, Tx) at 1:200 dilution, and then incubated with polymer-HRP conjugated anti-rabbit antibody (DAKO, Hamburg, Germany) followed by diaminobenzidine substrate to develop the colorimetric reaction. CD8 was stained with Rabbit anti-CD8 Ab (polyclonal, RB-9009-P0, Thermo Fisher Scientific), mesothelin was stained with mouse mesothelin Ab (Ab-1, MS-1320-50, Thermo Fisher Scientific) Stained slides were scanned by 20× magnification. The number of CD8 positive cells and mesothelin intensity were quantified with Aperio ImageScope software (Leica biosystems, Wetzlar Germany).

T Cell Trafficking Assay

CAR T cell trafficking assays were performed as previously described using click beetle luciferase green (CBG) labeled CAR T cells (Barrett D M, Human gene therapy. 2013; 24(8):717-27). Bioluminescent imaging was performed using a Xenogen IVIS-200 Spectrum camera and analyzed with LivingImage software (Caliper LifeSciences, Hopkinton, MA).

Flow Cytometry and Antibodies

For FCM analysis, antibodies specific for human CD45 (2D1) and mouse CD3 (17A2) were purchased from Affymetrix. Antibodies specific for human CD3 (OKT3), human CD4 (OKT4) human CD69 (FN50), human CD95 (DX2), mouse CD45.1 (A20), mouse CD45.2 (104), mouse CD3 (17A2), mouse CD11c (N418), mouse F4/80 (BM8) and CD80 (16-10A1) were purchased from BioLegend. Antibodies specific for human CD45 (H130), human CD8 (SKI), human CD25 (2A3), human Ki67 (B56), mouse CD45 (30-F11), mouse CD4 (RM4-5), mouse CD8a (53-6.7), mouse NK-1.1(PK136), mouse CD11b (M1/70), mouse Ly6C (AL-21), mouse Ly6G (1A8) and mouse CD86 (GL1) were purchased from BD Bioscience. An antibody specific for human-mesothelin (K1) was purchased from Covance. Expression of meso-CAR on human T cells was detected with biotinylated goat anti-mouse IgG (specific for scFv of murine origin) (Jackson ImmunoResearch, West Grove, PA). Expression of mmeso-CAR on mouse T cells was detected with biotinylated goat anti-human IgG specific for scFv of human origin) (Jackson ImmunoResearch). Cells were stained for viability with violet amine-reactive viability dye (Invitrogen, Frederick, MD). Surface markers were stained in PBS containing 2% FBS. Intracellular (nuclear) staining was performed using the Foxp3/Transcription Factor Staining Kit (Affymetrix, Santa Clara, CA) per manufacturer's instructions. Mouse tumor and spleen samples were stained after Fc blocking using purified rat anti-mouse CD16/32 antibody (BD Bioscience). All data were collected by the Fortessa LSRII cytometer (BD Biosciences, San Jose, CA) and analyzed using FlowJo ver.10 software (TreeStar, Eugene, OR).

Statistics

Statistical analysis was performed with GraphPad Prism 5 (GraphPad Software, San Diego, CA). Two-tailed Student t test was used to compare the two groups and one-way ANOVA with Tukey's post-hoc test was used to compare three or more groups. Repeated measures two-way ANOVA with Bonferroni correction was used to compare the effect of multiple levels of two factors with multiple observations at each level (for tumor volumes, luminescence and T cell engraftment data). Strength of relationship between two factors was presented as Pearson's correlation coefficient. Pearson's R values are shown. Survival curves were drawn using the Kaplan-Meier method and the difference of two curves were compared with Log-rank test. P values of $<0.05$ were considered significant.

Example 2: Combined Mesothelin-Redirected Chimeric Antigen Receptor T Cells with Cytokine-Armed Oncolytic Adenoviruses for the Treatment of Pancreatic Cancer Pancreatic ductal adenocarcinoma (PDA) is characterized by its highly immunosuppressive tumor microenvironment (TME) that can limit T cell infiltration and induce T cell hypofunction. Mesothelin-redirected CAR T cell (meso-CAR T cell) therapy has shown feasibility and some efficacy in clinical trials but antitumor efficacy remains modest. This study tested the hypothesis that combined meso-CAR T cell therapy with an oncolytic adenovirus expressing TNF-α and IL-2 (Ad5/3-E2F-D24-TNFα-IRES-IL2 or TILT-123)

would improve efficacy in syngeneic and xenogeneic mouse pancreatic tumor models. Ad5/3-E2F-D24-TNFα-IRES-IL2 enhanced the anti-tumor efficacy of human meso-CAR T cells in immune-deficient mice engrafted with human PDA and efficacy was associated with robustly increased tumor infiltrating lymphocytes (TILs) and enhanced CAR T cell function. Importantly, the combined therapy prevented metastasis while neither therapy alone prevented metastasis, indicating a systemic effect of the intratumorally injected Ad5/3-E2F-D24-TNFα-IRES-IL2 in combination with intravenously injected meso-CAR T cells. Combining Ad5/3-E2F-D24-TNFα-IRES-IL2 with meso-CAR T cells also induced mesothelin downregulation in tumors, indicating enhanced on-target CAR T cell activity. Further analyses of TILs at later phases of treatment revealed that Ki67 positive CD3+ TILs are associated with sustained tumor regression. We also evaluated this approach in a syngeneic mouse tumor model by combining adenovirus expressing murine TNF-α and murine IL-2 (Ad-mTNFα-mIL2) and newly established mouse CAR T cells. This approach induced significant tumor regression in mice engrafted with highly immunosuppressive PDA tumors. In contrast, multiple dosing of CAR T cells failed to suppress tumor growth. Ad-mTNFα-mIL2 increased both CAR T cell and host T cell infiltration to the tumor and altered host tumor immune status with M1 polarization of macrophages and increased dendritic cell maturation. These findings indicate that combining cytokine armed-oncolytic adenovirus to enhance the efficacy of CAR T cells is a promising approach to overcome the immunosuppressive TME by inducing both CAR-dependent and CAR-independent host immunity for the treatment of PDA.

EQUIVALENTS

The disclosures of each and every patent, patent application, and publication cited herein are hereby incorporated herein by reference in their entirety. While this invention has been disclosed with reference to specific aspects, it is apparent that other aspects and variations of this invention may be devised by others skilled in the art without departing from the true spirit and scope of the invention. The appended claims are intended to be construed to include all such aspects and equivalent variations.

What is claimed is:

1. A method of treating a mesothelin expressing solid tumor in a subject in need thereof, the method comprising administering a therapeutically effective amount of T cells that express a chimeric antigen receptor (CAR) molecule that binds to mesothelin ("mesothelin CAR-expressing cells") to the subject, and administering a chimeric serotype 5/3 oncolytic adenovirus comprising a nucleic acid molecule encoding a TNFα molecule and an IL-2 molecule to the subject, thereby treating the mesothelin expressing solid tumor, wherein the nucleic acid molecule comprises the sequence of SEQ ID NO: 612 and 614, wherein the subject is an immunocompetent human subject, wherein the CAR comprises the amino acid sequence of SEQ ID NO: 67; SEQ ID NO: 73, SEQ ID NO: 278, SEQ ID NO: 63, SEQ ID NO: 64, SEQ ID NO: 65, SEQ ID NO: 66, SEQ ID NO: 68, SEQ ID NO: 69, SEQ ID NO: 70, SEQ ID NO: 71, SEQ ID NO: 72, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, or SEQ ID NO: 86, each with or without the signal peptide MALPVTALLLPLALLLHAARP (SEQ ID NO: 1), and wherein the mesothelin CAR-expressing cells target a cell of the mesothelin expressing solid tumor systemically; and/or prevent the cell from egressing from the mesothelin expressing solid tumor.

2. The method of claim 1, wherein the mesothelin expressing solid tumor is mesothelioma, malignant pleural mesothelioma, pancreatic cancer, or pancreatic ductal adenocarcinoma.

3. The method of claim 1, wherein:

the chimeric serotype 5/3 oncolytic adenovirus is administered about 1, 2, 3, 4, or 5 days prior to or after the administration of the therapeutically effective amount of the mesothelin CAR-expressing cells.

4. The method of claim 1, wherein (i) the therapeutically effective amount of the mesothelin CAR-expressing cells and (ii) the chimeric serotype 5/3 oncolytic adenovirus are administered for a first treatment interval, wherein the first treatment interval comprises a single dose of the therapeutically effective amount of the mesothelin CAR-expressing cells and a single dose of the chimeric serotype 5/3 oncolytic adenovirus.

5. The method of claim 4, wherein:

(i)) the first treatment interval is initiated upon administration of the single dose of the chimeric serotype 5/3 oncolytic adenovirus, and completed upon administration of the single dose of the therapeutically effective amount of the mesothelin CAR-expressing cells;

(ii) the single dose of the therapeutically effective amount of the mesothelin CAR-expressing cells is administered after the administration of the single dose of the chimeric serotype 5/3 oncolytic adenovirus;

(iii) the first treatment interval is repeated one or more times;

(iv) the first treatment interval is followed by one or more subsequent treatment intervals; or (v) the first treatment interval is followed by one or more subsequent treatment intervals and the one or more subsequent treatment intervals are different from the first treatment interval.

6. The method of claim 1, wherein:

(i) the nucleic acid molecule encoding the TNFα molecule and the nucleic acid molecule encoding the IL-2 molecule are encapsulated in a single viral particle, (ii) the nucleic acid molecule encoding the TNFα molecule and the nucleic acid molecule encoding the IL-2 molecule are disposed on a single nucleic acid molecule, or (iii) the nucleic acid molecule encoding the TNFα molecule and the nucleic acid molecule encoding the IL-2 molecule are separated by a nucleic acid molecule encoding a self-cleavage site or an internal ribosomal entry site.

7. The method of claim 1, wherein the CAR molecule that binds to mesothelin comprises: the amino acid sequence of SEQ ID NO: 67 with or without the signal peptide MALPVTALLLPLALLLHAARP (SEQ ID NO: 1).

8. The method of claim 1, wherein the CAR molecule that binds to mesothelin comprises: the amino acid sequence of SEQ ID NO: 73 with or without the signal peptide MALPVTALLLPLALLLHAARP (SEQ ID NO: 1).

9. The method of claim 1, wherein the mesothelin expressing solid tumor is a metastatic solid tumor.

* * * * *

SEQUENCE LISTING

```
<160> NUMBER OF SEQ ID NOS: 628

<210> SEQ ID NO 1
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 1

Met Ala Leu Pro Val Thr Ala Leu Leu Leu Pro Leu Ala Leu Leu Leu
1               5                   10                  15

His Ala Ala Arg Pro
            20


<210> SEQ ID NO 2
<211> LENGTH: 45
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 2

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45


<210> SEQ ID NO 3
<211> LENGTH: 230
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

<400> SEQUENCE: 3

Glu Ser Lys Tyr Gly Pro Pro Cys Pro Pro Cys Pro Ala Pro Glu Phe
1 5 10 15

Leu Gly Gly Pro Ser Val Phe Leu Phe Pro Pro Lys Pro Lys Asp Thr
20 25 30

Leu Met Ile Ser Arg Thr Pro Glu Val Thr Cys Val Val Val Asp Val
35 40 45

Ser Gln Glu Asp Pro Glu Val Gln Phe Asn Trp Tyr Val Asp Gly Val
50 55 60

Glu Val His Asn Ala Lys Thr Lys Pro Arg Glu Glu Gln Phe Asn Ser
65 70 75 80

Thr Tyr Arg Val Val Ser Val Leu Thr Val Leu His Gln Asp Trp Leu
85 90 95

Asn Gly Lys Glu Tyr Lys Cys Lys Val Ser Asn Lys Gly Leu Pro Ser
100 105 110

Ser Ile Glu Lys Thr Ile Ser Lys Ala Lys Gly Gln Pro Arg Glu Pro
115 120 125

Gln Val Tyr Thr Leu Pro Pro Ser Gln Glu Glu Met Thr Lys Asn Gln
130 135 140

Val Ser Leu Thr Cys Leu Val Lys Gly Phe Tyr Pro Ser Asp Ile Ala
145 150 155 160

Val Glu Trp Glu Ser Asn Gly Gln Pro Glu Asn Asn Tyr Lys Thr Thr
165 170 175

Pro Pro Val Leu Asp Ser Asp Gly Ser Phe Phe Leu Tyr Ser Arg Leu
180 185 190

Thr Val Asp Lys Ser Arg Trp Gln Glu Gly Asn Val Phe Ser Cys Ser
195 200 205

Val Met His Glu Ala Leu His Asn His Tyr Thr Gln Lys Ser Leu Ser
210 215 220

Leu Ser Leu Gly Lys Met
225 230

<210> SEQ ID NO 4
<211> LENGTH: 282
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 4

Arg Trp Pro Glu Ser Pro Lys Ala Gln Ala Ser Ser Val Pro Thr Ala
1 5 10 15

Gln Pro Gln Ala Glu Gly Ser Leu Ala Lys Ala Thr Thr Ala Pro Ala
20 25 30

Thr Thr Arg Asn Thr Gly Arg Gly Gly Glu Glu Lys Lys Lys Glu Lys
35 40 45

Glu Lys Glu Glu Gln Glu Glu Arg Glu Thr Lys Thr Pro Glu Cys Pro
50 55 60

Ser His Thr Gln Pro Leu Gly Val Tyr Leu Leu Thr Pro Ala Val Gln
65 70 75 80

Asp Leu Trp Leu Arg Asp Lys Ala Thr Phe Thr Cys Phe Val Val Gly
85 90 95

Ser Asp Leu Lys Asp Ala His Leu Thr Trp Glu Val Ala Gly Lys Val
100 105 110

-continued

```
Pro Thr Gly Gly Val Glu Glu Gly Leu Leu Glu Arg His Ser Asn Gly
        115                 120                 125

Ser Gln Ser Gln His Ser Arg Leu Thr Leu Pro Arg Ser Leu Trp Asn
    130                 135                 140

Ala Gly Thr Ser Val Thr Cys Thr Leu Asn His Pro Ser Leu Pro Pro
145                 150                 155                 160

Gln Arg Leu Met Ala Leu Arg Glu Pro Ala Ala Gln Ala Pro Val Lys
                165                 170                 175

Leu Ser Leu Asn Leu Leu Ala Ser Ser Asp Pro Pro Glu Ala Ala Ser
            180                 185                 190

Trp Leu Leu Cys Glu Val Ser Gly Phe Ser Pro Pro Asn Ile Leu Leu
        195                 200                 205

Met Trp Leu Glu Asp Gln Arg Glu Val Asn Thr Ser Gly Phe Ala Pro
    210                 215                 220

Ala Arg Pro Pro Pro Gln Pro Gly Ser Thr Thr Phe Trp Ala Trp Ser
225                 230                 235                 240

Val Leu Arg Val Pro Ala Pro Pro Ser Pro Gln Pro Ala Thr Tyr Thr
                245                 250                 255

Cys Val Val Ser His Glu Asp Ser Arg Thr Leu Leu Asn Ala Ser Arg
            260                 265                 270

Ser Leu Glu Val Ser Tyr Val Thr Asp His
        275                 280


<210> SEQ ID NO 5
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 5

Gly Gly Gly Gly Ser Gly Gly Gly Gly Ser
1               5                   10


<210> SEQ ID NO 6
<211> LENGTH: 24
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

Ile Tyr Ile Trp Ala Pro Leu Ala Gly Thr Cys Gly Val Leu Leu Leu
1               5                   10                  15

Ser Leu Val Ile Thr Leu Tyr Cys
            20


<210> SEQ ID NO 7
<211> LENGTH: 42
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7
```

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 8
<211> LENGTH: 48
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 8

Gln Arg Arg Lys Tyr Arg Ser Asn Lys Gly Glu Ser Pro Val Glu Pro
1               5                   10                  15

Ala Glu Pro Cys Arg Tyr Ser Cys Pro Arg Glu Glu Glu Gly Ser Thr
            20                  25                  30

Ile Pro Ile Gln Glu Asp Tyr Arg Lys Pro Glu Pro Ala Cys Ser Pro
        35                  40                  45

<210> SEQ ID NO 9
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 9

Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 10
<211> LENGTH: 112
<212> TYPE: PRT
<213> ORGANISM: Homo sapiens

<400> SEQUENCE: 10

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

-continued

```
Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110
```

<210> SEQ ID NO 11
<211> LENGTH: 1184
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 11

```
cgtgaggctc cggtgcccgt cagtgggcag agcgcacatc gcccacagtc cccgagaagt      60

tggggggagg ggtcggcaat tgaaccggtg cctagagaag gtggcgcggg gtaaactggg     120

aaagtgatgt cgtgtactgg ctccgccttt ttcccgaggg tgggggagaa ccgtatataa     180

gtgcagtagt cgccgtgaac gttctttttc gcaacgggtt tgccgccaga acacaggtaa     240

gtgccgtgtg tggttcccgc gggcctggcc tctttacggg ttatggccct tgcgtgcctt     300

gaattacttc cacctggctg cagtacgtga ttcttgatcc cgagcttcgg gttggaagtg     360

ggtgggagag ttcgaggcct tgcgcttaag gagccccttc gcctcgtgct tgagttgagg     420

cctggcctgg gcgctggggc cgccgcgtgc gaatctggtg gcaccttcgc gcctgtctcg     480

ctgctttcga taagtctcta gccatttaaa atttttgatg acctgctgcg acgctttttt     540

tctggcaaga tagtcttgta aatgcgggcc aagatctgca cactggtatt tcggtttttg     600

gggccgcggg cggcgacggg gcccgtgcgt cccagcgcac atgttcggcg aggcggggcc     660

tgcgagcgcg gccaccgaga atcggacggg ggtagtctca agctggccgg cctgctctgg     720

tgcctggcct cgcgccgccg tgtatcgccc cgccctgggc ggcaaggctg gcccggtcgg     780

caccagttgc gtgagcggaa agatggccgc ttcccggccc tgctgcaggg agctcaaaat     840

ggaggacgcg gcgctcggga gagcgggcgg gtgagtcacc cacacaaagg aaaagggcct     900

ttccgtcctc agccgtcgct tcatgtgact ccacggagta ccgggcgccg tccaggcacc     960

tcgattagtt ctcgagcttt tggagtacgt cgtctttagg ttggggggag gggtttttatg    1020

cgatggagtt tccccacact gagtgggtgg agactgaagt taggccagct tggcacttga    1080

tgtaattctc cttggaattt gccctttttg agtttggatc ttggttcatt ctcaagcctc    1140

agacagtggt tcaaagtttt tttcttccat ttcaggtgtc gtga                      1184
```

<210> SEQ ID NO 12
<211> LENGTH: 63
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 12

```
atggccctgc ctgtgacagc cctgctgctg cctctggctc tgctgctgca tgccgctaga      60
```

-continued

```
ccc                                                                  63


<210> SEQ ID NO 13
<211> LENGTH: 135
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 13

accacgacgc cagcgccgcg accaccaaca ccggcgccca ccatcgcgtc gcagcccctg     60

tccctgcgcc cagaggcgtg ccggccagcg gcggggggcg cagtgcacac gagggggctg    120

gacttcgcct gtgat                                                     135


<210> SEQ ID NO 14
<211> LENGTH: 690
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 14

gagagcaagt acggccctcc ctgccccct tgccctgccc ccgagttcct gggcggaccc     60

agcgtgttcc tgttcccccc caagcccaag gacaccctga tgatcagccg gacccccgag    120

gtgacctgtg tggtggtgga cgtgtcccag gaggaccccg aggtccagtt caactggtac    180

gtggacggcg tggaggtgca caacgccaag accaagcccc gggaggagca gttcaatagc    240

acctaccggg tggtgtccgt gctgaccgtg ctgcaccagg actggctgaa cggcaaggaa    300

tacaagtgta aggtgtccaa caagggcctg cccagcagca tcgagaaaac catcagcaag    360

gccaagggcc agcctcggga gccccaggtg tacaccctgc cccctagcca agaggagatg    420

accaagaacc aggtgtccct gacctgcctg gtgaagggct tctaccccag cgacatcgcc    480

gtggagtggg agagcaacgg ccagcccgag aacaactaca agaccacccc ccctgtgctg    540

gacagcgacg gcagcttctt cctgtacagc cggctgaccg tggacaagag ccggtggcag    600

gagggcaacg tctttagctg ctccgtgatg cacgaggccc tgcacaacca ctacacccag    660

aagagcctga gcctgtccct gggcaagatg                                     690


<210> SEQ ID NO 15
<211> LENGTH: 847
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 15

aggtggcccg aaagtcccaa ggcccaggca tctagtgttc ctactgcaca gccccaggca     60

gaaggcagcc tagccaaagc tactactgca cctgccacta cgcgcaatac tggccgtggc    120

ggggaggaga agaaaaagga gaaagagaaa gaagaacagg aagagaggga gaccaagacc    180

cctgaatgtc catcccatac ccagccgctg ggcgtctatc tcttgactcc cgcagtacag    240

gacttgtggc ttagagataa ggccaccttt acatgtttcg tcgtgggctc tgacctgaag    300

gatgcccatt tgacttggga ggttgccgga aaggtaccca caggggggt tgaggaaggg    360
```

ttgctggagc gccattccaa tggctctcag agccagcact caagactcac ccttccgaga 420
tccctgtgga acgccgggac ctctgtcaca tgtactctaa atcatcctag cctgccccca 480
cagcgtctga tggcccttag agagccagcc gcccaggcac cagttaagct tagcctgaat 540
ctgctcgcca gtagtgatcc cccagaggcc gccagctggc tcttatgcga agtgtccggc 600
tttagcccgc ccaacatctt gctcatgtgg ctggaggacc agcgagaagt gaacaccagc 660
ggcttcgctc cagcccggcc cccaccccag ccgggttcta ccacattctg ggcctggagt 720
gtcttaaggg tcccagcacc acctagcccc cagccagcca catacacctg tgttgtgtcc 780
catgaagata gcaggaccct gctaaatgct tctaggagtc tggaggtttc ctacgtgact 840
gaccatt 847

<210> SEQ ID NO 16
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 16
ggtggcggag gttctggagg tggaggttcc 30

<210> SEQ ID NO 17
<211> LENGTH: 72
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 17
atctacatct gggcgccctt ggccgggact tgtggggtcc ttctcctgtc actggttatc 60
accctttact gc 72

<210> SEQ ID NO 18
<211> LENGTH: 126
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 18
aaacggggca gaaagaaact cctgtatata ttcaaacaac catttatgag accagtacaa 60
actactcaag aggaagatgg ctgtagctgc cgatttccag aagaagaaga aggaggatgt 120
gaactg 126

<210> SEQ ID NO 19
<211> LENGTH: 123
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 19

-continued

```
aggagtaaga ggagcaggct cctgcacagt gactacatga acatgactcc ccgccgcccc     60

gggcccaccc gcaagcatta ccagccctat gccccaccac gcgacttcgc agcctatcgc    120

tcc                                                                  123


<210> SEQ ID NO 20
<211> LENGTH: 336
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 20

agagtgaagt tcagcaggag cgcagacgcc cccgcgtaca agcagggcca gaaccagctc     60

tataacgagc tcaatctagg acgaagagag gagtacgatg ttttggacaa gagacgtggc    120

cgggaccctg agatgggggg aaagccgaga aggaagaacc ctcaggaagg cctgtacaat    180

gaactgcaga aagataagat ggcggaggcc tacagtgaga ttgggatgaa aggcgagcgc    240

cggaggggca aggggcacga tggcctttac cagggtctca gtacagccac caaggacacc    300

tacgacgccc ttcacatgca ggccctgccc cctcgc                              336


<210> SEQ ID NO 21
<211> LENGTH: 336
<212> TYPE: DNA
<213> ORGANISM: Homo sapiens

<400> SEQUENCE: 21

agagtgaagt tcagcaggag cgcagacgcc cccgcgtacc agcagggcca gaaccagctc     60

tataacgagc tcaatctagg acgaagagag gagtacgatg ttttggacaa gagacgtggc    120

cgggaccctg agatgggggg aaagccgaga aggaagaacc ctcaggaagg cctgtacaat    180

gaactgcaga aagataagat ggcggaggcc tacagtgaga ttgggatgaa aggcgagcgc    240

cggaggggca aggggcacga tggcctttac cagggtctca gtacagccac caaggacacc    300

tacgacgccc ttcacatgca ggccctgccc cctcgc                              336


<210> SEQ ID NO 22
<211> LENGTH: 373
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 22

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95
```

```
Asp Ser Gly Thr Tyr Leu Cys Gly Ala Ile Ser Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val Thr Thr Thr Pro Ala Pro Arg Pro Pro Thr
145                 150                 155                 160

Pro Ala Pro Thr Ile Ala Ser Gln Pro Leu Ser Leu Arg Pro Glu Ala
                165                 170                 175

Cys Arg Pro Ala Ala Gly Gly Ala Val His Thr Arg Gly Leu Asp Phe
            180                 185                 190

Ala Cys Asp Ile Tyr Ile Trp Ala Pro Leu Ala Gly Thr Cys Gly Val
        195                 200                 205

Leu Leu Leu Ser Leu Val Ile Thr Leu Tyr Cys Lys Arg Gly Arg Lys
    210                 215                 220

Lys Leu Leu Tyr Ile Phe Lys Gln Pro Phe Met Arg Pro Val Gln Thr
225                 230                 235                 240

Thr Gln Glu Glu Asp Gly Cys Ser Cys Arg Phe Pro Glu Glu Glu Glu
                245                 250                 255

Gly Gly Cys Glu Leu Arg Val Lys Phe Ser Arg Ser Ala Asp Ala Pro
            260                 265                 270

Ala Tyr Lys Gln Gly Gln Asn Gln Leu Tyr Asn Glu Leu Asn Leu Gly
        275                 280                 285

Arg Arg Glu Glu Tyr Asp Val Leu Asp Lys Arg Arg Gly Arg Asp Pro
    290                 295                 300

Glu Met Gly Gly Lys Pro Arg Arg Lys Asn Pro Gln Glu Gly Leu Tyr
305                 310                 315                 320

Asn Glu Leu Gln Lys Asp Lys Met Ala Glu Ala Tyr Ser Glu Ile Gly
                325                 330                 335

Met Lys Gly Glu Arg Arg Arg Gly Lys Gly His Asp Gly Leu Tyr Gln
            340                 345                 350

Gly Leu Ser Thr Ala Thr Lys Asp Thr Tyr Asp Ala Leu His Met Gln
        355                 360                 365

Ala Leu Pro Pro Arg
    370


<210> SEQ ID NO 23
<211> LENGTH: 1182
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 23

atggccctcc ctgtcactgc cctgcttctc cccctcgcac tcctgctcca cgccgctaga     60

ccacccggat ggtttctgga ctctccggat cgcccgtgga atcccccaac cttctcaccg    120

gcactcttgg ttgtgactga gggcgataat gcgaccttca cgtgctcgtt ctccaacacc    180

tccgaatcat tcgtgctgaa ctggtaccgc atgagcccgt caaaccagac cgacaagctc    240

gccgcgtttc cggaagatcg gtcgcaaccg ggacaggatt gtcggttccg cgtgactcaa    300

ctgccgaatg gcagagactt ccacatgagc gtggtccgcg ctaggcgaaa cgactccggg    360
```

-continued

```
acctacctgt gcggagccat ctcgctggcg cctaaggccc aaatcaaaga gagcttgagg    420

gccgaactga gagtgaccga gcgcagagct gaggtgccaa ctgcacatcc atccccatcg    480

cctcggcctg cggggcagtt tcagaccctg gtcacgacca ctccggcgcc gcgcccaccg    540

actccggccc caactatcgc gagccagccc ctgtcgctga ggccggaagc atgccgccct    600

gccgccggag gtgctgtgca tacccgggga ttggacttcg catgcgacat ctacatttgg    660

gctcctctcg ccggaacttg tggcgtgctc cttctgtccc tggtcatcac cctgtactgc    720

aagcggggtc ggaaaaagct tctgtacatt ttcaagcagc ccttcatgag gcccgtgcaa    780

accacccagg aggaggacgg ttgctcctgc cggttccccg aagaggaaga aggaggttgc    840

gagctgcgcg tgaagttctc ccggagcgcc gacgcccccg cctataagca gggccagaac    900

cagctgtaca acgaactgaa cctgggacgg cgggaagagt acgatgtgct ggacaagcgg    960

cgcggccggg accccgaaat gggcgggaag cctagaagaa agaaccctca ggaaggcctg   1020

tataacgagc tgcagaagga caagatggcc gaggcctact ccgaaattgg gatgaaggga   1080

gagcggcgga ggggaaaggg gcacgacggc ctgtaccaag gactgtccac cgccaccaag   1140

gacacatacg atgccctgca catgcaggcc cttccccctc gc                      1182
```

<210> SEQ ID NO 24
<211> LENGTH: 394
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 24

```
Met Ala Leu Pro Val Thr Ala Leu Leu Leu Pro Leu Ala Leu Leu Leu
1               5                   10                  15

His Ala Ala Arg Pro Pro Gly Trp Phe Leu Asp Ser Pro Asp Arg Pro
            20                  25                  30

Trp Asn Pro Pro Thr Phe Ser Pro Ala Leu Leu Val Val Thr Glu Gly
        35                  40                  45

Asp Asn Ala Thr Phe Thr Cys Ser Phe Ser Asn Thr Ser Glu Ser Phe
    50                  55                  60

Val Leu Asn Trp Tyr Arg Met Ser Pro Ser Asn Gln Thr Asp Lys Leu
65                  70                  75                  80

Ala Ala Phe Pro Glu Asp Arg Ser Gln Pro Gly Gln Asp Cys Arg Phe
                85                  90                  95

Arg Val Thr Gln Leu Pro Asn Gly Arg Asp Phe His Met Ser Val Val
            100                 105                 110

Arg Ala Arg Arg Asn Asp Ser Gly Thr Tyr Leu Cys Gly Ala Ile Ser
        115                 120                 125

Leu Ala Pro Lys Ala Gln Ile Lys Glu Ser Leu Arg Ala Glu Leu Arg
    130                 135                 140

Val Thr Glu Arg Arg Ala Glu Val Pro Thr Ala His Pro Ser Pro Ser
145                 150                 155                 160

Pro Arg Pro Ala Gly Gln Phe Gln Thr Leu Val Thr Thr Thr Pro Ala
                165                 170                 175

Pro Arg Pro Pro Thr Pro Ala Pro Thr Ile Ala Ser Gln Pro Leu Ser
            180                 185                 190

Leu Arg Pro Glu Ala Cys Arg Pro Ala Ala Gly Gly Ala Val His Thr
        195                 200                 205
```

-continued

```
Arg Gly Leu Asp Phe Ala Cys Asp Ile Tyr Ile Trp Ala Pro Leu Ala
    210                 215                 220

Gly Thr Cys Gly Val Leu Leu Leu Ser Leu Val Ile Thr Leu Tyr Cys
225                 230                 235                 240

Lys Arg Gly Arg Lys Lys Leu Leu Tyr Ile Phe Lys Gln Pro Phe Met
                245                 250                 255

Arg Pro Val Gln Thr Thr Gln Glu Glu Asp Gly Cys Ser Cys Arg Phe
            260                 265                 270

Pro Glu Glu Glu Glu Gly Gly Cys Glu Leu Arg Val Lys Phe Ser Arg
        275                 280                 285

Ser Ala Asp Ala Pro Ala Tyr Lys Gln Gly Gln Asn Gln Leu Tyr Asn
    290                 295                 300

Glu Leu Asn Leu Gly Arg Arg Glu Glu Tyr Asp Val Leu Asp Lys Arg
305                 310                 315                 320

Arg Gly Arg Asp Pro Glu Met Gly Gly Lys Pro Arg Arg Lys Asn Pro
                325                 330                 335

Gln Glu Gly Leu Tyr Asn Glu Leu Gln Lys Asp Lys Met Ala Glu Ala
            340                 345                 350

Tyr Ser Glu Ile Gly Met Lys Gly Glu Arg Arg Arg Gly Lys Gly His
        355                 360                 365

Asp Gly Leu Tyr Gln Gly Leu Ser Thr Ala Thr Lys Asp Thr Tyr Asp
    370                 375                 380

Ala Leu His Met Gln Ala Leu Pro Pro Arg
385                 390
```

<210> SEQ ID NO 25
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 25

```
Gly Gly Gly Gly Ser
1               5
```

<210> SEQ ID NO 26
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: SITE
<222> LOCATION: (1)..(30)
<223> OTHER INFORMATION: /note="This sequence may encompass 1-6 'Gly Gly Gly Gly Ser' repeating units"
<220> FEATURE:
<221> NAME/KEY: source
<223> OTHER INFORMATION: /note="See specification as filed for detailed description of substitutions and preferred embodiments"

<400> SEQUENCE: 26

```
Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30
```

<210> SEQ ID NO 27
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 27

Gly Gly Gly Gly Ser Gly Gly Gly Gly Ser Gly Gly Gly Gly Ser Gly
1 5 10 15

Gly Gly Gly Ser
20

<210> SEQ ID NO 28
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 28

Gly Gly Gly Gly Ser Gly Gly Gly Gly Ser Gly Gly Gly Gly Ser
1 5 10 15

<210> SEQ ID NO 29
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 29

Gly Gly Gly Ser
1

<210> SEQ ID NO 30
<211> LENGTH: 5000
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: misc_feature
<222> LOCATION: (1)..(5000)
<223> OTHER INFORMATION: /note="This sequence may encompass 50-5000 nucleotides"
<220> FEATURE:
<221> NAME/KEY: source
<223> OTHER INFORMATION: /note="See specification as filed for detailed description of substitutions and preferred embodiments"

<400> SEQUENCE: 30
aaaaaaaaaa aaaaaaaaaa aaaaaaaaaa aaaaaaaaaa aaaaaaaaaa aaaaaaaaaa 60
aaaaaaaaaa aaaaaaaaaa aaaaaaaaaa aaaaaaaaaa aaaaaaaaaa aaaaaaaaaa 120
aaaaaaaaaa aaaaaaaaaa aaaaaaaaaa aaaaaaaaaa aaaaaaaaaa aaaaaaaaaa 180
aaaaaaaaaa aaaaaaaaaa aaaaaaaaaa aaaaaaaaaa aaaaaaaaaa aaaaaaaaaa 240
aaaaaaaaaa aaaaaaaaaa aaaaaaaaaa aaaaaaaaaa aaaaaaaaaa aaaaaaaaaa 300
aaaaaaaaaa aaaaaaaaaa aaaaaaaaaa aaaaaaaaaa aaaaaaaaaa aaaaaaaaaa 360

-continued

```
aaaaaaaaaa aaaaaaaaaa aaaaaaaaaa aaaaaaaaaa aaaaaaaaaa aaaaaaaaaa    420
aaaaaaaaaa aaaaaaaaaa aaaaaaaaaa aaaaaaaaaa aaaaaaaaaa aaaaaaaaaa    480
aaaaaaaaaa aaaaaaaaaa aaaaaaaaaa aaaaaaaaaa aaaaaaaaaa aaaaaaaaaa    540
aaaaaaaaaa aaaaaaaaaa aaaaaaaaaa aaaaaaaaaa aaaaaaaaaa aaaaaaaaaa    600
aaaaaaaaaa aaaaaaaaaa aaaaaaaaaa aaaaaaaaaa aaaaaaaaaa aaaaaaaaaa    660
aaaaaaaaaa aaaaaaaaaa aaaaaaaaaa aaaaaaaaaa aaaaaaaaaa aaaaaaaaaa    720
aaaaaaaaaa aaaaaaaaaa aaaaaaaaaa aaaaaaaaaa aaaaaaaaaa aaaaaaaaaa    780
aaaaaaaaaa aaaaaaaaaa aaaaaaaaaa aaaaaaaaaa aaaaaaaaaa aaaaaaaaaa    840
aaaaaaaaaa aaaaaaaaaa aaaaaaaaaa aaaaaaaaaa aaaaaaaaaa aaaaaaaaaa    900
aaaaaaaaaa aaaaaaaaaa aaaaaaaaaa aaaaaaaaaa aaaaaaaaaa aaaaaaaaaa    960
aaaaaaaaaa aaaaaaaaaa aaaaaaaaaa aaaaaaaaaa aaaaaaaaaa aaaaaaaaaa   1020
aaaaaaaaaa aaaaaaaaaa aaaaaaaaaa aaaaaaaaaa aaaaaaaaaa aaaaaaaaaa   1080
aaaaaaaaaa aaaaaaaaaa aaaaaaaaaa aaaaaaaaaa aaaaaaaaaa aaaaaaaaaa   1140
aaaaaaaaaa aaaaaaaaaa aaaaaaaaaa aaaaaaaaaa aaaaaaaaaa aaaaaaaaaa   1200
aaaaaaaaaa aaaaaaaaaa aaaaaaaaaa aaaaaaaaaa aaaaaaaaaa aaaaaaaaaa   1260
aaaaaaaaaa aaaaaaaaaa aaaaaaaaaa aaaaaaaaaa aaaaaaaaaa aaaaaaaaaa   1320
aaaaaaaaaa aaaaaaaaaa aaaaaaaaaa aaaaaaaaaa aaaaaaaaaa aaaaaaaaaa   1380
aaaaaaaaaa aaaaaaaaaa aaaaaaaaaa aaaaaaaaaa aaaaaaaaaa aaaaaaaaaa   1440
aaaaaaaaaa aaaaaaaaaa aaaaaaaaaa aaaaaaaaaa aaaaaaaaaa aaaaaaaaaa   1500
aaaaaaaaaa aaaaaaaaaa aaaaaaaaaa aaaaaaaaaa aaaaaaaaaa aaaaaaaaaa   1560
aaaaaaaaaa aaaaaaaaaa aaaaaaaaaa aaaaaaaaaa aaaaaaaaaa aaaaaaaaaa   1620
aaaaaaaaaa aaaaaaaaaa aaaaaaaaaa aaaaaaaaaa aaaaaaaaaa aaaaaaaaaa   1680
aaaaaaaaaa aaaaaaaaaa aaaaaaaaaa aaaaaaaaaa aaaaaaaaaa aaaaaaaaaa   1740
aaaaaaaaaa aaaaaaaaaa aaaaaaaaaa aaaaaaaaaa aaaaaaaaaa aaaaaaaaaa   1800
aaaaaaaaaa aaaaaaaaaa aaaaaaaaaa aaaaaaaaaa aaaaaaaaaa aaaaaaaaaa   1860
aaaaaaaaaa aaaaaaaaaa aaaaaaaaaa aaaaaaaaaa aaaaaaaaaa aaaaaaaaaa   1920
aaaaaaaaaa aaaaaaaaaa aaaaaaaaaa aaaaaaaaaa aaaaaaaaaa aaaaaaaaaa   1980
aaaaaaaaaa aaaaaaaaaa aaaaaaaaaa aaaaaaaaaa aaaaaaaaaa aaaaaaaaaa   2040
aaaaaaaaaa aaaaaaaaaa aaaaaaaaaa aaaaaaaaaa aaaaaaaaaa aaaaaaaaaa   2100
aaaaaaaaaa aaaaaaaaaa aaaaaaaaaa aaaaaaaaaa aaaaaaaaaa aaaaaaaaaa   2160
aaaaaaaaaa aaaaaaaaaa aaaaaaaaaa aaaaaaaaaa aaaaaaaaaa aaaaaaaaaa   2220
aaaaaaaaaa aaaaaaaaaa aaaaaaaaaa aaaaaaaaaa aaaaaaaaaa aaaaaaaaaa   2280
aaaaaaaaaa aaaaaaaaaa aaaaaaaaaa aaaaaaaaaa aaaaaaaaaa aaaaaaaaaa   2340
aaaaaaaaaa aaaaaaaaaa aaaaaaaaaa aaaaaaaaaa aaaaaaaaaa aaaaaaaaaa   2400
aaaaaaaaaa aaaaaaaaaa aaaaaaaaaa aaaaaaaaaa aaaaaaaaaa aaaaaaaaaa   2460
aaaaaaaaaa aaaaaaaaaa aaaaaaaaaa aaaaaaaaaa aaaaaaaaaa aaaaaaaaaa   2520
aaaaaaaaaa aaaaaaaaaa aaaaaaaaaa aaaaaaaaaa aaaaaaaaaa aaaaaaaaaa   2580
aaaaaaaaaa aaaaaaaaaa aaaaaaaaaa aaaaaaaaaa aaaaaaaaaa aaaaaaaaaa   2640
aaaaaaaaaa aaaaaaaaaa aaaaaaaaaa aaaaaaaaaa aaaaaaaaaa aaaaaaaaaa   2700
```

-continued

```
aaaaaaaaaa aaaaaaaaaa aaaaaaaaaa aaaaaaaaaa aaaaaaaaaa aaaaaaaaaa   2760
aaaaaaaaaa aaaaaaaaaa aaaaaaaaaa aaaaaaaaaa aaaaaaaaaa aaaaaaaaaa   2820
aaaaaaaaaa aaaaaaaaaa aaaaaaaaaa aaaaaaaaaa aaaaaaaaaa aaaaaaaaaa   2880
aaaaaaaaaa aaaaaaaaaa aaaaaaaaaa aaaaaaaaaa aaaaaaaaaa aaaaaaaaaa   2940
aaaaaaaaaa aaaaaaaaaa aaaaaaaaaa aaaaaaaaaa aaaaaaaaaa aaaaaaaaaa   3000
aaaaaaaaaa aaaaaaaaaa aaaaaaaaaa aaaaaaaaaa aaaaaaaaaa aaaaaaaaaa   3060
aaaaaaaaaa aaaaaaaaaa aaaaaaaaaa aaaaaaaaaa aaaaaaaaaa aaaaaaaaaa   3120
aaaaaaaaaa aaaaaaaaaa aaaaaaaaaa aaaaaaaaaa aaaaaaaaaa aaaaaaaaaa   3180
aaaaaaaaaa aaaaaaaaaa aaaaaaaaaa aaaaaaaaaa aaaaaaaaaa aaaaaaaaaa   3240
aaaaaaaaaa aaaaaaaaaa aaaaaaaaaa aaaaaaaaaa aaaaaaaaaa aaaaaaaaaa   3300
aaaaaaaaaa aaaaaaaaaa aaaaaaaaaa aaaaaaaaaa aaaaaaaaaa aaaaaaaaaa   3360
aaaaaaaaaa aaaaaaaaaa aaaaaaaaaa aaaaaaaaaa aaaaaaaaaa aaaaaaaaaa   3420
aaaaaaaaaa aaaaaaaaaa aaaaaaaaaa aaaaaaaaaa aaaaaaaaaa aaaaaaaaaa   3480
aaaaaaaaaa aaaaaaaaaa aaaaaaaaaa aaaaaaaaaa aaaaaaaaaa aaaaaaaaaa   3540
aaaaaaaaaa aaaaaaaaaa aaaaaaaaaa aaaaaaaaaa aaaaaaaaaa aaaaaaaaaa   3600
aaaaaaaaaa aaaaaaaaaa aaaaaaaaaa aaaaaaaaaa aaaaaaaaaa aaaaaaaaaa   3660
aaaaaaaaaa aaaaaaaaaa aaaaaaaaaa aaaaaaaaaa aaaaaaaaaa aaaaaaaaaa   3720
aaaaaaaaaa aaaaaaaaaa aaaaaaaaaa aaaaaaaaaa aaaaaaaaaa aaaaaaaaaa   3780
aaaaaaaaaa aaaaaaaaaa aaaaaaaaaa aaaaaaaaaa aaaaaaaaaa aaaaaaaaaa   3840
aaaaaaaaaa aaaaaaaaaa aaaaaaaaaa aaaaaaaaaa aaaaaaaaaa aaaaaaaaaa   3900
aaaaaaaaaa aaaaaaaaaa aaaaaaaaaa aaaaaaaaaa aaaaaaaaaa aaaaaaaaaa   3960
aaaaaaaaaa aaaaaaaaaa aaaaaaaaaa aaaaaaaaaa aaaaaaaaaa aaaaaaaaaa   4020
aaaaaaaaaa aaaaaaaaaa aaaaaaaaaa aaaaaaaaaa aaaaaaaaaa aaaaaaaaaa   4080
aaaaaaaaaa aaaaaaaaaa aaaaaaaaaa aaaaaaaaaa aaaaaaaaaa aaaaaaaaaa   4140
aaaaaaaaaa aaaaaaaaaa aaaaaaaaaa aaaaaaaaaa aaaaaaaaaa aaaaaaaaaa   4200
aaaaaaaaaa aaaaaaaaaa aaaaaaaaaa aaaaaaaaaa aaaaaaaaaa aaaaaaaaaa   4260
aaaaaaaaaa aaaaaaaaaa aaaaaaaaaa aaaaaaaaaa aaaaaaaaaa aaaaaaaaaa   4320
aaaaaaaaaa aaaaaaaaaa aaaaaaaaaa aaaaaaaaaa aaaaaaaaaa aaaaaaaaaa   4380
aaaaaaaaaa aaaaaaaaaa aaaaaaaaaa aaaaaaaaaa aaaaaaaaaa aaaaaaaaaa   4440
aaaaaaaaaa aaaaaaaaaa aaaaaaaaaa aaaaaaaaaa aaaaaaaaaa aaaaaaaaaa   4500
aaaaaaaaaa aaaaaaaaaa aaaaaaaaaa aaaaaaaaaa aaaaaaaaaa aaaaaaaaaa   4560
aaaaaaaaaa aaaaaaaaaa aaaaaaaaaa aaaaaaaaaa aaaaaaaaaa aaaaaaaaaa   4620
aaaaaaaaaa aaaaaaaaaa aaaaaaaaaa aaaaaaaaaa aaaaaaaaaa aaaaaaaaaa   4680
aaaaaaaaaa aaaaaaaaaa aaaaaaaaaa aaaaaaaaaa aaaaaaaaaa aaaaaaaaaa   4740
aaaaaaaaaa aaaaaaaaaa aaaaaaaaaa aaaaaaaaaa aaaaaaaaaa aaaaaaaaaa   4800
aaaaaaaaaa aaaaaaaaaa aaaaaaaaaa aaaaaaaaaa aaaaaaaaaa aaaaaaaaaa   4860
aaaaaaaaaa aaaaaaaaaa aaaaaaaaaa aaaaaaaaaa aaaaaaaaaa aaaaaaaaaa   4920
aaaaaaaaaa aaaaaaaaaa aaaaaaaaaa aaaaaaaaaa aaaaaaaaaa aaaaaaaaaa   4980
aaaaaaaaaa aaaaaaaaaa                                               5000
```

-continued

<210> SEQ ID NO 31
<211> LENGTH: 100
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 31
tttttttttt tttttttttt tttttttttt tttttttttt tttttttttt tttttttttt 60
tttttttttt tttttttttt tttttttttt tttttttttt 100

<210> SEQ ID NO 32
<211> LENGTH: 5000
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: misc_feature
<222> LOCATION: (1)..(5000)
<223> OTHER INFORMATION: /note="This sequence may encompass 50-5000 nucleotides"

<400> SEQUENCE: 32
tttttttttt tttttttttt tttttttttt tttttttttt tttttttttt tttttttttt 60
tttttttttt tttttttttt tttttttttt tttttttttt tttttttttt tttttttttt 120
tttttttttt tttttttttt tttttttttt tttttttttt tttttttttt tttttttttt 180
tttttttttt tttttttttt tttttttttt tttttttttt tttttttttt tttttttttt 240
tttttttttt tttttttttt tttttttttt tttttttttt tttttttttt tttttttttt 300
tttttttttt tttttttttt tttttttttt tttttttttt tttttttttt tttttttttt 360
tttttttttt tttttttttt tttttttttt tttttttttt tttttttttt tttttttttt 420
tttttttttt tttttttttt tttttttttt tttttttttt tttttttttt tttttttttt 480
tttttttttt tttttttttt tttttttttt tttttttttt tttttttttt tttttttttt 540
tttttttttt tttttttttt tttttttttt tttttttttt tttttttttt tttttttttt 600
tttttttttt tttttttttt tttttttttt tttttttttt tttttttttt tttttttttt 660
tttttttttt tttttttttt tttttttttt tttttttttt tttttttttt tttttttttt 720
tttttttttt tttttttttt tttttttttt tttttttttt tttttttttt tttttttttt 780
tttttttttt tttttttttt tttttttttt tttttttttt tttttttttt tttttttttt 840
tttttttttt tttttttttt tttttttttt tttttttttt tttttttttt tttttttttt 900
tttttttttt tttttttttt tttttttttt tttttttttt tttttttttt tttttttttt 960
tttttttttt tttttttttt tttttttttt tttttttttt tttttttttt tttttttttt 1020
tttttttttt tttttttttt tttttttttt tttttttttt tttttttttt tttttttttt 1080
tttttttttt tttttttttt tttttttttt tttttttttt tttttttttt tttttttttt 1140
tttttttttt tttttttttt tttttttttt tttttttttt tttttttttt tttttttttt 1200
tttttttttt tttttttttt tttttttttt tttttttttt tttttttttt tttttttttt 1260
tttttttttt tttttttttt tttttttttt tttttttttt tttttttttt tttttttttt 1320
tttttttttt tttttttttt tttttttttt tttttttttt tttttttttt tttttttttt 1380
tttttttttt tttttttttt tttttttttt tttttttttt tttttttttt tttttttttt 1440

-continued tttttttttt tttttttttt tttttttttt tttttttttt tttttttttt tttttttttt 1500
tttttttttt tttttttttt tttttttttt tttttttttt tttttttttt tttttttttt 1560
tttttttttt tttttttttt tttttttttt tttttttttt tttttttttt tttttttttt 1620
tttttttttt tttttttttt tttttttttt tttttttttt tttttttttt tttttttttt 1680
tttttttttt tttttttttt tttttttttt tttttttttt tttttttttt tttttttttt 1740
tttttttttt tttttttttt tttttttttt tttttttttt tttttttttt tttttttttt 1800
tttttttttt tttttttttt tttttttttt tttttttttt tttttttttt tttttttttt 1860
tttttttttt tttttttttt tttttttttt tttttttttt tttttttttt tttttttttt 1920
tttttttttt tttttttttt tttttttttt tttttttttt tttttttttt tttttttttt 1980
tttttttttt tttttttttt tttttttttt tttttttttt tttttttttt tttttttttt 2040
tttttttttt tttttttttt tttttttttt tttttttttt tttttttttt tttttttttt 2100
tttttttttt tttttttttt tttttttttt tttttttttt tttttttttt tttttttttt 2160
tttttttttt tttttttttt tttttttttt tttttttttt tttttttttt tttttttttt 2220
tttttttttt tttttttttt tttttttttt tttttttttt tttttttttt tttttttttt 2280
tttttttttt tttttttttt tttttttttt tttttttttt tttttttttt tttttttttt 2340
tttttttttt tttttttttt tttttttttt tttttttttt tttttttttt tttttttttt 2400
tttttttttt tttttttttt tttttttttt tttttttttt tttttttttt tttttttttt 2460
tttttttttt tttttttttt tttttttttt tttttttttt tttttttttt tttttttttt 2520
tttttttttt tttttttttt tttttttttt tttttttttt tttttttttt tttttttttt 2580
tttttttttt tttttttttt tttttttttt tttttttttt tttttttttt tttttttttt 2640
tttttttttt tttttttttt tttttttttt tttttttttt tttttttttt tttttttttt 2700
tttttttttt tttttttttt tttttttttt tttttttttt tttttttttt tttttttttt 2760
tttttttttt tttttttttt tttttttttt tttttttttt tttttttttt tttttttttt 2820
tttttttttt tttttttttt tttttttttt tttttttttt tttttttttt tttttttttt 2880
tttttttttt tttttttttt tttttttttt tttttttttt tttttttttt tttttttttt 2940
tttttttttt tttttttttt tttttttttt tttttttttt tttttttttt tttttttttt 3000
tttttttttt tttttttttt tttttttttt tttttttttt tttttttttt tttttttttt 3060
tttttttttt tttttttttt tttttttttt tttttttttt tttttttttt tttttttttt 3120
tttttttttt tttttttttt tttttttttt tttttttttt tttttttttt tttttttttt 3180
tttttttttt tttttttttt tttttttttt tttttttttt tttttttttt tttttttttt 3240
tttttttttt tttttttttt tttttttttt tttttttttt tttttttttt tttttttttt 3300
tttttttttt tttttttttt tttttttttt tttttttttt tttttttttt tttttttttt 3360
tttttttttt tttttttttt tttttttttt tttttttttt tttttttttt tttttttttt 3420
tttttttttt tttttttttt tttttttttt tttttttttt tttttttttt tttttttttt 3480
tttttttttt tttttttttt tttttttttt tttttttttt tttttttttt tttttttttt 3540
tttttttttt tttttttttt tttttttttt tttttttttt tttttttttt tttttttttt 3600
tttttttttt tttttttttt tttttttttt tttttttttt tttttttttt tttttttttt 3660
tttttttttt tttttttttt tttttttttt tttttttttt tttttttttt tttttttttt 3720
tttttttttt tttttttttt tttttttttt tttttttttt tttttttttt tttttttttt 3780

```
tttttttttt tttttttttt tttttttttt tttttttttt tttttttttt tttttttttt   3840

tttttttttt tttttttttt tttttttttt tttttttttt tttttttttt tttttttttt   3900

tttttttttt tttttttttt tttttttttt tttttttttt tttttttttt tttttttttt   3960

tttttttttt tttttttttt tttttttttt tttttttttt tttttttttt tttttttttt   4020

tttttttttt tttttttttt tttttttttt tttttttttt tttttttttt tttttttttt   4080

tttttttttt tttttttttt tttttttttt tttttttttt tttttttttt tttttttttt   4140

tttttttttt tttttttttt tttttttttt tttttttttt tttttttttt tttttttttt   4200

tttttttttt tttttttttt tttttttttt tttttttttt tttttttttt tttttttttt   4260

tttttttttt tttttttttt tttttttttt tttttttttt tttttttttt tttttttttt   4320

tttttttttt tttttttttt tttttttttt tttttttttt tttttttttt tttttttttt   4380

tttttttttt tttttttttt tttttttttt tttttttttt tttttttttt tttttttttt   4440

tttttttttt tttttttttt tttttttttt tttttttttt tttttttttt tttttttttt   4500

tttttttttt tttttttttt tttttttttt tttttttttt tttttttttt tttttttttt   4560

tttttttttt tttttttttt tttttttttt tttttttttt tttttttttt tttttttttt   4620

tttttttttt tttttttttt tttttttttt tttttttttt tttttttttt tttttttttt   4680

tttttttttt tttttttttt tttttttttt tttttttttt tttttttttt tttttttttt   4740

tttttttttt tttttttttt tttttttttt tttttttttt tttttttttt tttttttttt   4800

tttttttttt tttttttttt tttttttttt tttttttttt tttttttttt tttttttttt   4860

tttttttttt tttttttttt tttttttttt tttttttttt tttttttttt tttttttttt   4920

tttttttttt tttttttttt tttttttttt tttttttttt tttttttttt tttttttttt   4980

tttttttttt tttttttttt                                               5000
```

<210> SEQ ID NO 33
<211> LENGTH: 5000
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: misc_feature
<222> LOCATION: (1)..(5000)
<223> OTHER INFORMATION: /note="This sequence may encompass 100-5000 nucleotides"

<400> SEQUENCE: 33

```
aaaaaaaaaa aaaaaaaaaa aaaaaaaaaa aaaaaaaaaa aaaaaaaaaa aaaaaaaaaa     60

aaaaaaaaaa aaaaaaaaaa aaaaaaaaaa aaaaaaaaaa aaaaaaaaaa aaaaaaaaaa    120

aaaaaaaaaa aaaaaaaaaa aaaaaaaaaa aaaaaaaaaa aaaaaaaaaa aaaaaaaaaa    180

aaaaaaaaaa aaaaaaaaaa aaaaaaaaaa aaaaaaaaaa aaaaaaaaaa aaaaaaaaaa    240

aaaaaaaaaa aaaaaaaaaa aaaaaaaaaa aaaaaaaaaa aaaaaaaaaa aaaaaaaaaa    300

aaaaaaaaaa aaaaaaaaaa aaaaaaaaaa aaaaaaaaaa aaaaaaaaaa aaaaaaaaaa    360

aaaaaaaaaa aaaaaaaaaa aaaaaaaaaa aaaaaaaaaa aaaaaaaaaa aaaaaaaaaa    420

aaaaaaaaaa aaaaaaaaaa aaaaaaaaaa aaaaaaaaaa aaaaaaaaaa aaaaaaaaaa    480

aaaaaaaaaa aaaaaaaaaa aaaaaaaaaa aaaaaaaaaa aaaaaaaaaa aaaaaaaaaa    540

aaaaaaaaaa aaaaaaaaaa aaaaaaaaaa aaaaaaaaaa aaaaaaaaaa aaaaaaaaaa    600
```

-continued

```
aaaaaaaaaa aaaaaaaaaa aaaaaaaaaa aaaaaaaaaa aaaaaaaaaa aaaaaaaaaa    660
aaaaaaaaaa aaaaaaaaaa aaaaaaaaaa aaaaaaaaaa aaaaaaaaaa aaaaaaaaaa    720
aaaaaaaaaa aaaaaaaaaa aaaaaaaaaa aaaaaaaaaa aaaaaaaaaa aaaaaaaaaa    780
aaaaaaaaaa aaaaaaaaaa aaaaaaaaaa aaaaaaaaaa aaaaaaaaaa aaaaaaaaaa    840
aaaaaaaaaa aaaaaaaaaa aaaaaaaaaa aaaaaaaaaa aaaaaaaaaa aaaaaaaaaa    900
aaaaaaaaaa aaaaaaaaaa aaaaaaaaaa aaaaaaaaaa aaaaaaaaaa aaaaaaaaaa    960
aaaaaaaaaa aaaaaaaaaa aaaaaaaaaa aaaaaaaaaa aaaaaaaaaa aaaaaaaaaa   1020
aaaaaaaaaa aaaaaaaaaa aaaaaaaaaa aaaaaaaaaa aaaaaaaaaa aaaaaaaaaa   1080
aaaaaaaaaa aaaaaaaaaa aaaaaaaaaa aaaaaaaaaa aaaaaaaaaa aaaaaaaaaa   1140
aaaaaaaaaa aaaaaaaaaa aaaaaaaaaa aaaaaaaaaa aaaaaaaaaa aaaaaaaaaa   1200
aaaaaaaaaa aaaaaaaaaa aaaaaaaaaa aaaaaaaaaa aaaaaaaaaa aaaaaaaaaa   1260
aaaaaaaaaa aaaaaaaaaa aaaaaaaaaa aaaaaaaaaa aaaaaaaaaa aaaaaaaaaa   1320
aaaaaaaaaa aaaaaaaaaa aaaaaaaaaa aaaaaaaaaa aaaaaaaaaa aaaaaaaaaa   1380
aaaaaaaaaa aaaaaaaaaa aaaaaaaaaa aaaaaaaaaa aaaaaaaaaa aaaaaaaaaa   1440
aaaaaaaaaa aaaaaaaaaa aaaaaaaaaa aaaaaaaaaa aaaaaaaaaa aaaaaaaaaa   1500
aaaaaaaaaa aaaaaaaaaa aaaaaaaaaa aaaaaaaaaa aaaaaaaaaa aaaaaaaaaa   1560
aaaaaaaaaa aaaaaaaaaa aaaaaaaaaa aaaaaaaaaa aaaaaaaaaa aaaaaaaaaa   1620
aaaaaaaaaa aaaaaaaaaa aaaaaaaaaa aaaaaaaaaa aaaaaaaaaa aaaaaaaaaa   1680
aaaaaaaaaa aaaaaaaaaa aaaaaaaaaa aaaaaaaaaa aaaaaaaaaa aaaaaaaaaa   1740
aaaaaaaaaa aaaaaaaaaa aaaaaaaaaa aaaaaaaaaa aaaaaaaaaa aaaaaaaaaa   1800
aaaaaaaaaa aaaaaaaaaa aaaaaaaaaa aaaaaaaaaa aaaaaaaaaa aaaaaaaaaa   1860
aaaaaaaaaa aaaaaaaaaa aaaaaaaaaa aaaaaaaaaa aaaaaaaaaa aaaaaaaaaa   1920
aaaaaaaaaa aaaaaaaaaa aaaaaaaaaa aaaaaaaaaa aaaaaaaaaa aaaaaaaaaa   1980
aaaaaaaaaa aaaaaaaaaa aaaaaaaaaa aaaaaaaaaa aaaaaaaaaa aaaaaaaaaa   2040
aaaaaaaaaa aaaaaaaaaa aaaaaaaaaa aaaaaaaaaa aaaaaaaaaa aaaaaaaaaa   2100
aaaaaaaaaa aaaaaaaaaa aaaaaaaaaa aaaaaaaaaa aaaaaaaaaa aaaaaaaaaa   2160
aaaaaaaaaa aaaaaaaaaa aaaaaaaaaa aaaaaaaaaa aaaaaaaaaa aaaaaaaaaa   2220
aaaaaaaaaa aaaaaaaaaa aaaaaaaaaa aaaaaaaaaa aaaaaaaaaa aaaaaaaaaa   2280
aaaaaaaaaa aaaaaaaaaa aaaaaaaaaa aaaaaaaaaa aaaaaaaaaa aaaaaaaaaa   2340
aaaaaaaaaa aaaaaaaaaa aaaaaaaaaa aaaaaaaaaa aaaaaaaaaa aaaaaaaaaa   2400
aaaaaaaaaa aaaaaaaaaa aaaaaaaaaa aaaaaaaaaa aaaaaaaaaa aaaaaaaaaa   2460
aaaaaaaaaa aaaaaaaaaa aaaaaaaaaa aaaaaaaaaa aaaaaaaaaa aaaaaaaaaa   2520
aaaaaaaaaa aaaaaaaaaa aaaaaaaaaa aaaaaaaaaa aaaaaaaaaa aaaaaaaaaa   2580
aaaaaaaaaa aaaaaaaaaa aaaaaaaaaa aaaaaaaaaa aaaaaaaaaa aaaaaaaaaa   2640
aaaaaaaaaa aaaaaaaaaa aaaaaaaaaa aaaaaaaaaa aaaaaaaaaa aaaaaaaaaa   2700
aaaaaaaaaa aaaaaaaaaa aaaaaaaaaa aaaaaaaaaa aaaaaaaaaa aaaaaaaaaa   2760
aaaaaaaaaa aaaaaaaaaa aaaaaaaaaa aaaaaaaaaa aaaaaaaaaa aaaaaaaaaa   2820
aaaaaaaaaa aaaaaaaaaa aaaaaaaaaa aaaaaaaaaa aaaaaaaaaa aaaaaaaaaa   2880
aaaaaaaaaa aaaaaaaaaa aaaaaaaaaa aaaaaaaaaa aaaaaaaaaa aaaaaaaaaa   2940
aaaaaaaaaa aaaaaaaaaa aaaaaaaaaa aaaaaaaaaa aaaaaaaaaa aaaaaaaaaa   3000
```

```
aaaaaaaaaa aaaaaaaaaa aaaaaaaaaa aaaaaaaaaa aaaaaaaaaa aaaaaaaaaa   3060

aaaaaaaaaa aaaaaaaaaa aaaaaaaaaa aaaaaaaaaa aaaaaaaaaa aaaaaaaaaa   3120

aaaaaaaaaa aaaaaaaaaa aaaaaaaaaa aaaaaaaaaa aaaaaaaaaa aaaaaaaaaa   3180

aaaaaaaaaa aaaaaaaaaa aaaaaaaaaa aaaaaaaaaa aaaaaaaaaa aaaaaaaaaa   3240

aaaaaaaaaa aaaaaaaaaa aaaaaaaaaa aaaaaaaaaa aaaaaaaaaa aaaaaaaaaa   3300

aaaaaaaaaa aaaaaaaaaa aaaaaaaaaa aaaaaaaaaa aaaaaaaaaa aaaaaaaaaa   3360

aaaaaaaaaa aaaaaaaaaa aaaaaaaaaa aaaaaaaaaa aaaaaaaaaa aaaaaaaaaa   3420

aaaaaaaaaa aaaaaaaaaa aaaaaaaaaa aaaaaaaaaa aaaaaaaaaa aaaaaaaaaa   3480

aaaaaaaaaa aaaaaaaaaa aaaaaaaaaa aaaaaaaaaa aaaaaaaaaa aaaaaaaaaa   3540

aaaaaaaaaa aaaaaaaaaa aaaaaaaaaa aaaaaaaaaa aaaaaaaaaa aaaaaaaaaa   3600

aaaaaaaaaa aaaaaaaaaa aaaaaaaaaa aaaaaaaaaa aaaaaaaaaa aaaaaaaaaa   3660

aaaaaaaaaa aaaaaaaaaa aaaaaaaaaa aaaaaaaaaa aaaaaaaaaa aaaaaaaaaa   3720

aaaaaaaaaa aaaaaaaaaa aaaaaaaaaa aaaaaaaaaa aaaaaaaaaa aaaaaaaaaa   3780

aaaaaaaaaa aaaaaaaaaa aaaaaaaaaa aaaaaaaaaa aaaaaaaaaa aaaaaaaaaa   3840

aaaaaaaaaa aaaaaaaaaa aaaaaaaaaa aaaaaaaaaa aaaaaaaaaa aaaaaaaaaa   3900

aaaaaaaaaa aaaaaaaaaa aaaaaaaaaa aaaaaaaaaa aaaaaaaaaa aaaaaaaaaa   3960

aaaaaaaaaa aaaaaaaaaa aaaaaaaaaa aaaaaaaaaa aaaaaaaaaa aaaaaaaaaa   4020

aaaaaaaaaa aaaaaaaaaa aaaaaaaaaa aaaaaaaaaa aaaaaaaaaa aaaaaaaaaa   4080

aaaaaaaaaa aaaaaaaaaa aaaaaaaaaa aaaaaaaaaa aaaaaaaaaa aaaaaaaaaa   4140

aaaaaaaaaa aaaaaaaaaa aaaaaaaaaa aaaaaaaaaa aaaaaaaaaa aaaaaaaaaa   4200

aaaaaaaaaa aaaaaaaaaa aaaaaaaaaa aaaaaaaaaa aaaaaaaaaa aaaaaaaaaa   4260

aaaaaaaaaa aaaaaaaaaa aaaaaaaaaa aaaaaaaaaa aaaaaaaaaa aaaaaaaaaa   4320

aaaaaaaaaa aaaaaaaaaa aaaaaaaaaa aaaaaaaaaa aaaaaaaaaa aaaaaaaaaa   4380

aaaaaaaaaa aaaaaaaaaa aaaaaaaaaa aaaaaaaaaa aaaaaaaaaa aaaaaaaaaa   4440

aaaaaaaaaa aaaaaaaaaa aaaaaaaaaa aaaaaaaaaa aaaaaaaaaa aaaaaaaaaa   4500

aaaaaaaaaa aaaaaaaaaa aaaaaaaaaa aaaaaaaaaa aaaaaaaaaa aaaaaaaaaa   4560

aaaaaaaaaa aaaaaaaaaa aaaaaaaaaa aaaaaaaaaa aaaaaaaaaa aaaaaaaaaa   4620

aaaaaaaaaa aaaaaaaaaa aaaaaaaaaa aaaaaaaaaa aaaaaaaaaa aaaaaaaaaa   4680

aaaaaaaaaa aaaaaaaaaa aaaaaaaaaa aaaaaaaaaa aaaaaaaaaa aaaaaaaaaa   4740

aaaaaaaaaa aaaaaaaaaa aaaaaaaaaa aaaaaaaaaa aaaaaaaaaa aaaaaaaaaa   4800

aaaaaaaaaa aaaaaaaaaa aaaaaaaaaa aaaaaaaaaa aaaaaaaaaa aaaaaaaaaa   4860

aaaaaaaaaa aaaaaaaaaa aaaaaaaaaa aaaaaaaaaa aaaaaaaaaa aaaaaaaaaa   4920

aaaaaaaaaa aaaaaaaaaa aaaaaaaaaa aaaaaaaaaa aaaaaaaaaa aaaaaaaaaa   4980

aaaaaaaaaa aaaaaaaaaa                                               5000
```

```
<210> SEQ ID NO 34
<211> LENGTH: 400
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
```

```
<221> NAME/KEY: misc_feature
<222> LOCATION: (1)..(400)
<223> OTHER INFORMATION: /note="This sequence may encompass 100-400
      nucleotides"
<220> FEATURE:
<221> NAME/KEY: source
<223> OTHER INFORMATION: /note="See specification as filed for detailed
      description of substitutions and preferred embodiments"

<400> SEQUENCE: 34

aaaaaaaaaa aaaaaaaaaa aaaaaaaaaa aaaaaaaaaa aaaaaaaaaa aaaaaaaaaa     60

aaaaaaaaaa aaaaaaaaaa aaaaaaaaaa aaaaaaaaaa aaaaaaaaaa aaaaaaaaaa    120

aaaaaaaaaa aaaaaaaaaa aaaaaaaaaa aaaaaaaaaa aaaaaaaaaa aaaaaaaaaa    180

aaaaaaaaaa aaaaaaaaaa aaaaaaaaaa aaaaaaaaaa aaaaaaaaaa aaaaaaaaaa    240

aaaaaaaaaa aaaaaaaaaa aaaaaaaaaa aaaaaaaaaa aaaaaaaaaa aaaaaaaaaa    300

aaaaaaaaaa aaaaaaaaaa aaaaaaaaaa aaaaaaaaaa aaaaaaaaaa aaaaaaaaaa    360

aaaaaaaaaa aaaaaaaaaa aaaaaaaaaa aaaaaaaaaa                          400


<210> SEQ ID NO 35
<211> LENGTH: 2000
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: misc_feature
<222> LOCATION: (1)..(2000)
<223> OTHER INFORMATION: /note="This sequence may encompass 50-2000
      nucleotides"

<400> SEQUENCE: 35

aaaaaaaaaa aaaaaaaaaa aaaaaaaaaa aaaaaaaaaa aaaaaaaaaa aaaaaaaaaa     60

aaaaaaaaaa aaaaaaaaaa aaaaaaaaaa aaaaaaaaaa aaaaaaaaaa aaaaaaaaaa    120

aaaaaaaaaa aaaaaaaaaa aaaaaaaaaa aaaaaaaaaa aaaaaaaaaa aaaaaaaaaa    180

aaaaaaaaaa aaaaaaaaaa aaaaaaaaaa aaaaaaaaaa aaaaaaaaaa aaaaaaaaaa    240

aaaaaaaaaa aaaaaaaaaa aaaaaaaaaa aaaaaaaaaa aaaaaaaaaa aaaaaaaaaa    300

aaaaaaaaaa aaaaaaaaaa aaaaaaaaaa aaaaaaaaaa aaaaaaaaaa aaaaaaaaaa    360

aaaaaaaaaa aaaaaaaaaa aaaaaaaaaa aaaaaaaaaa aaaaaaaaaa aaaaaaaaaa    420

aaaaaaaaaa aaaaaaaaaa aaaaaaaaaa aaaaaaaaaa aaaaaaaaaa aaaaaaaaaa    480

aaaaaaaaaa aaaaaaaaaa aaaaaaaaaa aaaaaaaaaa aaaaaaaaaa aaaaaaaaaa    540

aaaaaaaaaa aaaaaaaaaa aaaaaaaaaa aaaaaaaaaa aaaaaaaaaa aaaaaaaaaa    600

aaaaaaaaaa aaaaaaaaaa aaaaaaaaaa aaaaaaaaaa aaaaaaaaaa aaaaaaaaaa    660

aaaaaaaaaa aaaaaaaaaa aaaaaaaaaa aaaaaaaaaa aaaaaaaaaa aaaaaaaaaa    720

aaaaaaaaaa aaaaaaaaaa aaaaaaaaaa aaaaaaaaaa aaaaaaaaaa aaaaaaaaaa    780

aaaaaaaaaa aaaaaaaaaa aaaaaaaaaa aaaaaaaaaa aaaaaaaaaa aaaaaaaaaa    840

aaaaaaaaaa aaaaaaaaaa aaaaaaaaaa aaaaaaaaaa aaaaaaaaaa aaaaaaaaaa    900

aaaaaaaaaa aaaaaaaaaa aaaaaaaaaa aaaaaaaaaa aaaaaaaaaa aaaaaaaaaa    960

aaaaaaaaaa aaaaaaaaaa aaaaaaaaaa aaaaaaaaaa aaaaaaaaaa aaaaaaaaaa   1020

aaaaaaaaaa aaaaaaaaaa aaaaaaaaaa aaaaaaaaaa aaaaaaaaaa aaaaaaaaaa   1080

aaaaaaaaaa aaaaaaaaaa aaaaaaaaaa aaaaaaaaaa aaaaaaaaaa aaaaaaaaaa   1140
```

aaaaaaaaaa aaaaaaaaaa aaaaaaaaaa aaaaaaaaaa aaaaaaaaaa aaaaaaaaaa 1200
aaaaaaaaaa aaaaaaaaaa aaaaaaaaaa aaaaaaaaaa aaaaaaaaaa aaaaaaaaaa 1260
aaaaaaaaaa aaaaaaaaaa aaaaaaaaaa aaaaaaaaaa aaaaaaaaaa aaaaaaaaaa 1320
aaaaaaaaaa aaaaaaaaaa aaaaaaaaaa aaaaaaaaaa aaaaaaaaaa aaaaaaaaaa 1380
aaaaaaaaaa aaaaaaaaaa aaaaaaaaaa aaaaaaaaaa aaaaaaaaaa aaaaaaaaaa 1440
aaaaaaaaaa aaaaaaaaaa aaaaaaaaaa aaaaaaaaaa aaaaaaaaaa aaaaaaaaaa 1500
aaaaaaaaaa aaaaaaaaaa aaaaaaaaaa aaaaaaaaaa aaaaaaaaaa aaaaaaaaaa 1560
aaaaaaaaaa aaaaaaaaaa aaaaaaaaaa aaaaaaaaaa aaaaaaaaaa aaaaaaaaaa 1620
aaaaaaaaaa aaaaaaaaaa aaaaaaaaaa aaaaaaaaaa aaaaaaaaaa aaaaaaaaaa 1680
aaaaaaaaaa aaaaaaaaaa aaaaaaaaaa aaaaaaaaaa aaaaaaaaaa aaaaaaaaaa 1740
aaaaaaaaaa aaaaaaaaaa aaaaaaaaaa aaaaaaaaaa aaaaaaaaaa aaaaaaaaaa 1800
aaaaaaaaaa aaaaaaaaaa aaaaaaaaaa aaaaaaaaaa aaaaaaaaaa aaaaaaaaaa 1860
aaaaaaaaaa aaaaaaaaaa aaaaaaaaaa aaaaaaaaaa aaaaaaaaaa aaaaaaaaaa 1920
aaaaaaaaaa aaaaaaaaaa aaaaaaaaaa aaaaaaaaaa aaaaaaaaaa aaaaaaaaaa 1980
aaaaaaaaaa aaaaaaaaaa 2000

<210> SEQ ID NO 36
<211> LENGTH: 41
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 36

Arg Ser Lys Arg Ser Arg Leu Leu His Ser Asp Tyr Met Asn Met Thr
1 5 10 15

Pro Arg Arg Pro Gly Pro Thr Arg Lys His Tyr Gln Pro Tyr Ala Pro
20 25 30

Pro Arg Asp Phe Ala Ala Tyr Arg Ser
35 40

<210> SEQ ID NO 37
<211> LENGTH: 123
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 37
aggagtaaga ggagcaggct cctgcacagt gactacatga acatgactcc ccgccgcccc 60
gggcccaccc gcaagcatta ccagccctat gccccaccac gcgacttcgc agcctatcgc 120
tcc 123

<210> SEQ ID NO 38
<211> LENGTH: 35
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 38

Thr Lys Lys Lys Tyr Ser Ser Ser Val His Asp Pro Asn Gly Glu Tyr
1               5                   10                  15

Met Phe Met Arg Ala Val Asn Thr Ala Lys Lys Ser Arg Leu Thr Asp
            20                  25                  30

Val Thr Leu
        35

<210> SEQ ID NO 39
<211> LENGTH: 244
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 39

Gln Val Gln Leu Gln Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Arg Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Glu Asp Thr Ala Val Tyr Tyr Cys
                85                  90                  95

Ala Arg Gly Arg Tyr Tyr Gly Met Asp Val Trp Gly Gln Gly Thr Met
            100                 105                 110

Val Thr Val Ser Ser Gly Gly Gly Gly Ser Gly Gly Gly Gly Ser Gly
        115                 120                 125

Gly Gly Gly Ser Gly Gly Gly Gly Ser Glu Ile Val Leu Thr Gln Ser
    130                 135                 140

Pro Ala Thr Leu Ser Leu Ser Pro Gly Glu Arg Ala Thr Ile Ser Cys
145                 150                 155                 160

Arg Ala Ser Gln Ser Val Ser Ser Asn Phe Ala Trp Tyr Gln Gln Arg
                165                 170                 175

Pro Gly Gln Ala Pro Arg Leu Leu Ile Tyr Asp Ala Ser Asn Arg Ala
            180                 185                 190

Thr Gly Ile Pro Pro Arg Phe Ser Gly Ser Gly Ser Gly Thr Asp Phe
        195                 200                 205

Thr Leu Thr Ile Ser Ser Leu Glu Pro Glu Asp Phe Ala Ala Tyr Tyr
    210                 215                 220

Cys His Gln Arg Ser Asn Trp Leu Tyr Thr Phe Gly Gln Gly Thr Lys
225                 230                 235                 240

Val Asp Ile Lys

<210> SEQ ID NO 40
<211> LENGTH: 253
<212> TYPE: PRT
<213> ORGANISM: Artificial Sequence
<220> FEATURE:
<221> NAME/KEY: source
<223> OTHER INFORMATION: /note="Description of Artificial Sequence:

Synthetic polypeptide"

<400> SEQUENCE: 40

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

Tyr Met His Trp Val Arg Gln Ala Pro Gly Gln Gly Leu Glu Trp Met
35 40 45

Gly Trp Ile Asn Pro Asn Ser Gly Gly Thr Asn Tyr Ala Gln Lys Phe
50 55 60

Gln Gly Arg Val Thr Met Thr Arg Asp Thr Ser Ile Ser Thr Ala Tyr
65 70 75 80

Met Glu Leu Ser Arg Leu Arg Ser Asp Asp Thr Ala Val Tyr Tyr Cys
85 90 95

Ala Arg Asp Leu Arg Arg Thr Val Val Thr Pro Arg Ala Tyr Tyr Gly
100 105 110

Met Asp Val Trp Gly Gln Gly Thr Thr Val Thr Val Ser Ser Gly Gly
115 120 125

Gly Gly Ser Gly Gly Gly Gly Ser Gly Gly Gly Gly Ser Gly Gly Gly
130 135 140

Gly Ser Asp Ile Gln Leu Thr Gln Ser Pro Ser Thr Leu Ser Ala Ser
145 150 155 160

Val Gly Asp Arg Val Thr Ile Thr Cys Gln Ala Ser Gln Asp Ile Ser
165 170 175

Asn Ser Leu Asn Trp Tyr Gln Gln Lys Ala Gly Lys Ala Pro Lys Leu
180 185 190

Leu Ile Tyr Asp Ala Ser Thr Leu Glu Thr Gly Val Pro Ser Arg Phe
195 200 205

Ser Gly Ser Gly Ser Gly Thr Asp Phe Ser Phe Thr Ile Ser Ser Leu
210 215 220

Gln Pro Glu Asp Ile Ala Thr Tyr Tyr Cys Gln Gln His Asp Asn Leu
225 230 235 240

Pro Leu Thr Phe Gly Gln Gly Thr Lys Val Glu Ile Lys
245 250

<210> SEQ ID NO 41
<211> LENGTH: 246
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 41

Gln Val Gln Leu Val Gln Ser Gly Ala Glu Val Lys Lys Pro Gly Ala
1 5 10 15

Pro Val Lys Val Ser Cys Lys Ala Ser Gly Tyr Thr Phe Thr Gly Tyr
20 25 30

Tyr Met His Trp Val Arg Gln Ala Pro Gly Gln Gly Leu Glu Trp Met
35 40 45

Gly Trp Ile Asn Pro Asn Ser Gly Gly Thr Asn Tyr Ala Gln Lys Phe
50 55 60

Gln Gly Arg Val Thr Met Thr Arg Asp Thr Ser Ile Ser Thr Ala Tyr
65 70 75 80

-continued

```
Met Glu Leu Ser Arg Leu Arg Ser Asp Asp Thr Ala Val Tyr Tyr Cys
                85                  90                  95

Ala Arg Gly Glu Trp Asp Gly Ser Tyr Tyr Tyr Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Gly Gly Gly Gly Ser Asp Ile Val Leu
    130                 135                 140

Thr Gln Thr Pro Ser Ser Leu Ser Ala Ser Val Gly Asp Arg Val Thr
145                 150                 155                 160

Ile Thr Cys Arg Ala Ser Gln Ser Ile Asn Thr Tyr Leu Asn Trp Tyr
                165                 170                 175

Gln His Lys Pro Gly Lys Ala Pro Lys Leu Leu Ile Tyr Ala Ala Ser
            180                 185                 190

Ser Leu Gln Ser Gly Val Pro Ser Arg Phe Ser Gly Ser Gly Ser Gly
        195                 200                 205

Thr Asp Phe Thr Leu Thr Ile Ser Ser Leu Gln Pro Glu Asp Phe Ala
    210                 215                 220

Thr Tyr Tyr Cys Gln Gln Ser Phe Ser Pro Leu Thr Phe Gly Gly Gly
225                 230                 235                 240

Thr Lys Leu Glu Ile Lys
                245


<210> SEQ ID NO 42
<211> LENGTH: 242
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 42

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met His Trp Val Arg Gln Val Pro Gly Lys Gly Leu Val Trp Val
        35                  40                  45

Ser Arg Ile Asn Thr Asp Gly Ser Thr Thr Thr Tyr Ala Asp Ser Val
    50                  55                  60

Glu Gly Arg Phe Thr Ile Ser Arg Asp Asn Ala Lys Asn Thr Leu Tyr
65                  70                  75                  80

Leu Gln Met Asn Ser Leu Arg Asp Asp Asp Thr Ala Val Tyr Tyr Cys
                85                  90                  95

Val Gly Gly His Trp Ala Val Trp Gly Gln Gly Thr Thr Val Thr Val
            100                 105                 110

Ser Ser Gly Gly Gly Gly Ser Gly Gly Gly Gly Ser Gly Gly Gly Gly
        115                 120                 125

Ser Gly Gly Gly Gly Ser Asp Ile Gln Met Thr Gln Ser Pro Ser Thr
    130                 135                 140

Leu Ser Ala Ser Val Gly Asp Arg Val Thr Ile Thr Cys Arg Ala Ser
145                 150                 155                 160

Gln Ser Ile Ser Asp Arg Leu Ala Trp Tyr Gln Gln Lys Pro Gly Lys
                165                 170                 175

Ala Pro Lys Leu Leu Ile Tyr Lys Ala Ser Ser Leu Glu Ser Gly Val
```

```
            180                 185                 190

Pro Ser Arg Phe Ser Gly Ser Gly Ser Gly Thr Glu Phe Thr Leu Thr
        195                 200                 205

Ile Ser Ser Leu Gln Pro Asp Asp Phe Ala Val Tyr Tyr Cys Gln Gln
    210                 215                 220

Tyr Gly His Leu Pro Met Tyr Thr Phe Gly Gln Gly Thr Lys Val Glu
225                 230                 235                 240

Ile Lys


<210> SEQ ID NO 43
<211> LENGTH: 241
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 43

Gln Val Gln Leu Val Gln Ser Gly Ala Glu Val Glu Lys Pro Gly Ala
1               5                   10                  15

Ser Val Lys Val Ser Cys Lys Ala Ser Gly Tyr Thr Phe Thr Asp Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Ser Gly Trp Asp Phe Asp Tyr Trp Gly Gln Gly Thr Leu Val Thr
            100                 105                 110

Val Ser Ser Gly Gly Gly Gly Ser Gly Gly Gly Gly Ser Gly Gly Gly
        115                 120                 125

Gly Ser Gly Gly Gly Gly Ser Asp Ile Val Met Thr Gln Ser Pro Ser
    130                 135                 140

Ser Leu Ser Ala Ser Val Gly Asp Arg Val Thr Ile Thr Cys Arg Ala
145                 150                 155                 160

Ser Gln Ser Ile Arg Tyr Tyr Leu Ser Trp Tyr Gln Gln Lys Pro Gly
                165                 170                 175

Lys Ala Pro Lys Leu Leu Ile Tyr Thr Ala Ser Ile Leu Gln Asn Gly
            180                 185                 190

Val Pro Ser Arg Phe Ser Gly Ser Gly Ser Gly Thr Asp Phe Thr Leu
        195                 200                 205

Thr Ile Ser Ser Leu Gln Pro Glu Asp Phe Ala Thr Tyr Tyr Cys Leu
    210                 215                 220

Gln Thr Tyr Thr Thr Pro Asp Phe Gly Pro Gly Thr Lys Val Glu Ile
225                 230                 235                 240

Lys


<210> SEQ ID NO 44
<211> LENGTH: 253
<212> TYPE: PRT
<213> ORGANISM: Artificial Sequence
<220> FEATURE:
<221> NAME/KEY: source
```

<223> OTHER INFORMATION: /note="Description of Artificial Sequence: Synthetic polypeptide"

<400> SEQUENCE: 44

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Ser Tyr
20 25 30

Tyr Met His Trp Val Arg Gln Ala Pro Gly Gln Gly Leu Glu Trp Met
35 40 45

Gly Ile Ile Asn Pro Ser Gly Gly Ser Thr Ser Tyr Ala Gln Lys Phe
50 55 60

Gln Gly Arg Val Thr Met Thr Arg Asp Thr Ser Thr Ser Thr Val Tyr
65 70 75 80

Met Glu Leu Ser Ser Leu Arg Ser Glu Asp Thr Ala Val Tyr Tyr Cys
85 90 95

Ala Arg Tyr Arg Leu Ile Ala Val Ala Gly Asp Tyr Tyr Tyr Tyr Gly
100 105 110

Met Asp Val Trp Gly Gln Gly Thr Met Val Thr Val Ser Ser Gly Gly
115 120 125

Gly Gly Ser Gly Gly Gly Gly Ser Gly Gly Gly Gly Ser Gly Gly Gly
130 135 140

Gly Ser Asp Ile Gln Met Thr Gln Ser Pro Ser Ser Val Ser Ala Ser
145 150 155 160

Val Gly Asp Arg Val Thr Ile Thr Cys Arg Ala Ser Gln Gly Val Gly
165 170 175

Arg Trp Leu Ala Trp Tyr Gln Gln Lys Pro Gly Thr Ala Pro Lys Leu
180 185 190

Leu Ile Tyr Ala Ala Ser Thr Leu Gln Ser Gly Val Pro Ser Arg Phe
195 200 205

Ser Gly Ser Gly Ser Gly Thr Asp Phe Thr Leu Thr Ile Asn Asn Leu
210 215 220

Gln Pro Glu Asp Phe Ala Thr Tyr Tyr Cys Gln Gln Ala Asn Ser Phe
225 230 235 240

Pro Leu Thr Phe Gly Gly Gly Thr Arg Leu Glu Ile Lys
245 250

<210> SEQ ID NO 45
<211> LENGTH: 250
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 45

Gln Val Gln Leu Val Gln Ser Gly Gly Gly Val Val Gln Pro Gly Arg
1 5 10 15

Ser Leu Arg Leu Ser Cys Ala Ala Ser Gly Phe Thr Phe Ser Ser Tyr
20 25 30

Ala Met His Trp Val Arg Gln Ala Pro Gly Lys Gly Leu Glu Trp Val
35 40 45

Ala Val Ile Ser Tyr Asp Gly Ser Asn Lys Tyr Tyr Ala Asp Ser Val
50 55 60

Lys Gly Arg Phe Thr Ile Ser Arg Asp Asn Ser Lys Asn Thr Leu Tyr
65 70 75 80

```
Leu Gln Met Asn Ser Leu Arg Ala Glu Asp Thr Ala Val Tyr Tyr Cys
                85                  90                  95

Ala Arg Trp Lys Val Ser Ser Ser Ser Pro Ala Phe Asp Tyr Trp Gly
            100                 105                 110

Gln Gly Thr Leu Val Thr Val Ser Ser Gly Gly Gly Gly Ser Gly Gly
        115                 120                 125

Gly Gly Ser Gly Gly Gly Gly Ser Gly Gly Gly Gly Ser Glu Ile Val
    130                 135                 140

Leu Thr Gln Ser Pro Ala Thr Leu Ser Leu Ser Pro Gly Glu Arg Ala
145                 150                 155                 160

Ile Leu Ser Cys Arg Ala Ser Gln Ser Val Tyr Thr Lys Tyr Leu Gly
                165                 170                 175

Trp Tyr Gln Gln Lys Pro Gly Gln Ala Pro Arg Leu Leu Ile Tyr Asp
            180                 185                 190

Ala Ser Thr Arg Ala Thr Gly Ile Pro Asp Arg Phe Ser Gly Ser Gly
        195                 200                 205

Ser Gly Thr Asp Phe Thr Leu Thr Ile Asn Arg Leu Glu Pro Glu Asp
    210                 215                 220

Phe Ala Val Tyr Tyr Cys Gln His Tyr Gly Gly Ser Pro Leu Ile Thr
225                 230                 235                 240

Phe Gly Gln Gly Thr Arg Leu Glu Ile Lys
                245                 250


<210> SEQ ID NO 46
<211> LENGTH: 246
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 46

Gln Val Gln Leu Gln Gln Ser Gly Ala Glu Val Lys Lys Pro Gly Ala
1               5                   10                  15

Ser Val Lys Val Ser Cys Lys Thr Ser Gly Tyr Pro Phe Thr Gly Tyr
            20                  25                  30

Ser Leu His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp His Tyr Gly Gly Asn Ser Leu Phe Tyr Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Gly Gly Gly Gly Ser Asp Ile Gln Leu Thr
    130                 135                 140

Gln Ser Pro Ser Ser Ile Ser Ala Ser Val Gly Asp Thr Val Ser Ile
145                 150                 155                 160

Thr Cys Arg Ala Ser Gln Asp Ser Gly Thr Trp Leu Ala Trp Tyr Gln
                165                 170                 175
```

```
Gln Lys Pro Gly Lys Ala Pro Asn Leu Leu Met Tyr Asp Ala Ser Thr
            180                 185                 190

Leu Glu Asp Gly Val Pro Ser Arg Phe Ser Gly Ser Ala Ser Gly Thr
        195                 200                 205

Glu Phe Thr Leu Thr Val Asn Arg Leu Gln Pro Glu Asp Ser Ala Thr
    210                 215                 220

Tyr Tyr Cys Gln Gln Tyr Asn Ser Tyr Pro Leu Thr Phe Gly Gly Gly
225                 230                 235                 240

Thr Lys Val Asp Ile Lys
                245


<210> SEQ ID NO 47
<211> LENGTH: 248
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 47

Gln Val Gln Leu Val Gln Ser Gly Ala Glu Val Lys Lys Pro Gly Ala
1               5                   10                  15

Ser Val Glu Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Gly Tyr Ala Gln Lys Phe
    50                  55                  60

Gln Gly Arg Val Thr Met Thr Arg Asp Thr Ser Thr Ser Thr Val His
65                  70                  75                  80

Met Glu Leu Ser Ser Leu Arg Ser Glu Asp Thr Ala Val Tyr Tyr Cys
                85                  90                  95

Ala Arg Gly Gly Tyr Ser Ser Ser Ser Asp Ala Phe Asp Ile Trp Gly
            100                 105                 110

Gln Gly Thr Met Val Thr Val Ser Ser Gly Gly Gly Gly Ser Gly Gly
        115                 120                 125

Gly Gly Ser Gly Gly Gly Gly Ser Gly Gly Gly Gly Ser Asp Ile Gln
    130                 135                 140

Met Thr Gln Ser Pro Pro Ser Leu Ser Ala Ser Val Gly Asp Arg Val
145                 150                 155                 160

Thr Ile Thr Cys Arg Ala Ser Gln Asp Ile Ser Ser Ala Leu Ala Trp
                165                 170                 175

Tyr Gln Gln Lys Pro Gly Thr Pro Pro Lys Leu Leu Ile Tyr Asp Ala
            180                 185                 190

Ser Ser Leu Glu Ser Gly Val Pro Ser Arg Phe Ser Gly Ser Gly Ser
        195                 200                 205

Gly Thr Asp Phe Thr Leu Thr Ile Ser Ser Leu Gln Pro Glu Asp Phe
    210                 215                 220

Ala Thr Tyr Tyr Cys Gln Gln Phe Ser Ser Tyr Pro Leu Thr Phe Gly
225                 230                 235                 240

Gly Gly Thr Arg Leu Glu Ile Lys
                245


<210> SEQ ID NO 48
<211> LENGTH: 255
<212> TYPE: PRT
```

<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 48

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Ser Tyr
20 25 30

Gly Ile Ser Trp Val Arg Gln Ala Pro Gly Gln Gly Leu Glu Trp Met
35 40 45

Gly Trp Ile Ser Ala Tyr Asn Gly Asn Thr Asn Tyr Ala Gln Lys Leu
50 55 60

Gln Gly Arg Val Thr Met Thr Thr Asp Thr Ser Thr Ser Thr Ala Tyr
65 70 75 80

Met Glu Leu Arg Ser Leu Arg Ser Asp Asp Thr Ala Val Tyr Tyr Cys
85 90 95

Ala Arg Val Ala Gly Gly Ile Tyr Tyr Tyr Tyr Gly Met Asp Val Trp
100 105 110

Gly Gln Gly Thr Thr Ile Thr Val Ser Ser Gly Gly Gly Gly Ser Gly
115 120 125

Gly Gly Gly Ser Gly Gly Gly Gly Ser Gly Gly Gly Gly Ser Asp Ile
130 135 140

Val Met Thr Gln Thr Pro Asp Ser Leu Ala Val Ser Leu Gly Glu Arg
145 150 155 160

Ala Thr Ile Ser Cys Lys Ser Ser His Ser Val Leu Tyr Asn Arg Asn
165 170 175

Asn Lys Asn Tyr Leu Ala Trp Tyr Gln Gln Lys Pro Gly Gln Pro Pro
180 185 190

Lys Leu Leu Phe Tyr Trp Ala Ser Thr Arg Lys Ser Gly Val Pro Asp
195 200 205

Arg Phe Ser Gly Ser Gly Ser Gly Thr Asp Phe Thr Leu Thr Ile Ser
210 215 220

Ser Leu Gln Pro Glu Asp Phe Ala Thr Tyr Phe Cys Gln Gln Thr Gln
225 230 235 240

Thr Phe Pro Leu Thr Phe Gly Gln Gly Thr Arg Leu Glu Ile Asn
245 250 255

<210> SEQ ID NO 49
<211> LENGTH: 241
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 49

Gln Val Gln Leu Gln Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

Tyr Met His Trp Val Arg Gln Ala Pro Gly Gln Gly Leu Glu Trp Met
35 40 45

Gly Trp Ile Asn Pro Asn Ser Gly Gly Thr Asn Tyr Ala Gln Asn Phe
50 55 60

```
Gln Gly Arg Val Thr Met Thr Arg Asp Thr Ser Ile Ser Thr Ala Tyr
65                  70                  75                  80

Met Glu Leu Arg Arg Leu Arg Ser Asp Asp Thr Ala Val Tyr Tyr Cys
                85                  90                  95

Ala Ser Gly Trp Asp Phe Asp Tyr Trp Gly Gln Gly Thr Leu Val Thr
            100                 105                 110

Val Ser Ser Gly Gly Gly Gly Ser Gly Gly Gly Gly Ser Gly Gly Gly
        115                 120                 125

Gly Ser Gly Gly Gly Gly Ser Asp Ile Arg Met Thr Gln Ser Pro Ser
    130                 135                 140

Ser Leu Ser Ala Ser Val Gly Asp Arg Val Thr Ile Thr Cys Arg Ala
145                 150                 155                 160

Ser Gln Ser Ile Arg Tyr Tyr Leu Ser Trp Tyr Gln Gln Lys Pro Gly
                165                 170                 175

Lys Ala Pro Lys Leu Leu Ile Tyr Thr Ala Ser Ile Leu Gln Asn Gly
            180                 185                 190

Val Pro Ser Arg Phe Ser Gly Ser Gly Ser Gly Thr Asp Phe Thr Leu
        195                 200                 205

Thr Ile Ser Ser Leu Gln Pro Glu Asp Phe Ala Thr Tyr Tyr Cys Leu
    210                 215                 220

Gln Thr Tyr Thr Thr Pro Asp Phe Gly Pro Gly Thr Lys Val Glu Ile
225                 230                 235                 240

Lys


<210> SEQ ID NO 50
<211> LENGTH: 246
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 50

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Arg Ile Asn Pro Asn Ser Gly Gly Thr Asn Tyr Ala Gln Lys Phe
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Thr Thr Thr Ser Tyr Ala Phe Asp Ile Trp Gly Gln Gly Thr
            100                 105                 110

Met Val Thr Val Ser Ser Gly Gly Gly Gly Ser Gly Gly Gly Gly Ser
        115                 120                 125

Gly Gly Gly Gly Ser Gly Gly Gly Gly Ser Asp Ile Gln Leu Thr Gln
    130                 135                 140

Ser Pro Ser Thr Leu Ser Ala Ser Val Gly Asp Arg Val Thr Ile Thr
145                 150                 155                 160

Cys Arg Ala Ser Gln Ser Ile Ser Thr Trp Leu Ala Trp Tyr Gln Gln
```

-continued

```
                165                 170                 175

Lys Pro Gly Lys Ala Pro Asn Leu Leu Ile Tyr Lys Ala Ser Thr Leu
            180                 185                 190

Glu Ser Gly Val Pro Ser Arg Phe Ser Gly Ser Gly Ser Gly Thr Glu
        195                 200                 205

Phe Thr Leu Thr Ile Ser Ser Leu Gln Pro Asp Asp Phe Ala Thr Tyr
    210                 215                 220

Tyr Cys Gln Gln Tyr Asn Thr Tyr Ser Pro Tyr Thr Phe Gly Gln Gly
225                 230                 235                 240

Thr Lys Leu Glu Ile Lys
                245


<210> SEQ ID NO 51
<211> LENGTH: 249
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 51

Gln Val Gln Leu Val Gln Ser Gly Gly Gly Leu Val Lys Pro Gly Gly
1               5                   10                  15

Ser Leu Arg Leu Ser Cys Glu Ala Ser Gly Phe Ile Phe Ser Asp Tyr
            20                  25                  30

Tyr Met Gly Trp Ile Arg Gln Ala Pro Gly Lys Gly Leu Glu Trp Val
        35                  40                  45

Ser Tyr Ile Gly Arg Ser Gly Ser Ser Met Tyr Tyr Ala Asp Ser Val
    50                  55                  60

Lys Gly Arg Phe Thr Phe Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Ala Ser Pro Val Val Ala Ala Thr Glu Asp Phe Gln His Trp Gly
            100                 105                 110

Gln Gly Thr Leu Val Thr Val Ser Ser Gly Gly Gly Gly Ser Gly Gly
        115                 120                 125

Gly Gly Ser Gly Gly Gly Gly Ser Gly Gly Gly Gly Ser Asp Ile Val
    130                 135                 140

Met Thr Gln Thr Pro Ala Thr Leu Ser Leu Ser Pro Gly Glu Arg Ala
145                 150                 155                 160

Thr Leu Ser Cys Arg Ala Ser Gln Ser Val Thr Ser Asn Tyr Leu Ala
                165                 170                 175

Trp Tyr Gln Gln Lys Pro Gly Gln Ala Pro Arg Leu Leu Leu Phe Gly
            180                 185                 190

Ala Ser Thr Arg Ala Thr Gly Ile Pro Asp Arg Phe Ser Gly Ser Gly
        195                 200                 205

Ser Gly Thr Asp Phe Thr Leu Thr Ile Asn Arg Leu Glu Pro Glu Asp
    210                 215                 220

Phe Ala Met Tyr Tyr Cys Gln Gln Tyr Gly Ser Ala Pro Val Thr Phe
225                 230                 235                 240

Gly Gln Gly Thr Lys Leu Glu Ile Lys
                245


<210> SEQ ID NO 52
```

<211> LENGTH: 249
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 52

Gln Val Gln Leu Val Gln Ser Gly Ala Glu Val Arg Ala Pro Gly Ala
1 5 10 15

Ser Val Lys Ile Ser Cys Lys Ala Ser Gly Phe Thr Phe Arg Gly Tyr
20 25 30

Tyr Ile His Trp Val Arg Gln Ala Pro Gly Gln Gly Leu Glu Trp Met
35 40 45

Gly Ile Ile Asn Pro Ser Gly Gly Ser Arg Ala Tyr Ala Gln Lys Phe
50 55 60

Gln Gly Arg Val Thr Met Thr Arg Asp Thr Ser Thr Ser Thr Val Tyr
65 70 75 80

Met Glu Leu Ser Ser Leu Arg Ser Asp Asp Thr Ala Met Tyr Tyr Cys
85 90 95

Ala Arg Thr Ala Ser Cys Gly Gly Asp Cys Tyr Tyr Leu Asp Tyr Trp
100 105 110

Gly Gln Gly Thr Leu Val Thr Val Ser Ser Gly Gly Gly Gly Ser Gly
115 120 125

Gly Gly Gly Ser Gly Gly Gly Gly Ser Gly Gly Gly Gly Ser Asp Ile
130 135 140

Gln Met Thr Gln Ser Pro Pro Thr Leu Ser Ala Ser Val Gly Asp Arg
145 150 155 160

Val Thr Ile Thr Cys Arg Ala Ser Glu Asn Val Asn Ile Trp Leu Ala
165 170 175

Trp Tyr Gln Gln Lys Pro Gly Lys Ala Pro Lys Leu Leu Ile Tyr Lys
180 185 190

Ser Ser Ser Leu Ala Ser Gly Val Pro Ser Arg Phe Ser Gly Ser Gly
195 200 205

Ser Gly Ala Glu Phe Thr Leu Thr Ile Ser Ser Leu Gln Pro Asp Asp
210 215 220

Phe Ala Thr Tyr Tyr Cys Gln Gln Tyr Gln Ser Tyr Pro Leu Thr Phe
225 230 235 240

Gly Gly Gly Thr Lys Val Asp Ile Lys
245

<210> SEQ ID NO 53
<211> LENGTH: 244
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 53

Gln Val Gln Leu Val Gln Ser Gly Gly Gly Leu Val Gln Pro Gly Arg
1 5 10 15

Ser Leu Arg Leu Ser Cys Ala Ala Ser Gly Phe Thr Phe Asp Asp Tyr
20 25 30

Ala Met His Trp Val Arg Gln Ala Pro Gly Lys Gly Leu Glu Trp Val
35 40 45

Ser Gly Ile Ser Trp Asn Ser Gly Ser Ile Gly Tyr Ala Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Tyr Cys
85 90 95

Ala Lys Asp Gly Ser Ser Ser Trp Ser Trp Gly Tyr Phe Asp Tyr Trp
100 105 110

Gly Gln Gly Thr Leu Val Thr Val Ser Ser Gly Gly Gly Gly Ser Gly
115 120 125

Gly Gly Gly Ser Gly Gly Gly Gly Ser Ser Ser Glu Leu Thr Gln Asp
130 135 140

Pro Ala Val Ser Val Ala Leu Gly Gln Thr Val Arg Thr Thr Cys Gln
145 150 155 160

Gly Asp Ala Leu Arg Ser Tyr Tyr Ala Ser Trp Tyr Gln Gln Lys Pro
165 170 175

Gly Gln Ala Pro Met Leu Val Ile Tyr Gly Lys Asn Asn Arg Pro Ser
180 185 190

Gly Ile Pro Asp Arg Phe Ser Gly Ser Asp Ser Gly Asp Thr Ala Ser
195 200 205

Leu Thr Ile Thr Gly Ala Gln Ala Glu Asp Glu Ala Asp Tyr Tyr Cys
210 215 220

Asn Ser Arg Asp Ser Ser Gly Tyr Pro Val Phe Gly Thr Gly Thr Lys
225 230 235 240

Val Thr Val Leu

<210> SEQ ID NO 54
<211> LENGTH: 246
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 54

Glu Val Gln Leu Val Glu Ser Gly Gly Gly Leu Val Gln Pro Gly Arg
1 5 10 15

Ser Leu Arg Leu Ser Cys Ala Ala Ser Gly Phe Thr Phe Asp Asp Tyr
20 25 30

Ala Met His Trp Val Arg Gln Ala Pro Gly Lys Gly Leu Glu Trp Val
35 40 45

Ser Gly Ile Ser Trp Asn Ser Gly Ser Thr Gly Tyr Ala Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Leu Tyr Tyr Cys
85 90 95

Ala Lys Asp Ser Ser Ser Trp Tyr Gly Gly Gly Ser Ala Phe Asp Ile
100 105 110

Trp Gly Gln Gly Thr Met Val Thr Val Ser Ser Gly Gly Gly Gly Ser
115 120 125

Gly Gly Gly Gly Ser Gly Gly Gly Gly Ser Ser Ser Glu Leu Thr Gln
130 135 140

Glu Pro Ala Val Ser Val Ala Leu Gly Gln Thr Val Arg Ile Thr Cys
145 150 155 160

```
Gln Gly Asp Ser Leu Arg Ser Tyr Tyr Ala Ser Trp Tyr Gln Gln Lys
                165                 170                 175

Pro Gly Gln Ala Pro Val Leu Val Ile Phe Gly Arg Ser Arg Arg Pro
            180                 185                 190

Ser Gly Ile Pro Asp Arg Phe Ser Gly Ser Ser Ser Gly Asn Thr Ala
        195                 200                 205

Ser Leu Ile Ile Thr Gly Ala Gln Ala Glu Asp Glu Ala Asp Tyr Tyr
    210                 215                 220

Cys Asn Ser Arg Asp Asn Thr Ala Asn His Tyr Val Phe Gly Thr Gly
225                 230                 235                 240

Thr Lys Leu Thr Val Leu
                245


<210> SEQ ID NO 55
<211> LENGTH: 246
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 55

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Thr Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Ser Ser Ser Trp Tyr Gly Gly Gly Ser Ala Phe Asp Ile
            100                 105                 110

Trp Gly Gln Gly Thr Met Val Thr Val Ser Ser Gly Gly Gly Gly Ser
        115                 120                 125

Gly Gly Gly Gly Ser Gly Gly Gly Gly Ser Ser Ser Glu Leu Thr Gln
    130                 135                 140

Asp Pro Ala Val Ser Val Ala Leu Gly Gln Thr Val Arg Ile Thr Cys
145                 150                 155                 160

Gln Gly Asp Ser Leu Arg Ser Tyr Tyr Ala Ser Trp Tyr Gln Gln Lys
                165                 170                 175

Pro Gly Gln Ala Pro Val Leu Val Ile Tyr Gly Lys Asn Asn Arg Pro
            180                 185                 190

Ser Gly Ile Pro Asp Arg Phe Ser Gly Ser Ser Ser Gly Asn Thr Ala
        195                 200                 205

Ser Leu Thr Ile Thr Gly Ala Gln Ala Glu Asp Glu Ala Asp Tyr Tyr
    210                 215                 220

Cys Asn Ser Arg Gly Ser Ser Gly Asn His Tyr Val Phe Gly Thr Gly
225                 230                 235                 240

Thr Lys Val Thr Val Leu
                245
```

<210> SEQ ID NO 56
<211> LENGTH: 251
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 56

Gln Val Gln Leu Val Gln Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Trp Met His Trp Val Arg Gln Ala Pro Gly Lys Gly Leu Val Trp Val
35 40 45

Ser Arg Ile Asn Ser Asp Gly Ser Ser Thr Ser Tyr Ala Asp Ser Val
50 55 60

Lys Gly Arg Phe Thr Ile Ser Arg Asp Asn Ala Lys Asn Thr Leu Tyr
65 70 75 80

Leu Gln Met Asn Ser Leu Arg Ala Glu Asp Thr Ala Val Tyr Tyr Cys
85 90 95

Val Arg Thr Gly Trp Val Gly Ser Tyr Tyr Tyr Tyr Met Asp Val Trp
100 105 110

Gly Lys Gly Thr Thr Val Thr Val Ser Ser Gly Gly Gly Gly Ser Gly
115 120 125

Gly Gly Gly Ser Gly Gly Gly Gly Ser Gly Gly Gly Gly Ser Glu Ile
130 135 140

Val Leu Thr Gln Ser Pro Gly Thr Leu Ser Leu Ser Pro Gly Glu Arg
145 150 155 160

Ala Thr Leu Ser Cys Arg Ala Ser Gln Ser Val Ser Ser Asn Tyr Leu
165 170 175

Ala Trp Tyr Gln Gln Lys Pro Gly Gln Pro Pro Arg Leu Leu Ile Tyr
180 185 190

Asp Val Ser Thr Arg Ala Thr Gly Ile Pro Ala Arg Phe Ser Gly Gly
195 200 205

Gly Ser Gly Thr Asp Phe Thr Leu Thr Ile Ser Ser Leu Glu Pro Glu
210 215 220

Asp Phe Ala Val Tyr Tyr Cys Gln Gln Arg Ser Asn Trp Pro Pro Trp
225 230 235 240

Thr Phe Gly Gln Gly Thr Lys Val Glu Ile Lys
245 250

<210> SEQ ID NO 57
<211> LENGTH: 250
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 57

Gln Val Gln Leu Val Gln Ser Gly Gly Gly Val Val Gln Pro Gly Arg
1 5 10 15

Ser Leu Arg Leu Ser Cys Ala Ala Ser Gly Phe Thr Phe Ser Ser Tyr
20 25 30

Gly Met His Trp Val Arg Gln Ala Pro Gly Lys Gly Leu Glu Trp Val

```
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Tyr Ser Arg Tyr Tyr Tyr Tyr Gly Met Asp Val Trp Gly
            100                 105                 110

Gln Gly Thr Thr Val Thr Val Ser Ser Gly Gly Gly Gly Ser Gly Gly
        115                 120                 125

Gly Gly Ser Gly Gly Gly Gly Ser Gly Gly Gly Gly Ser Glu Ile Val
    130                 135                 140

Met Thr Gln Ser Pro Ala Thr Leu Ser Leu Ser Pro Gly Glu Arg Ala
145                 150                 155                 160

Ile Leu Ser Cys Arg Ala Ser Gln Ser Val Tyr Thr Lys Tyr Leu Gly
                165                 170                 175

Trp Tyr Gln Gln Lys Pro Gly Gln Ala Pro Arg Leu Leu Ile Tyr Asp
            180                 185                 190

Ala Ser Thr Arg Ala Thr Gly Ile Pro Asp Arg Phe Ser Gly Ser Gly
        195                 200                 205

Ser Gly Thr Asp Phe Thr Leu Thr Ile Asn Arg Leu Glu Pro Glu Asp
    210                 215                 220

Phe Ala Val Tyr Tyr Cys Gln His Tyr Gly Gly Ser Pro Leu Ile Thr
225                 230                 235                 240

Phe Gly Gln Gly Thr Lys Val Asp Ile Lys
                245                 250


<210> SEQ ID NO 58
<211> LENGTH: 249
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 58

Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Arg Glu Ala Ala Ala Gly His Asp Trp Tyr Phe Asp Leu Trp
            100                 105                 110

Gly Arg Gly Thr Leu Val Thr Val Ser Ser Gly Gly Gly Gly Ser Gly
        115                 120                 125

Gly Gly Gly Ser Gly Gly Gly Gly Ser Gly Gly Gly Gly Ser Asp Ile
    130                 135                 140
```

-continued

Arg Val Thr Gln Ser Pro Ser Ser Leu Ser Ala Ser Val Gly Asp Arg
145 150 155 160

Val Thr Ile Thr Cys Arg Ala Ser Gln Ser Ile Ser Ser Tyr Leu Asn
165 170 175

Trp Tyr Gln Gln Lys Pro Gly Lys Ala Pro Lys Leu Leu Ile Tyr Ala
180 185 190

Ala Ser Ser Leu Gln Ser Gly Val Pro Ser Arg Phe Ser Gly Ser Gly
195 200 205

Ser Gly Thr Asp Phe Thr Leu Thr Ile Ser Ser Leu Gln Pro Glu Asp
210 215 220

Phe Ala Thr Tyr Tyr Cys Gln Gln Ser Tyr Ser Ile Pro Leu Thr Phe
225 230 235 240

Gly Gln Gly Thr Lys Val Glu Ile Lys
245

<210> SEQ ID NO 59
<211> LENGTH: 247
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 59

Gln Val Gln Leu Val Gln Ser Trp Ala Glu Val Lys Lys Pro Gly Ala
1 5 10 15

Ser Val Lys Val Ser Cys Lys Ala Ser Gly Tyr Thr Phe Thr Ser Tyr
20 25 30

Tyr Met His Trp Val Arg Gln Ala Pro Gly Gln Gly Leu Glu Trp Met
35 40 45

Gly Ile Ile Asn Pro Ser Gly Gly Ser Thr Ser Tyr Ala Gln Lys Phe
50 55 60

Gln Gly Arg Val Thr Met Thr Arg Asp Thr Ser Thr Ser Thr Val Tyr
65 70 75 80

Met Glu Leu Ser Asn Leu Arg Ser Glu Asp Thr Ala Val Tyr Tyr Cys
85 90 95

Ala Arg Ser Pro Arg Val Thr Thr Gly Tyr Phe Asp Tyr Trp Gly Gln
100 105 110

Gly Thr Leu Val Thr Val Ser Ser Gly Gly Gly Gly Ser Gly Gly Gly
115 120 125

Gly Ser Gly Gly Gly Gly Ser Gly Gly Gly Gly Ser Asp Ile Gln Leu
130 135 140

Thr Gln Ser Pro Ser Thr Leu Ser Ala Ser Val Gly Asp Arg Val Thr
145 150 155 160

Ile Thr Cys Arg Ala Ser Gln Ser Ile Ser Ser Trp Leu Ala Trp Tyr
165 170 175

Gln Gln Lys Pro Gly Lys Ala Pro Lys Leu Leu Ile Tyr Lys Ala Ser
180 185 190

Ser Leu Glu Ser Gly Val Pro Ser Arg Phe Ser Gly Ser Gly Ser Gly
195 200 205

Thr Glu Phe Thr Leu Thr Ile Ser Ser Leu Gln Pro Asp Asp Phe Ala
210 215 220

Thr Tyr Tyr Cys Gln Gln Tyr Ser Ser Tyr Pro Leu Thr Phe Gly Gly
225 230 235 240

Gly Thr Arg Leu Glu Ile Lys
245

<210> SEQ ID NO 60
<211> LENGTH: 253
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 60

Gln Val Gln Leu Val Gln Ser Gly Ala Glu Val Arg Arg Pro Gly Ala
1 5 10 15

Ser Val Lys Ile Ser Cys Arg Ala Ser Gly Asp Thr Ser Thr Arg His
20 25 30

Tyr Ile His Trp Leu Arg Gln Ala Pro Gly Gln Gly Pro Glu Trp Met
35 40 45

Gly Val Ile Asn Pro Thr Thr Gly Pro Ala Thr Gly Ser Pro Ala Tyr
50 55 60

Ala Gln Met Leu Gln Gly Arg Val Thr Met Thr Arg Asp Thr Ser Thr
65 70 75 80

Arg Thr Val Tyr Met Glu Leu Arg Ser Leu Arg Phe Glu Asp Thr Ala
85 90 95

Val Tyr Tyr Cys Ala Arg Ser Val Val Gly Arg Ser Ala Pro Tyr Tyr
100 105 110

Phe Asp Tyr Trp Gly Gln Gly Thr Leu Val Thr Val Ser Ser Gly Gly
115 120 125

Gly Gly Ser Gly Gly Gly Gly Ser Gly Gly Gly Gly Ser Gly Gly Gly
130 135 140

Gly Ser Asp Ile Gln Met Thr Gln Ser Pro Ser Ser Leu Ser Ala Ser
145 150 155 160

Val Gly Asp Arg Val Thr Ile Thr Cys Arg Ala Ser Gln Gly Ile Ser
165 170 175

Asp Tyr Ser Ala Trp Tyr Gln Gln Lys Pro Gly Lys Ala Pro Lys Leu
180 185 190

Leu Ile Tyr Ala Ala Ser Thr Leu Gln Ser Gly Val Pro Ser Arg Phe
195 200 205

Ser Gly Ser Gly Ser Gly Thr Asp Phe Thr Leu Thr Ile Ser Tyr Leu
210 215 220

Gln Ser Glu Asp Phe Ala Thr Tyr Tyr Cys Gln Gln Tyr Tyr Ser Tyr
225 230 235 240

Pro Leu Thr Phe Gly Gly Gly Thr Lys Val Asp Ile Lys
245 250

<210> SEQ ID NO 61
<211> LENGTH: 249
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 61

Gln Val Gln Leu Gln Gln Ser Gly Ala Glu Val Lys Lys Pro Gly Ala
1 5 10 15

Ser Val Lys Val Ser Cys Lys Ala Ser Gly Tyr Thr Phe Thr Asn Tyr

```
            20                  25                  30

Tyr Met His Trp Val Arg Gln Ala Pro Gly Gln Gly Leu Glu Trp Met
        35                  40                  45

Gly Ile Ile Asn Pro Ser Gly Gly Tyr Thr Thr Tyr Ala Gln Lys Phe
    50                  55                  60

Gln Gly Arg Leu Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ile Arg Ser Cys Gly Gly Asp Cys Tyr Tyr Phe Asp Asn Trp
            100                 105                 110

Gly Gln Gly Thr Leu Val Thr Val Ser Ser Gly Gly Gly Gly Ser Gly
        115                 120                 125

Gly Gly Gly Ser Gly Gly Gly Gly Ser Gly Gly Gly Gly Ser Asp Ile
    130                 135                 140

Gln Leu Thr Gln Ser Pro Ser Thr Leu Ser Ala Ser Val Gly Asp Arg
145                 150                 155                 160

Val Thr Ile Thr Cys Arg Ala Ser Glu Asn Val Asn Ile Trp Leu Ala
                165                 170                 175

Trp Tyr Gln Gln Lys Pro Gly Lys Ala Pro Lys Leu Leu Ile Tyr Lys
            180                 185                 190

Ser Ser Ser Leu Ala Ser Gly Val Pro Ser Arg Phe Ser Gly Ser Gly
        195                 200                 205

Ser Gly Ala Glu Phe Thr Leu Thr Ile Ser Ser Leu Gln Pro Asp Asp
    210                 215                 220

Phe Ala Thr Tyr Tyr Cys Gln Gln Tyr Gln Ser Tyr Pro Leu Thr Phe
225                 230                 235                 240

Gly Gly Gly Thr Lys Val Asp Ile Lys
                245


<210> SEQ ID NO 62
<211> LENGTH: 246
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 62

Gln Ile Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ala
            20                  25                  30

Gly Val His Val Gly Trp Ile Arg Gln Pro Pro Gly Lys Ala Leu Glu
        35                  40                  45

Trp Leu Ala Leu Ile Ser Trp Ala Asp Asp Lys Arg Tyr Arg Pro Ser
    50                  55                  60

Leu Arg Ser Arg Leu Asp Ile Thr Arg Val Thr Ser Lys Asp Gln Val
65                  70                  75                  80

Val Leu Ser Met Thr Asn Met Gln Pro Glu Asp Thr Ala Thr Tyr Tyr
                85                  90                  95

Cys Ala Leu Gln Gly Phe Asp Gly Tyr Glu Ala Asn Trp Gly Pro Gly
            100                 105                 110

Thr Leu Val Thr Val Ser Ser Gly Gly Gly Gly Ser Gly Gly Gly Gly
        115                 120                 125
```

Ser Gly Gly Gly Gly Ser Gly Gly Gly Gly Ser Asp Ile Val Met Thr
130 135 140

Gln Ser Pro Ser Ser Leu Ser Ala Ser Ala Gly Asp Arg Val Thr Ile
145 150 155 160

Thr Cys Arg Ala Ser Arg Gly Ile Ser Ser Ala Leu Ala Trp Tyr Gln
165 170 175

Gln Lys Pro Gly Lys Pro Pro Lys Leu Leu Ile Tyr Asp Ala Ser Ser
180 185 190

Leu Glu Ser Gly Val Pro Ser Arg Phe Ser Gly Ser Gly Ser Gly Thr
195 200 205

Asp Phe Thr Leu Thr Ile Asp Ser Leu Glu Pro Glu Asp Phe Ala Thr
210 215 220

Tyr Tyr Cys Gln Gln Ser Tyr Ser Thr Pro Trp Thr Phe Gly Gln Gly
225 230 235 240

Thr Lys Val Asp Ile Lys
245

<210> SEQ ID NO 63
<211> LENGTH: 488
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 63

Met Ala Leu Pro Val Thr Ala Leu Leu Leu Pro Leu Ala Leu Leu Leu
1 5 10 15

His Ala Ala Arg Pro Gln Val Gln Leu Gln Gln Ser Gly Ala Glu Val
20 25 30

Lys Lys Pro Gly Ala Ser Val Lys Val Ser Cys Lys Ala Ser Gly Tyr
35 40 45

Thr Phe Thr Gly Tyr Tyr Met His Trp Val Arg Gln Ala Pro Gly Gln
50 55 60

Gly Leu Glu Trp Met Gly Arg Ile Asn Pro Asn Ser Gly Gly Thr Asn
65 70 75 80

Tyr Ala Gln Lys Phe Gln Gly Arg Val Thr Met Thr Arg Asp Thr Ser
85 90 95

Ile Ser Thr Ala Tyr Met Glu Leu Ser Arg Leu Arg Ser Glu Asp Thr
100 105 110

Ala Val Tyr Tyr Cys Ala Arg Gly Arg Tyr Tyr Gly Met Asp Val Trp
115 120 125

Gly Gln Gly Thr Met Val Thr Val Ser Ser Gly Gly Gly Gly Ser Gly
130 135 140

Gly Gly Gly Ser Gly Gly Gly Gly Ser Gly Gly Gly Gly Ser Glu Ile
145 150 155 160

Val Leu Thr Gln Ser Pro Ala Thr Leu Ser Leu Ser Pro Gly Glu Arg
165 170 175

Ala Thr Ile Ser Cys Arg Ala Ser Gln Ser Val Ser Ser Asn Phe Ala
180 185 190

Trp Tyr Gln Gln Arg Pro Gly Gln Ala Pro Arg Leu Leu Ile Tyr Asp
195 200 205

Ala Ser Asn Arg Ala Thr Gly Ile Pro Pro Arg Phe Ser Gly Ser Gly
210 215 220

Ser Gly Thr Asp Phe Thr Leu Thr Ile Ser Ser Leu Glu Pro Glu Asp
225 230 235 240

Phe Ala Ala Tyr Tyr Cys His Gln Arg Ser Asn Trp Leu Tyr Thr Phe
245 250 255

Gly Gln Gly Thr Lys Val Asp Ile Lys Thr Thr Thr Pro Ala Pro Arg
260 265 270

Pro Pro Thr Pro Ala Pro Thr Ile Ala Ser Gln Pro Leu Ser Leu Arg
275 280 285

Pro Glu Ala Cys Arg Pro Ala Ala Gly Gly Ala Val His Thr Arg Gly
290 295 300

Leu Asp Phe Ala Cys Asp Ile Tyr Ile Trp Ala Pro Leu Ala Gly Thr
305 310 315 320

Cys Gly Val Leu Leu Leu Ser Leu Val Ile Thr Leu Tyr Cys Lys Arg
325 330 335

Gly Arg Lys Lys Leu Leu Tyr Ile Phe Lys Gln Pro Phe Met Arg Pro
340 345 350

Val Gln Thr Thr Gln Glu Glu Asp Gly Cys Ser Cys Arg Phe Pro Glu
355 360 365

Glu Glu Glu Gly Gly Cys Glu Leu Arg Val Lys Phe Ser Arg Ser Ala
370 375 380

Asp Ala Pro Ala Tyr Lys Gln Gly Gln Asn Gln Leu Tyr Asn Glu Leu
385 390 395 400

Asn Leu Gly Arg Arg Glu Glu Tyr Asp Val Leu Asp Lys Arg Arg Gly
405 410 415

Arg Asp Pro Glu Met Gly Gly Lys Pro Arg Arg Lys Asn Pro Gln Glu
420 425 430

Gly Leu Tyr Asn Glu Leu Gln Lys Asp Lys Met Ala Glu Ala Tyr Ser
435 440 445

Glu Ile Gly Met Lys Gly Glu Arg Arg Arg Gly Lys Gly His Asp Gly
450 455 460

Leu Tyr Gln Gly Leu Ser Thr Ala Thr Lys Asp Thr Tyr Asp Ala Leu
465 470 475 480

His Met Gln Ala Leu Pro Pro Arg
485

<210> SEQ ID NO 64
<211> LENGTH: 497
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 64

Met Ala Leu Pro Val Thr Ala Leu Leu Leu Pro Leu Ala Leu Leu Leu
1 5 10 15

His Ala Ala Arg Pro Gln Val Gln Leu Val Gln Ser Gly Ala Glu Val
20 25 30

Lys Lys Pro Gly Ala Ser Val Lys Val Ser Cys Lys Ala Ser Gly Tyr
35 40 45

Thr Phe Thr Gly Tyr Tyr Met His Trp Val Arg Gln Ala Pro Gly Gln
50 55 60

Gly Leu Glu Trp Met Gly Trp Ile Asn Pro Asn Ser Gly Gly Thr Asn
65 70 75 80

Tyr Ala Gln Lys Phe Gln Gly Arg Val Thr Met Thr Arg Asp Thr Ser

-continued

```
                85                  90                  95

Ile Ser Thr Ala Tyr Met Glu Leu Ser Arg Leu Arg Ser Asp Asp Thr
            100                 105                 110

Ala Val Tyr Tyr Cys Ala Arg Asp Leu Arg Arg Thr Val Val Thr Pro
        115                 120                 125

Arg Ala Tyr Tyr Gly Met Asp Val Trp Gly Gln Gly Thr Thr Val Thr
    130                 135                 140

Val Ser Ser Gly Gly Gly Gly Ser Gly Gly Gly Gly Ser Gly Gly Gly
145                 150                 155                 160

Gly Ser Gly Gly Gly Gly Ser Asp Ile Gln Leu Thr Gln Ser Pro Ser
                165                 170                 175

Thr Leu Ser Ala Ser Val Gly Asp Arg Val Thr Ile Thr Cys Gln Ala
            180                 185                 190

Ser Gln Asp Ile Ser Asn Ser Leu Asn Trp Tyr Gln Gln Lys Ala Gly
        195                 200                 205

Lys Ala Pro Lys Leu Leu Ile Tyr Asp Ala Ser Thr Leu Glu Thr Gly
    210                 215                 220

Val Pro Ser Arg Phe Ser Gly Ser Gly Ser Gly Thr Asp Phe Ser Phe
225                 230                 235                 240

Thr Ile Ser Ser Leu Gln Pro Glu Asp Ile Ala Thr Tyr Tyr Cys Gln
                245                 250                 255

Gln His Asp Asn Leu Pro Leu Thr Phe Gly Gln Gly Thr Lys Val Glu
            260                 265                 270

Ile Lys Thr Thr Thr Pro Ala Pro Arg Pro Pro Thr Pro Ala Pro Thr
        275                 280                 285

Ile Ala Ser Gln Pro Leu Ser Leu Arg Pro Glu Ala Cys Arg Pro Ala
    290                 295                 300

Ala Gly Gly Ala Val His Thr Arg Gly Leu Asp Phe Ala Cys Asp Ile
305                 310                 315                 320

Tyr Ile Trp Ala Pro Leu Ala Gly Thr Cys Gly Val Leu Leu Leu Ser
                325                 330                 335

Leu Val Ile Thr Leu Tyr Cys Lys Arg Gly Arg Lys Lys Leu Leu Tyr
            340                 345                 350

Ile Phe Lys Gln Pro Phe Met Arg Pro Val Gln Thr Thr Gln Glu Glu
        355                 360                 365

Asp Gly Cys Ser Cys Arg Phe Pro Glu Glu Glu Glu Gly Gly Cys Glu
    370                 375                 380

Leu Arg Val Lys Phe Ser Arg Ser Ala Asp Ala Pro Ala Tyr Lys Gln
385                 390                 395                 400

Gly Gln Asn Gln Leu Tyr Asn Glu Leu Asn Leu Gly Arg Arg Glu Glu
                405                 410                 415

Tyr Asp Val Leu Asp Lys Arg Arg Gly Arg Asp Pro Glu Met Gly Gly
            420                 425                 430

Lys Pro Arg Arg Lys Asn Pro Gln Glu Gly Leu Tyr Asn Glu Leu Gln
        435                 440                 445

Lys Asp Lys Met Ala Glu Ala Tyr Ser Glu Ile Gly Met Lys Gly Glu
    450                 455                 460

Arg Arg Arg Gly Lys Gly His Asp Gly Leu Tyr Gln Gly Leu Ser Thr
465                 470                 475                 480

Ala Thr Lys Asp Thr Tyr Asp Ala Leu His Met Gln Ala Leu Pro Pro
                485                 490                 495

Arg
```

<210> SEQ ID NO 65
<211> LENGTH: 490
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 65

```
Met Ala Leu Pro Val Thr Ala Leu Leu Leu Pro Leu Ala Leu Leu Leu
1               5                   10                  15

His Ala Ala Arg Pro Gln Val Gln Leu Val Gln Ser Gly Ala Glu Val
            20                  25                  30

Lys Lys Pro Gly Ala Pro Val Lys Val Ser Cys Lys Ala Ser Gly Tyr
        35                  40                  45

Thr Phe Thr Gly Tyr Tyr Met His Trp Val Arg Gln Ala Pro Gly Gln
    50                  55                  60

Gly Leu Glu Trp Met Gly Trp Ile Asn Pro Asn Ser Gly Gly Thr Asn
65                  70                  75                  80

Tyr Ala Gln Lys Phe Gln Gly Arg Val Thr Met Thr Arg Asp Thr Ser
                85                  90                  95

Ile Ser Thr Ala Tyr Met Glu Leu Ser Arg Leu Arg Ser Asp Asp Thr
            100                 105                 110

Ala Val Tyr Tyr Cys Ala Arg Gly Glu Trp Asp Gly Ser Tyr Tyr Tyr
        115                 120                 125

Asp Tyr Trp Gly Gln Gly Thr Leu Val Thr Val Ser Ser Gly Gly Gly
    130                 135                 140

Gly Ser Gly Gly Gly Gly Ser Gly Gly Gly Gly Ser Gly Gly Gly Gly
145                 150                 155                 160

Ser Asp Ile Val Leu Thr Gln Thr Pro Ser Ser Leu Ser Ala Ser Val
                165                 170                 175

Gly Asp Arg Val Thr Ile Thr Cys Arg Ala Ser Gln Ser Ile Asn Thr
            180                 185                 190

Tyr Leu Asn Trp Tyr Gln His Lys Pro Gly Lys Ala Pro Lys Leu Leu
        195                 200                 205

Ile Tyr Ala Ala Ser Ser Leu Gln Ser Gly Val Pro Ser Arg Phe Ser
    210                 215                 220

Gly Ser Gly Ser Gly Thr Asp Phe Thr Leu Thr Ile Ser Ser Leu Gln
225                 230                 235                 240

Pro Glu Asp Phe Ala Thr Tyr Tyr Cys Gln Gln Ser Phe Ser Pro Leu
                245                 250                 255

Thr Phe Gly Gly Gly Thr Lys Leu Glu Ile Lys Thr Thr Thr Pro Ala
            260                 265                 270

Pro Arg Pro Pro Thr Pro Ala Pro Thr Ile Ala Ser Gln Pro Leu Ser
        275                 280                 285

Leu Arg Pro Glu Ala Cys Arg Pro Ala Ala Gly Gly Ala Val His Thr
    290                 295                 300

Arg Gly Leu Asp Phe Ala Cys Asp Ile Tyr Ile Trp Ala Pro Leu Ala
305                 310                 315                 320

Gly Thr Cys Gly Val Leu Leu Leu Ser Leu Val Ile Thr Leu Tyr Cys
                325                 330                 335

Lys Arg Gly Arg Lys Lys Leu Leu Tyr Ile Phe Lys Gln Pro Phe Met
            340                 345                 350

Arg Pro Val Gln Thr Thr Gln Glu Glu Asp Gly Cys Ser Cys Arg Phe
```

```
        355                 360                 365

Pro Glu Glu Glu Glu Gly Gly Cys Glu Leu Arg Val Lys Phe Ser Arg
    370                 375                 380

Ser Ala Asp Ala Pro Ala Tyr Lys Gln Gly Gln Asn Gln Leu Tyr Asn
385                 390                 395                 400

Glu Leu Asn Leu Gly Arg Arg Glu Glu Tyr Asp Val Leu Asp Lys Arg
                405                 410                 415

Arg Gly Arg Asp Pro Glu Met Gly Gly Lys Pro Arg Arg Lys Asn Pro
            420                 425                 430

Gln Glu Gly Leu Tyr Asn Glu Leu Gln Lys Asp Lys Met Ala Glu Ala
        435                 440                 445

Tyr Ser Glu Ile Gly Met Lys Gly Glu Arg Arg Arg Gly Lys Gly His
    450                 455                 460

Asp Gly Leu Tyr Gln Gly Leu Ser Thr Ala Thr Lys Asp Thr Tyr Asp
465                 470                 475                 480

Ala Leu His Met Gln Ala Leu Pro Pro Arg
                485                 490


<210> SEQ ID NO 66
<211> LENGTH: 486
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 66

Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Leu
            20                  25                  30

Val Gln Pro Gly Gly Ser Leu Arg Leu Ser Cys Ala Ala Ser Gly Phe
        35                  40                  45

Thr Phe Ser Ser Tyr Trp Met His Trp Val Arg Gln Val Pro Gly Lys
    50                  55                  60

Gly Leu Val Trp Val Ser Arg Ile Asn Thr Asp Gly Ser Thr Thr Thr
65                  70                  75                  80

Tyr Ala Asp Ser Val Glu Gly Arg Phe Thr Ile Ser Arg Asp Asn Ala
                85                  90                  95

Lys Asn Thr Leu Tyr Leu Gln Met Asn Ser Leu Arg Asp Asp Asp Thr
            100                 105                 110

Ala Val Tyr Tyr Cys Val Gly Gly His Trp Ala Val Trp Gly Gln Gly
        115                 120                 125

Thr Thr Val Thr Val Ser Ser Gly Gly Gly Gly Ser Gly Gly Gly Gly
    130                 135                 140

Ser Gly Gly Gly Gly Ser Gly Gly Gly Gly Ser Asp Ile Gln Met Thr
145                 150                 155                 160

Gln Ser Pro Ser Thr Leu Ser Ala Ser Val Gly Asp Arg Val Thr Ile
                165                 170                 175

Thr Cys Arg Ala Ser Gln Ser Ile Ser Asp Arg Leu Ala Trp Tyr Gln
            180                 185                 190

Gln Lys Pro Gly Lys Ala Pro Lys Leu Leu Ile Tyr Lys Ala Ser Ser
        195                 200                 205

Leu Glu Ser Gly Val Pro Ser Arg Phe Ser Gly Ser Gly Ser Gly Thr
    210                 215                 220
```

Glu Phe Thr Leu Thr Ile Ser Ser Leu Gln Pro Asp Asp Phe Ala Val
225 230 235 240

Tyr Tyr Cys Gln Gln Tyr Gly His Leu Pro Met Tyr Thr Phe Gly Gln
245 250 255

Gly Thr Lys Val Glu Ile Lys Thr Thr Thr Pro Ala Pro Arg Pro Pro
260 265 270

Thr Pro Ala Pro Thr Ile Ala Ser Gln Pro Leu Ser Leu Arg Pro Glu
275 280 285

Ala Cys Arg Pro Ala Ala Gly Gly Ala Val His Thr Arg Gly Leu Asp
290 295 300

Phe Ala Cys Asp Ile Tyr Ile Trp Ala Pro Leu Ala Gly Thr Cys Gly
305 310 315 320

Val Leu Leu Leu Ser Leu Val Ile Thr Leu Tyr Cys Lys Arg Gly Arg
325 330 335

Lys Lys Leu Leu Tyr Ile Phe Lys Gln Pro Phe Met Arg Pro Val Gln
340 345 350

Thr Thr Gln Glu Glu Asp Gly Cys Ser Cys Arg Phe Pro Glu Glu Glu
355 360 365

Glu Gly Gly Cys Glu Leu Arg Val Lys Phe Ser Arg Ser Ala Asp Ala
370 375 380

Pro Ala Tyr Lys Gln Gly Gln Asn Gln Leu Tyr Asn Glu Leu Asn Leu
385 390 395 400

Gly Arg Arg Glu Glu Tyr Asp Val Leu Asp Lys Arg Arg Gly Arg Asp
405 410 415

Pro Glu Met Gly Gly Lys Pro Arg Arg Lys Asn Pro Gln Glu Gly Leu
420 425 430

Tyr Asn Glu Leu Gln Lys Asp Lys Met Ala Glu Ala Tyr Ser Glu Ile
435 440 445

Gly Met Lys Gly Glu Arg Arg Arg Gly Lys Gly His Asp Gly Leu Tyr
450 455 460

Gln Gly Leu Ser Thr Ala Thr Lys Asp Thr Tyr Asp Ala Leu His Met
465 470 475 480

Gln Ala Leu Pro Pro Arg
485

<210> SEQ ID NO 67
<211> LENGTH: 485
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 67

Met Ala Leu Pro Val Thr Ala Leu Leu Leu Pro Leu Ala Leu Leu Leu
1 5 10 15

His Ala Ala Arg Pro Gln Val Gln Leu Val Gln Ser Gly Ala Glu Val
20 25 30

Glu Lys Pro Gly Ala Ser Val Lys Val Ser Cys Lys Ala Ser Gly Tyr
35 40 45

Thr Phe Thr Asp Tyr Tyr Met His Trp Val Arg Gln Ala Pro Gly Gln
50 55 60

Gly Leu Glu Trp Met Gly Trp Ile Asn Pro Asn Ser Gly Gly Thr Asn
65 70 75 80

-continued

```
Tyr Ala Gln Lys Phe Gln Gly Arg Val Thr Met Thr Arg Asp Thr Ser
                85                  90                  95

Ile Ser Thr Ala Tyr Met Glu Leu Ser Arg Leu Arg Ser Asp Asp Thr
            100                 105                 110

Ala Val Tyr Tyr Cys Ala Ser Gly Trp Asp Phe Asp Tyr Trp Gly Gln
        115                 120                 125

Gly Thr Leu Val Thr Val Ser Ser Gly Gly Gly Gly Ser Gly Gly Gly
    130                 135                 140

Gly Ser Gly Gly Gly Gly Ser Gly Gly Gly Gly Ser Asp Ile Val Met
145                 150                 155                 160

Thr Gln Ser Pro Ser Ser Leu Ser Ala Ser Val Gly Asp Arg Val Thr
                165                 170                 175

Ile Thr Cys Arg Ala Ser Gln Ser Ile Arg Tyr Tyr Leu Ser Trp Tyr
            180                 185                 190

Gln Gln Lys Pro Gly Lys Ala Pro Lys Leu Leu Ile Tyr Thr Ala Ser
        195                 200                 205

Ile Leu Gln Asn Gly Val Pro Ser Arg Phe Ser Gly Ser Gly Ser Gly
    210                 215                 220

Thr Asp Phe Thr Leu Thr Ile Ser Ser Leu Gln Pro Glu Asp Phe Ala
225                 230                 235                 240

Thr Tyr Tyr Cys Leu Gln Thr Tyr Thr Thr Pro Asp Phe Gly Pro Gly
                245                 250                 255

Thr Lys Val Glu Ile Lys Thr Thr Thr Pro Ala Pro Arg Pro Pro Thr
            260                 265                 270

Pro Ala Pro Thr Ile Ala Ser Gln Pro Leu Ser Leu Arg Pro Glu Ala
        275                 280                 285

Cys Arg Pro Ala Ala Gly Gly Ala Val His Thr Arg Gly Leu Asp Phe
    290                 295                 300

Ala Cys Asp Ile Tyr Ile Trp Ala Pro Leu Ala Gly Thr Cys Gly Val
305                 310                 315                 320

Leu Leu Leu Ser Leu Val Ile Thr Leu Tyr Cys Lys Arg Gly Arg Lys
                325                 330                 335

Lys Leu Leu Tyr Ile Phe Lys Gln Pro Phe Met Arg Pro Val Gln Thr
            340                 345                 350

Thr Gln Glu Glu Asp Gly Cys Ser Cys Arg Phe Pro Glu Glu Glu Glu
        355                 360                 365

Gly Gly Cys Glu Leu Arg Val Lys Phe Ser Arg Ser Ala Asp Ala Pro
    370                 375                 380

Ala Tyr Lys Gln Gly Gln Asn Gln Leu Tyr Asn Glu Leu Asn Leu Gly
385                 390                 395                 400

Arg Arg Glu Glu Tyr Asp Val Leu Asp Lys Arg Arg Gly Arg Asp Pro
                405                 410                 415

Glu Met Gly Gly Lys Pro Arg Arg Lys Asn Pro Gln Glu Gly Leu Tyr
            420                 425                 430

Asn Glu Leu Gln Lys Asp Lys Met Ala Glu Ala Tyr Ser Glu Ile Gly
        435                 440                 445

Met Lys Gly Glu Arg Arg Arg Gly Lys Gly His Asp Gly Leu Tyr Gln
    450                 455                 460

Gly Leu Ser Thr Ala Thr Lys Asp Thr Tyr Asp Ala Leu His Met Gln
465                 470                 475                 480

Ala Leu Pro Pro Arg
                485
```

<210> SEQ ID NO 68
<211> LENGTH: 497
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 68

```
Met Ala Leu Pro Val Thr Ala Leu Leu Leu Pro Leu Ala Leu Leu Leu
1               5                   10                  15

His Ala Ala Arg Pro Gln Val Gln Leu Val Gln Ser Gly Ala Glu Val
            20                  25                  30

Lys Lys Pro Gly Ala Ser Val Lys Val Ser Cys Lys Ala Ser Gly Tyr
        35                  40                  45

Thr Phe Thr Ser Tyr Tyr Met His Trp Val Arg Gln Ala Pro Gly Gln
    50                  55                  60

Gly Leu Glu Trp Met Gly Ile Ile Asn Pro Ser Gly Gly Ser Thr Ser
65                  70                  75                  80

Tyr Ala Gln Lys Phe Gln Gly Arg Val Thr Met Thr Arg Asp Thr Ser
                85                  90                  95

Thr Ser Thr Val Tyr Met Glu Leu Ser Ser Leu Arg Ser Glu Asp Thr
            100                 105                 110

Ala Val Tyr Tyr Cys Ala Arg Tyr Arg Leu Ile Ala Val Ala Gly Asp
        115                 120                 125

Tyr Tyr Tyr Tyr Gly Met Asp Val Trp Gly Gln Gly Thr Met Val Thr
    130                 135                 140

Val Ser Ser Gly Gly Gly Gly Ser Gly Gly Gly Gly Ser Gly Gly Gly
145                 150                 155                 160

Gly Ser Gly Gly Gly Gly Ser Asp Ile Gln Met Thr Gln Ser Pro Ser
                165                 170                 175

Ser Val Ser Ala Ser Val Gly Asp Arg Val Thr Ile Thr Cys Arg Ala
            180                 185                 190

Ser Gln Gly Val Gly Arg Trp Leu Ala Trp Tyr Gln Gln Lys Pro Gly
        195                 200                 205

Thr Ala Pro Lys Leu Leu Ile Tyr Ala Ala Ser Thr Leu Gln Ser Gly
    210                 215                 220

Val Pro Ser Arg Phe Ser Gly Ser Gly Ser Gly Thr Asp Phe Thr Leu
225                 230                 235                 240

Thr Ile Asn Asn Leu Gln Pro Glu Asp Phe Ala Thr Tyr Tyr Cys Gln
                245                 250                 255

Gln Ala Asn Ser Phe Pro Leu Thr Phe Gly Gly Gly Thr Arg Leu Glu
            260                 265                 270

Ile Lys Thr Thr Thr Pro Ala Pro Arg Pro Pro Thr Pro Ala Pro Thr
        275                 280                 285

Ile Ala Ser Gln Pro Leu Ser Leu Arg Pro Glu Ala Cys Arg Pro Ala
    290                 295                 300

Ala Gly Gly Ala Val His Thr Arg Gly Leu Asp Phe Ala Cys Asp Ile
305                 310                 315                 320

Tyr Ile Trp Ala Pro Leu Ala Gly Thr Cys Gly Val Leu Leu Leu Ser
                325                 330                 335

Leu Val Ile Thr Leu Tyr Cys Lys Arg Gly Arg Lys Lys Leu Leu Tyr
            340                 345                 350

Ile Phe Lys Gln Pro Phe Met Arg Pro Val Gln Thr Thr Gln Glu Glu
        355                 360                 365
```

```
Asp Gly Cys Ser Cys Arg Phe Pro Glu Glu Glu Glu Gly Gly Cys Glu
    370                 375                 380

Leu Arg Val Lys Phe Ser Arg Ser Ala Asp Ala Pro Ala Tyr Lys Gln
385                 390                 395                 400

Gly Gln Asn Gln Leu Tyr Asn Glu Leu Asn Leu Gly Arg Arg Glu Glu
                405                 410                 415

Tyr Asp Val Leu Asp Lys Arg Arg Gly Arg Asp Pro Glu Met Gly Gly
            420                 425                 430

Lys Pro Arg Arg Lys Asn Pro Gln Glu Gly Leu Tyr Asn Glu Leu Gln
        435                 440                 445

Lys Asp Lys Met Ala Glu Ala Tyr Ser Glu Ile Gly Met Lys Gly Glu
    450                 455                 460

Arg Arg Arg Gly Lys Gly His Asp Gly Leu Tyr Gln Gly Leu Ser Thr
465                 470                 475                 480

Ala Thr Lys Asp Thr Tyr Asp Ala Leu His Met Gln Ala Leu Pro Pro
                485                 490                 495

Arg


<210> SEQ ID NO 69
<211> LENGTH: 494
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 69

Met Ala Leu Pro Val Thr Ala Leu Leu Leu Pro Leu Ala Leu Leu Leu
1               5                   10                  15

His Ala Ala Arg Pro Gln Val Gln Leu Val Gln Ser Gly Gly Gly Val
            20                  25                  30

Val Gln Pro Gly Arg Ser Leu Arg Leu Ser Cys Ala Ala Ser Gly Phe
        35                  40                  45

Thr Phe Ser Ser Tyr Ala Met His Trp Val Arg Gln Ala Pro Gly Lys
    50                  55                  60

Gly Leu Glu Trp Val Ala Val Ile Ser Tyr Asp Gly Ser Asn Lys Tyr
65                  70                  75                  80

Tyr Ala Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Ala Arg Trp Lys Val Ser Ser Ser Ser Pro Ala
        115                 120                 125

Phe Asp Tyr Trp Gly Gln Gly Thr Leu Val Thr Val Ser Ser Gly Gly
    130                 135                 140

Gly Gly Ser Gly Gly Gly Gly Ser Gly Gly Gly Gly Ser Gly Gly Gly
145                 150                 155                 160

Gly Ser Glu Ile Val Leu Thr Gln Ser Pro Ala Thr Leu Ser Leu Ser
                165                 170                 175

Pro Gly Glu Arg Ala Ile Leu Ser Cys Arg Ala Ser Gln Ser Val Tyr
            180                 185                 190

Thr Lys Tyr Leu Gly Trp Tyr Gln Gln Lys Pro Gly Gln Ala Pro Arg
        195                 200                 205

Leu Leu Ile Tyr Asp Ala Ser Thr Arg Ala Thr Gly Ile Pro Asp Arg
```

```
    210                 215                 220

Phe Ser Gly Ser Gly Ser Gly Thr Asp Phe Thr Leu Thr Ile Asn Arg
225                 230                 235                 240

Leu Glu Pro Glu Asp Phe Ala Val Tyr Tyr Cys Gln His Tyr Gly Gly
                245                 250                 255

Ser Pro Leu Ile Thr Phe Gly Gln Gly Thr Arg Leu Glu Ile Lys Thr
            260                 265                 270

Thr Thr Pro Ala Pro Arg Pro Pro Thr Pro Ala Pro Thr Ile Ala Ser
        275                 280                 285

Gln Pro Leu Ser Leu Arg Pro Glu Ala Cys Arg Pro Ala Ala Gly Gly
    290                 295                 300

Ala Val His Thr Arg Gly Leu Asp Phe Ala Cys Asp Ile Tyr Ile Trp
305                 310                 315                 320

Ala Pro Leu Ala Gly Thr Cys Gly Val Leu Leu Leu Ser Leu Val Ile
                325                 330                 335

Thr Leu Tyr Cys Lys Arg Gly Arg Lys Lys Leu Leu Tyr Ile Phe Lys
            340                 345                 350

Gln Pro Phe Met Arg Pro Val Gln Thr Thr Gln Glu Glu Asp Gly Cys
        355                 360                 365

Ser Cys Arg Phe Pro Glu Glu Glu Glu Gly Gly Cys Glu Leu Arg Val
    370                 375                 380

Lys Phe Ser Arg Ser Ala Asp Ala Pro Ala Tyr Lys Gln Gly Gln Asn
385                 390                 395                 400

Gln Leu Tyr Asn Glu Leu Asn Leu Gly Arg Arg Glu Glu Tyr Asp Val
                405                 410                 415

Leu Asp Lys Arg Arg Gly Arg Asp Pro Glu Met Gly Gly Lys Pro Arg
            420                 425                 430

Arg Lys Asn Pro Gln Glu Gly Leu Tyr Asn Glu Leu Gln Lys Asp Lys
        435                 440                 445

Met Ala Glu Ala Tyr Ser Glu Ile Gly Met Lys Gly Glu Arg Arg Arg
    450                 455                 460

Gly Lys Gly His Asp Gly Leu Tyr Gln Gly Leu Ser Thr Ala Thr Lys
465                 470                 475                 480

Asp Thr Tyr Asp Ala Leu His Met Gln Ala Leu Pro Pro Arg
                485                 490
```

<210> SEQ ID NO 70
<211> LENGTH: 490
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 70

```
Met Ala Leu Pro Val Thr Ala Leu Leu Leu Pro Leu Ala Leu Leu Leu
1               5                   10                  15

His Ala Ala Arg Pro Gln Val Gln Leu Gln Gln Ser Gly Ala Glu Val
            20                  25                  30

Lys Lys Pro Gly Ala Ser Val Lys Val Ser Cys Lys Thr Ser Gly Tyr
        35                  40                  45

Pro Phe Thr Gly Tyr Ser Leu His Trp Val Arg Gln Ala Pro Gly Gln
    50                  55                  60

Gly Leu Glu Trp Met Gly Trp Ile Asn Pro Asn Ser Gly Gly Thr Asn
65                  70                  75                  80
```

```
Tyr Ala Gln Lys Phe Gln Gly Arg Val Thr Met Thr Arg Asp Thr Ser
                85                  90                  95

Ile Ser Thr Ala Tyr Met Glu Leu Ser Arg Leu Arg Ser Asp Asp Thr
            100                 105                 110

Ala Val Tyr Tyr Cys Ala Arg Asp His Tyr Gly Gly Asn Ser Leu Phe
        115                 120                 125

Tyr Trp Gly Gln Gly Thr Leu Val Thr Val Ser Ser Gly Gly Gly Gly
    130                 135                 140

Ser Gly Gly Gly Gly Ser Gly Gly Gly Gly Ser Gly Gly Gly Gly Ser
145                 150                 155                 160

Asp Ile Gln Leu Thr Gln Ser Pro Ser Ser Ile Ser Ala Ser Val Gly
                165                 170                 175

Asp Thr Val Ser Ile Thr Cys Arg Ala Ser Gln Asp Ser Gly Thr Trp
            180                 185                 190

Leu Ala Trp Tyr Gln Gln Lys Pro Gly Lys Ala Pro Asn Leu Leu Met
        195                 200                 205

Tyr Asp Ala Ser Thr Leu Glu Asp Gly Val Pro Ser Arg Phe Ser Gly
    210                 215                 220

Ser Ala Ser Gly Thr Glu Phe Thr Leu Thr Val Asn Arg Leu Gln Pro
225                 230                 235                 240

Glu Asp Ser Ala Thr Tyr Tyr Cys Gln Gln Tyr Asn Ser Tyr Pro Leu
                245                 250                 255

Thr Phe Gly Gly Gly Thr Lys Val Asp Ile Lys Thr Thr Thr Pro Ala
            260                 265                 270

Pro Arg Pro Pro Thr Pro Ala Pro Thr Ile Ala Ser Gln Pro Leu Ser
        275                 280                 285

Leu Arg Pro Glu Ala Cys Arg Pro Ala Ala Gly Gly Ala Val His Thr
    290                 295                 300

Arg Gly Leu Asp Phe Ala Cys Asp Ile Tyr Ile Trp Ala Pro Leu Ala
305                 310                 315                 320

Gly Thr Cys Gly Val Leu Leu Leu Ser Leu Val Ile Thr Leu Tyr Cys
                325                 330                 335

Lys Arg Gly Arg Lys Lys Leu Leu Tyr Ile Phe Lys Gln Pro Phe Met
            340                 345                 350

Arg Pro Val Gln Thr Thr Gln Glu Glu Asp Gly Cys Ser Cys Arg Phe
        355                 360                 365

Pro Glu Glu Glu Glu Gly Gly Cys Glu Leu Arg Val Lys Phe Ser Arg
    370                 375                 380

Ser Ala Asp Ala Pro Ala Tyr Lys Gln Gly Gln Asn Gln Leu Tyr Asn
385                 390                 395                 400

Glu Leu Asn Leu Gly Arg Arg Glu Glu Tyr Asp Val Leu Asp Lys Arg
                405                 410                 415

Arg Gly Arg Asp Pro Glu Met Gly Gly Lys Pro Arg Arg Lys Asn Pro
            420                 425                 430

Gln Glu Gly Leu Tyr Asn Glu Leu Gln Lys Asp Lys Met Ala Glu Ala
        435                 440                 445

Tyr Ser Glu Ile Gly Met Lys Gly Glu Arg Arg Arg Gly Lys Gly His
    450                 455                 460

Asp Gly Leu Tyr Gln Gly Leu Ser Thr Ala Thr Lys Asp Thr Tyr Asp
465                 470                 475                 480

Ala Leu His Met Gln Ala Leu Pro Pro Arg
                485                 490
```

<210> SEQ ID NO 71
<211> LENGTH: 492
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 71

Met Ala Leu Pro Val Thr Ala Leu Leu Leu Pro Leu Ala Leu Leu Leu
1 5 10 15

His Ala Ala Arg Pro Gln Val Gln Leu Val Gln Ser Gly Ala Glu Val
20 25 30

Lys Lys Pro Gly Ala Ser Val Glu Val Ser Cys Lys Ala Ser Gly Tyr
35 40 45

Thr Phe Thr Ser Tyr Tyr Met His Trp Val Arg Gln Ala Pro Gly Gln
50 55 60

Gly Leu Glu Trp Met Gly Ile Ile Asn Pro Ser Gly Gly Ser Thr Gly
65 70 75 80

Tyr Ala Gln Lys Phe Gln Gly Arg Val Thr Met Thr Arg Asp Thr Ser
85 90 95

Thr Ser Thr Val His Met Glu Leu Ser Ser Leu Arg Ser Glu Asp Thr
100 105 110

Ala Val Tyr Tyr Cys Ala Arg Gly Gly Tyr Ser Ser Ser Ser Asp Ala
115 120 125

Phe Asp Ile Trp Gly Gln Gly Thr Met Val Thr Val Ser Ser Gly Gly
130 135 140

Gly Gly Ser Gly Gly Gly Gly Ser Gly Gly Gly Gly Ser Gly Gly Gly
145 150 155 160

Gly Ser Asp Ile Gln Met Thr Gln Ser Pro Pro Ser Leu Ser Ala Ser
165 170 175

Val Gly Asp Arg Val Thr Ile Thr Cys Arg Ala Ser Gln Asp Ile Ser
180 185 190

Ser Ala Leu Ala Trp Tyr Gln Gln Lys Pro Gly Thr Pro Pro Lys Leu
195 200 205

Leu Ile Tyr Asp Ala Ser Ser Leu Glu Ser Gly Val Pro Ser Arg Phe
210 215 220

Ser Gly Ser Gly Ser Gly Thr Asp Phe Thr Leu Thr Ile Ser Ser Leu
225 230 235 240

Gln Pro Glu Asp Phe Ala Thr Tyr Tyr Cys Gln Gln Phe Ser Ser Tyr
245 250 255

Pro Leu Thr Phe Gly Gly Gly Thr Arg Leu Glu Ile Lys Thr Thr Thr
260 265 270

Pro Ala Pro Arg Pro Pro Thr Pro Ala Pro Thr Ile Ala Ser Gln Pro
275 280 285

Leu Ser Leu Arg Pro Glu Ala Cys Arg Pro Ala Ala Gly Gly Ala Val
290 295 300

His Thr Arg Gly Leu Asp Phe Ala Cys Asp Ile Tyr Ile Trp Ala Pro
305 310 315 320

Leu Ala Gly Thr Cys Gly Val Leu Leu Leu Ser Leu Val Ile Thr Leu
325 330 335

Tyr Cys Lys Arg Gly Arg Lys Lys Leu Leu Tyr Ile Phe Lys Gln Pro
340 345 350

Phe Met Arg Pro Val Gln Thr Thr Gln Glu Glu Asp Gly Cys Ser Cys

```
        355                 360                 365

Arg Phe Pro Glu Glu Glu Glu Gly Gly Cys Glu Leu Arg Val Lys Phe
    370                 375                 380

Ser Arg Ser Ala Asp Ala Pro Ala Tyr Lys Gln Gly Gln Asn Gln Leu
385                 390                 395                 400

Tyr Asn Glu Leu Asn Leu Gly Arg Arg Glu Glu Tyr Asp Val Leu Asp
                405                 410                 415

Lys Arg Arg Gly Arg Asp Pro Glu Met Gly Gly Lys Pro Arg Arg Lys
            420                 425                 430

Asn Pro Gln Glu Gly Leu Tyr Asn Glu Leu Gln Lys Asp Lys Met Ala
        435                 440                 445

Glu Ala Tyr Ser Glu Ile Gly Met Lys Gly Glu Arg Arg Arg Gly Lys
    450                 455                 460

Gly His Asp Gly Leu Tyr Gln Gly Leu Ser Thr Ala Thr Lys Asp Thr
465                 470                 475                 480

Tyr Asp Ala Leu His Met Gln Ala Leu Pro Pro Arg
                485                 490


<210> SEQ ID NO 72
<211> LENGTH: 499
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 72

Met Ala Leu Pro Val Thr Ala Leu Leu Leu Pro Leu Ala Leu Leu Leu
1               5                   10                  15

His Ala Ala Arg Pro Gln Val Gln Leu Val Gln Ser Gly Ala Glu Val
            20                  25                  30

Lys Lys Pro Gly Ala Ser Val Lys Val Ser Cys Lys Ala Ser Gly Tyr
        35                  40                  45

Thr Phe Thr Ser Tyr Gly Ile Ser Trp Val Arg Gln Ala Pro Gly Gln
    50                  55                  60

Gly Leu Glu Trp Met Gly Trp Ile Ser Ala Tyr Asn Gly Asn Thr Asn
65                  70                  75                  80

Tyr Ala Gln Lys Leu Gln Gly Arg Val Thr Met Thr Thr Asp Thr Ser
                85                  90                  95

Thr Ser Thr Ala Tyr Met Glu Leu Arg Ser Leu Arg Ser Asp Asp Thr
            100                 105                 110

Ala Val Tyr Tyr Cys Ala Arg Val Ala Gly Gly Ile Tyr Tyr Tyr Tyr
        115                 120                 125

Gly Met Asp Val Trp Gly Gln Gly Thr Thr Ile Thr Val Ser Ser Gly
    130                 135                 140

Gly Gly Gly Ser Gly Gly Gly Gly Ser Gly Gly Gly Gly Ser Gly Gly
145                 150                 155                 160

Gly Gly Ser Asp Ile Val Met Thr Gln Thr Pro Asp Ser Leu Ala Val
                165                 170                 175

Ser Leu Gly Glu Arg Ala Thr Ile Ser Cys Lys Ser Ser His Ser Val
            180                 185                 190

Leu Tyr Asn Arg Asn Asn Lys Asn Tyr Leu Ala Trp Tyr Gln Gln Lys
        195                 200                 205

Pro Gly Gln Pro Pro Lys Leu Leu Phe Tyr Trp Ala Ser Thr Arg Lys
    210                 215                 220
```

Ser Gly Val Pro Asp Arg Phe Ser Gly Ser Gly Ser Gly Thr Asp Phe
225 230 235 240

Thr Leu Thr Ile Ser Ser Leu Gln Pro Glu Asp Phe Ala Thr Tyr Phe
245 250 255

Cys Gln Gln Thr Gln Thr Phe Pro Leu Thr Phe Gly Gln Gly Thr Arg
260 265 270

Leu Glu Ile Asn Thr Thr Thr Pro Ala Pro Arg Pro Pro Thr Pro Ala
275 280 285

Pro Thr Ile Ala Ser Gln Pro Leu Ser Leu Arg Pro Glu Ala Cys Arg
290 295 300

Pro Ala Ala Gly Gly Ala Val His Thr Arg Gly Leu Asp Phe Ala Cys
305 310 315 320

Asp Ile Tyr Ile Trp Ala Pro Leu Ala Gly Thr Cys Gly Val Leu Leu
325 330 335

Leu Ser Leu Val Ile Thr Leu Tyr Cys Lys Arg Gly Arg Lys Lys Leu
340 345 350

Leu Tyr Ile Phe Lys Gln Pro Phe Met Arg Pro Val Gln Thr Thr Gln
355 360 365

Glu Glu Asp Gly Cys Ser Cys Arg Phe Pro Glu Glu Glu Glu Gly Gly
370 375 380

Cys Glu Leu Arg Val Lys Phe Ser Arg Ser Ala Asp Ala Pro Ala Tyr
385 390 395 400

Lys Gln Gly Gln Asn Gln Leu Tyr Asn Glu Leu Asn Leu Gly Arg Arg
405 410 415

Glu Glu Tyr Asp Val Leu Asp Lys Arg Arg Gly Arg Asp Pro Glu Met
420 425 430

Gly Gly Lys Pro Arg Arg Lys Asn Pro Gln Glu Gly Leu Tyr Asn Glu
435 440 445

Leu Gln Lys Asp Lys Met Ala Glu Ala Tyr Ser Glu Ile Gly Met Lys
450 455 460

Gly Glu Arg Arg Arg Gly Lys Gly His Asp Gly Leu Tyr Gln Gly Leu
465 470 475 480

Ser Thr Ala Thr Lys Asp Thr Tyr Asp Ala Leu His Met Gln Ala Leu
485 490 495

Pro Pro Arg

<210> SEQ ID NO 73
<211> LENGTH: 485
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 73

Met Ala Leu Pro Val Thr Ala Leu Leu Leu Pro Leu Ala Leu Leu Leu
1 5 10 15

His Ala Ala Arg Pro Gln Val Gln Leu Gln Gln Ser Gly Ala Glu Val
20 25 30

Lys Lys Pro Gly Ala Ser Val Lys Val Ser Cys Lys Ala Ser Gly Tyr
35 40 45

Thr Phe Thr Gly Tyr Tyr Met His Trp Val Arg Gln Ala Pro Gly Gln
50 55 60

Gly Leu Glu Trp Met Gly Trp Ile Asn Pro Asn Ser Gly Gly Thr Asn 65 70 75 80

Tyr Ala Gln Asn Phe Gln Gly Arg Val Thr Met Thr Arg Asp Thr Ser
85 90 95

Ile Ser Thr Ala Tyr Met Glu Leu Arg Arg Leu Arg Ser Asp Asp Thr
100 105 110

Ala Val Tyr Tyr Cys Ala Ser Gly Trp Asp Phe Asp Tyr Trp Gly Gln
115 120 125

Gly Thr Leu Val Thr Val Ser Ser Gly Gly Gly Gly Ser Gly Gly Gly
130 135 140

Gly Ser Gly Gly Gly Gly Ser Gly Gly Gly Gly Ser Asp Ile Arg Met
145 150 155 160

Thr Gln Ser Pro Ser Ser Leu Ser Ala Ser Val Gly Asp Arg Val Thr
165 170 175

Ile Thr Cys Arg Ala Ser Gln Ser Ile Arg Tyr Tyr Leu Ser Trp Tyr
180 185 190

Gln Gln Lys Pro Gly Lys Ala Pro Lys Leu Leu Ile Tyr Thr Ala Ser
195 200 205

Ile Leu Gln Asn Gly Val Pro Ser Arg Phe Ser Gly Ser Gly Ser Gly
210 215 220

Thr Asp Phe Thr Leu Thr Ile Ser Ser Leu Gln Pro Glu Asp Phe Ala
225 230 235 240

Thr Tyr Tyr Cys Leu Gln Thr Tyr Thr Thr Pro Asp Phe Gly Pro Gly
245 250 255

Thr Lys Val Glu Ile Lys Thr Thr Thr Pro Ala Pro Arg Pro Pro Thr
260 265 270

Pro Ala Pro Thr Ile Ala Ser Gln Pro Leu Ser Leu Arg Pro Glu Ala
275 280 285

Cys Arg Pro Ala Ala Gly Gly Ala Val His Thr Arg Gly Leu Asp Phe
290 295 300

Ala Cys Asp Ile Tyr Ile Trp Ala Pro Leu Ala Gly Thr Cys Gly Val
305 310 315 320

Leu Leu Leu Ser Leu Val Ile Thr Leu Tyr Cys Lys Arg Gly Arg Lys
325 330 335

Lys Leu Leu Tyr Ile Phe Lys Gln Pro Phe Met Arg Pro Val Gln Thr
340 345 350

Thr Gln Glu Glu Asp Gly Cys Ser Cys Arg Phe Pro Glu Glu Glu Glu
355 360 365

Gly Gly Cys Glu Leu Arg Val Lys Phe Ser Arg Ser Ala Asp Ala Pro
370 375 380

Ala Tyr Lys Gln Gly Gln Asn Gln Leu Tyr Asn Glu Leu Asn Leu Gly
385 390 395 400

Arg Arg Glu Glu Tyr Asp Val Leu Asp Lys Arg Arg Gly Arg Asp Pro
405 410 415

Glu Met Gly Gly Lys Pro Arg Arg Lys Asn Pro Gln Glu Gly Leu Tyr
420 425 430

Asn Glu Leu Gln Lys Asp Lys Met Ala Glu Ala Tyr Ser Glu Ile Gly
435 440 445

Met Lys Gly Glu Arg Arg Arg Gly Lys Gly His Asp Gly Leu Tyr Gln
450 455 460

Gly Leu Ser Thr Ala Thr Lys Asp Thr Tyr Asp Ala Leu His Met Gln
465 470 475 480

Ala Leu Pro Pro Arg
485

<210> SEQ ID NO 74
<211> LENGTH: 490
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 74

```
Met Ala Leu Pro Val Thr Ala Leu Leu Leu Pro Leu Ala Leu Leu Leu
1               5                   10                  15

His Ala Ala Arg Pro Gln Val Gln Leu Val Gln Ser Gly Ala Glu Val
            20                  25                  30

Lys Lys Pro Gly Ala Ser Val Lys Val Ser Cys Lys Ala Ser Gly Tyr
        35                  40                  45

Thr Phe Thr Gly Tyr Tyr Met His Trp Val Arg Gln Ala Pro Gly Gln
    50                  55                  60

Gly Leu Glu Trp Met Gly Arg Ile Asn Pro Asn Ser Gly Gly Thr Asn
65                  70                  75                  80

Tyr Ala Gln Lys Phe Gln Gly Arg Val Thr Met Thr Thr Asp Thr Ser
                85                  90                  95

Thr Ser Thr Ala Tyr Met Glu Leu Arg Ser Leu Arg Ser Asp Asp Thr
            100                 105                 110

Ala Val Tyr Tyr Cys Ala Arg Thr Thr Thr Ser Tyr Ala Phe Asp Ile
        115                 120                 125

Trp Gly Gln Gly Thr Met Val Thr Val Ser Ser Gly Gly Gly Gly Ser
    130                 135                 140

Gly Gly Gly Gly Ser Gly Gly Gly Gly Ser Gly Gly Gly Gly Ser Asp
145                 150                 155                 160

Ile Gln Leu Thr Gln Ser Pro Ser Thr Leu Ser Ala Ser Val Gly Asp
                165                 170                 175

Arg Val Thr Ile Thr Cys Arg Ala Ser Gln Ser Ile Ser Thr Trp Leu
            180                 185                 190

Ala Trp Tyr Gln Gln Lys Pro Gly Lys Ala Pro Asn Leu Leu Ile Tyr
        195                 200                 205

Lys Ala Ser Thr Leu Glu Ser Gly Val Pro Ser Arg Phe Ser Gly Ser
    210                 215                 220

Gly Ser Gly Thr Glu Phe Thr Leu Thr Ile Ser Ser Leu Gln Pro Asp
225                 230                 235                 240

Asp Phe Ala Thr Tyr Tyr Cys Gln Gln Tyr Asn Thr Tyr Ser Pro Tyr
                245                 250                 255

Thr Phe Gly Gln Gly Thr Lys Leu Glu Ile Lys Thr Thr Thr Pro Ala
            260                 265                 270

Pro Arg Pro Pro Thr Pro Ala Pro Thr Ile Ala Ser Gln Pro Leu Ser
        275                 280                 285

Leu Arg Pro Glu Ala Cys Arg Pro Ala Ala Gly Gly Ala Val His Thr
    290                 295                 300

Arg Gly Leu Asp Phe Ala Cys Asp Ile Tyr Ile Trp Ala Pro Leu Ala
305                 310                 315                 320

Gly Thr Cys Gly Val Leu Leu Leu Ser Leu Val Ile Thr Leu Tyr Cys
                325                 330                 335

Lys Arg Gly Arg Lys Lys Leu Leu Tyr Ile Phe Lys Gln Pro Phe Met
            340                 345                 350
```

```
Arg Pro Val Gln Thr Thr Gln Glu Glu Asp Gly Cys Ser Cys Arg Phe
        355                 360                 365

Pro Glu Glu Glu Glu Gly Gly Cys Glu Leu Arg Val Lys Phe Ser Arg
    370                 375                 380

Ser Ala Asp Ala Pro Ala Tyr Lys Gln Gly Gln Asn Gln Leu Tyr Asn
385                 390                 395                 400

Glu Leu Asn Leu Gly Arg Arg Glu Glu Tyr Asp Val Leu Asp Lys Arg
                405                 410                 415

Arg Gly Arg Asp Pro Glu Met Gly Gly Lys Pro Arg Arg Lys Asn Pro
            420                 425                 430

Gln Glu Gly Leu Tyr Asn Glu Leu Gln Lys Asp Lys Met Ala Glu Ala
        435                 440                 445

Tyr Ser Glu Ile Gly Met Lys Gly Glu Arg Arg Arg Gly Lys Gly His
    450                 455                 460

Asp Gly Leu Tyr Gln Gly Leu Ser Thr Ala Thr Lys Asp Thr Tyr Asp
465                 470                 475                 480

Ala Leu His Met Gln Ala Leu Pro Pro Arg
                485                 490


<210> SEQ ID NO 75
<211> LENGTH: 493
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 75

Met Ala Leu Pro Val Thr Ala Leu Leu Leu Pro Leu Ala Leu Leu Leu
1               5                   10                  15

His Ala Ala Arg Pro Gln Val Gln Leu Val Gln Ser Gly Gly Gly Leu
            20                  25                  30

Val Lys Pro Gly Gly Ser Leu Arg Leu Ser Cys Glu Ala Ser Gly Phe
        35                  40                  45

Ile Phe Ser Asp Tyr Tyr Met Gly Trp Ile Arg Gln Ala Pro Gly Lys
    50                  55                  60

Gly Leu Glu Trp Val Ser Tyr Ile Gly Arg Ser Gly Ser Ser Met Tyr
65                  70                  75                  80

Tyr Ala Asp Ser Val Lys Gly Arg Phe Thr Phe Ser Arg Asp Asn Ala
                85                  90                  95

Lys Asn Ser Leu Tyr Leu Gln Met Asn Ser Leu Arg Ala Glu Asp Thr
            100                 105                 110

Ala Val Tyr Tyr Cys Ala Ala Ser Pro Val Val Ala Ala Thr Glu Asp
        115                 120                 125

Phe Gln His Trp Gly Gln Gly Thr Leu Val Thr Val Ser Ser Gly Gly
    130                 135                 140

Gly Gly Ser Gly Gly Gly Gly Ser Gly Gly Gly Gly Ser Gly Gly Gly
145                 150                 155                 160

Gly Ser Asp Ile Val Met Thr Gln Thr Pro Ala Thr Leu Ser Leu Ser
                165                 170                 175

Pro Gly Glu Arg Ala Thr Leu Ser Cys Arg Ala Ser Gln Ser Val Thr
            180                 185                 190

Ser Asn Tyr Leu Ala Trp Tyr Gln Gln Lys Pro Gly Gln Ala Pro Arg
        195                 200                 205

Leu Leu Leu Phe Gly Ala Ser Thr Arg Ala Thr Gly Ile Pro Asp Arg
```

```
    210                 215                 220

Phe Ser Gly Ser Gly Ser Gly Thr Asp Phe Thr Leu Thr Ile Asn Arg
225                 230                 235                 240

Leu Glu Pro Glu Asp Phe Ala Met Tyr Tyr Cys Gln Gln Tyr Gly Ser
                245                 250                 255

Ala Pro Val Thr Phe Gly Gln Gly Thr Lys Leu Glu Ile Lys Thr Thr
            260                 265                 270

Thr Pro Ala Pro Arg Pro Pro Thr Pro Ala Pro Thr Ile Ala Ser Gln
        275                 280                 285

Pro Leu Ser Leu Arg Pro Glu Ala Cys Arg Pro Ala Ala Gly Gly Ala
    290                 295                 300

Val His Thr Arg Gly Leu Asp Phe Ala Cys Asp Ile Tyr Ile Trp Ala
305                 310                 315                 320

Pro Leu Ala Gly Thr Cys Gly Val Leu Leu Leu Ser Leu Val Ile Thr
                325                 330                 335

Leu Tyr Cys Lys Arg Gly Arg Lys Lys Leu Leu Tyr Ile Phe Lys Gln
            340                 345                 350

Pro Phe Met Arg Pro Val Gln Thr Thr Gln Glu Glu Asp Gly Cys Ser
        355                 360                 365

Cys Arg Phe Pro Glu Glu Glu Glu Gly Gly Cys Glu Leu Arg Val Lys
    370                 375                 380

Phe Ser Arg Ser Ala Asp Ala Pro Ala Tyr Lys Gln Gly Gln Asn Gln
385                 390                 395                 400

Leu Tyr Asn Glu Leu Asn Leu Gly Arg Arg Glu Glu Tyr Asp Val Leu
                405                 410                 415

Asp Lys Arg Arg Gly Arg Asp Pro Glu Met Gly Gly Lys Pro Arg Arg
            420                 425                 430

Lys Asn Pro Gln Glu Gly Leu Tyr Asn Glu Leu Gln Lys Asp Lys Met
        435                 440                 445

Ala Glu Ala Tyr Ser Glu Ile Gly Met Lys Gly Glu Arg Arg Arg Gly
    450                 455                 460

Lys Gly His Asp Gly Leu Tyr Gln Gly Leu Ser Thr Ala Thr Lys Asp
465                 470                 475                 480

Thr Tyr Asp Ala Leu His Met Gln Ala Leu Pro Pro Arg
                485                 490
```

<210> SEQ ID NO 76
<211> LENGTH: 493
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 76

```
Met Ala Leu Pro Val Thr Ala Leu Leu Leu Pro Leu Ala Leu Leu Leu
1               5                   10                  15

His Ala Ala Arg Pro Gln Val Gln Leu Val Gln Ser Gly Ala Glu Val
            20                  25                  30

Arg Ala Pro Gly Ala Ser Val Lys Ile Ser Cys Lys Ala Ser Gly Phe
        35                  40                  45

Thr Phe Arg Gly Tyr Tyr Ile His Trp Val Arg Gln Ala Pro Gly Gln
    50                  55                  60

Gly Leu Glu Trp Met Gly Ile Ile Asn Pro Ser Gly Gly Ser Arg Ala
65                  70                  75                  80
```

```
Tyr Ala Gln Lys Phe Gln Gly Arg Val Thr Met Thr Arg Asp Thr Ser
                85                  90                  95

Thr Ser Thr Val Tyr Met Glu Leu Ser Ser Leu Arg Ser Asp Asp Thr
            100                 105                 110

Ala Met Tyr Tyr Cys Ala Arg Thr Ala Ser Cys Gly Gly Asp Cys Tyr
        115                 120                 125

Tyr Leu Asp Tyr Trp Gly Gln Gly Thr Leu Val Thr Val Ser Ser Gly
    130                 135                 140

Gly Gly Gly Ser Gly Gly Gly Gly Ser Gly Gly Gly Gly Ser Gly Gly
145                 150                 155                 160

Gly Gly Ser Asp Ile Gln Met Thr Gln Ser Pro Pro Thr Leu Ser Ala
                165                 170                 175

Ser Val Gly Asp Arg Val Thr Ile Thr Cys Arg Ala Ser Glu Asn Val
            180                 185                 190

Asn Ile Trp Leu Ala Trp Tyr Gln Gln Lys Pro Gly Lys Ala Pro Lys
        195                 200                 205

Leu Leu Ile Tyr Lys Ser Ser Ser Leu Ala Ser Gly Val Pro Ser Arg
    210                 215                 220

Phe Ser Gly Ser Gly Ser Gly Ala Glu Phe Thr Leu Thr Ile Ser Ser
225                 230                 235                 240

Leu Gln Pro Asp Asp Phe Ala Thr Tyr Tyr Cys Gln Gln Tyr Gln Ser
                245                 250                 255

Tyr Pro Leu Thr Phe Gly Gly Gly Thr Lys Val Asp Ile Lys Thr Thr
            260                 265                 270

Thr Pro Ala Pro Arg Pro Pro Thr Pro Ala Pro Thr Ile Ala Ser Gln
        275                 280                 285

Pro Leu Ser Leu Arg Pro Glu Ala Cys Arg Pro Ala Ala Gly Gly Ala
    290                 295                 300

Val His Thr Arg Gly Leu Asp Phe Ala Cys Asp Ile Tyr Ile Trp Ala
305                 310                 315                 320

Pro Leu Ala Gly Thr Cys Gly Val Leu Leu Leu Ser Leu Val Ile Thr
                325                 330                 335

Leu Tyr Cys Lys Arg Gly Arg Lys Lys Leu Leu Tyr Ile Phe Lys Gln
            340                 345                 350

Pro Phe Met Arg Pro Val Gln Thr Thr Gln Glu Glu Asp Gly Cys Ser
        355                 360                 365

Cys Arg Phe Pro Glu Glu Glu Glu Gly Gly Cys Glu Leu Arg Val Lys
    370                 375                 380

Phe Ser Arg Ser Ala Asp Ala Pro Ala Tyr Lys Gln Gly Gln Asn Gln
385                 390                 395                 400

Leu Tyr Asn Glu Leu Asn Leu Gly Arg Arg Glu Glu Tyr Asp Val Leu
                405                 410                 415

Asp Lys Arg Arg Gly Arg Asp Pro Glu Met Gly Gly Lys Pro Arg Arg
            420                 425                 430

Lys Asn Pro Gln Glu Gly Leu Tyr Asn Glu Leu Gln Lys Asp Lys Met
        435                 440                 445

Ala Glu Ala Tyr Ser Glu Ile Gly Met Lys Gly Glu Arg Arg Arg Gly
    450                 455                 460

Lys Gly His Asp Gly Leu Tyr Gln Gly Leu Ser Thr Ala Thr Lys Asp
465                 470                 475                 480

Thr Tyr Asp Ala Leu His Met Gln Ala Leu Pro Pro Arg
                485                 490
```

<210> SEQ ID NO 77
<211> LENGTH: 488
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 77

```
Met Ala Leu Pro Val Thr Ala Leu Leu Leu Pro Leu Ala Leu Leu Leu
1               5                   10                  15

His Ala Ala Arg Pro Gln Val Gln Leu Val Gln Ser Gly Gly Gly Leu
            20                  25                  30

Val Gln Pro Gly Arg Ser Leu Arg Leu Ser Cys Ala Ala Ser Gly Phe
        35                  40                  45

Thr Phe Asp Asp Tyr Ala Met His Trp Val Arg Gln Ala Pro Gly Lys
    50                  55                  60

Gly Leu Glu Trp Val Ser Gly Ile Ser Trp Asn Ser Gly Ser Ile Gly
65                  70                  75                  80

Tyr Ala Asp Ser Val Lys Gly Arg Phe Thr Ile Ser Arg Asp Asn Ala
                85                  90                  95

Lys Asn Ser Leu Tyr Leu Gln Met Asn Ser Leu Arg Ala Glu Asp Thr
            100                 105                 110

Ala Val Tyr Tyr Cys Ala Lys Asp Gly Ser Ser Ser Trp Ser Trp Gly
        115                 120                 125

Tyr Phe Asp Tyr Trp Gly Gln Gly Thr Leu Val Thr Val Ser Ser Gly
    130                 135                 140

Gly Gly Gly Ser Gly Gly Gly Gly Ser Gly Gly Gly Gly Ser Ser Ser
145                 150                 155                 160

Glu Leu Thr Gln Asp Pro Ala Val Ser Val Ala Leu Gly Gln Thr Val
                165                 170                 175

Arg Thr Thr Cys Gln Gly Asp Ala Leu Arg Ser Tyr Tyr Ala Ser Trp
            180                 185                 190

Tyr Gln Gln Lys Pro Gly Gln Ala Pro Met Leu Val Ile Tyr Gly Lys
        195                 200                 205

Asn Asn Arg Pro Ser Gly Ile Pro Asp Arg Phe Ser Gly Ser Asp Ser
    210                 215                 220

Gly Asp Thr Ala Ser Leu Thr Ile Thr Gly Ala Gln Ala Glu Asp Glu
225                 230                 235                 240

Ala Asp Tyr Tyr Cys Asn Ser Arg Asp Ser Ser Gly Tyr Pro Val Phe
                245                 250                 255

Gly Thr Gly Thr Lys Val Thr Val Leu Thr Thr Thr Pro Ala Pro Arg
            260                 265                 270

Pro Pro Thr Pro Ala Pro Thr Ile Ala Ser Gln Pro Leu Ser Leu Arg
        275                 280                 285

Pro Glu Ala Cys Arg Pro Ala Ala Gly Gly Ala Val His Thr Arg Gly
    290                 295                 300

Leu Asp Phe Ala Cys Asp Ile Tyr Ile Trp Ala Pro Leu Ala Gly Thr
305                 310                 315                 320

Cys Gly Val Leu Leu Leu Ser Leu Val Ile Thr Leu Tyr Cys Lys Arg
                325                 330                 335

Gly Arg Lys Lys Leu Leu Tyr Ile Phe Lys Gln Pro Phe Met Arg Pro
            340                 345                 350

Val Gln Thr Thr Gln Glu Glu Asp Gly Cys Ser Cys Arg Phe Pro Glu
```

```
        355                 360                 365

Glu Glu Glu Gly Gly Cys Glu Leu Arg Val Lys Phe Ser Arg Ser Ala
    370                 375                 380

Asp Ala Pro Ala Tyr Lys Gln Gly Gln Asn Gln Leu Tyr Asn Glu Leu
385                 390                 395                 400

Asn Leu Gly Arg Arg Glu Glu Tyr Asp Val Leu Asp Lys Arg Arg Gly
                405                 410                 415

Arg Asp Pro Glu Met Gly Gly Lys Pro Arg Arg Lys Asn Pro Gln Glu
            420                 425                 430

Gly Leu Tyr Asn Glu Leu Gln Lys Asp Lys Met Ala Glu Ala Tyr Ser
        435                 440                 445

Glu Ile Gly Met Lys Gly Glu Arg Arg Arg Gly Lys Gly His Asp Gly
    450                 455                 460

Leu Tyr Gln Gly Leu Ser Thr Ala Thr Lys Asp Thr Tyr Asp Ala Leu
465                 470                 475                 480

His Met Gln Ala Leu Pro Pro Arg
                485


<210> SEQ ID NO 78
<211> LENGTH: 490
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 78

Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Leu
            20                  25                  30

Val Gln Pro Gly Arg Ser Leu Arg Leu Ser Cys Ala Ala Ser Gly Phe
        35                  40                  45

Thr Phe Asp Asp Tyr Ala Met His Trp Val Arg Gln Ala Pro Gly Lys
    50                  55                  60

Gly Leu Glu Trp Val Ser Gly Ile Ser Trp Asn Ser Gly Ser Thr Gly
65                  70                  75                  80

Tyr Ala Asp Ser Val Lys Gly Arg Phe Thr Ile Ser Arg Asp Asn Ala
                85                  90                  95

Lys Asn Ser Leu Tyr Leu Gln Met Asn Ser Leu Arg Ala Glu Asp Thr
            100                 105                 110

Ala Leu Tyr Tyr Cys Ala Lys Asp Ser Ser Ser Trp Tyr Gly Gly Gly
        115                 120                 125

Ser Ala Phe Asp Ile Trp Gly Gln Gly Thr Met Val Thr Val Ser Ser
    130                 135                 140

Gly Gly Gly Gly Ser Gly Gly Gly Gly Ser Gly Gly Gly Gly Ser Ser
145                 150                 155                 160

Ser Glu Leu Thr Gln Glu Pro Ala Val Ser Val Ala Leu Gly Gln Thr
                165                 170                 175

Val Arg Ile Thr Cys Gln Gly Asp Ser Leu Arg Ser Tyr Tyr Ala Ser
            180                 185                 190

Trp Tyr Gln Gln Lys Pro Gly Gln Ala Pro Val Leu Val Ile Phe Gly
        195                 200                 205

Arg Ser Arg Arg Pro Ser Gly Ile Pro Asp Arg Phe Ser Gly Ser Ser
    210                 215                 220
```

```
Ser Gly Asn Thr Ala Ser Leu Ile Ile Thr Gly Ala Gln Ala Glu Asp
225                 230                 235                 240

Glu Ala Asp Tyr Tyr Cys Asn Ser Arg Asp Asn Thr Ala Asn His Tyr
                245                 250                 255

Val Phe Gly Thr Gly Thr Lys Leu Thr Val Leu Thr Thr Thr Pro Ala
            260                 265                 270

Pro Arg Pro Pro Thr Pro Ala Pro Thr Ile Ala Ser Gln Pro Leu Ser
        275                 280                 285

Leu Arg Pro Glu Ala Cys Arg Pro Ala Ala Gly Gly Ala Val His Thr
    290                 295                 300

Arg Gly Leu Asp Phe Ala Cys Asp Ile Tyr Ile Trp Ala Pro Leu Ala
305                 310                 315                 320

Gly Thr Cys Gly Val Leu Leu Leu Ser Leu Val Ile Thr Leu Tyr Cys
                325                 330                 335

Lys Arg Gly Arg Lys Lys Leu Leu Tyr Ile Phe Lys Gln Pro Phe Met
            340                 345                 350

Arg Pro Val Gln Thr Thr Gln Glu Glu Asp Gly Cys Ser Cys Arg Phe
        355                 360                 365

Pro Glu Glu Glu Glu Gly Gly Cys Glu Leu Arg Val Lys Phe Ser Arg
    370                 375                 380

Ser Ala Asp Ala Pro Ala Tyr Lys Gln Gly Gln Asn Gln Leu Tyr Asn
385                 390                 395                 400

Glu Leu Asn Leu Gly Arg Arg Glu Glu Tyr Asp Val Leu Asp Lys Arg
                405                 410                 415

Arg Gly Arg Asp Pro Glu Met Gly Gly Lys Pro Arg Arg Lys Asn Pro
            420                 425                 430

Gln Glu Gly Leu Tyr Asn Glu Leu Gln Lys Asp Lys Met Ala Glu Ala
        435                 440                 445

Tyr Ser Glu Ile Gly Met Lys Gly Glu Arg Arg Arg Gly Lys Gly His
    450                 455                 460

Asp Gly Leu Tyr Gln Gly Leu Ser Thr Ala Thr Lys Asp Thr Tyr Asp
465                 470                 475                 480

Ala Leu His Met Gln Ala Leu Pro Pro Arg
                485                 490


<210> SEQ ID NO 79
<211> LENGTH: 490
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 79

Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Leu
            20                  25                  30

Val Gln Pro Gly Arg Ser Leu Arg Leu Ser Cys Ala Ala Ser Gly Phe
        35                  40                  45

Thr Phe Asp Asp Tyr Ala Met His Trp Val Arg Gln Ala Pro Gly Lys
    50                  55                  60

Gly Leu Glu Trp Val Ser Gly Ile Ser Trp Asn Ser Gly Ser Thr Gly
65                  70                  75                  80
```

-continued

```
Tyr Ala Asp Ser Val Lys Gly Arg Phe Thr Ile Ser Arg Asp Asn Ala
                85                  90                  95

Lys Asn Ser Leu Tyr Leu Gln Met Asn Ser Leu Arg Ala Glu Asp Thr
            100                 105                 110

Ala Leu Tyr Tyr Cys Ala Lys Asp Ser Ser Ser Trp Tyr Gly Gly Gly
        115                 120                 125

Ser Ala Phe Asp Ile Trp Gly Gln Gly Thr Met Val Thr Val Ser Ser
    130                 135                 140

Gly Gly Gly Gly Ser Gly Gly Gly Gly Ser Gly Gly Gly Gly Ser Ser
145                 150                 155                 160

Ser Glu Leu Thr Gln Asp Pro Ala Val Ser Val Ala Leu Gly Gln Thr
                165                 170                 175

Val Arg Ile Thr Cys Gln Gly Asp Ser Leu Arg Ser Tyr Tyr Ala Ser
            180                 185                 190

Trp Tyr Gln Gln Lys Pro Gly Gln Ala Pro Val Leu Val Ile Tyr Gly
        195                 200                 205

Lys Asn Asn Arg Pro Ser Gly Ile Pro Asp Arg Phe Ser Gly Ser Ser
    210                 215                 220

Ser Gly Asn Thr Ala Ser Leu Thr Ile Thr Gly Ala Gln Ala Glu Asp
225                 230                 235                 240

Glu Ala Asp Tyr Tyr Cys Asn Ser Arg Gly Ser Ser Gly Asn His Tyr
                245                 250                 255

Val Phe Gly Thr Gly Thr Lys Val Thr Val Leu Thr Thr Thr Pro Ala
            260                 265                 270

Pro Arg Pro Pro Thr Pro Ala Pro Thr Ile Ala Ser Gln Pro Leu Ser
        275                 280                 285

Leu Arg Pro Glu Ala Cys Arg Pro Ala Ala Gly Gly Ala Val His Thr
    290                 295                 300

Arg Gly Leu Asp Phe Ala Cys Asp Ile Tyr Ile Trp Ala Pro Leu Ala
305                 310                 315                 320

Gly Thr Cys Gly Val Leu Leu Leu Ser Leu Val Ile Thr Leu Tyr Cys
                325                 330                 335

Lys Arg Gly Arg Lys Lys Leu Leu Tyr Ile Phe Lys Gln Pro Phe Met
            340                 345                 350

Arg Pro Val Gln Thr Thr Gln Glu Glu Asp Gly Cys Ser Cys Arg Phe
        355                 360                 365

Pro Glu Glu Glu Glu Gly Gly Cys Glu Leu Arg Val Lys Phe Ser Arg
    370                 375                 380

Ser Ala Asp Ala Pro Ala Tyr Lys Gln Gly Gln Asn Gln Leu Tyr Asn
385                 390                 395                 400

Glu Leu Asn Leu Gly Arg Arg Glu Glu Tyr Asp Val Leu Asp Lys Arg
                405                 410                 415

Arg Gly Arg Asp Pro Glu Met Gly Gly Lys Pro Arg Arg Lys Asn Pro
            420                 425                 430

Gln Glu Gly Leu Tyr Asn Glu Leu Gln Lys Asp Lys Met Ala Glu Ala
        435                 440                 445

Tyr Ser Glu Ile Gly Met Lys Gly Glu Arg Arg Arg Gly Lys Gly His
    450                 455                 460

Asp Gly Leu Tyr Gln Gly Leu Ser Thr Ala Thr Lys Asp Thr Tyr Asp
465                 470                 475                 480

Ala Leu His Met Gln Ala Leu Pro Pro Arg
                485                 490
```

<210> SEQ ID NO 80
<211> LENGTH: 495
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 80

Met Ala Leu Pro Val Thr Ala Leu Leu Leu Pro Leu Ala Leu Leu Leu
1 5 10 15

His Ala Ala Arg Pro Gln Val Gln Leu Val Gln Ser Gly Gly Gly Leu
20 25 30

Val Gln Pro Gly Gly Ser Leu Arg Leu Ser Cys Ala Ala Ser Gly Phe
35 40 45

Thr Phe Ser Ser Tyr Trp Met His Trp Val Arg Gln Ala Pro Gly Lys
50 55 60

Gly Leu Val Trp Val Ser Arg Ile Asn Ser Asp Gly Ser Ser Thr Ser
65 70 75 80

Tyr Ala Asp Ser Val Lys Gly Arg Phe Thr Ile Ser Arg Asp Asn Ala
85 90 95

Lys Asn Thr Leu Tyr Leu Gln Met Asn Ser Leu Arg Ala Glu Asp Thr
100 105 110

Ala Val Tyr Tyr Cys Val Arg Thr Gly Trp Val Gly Ser Tyr Tyr Tyr
115 120 125

Tyr Met Asp Val Trp Gly Lys Gly Thr Thr Val Thr Val Ser Ser Gly
130 135 140

Gly Gly Gly Ser Gly Gly Gly Gly Ser Gly Gly Gly Gly Ser Gly Gly
145 150 155 160

Gly Gly Ser Glu Ile Val Leu Thr Gln Ser Pro Gly Thr Leu Ser Leu
165 170 175

Ser Pro Gly Glu Arg Ala Thr Leu Ser Cys Arg Ala Ser Gln Ser Val
180 185 190

Ser Ser Asn Tyr Leu Ala Trp Tyr Gln Gln Lys Pro Gly Gln Pro Pro
195 200 205

Arg Leu Leu Ile Tyr Asp Val Ser Thr Arg Ala Thr Gly Ile Pro Ala
210 215 220

Arg Phe Ser Gly Gly Gly Ser Gly Thr Asp Phe Thr Leu Thr Ile Ser
225 230 235 240

Ser Leu Glu Pro Glu Asp Phe Ala Val Tyr Tyr Cys Gln Gln Arg Ser
245 250 255

Asn Trp Pro Pro Trp Thr Phe Gly Gln Gly Thr Lys Val Glu Ile Lys
260 265 270

Thr Thr Thr Pro Ala Pro Arg Pro Pro Thr Pro Ala Pro Thr Ile Ala
275 280 285

Ser Gln Pro Leu Ser Leu Arg Pro Glu Ala Cys Arg Pro Ala Ala Gly
290 295 300

Gly Ala Val His Thr Arg Gly Leu Asp Phe Ala Cys Asp Ile Tyr Ile
305 310 315 320

Trp Ala Pro Leu Ala Gly Thr Cys Gly Val Leu Leu Leu Ser Leu Val
325 330 335

Ile Thr Leu Tyr Cys Lys Arg Gly Arg Lys Lys Leu Leu Tyr Ile Phe
340 345 350

Lys Gln Pro Phe Met Arg Pro Val Gln Thr Thr Gln Glu Glu Asp Gly
355 360 365

```
Cys Ser Cys Arg Phe Pro Glu Glu Glu Glu Gly Gly Cys Glu Leu Arg
    370                 375                 380

Val Lys Phe Ser Arg Ser Ala Asp Ala Pro Ala Tyr Lys Gln Gly Gln
385                 390                 395                 400

Asn Gln Leu Tyr Asn Glu Leu Asn Leu Gly Arg Arg Glu Glu Tyr Asp
                405                 410                 415

Val Leu Asp Lys Arg Arg Gly Arg Asp Pro Glu Met Gly Gly Lys Pro
            420                 425                 430

Arg Arg Lys Asn Pro Gln Glu Gly Leu Tyr Asn Glu Leu Gln Lys Asp
        435                 440                 445

Lys Met Ala Glu Ala Tyr Ser Glu Ile Gly Met Lys Gly Glu Arg Arg
    450                 455                 460

Arg Gly Lys Gly His Asp Gly Leu Tyr Gln Gly Leu Ser Thr Ala Thr
465                 470                 475                 480

Lys Asp Thr Tyr Asp Ala Leu His Met Gln Ala Leu Pro Pro Arg
                485                 490                 495
```

<210> SEQ ID NO 81
<211> LENGTH: 494
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 81

```
Met Ala Leu Pro Val Thr Ala Leu Leu Leu Pro Leu Ala Leu Leu Leu
1               5                   10                  15

His Ala Ala Arg Pro Gln Val Gln Leu Val Gln Ser Gly Gly Gly Val
            20                  25                  30

Val Gln Pro Gly Arg Ser Leu Arg Leu Ser Cys Ala Ala Ser Gly Phe
        35                  40                  45

Thr Phe Ser Ser Tyr Gly Met His Trp Val Arg Gln Ala Pro Gly Lys
    50                  55                  60

Gly Leu Glu Trp Val Ala Val Ile Ser Tyr Asp Gly Ser Asn Lys Tyr
65                  70                  75                  80

Tyr Ala Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Ala Lys Gly Tyr Ser Arg Tyr Tyr Tyr Tyr Gly
        115                 120                 125

Met Asp Val Trp Gly Gln Gly Thr Thr Val Thr Val Ser Ser Gly Gly
    130                 135                 140

Gly Gly Ser Gly Gly Gly Gly Ser Gly Gly Gly Gly Ser Gly Gly Gly
145                 150                 155                 160

Gly Ser Glu Ile Val Met Thr Gln Ser Pro Ala Thr Leu Ser Leu Ser
                165                 170                 175

Pro Gly Glu Arg Ala Ile Leu Ser Cys Arg Ala Ser Gln Ser Val Tyr
            180                 185                 190

Thr Lys Tyr Leu Gly Trp Tyr Gln Gln Lys Pro Gly Gln Ala Pro Arg
        195                 200                 205

Leu Leu Ile Tyr Asp Ala Ser Thr Arg Ala Thr Gly Ile Pro Asp Arg
    210                 215                 220
```

```
Phe Ser Gly Ser Gly Ser Gly Thr Asp Phe Thr Leu Thr Ile Asn Arg
225                 230                 235                 240

Leu Glu Pro Glu Asp Phe Ala Val Tyr Tyr Cys Gln His Tyr Gly Gly
                245                 250                 255

Ser Pro Leu Ile Thr Phe Gly Gln Gly Thr Lys Val Asp Ile Lys Thr
            260                 265                 270

Thr Thr Pro Ala Pro Arg Pro Pro Thr Pro Ala Pro Thr Ile Ala Ser
        275                 280                 285

Gln Pro Leu Ser Leu Arg Pro Glu Ala Cys Arg Pro Ala Ala Gly Gly
    290                 295                 300

Ala Val His Thr Arg Gly Leu Asp Phe Ala Cys Asp Ile Tyr Ile Trp
305                 310                 315                 320

Ala Pro Leu Ala Gly Thr Cys Gly Val Leu Leu Leu Ser Leu Val Ile
                325                 330                 335

Thr Leu Tyr Cys Lys Arg Gly Arg Lys Lys Leu Leu Tyr Ile Phe Lys
            340                 345                 350

Gln Pro Phe Met Arg Pro Val Gln Thr Thr Gln Glu Glu Asp Gly Cys
        355                 360                 365

Ser Cys Arg Phe Pro Glu Glu Glu Glu Gly Gly Cys Glu Leu Arg Val
    370                 375                 380

Lys Phe Ser Arg Ser Ala Asp Ala Pro Ala Tyr Lys Gln Gly Gln Asn
385                 390                 395                 400

Gln Leu Tyr Asn Glu Leu Asn Leu Gly Arg Arg Glu Glu Tyr Asp Val
                405                 410                 415

Leu Asp Lys Arg Arg Gly Arg Asp Pro Glu Met Gly Gly Lys Pro Arg
            420                 425                 430

Arg Lys Asn Pro Gln Glu Gly Leu Tyr Asn Glu Leu Gln Lys Asp Lys
        435                 440                 445

Met Ala Glu Ala Tyr Ser Glu Ile Gly Met Lys Gly Glu Arg Arg Arg
    450                 455                 460

Gly Lys Gly His Asp Gly Leu Tyr Gln Gly Leu Ser Thr Ala Thr Lys
465                 470                 475                 480

Asp Thr Tyr Asp Ala Leu His Met Gln Ala Leu Pro Pro Arg
                485                 490


<210> SEQ ID NO 82
<211> LENGTH: 493
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 82

Met Ala Leu Pro Val Thr Ala Leu Leu Leu Pro Leu Ala Leu Leu Leu
1               5                   10                  15

His Ala Ala Arg Pro Gln Val Gln Leu Val Gln Ser Gly Gly Gly Leu
            20                  25                  30

Val Gln Pro Gly Gly Ser Leu Arg Leu Ser Cys Ala Ala Ser Gly Phe
        35                  40                  45

Thr Phe Ser Ser Tyr Ala Met Ser Trp Val Arg Gln Ala Pro Gly Lys
    50                  55                  60

Gly Leu Glu Trp Val Ser Ala Ile Ser Gly Ser Gly Gly Ser Thr Tyr
65                  70                  75                  80

Tyr Ala Asp Ser Val Lys Gly Arg Phe Thr Ile Ser Arg Asp Asn Ser
```

```
                85                  90                  95

Lys Asn Thr Leu Tyr Leu Gln Met Asn Ser Leu Arg Ala Glu Asp Thr
            100                 105                 110

Ala Val Tyr Tyr Cys Ala Lys Arg Glu Ala Ala Ala Gly His Asp Trp
        115                 120                 125

Tyr Phe Asp Leu Trp Gly Arg Gly Thr Leu Val Thr Val Ser Ser Gly
    130                 135                 140

Gly Gly Gly Ser Gly Gly Gly Gly Ser Gly Gly Gly Gly Ser Gly Gly
145                 150                 155                 160

Gly Gly Ser Asp Ile Arg Val Thr Gln Ser Pro Ser Ser Leu Ser Ala
                165                 170                 175

Ser Val Gly Asp Arg Val Thr Ile Thr Cys Arg Ala Ser Gln Ser Ile
            180                 185                 190

Ser Ser Tyr Leu Asn Trp Tyr Gln Gln Lys Pro Gly Lys Ala Pro Lys
        195                 200                 205

Leu Leu Ile Tyr Ala Ala Ser Ser Leu Gln Ser Gly Val Pro Ser Arg
    210                 215                 220

Phe Ser Gly Ser Gly Ser Gly Thr Asp Phe Thr Leu Thr Ile Ser Ser
225                 230                 235                 240

Leu Gln Pro Glu Asp Phe Ala Thr Tyr Tyr Cys Gln Gln Ser Tyr Ser
                245                 250                 255

Ile Pro Leu Thr Phe Gly Gln Gly Thr Lys Val Glu Ile Lys Thr Thr
            260                 265                 270

Thr Pro Ala Pro Arg Pro Pro Thr Pro Ala Pro Thr Ile Ala Ser Gln
        275                 280                 285

Pro Leu Ser Leu Arg Pro Glu Ala Cys Arg Pro Ala Ala Gly Gly Ala
    290                 295                 300

Val His Thr Arg Gly Leu Asp Phe Ala Cys Asp Ile Tyr Ile Trp Ala
305                 310                 315                 320

Pro Leu Ala Gly Thr Cys Gly Val Leu Leu Leu Ser Leu Val Ile Thr
                325                 330                 335

Leu Tyr Cys Lys Arg Gly Arg Lys Lys Leu Leu Tyr Ile Phe Lys Gln
            340                 345                 350

Pro Phe Met Arg Pro Val Gln Thr Thr Gln Glu Glu Asp Gly Cys Ser
        355                 360                 365

Cys Arg Phe Pro Glu Glu Glu Glu Gly Gly Cys Glu Leu Arg Val Lys
    370                 375                 380

Phe Ser Arg Ser Ala Asp Ala Pro Ala Tyr Lys Gln Gly Gln Asn Gln
385                 390                 395                 400

Leu Tyr Asn Glu Leu Asn Leu Gly Arg Arg Glu Glu Tyr Asp Val Leu
                405                 410                 415

Asp Lys Arg Arg Gly Arg Asp Pro Glu Met Gly Gly Lys Pro Arg Arg
            420                 425                 430

Lys Asn Pro Gln Glu Gly Leu Tyr Asn Glu Leu Gln Lys Asp Lys Met
        435                 440                 445

Ala Glu Ala Tyr Ser Glu Ile Gly Met Lys Gly Glu Arg Arg Arg Gly
    450                 455                 460

Lys Gly His Asp Gly Leu Tyr Gln Gly Leu Ser Thr Ala Thr Lys Asp
465                 470                 475                 480

Thr Tyr Asp Ala Leu His Met Gln Ala Leu Pro Pro Arg
                485                 490
```

<210> SEQ ID NO 83

<211> LENGTH: 491
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 83

```
Met Ala Leu Pro Val Thr Ala Leu Leu Leu Pro Leu Ala Leu Leu Leu
1               5                   10                  15

His Ala Ala Arg Pro Gln Val Gln Leu Val Gln Ser Trp Ala Glu Val
            20                  25                  30

Lys Lys Pro Gly Ala Ser Val Lys Val Ser Cys Lys Ala Ser Gly Tyr
        35                  40                  45

Thr Phe Thr Ser Tyr Tyr Met His Trp Val Arg Gln Ala Pro Gly Gln
    50                  55                  60

Gly Leu Glu Trp Met Gly Ile Ile Asn Pro Ser Gly Gly Ser Thr Ser
65                  70                  75                  80

Tyr Ala Gln Lys Phe Gln Gly Arg Val Thr Met Thr Arg Asp Thr Ser
                85                  90                  95

Thr Ser Thr Val Tyr Met Glu Leu Ser Asn Leu Arg Ser Glu Asp Thr
            100                 105                 110

Ala Val Tyr Tyr Cys Ala Arg Ser Pro Arg Val Thr Thr Gly Tyr Phe
        115                 120                 125

Asp Tyr Trp Gly Gln Gly Thr Leu Val Thr Val Ser Ser Gly Gly Gly
    130                 135                 140

Gly Ser Gly Gly Gly Gly Ser Gly Gly Gly Gly Ser Gly Gly Gly Gly
145                 150                 155                 160

Ser Asp Ile Gln Leu Thr Gln Ser Pro Ser Thr Leu Ser Ala Ser Val
                165                 170                 175

Gly Asp Arg Val Thr Ile Thr Cys Arg Ala Ser Gln Ser Ile Ser Ser
            180                 185                 190

Trp Leu Ala Trp Tyr Gln Gln Lys Pro Gly Lys Ala Pro Lys Leu Leu
        195                 200                 205

Ile Tyr Lys Ala Ser Ser Leu Glu Ser Gly Val Pro Ser Arg Phe Ser
    210                 215                 220

Gly Ser Gly Ser Gly Thr Glu Phe Thr Leu Thr Ile Ser Ser Leu Gln
225                 230                 235                 240

Pro Asp Asp Phe Ala Thr Tyr Tyr Cys Gln Gln Tyr Ser Ser Tyr Pro
                245                 250                 255

Leu Thr Phe Gly Gly Gly Thr Arg Leu Glu Ile Lys Thr Thr Thr Pro
            260                 265                 270

Ala Pro Arg Pro Pro Thr Pro Ala Pro Thr Ile Ala Ser Gln Pro Leu
        275                 280                 285

Ser Leu Arg Pro Glu Ala Cys Arg Pro Ala Ala Gly Gly Ala Val His
    290                 295                 300

Thr Arg Gly Leu Asp Phe Ala Cys Asp Ile Tyr Ile Trp Ala Pro Leu
305                 310                 315                 320

Ala Gly Thr Cys Gly Val Leu Leu Leu Ser Leu Val Ile Thr Leu Tyr
                325                 330                 335

Cys Lys Arg Gly Arg Lys Lys Leu Leu Tyr Ile Phe Lys Gln Pro Phe
            340                 345                 350

Met Arg Pro Val Gln Thr Thr Gln Glu Glu Asp Gly Cys Ser Cys Arg
        355                 360                 365
```

```
Phe Pro Glu Glu Glu Glu Gly Gly Cys Glu Leu Arg Val Lys Phe Ser
    370                 375                 380

Arg Ser Ala Asp Ala Pro Ala Tyr Lys Gln Gly Gln Asn Gln Leu Tyr
385                 390                 395                 400

Asn Glu Leu Asn Leu Gly Arg Arg Glu Glu Tyr Asp Val Leu Asp Lys
                405                 410                 415

Arg Arg Gly Arg Asp Pro Glu Met Gly Gly Lys Pro Arg Arg Lys Asn
            420                 425                 430

Pro Gln Glu Gly Leu Tyr Asn Glu Leu Gln Lys Asp Lys Met Ala Glu
        435                 440                 445

Ala Tyr Ser Glu Ile Gly Met Lys Gly Glu Arg Arg Arg Gly Lys Gly
    450                 455                 460

His Asp Gly Leu Tyr Gln Gly Leu Ser Thr Ala Thr Lys Asp Thr Tyr
465                 470                 475                 480

Asp Ala Leu His Met Gln Ala Leu Pro Pro Arg
                485                 490


<210> SEQ ID NO 84
<211> LENGTH: 497
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 84

Met Ala Leu Pro Val Thr Ala Leu Leu Leu Pro Leu Ala Leu Leu Leu
1               5                   10                  15

His Ala Ala Arg Pro Gln Val Gln Leu Val Gln Ser Gly Ala Glu Val
            20                  25                  30

Arg Arg Pro Gly Ala Ser Val Lys Ile Ser Cys Arg Ala Ser Gly Asp
        35                  40                  45

Thr Ser Thr Arg His Tyr Ile His Trp Leu Arg Gln Ala Pro Gly Gln
    50                  55                  60

Gly Pro Glu Trp Met Gly Val Ile Asn Pro Thr Thr Gly Pro Ala Thr
65                  70                  75                  80

Gly Ser Pro Ala Tyr Ala Gln Met Leu Gln Gly Arg Val Thr Met Thr
                85                  90                  95

Arg Asp Thr Ser Thr Arg Thr Val Tyr Met Glu Leu Arg Ser Leu Arg
            100                 105                 110

Phe Glu Asp Thr Ala Val Tyr Tyr Cys Ala Arg Ser Val Val Gly Arg
        115                 120                 125

Ser Ala Pro Tyr Tyr Phe Asp Tyr Trp Gly Gln Gly Thr Leu Val Thr
    130                 135                 140

Val Ser Ser Gly Gly Gly Gly Ser Gly Gly Gly Gly Ser Gly Gly Gly
145                 150                 155                 160

Gly Ser Gly Gly Gly Gly Ser Asp Ile Gln Met Thr Gln Ser Pro Ser
                165                 170                 175

Ser Leu Ser Ala Ser Val Gly Asp Arg Val Thr Ile Thr Cys Arg Ala
            180                 185                 190

Ser Gln Gly Ile Ser Asp Tyr Ser Ala Trp Tyr Gln Gln Lys Pro Gly
        195                 200                 205

Lys Ala Pro Lys Leu Leu Ile Tyr Ala Ala Ser Thr Leu Gln Ser Gly
    210                 215                 220

Val Pro Ser Arg Phe Ser Gly Ser Gly Ser Gly Thr Asp Phe Thr Leu
```

225 230 235 240

Thr Ile Ser Tyr Leu Gln Ser Glu Asp Phe Ala Thr Tyr Tyr Cys Gln
245 250 255

Gln Tyr Tyr Ser Tyr Pro Leu Thr Phe Gly Gly Gly Thr Lys Val Asp
260 265 270

Ile Lys Thr Thr Thr Pro Ala Pro Arg Pro Pro Thr Pro Ala Pro Thr
275 280 285

Ile Ala Ser Gln Pro Leu Ser Leu Arg Pro Glu Ala Cys Arg Pro Ala
290 295 300

Ala Gly Gly Ala Val His Thr Arg Gly Leu Asp Phe Ala Cys Asp Ile
305 310 315 320

Tyr Ile Trp Ala Pro Leu Ala Gly Thr Cys Gly Val Leu Leu Leu Ser
325 330 335

Leu Val Ile Thr Leu Tyr Cys Lys Arg Gly Arg Lys Lys Leu Leu Tyr
340 345 350

Ile Phe Lys Gln Pro Phe Met Arg Pro Val Gln Thr Thr Gln Glu Glu
355 360 365

Asp Gly Cys Ser Cys Arg Phe Pro Glu Glu Glu Glu Gly Gly Cys Glu
370 375 380

Leu Arg Val Lys Phe Ser Arg Ser Ala Asp Ala Pro Ala Tyr Lys Gln
385 390 395 400

Gly Gln Asn Gln Leu Tyr Asn Glu Leu Asn Leu Gly Arg Arg Glu Glu
405 410 415

Tyr Asp Val Leu Asp Lys Arg Arg Gly Arg Asp Pro Glu Met Gly Gly
420 425 430

Lys Pro Arg Arg Lys Asn Pro Gln Glu Gly Leu Tyr Asn Glu Leu Gln
435 440 445

Lys Asp Lys Met Ala Glu Ala Tyr Ser Glu Ile Gly Met Lys Gly Glu
450 455 460

Arg Arg Arg Gly Lys Gly His Asp Gly Leu Tyr Gln Gly Leu Ser Thr
465 470 475 480

Ala Thr Lys Asp Thr Tyr Asp Ala Leu His Met Gln Ala Leu Pro Pro
485 490 495

Arg

<210> SEQ ID NO 85
<211> LENGTH: 493
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 85

Met Ala Leu Pro Val Thr Ala Leu Leu Leu Pro Leu Ala Leu Leu Leu
1 5 10 15

His Ala Ala Arg Pro Gln Val Gln Leu Gln Gln Ser Gly Ala Glu Val
20 25 30

Lys Lys Pro Gly Ala Ser Val Lys Val Ser Cys Lys Ala Ser Gly Tyr
35 40 45

Thr Phe Thr Asn Tyr Tyr Met His Trp Val Arg Gln Ala Pro Gly Gln
50 55 60

Gly Leu Glu Trp Met Gly Ile Ile Asn Pro Ser Gly Gly Tyr Thr Thr
65 70 75 80

```
Tyr Ala Gln Lys Phe Gln Gly Arg Leu Thr Met Thr Arg Asp Thr Ser
                85                  90                  95

Thr Ser Thr Val Tyr Met Glu Leu Ser Ser Leu Arg Ser Glu Asp Thr
            100                 105                 110

Ala Val Tyr Tyr Cys Ala Arg Ile Arg Ser Cys Gly Gly Asp Cys Tyr
        115                 120                 125

Tyr Phe Asp Asn Trp Gly Gln Gly Thr Leu Val Thr Val Ser Ser Gly
    130                 135                 140

Gly Gly Gly Ser Gly Gly Gly Gly Ser Gly Gly Gly Gly Ser Gly Gly
145                 150                 155                 160

Gly Gly Ser Asp Ile Gln Leu Thr Gln Ser Pro Ser Thr Leu Ser Ala
                165                 170                 175

Ser Val Gly Asp Arg Val Thr Ile Thr Cys Arg Ala Ser Glu Asn Val
            180                 185                 190

Asn Ile Trp Leu Ala Trp Tyr Gln Gln Lys Pro Gly Lys Ala Pro Lys
        195                 200                 205

Leu Leu Ile Tyr Lys Ser Ser Ser Leu Ala Ser Gly Val Pro Ser Arg
    210                 215                 220

Phe Ser Gly Ser Gly Ser Gly Ala Glu Phe Thr Leu Thr Ile Ser Ser
225                 230                 235                 240

Leu Gln Pro Asp Asp Phe Ala Thr Tyr Tyr Cys Gln Gln Tyr Gln Ser
                245                 250                 255

Tyr Pro Leu Thr Phe Gly Gly Gly Thr Lys Val Asp Ile Lys Thr Thr
            260                 265                 270

Thr Pro Ala Pro Arg Pro Pro Thr Pro Ala Pro Thr Ile Ala Ser Gln
        275                 280                 285

Pro Leu Ser Leu Arg Pro Glu Ala Cys Arg Pro Ala Ala Gly Gly Ala
    290                 295                 300

Val His Thr Arg Gly Leu Asp Phe Ala Cys Asp Ile Tyr Ile Trp Ala
305                 310                 315                 320

Pro Leu Ala Gly Thr Cys Gly Val Leu Leu Leu Ser Leu Val Ile Thr
                325                 330                 335

Leu Tyr Cys Lys Arg Gly Arg Lys Lys Leu Leu Tyr Ile Phe Lys Gln
            340                 345                 350

Pro Phe Met Arg Pro Val Gln Thr Thr Gln Glu Glu Asp Gly Cys Ser
        355                 360                 365

Cys Arg Phe Pro Glu Glu Glu Glu Gly Gly Cys Glu Leu Arg Val Lys
    370                 375                 380

Phe Ser Arg Ser Ala Asp Ala Pro Ala Tyr Lys Gln Gly Gln Asn Gln
385                 390                 395                 400

Leu Tyr Asn Glu Leu Asn Leu Gly Arg Arg Glu Glu Tyr Asp Val Leu
                405                 410                 415

Asp Lys Arg Arg Gly Arg Asp Pro Glu Met Gly Gly Lys Pro Arg Arg
            420                 425                 430

Lys Asn Pro Gln Glu Gly Leu Tyr Asn Glu Leu Gln Lys Asp Lys Met
        435                 440                 445

Ala Glu Ala Tyr Ser Glu Ile Gly Met Lys Gly Glu Arg Arg Arg Gly
    450                 455                 460

Lys Gly His Asp Gly Leu Tyr Gln Gly Leu Ser Thr Ala Thr Lys Asp
465                 470                 475                 480

Thr Tyr Asp Ala Leu His Met Gln Ala Leu Pro Pro Arg
                485                 490
```

```
<210> SEQ ID NO 86
<211> LENGTH: 490
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 86

Met Ala Leu Pro Val Thr Ala Leu Leu Leu Pro Leu Ala Leu Leu Leu
1               5                   10                  15

His Ala Ala Arg Pro Gln Ile Thr Leu Lys Glu Ser Gly Pro Ala Leu
            20                  25                  30

Val Lys Pro Thr Gln Thr Leu Thr Leu Thr Cys Thr Phe Ser Gly Phe
        35                  40                  45

Ser Leu Ser Thr Ala Gly Val His Val Gly Trp Ile Arg Gln Pro Pro
    50                  55                  60

Gly Lys Ala Leu Glu Trp Leu Ala Leu Ile Ser Trp Ala Asp Asp Lys
65                  70                  75                  80

Arg Tyr Arg Pro Ser Leu Arg Ser Arg Leu Asp Ile Thr Arg Val Thr
                85                  90                  95

Ser Lys Asp Gln Val Val Leu Ser Met Thr Asn Met Gln Pro Glu Asp
            100                 105                 110

Thr Ala Thr Tyr Tyr Cys Ala Leu Gln Gly Phe Asp Gly Tyr Glu Ala
        115                 120                 125

Asn Trp Gly Pro Gly Thr Leu Val Thr Val Ser Ser Gly Gly Gly Gly
    130                 135                 140

Ser Gly Gly Gly Gly Ser Gly Gly Gly Gly Ser Gly Gly Gly Gly Ser
145                 150                 155                 160

Asp Ile Val Met Thr Gln Ser Pro Ser Ser Leu Ser Ala Ser Ala Gly
                165                 170                 175

Asp Arg Val Thr Ile Thr Cys Arg Ala Ser Arg Gly Ile Ser Ser Ala
            180                 185                 190

Leu Ala Trp Tyr Gln Gln Lys Pro Gly Lys Pro Pro Lys Leu Leu Ile
        195                 200                 205

Tyr Asp Ala Ser Ser Leu Glu Ser Gly Val Pro Ser Arg Phe Ser Gly
    210                 215                 220

Ser Gly Ser Gly Thr Asp Phe Thr Leu Thr Ile Asp Ser Leu Glu Pro
225                 230                 235                 240

Glu Asp Phe Ala Thr Tyr Tyr Cys Gln Gln Ser Tyr Ser Thr Pro Trp
                245                 250                 255

Thr Phe Gly Gln Gly Thr Lys Val Asp Ile Lys Thr Thr Thr Pro Ala
            260                 265                 270

Pro Arg Pro Pro Thr Pro Ala Pro Thr Ile Ala Ser Gln Pro Leu Ser
        275                 280                 285

Leu Arg Pro Glu Ala Cys Arg Pro Ala Ala Gly Gly Ala Val His Thr
    290                 295                 300

Arg Gly Leu Asp Phe Ala Cys Asp Ile Tyr Ile Trp Ala Pro Leu Ala
305                 310                 315                 320

Gly Thr Cys Gly Val Leu Leu Leu Ser Leu Val Ile Thr Leu Tyr Cys
                325                 330                 335

Lys Arg Gly Arg Lys Lys Leu Leu Tyr Ile Phe Lys Gln Pro Phe Met
            340                 345                 350

Arg Pro Val Gln Thr Thr Gln Glu Glu Asp Gly Cys Ser Cys Arg Phe
        355                 360                 365
```

-continued

```
Pro Glu Glu Glu Glu Gly Gly Cys Glu Leu Arg Val Lys Phe Ser Arg
    370                 375                 380

Ser Ala Asp Ala Pro Ala Tyr Lys Gln Gly Gln Asn Gln Leu Tyr Asn
385                 390                 395                 400

Glu Leu Asn Leu Gly Arg Arg Glu Glu Tyr Asp Val Leu Asp Lys Arg
                405                 410                 415

Arg Gly Arg Asp Pro Glu Met Gly Gly Lys Pro Arg Arg Lys Asn Pro
            420                 425                 430

Gln Glu Gly Leu Tyr Asn Glu Leu Gln Lys Asp Lys Met Ala Glu Ala
        435                 440                 445

Tyr Ser Glu Ile Gly Met Lys Gly Glu Arg Arg Arg Gly Lys Gly His
    450                 455                 460

Asp Gly Leu Tyr Gln Gly Leu Ser Thr Ala Thr Lys Asp Thr Tyr Asp
465                 470                 475                 480

Ala Leu His Met Gln Ala Leu Pro Pro Arg
                485                 490


<210> SEQ ID NO 87
<211> LENGTH: 732
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 87

caagtccaac tgcagcagtc aggagcggaa gtgaagaaac caggagcgtc agtcaaagtg     60

tcgtgcaagg ctagcggcta caccttcacc ggctactaca tgcactgggt tcgacaggct    120

ccagggcagg gtctggagtg gatgggccgc atcaacccga attccggtgg gactaactac    180

gcccagaagt tccagggaag agtgaccatg actagggaca cgtcgatcag cactgcgtac    240

atggaactga gccgcctgcg gtccgaggat actgccgtct actactgcgc acgcggaagg    300

tactatggaa tggacgtgtg gggccaaggg actatggtga ctgtgagctc gggaggggga    360

ggctccggtg gcgggggatc aggaggagga ggatcagggg gaggaggttc cgaaattgtc    420

ctcacccaga gcccggcaac cctctcactt tccccgggag agcgcgcaac catctcttgc    480

cgggctagcc aatccgtgtc gtccaatttc gcctggtacc agcaacggcc gggacaagcc    540

cctagactcc tgatctacga cgccagcaac agagcgactg gaattcctcc acgcttttcg    600

ggatcaggct ccggtaccga cttcaccctg actatctcgt cgctcgaacc cgaggatttc    660

gccgcctact actgtcatca gcggtcgaac tggttgtata cgtttggcca gggcaccaag    720

gtggatatca ag                                                         732


<210> SEQ ID NO 88
<211> LENGTH: 759
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 88

caagtccaac tcgtccagtc aggagcagaa gtcaagaaac caggtgctag cgtgaaagtg     60

tcgtgcaagg cgtcgggata cactttcacc ggatactaca tgcactgggt ccgccaggcc    120
```

```
cccggacaag gactggaatg gatgggctgg atcaacccga atagcggggg aactaattac    180
gcccagaagt ttcagggacg agtgaccatg acccgcgata cctctatctc gaccgcctac    240
atggagctct ccagactgcg ctccgacgat actgcagtgt actactgcgc ccgggacctg    300
aggcggactg tggttactcc tcgcgcctat tatggcatgg acgtgtgggg ccaaggaact    360
actgtgactg tgagctcggg aggcggtggg tcaggcggag gagggtcggg cggtggtggc    420
tcgggagggg gaggaagcga cattcaactt acgcagagcc cgtcaaccct gtcagcgtca    480
gtgggagatc gggtgaccat cacgtgtcag gccagccagg atatctccaa ctcgctcaac    540
tggtaccagc aaaaggcggg taaagctccg aagctgctga tctacgacgc ttccaccctc    600
gagactggag tcccatccag attttccggg tcaggaagcg gcaccgattt ctccttcacc    660
atttcgtcct tgcaaccgga ggacatcgca acctactact gccagcagca tgacaacttg    720
cctctgacgt tcgggcaggg caccaaggtg gaaatcaag                           759
```

```
<210> SEQ ID NO 89
<211> LENGTH: 738
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 89

caagtccaac tcgtccaatc aggagcggaa gtcaaaaagc ccggagctcc agtgaaagtg     60
tcatgcaagg cctccggcta caccttcacc ggttactata tgcactgggt gcggcaggcc    120
ccgggccagg ggttggaatg gatgggatgg atcaatccaa actcgggtgg gactaactac    180
gcccagaagt tccaaggacg ggtgaccatg actagggaca cctcgatctc caccgcatac    240
atggagctta gcagactccg ctccgacgat accgcagtct actattgcgc gcggggagag    300
tgggacggat cgtactacta cgattactgg ggccagggaa ctctggtgac tgtttcctcg    360
ggtggaggag gttcaggcgg aggcggctcg ggcgggggag gatctggagg aggagggtcc    420
gacattgtgc tgacccaaac tccttcgtcc ctgtcggcca gcgtgggcga ccgcgtgacg    480
attacgtgca gagctagcca atccatcaat acttacctca actggtacca gcataagccg    540
gggaaagcac caaagctgct gatctacgcc gcctcatcct tgcagagcgg tgtgccttca    600
cgctttagcg gatcgggatc gggaacggat ttcaccctga ctatcagctc cctccagccg    660
gaggattttg cgacctacta ctgtcagcag agcttctcac cgctgacttt cggcggcggg    720
accaagctgg aaatcaag                                                  738
```

```
<210> SEQ ID NO 90
<211> LENGTH: 726
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 90

caagtgcaac tcgttgaatc aggtggaggt ttggtgcaac ccggaggatc tctcagactg     60
tcgtgtgcgg cgtccgggtt caccttttcg tcctactgga tgcactgggt gcgccaggtg    120
ccgggaaaag gactggtgtg ggtgtccaga atcaacaccg acgggtcaac gactacctac    180
gcagatagcg tggaaggtcg gttcaccatt tcgcgggaca acgctaaaaa cactctgtac    240
```

```
cttcagatga attcactgcg cgatgacgac accgcagtct actactgcgt cggtggacac    300

tgggcggtct ggggacaggg aactacggtg actgtgtcca gcggcggggg aggaagcggc    360

ggaggggggga gcggaggcgg aggatcagga ggaggcggct ccgatatcca gatgacccag    420

tcgccatcga ccctctccgc tagcgtgggg gatagggtca ctatcacttg ccgagccagc    480

caatccatta gcgaccggct tgcctggtac caacagaaac ctggaaaggc cccgaagctg    540

ctcatctaca aggcctcgtc actggagtcg ggagtcccgt cccgcttttc cggctcgggc    600

tcaggcaccg agttcactct gaccatctcg agcctgcagc cggacgattt cgccgtgtat    660

tactgccagc aatacggaca tctcccaatg tacacgttcg gtcagggcac caaggtcgaa    720

atcaag                                                               726
```

<210> SEQ ID NO 91
<211> LENGTH: 723
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 91

```
caagtccaac tcgttcaatc aggcgcagaa gtcgaaaagc ccggagcatc agtcaaagtc     60

tcttgcaagg cttccggcta caccttcacg gactactaca tgcactgggt gcgccaggct    120

ccaggccagg gactggagtg gatgggatgg atcaacccga attccggggg aactaactac    180

gcccagaagt ttcagggccg ggtgactatg actcgcgata cctcgatctc gactgcgtac    240

atggagctca gccgcctccg gtcggacgat accgccgtgt actattgtgc gtcgggatgg    300

gacttcgact actgggggca gggcactctg gtcactgtgt caagcggagg aggtggatca    360

ggtggaggtg gaagcggggg aggaggttcc ggcggcggag gatcagatat cgtgatgacg    420

caatcgcctt cctcgttgtc cgcatccgtg ggagacaggg tgaccattac ttgcagagcg    480

tcccagtcca ttcggtacta cctgtcgtgg taccagcaga agccggggaa agccccaaaa    540

ctgcttatct atactgcctc gatcctccaa aacggcgtgc catcaagatt cagcggttcg    600

ggcagcggga ccgactttac cctgactatc agcagcctgc agccggaaga tttcgccacg    660

tactactgcc tgcaaaccta caccaccccg gacttcggac ctggaaccaa ggtggagatc    720

aag                                                                  723
```

<210> SEQ ID NO 92
<211> LENGTH: 759
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 92

```
caagtgcaac tcgtccagtc aggtgcagaa gtgaagaaac ccggagcgtc agtcaaagtg     60

tcatgcaagg cgtcaggcta caccttcacc agctactaca tgcactgggt gcggcaggcc    120

ccaggccaag gcttggagtg gatgggaatc attaacccgt caggaggctc cacctcctac    180

gcccagaagt ttcagggaag agtgacgatg actcgggata cgtcgacctc gaccgtgtac    240

atggaactga gctcgctgcg ctccgaggac actgctgtgt actactgcgc acggtacaga    300
```

```
ctcattgccg tggcaggaga ctactactac tatggcatgg acgtctgggg gcagggcact    360

atggtcactg tgtcgtccgg cggaggaggc tcgggtggag gaggtagcgg aggaggggga    420

agcggagggg ggggctccga tatccagatg actcagtcgc cttcctccgt gtcggcctcg    480

gttggagatc gcgtcaccat cacttgtcga gcttcccaag gagtcggtag gtggctggcg    540

tggtaccagc aaaagccggg aactgccccg aagctcctga tctacgcggc tagcaccctg    600

cagtcgggag tgccatcccg cttcagcgga tctgggtcag gtaccgactt caccettacg    660

atcaacaatc tccagccgga ggactttgcc acctattact gccaacaggc caacagcttc    720

cctctgactt tcggaggggg cactcgcctg gaaatcaag                           759
```

<210> SEQ ID NO 93
<211> LENGTH: 750
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 93

```
caagtgcaat tggttcaatc aggaggagga gtggtgcaac ctggaagatc tctcagactg     60

tcgtgtgcgg catcgggatt cactttctca tcatacgcaa tgcactgggt ccgccaggcc    120

ccgggcaaag gcttggaatg ggtggcggtc atttcatacg acggctcgaa caagtactac    180

gctgacagcg tgaagggacg ctttactatt tcccgggaca attcgaagaa cactctgtac    240

ctccagatga actcccttag ggctgaggac accgccgtct actactgcgc acgctggaaa    300

gtgtcgtcca gctccccagc ttttgactac tggggacagg gaacccttgt gaccgtgtcg    360

tccggtggag ggggaagcgg cggaggggga tcaggtggcg gcggatcggg aggcggggga    420

tcagaaatcg tgctgactca gtccccggcc acgctgtctc tcagcccggg agagagagcg    480

atcctgtcct gccgcgcctc gcagagcgtg tacactaagt acctggggtg gtaccagcag    540

aaaccgggtc aagcgcctcg gctgctgatc tacgatgcct ccacccgggc caccggaatc    600

cccgatcggt tctccggcag cggctcggga actgatttca cgctgaccat caatcgcctg    660

gagccggaag atttcgccgt ctattactgc cagcattacg gcgggagccc actcatcacc    720

ttcggtcaag gaacccgact cgaaatcaag                                     750
```

<210> SEQ ID NO 94
<211> LENGTH: 738
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 94

```
caagtccaac tccagcagtc aggtgcagaa gtcaaaaagc caggagcatc cgtgaaggtt     60

tcgtgcaaga cttccggcta cccttttacc gggtactccc tccattgggt gagacaagca    120

ccgggccagg gactggagtg gatgggatgg atcaacccaa attcgggcgg caccaactat    180

gcgcagaagt tccagggacg ggtgaccatg actcgcgaca cttcgatctc cactgcctac    240

atggagctgt cccgcttgag atctgacgac acggccgtct actactgcgc ccgggatcac    300

tacggaggta attcgctgtt ctactggggg cagggaaccc ttgtgactgt gtcctcgggt    360

ggtggagggt caggaggcgg aggctcaggg ggaggaggta gcggaggagg cggatcagac    420
```

atccaactga cccagtcacc atcctccatc tcggctagcg tcggagacac cgtgtcgatt 480
acttgtaggg cctcccaaga ctcagggacg tggctggcgt ggtatcagca aaaaccgggc 540
aaagctccga acctgttgat gtacgacgcc agcaccctcg aagatggagt gcctagccgc 600
ttcagcggaa gcgcctcggg cactgaattc acgctgactg tgaatcggct ccagccggag 660
gattcggcga cctactactg ccagcagtac aacagctacc ccctgacctt tggaggcggg 720
accaaggtgg atatcaag 738

<210> SEQ ID NO 95
<211> LENGTH: 744
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 95
caagtgcaac tcgtccagtc aggtgcagaa gtgaagaaac caggagcgtc cgtcgaagtg 60
tcgtgtaagg cgtccggcta cactttcacc tcgtactaca tgcactgggt gcggcaggcc 120
ccgggacaag gcctcgaatg gatgggaatc atcaacccga gcggaggctc gactggttac 180
gcccagaagt tccagggaag ggtgacgatg acccgcgata cctcgacttc gaccgttcat 240
atggagctct cgtccctgcg gagcgaggac actgctgtct actattgcgc gcggggagga 300
tactctagct cctccgatgc atttgacatt tggggccagg gaactatggt gaccgtgtca 360
tcaggcggag gtggatcagg aggaggaggg tcgggagggg gaggcagcgg cgggggtggg 420
tcggacattc agatgacgca gtcccctcct agcctgagcg cctcggtggg tgacagagtg 480
accatcactt gcagagcctc gcaagacatc tcctccgcat tggcttggta ccagcaaaag 540
ccgggcactc cgccgaaact gctcatctac gatgcctcct cactggagtc aggagtccca 600
tctcgcttct cggggtcagg aagcggcacc gattttaccc ttaccatctc cagcctgcag 660
cccgaggact tcgccacgta ctactgccaa cagttcagct cctacccact gaccttcggg 720
ggcggaactc gcctggaaat caag 744

<210> SEQ ID NO 96
<211> LENGTH: 765
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 96
caagtgcaac tcgtccagag cggagcagaa gtcaagaagc caggagcgtc agtgaaagtg 60
tcatgcaagg ccagcggcta tacctttact tcgtatggga tctcctgggt gcggcaggca 120
ccgggccaag gactggagtg gatgggatgg atctcagcct acaacggtaa caccaactac 180
gcccagaagc tgcaaggacg cgtgaccatg actactgata cgagcacctc cactgcctac 240
atggaattgc ggtcccttcg gtcggacgat actgctgtgt actactgcgc aagagtcgcc 300
ggagggatct actactacta cggcatggac gtctggggac agggaaccac cattacggtg 360
tcgagcggag ggggaggctc ggggggagga ggaagcggag gtggcggctc cgggggcggc 420
ggatcggaca ttgtgatgac ccagactcct gactccctgg ctgtttcgtt gggagagcgc 480

```
gcgactatct cgtgtaagtc cagccactca gtcctgtaca atcgcaataa caagaactac    540

ctcgcgtggt accagcaaaa accgggtcag ccgcctaaac tcctgttcta ctgggcctcc    600

accagaaaga gcggggtgcc agatcgattc tctggatcag gatcaggtac cgactttacg    660

ctgaccatct cgtccctgca gccggaggat ttcgcgactt acttctgcca gcagactcag    720

actttccccc tcaccttcgg tcaaggcacc aggctggaaa tcaat                    765
```

<210> SEQ ID NO 97
<211> LENGTH: 723
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 97

```
caagtccaat tgcagcagag cggagcagaa gtgaagaagc caggagcgtc agtcaaagtg     60

tcgtgtaagg cgtcaggata caccttcacg ggatactaca tgcactgggt gcgccaggcc    120

ccgggccaag gactcgagtg gatgggctgg atcaacccta actctggagg caccaactac    180

gcccagaatt tccaaggcag agtgaccatg acccgggaca cctccatctc gactgcctat    240

atggaactgc ggcggctgcg ctcggacgat actgctgtgt attactgcgc cagcggctgg    300

gactttgact actggggaca gggtactctg gtgactgttt cctcgggagg aggcggatcg    360

ggtggaggag gtagcggggg agggggggtcg ggaggcggag gcagcgatat tcgcatgact    420

caatcgccgt cctccctgag cgctagcgtg ggagatcgag tcaccatcac ttgcagagcg    480

tcacagtcga ttcgctacta cctgtcctgg taccagcaga aaccgggaaa ggcaccaaag    540

cttctgatct acacggcctc catcctgcaa aatggtgtcc catcaaggtt ctccgggtca    600

gggagcggca ctgacttcac tctcaccatc tcctcactcc agcccgagga ctttgcaacc    660

tactactgcc tccagacgta caccaccccg gatttcggtc ctggaaccaa ggtggaaatc    720

aaa                                                                  723
```

<210> SEQ ID NO 98
<211> LENGTH: 738
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 98

```
caagtccaac tcgtccaaag cggagcagaa gtcaaaaagc caggagcgtc ggtgaaagtg     60

tcttgcaaag ccagcggcta caccttcacg ggttactaca tgcactgggt gcgccaggcg    120

ccgggccagg ggctggagtg gatgggccgg attaacccta acagcggggg aactaattac    180

gctcagaagt tccagggtag agtcaccatg actacggaca cttccacttc caccgcctat    240

atggaactgc gctccctccg ctcagatgat actgccgtgt attactgcgc gcggactacc    300

acgtcatacg catttgacat ctggggccag ggaactatgg tgaccgtgag ctcgggcgga    360

ggcggttcag gggaggaggg aagcggagga ggaggatcgg gaggaggtgg ctccgatatc    420

cagctgactc agtccccgag caccctgtcg gcgtcggtgg gggacagggt taccatcacc    480

tgtagagctt cccaatccat ttcgacttgg ctggcctggt accagcaaaa gccgggaaag    540

gcccctaatt tgcttatcta caaggcatcg accctcgaaa gcggtgtgcc ctcccggttt    600
```

tcgggatcag gatcagggac cgagttcacc ctgaccatct catccctcca gccggacgac 660
ttcgccactt actactgcca gcagtacaac acctactcgc catacacttt cggccaaggc 720
accaagctgg agatcaag 738

<210> SEQ ID NO 99
<211> LENGTH: 747
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 99
caagttcaac tcgtgcaatc aggtggagga ctcgtcaaac ccggaggatc attgagactg 60
tcatgcgaag cgagcggttt tatcttctcc gattactata tgggatggat tcggcaggcc 120
ccgggaaagg gactcgaatg ggtgtcatac atcggaaggt caggctcgtc catgtactac 180
gcagactcgg tgaaaggcag attcaccttt agccgggaca acgccaagaa ttccctctac 240
ttgcagatga acagcctgcg agccgaggat actgctgtct actactgtgc cgcgtcgccg 300
gtggtggcag ctactgaaga tttccagcac tggggacagg gaactctggt cacggtgtcg 360
agcggtgggg gcggaagcgg aggcggagga tcgggcggcg gaggttcggg ggggggaggg 420
tctgacatcg tgatgaccca aaccccagcc accctgagcc tctcccctgg agagcgcgcg 480
actctttcgt gccgcgcttc ccagtcagtg accagcaatt acttggcttg gtaccaacag 540
aagccgggac aggcgccacg gctgctgctt tttggtgcca gcactcgcgc caccggaatc 600
ccggatcgct tctcgggctc agggtccggg acggacttca ccctgactat caaccggctg 660
gaacctgagg acttcgcgat gtactactgc cagcagtacg gctccgcacc agtcactttc 720
ggacaaggca ccaagctgga gatcaag 747

<210> SEQ ID NO 100
<211> LENGTH: 747
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 100
caagtccaac tcgtccagtc gggagcagaa gttagagcac caggagcgtc agtgaaaatc 60
tcatgcaagg cctcgggctt cacgttccgc ggatactaca tccactgggt gcgccaagcc 120
ccgggtcagg gattggagtg gatgggaatc attaacccat caggagggag ccgggcttac 180
gcgcagaagt tccagggacg cgtcactatg acccgagata cttccacctc gactgtgtac 240
atggaactct cgtccctgag gtccgacgac actgcgatgt attactgtgc tcggactgcc 300
agctgcggtg gggactgtta ctacctcgat tactggggcc agggaactct ggtgaccgtg 360
tccagcggag gtggcgggtc agggggtggc ggaagcggag gcggcggttc aggcggagga 420
ggctcggaca tccaaatgac gcaatcgccg cctaccctga gcgcttccgt gggagatcgg 480
gtgaccatta cttgcagagc atccgagaac gtcaatatct ggctggcctg gtaccaacag 540
aagccgggga aggcccctaa actgctgatc tacaagtcga gcagccttgc ctctggagtg 600
ccctcccgct tctcgggctc gggatcagga gcggaattca ccctcaccat ctcctccctg 660
cagccagatg actttgccac ctactactgc cagcagtacc agagctatcc gttgaccttt 720
gggggaggca ctaaagtgga catcaag 747

<210> SEQ ID NO 101
<211> LENGTH: 732
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 101
caagttcaac tcgttcaatc aggtggagga ctcgtgcaac caggaagatc actcagactc 60
agctgcgccg cgtcgggatt cactttcgat gactacgcaa tgcactgggt gcggcaggcc 120
ccgggcaaag gactggaatg ggtgagcgga attagctgga actcggggtc catcgggtac 180
gccgactcgg tgaagggacg ctttacgatc tcccgggaca atgccaagaa ctccctgtat 240
ttgcagatga actccttgag ggctgaggac accgccgtgt actactgcgc taaagatgga 300
tcatcgtcct ggtcctgggg atacttcgat tactggggcc agggcactct ggtgaccgtg 360
tcgtcaggcg gtggagggtc gggcggagga ggtagcggag gcggagggag cagctctgaa 420
ctgacccaag acccggcggt gtcggtcgcc cttggtcaga ctgtgcggac tacctgtcag 480
ggggacgcgc tgcgctcgta ctacgcttca tggtaccagc agaagcccgg acaggcacct 540
atgctggtca tctacggaaa gaataaccgc ccatccggca tcccggatcg cttctcgggt 600
tcggacagcg gcgacaccgc atccctgacg atcactggag cgcaggccga ggatgaagcc 660
gactactact gcaattcccg agattcaagc ggctaccctg tgtttgggac cggaactaag 720
gtcaccgtcc tg 732

<210> SEQ ID NO 102
<211> LENGTH: 738
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 102
gaagtgcaac tcgtggaatc tggtggagga cttgtgcaac ctggaagatc gttgagactc 60
tcatgtgctg cctccgggtt cacctttgac gactacgcca tgcactgggt gcgccaggca 120
ccaggaaagg gtctggagtg ggtttcgggt atctcgtgga actccgggag cactggctac 180
gctgattcgg tgaaaggccg gtttaccatc tcccgagaca atgcgaagaa ttccctctat 240
ctgcagatga acagcctccg ggccgaggat actgccctgt actactgcgc caaggatagc 300
tcatcatggt acggaggtgg atcggctttc gatatctggg gccagggcac gatggtcacc 360
gtgtcctcgg ggggcggagg ctccggggga ggaggtagcg gaggaggagg atcgagctca 420
gagttgactc aagaacccgc agtgtccgtg gcactgggcc aaaccgtcag gatcacttgc 480
cagggagaca gcctgaggtc gtactacgcg tcctggtacc agcagaagcc gggacaggcc 540
ccggtcctgg tcattttcgg acgctcaaga cgcccatcgg gcatcccgga ccggttcagc 600
ggaagctcct cgggaaacac cgcgtcactt atcattaccg gcgcacaggc tgaggacgaa 660
gcggattact actgcaactc ccgcgacaat actgccaacc attacgtgtt cgggaccgga 720
acgaaactga ctgtcctg 738

<210> SEQ ID NO 103
<211> LENGTH: 738
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 103
gaagttcaat tggtggaatc tggaggagga cttgtgcaac ccggtagatc tctgagactg 60
tcctgtgcgg catcgggatt caccttcgac gactacgcta tgcactgggt gagacaagcc 120
cctggaaaag gactggagtg ggtgtcaggc atctcctgga atagcgggtc cactggatac 180
gccgattcgg tcaagggtcg cttcaccatt tcccgggaca atgccaagaa ctccctgtac 240
cttcaaatga actccctccg ggccgaggat accgccctct actactgcgc caaagacagc 300
tcgtcatggt atggcggagg gtcggcattt gacatctggg gacagggaac tatggtgact 360
gtgtcatcag gaggcggcgg aagcggcggc ggcgggtccg gcggaggagg gtcgtccagc 420
gaactcaccc aagatccagc agtgagcgtc gcgctgggcc agaccgtcag gatcacgtgc 480
cagggagatt cactgcgctc atactacgcg tcctggtacc agcagaagcc ggggcaggcc 540
ccggtcctcg tgatctacgg aaagaacaac cgcccgtcgg gtatcccaga ccgcttttcg 600
ggtagctcca gcggaaatac ggctagcctg accatcactg gagcacaggc tgaggatgaa 660
gcggactact actgcaattc gcggggctca tcggggaacc attacgtgtt cggaactggt 720
accaaggtga ctgtcctg 738

<210> SEQ ID NO 104
<211> LENGTH: 753
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 104
caagtgcagc tcgttcaatc aggcggagga ctcgttcaac caggaggatc attgcgactc 60
tcatgtgcgg cctctggatt cacgtttagc tcatattgga tgcactgggt gcggcaggcg 120
ccggggaaag gtctggtgtg ggtcagccgc atcaactcag acggctcctc gacttcgtac 180
gccgactccg tgaagggacg ctttaccatt tcccgcgaca acgccaagaa taccctttac 240
cttcagatga actccctccg cgctgaggat accgccgtgt actactgcgt gaggactggc 300
tgggtcggca gctactacta ctacatggac gtgtggggca aaggaactac tgtcaccgtg 360
tcaagcggcg gtggaggttc cggcgggggga ggatcggggg ggggcggatc gggtggcgga 420
ggatcggaga tcgtgttgac ccagtcgccg ggaaccctgt cgctgtcgcc tggggagaga 480
gcaactctgt cctgccgggc ttcccagtcg gtgtcgagca attacctggc atggtaccaa 540
cagaagccgg gacagccgcc acgcctgctg atctatgacg tgtcaactcg ggcaactgga 600
atccctgcgc ggttcagcgg cggagggagc ggtaccgatt tcaccctgac tatttcctcc 660
ctcgaaccag aagatttcgc cgtctactac tgccagcaga gaagcaactg gccgccctgg 720
acgttcggac aaggaaccaa ggtcgaaatc aag 753

<210> SEQ ID NO 105

<211> LENGTH: 750
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 105

```
caagtgcaat tggttcaatc aggaggagga gtcgtgcagc ccggaagatc gttgagactg     60
tcatgtgccg cgagcggctt tactttctca agctacggaa tgcattgggt gcgacaggct    120
ccgggaaaag gactggaatg ggtcgcagtg atctcatacg acggctcgaa caagtactac    180
gccgactccg tcaagggtcg gttcacgatt tcgcgcgata attccaagaa cactctgtac    240
ctccaaatga acagcctccg ggcagaggac accgccgtct actactgcgc taagggatac    300
tcgcgctact actactatgg aatggatgtg tggggccagg gaactaccgt gacggtgtcg    360
tccggcggcg gtgggtcggg cggaggcgga tcaggtggag gtggaagcgg aggaggaggg    420
agcgaaatcg tcatgactca gtcccctgct accctttctc tgtcgccggg agaaagagcc    480
atcctgagct gccgggcctc ccagagcgtg tacaccaaat acctgggatg gtaccagcag    540
aagccggggc aggcaccaag gctcctgatc tacgatgcgt ccacccgcgc gactggtatc    600
ccagaccgct tttccggctc ggggtcaggg actgacttca cccttactat caatcggctc    660
gagcctgagg atttcgccgt gtattactgc cagcactacg gagggtcccc gctgattacc    720
ttcggccaag gcaccaaagt ggacatcaag                                     750
```

<210> SEQ ID NO 106
<211> LENGTH: 747
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 106

```
caagtgcaac ttgttcaatc aggaggagga ctcgttcaac ccggaggatc actgcgactc     60
tcatgtgcag cgtcggggtt caccttctcc agctacgcaa tgtcctgggt gcgccaagcc    120
cctggaaaag gcctggagtg ggtgtcggcc atctctggga gcgggggatc aacttactac    180
gctgactccg tcaagggccg ctttaccatc tcccgggaca acagcaagaa cactctctat    240
ctccagatga actcgctgag agccgaagat accgctgtct actactgcgc gaagagagaa    300
gctgccgcag ggcacgattg gtacttcgac ttgtggggca ggggcaccct tgtgaccgtg    360
tcctccggtg gaggcggatc aggaggtggg ggatcgggtg gaggaggaag cggaggcggc    420
ggttcggaca ttcgcgtcac ccagtcaccg agctccctca gcgcatcggt gggcgaccgg    480
gtcactatca cttgccgggc gtcccagtcg atctcatcgt atctgaattg gtaccagcag    540
aaaccgggaa aggcgccgaa gctgttgatc tacgctgcca gctccctgca gtcgggtgtg    600
ccatcacgct tttccggctc gggatcggga accgatttca ctctgacgat ctctagcctg    660
cagccagaag atttcgccac ttactactgc cagcagtcct acagcatccc tctgactttc    720
ggacaaggga cgaaagtgga gattaag                                        747
```

<210> SEQ ID NO 107
<211> LENGTH: 741
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 107

```
caagtccaac tcgttcagtc atgggcagaa gtcaagaaac ccggtgcaag cgtcaaagtg     60

tcgtgtaagg cctccggcta cactttcact tcctactaca tgcactgggt gcgccaagcc    120

ccgggacagg gccttgaatg gatgggcatc atcaacccat caggaggttc cacgagctac    180

gcgcagaagt tccaggggag agtgacgatg actagagata cctccacgag caccgtctac    240

atggagctgt cgaatctgcg gtcagaggac actgctgtgt attactgcgc gcgctccccg    300

cgggtgacca ctggctactt tgactactgg ggacaaggga ccctggtgac cgtcagctcg    360

ggaggcggag gatcgggagg tggagggtcc ggtggaggcg gctctggagg aggcgggtcg    420

gacattcaat tgacccagag cccatccacc ctctcagcct cggtggggga tagggtgact    480

atcacttgcc gggcctccca gtcaatttcc agctggctgg cttggtacca gcaaaagcct    540

ggaaaggcac cgaagctcct gatctacaag gcctcatctc tggaatcagg agtgccttcg    600

cgcttcagcg gaagcggctc gggaactgag tttaccctga ccatctcgag cctgcagcca    660

gatgacttcg cgacctatta ctgccagcag tactcgtcct acccgttgac tttcggagga    720

ggtacccgcc tcgaaatcaa a                                              741
```

<210> SEQ ID NO 108
<211> LENGTH: 759
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 108

```
caagtccaac tcgtccagtc cggtgcagaa gtcagaaggc caggagcaag cgtgaagatc     60

tcgtgtagag cgtcaggaga caccagcact cgccattaca tccactggct gcgccaggct    120

ccgggccaag ggccggagtg gatgggtgtg atcaacccga ctacgggacc ggctaccgga    180

agccctgcgt acgcacagat gctgcaggga cgggtgacta tgacccgcga tactagcact    240

aggaccgtgt acatggaact ccgctcgttg cggttcgaag ataccgccgt ctactactgc    300

gcccggtccg tggtgggccg aagcgcccct tactacttcg attactgggg acagggcact    360

ctggtgaccg ttagctccgg tgggggaggc tcgggtggag gcggatcggg aggaggaggc    420

agcggtggag gggatcgga cattcagatg acccagtcac cctcctccct ctcagcctcg    480

gtcggggacc gggtgaccat tacgtgcaga gcctcacaag ggatctcgga ctactccgcc    540

tggtaccagc agaaaccggg aaaagcgcca aagctcctga tctacgccgc gagcaccctg    600

caatcaggag tgccatcgcg cttttctgga tcgggctcag ggactgactt cacgctgact    660

atctcctacc ttcagtccga ggatttcgct acctactact gccaacagta ttactcctat    720

cccctgacct ttggcggagg cactaaggtg gacatcaag                           759
```

<210> SEQ ID NO 109
<211> LENGTH: 747
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic polynucleotide"

<400> SEQUENCE: 109
caagtccaac tccagcaatc gggagcagaa gtcaagaaac caggcgcatc ggtgaaagtg 60
tcgtgtaagg cgtcagggta caccttcacc aactactata tgcactgggt gcgccaggct 120
ccaggccagg ggttggagtg gatggggatc atcaatccgt caggtggcta caccacttac 180
gctcagaagt tccagggacg cctcactatg actcgcgata ctagcacctc cacggtgtac 240
atggaactgt catcgctgag gtccgaagat accgccgtct actactgcgc acggatcaga 300
tcctgcggag gagattgtta ctactttgac aactggggac agggcaccct tgttactgtg 360
tcatcgggag gagggggaag cggaggaggt ggatcaggcg gcggtggcag cgggggcgga 420
ggatcggaca ttcagctgac tcagtccccc tccactttgt cggccagcgt gggagacaga 480
gtgaccatca cttgccgggc gtccgagaac gtcaatatct ggctggcctg gtaccagcaa 540
aagcctggaa aagccccgaa gctgctcatc tataagtcat ccagcctggc gtctggtgtg 600
ccgtcgcggt tctccggcag cgggagcgga gccgagttca ctctcaccat ttcgagcctt 660
caaccggacg atttcgccac ctactactgc cagcagtacc aatcctaccc tctgacgttt 720
ggaggtggaa ccaaggtgga catcaag 747

<210> SEQ ID NO 110
<211> LENGTH: 738
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 110
caaatcactc tgaaagaatc tggaccggcc ctggttaagc cgactcaaac gctcaccctt 60
acttgcacct tcagcggatt ctcactcagc actgctggtg tgcacgtcgg atggattaga 120
cagccgcctg gaaaggccct ggaatggctc gccctcatct cctgggccga tgacaagaga 180
tacaggccct cgcttcgatc ccggttggac attacccggg tgacctcgaa agatcaggtg 240
gtgctctcaa tgaccaatat gcagccggag gacaccgcta cgtactactg cgcactgcaa 300
ggatttgacg gctacgaggc taactgggga ccaggtactc tggtcaccgt gagctccggc 360
gggggaggat caggcggggg ggggtcagga ggcggaggct ccggtggagg aggatcggat 420
atcgtcatga cccagtcccc aagctcgctg agcgcgtcag cgggcgaccg cgtgactatc 480
acttgccggg ccagccgcgg catctcctcc gcactggcgt ggtaccagca gaagcctgga 540
aaaccgccaa agctcctgat ctatgatgcc tccagcctgg agtcaggtgt ccccagccgc 600
ttctcgggtt cgggctcggg aaccgacttc actttgacca tcgactcgct ggaaccggaa 660
gatttcgcaa cctactactg tcagcagtcc tactcgaccc cttggacttt tggacaaggg 720
acgaaggtgg acatcaag 738

<210> SEQ ID NO 111
<211> LENGTH: 1464
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 111

-continued

```
atggccctcc ctgtcaccgc cctgctgctt ccgctggctc ttctgctcca cgccgctcgg      60

ccccaagtcc aactgcagca gtcaggagcg gaagtgaaga aaccaggagc gtcagtcaaa     120

gtgtcgtgca aggctagcgg ctacaccttc accggctact acatgcactg ggttcgacag     180

gctccagggc agggtctgga gtggatgggc cgcatcaacc cgaattccgg tgggactaac     240

tacgcccaga agttccaggg aagagtgacc atgactaggg acacgtcgat cagcactgcg     300

tacatggaac tgagccgcct gcggtccgag gatactgccg tctactactg cgcacgcgga     360

aggtactatg gaatggacgt gtggggccaa gggactatgg tgactgtgag ctcgggaggg     420

ggaggctccg gtggcggggg atcaggagga ggaggatcag gggaggagg ttccgaaatt      480

gtcctcaccc agagcccggc aaccctctca ctttccccgg gagagcgcgc aaccatctct     540

tgccgggcta gccaatccgt gtcgtccaat ttcgcctggt accagcaacg gccgggacaa     600

gcccctagac tcctgatcta cgacgccagc aacagagcga ctggaattcc tccacgcttt     660

tcgggatcag gctccggtac cgacttcacc ctgactatct cgtcgctcga acccgaggat     720

ttcgccgcct actactgtca tcagcggtcg aactggttgt atacgtttgg ccagggcacc     780

aaggtggata tcaagaccac taccccagca ccgaggccac ccaccccggc tcctaccatc     840

gcctcccagc ctctgtccct gcgtccggag gcatgtagac ccgcagctgg tggggccgtg     900

catacccggg gtcttgactt cgcctgcgat atctacattt gggcccctct ggctggtact     960

tgcggggtcc tgctgctttc actcgtgatc actctttact gtaagcgcgg tcggaagaag    1020

ctgctgtaca tctttaagca acccttcatg aggcctgtgc agactactca agaggaggac    1080

ggctgttcat gccggttccc agaggaggag gaaggcggct gcgaactgcg cgtgaaattc    1140

agccgcagcg cagatgctcc agcctacaag caggggcaga accagctcta caacgaactc    1200

aatcttggtc ggagagagga gtacgacgtg ctggacaagc ggagaggacg ggacccagaa    1260

atgggcggga agccgcgcag aaagaatccc caagagggcc tgtacaacga gctccaaaag    1320

gataagatgg cagaagccta tagcgagatt ggtatgaaag gggaacgcag aagaggcaaa    1380

ggccacgacg gactgtacca gggactcagc accgccacca aggacaccta tgacgctctt    1440

cacatgcagg ccctgccgcc tcgg                                            1464
```

```
<210> SEQ ID NO 112
<211> LENGTH: 1491
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 112

atggccctcc ctgtcaccgc cctgctgctt ccgctggctc ttctgctcca cgccgctcgg      60

ccccaagtcc aactcgtcca gtcaggagca gaagtcaaga aaccaggtgc tagcgtgaaa     120

gtgtcgtgca aggcgtcggg atacactttc accggatact acatgcactg ggtccgccag     180

gcccccggac aaggactgga atggatgggc tggatcaacc cgaatagcgg gggaactaat     240

tacgcccaga agtttcaggg acgagtgacc atgacccgcg atacctctat ctcgaccgcc     300

tacatggagc tctccagact gcgctccgac gatactgcag tgtactactg cgcccgggac     360

ctgaggcgga ctgtggttac tcctcgcgcc tattatggca tggacgtgtg gggccaagga     420

actactgtga ctgtgagctc gggaggcggt gggtcaggcg gaggagggtc gggcggtggt     480
```

```
ggctcgggag ggggaggaag cgacattcaa cttacgcaga gcccgtcaac cctgtcagcg    540

tcagtgggag atcgggtgac catcacgtgt caggccagcc aggatatctc caactcgctc    600

aactggtacc agcaaaaggc gggtaaagct ccgaagctgc tgatctacga cgcttccacc    660

ctcgagactg gagtcccatc cagattttcc gggtcaggaa gcggcaccga tttctccttc    720

accatttcgt ccttgcaacc ggaggacatc gcaacctact actgccagca gcatgacaac    780

ttgcctctga cgttcgggca gggcaccaag gtggaaatca agaccactac cccagcaccg    840

aggccaccca ccccggctcc taccatcgcc tcccagcctc tgtccctgcg tccggaggca    900

tgtagacccg cagctggtgg ggccgtgcat acccggggtc ttgacttcgc ctgcgatatc    960

tacatttggg cccctctggc tggtacttgc ggggtcctgc tgctttcact cgtgatcact   1020

ctttactgta agcgcggtcg gaagaagctg ctgtacatct ttaagcaacc cttcatgagg   1080

cctgtgcaga ctactcaaga ggaggacggc tgttcatgcc ggttcccaga ggaggaggaa   1140

ggcggctgcg aactgcgcgt gaaattcagc cgcagcgcag atgctccagc ctacaagcag   1200

gggcagaacc agctctacaa cgaactcaat cttggtcgga gagaggagta cgacgtgctg   1260

gacaagcgga gaggacggga cccagaaatg ggcgggaagc cgcgcagaaa gaatccccaa   1320

gagggcctgt acaacgagct ccaaaaggat aagatggcag aagcctatag cgagattggt   1380

atgaaagggg aacgcagaag aggcaaaggc cacgacggac tgtaccaggg actcagcacc   1440

gccaccaagg acacctatga cgctcttcac atgcaggccc tgccgcctcg g            1491
```

<210> SEQ ID NO 113
<211> LENGTH: 1470
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 113

```
atggccctcc ctgtcaccgc cctgctgctt ccgctggctc ttctgctcca cgccgctcgg     60

ccccaagtcc aactcgtcca atcaggagcg gaagtcaaaa agcccggagc tccagtgaaa    120

gtgtcatgca aggcctccgg ctacaccttc accggttact atatgcactg ggtgcggcag    180

gccccgggcc aggggttgga atggatggga tggatcaatc caaactcggg tgggactaac    240

tacgcccaga agttccaagg acgggtgacc atgactaggg acacctcgat ctccaccgca    300

tacatggagc ttagcagact ccgctccgac gataccgcag tctactattg cgcgcgggga    360

gagtgggacg gatcgtacta ctacgattac tggggccagg gaactctggt gactgtttcc    420

tcgggtggag gaggttcagg cggaggcggc tcgggcgggg gaggatctgg aggaggaggg    480

tccgacattg tgctgaccca aactccttcg tccctgtcgg ccagcgtggg cgaccgcgtg    540

acgattacgt gcagagctag ccaatccatc aatacttacc tcaactggta ccagcataag    600

ccggggaaag caccaaagct gctgatctac gccgcctcat ccttgcagag cggtgtgcct    660

tcacgcttta gcggatcggg atcgggaacg gatttcaccc tgactatcag ctccctccag    720

ccggaggatt ttgcgaccta ctactgtcag cagagcttct caccgctgac tttcggcggc    780

gggaccaagc tggaaatcaa gaccactacc ccagcaccga ggccacccac cccggctcct    840

accatcgcct cccagcctct gtccctgcgt ccggaggcat gtagacccgc agctggtggg    900

gccgtgcata cccggggtct tgacttcgcc tgcgatatct acatttgggc ccctctggct    960

ggtacttgcg gggtcctgct gctttcactc gtgatcactc tttactgtaa gcgcggtcgg   1020
```

```
aagaagctgc tgtacatctt taagcaaccc ttcatgaggc ctgtgcagac tactcaagag   1080

gaggacggct gttcatgccg gttcccagag gaggaggaag gcggctgcga actgcgcgtg   1140

aaattcagcc gcagcgcaga tgctccagcc tacaagcagg ggcagaacca gctctacaac   1200

gaactcaatc ttggtcggag agaggagtac gacgtgctgg acaagcggag aggacgggac   1260

ccagaaatgg gcgggaagcc gcgcagaaag aatccccaag agggcctgta caacgagctc   1320

caaaaggata agatggcaga agcctatagc gagattggta tgaaagggga acgcagaaga   1380

ggcaaaggcc acgacggact gtaccaggga ctcagcaccg ccaccaagga cacctatgac   1440

gctcttcaca tgcaggccct gccgcctcgg                                    1470
```

```
<210> SEQ ID NO 114
<211> LENGTH: 1458
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 114

atggccctcc ctgtcaccgc cctgctgctt ccgctggctc ttctgctcca cgccgctcgg     60

ccccaagtgc aactcgttga atcaggtgga ggtttggtgc aacccggagg atctctcaga    120

ctgtcgtgtg cggcgtccgg gttcaccttt tcgtcctact ggatgcactg ggtgcgccag    180

gtgccgggaa aaggactggt gtgggtgtcc agaatcaaca ccgacgggtc aacgactacc    240

tacgcagata gcgtggaagg tcggttcacc atttcgcggg acaacgctaa aaacactctg    300

taccttcaga tgaattcact gcgcgatgac gacaccgcag tctactactg cgtcggtgga    360

cactgggcgg tctggggaca gggaactacg gtgactgtgt ccagcggcgg gggaggaagc    420

ggcggagggg ggagcggagg cggaggatca ggaggaggcg gctccgatat ccagatgacc    480

cagtcgccat cgaccctctc cgctagcgtg gggataggg tcactatcac ttgccgagcc     540

agccaatcca ttagcgaccg gcttgcctgg taccaacaga aacctggaaa ggccccgaag    600

ctgctcatct acaaggcctc gtcactggag tcgggagtcc cgtcccgctt ttccggctcg    660

ggctcaggca ccgagttcac tctgaccatc tcgagcctgc agccggacga tttcgccgtg    720

tattactgcc agcaatacgg acatctccca atgtacacgt tcggtcaggg caccaaggtc    780

gaaatcaaga ccactacccc agcaccgagg ccacccaccc cggctcctac catcgcctcc    840

cagcctctgt ccctgcgtcc ggaggcatgt agacccgcag ctggtggggc cgtgcatacc    900

cggggtcttg acttcgcctg cgatatctac atttgggccc ctctggctgg tacttgcggg    960

gtcctgctgc tttcactcgt gatcactctt tactgtaagc gcggtcggaa gaagctgctg   1020

tacatcttta agcaaccctt catgaggcct gtgcagacta ctcaagagga ggacggctgt   1080

tcatgccggt tcccagagga ggaggaaggc ggctgcgaac tgcgcgtgaa attcagccgc   1140

agcgcagatg ctccagccta caagcagggg cagaaccagc tctacaacga actcaatctt   1200

ggtcggagag aggagtacga cgtgctggac aagcggagag gacgggaccc agaaatgggc   1260

gggaagccgc gcagaaagaa tccccaagag ggcctgtaca acgagctcca aaaggataag   1320

atggcagaag cctatagcga gattggtatg aaaggggaac gcagaagagg caaaggccac   1380

gacggactgt accagggact cagcaccgcc accaaggaca cctatgacgc tcttcacatg   1440

caggccctgc cgcctcgg                                                 1458
```

<210> SEQ ID NO 115
<211> LENGTH: 1455
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 115
atggccctcc ctgtcaccgc cctgctgctt ccgctggctc ttctgctcca cgccgctcgg 60
ccccaagtcc aactcgttca atcaggcgca gaagtcgaaa agcccggagc atcagtcaaa 120
gtctcttgca aggcttccgg ctacaccttc acggactact acatgcactg ggtgcgccag 180
gctccaggcc agggactgga gtggatggga tggatcaacc cgaattccgg gggaactaac 240
tacgcccaga agtttcaggg ccgggtgact atgactcgcg atacctcgat ctcgactgcg 300
tacatggagc tcagccgcct ccggtcggac gataccgccg tgtactattg tgcgtcggga 360
tgggacttcg actactgggg gcagggcact ctggtcactg tgtcaagcgg aggaggtgga 420
tcaggtggag gtggaagcgg gggaggaggt tccggcggcg gaggatcaga tatcgtgatg 480
acgcaatcgc cttcctcgtt gtccgcatcc gtgggagaca gggtgaccat tacttgcaga 540
gcgtcccagt ccattcggta ctacctgtcg tggtaccagc agaagccggg gaaagcccca 600
aaactgctta tctatactgc ctcgatcctc caaaacggcg tgccatcaag attcagcggt 660
tcgggcagcg ggaccgactt taccctgact atcagcagcc tgcagccgga agatttcgcc 720
acgtactact gcctgcaaac ctacaccacc ccggacttcg gacctggaac caaggtggag 780
atcaagacca ctaccccagc accgaggcca cccaccccgg ctcctaccat cgcctcccag 840
cctctgtccc tgcgtccgga ggcatgtaga cccgcagctg gtggggccgt gcatacccgg 900
ggtcttgact tcgcctgcga tatctacatt tgggcccctc tggctggtac ttgcggggtc 960
ctgctgcttt cactcgtgat cactctttac tgtaagcgcg gtcggaagaa gctgctgtac 1020
atctttaagc aacccttcat gaggcctgtg cagactactc aagaggagga cggctgttca 1080
tgccggttcc cagaggagga ggaaggcggc tgcgaactgc gcgtgaaatt cagccgcagc 1140
gcagatgctc cagcctacaa gcaggggcag aaccagctct acaacgaact caatcttggt 1200
cggagagagg agtacgacgt gctggacaag cggagaggac gggacccaga aatgggcggg 1260
aagccgcgca gaaagaatcc ccaagagggc ctgtacaacg agctccaaaa ggataagatg 1320
gcagaagcct atagcgagat tggtatgaaa ggggaacgca gaagaggcaa aggccacgac 1380
ggactgtacc agggactcag caccgccacc aaggacacct atgacgctct tcacatgcag 1440
gccctgccgc ctcgg 1455

<210> SEQ ID NO 116
<211> LENGTH: 1491
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 116
atggccctcc ctgtcaccgc cctgctgctt ccgctggctc ttctgctcca cgccgctcgg 60
ccccaagtgc aactcgtcca gtcaggtgca gaagtgaaga aacccggagc gtcagtcaaa 120
gtgtcatgca aggcgtcagg ctacaccttc accagctact acatgcactg ggtgcggcag 180
gccccaggcc aaggcttgga gtggatggga atcattaacc cgtcaggagg ctccacctcc 240
tacgcccaga agtttcaggg aagagtgacg atgactcggg atacgtcgac ctcgaccgtg 300
tacatggaac tgagctcgct gcgctccgag gacactgctg tgtactactg cgcacggtac 360
agactcattg ccgtggcagg agactactac tactatggca tggacgtctg gggcagggc 420 actatggtca ctgtgtcgtc cggcggagga ggctcgggtg gaggaggtag cggaggaggg 480
ggaagcggag ggggggctc cgatatccag atgactcagt cgccttcctc cgtgtcggcc 540
tcggttggag atcgcgtcac catcacttgt cgagcttccc aaggagtcgg taggtggctg 600
gcgtggtacc agcaaaagcc gggaactgcc ccgaagctcc tgatctacgc ggctagcacc 660
ctgcagtcgg gagtgccatc ccgcttcagc ggatctgggt caggtaccga cttcaccctt 720
acgatcaaca atctccagcc ggaggacttt gccacctatt actgccaaca ggccaacagc 780
ttccctctga ctttcggagg gggcactcgc ctggaaatca agaccactac cccagcaccg 840
aggccaccca ccccggctcc taccatcgcc tcccagcctc tgtccctgcg tccggaggca 900
tgtagacccg cagctggtgg ggccgtgcat acccggggtc ttgacttcgc ctgcgatatc 960
tacatttggg cccctctggc tggtacttgc ggggtcctgc tgctttcact cgtgatcact 1020
ctttactgta agcgcggtcg gaagaagctg ctgtacatct ttaagcaacc cttcatgagg 1080
cctgtgcaga ctactcaaga ggaggacggc tgttcatgcc ggttcccaga ggaggaggaa 1140
ggcggctgcg aactgcgcgt gaaattcagc cgcagcgcag atgctccagc ctacaagcag 1200
gggcagaacc agctctacaa cgaactcaat cttggtcgga gagaggagta cgacgtgctg 1260
gacaagcgga gaggacggga cccagaaatg ggcgggaagc cgcgcagaaa gaatccccaa 1320
gagggcctgt acaacgagct ccaaaaggat aagatggcag aagcctatag cgagattggt 1380
atgaaagggg aacgcagaag aggcaaaggc cacgacggac tgtaccaggg actcagcacc 1440
gccaccaagg acacctatga cgctcttcac atgcaggccc tgccgcctcg g 1491

<210> SEQ ID NO 117
<211> LENGTH: 1482
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 117
atggccctcc ctgtcaccgc cctgctgctt ccgctggctc ttctgctcca cgccgctcgg 60
ccccaagtgc aattggttca atcaggagga ggagtggtgc aacctggaag atctctcaga 120
ctgtcgtgtg cggcatcggg attcactttc tcatcatacg caatgcactg ggtccgccag 180
gccccgggca aaggcttgga atgggtggcg gtcatttcat acgacggctc gaacaagtac 240
tacgctgaca gcgtgaaggg acgctttact atttcccggg acaattcgaa gaacactctg 300
tacctccaga tgaactccct tagggctgag gacaccgccg tctactactg cgcacgctgg 360
aaagtgtcgt ccagctcccc agcttttgac tactggggac agggaaccct tgtgaccgtg 420
tcgtccggtg gagggggaag cggcggaggg ggatcaggtg gcggcggatc gggaggcggg 480
ggatcagaaa tcgtgctgac tcagtccccg gccacgctgt ctctcagccc gggagagaga 540
gcgatcctgt cctgccgcgc ctcgcagagc gtgtacacta agtacctggg gtggtaccag 600
cagaaaccgg gtcaagcgcc tcggctgctg atctacgatg cctccacccg ggccaccgga 660

```
atccccgatc ggttctccgg cagcggctcg ggaactgatt tcacgctgac catcaatcgc    720

ctggagccgg aagatttcgc cgtctattac tgccagcatt acggcgggag cccactcatc    780

accttcggtc aaggaacccg actcgaaatc aagaccacta ccccagcacc gaggccaccc    840

accccggctc ctaccatcgc ctcccagcct ctgtccctgc gtccggaggc atgtagaccc    900

gcagctggtg ggccgtgca tacccggggt cttgacttcg cctgcgatat ctacatttgg     960

gcccctctgg ctggtacttg cggggtcctg ctgctttcac tcgtgatcac tctttactgt   1020

aagcgcggtc ggaagaagct gctgtacatc tttaagcaac ccttcatgag gcctgtgcag   1080

actactcaag aggaggacgg ctgttcatgc cggttcccag aggaggagga aggcggctgc   1140

gaactgcgcg tgaaattcag ccgcagcgca gatgctccag cctacaagca ggggcagaac   1200

cagctctaca acgaactcaa tcttggtcgg agagaggagt acgacgtgct ggacaagcgg   1260

agaggacggg acccagaaat gggcgggaag ccgcgcagaa agaatcccca agagggcctg   1320

tacaacgagc tccaaaagga taagatggca gaagcctata gcgagattgg tatgaaaggg   1380

gaacgcagaa gaggcaaagg ccacgacgga ctgtaccagg gactcagcac cgccaccaag   1440

gacacctatg acgctcttca catgcaggcc ctgccgcctc gg                      1482
```

<210> SEQ ID NO 118
<211> LENGTH: 1470
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 118

```
atggccctcc ctgtcaccgc cctgctgctt ccgctggctc ttctgctcca cgccgctcgg     60

ccccaagtcc aactccagca gtcaggtgca gaagtcaaaa agccaggagc atccgtgaag    120

gtttcgtgca agacttccgg ctaccctttt accgggtact ccctccattg ggtgagacaa    180

gcaccgggcc agggactgga gtggatggga tggatcaacc caaattcggg cggcaccaac    240

tatgcgcaga agttccaggg acgggtgacc atgactcgcg acacttcgat ctccactgcc    300

tacatggagc tgtcccgctt gagatctgac gacacggccg tctactactg cgcccgggat    360

cactacggag gtaattcgct gttctactgg gggcagggaa cccttgtgac tgtgtcctcg    420

ggtggtggag ggtcaggagg cggaggctca gggggaggag gtagcggagg aggcggatca    480

gacatccaac tgacccagtc accatcctcc atctcggcta gcgtcggaga caccgtgtcg    540

attacttgta gggcctccca agactcaggg acgtggctgg cgtggtatca gcaaaaaccg    600

ggcaaagctc cgaacctgtt gatgtacgac gccagcaccc tcgaagatgg agtgcctagc    660

cgcttcagcg gaagcgcctc gggcactgaa ttcacgctga ctgtgaatcg gctccagccg    720

gaggattcgg cgacctacta ctgccagcag tacaacagct accccctgac ctttggaggc    780

gggaccaagg tggatatcaa gaccactacc ccagcaccga ggccacccac cccggctcct    840

accatcgcct cccagcctct gtccctgcgt ccggaggcat gtagacccgc agctggtggg    900

gccgtgcata cccggggtct tgacttcgcc tgcgatatct acatttgggc ccctctggct    960

ggtacttgcg gggtcctgct gctttcactc gtgatcactc tttactgtaa gcgcggtcgg   1020

aagaagctgc tgtacatctt taagcaaccc ttcatgaggc ctgtgcagac tactcaagag   1080

gaggacggct gttcatgccg gttcccagag gaggaggaag gcggctgcga actgcgcgtg   1140

aaattcagcc gcagcgcaga tgctccagcc tacaagcagg ggcagaacca gctctacaac   1200
```

```
gaactcaatc ttggtcggag agaggagtac gacgtgctgg acaagcggag aggacgggac   1260

ccagaaatgg gcgggaagcc gcgcagaaag aatccccaag agggcctgta caacgagctc   1320

caaaaggata agatggcaga agcctatagc gagattggta tgaaagggga acgcagaaga   1380

ggcaaaggcc acgacggact gtaccaggga ctcagcaccg ccaccaagga cacctatgac   1440

gctcttcaca tgcaggccct gccgcctcgg                                    1470
```

<210> SEQ ID NO 119
<211> LENGTH: 1476
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 119

```
atggccctcc ctgtcaccgc cctgctgctt ccgctggctc ttctgctcca cgccgctcgg     60

ccccaagtgc aactcgtcca gtcaggtgca gaagtgaaga aaccaggagc gtccgtcgaa    120

gtgtcgtgta aggcgtccgg ctacactttc acctcgtact acatgcactg ggtgcggcag    180

gccccgggac aaggcctcga atggatggga atcatcaacc cgagcggagg ctcgactggt    240

tacgcccaga agttccaggg aagggtgacg atgacccgcg atacctcgac ttcgaccgtt    300

catatggagc tctcgtccct gcggagcgag gacactgctg tctactattg cgcgcgggga    360

ggatactcta gctcctccga tgcatttgac atttggggcc agggaactat ggtgaccgtg    420

tcatcaggcg gaggtggatc aggaggagga gggtcgggag gggaggcag cggcgggggt     480

gggtcggaca ttcagatgac gcagtcccct cctagcctga gcgcctcggt gggtgacaga    540

gtgaccatca cttgcagagc ctcgcaagac atctcctccg cattggcttg gtaccagcaa    600

aagccgggca ctccgccgaa actgctcatc tacgatgcct cctcactgga gtcaggagtc    660

ccatctcgct tctcggggtc aggaagcggc accgatttta cccttaccat ctccagcctg    720

cagcccgagg acttcgccac gtactactgc caacagttca gctcctaccc actgaccttc    780

gggggcggaa ctcgcctgga aatcaagacc actaccccag caccgaggcc acccaccccg    840

gctcctacca tcgcctccca gcctctgtcc ctgcgtccgg aggcatgtag acccgcagct    900

ggtggggccg tgcatacccg gggtcttgac ttcgcctgcg atatctacat ttgggcccct    960

ctggctggta cttgcggggt cctgctgctt tcactcgtga tcactcttta ctgtaagcgc   1020

ggtcggaaga agctgctgta catctttaag caacccttca tgaggcctgt gcagactact   1080

caagaggagg acggctgttc atgccggttc ccagaggagg aggaaggcgg ctgcgaactg   1140

cgcgtgaaat tcagccgcag cgcagatgct ccagcctaca agcaggggca gaaccagctc   1200

tacaacgaac tcaatcttgg tcggagagag gagtacgacg tgctggacaa gcggagagga   1260

cgggacccag aaatgggcgg gaagccgcgc agaaagaatc cccaagaggg cctgtacaac   1320

gagctccaaa aggataagat ggcagaagcc tatagcgaga ttggtatgaa aggggaacgc   1380

agaagaggca aaggccacga cggactgtac cagggactca gcaccgccac caaggacacc   1440

tatgacgctc ttcacatgca ggccctgccg cctcgg                             1476
```

<210> SEQ ID NO 120
<211> LENGTH: 1497
<212> TYPE: DNA
<213> ORGANISM: Artificial Sequence
<220> FEATURE:

<221> NAME/KEY: source
<223> OTHER INFORMATION: /note="Description of Artificial Sequence: Synthetic polynucleotide"

<400> SEQUENCE: 120

```
atggccctcc ctgtcaccgc cctgctgctt ccgctggctc ttctgctcca cgccgctcgg     60

ccccaagtgc aactcgtcca gagcggagca gaagtcaaga agccaggagc gtcagtgaaa    120

gtgtcatgca aggccagcgg ctataccttt acttcgtatg ggatctcctg ggtgcggcag    180

gcaccgggcc aaggactgga gtggatggga tggatctcag cctacaacgg taacaccaac    240

tacgcccaga agctgcaagg acgcgtgacc atgactactg atacgagcac ctccactgcc    300

tacatggaat tgcggtccct tcggtcggac gatactgctg tgtactactg cgcaagagtc    360

gccggaggga tctactacta ctacggcatg gacgtctggg gacagggaac caccattacg    420

gtgtcgagcg gagggggagg ctcgggggga ggaggaagcg gaggtggcgg ctccgggggc    480

ggcggatcgg acattgtgat gacccagact cctgactccc tggctgtttc gttgggagag    540

cgcgcgacta tctcgtgtaa gtccagccac tcagtcctgt acaatcgcaa taacaagaac    600

tacctcgcgt ggtaccagca aaaaccgggt cagccgccta aactcctgtt ctactgggcc    660

tccaccagaa agagcggggt gccagatcga ttctctggat caggatcagg taccgacttt    720

acgctgacca tctcgtccct gcagccggag gatttcgcga cttacttctg ccagcagact    780

cagactttcc ccctcacctt cggtcaaggc accaggctgg aaatcaatac cactacccca    840

gcaccgaggc cacccacccc ggctcctacc atcgcctccc agcctctgtc cctgcgtccg    900

gaggcatgta gacccgcagc tggtggggcc gtgcataccc ggggtcttga cttcgcctgc    960

gatatctaca tttgggcccc tctggctggt acttgcgggg tcctgctgct ttcactcgtg   1020

atcactcttt actgtaagcg cggtcggaag aagctgctgt acatctttaa gcaacccttc   1080

atgaggcctg tgcagactac tcaagaggag gacggctgtt catgccggtt cccagaggag   1140

gaggaaggcg gctgcgaact gcgcgtgaaa ttcagccgca gcgcagatgc tccagcctac   1200

aagcaggggc agaaccagct ctacaacgaa ctcaatcttg gtcggagaga ggagtacgac   1260

gtgctggaca agcggagagg acgggaccca gaaatgggcg ggaagccgcg cagaaagaat   1320

ccccaagagg gcctgtacaa cgagctccaa aaggataaga tggcagaagc ctatagcgag   1380

attggtatga aaggggaacg cagaagaggc aaaggccacg acggactgta ccagggactc   1440

agcaccgcca ccaaggacac ctatgacgct cttcacatgc aggccctgcc gcctcgg      1497
```

<210> SEQ ID NO 121
<211> LENGTH: 1455
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 121

```
atggccctcc ctgtcaccgc cctgctgctt ccgctggctc ttctgctcca cgccgctcgg     60

ccccaagtcc aattgcagca gagcggagca gaagtgaaga agccaggagc gtcagtcaaa    120

gtgtcgtgta aggcgtcagg atacaccttc acgggatact acatgcactg ggtgcgccag    180

gccccgggcc aaggactcga gtggatgggc tggatcaacc ctaactctgg aggcaccaac    240

tacgcccaga atttccaagg cagagtgacc atgacccggg acacctccat ctcgactgcc    300

tatatggaac tgcggcggct gcgctcggac gatactgctg tgtattactg cgccagcggc    360
```

tgggactttg actactgggg acagggtact ctggtgactg tttcctcggg aggaggcgga 420
tcgggtggag gaggtagcgg gggagggggg tcgggaggcg gaggcagcga tattcgcatg 480
actcaatcgc cgtcctccct gagcgctagc gtgggagatc gagtcaccat cacttgcaga 540
gcgtcacagt cgattcgcta ctacctgtcc tggtaccagc agaaaccggg aaaggcacca 600
aagcttctga tctacacggc ctccatcctg caaaatggtg tcccatcaag gttctccggg 660
tcagggagcg gcactgactt cactctcacc atctcctcac tccagcccga ggactttgca 720
acctactact gcctccagac gtacaccacc ccggatttcg gtcctggaac caaggtggaa 780
atcaaaacca ctaccccagc accgaggcca cccaccccgg ctcctaccat cgcctcccag 840
cctctgtccc tgcgtccgga ggcatgtaga cccgcagctg gtggggccgt gcatacccgg 900
ggtcttgact tcgcctgcga tatctacatt tgggcccctc tggctggtac ttgcggggtc 960
ctgctgcttt cactcgtgat cactctttac tgtaagcgcg gtcggaagaa gctgctgtac 1020
atctttaagc aacccttcat gaggcctgtg cagactactc aagaggagga cggctgttca 1080
tgccggttcc cagaggagga ggaaggcggc tgcgaactgc gcgtgaaatt cagccgcagc 1140
gcagatgctc cagcctacaa gcaggggcag aaccagctct acaacgaact caatcttggt 1200
cggagagagg agtacgacgt gctggacaag cggagaggac gggacccaga aatgggcggg 1260
aagccgcgca gaaagaatcc ccaagagggc ctgtacaacg agctccaaaa ggataagatg 1320
gcagaagcct atagcgagat tggtatgaaa ggggaacgca gaagaggcaa aggccacgac 1380
ggactgtacc agggactcag caccgccacc aaggacacct atgacgctct tcacatgcag 1440
gccctgccgc ctcgg 1455

<210> SEQ ID NO 122
<211> LENGTH: 1470
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 122
atggccctcc ctgtcaccgc cctgctgctt ccgctggctc ttctgctcca cgccgctcgg 60
ccccaagtcc aactcgtcca aagcggagca gaagtcaaaa agccaggagc gtcggtgaaa 120
gtgtcttgca aagccagcgg ctacaccttc acgggttact acatgcactg ggtgcgccag 180
gcgccgggcc aggggctgga gtggatgggc cggattaacc ctaacagcgg gggaactaat 240
tacgctcaga agttccaggg tagagtcacc atgactacgg acacttccac ttccaccgcc 300
tatatggaac tgcgctccct ccgctcagat gatactgccg tgtattactg cgcgcggact 360
accacgtcat acgcatttga catctggggc cagggaacta tggtgaccgt gagctcgggc 420
ggaggcggtt caggggggagg aggaagcgga ggaggaggat cgggaggagg tggctccgat 480
atccagctga ctcagtcccc gagcaccctg tcggcgtcgg tgggggacag ggttaccatc 540
acctgtagag cttcccaatc catttcgact tggctggcct ggtaccagca aaagccggga 600
aaggccccta atttgcttat ctacaaggca tcgaccctcg aaagcggtgt gccctcccgg 660
ttttcgggat caggatcagg gaccgagttc accctgacca tctcatccct ccagccggac 720
gacttcgcca cttactactg ccagcagtac aacacctact cgccatacac tttcggccaa 780
ggcaccaagc tggagatcaa gaccactacc ccagcaccga ggccacccac cccggctcct 840

```
accatcgcct cccagcctct gtccctgcgt ccggaggcat gtagacccgc agctggtggg     900

gccgtgcata cccggggtct tgacttcgcc tgcgatatct acatttgggc ccctctggct     960

ggtacttgcg ggtcctgctc gctttcactc gtgatcactc tttactgtaa gcgcggtcgg    1020

aagaagctgc tgtacatctt taagcaaccc ttcatgaggc ctgtgcagac tactcaagag    1080

gaggacggct gttcatgccg gttcccagag gaggaggaag gcggctgcga actgcgcgtg    1140

aaattcagcc gcagcgcaga tgctccagcc tacaagcagg ggcagaacca gctctacaac    1200

gaactcaatc ttggtcggag agaggagtac gacgtgctgg acaagcggag aggacgggac    1260

ccagaaatgg gcgggaagcc gcgcagaaag aatccccaag agggcctgta caacgagctc    1320

caaaaggata agatggcaga agcctatagc gagattggta tgaaagggga acgcagaaga    1380

ggcaaaggcc acgacggact gtaccaggga ctcagcaccg ccaccaagga cacctatgac    1440

gctcttcaca tgcaggccct gccgcctcgg                                     1470
```

```
<210> SEQ ID NO 123
<211> LENGTH: 1479
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 123

atggccctcc ctgtcaccgc cctgctgctt ccgctggctc ttctgctcca cgccgctcgg      60

ccccaagttc aactcgtgca atcaggtgga ggactcgtca aacccggagg atcattgaga     120

ctgtcatgcg aagcgagcgg ttttatcttc tccgattact atatgggatg gattcggcag     180

gccccgggaa agggactcga atgggtgtca tacatcggaa ggtcaggctc gtccatgtac     240

tacgcagact cggtgaaagg cagattcacc tttagccggg acaacgccaa gaattccctc     300

tacttgcaga tgaacagcct gcgagccgag gatactgctg tctactactg tgccgcgtcg     360

ccggtggtgg cagctactga agatttccag cactggggac agggaactct ggtcacggtg     420

tcgagcggtg gggcggaag cggaggcgga ggatcgggcg gcggaggttc gggggggga      480

gggtctgaca tcgtgatgac ccaaacccca gccaccctga gcctctcccc tggagagcgc     540

gcgactcttt cgtgccgcgc ttcccagtca gtgaccagca attacttggc ttggtaccaa     600

cagaagccgg gacaggcgcc acggctgctg ctttttggtg ccagcactcg cgccaccgga     660

atcccggatc gcttctcggg ctcagggtcc gggacggact tcaccctgac tatcaaccgg     720

ctggaacctg aggacttcgc gatgtactac tgccagcagt acggctccgc accagtcact     780

ttcggacaag gcaccaagct ggagatcaag accactaccc cagcaccgag gccacccacc     840

ccggctccta ccatcgcctc ccagcctctg tccctgcgtc cggaggcatg tagacccgca     900

gctggtgggg ccgtgcatac ccggggtctt gacttcgcct gcgatatcta catttgggcc     960

cctctggctg gtacttgcgg ggtcctgctg ctttcactcg tgatcactct ttactgtaag    1020

cgcggtcgga agaagctgct gtacatcttt aagcaaccct tcatgaggcc tgtgcagact    1080

actcaagagg aggacggctg ttcatgccgg ttcccagagg aggaggaagg cggctgcgaa    1140

ctgcgcgtga aattcagccg cagcgcagat gctccagcct acaagcaggg gcagaaccag    1200

ctctacaacg aactcaatct tggtcggaga gaggagtacg acgtgctgga caagcggaga    1260

ggacgggacc cagaaatggg cgggaagccg cgcagaaaga atccccaaga gggcctgtac    1320

aacgagctcc aaaaggataa gatggcagaa gcctatagcg agattggtat gaaaggggaa    1380
```

cgcagaagag gcaaaggcca cgacggactg taccagggac tcagcaccgc caccaaggac 1440
acctatgacg ctcttcacat gcaggccctg ccgcctcgg 1479

<210> SEQ ID NO 124
<211> LENGTH: 1479
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 124
atggccctcc ctgtcaccgc cctgctgctt ccgctggctc ttctgctcca cgccgctcgg 60
ccccaagtcc aactcgtcca gtcgggagca gaagttagag caccaggagc gtcagtgaaa 120
atctcatgca aggcctcggg cttcacgttc cgcggatact acatccactg ggtgcgccaa 180
gccccgggtc agggattgga gtggatggga atcattaacc catcaggagg gagccgggct 240
tacgcgcaga agttccaggg acgcgtcact atgacccgag atacttccac ctcgactgtg 300
tacatggaac tctcgtccct gaggtccgac gacactgcga tgtattactg tgctcggact 360
gccagctgcg gtggggactg ttactacctc gattactggg gccagggaac tctggtgacc 420
gtgtccagcg gaggtggcgg gtcagggggt ggcggaagcg gaggcggcgg ttcaggcgga 480
ggaggctcgg acatccaaat gacgcaatcg ccgcctaccc tgagcgcttc cgtgggagat 540
cgggtgacca ttacttgcag agcatccgag aacgtcaata tctggctggc ctggtaccaa 600
cagaagccgg ggaaggcccc taaactgctg atctacaagt cgagcagcct tgcctctgga 660
gtgccctccc gcttctcggg ctcgggatca ggagcggaat tcaccctcac catctcctcc 720
ctgcagccag atgactttgc cacctactac tgccagcagt accagagcta tccgttgacc 780
tttgggggag gcactaaagt ggacatcaag accactaccc cagcaccgag gccacccacc 840
ccggctccta ccatcgcctc ccagcctctg tccctgcgtc cggaggcatg tagacccgca 900
gctggtgggg ccgtgcatac ccggggtctt gacttcgcct gcgatatcta catttgggcc 960
cctctggctg gtacttgcgg ggtcctgctg ctttcactcg tgatcactct ttactgtaag 1020
cgcggtcgga agaagctgct gtacatcttt aagcaaccct tcatgaggcc tgtgcagact 1080
actcaagagg aggacggctg ttcatgccgg ttcccagagg aggaggaagg cggctgcgaa 1140
ctgcgcgtga aattcagccg cagcgcagat gctccagcct acaagcaggg gcagaaccag 1200
ctctacaacg aactcaatct tggtcggaga gaggagtacg acgtgctgga caagcggaga 1260
ggacgggacc cagaaatggg cgggaagccg cgcagaaaga atccccaaga gggcctgtac 1320
aacgagctcc aaaaggataa gatggcagaa gcctatagcg agattggtat gaaaggggaa 1380
cgcagaagag gcaaaggcca cgacggactg taccagggac tcagcaccgc caccaaggac 1440
acctatgacg ctcttcacat gcaggccctg ccgcctcgg 1479

<210> SEQ ID NO 125
<211> LENGTH: 1464
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 125

```
atggccctcc ctgtcaccgc cctgctgctt ccgctggctc ttctgctcca cgccgctcgg     60
ccccaagttc aactcgttca atcaggtgga ggactcgtgc aaccaggaag atcactcaga    120
ctcagctgcg ccgcgtcggg attcactttc gatgactacg caatgcactg ggtgcggcag    180
gccccgggca aaggactgga atgggtgagc ggaattagct ggaactcggg gtccatcggg    240
tacgccgact cggtgaaggg acgctttacg atctcccggg acaatgccaa gaactccctg    300
tatttgcaga tgaactcctt gagggctgag gacaccgccg tgtactactg cgctaaagat    360
ggatcatcgt cctggtcctg ggatacttc gattactggg gccagggcac tctggtgacc    420
gtgtcgtcag gcggtggagg gtcgggcgga ggaggtagcg gaggcggagg gagcagctct    480
gaactgaccc aagacccggc ggtgtcggtc gcccttggtc agactgtgcg gactacctgt    540
cagggggacg cgctgcgctc gtactacgct tcatggtacc agcagaagcc cggacaggca    600
cctatgctgg tcatctacgg aaagaataac cgcccatccg gcatcccgga tcgcttctcg    660
ggttcggaca gcggcgacac cgcatccctg acgatcactg gagcgcaggc cgaggatgaa    720
gccgactact actgcaattc ccgagattca agcggctacc ctgtgtttgg gaccggaact    780
aaggtcaccg tcctgaccac taccccagca ccgaggccac ccaccccggc tcctaccatc    840
gcctcccagc ctctgtccct gcgtccggag gcatgtagac ccgcagctgg tggggccgtg    900
catacccggg gtcttgactt cgcctgcgat atctacattt gggcccctct ggctggtact    960
tgcggggtcc tgctgctttc actcgtgatc actctttact gtaagcgcgg tcggaagaag   1020
ctgctgtaca tctttaagca acccttcatg aggcctgtgc agactactca agaggaggac   1080
ggctgttcat gccggttccc agaggaggag gaaggcggct gcgaactgcg cgtgaaattc   1140
agccgcagcg cagatgctcc agcctacaag caggggcaga accagctcta caacgaactc   1200
aatcttggtc ggagagagga gtacgacgtg ctggacaagc ggagaggacg ggacccagaa   1260
atgggcggga agccgcgcag aaagaatccc caagagggcc tgtacaacga gctccaaaag   1320
gataagatgg cagaagccta tagcgagatt ggtatgaaag gggaacgcag aagaggcaaa   1380
ggccacgacg gactgtacca gggactcagc accgccacca aggacaccta tgacgctctt   1440
cacatgcagg ccctgccgcc tcgg                                          1464
```

<210> SEQ ID NO 126
<211> LENGTH: 1470
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 126

```
atggccctcc ctgtcaccgc cctgctgctt ccgctggctc ttctgctcca cgccgctcgg     60
cccgaagtgc aactcgtgga atctggtgga ggacttgtgc aacctggaag atcgttgaga    120
ctctcatgtg ctgcctccgg gttcaccttt gacgactacg ccatgcactg ggtgcgccag    180
gcaccaggaa agggtctgga gtgggtttcg ggtatctcgt ggaactccgg gagcactggc    240
tacgctgatt cggtgaaagg ccggtttacc atctcccgag acaatgcgaa gaattccctc    300
tatctgcaga tgaacagcct ccgggccgag gatactgccc tgtactactg cgccaaggat    360
agctcatcat ggtacggagg tggatcggct ttcgatatct ggggccaggg cacgatggtc    420
accgtgtcct cgggggggcgg aggctccggg ggaggaggta gcggaggagg aggatcgagc    480
tcagagttga ctcaagaacc cgcagtgtcc gtggcactgg gccaaaccgt caggatcact    540
```

```
tgccagggag acagcctgag gtcgtactac gcgtcctggt accagcagaa gccgggacag    600

gccccggtcc tggtcatttt cggacgctca agacgcccat cgggcatccc ggaccggttc    660

agcggaagct cctcgggaaa caccgcgtca cttatcatta ccggcgcaca ggctgaggac    720

gaagcggatt actactgcaa ctcccgcgac aatactgcca accattacgt gttcgggacc    780

ggaacgaaac tgactgtcct gaccactacc ccagcaccga ggccacccac cccggctcct    840

accatcgcct cccagcctct gtccctgcgt ccggaggcat gtagacccgc agctggtggg    900

gccgtgcata cccggggtct tgacttcgcc tgcgatatct acatttgggc ccctctggct    960

ggtacttgcg ggtcctgct gctttcactc gtgatcactc tttactgtaa gcgcggtcgg   1020

aagaagctgc tgtacatctt taagcaaccc ttcatgaggc ctgtgcagac tactcaagag   1080

gaggacggct gttcatgccg gttcccagag gaggaggaag gcggctgcga actgcgcgtg   1140

aaattcagcc gcagcgcaga tgctccagcc tacaagcagg ggcagaacca gctctacaac   1200

gaactcaatc ttggtcggag agaggagtac gacgtgctgg acaagcggag aggacgggac   1260

ccagaaatgg gcgggaagcc gcgcagaaag aatccccaag agggcctgta caacgagctc   1320

caaaaggata agatggcaga agcctatagc gagattggta tgaaagggga acgcagaaga   1380

ggcaaaggcc acgacggact gtaccaggga ctcagcaccg ccaccaagga cacctatgac   1440

gctcttcaca tgcaggccct gccgcctcgg                                    1470
```

<210> SEQ ID NO 127
<211> LENGTH: 1470
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 127

```
atggccctcc ctgtcaccgc cctgctgctt ccgctggctc ttctgctcca cgccgctcgg     60

cccgaagttc aattggtgga atctggagga ggacttgtgc aacccggtag atctctgaga    120

ctgtcctgtg cggcatcggg attcaccttc gacgactacg ctatgcactg ggtgagacaa    180

gcccctggaa aaggactgga gtgggtgtca ggcatctcct ggaatagcgg gtccactgga    240

tacgccgatt cggtcaaggg tcgcttcacc atttcccggg acaatgccaa gaactccctg    300

taccttcaaa tgaactccct ccgggccgag gataccgccc tctactactg cgccaaagac    360

agctcgtcat ggtatggcgg agggtcggca tttgacatct ggggacaggg aactatggtg    420

actgtgtcat caggaggcgg cggaagcggc ggcggcgggt ccggcggagg agggtcgtcc    480

agcgaactca cccaagatcc agcagtgagc gtcgcgctgg gccagaccgt caggatcacg    540

tgccagggag attcactgcg ctcatactac gcgtcctggt accagcagaa gccggggcag    600

gccccggtcc tcgtgatcta cggaaagaac aaccgcccgt cgggtatccc agaccgcttt    660

tcgggtagct ccagcggaaa tacggctagc ctgaccatca ctggagcaca ggctgaggat    720

gaagcggact actactgcaa ttcgcggggc tcatcgggga accattacgt gttcggaact    780

ggtaccaagg tgactgtcct gaccactacc ccagcaccga ggccacccac cccggctcct    840

accatcgcct cccagcctct gtccctgcgt ccggaggcat gtagacccgc agctggtggg    900

gccgtgcata cccggggtct tgacttcgcc tgcgatatct acatttgggc ccctctggct    960

ggtacttgcg ggtcctgct gctttcactc gtgatcactc tttactgtaa gcgcggtcgg   1020
```

-continued

```
aagaagctgc tgtacatctt taagcaaccc ttcatgaggc ctgtgcagac tactcaagag   1080

gaggacggct gttcatgccg gttcccagag gaggaggaag gcggctgcga actgcgcgtg   1140

aaattcagcc gcagcgcaga tgctccagcc tacaagcagg ggcagaacca gctctacaac   1200

gaactcaatc ttggtcggag agaggagtac gacgtgctgg acaagcggag aggacgggac   1260

ccagaaatgg gcgggaagcc gcgcagaaag aatccccaag agggcctgta caacgagctc   1320

caaaaggata agatggcaga agcctatagc gagattggta tgaaagggga acgcagaaga   1380

ggcaaaggcc acgacggact gtaccaggga ctcagcaccg ccaccaagga cacctatgac   1440

gctcttcaca tgcaggccct gccgcctcgg                                    1470


<210> SEQ ID NO 128
<211> LENGTH: 1485
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 128

atggccctcc ctgtcaccgc cctgctgctt ccgctggctc ttctgctcca cgccgctcgg     60

ccccaagtgc agctcgttca atcaggcgga ggactcgttc aaccaggagg atcattgcga    120

ctctcatgtg cggcctctgg attcacgttt agctcatatt ggatgcactg ggtgcggcag    180

gcgccgggga aaggtctggt gtgggtcagc cgcatcaact cagacggctc ctcgacttcg    240

tacgccgact ccgtgaaggg acgctttacc atttcccgcg acaacgccaa gaataccctt    300

taccttcaga tgaactccct ccgcgctgag gataccgccg tgtactactg cgtgaggact    360

ggctgggtcg gcagctacta ctactacatg gacgtgtggg gcaaaggaac tactgtcacc    420

gtgtcaagcg gcggtggagg ttccggcggg ggaggatcgg ggggggcgg atcgggtggc     480

ggaggatcgg agatcgtgtt gacccagtcg ccgggaaccc tgtcgctgtc gcctggggag    540

agagcaactc tgtcctgccg ggcttcccag tcggtgtcga gcaattacct ggcatggtac    600

caacagaagc cgggacagcc gccacgcctg ctgatctatg acgtgtcaac tcgggcaact    660

ggaatccctg cgcggttcag cggcggaggg agcggtaccg atttcaccct gactatttcc    720

tccctcgaac cagaagattt cgccgtctac tactgccagc agagaagcaa ctggccgccc    780

tggacgttcg gacaaggaac caaggtcgaa atcaagacca ctaccccagc accgaggcca    840

cccaccccgg ctcctaccat cgcctcccag cctctgtccc tgcgtccgga ggcatgtaga    900

cccgcagctg gtggggccgt gcatacccgg ggtcttgact tcgcctgcga tatctacatt    960

tgggcccctc tggctggtac ttgcggggtc ctgctgcttt cactcgtgat cactctttac   1020

tgtaagcgcg gtcggaagaa gctgctgtac atctttaagc aacccttcat gaggcctgtg   1080

cagactactc aagaggagga cggctgttca tgccggttcc cagaggagga ggaaggcggc   1140

tgcgaactgc gcgtgaaatt cagccgcagc gcagatgctc cagcctacaa gcaggggcag   1200

aaccagctct acaacgaact caatcttggt cggagagagg agtacgacgt gctggacaag   1260

cggagaggac gggacccaga aatgggcggg aagccgcgca gaaagaatcc ccaagagggc   1320

ctgtacaacg agctccaaaa ggataagatg gcagaagcct atagcgagat tggtatgaaa   1380

ggggaacgca gaagaggcaa aggccacgac ggactgtacc agggactcag caccgccacc   1440

aaggacacct atgacgctct tcacatgcag gccctgccgc ctcgg                   1485
```

<210> SEQ ID NO 129
<211> LENGTH: 1482
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 129

```
atggccctcc ctgtcaccgc cctgctgctt ccgctggctc ttctgctcca cgccgctcgg     60
ccccaagtgc aattggttca atcaggagga ggagtcgtgc agcccggaag atcgttgaga    120
ctgtcatgtg ccgcgagcgg ctttactttc tcaagctacg gaatgcattg ggtgcgacag    180
gctccgggaa aaggactgga atgggtcgca gtgatctcat acgacggctc gaacaagtac    240
tacgccgact ccgtcaaggg tcggttcacg atttcgcgcg ataattccaa gaacactctg    300
tacctccaaa tgaacagcct ccgggcagag gacaccgccg tctactactg cgctaaggga    360
tactcgcgct actactacta tggaatggat gtgtggggcc agggaactac cgtgacggtg    420
tcgtccggcg gcggtgggtc gggcggaggc ggatcaggtg gaggtggaag cggaggagga    480
gggagcgaaa tcgtcatgac tcagtcccct gctacccttt ctctgtcgcc gggagaaaga    540
gccatcctga gctgccgggc ctcccagagc gtgtacacca aatacctggg atggtaccag    600
cagaagccgg ggcaggcacc aaggctcctg atctacgatg cgtccacccg cgcgactggt    660
atcccagacc gcttttccgg ctcggggtca gggactgact tcacccttac tatcaatcgg    720
ctcgagcctg aggatttcgc cgtgtattac tgccagcact acggagggtc cccgctgatt    780
accttcggcc aaggcaccaa agtggacatc aagaccacta ccccagcacc gaggccaccc    840
accccggctc ctaccatcgc ctcccagcct ctgtccctgc gtccggaggc atgtagaccc    900
gcagctggtg gggccgtgca tacccggggt cttgacttcg cctgcgatat ctacatttgg    960
gcccctctgg ctggtacttg cggggtcctg ctgctttcac tcgtgatcac tctttactgt   1020
aagcgcggtc ggaagaagct gctgtacatc tttaagcaac ccttcatgag gcctgtgcag   1080
actactcaag aggaggacgg ctgttcatgc cggttcccag aggaggagga aggcggctgc   1140
gaactgcgcg tgaaattcag ccgcagcgca gatgctccag cctacaagca ggggcagaac   1200
cagctctaca acgaactcaa tcttggtcgg agagaggagt acgacgtgct ggacaagcgg   1260
agaggacggg acccagaaat gggcgggaag ccgcgcagaa agaatcccca agagggcctg   1320
tacaacgagc tccaaaagga taagatggca gaagcctata gcgagattgg tatgaaaggg   1380
gaacgcagaa gaggcaaagg ccacgacgga ctgtaccagg gactcagcac cgccaccaag   1440
gacacctatg acgctcttca catgcaggcc ctgccgcctc gg                      1482
```

<210> SEQ ID NO 130
<211> LENGTH: 1479
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 130

```
atggccctcc ctgtcaccgc cctgctgctt ccgctggctc ttctgctcca cgccgctcgg     60
ccccaagtgc aacttgttca atcaggagga ggactcgttc aacccggagg atcactgcga    120
ctctcatgtg cagcgtcggg gttcaccttc tccagctacg caatgtcctg ggtgcgccaa    180
```

gcccctggaa aaggcctgga gtgggtgtcg gccatctctg ggagcggggg atcaacttac 240
tacgctgact ccgtcaaggg ccgctttacc atctcccggg acaacagcaa gaacactctc 300
tatctccaga tgaactcgct gagagccgaa gataccgctg tctactactg cgcgaagaga 360
gaagctgccg cagggcacga ttggtacttc gacttgtggg gcaggggcac ccttgtgacc 420
gtgtcctccg gtggaggcgg atcaggaggt gggggatcgg gtggaggagg aagcggaggc 480
ggcggttcgg acattcgcgt cacccagtca ccgagctccc tcagcgcatc ggtgggcgac 540
cgggtcacta tcacttgccg ggcgtcccag tcgatctcat cgtatctgaa ttggtaccag 600
cagaaaccgg gaaaggcgcc gaagctgttg atctacgctg ccagctccct gcagtcgggt 660
gtgccatcac gcttttccgg ctcgggatcg ggaaccgatt tcactctgac gatctctagc 720
ctgcagccag aagatttcgc cacttactac tgccagcagt cctacagcat ccctctgact 780
ttcggacaag ggacgaaagt ggagattaag accactaccc cagcaccgag gccacccacc 840
ccggctccta ccatcgcctc ccagcctctg tccctgcgtc cggaggcatg tagacccgca 900
gctggtgggg ccgtgcatac ccggggtctt gacttcgcct gcgatatcta catttgggcc 960
cctctggctg gtacttgcgg ggtcctgctg ctttcactcg tgatcactct ttactgtaag 1020
cgcggtcgga agaagctgct gtacatcttt aagcaaccct tcatgaggcc tgtgcagact 1080
actcaagagg aggacggctg ttcatgccgg ttcccagagg aggaggaagg cggctgcgaa 1140
ctgcgcgtga aattcagccg cagcgcagat gctccagcct acaagcaggg gcagaaccag 1200
ctctacaacg aactcaatct tggtcggaga gaggagtacg acgtgctgga caagcggaga 1260
ggacgggacc cagaaatggg cgggaagccg cgcagaaaga atccccaaga gggcctgtac 1320
aacgagctcc aaaaggataa gatggcagaa gcctatagcg agattggtat gaaaggggaa 1380
cgcagaagag gcaaaggcca cgacggactg taccagggac tcagcaccgc caccaaggac 1440
acctatgacg ctcttcacat gcaggccctg ccgcctcgg 1479

<210> SEQ ID NO 131
<211> LENGTH: 1473
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 131
atggccctcc ctgtcaccgc cctgctgctt ccgctggctc ttctgctcca cgccgctcgg 60
ccccaagtcc aactcgttca gtcatgggca gaagtcaaga aacccggtgc aagcgtcaaa 120
gtgtcgtgta aggcctccgg ctacactttc acttcctact acatgcactg ggtgcgccaa 180
gccccgggac agggccttga atggatgggc atcatcaacc catcaggagg ttccacgagc 240
tacgcgcaga agttccaggg gagagtgacg atgactagag atacctccac gagcaccgtc 300
tacatggagc tgtcgaatct gcggtcagag gacactgctg tgtattactg cgcgcgctcc 360
ccgcgggtga ccactggcta ctttgactac tggggacaag ggaccctggt gaccgtcagc 420
tcgggaggcg gaggatcggg aggtggaggg tccggtggag gcggctctgg aggaggcggg 480
tcggacattc aattgaccca gagcccatcc accctctcag cctcggtggg ggatagggtg 540
actatcactt gccgggcctc ccagtcaatt tccagctggc tggcttggta ccagcaaaag 600
cctggaaagg caccgaagct cctgatctac aaggcctcat ctctggaatc aggagtgcct 660
tcgcgcttca gcggaagcgg ctcgggaact gagtttaccc tgaccatctc gagcctgcag 720
ccagatgact tcgcgaccta ttactgccag cagtactcgt cctacccgtt gactttcgga 780
ggaggtaccc gcctcgaaat caaaaccact accccagcac cgaggccacc caccccggct 840
cctaccatcg cctcccagcc tctgtccctg cgtccggagg catgtagacc cgcagctggt 900
ggggccgtgc atacccgggg tcttgacttc gcctgcgata tctacatttg ggcccctctg 960
gctggtactt gcggggtcct gctgctttca ctcgtgatca ctctttactg taagcgcggt 1020
cggaagaagc tgctgtacat ctttaagcaa cccttcatga ggcctgtgca gactactcaa 1080
gaggaggacg gctgttcatg ccggttccca gaggaggagg aaggcggctg cgaactgcgc 1140
gtgaaattca gccgcagcgc agatgctcca gcctacaagc aggggcagaa ccagctctac 1200
aacgaactca atcttggtcg gagagaggag tacgacgtgc tggacaagcg gagaggacgg 1260
gacccagaaa tgggcgggaa gccgcgcaga aagaatcccc aagagggcct gtacaacgag 1320
ctccaaaagg ataagatggc agaagcctat agcgagattg gtatgaaagg ggaacgcaga 1380
agaggcaaag gccacgacgg actgtaccag ggactcagca ccgccaccaa ggacacctat 1440
gacgctcttc acatgcaggc cctgccgcct cgg 1473

<210> SEQ ID NO 132
<211> LENGTH: 1491
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 132
atggccctcc ctgtcaccgc cctgctgctt ccgctggctc ttctgctcca cgccgctcgg 60
ccccaagtcc aactcgtcca gtccggtgca gaagtcagaa ggccaggagc aagcgtgaag 120
atctcgtgta gagcgtcagg agacaccagc actcgccatt acatccactg gctgcgccag 180
gctccgggcc aagggccgga gtggatgggt gtgatcaacc cgactacggg accggctacc 240
ggaagccctg cgtacgcaca gatgctgcag ggacgggtga ctatgacccg cgatactagc 300
actaggaccg tgtacatgga actccgctcg ttgcggttcg aagataccgc cgtctactac 360
tgcgcccggt ccgtggtggg ccgaagcgcc ccttactact tcgattactg gggacagggc 420
actctggtga ccgttagctc cggtggggga ggctcgggtg gaggcggatc gggaggagga 480
ggcagcggtg gagggggatc ggacattcag atgacccagt caccctcctc cctctcagcc 540
tcggtcgggg accgggtgac cattacgtgc agagcctcac aagggatctc ggactactcc 600
gcctggtacc agcagaaacc gggaaaagcg ccaaagctcc tgatctacgc cgcgagcacc 660
ctgcaatcag gagtgccatc gcgcttttct ggatcgggct cagggactga cttcacgctg 720
actatctcct accttcagtc cgaggatttc gctacctact actgccaaca gtattactcc 780
tatcccctga cctttggcgg aggcactaag gtggacatca agaccactac cccagcaccg 840
aggccaccca ccccggctcc taccatcgcc tcccagcctc tgtccctgcg tccggaggca 900
tgtagacccg cagctggtgg ggccgtgcat acccggggtc ttgacttcgc ctgcgatatc 960
tacatttggg cccctctggc tggtacttgc ggggtcctgc tgctttcact cgtgatcact 1020
ctttactgta agcgcggtcg gaagaagctg ctgtacatct ttaagcaacc cttcatgagg 1080
cctgtgcaga ctactcaaga ggaggacggc tgttcatgcc ggttcccaga ggaggaggaa 1140
ggcggctgcg aactgcgcgt gaaattcagc cgcagcgcag atgctccagc ctacaagcag 1200

```
gggcagaacc agctctacaa cgaactcaat cttggtcgga gagaggagta cgacgtgctg   1260

gacaagcgga gaggacggga cccagaaatg ggcgggaagc cgcgcagaaa gaatccccaa   1320

gagggcctgt acaacgagct ccaaaaggat aagatggcag aagcctatag cgagattggt   1380

atgaaagggg aacgcagaag aggcaaaggc cacgacggac tgtaccaggg actcagcacc   1440

gccaccaagg acacctatga cgctcttcac atgcaggccc tgccgcctcg g            1491
```

<210> SEQ ID NO 133
<211> LENGTH: 1479
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 133

```
atggccctcc ctgtcaccgc cctgctgctt ccgctggctc ttctgctcca cgccgctcgg     60

ccccaagtcc aactccagca atcgggagca gaagtcaaga aaccaggcgc atcggtgaaa    120

gtgtcgtgta aggcgtcagg gtacaccttc accaactact atatgcactg ggtgcgccag    180

gctccaggcc aggggttgga gtggatgggg atcatcaatc cgtcaggtgg ctacaccact    240

tacgctcaga agttccaggg acgcctcact atgactcgcg atactagcac ctccacggtg    300

tacatggaac tgtcatcgct gaggtccgaa gataccgccg tctactactg cgcacggatc    360

agatcctgcg gaggagattg ttactacttt gacaactggg gacagggcac ccttgttact    420

gtgtcatcgg gaggaggggg aagcggagga ggtggatcag gcggcggtgg cagcgggggc    480

ggaggatcgg acattcagct gactcagtcc ccctccactt tgtcggccag cgtgggagac    540

agagtgacca tcacttgccg ggcgtccgag aacgtcaata tctggctggc ctggtaccag    600

caaaagcctg gaaaagcccc gaagctgctc atctataagt catccagcct ggcgtctggt    660

gtgccgtcgc ggttctccgg cagcgggagc ggagccgagt tcactctcac catttcgagc    720

cttcaaccgg acgatttcgc cacctactac tgccagcagt accaatccta ccctctgacg    780

tttggaggtg gaaccaaggt ggacatcaag accactaccc cagcaccgag gccacccacc    840

ccggctccta ccatcgcctc ccagcctctg tccctgcgtc cggaggcatg tagacccgca    900

gctggtgggg ccgtgcatac ccggggtctt gacttcgcct gcgatatcta catttgggcc    960

cctctggctg gtacttgcgg ggtcctgctg ctttcactcg tgatcactct ttactgtaag   1020

cgcggtcgga agaagctgct gtacatcttt aagcaaccct tcatgaggcc tgtgcagact   1080

actcaagagg aggacggctg ttcatgccgg ttcccagagg aggaggaagg cggctgcgaa   1140

ctgcgcgtga aattcagccg cagcgcagat gctccagcct acaagcaggg gcagaaccag   1200

ctctacaacg aactcaatct tggtcggaga gaggagtacg acgtgctgga caagcggaga   1260

ggacgggacc cagaaatggg cgggaagccg cgcagaaaga atccccaaga gggcctgtac   1320

aacgagctcc aaaaggataa gatggcagaa gcctatagcg agattggtat gaaaggggaa   1380

cgcagaagag gcaaaggcca cgacggactg taccagggac tcagcaccgc caccaaggac   1440

acctatgacg ctcttcacat gcaggccctg ccgcctcgg                          1479
```

<210> SEQ ID NO 134
<211> LENGTH: 1470
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 134
atggccctcc ctgtcaccgc cctgctgctt ccgctggctc ttctgctcca cgccgctcgg 60
ccccaaatca ctctgaaaga atctggaccg gccctggtta agccgactca aacgctcacc 120
cttacttgca ccttcagcgg attctcactc agcactgctg gtgtgcacgt cggatggatt 180
agacagccgc ctggaaaggc cctggaatgg ctcgccctca tctcctgggc cgatgacaag 240
agatacaggc cctcgcttcg atcccggttg gacattaccc gggtgacctc gaaagatcag 300
gtggtgctct caatgaccaa tatgcagccg gaggacaccg ctacgtacta ctgcgcactg 360
caaggatttg acggctacga ggctaactgg ggaccaggta ctctggtcac cgtgagctcc 420
ggcgggggag gatcaggcgg ggggggtca ggaggcggag gctccggtgg aggaggatcg 480
gatatcgtca tgacccagtc cccaagctcg ctgagcgcgt cagcgggcga ccgcgtgact 540
atcacttgcc gggccagccg cggcatctcc tccgcactgg cgtggtacca gcagaagcct 600
ggaaaaccgc caaagctcct gatctatgat gcctccagcc tggagtcagg tgtccccagc 660
cgcttctcgg gttcgggctc gggaaccgac ttcactttga ccatcgactc gctggaaccg 720
gaagatttcg caacctacta ctgtcagcag tcctactcga ccccttggac ttttggacaa 780
gggacgaagg tggacatcaa gaccactacc ccagcaccga ggccacccac cccggctcct 840
accatcgcct cccagcctct gtccctgcgt ccggaggcat gtagacccgc agctggtggg 900
gccgtgcata cccggggtct tgacttcgcc tgcgatatct acatttgggc ccctctggct 960
ggtacttgcg gggtcctgct gctttcactc gtgatcactc tttactgtaa gcgcggtcgg 1020
aagaagctgc tgtacatctt taagcaaccc ttcatgaggc ctgtgcagac tactcaagag 1080
gaggacggct gttcatgccg gttcccagag gaggaggaag gcggctgcga actgcgcgtg 1140
aaattcagcc gcagcgcaga tgctccagcc tacaagcagg ggcagaacca gctctacaac 1200
gaactcaatc ttggtcggag agaggagtac gacgtgctgg acaagcggag aggacgggac 1260
ccagaaatgg gcgggaagcc gcgcagaaag aatccccaag agggcctgta caacgagctc 1320
caaaaggata agatggcaga agcctatagc gagattggta tgaaagggga acgcagaaga 1380
ggcaaaggcc acgacggact gtaccaggga ctcagcaccg ccaccaagga cacctatgac 1440
gctcttcaca tgcaggccct gccgcctcgg 1470

<210> SEQ ID NO 135

<400> SEQUENCE: 135

000

<210> SEQ ID NO 136
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 136

Gly Tyr Thr Phe Thr Gly Tyr Tyr Met His
1 5 10

<210> SEQ ID NO 137

<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 137

Gly Phe Thr Phe Ser Ser Tyr Trp Met His
1 5 10

<210> SEQ ID NO 138
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 138

Gly Tyr Thr Phe Thr Asp Tyr Tyr Met His
1 5 10

<210> SEQ ID NO 139
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 139

Gly Tyr Thr Phe Thr Ser Tyr Tyr Met His
1 5 10

<210> SEQ ID NO 140
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 140

Gly Phe Thr Phe Ser Ser Tyr Ala Met His
1 5 10

<210> SEQ ID NO 141
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 141

Gly Tyr Pro Phe Thr Gly Tyr Ser Leu His
1 5 10

<210> SEQ ID NO 142
<211> LENGTH: 10
<212> TYPE: PRT
<213> ORGANISM: Artificial Sequence
<220> FEATURE:

<221> NAME/KEY: source
<223> OTHER INFORMATION: /note="Description of Artificial Sequence:
Synthetic peptide"

<400> SEQUENCE: 142

Gly Tyr Thr Phe Thr Ser Tyr Tyr Met His
1 5 10

<210> SEQ ID NO 143
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 143

Gly Tyr Thr Phe Thr Ser Tyr Gly Ile Ser
1 5 10

<210> SEQ ID NO 144
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 144

Gly Tyr Thr Phe Thr Gly Tyr Tyr Met His
1 5 10

<210> SEQ ID NO 145
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 145

Gly Phe Ile Phe Ser Asp Tyr Tyr Met Gly
1 5 10

<210> SEQ ID NO 146
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 146

Gly Phe Thr Phe Arg Gly Tyr Tyr Ile His
1 5 10

<210> SEQ ID NO 147
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 147

Gly Phe Thr Phe Asp Asp Tyr Ala Met His
1 5 10

<210> SEQ ID NO 148
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 148

Gly Phe Thr Phe Ser Ser Tyr Trp Met His
1 5 10

<210> SEQ ID NO 149
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 149

Gly Phe Thr Phe Ser Ser Tyr Gly Met His
1 5 10

<210> SEQ ID NO 150
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 150

Gly Phe Thr Phe Ser Ser Tyr Ala Met Ser
1 5 10

<210> SEQ ID NO 151
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 151

Gly Tyr Thr Phe Thr Ser Tyr Tyr Met His
1 5 10

<210> SEQ ID NO 152
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 152

Gly Asp Thr Ser Thr Arg His Tyr Ile His
1 5 10

<210> SEQ ID NO 153
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 153

Gly Tyr Thr Phe Thr Asn Tyr Tyr Met His
1 5 10

<210> SEQ ID NO 154
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 154

Gly Phe Ser Leu Ser Thr Ala Gly Val His Val Gly
1 5 10

<210> SEQ ID NO 155
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 155

Arg Ile Asn Pro Asn Ser Gly Gly Thr Asn Tyr Ala Gln Lys Phe Gln
1 5 10 15

Gly

<210> SEQ ID NO 156
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 156

Trp Ile Asn Pro Asn Ser Gly Gly Thr Asn Tyr Ala Gln Lys Phe Gln
1 5 10 15

Gly

<210> SEQ ID NO 157
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 157

Arg Ile Asn Thr Asp Gly Ser Thr Thr Thr Tyr Ala Asp Ser Val Glu
1 5 10 15

Gly

<210> SEQ ID NO 158
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 158

Ile Ile Asn Pro Ser Gly Gly Ser Thr Ser Tyr Ala Gln Lys Phe Gln
1 5 10 15

<210> SEQ ID NO 159
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 159

Trp Ile Asn Pro Asn Ser Gly Gly Thr Asn Tyr Ala Gln Lys Phe Gln
1 5 10 15

Gly

<210> SEQ ID NO 160
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 160

Ile Ile Asn Pro Ser Gly Gly Ser Thr Gly Tyr Ala Gln Lys Phe Gln
1 5 10 15

Gly

<210> SEQ ID NO 161
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 161

Trp Ile Ser Ala Tyr Asn Gly Asn Thr Asn Tyr Ala Gln Lys Leu Gln
1 5 10 15

<210> SEQ ID NO 162
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 162

```
Trp Ile Asn Pro Asn Ser Gly Gly Thr Asn Tyr Ala Gln Asn Phe Gln
1               5                   10                  15

Gly


<210> SEQ ID NO 163
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 163

Arg Ile Asn Pro Asn Ser Gly Gly Thr Asn Tyr Ala Gln Lys Phe Gln
1               5                   10                  15

Gly


<210> SEQ ID NO 164
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 164

Tyr Ile Gly Arg Ser Gly Ser Ser Met Tyr Tyr Ala Asp Ser Val Lys
1               5                   10                  15

Gly


<210> SEQ ID NO 165
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 165

Ile Ile Asn Pro Ser Gly Gly Ser Arg Ala Tyr Ala Gln Lys Phe Gln
1               5                   10                  15

Gly


<210> SEQ ID NO 166
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 166

Gly Ile Ser Trp Asn Ser Gly Ser Ile Gly Tyr Ala Asp Ser Val Lys
1               5                   10                  15


<210> SEQ ID NO 167
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
```

Synthetic peptide"

<400> SEQUENCE: 167

Gly Ile Ser Trp Asn Ser Gly Ser Thr Gly Tyr Ala Asp Ser Val Lys
1 5 10 15

Gly

<210> SEQ ID NO 168
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 168

Arg Ile Asn Ser Asp Gly Ser Ser Thr Ser Tyr Ala Asp Ser Val Lys
1 5 10 15

Gly

<210> SEQ ID NO 169
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 169

Val Ile Ser Tyr Asp Gly Ser Asn Lys Tyr Tyr Ala Asp Ser Val Lys
1 5 10 15

Gly

<210> SEQ ID NO 170
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 170

Ala Ile Ser Gly Ser Gly Gly Ser Thr Tyr Tyr Ala Asp Ser Val Lys
1 5 10 15

Gly

<210> SEQ ID NO 171
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 171

Ile Ile Asn Pro Ser Gly Gly Ser Thr Ser Tyr Ala Gln Lys Phe Gln
1 5 10 15

Gly

<210> SEQ ID NO 172

<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 172

Val Ile Asn Pro Thr Thr Gly Pro Ala Thr Gly Ser Pro Ala Tyr Ala
1 5 10 15

Gln Met Leu Gln Gly
20

<210> SEQ ID NO 173
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 173

Ile Ile Asn Pro Ser Gly Gly Tyr Thr Thr Tyr Ala Gln Lys Phe Gln
1 5 10 15

Gly

<210> SEQ ID NO 174
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 174

Leu Ile Ser Trp Ala Asp Asp Lys Arg Tyr Arg Pro Ser Leu Arg Ser
1 5 10 15

<210> SEQ ID NO 175
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 175

Gly Arg Tyr Tyr Gly Met Asp Val
1 5

<210> SEQ ID NO 176
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 176

Asp Leu Arg Arg Thr Val Val Thr Pro Arg Ala Tyr Tyr Gly Met Asp
1 5 10 15

Val

<210> SEQ ID NO 177
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 177

Gly Glu Trp Asp Gly Ser Tyr Tyr Tyr Asp Tyr
1 5 10

<210> SEQ ID NO 178
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 178

Gly His Trp Ala Val
1 5

<210> SEQ ID NO 179
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 179

Gly Trp Asp Phe Asp Tyr
1 5

<210> SEQ ID NO 180
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 180

Tyr Arg Leu Ile Ala Val Ala Gly Asp Tyr Tyr Tyr Tyr Gly Met Asp
1 5 10 15

Val

<210> SEQ ID NO 181
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 181

Trp Lys Val Ser Ser Ser Ser Pro Ala Phe Asp Tyr
1 5 10

<210> SEQ ID NO 182
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 182

Asp His Tyr Gly Gly Asn Ser Leu Phe Tyr
1 5 10

<210> SEQ ID NO 183
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 183

Gly Gly Tyr Ser Ser Ser Ser Asp Ala Phe Asp Ile
1 5 10

<210> SEQ ID NO 184
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 184

Val Ala Gly Gly Ile Tyr Tyr Tyr Tyr Gly Met Asp Val
1 5 10

<210> SEQ ID NO 185
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 185

Gly Trp Asp Phe Asp Tyr
1 5

<210> SEQ ID NO 186
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 186

Thr Thr Thr Ser Tyr Ala Phe Asp Ile
1 5

<210> SEQ ID NO 187
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 187

Ser Pro Val Val Ala Ala Thr Glu Asp Phe Gln His
1 5 10

<210> SEQ ID NO 188
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 188

Thr Ala Ser Cys Gly Gly Asp Cys Tyr Tyr Leu Asp Tyr
1 5 10

<210> SEQ ID NO 189
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 189

Asp Gly Ser Ser Ser Trp Ser Trp Gly Tyr Phe Asp Tyr
1 5 10

<210> SEQ ID NO 190
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 190

Asp Ser Ser Ser Trp Tyr Gly Gly Gly Ser Ala Phe Asp Ile
1 5 10

<210> SEQ ID NO 191
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 191

Asp Ser Ser Ser Trp Tyr Gly Gly Gly Ser Ala Phe Asp Ile
1 5 10

<210> SEQ ID NO 192
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 192

Thr Gly Trp Val Gly Ser Tyr Tyr Tyr Tyr Met Asp Val
1 5 10

<210> SEQ ID NO 193
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 193

Gly Tyr Ser Arg Tyr Tyr Tyr Tyr Gly Met Asp Val
1 5 10

<210> SEQ ID NO 194
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 194

Arg Glu Ala Ala Ala Gly His Asp Trp Tyr Phe Asp Leu
1 5 10

<210> SEQ ID NO 195
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 195

Ser Pro Arg Val Thr Thr Gly Tyr Phe Asp Tyr
1 5 10

<210> SEQ ID NO 196
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 196

Ser Val Val Gly Arg Ser Ala Pro Tyr Tyr Phe Asp Tyr
1 5 10

<210> SEQ ID NO 197
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 197

Ile Arg Ser Cys Gly Gly Asp Cys Tyr Tyr Phe Asp Asn

-continued 1 5 10

<210> SEQ ID NO 198
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 198

Gln Gly Phe Asp Gly Tyr Glu Ala Asn
1 5

<210> SEQ ID NO 199
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 199

Arg Ala Ser Gln Ser Val Ser Ser Asn Phe Ala
1 5 10

<210> SEQ ID NO 200
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 200

Gln Ala Ser Gln Asp Ile Ser Asn Ser Leu Asn
1 5 10

<210> SEQ ID NO 201
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 201

Arg Ala Ser Gln Ser Ile Asn Thr Tyr Leu Asn
1 5 10

<210> SEQ ID NO 202
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 202

Arg Ala Ser Gln Ser Ile Ser Asp Arg Leu Ala
1 5 10

<210> SEQ ID NO 203

<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 203

Arg Ala Ser Gln Ser Ile Arg Tyr Tyr Leu Ser
1               5                   10

<210> SEQ ID NO 204
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 204

Arg Ala Ser Gln Gly Val Gly Arg Trp Leu Ala
1               5                   10

<210> SEQ ID NO 205
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 205

Arg Ala Ser Gln Ser Val Tyr Thr Lys Tyr Leu Gly
1               5                   10

<210> SEQ ID NO 206
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 206

Arg Ala Ser Gln Asp Ser Gly Thr Trp Leu Ala
1               5                   10

<210> SEQ ID NO 207
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 207

Arg Ala Ser Gln Asp Ile Ser Ser Ala Leu Ala
1               5                   10

<210> SEQ ID NO 208
<211> LENGTH: 17
<212> TYPE: PRT
<213> ORGANISM: Artificial Sequence
<220> FEATURE:

<221> NAME/KEY: source
<223> OTHER INFORMATION: /note="Description of Artificial Sequence: Synthetic peptide"

<400> SEQUENCE: 208

Lys Ser Ser His Ser Val Leu Tyr Asn Arg Asn Asn Lys Asn Tyr Leu
1 5 10 15

Ala

<210> SEQ ID NO 209
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 209

Arg Ala Ser Gln Ser Ile Arg Tyr Tyr Leu Ser
1 5 10

<210> SEQ ID NO 210
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 210

Arg Ala Ser Gln Ser Ile Ser Thr Trp Leu Ala
1 5 10

<210> SEQ ID NO 211
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 211

Arg Ala Ser Gln Ser Val Thr Ser Asn Tyr Leu Ala
1 5 10

<210> SEQ ID NO 212
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 212

Arg Ala Ser Glu Asn Val Asn Ile Trp Leu Ala
1 5 10

<210> SEQ ID NO 213
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:

Synthetic peptide"

<400> SEQUENCE: 213

Gln Gly Asp Ala Leu Arg Ser Tyr Tyr Ala Ser
1 5 10

<210> SEQ ID NO 214
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 214

Gln Gly Asp Ser Leu Arg Ser Tyr Tyr Ala Ser
1 5 10

<210> SEQ ID NO 215
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 215

Gln Gly Asp Ser Leu Arg Ser Tyr Tyr Ala Ser
1 5 10

<210> SEQ ID NO 216
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 216

Arg Ala Ser Gln Ser Val Ser Ser Asn Tyr Leu Ala
1 5 10

<210> SEQ ID NO 217
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 217

Arg Ala Ser Gln Ser Val Tyr Thr Lys Tyr Leu Gly
1 5 10

<210> SEQ ID NO 218
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 218

```
Arg Ala Ser Gln Ser Ile Ser Ser Tyr Leu Asn
1               5                   10


<210> SEQ ID NO 219
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 219

Arg Ala Ser Gln Ser Ile Ser Ser Trp Leu Ala
1               5                   10


<210> SEQ ID NO 220
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 220

Arg Ala Ser Gln Gly Ile Ser Asp Tyr Ser
1               5                   10


<210> SEQ ID NO 221
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 221

Arg Ala Ser Glu Asn Val Asn Ile Trp Leu Ala
1               5                   10


<210> SEQ ID NO 222
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 222

Arg Ala Ser Arg Gly Ile Ser Ser Ala Leu Ala
1               5                   10


<210> SEQ ID NO 223
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 223

Asp Ala Ser Asn Arg Ala Thr
1               5
```

<210> SEQ ID NO 224
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 224

Asp Ala Ser Thr Leu Glu Thr
1 5

<210> SEQ ID NO 225
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 225

Ala Ala Ser Ser Leu Gln Ser
1 5

<210> SEQ ID NO 226
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 226

Lys Ala Ser Ser Leu Glu Ser
1 5

<210> SEQ ID NO 227
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 227

Thr Ala Ser Ile Leu Gln Asn
1 5

<210> SEQ ID NO 228
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 228

Ala Ala Ser Thr Leu Gln Ser
1 5

<210> SEQ ID NO 229
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 229

Asp Ala Ser Thr Arg Ala Thr
1 5

<210> SEQ ID NO 230
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 230

Asp Ala Ser Thr Leu Glu Asp
1 5

<210> SEQ ID NO 231
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 231

Asp Ala Ser Ser Leu Glu Ser
1 5

<210> SEQ ID NO 232
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 232

Trp Ala Ser Thr Arg Lys Ser
1 5

<210> SEQ ID NO 233
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 233

Thr Ala Ser Ile Leu Gln Asn
1 5

<210> SEQ ID NO 234
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 234

Lys Ala Ser Thr Leu Glu Ser
1               5

<210> SEQ ID NO 235
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 235

Gly Ala Ser Thr Arg Ala Thr
1               5

<210> SEQ ID NO 236
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 236

Lys Ser Ser Ser Leu Ala Ser
1               5

<210> SEQ ID NO 237
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 237

Gly Lys Asn Asn Arg Pro Ser
1               5

<210> SEQ ID NO 238
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 238

Gly Arg Ser Arg Arg Pro Ser
1               5

<210> SEQ ID NO 239
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 239

Gly Lys Asn Asn Arg Pro Ser 1 5

<210> SEQ ID NO 240
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 240

Asp Val Ser Thr Arg Ala Thr
1 5

<210> SEQ ID NO 241
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 241

Asp Ala Ser Thr Arg Ala Thr
1 5

<210> SEQ ID NO 242
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 242

Ala Ala Ser Ser Leu Gln Ser
1 5

<210> SEQ ID NO 243
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 243

Lys Ala Ser Ser Leu Glu Ser
1 5

<210> SEQ ID NO 244
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 244

Ala Ala Ser Thr Leu Gln Ser
1 5

<210> SEQ ID NO 245

<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 245

Lys Ser Ser Ser Leu Ala Ser
1 5

<210> SEQ ID NO 246
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 246

Asp Ala Ser Ser Leu Glu Ser
1 5

<210> SEQ ID NO 247
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 247

His Gln Arg Ser Asn Trp Leu Tyr Thr
1 5

<210> SEQ ID NO 248
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 248

Gln Gln His Asp Asn Leu Pro Leu Thr
1 5

<210> SEQ ID NO 249
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 249

Gln Gln Ser Phe Ser Pro Leu Thr
1 5

<210> SEQ ID NO 250
<211> LENGTH: 10
<212> TYPE: PRT
<213> ORGANISM: Artificial Sequence
<220> FEATURE:

<221> NAME/KEY: source
<223> OTHER INFORMATION: /note="Description of Artificial Sequence:
Synthetic peptide"

<400> SEQUENCE: 250

Gln Gln Tyr Gly His Leu Pro Met Tyr Thr
1 5 10

<210> SEQ ID NO 251
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 251

Leu Gln Thr Tyr Thr Thr Pro Asp
1 5

<210> SEQ ID NO 252
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 252

Gln Gln Ala Asn Ser Phe Pro Leu Thr
1 5

<210> SEQ ID NO 253
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 253

Gln His Tyr Gly Gly Ser Pro Leu Ile Thr
1 5 10

<210> SEQ ID NO 254
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 254

Gln Gln Tyr Asn Ser Tyr Pro Leu Thr
1 5

<210> SEQ ID NO 255
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 255

Gln Gln Phe Ser Ser Tyr Pro Leu Thr
1               5

<210> SEQ ID NO 256
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 256

Gln Gln Thr Gln Thr Phe Pro Leu Thr
1               5

<210> SEQ ID NO 257
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 257

Leu Gln Thr Tyr Thr Thr Pro Asp
1               5

<210> SEQ ID NO 258
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 258

Gln Gln Tyr Asn Thr Tyr Ser Pro Tyr Thr
1               5                   10

<210> SEQ ID NO 259
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 259

Gln Gln Tyr Gly Ser Ala Pro Val Thr
1               5

<210> SEQ ID NO 260
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 260

Gln Gln Tyr Gln Ser Tyr Pro Leu Thr
1               5

<210> SEQ ID NO 261
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 261

Asn Ser Arg Asp Ser Ser Gly Tyr Pro Val
1 5 10

<210> SEQ ID NO 262
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 262

Asn Ser Arg Asp Asn Thr Ala Asn His Tyr Val
1 5 10

<210> SEQ ID NO 263
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 263

Asn Ser Arg Gly Ser Ser Gly Asn His Tyr Val
1 5 10

<210> SEQ ID NO 264
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 264

Gln Gln Arg Ser Asn Trp Pro Pro Trp Thr
1 5 10

<210> SEQ ID NO 265
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 265

Gln His Tyr Gly Gly Ser Pro Leu Ile Thr
1 5 10

<210> SEQ ID NO 266
<211> LENGTH: 9

<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 266

Gln Gln Ser Tyr Ser Ile Pro Leu Thr
1 5

<210> SEQ ID NO 267
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 267

Gln Gln Tyr Ser Ser Tyr Pro Leu Thr
1 5

<210> SEQ ID NO 268
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 268

Gln Gln Tyr Tyr Ser Tyr Pro Leu Thr
1 5

<210> SEQ ID NO 269
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 269

Gln Gln Tyr Gln Ser Tyr Pro Leu Thr
1 5

<210> SEQ ID NO 270
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 270

Gln Gln Ser Tyr Ser Thr Pro Trp Thr
1 5

<210> SEQ ID NO 271

<400> SEQUENCE: 271

000

<210> SEQ ID NO 272

<400> SEQUENCE: 272

000

<210> SEQ ID NO 273

<400> SEQUENCE: 273

000

<210> SEQ ID NO 274
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 274

```
Val Ile Ser Tyr Asp Gly Ser Asn Lys Tyr Tyr Ala Asp Ser Val Lys
1               5                   10                  15

Gly
```

<210> SEQ ID NO 275
<211> LENGTH: 239
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 275

```
Gln Val Gln Leu Gln Gln Ser Gly Pro Glu Leu Glu Lys Pro Gly Ala
1               5                   10                  15

Ser Val Lys Ile Ser Cys Lys Ala Ser Gly Tyr Ser Phe Thr Gly Tyr
            20                  25                  30

Thr Met Asn Trp Val Lys Gln Ser His Gly Lys Ser Leu Glu Trp Ile
        35                  40                  45

Gly Leu Ile Thr Pro Tyr Asn Gly Ala Ser Ser Tyr Asn Gln Lys Phe
    50                  55                  60

Arg Gly Lys Ala Thr Leu Thr Val Asp Lys Ser Ser Ser Thr Ala Tyr
65                  70                  75                  80

Met Asp Leu Leu Ser Leu Thr Ser Glu Asp Ser Ala Val Tyr Phe Cys
                85                  90                  95

Ala Arg Gly Gly Tyr Asp Gly Arg Gly Phe Asp Tyr Trp Gly Gln Gly
            100                 105                 110

Thr Thr Val Thr Val Ser Ser Gly Gly Gly Gly Ser Gly Gly Gly Gly
        115                 120                 125

Ser Gly Gly Gly Gly Ser Asp Ile Glu Leu Thr Gln Ser Pro Ala Ile
    130                 135                 140

Met Ser Ala Ser Pro Gly Glu Lys Val Thr Met Thr Cys Ser Ala Ser
145                 150                 155                 160

Ser Ser Val Ser Tyr Met His Trp Tyr Gln Gln Lys Ser Gly Thr Ser
                165                 170                 175

Pro Lys Arg Trp Ile Tyr Asp Thr Ser Lys Leu Ala Ser Gly Val Pro
            180                 185                 190
```

Gly Arg Phe Ser Gly Ser Gly Ser Gly Asn Ser Tyr Ser Leu Thr Ile
195 200 205

Ser Ser Val Glu Ala Glu Asp Asp Ala Thr Tyr Tyr Cys Gln Gln Trp
210 215 220

Ser Gly Tyr Pro Leu Thr Phe Gly Ala Gly Thr Lys Leu Glu Ile
225 230 235

<210> SEQ ID NO 276

<400> SEQUENCE: 276

000

<210> SEQ ID NO 277

<400> SEQUENCE: 277

000

<210> SEQ ID NO 278
<211> LENGTH: 383
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 278

Met Ala Leu Pro Val Thr Ala Leu Leu Leu Pro Leu Ala Leu Leu Leu
1 5 10 15

His Ala Ala Arg Pro Gln Val Gln Leu Gln Gln Ser Gly Pro Glu Leu
20 25 30

Glu Lys Pro Gly Ala Ser Val Lys Ile Ser Cys Lys Ala Ser Gly Tyr
35 40 45

Ser Phe Thr Gly Tyr Thr Met Asn Trp Val Lys Gln Ser His Gly Lys
50 55 60

Ser Leu Glu Trp Ile Gly Leu Ile Thr Pro Tyr Asn Gly Ala Ser Ser
65 70 75 80

Tyr Asn Gln Lys Phe Arg Gly Lys Ala Thr Leu Thr Val Asp Lys Ser
85 90 95

Ser Ser Thr Ala Tyr Met Asp Leu Leu Ser Leu Thr Ser Glu Asp Ser
100 105 110

Ala Val Tyr Phe Cys Ala Arg Gly Gly Tyr Asp Gly Arg Gly Phe Asp
115 120 125

Tyr Trp Gly Gln Gly Thr Thr Val Thr Val Ser Ser Gly Gly Gly Gly
130 135 140

Ser Gly Gly Gly Gly Ser Gly Gly Gly Gly Ser Asp Ile Glu Leu Thr
145 150 155 160

Gln Ser Pro Ala Ile Met Ser Ala Ser Pro Gly Glu Lys Val Thr Met
165 170 175

Thr Cys Ser Ala Ser Ser Ser Val Ser Tyr Met His Trp Tyr Gln Gln
180 185 190

Lys Ser Gly Thr Ser Pro Lys Arg Trp Ile Tyr Asp Thr Ser Lys Leu
195 200 205

Ala Ser Gly Val Pro Gly Arg Phe Ser Gly Ser Gly Ser Gly Asn Ser
210 215 220

Tyr Ser Leu Thr Ile Ser Ser Val Glu Ala Glu Asp Asp Ala Thr Tyr
225 230 235 240

```
Tyr Cys Gln Gln Trp Ser Gly Tyr Pro Leu Thr Phe Gly Ala Gly Thr
                245                 250                 255

Lys Leu Glu Ile Thr Thr Thr Pro Ala Pro Arg Pro Pro Thr Pro Ala
            260                 265                 270

Pro Thr Ile Ala Ser Gln Pro Leu Ser Leu Arg Pro Glu Ala Cys Arg
        275                 280                 285

Pro Ala Ala Gly Gly Ala Val His Thr Arg Gly Leu Asp Phe Ala Cys
    290                 295                 300

Asp Ile Tyr Ile Trp Ala Pro Leu Ala Gly Thr Cys Gly Val Leu Leu
305                 310                 315                 320

Leu Ser Leu Val Ile Thr Leu Tyr Cys Lys Arg Gly Arg Lys Lys Leu
                325                 330                 335

Leu Tyr Ile Phe Lys Gln Pro Phe Met Arg Pro Val Gln Thr Thr Gln
            340                 345                 350

Glu Glu Asp Gly Cys Ser Cys Arg Phe Pro Glu Glu Glu Glu Gly Gly
        355                 360                 365

Cys Glu Leu Arg Val Lys Phe Ser Arg Ser Ala Asp Ala Pro Ala
    370                 375                 380
```

<210> SEQ ID NO 279
<211> LENGTH: 717
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 279

```
caagtccagc tccagcagtc gggcccagag ttggagaagc ctggggcgag cgtgaagatc     60

tcatgcaaag cctcaggcta ctcctttact ggatacacga tgaattgggt gaaacagtcg    120

catggaaagt cactggaatg gatcggtctg attacgccct acaacggcgc ctccagctac    180

aaccagaagt tcaggggaaa ggcgaccctt actgtcgaca agtcgtcaag caccgcctac    240

atggacctcc tgtccctgac ctccgaagat agcgcggtct acttttgtgc acgcggaggt    300

tacgatggac ggggattcga ctactggggc cagggaacca ctgtcaccgt gtcgagcgga    360

ggcggaggga gcggaggagg aggcagcgga ggtggagggt cggatatcga actcactcag    420

tccccagcaa tcatgtccgc ttcaccggga gaaaaggtga ccatgacttg ctcggcctcc    480

tcgtccgtgt catacatgca ctggtaccaa caaaaatcgg ggacctcccc taagagatgg    540

atctacgata ccagcaaact ggcttcaggc gtgccgggac gcttctcggg ttcggggagc    600

ggaaattcgt attcgttgac catttcgtcc gtggaagccg aggacgacgc aacttattac    660

tgccaacagt ggtcaggcta cccgctcact ttcggagccg gcactaagct ggagatc       717
```

<210> SEQ ID NO 280
<211> LENGTH: 1149
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 280

```
atggccctcc ctgtcaccgc cctgctgctt ccgctggctc ttctgctcca cgccgctcgg     60

ccccaagtcc agctccagca gtcgggccca gagttggaga agcctggggc gagcgtgaag    120
```

atctcatgca aagcctcagg ctactccttt actggataca cgatgaattg ggtgaaacag 180
tcgcatggaa agtcactgga atggatcggt ctgattacgc cctacaacgg cgcctccagc 240
tacaaccaga agttcagggg aaaggcgacc cttactgtcg acaagtcgtc aagcaccgcc 300
tacatggacc tcctgtccct gacctccgaa gatagcgcgg tctacttttg tgcacgcgga 360
ggttacgatg gacggggatt cgactactgg ggccagggaa ccactgtcac cgtgtcgagc 420
ggaggcggag ggagcggagg aggaggcagc ggaggtggag ggtcggatat cgaactcact 480
cagtccccag caatcatgtc cgcttcaccg ggagaaaagg tgaccatgac ttgctcggcc 540
tcctcgtccg tgtcatacat gcactggtac caacaaaaat cggggacctc ccctaagaga 600
tggatctacg ataccagcaa actggcttca ggcgtgccgg gacgcttctc gggttcgggg 660
agcggaaatt cgtattcgtt gaccatttcg tccgtggaag ccgaggacga cgcaacttat 720
tactgccaac agtggtcagg ctacccgctc actttcggag ccggcactaa gctggagatc 780
accactaccc cagcaccgag gccacccacc ccggctccta ccatcgcctc ccagcctctg 840
tccctgcgtc cggaggcatg tagacccgca gctggtgggg ccgtgcatac ccggggtctt 900
gacttcgcct gcgatatcta catttgggcc cctctggctg gtacttgcgg ggtcctgctg 960
ctttcactcg tgatcactct ttactgtaag cgcggtcgga agaagctgct gtacatcttt 1020
aagcaaccct tcatgaggcc tgtgcagact actcaagagg aggacggctg ttcatgccgg 1080
ttcccagagg aggaggaagg cggctgcgaa ctgcgcgtga aattcagccg cagcgcagat 1140
gctccagcc 1149

<210> SEQ ID NO 281
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 281

Gly Tyr Ser Phe Thr Gly Tyr Thr Met Asn
1 5 10

<210> SEQ ID NO 282
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 282

Leu Ile Thr Pro Tyr Asn Gly Ala Ser Ser Tyr Asn Gln Lys Phe Arg
1 5 10 15

Gly

<210> SEQ ID NO 283
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 283

Gly Gly Tyr Asp Gly Arg Gly Phe Asp Tyr
1 5 10

<210> SEQ ID NO 284
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 284

Ser Ala Ser Ser Ser Val Ser Tyr Met His
1 5 10

<210> SEQ ID NO 285
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 285

Asp Thr Ser Lys Leu Ala Ser
1 5

<210> SEQ ID NO 286
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 286

Gln Gln Trp Ser Gly Tyr Pro Leu Thr
1 5

<210> SEQ ID NO 287

<400> SEQUENCE: 287

000

<210> SEQ ID NO 288

<400> SEQUENCE: 288

000

<210> SEQ ID NO 289

<400> SEQUENCE: 289

000

<210> SEQ ID NO 290

<400> SEQUENCE: 290

000

<210> SEQ ID NO 291

<400> SEQUENCE: 291

000

<210> SEQ ID NO 292

<400> SEQUENCE: 292

000

<210> SEQ ID NO 293

<400> SEQUENCE: 293

000

<210> SEQ ID NO 294

<400> SEQUENCE: 294

000

<210> SEQ ID NO 295

<400> SEQUENCE: 295

000

<210> SEQ ID NO 296

<400> SEQUENCE: 296

000

<210> SEQ ID NO 297

<400> SEQUENCE: 297

000

<210> SEQ ID NO 298

<400> SEQUENCE: 298

000

<210> SEQ ID NO 299

<400> SEQUENCE: 299

000

<210> SEQ ID NO 300

<400> SEQUENCE: 300

000

<210> SEQ ID NO 301

<400> SEQUENCE: 301

000

<210> SEQ ID NO 302

<400> SEQUENCE: 302

000

<210> SEQ ID NO 303

<400> SEQUENCE: 303

000

<210> SEQ ID NO 304

<400> SEQUENCE: 304

000

<210> SEQ ID NO 305

<400> SEQUENCE: 305

000

<210> SEQ ID NO 306

<400> SEQUENCE: 306

000

<210> SEQ ID NO 307

<400> SEQUENCE: 307

000

<210> SEQ ID NO 308

<400> SEQUENCE: 308

000

<210> SEQ ID NO 309

<400> SEQUENCE: 309

000

<210> SEQ ID NO 310

<400> SEQUENCE: 310

000

<210> SEQ ID NO 311

<400> SEQUENCE: 311

000

<210> SEQ ID NO 312

<400> SEQUENCE: 312

000

<210> SEQ ID NO 313

<400> SEQUENCE: 313

000

<210> SEQ ID NO 314

<400> SEQUENCE: 314

000

<210> SEQ ID NO 315

<400> SEQUENCE: 315

000

<210> SEQ ID NO 316

<400> SEQUENCE: 316

000

<210> SEQ ID NO 317

<400> SEQUENCE: 317

000

<210> SEQ ID NO 318

<400> SEQUENCE: 318

000

<210> SEQ ID NO 319

<400> SEQUENCE: 319

000

<210> SEQ ID NO 320

<400> SEQUENCE: 320

000

<210> SEQ ID NO 321

<400> SEQUENCE: 321

000

<210> SEQ ID NO 322

<400> SEQUENCE: 322

000

<210> SEQ ID NO 323

<400> SEQUENCE: 323

000

<210> SEQ ID NO 324

<400> SEQUENCE: 324

000

<210> SEQ ID NO 325

<400> SEQUENCE: 325

000

<210> SEQ ID NO 326

<400> SEQUENCE: 326

000

<210> SEQ ID NO 327

<400> SEQUENCE: 327

000

<210> SEQ ID NO 328

<400> SEQUENCE: 328

000

<210> SEQ ID NO 329

<400> SEQUENCE: 329

000

<210> SEQ ID NO 330

<400> SEQUENCE: 330

000

<210> SEQ ID NO 331

<400> SEQUENCE: 331

000

<210> SEQ ID NO 332

<400> SEQUENCE: 332

000

<210> SEQ ID NO 333

<400> SEQUENCE: 333

000

<210> SEQ ID NO 334

<400> SEQUENCE: 334

000

<210> SEQ ID NO 335

<400> SEQUENCE: 335

000

<210> SEQ ID NO 336

<400> SEQUENCE: 336

000

<210> SEQ ID NO 337

<400> SEQUENCE: 337

000

<210> SEQ ID NO 338

<400> SEQUENCE: 338

000

<210> SEQ ID NO 339

<400> SEQUENCE: 339

000

<210> SEQ ID NO 340

<400> SEQUENCE: 340

000

<210> SEQ ID NO 341

<400> SEQUENCE: 341

000

<210> SEQ ID NO 342

<400> SEQUENCE: 342

000

<210> SEQ ID NO 343

<400> SEQUENCE: 343

000

<210> SEQ ID NO 344

<400> SEQUENCE: 344

000

<210> SEQ ID NO 345

<400> SEQUENCE: 345

000

<210> SEQ ID NO 346

<400> SEQUENCE: 346

000

<210> SEQ ID NO 347

<400> SEQUENCE: 347

000

<210> SEQ ID NO 348

<400> SEQUENCE: 348

000

<210> SEQ ID NO 349

<400> SEQUENCE: 349

000

<210> SEQ ID NO 350

<400> SEQUENCE: 350

000

<210> SEQ ID NO 351

<400> SEQUENCE: 351

000

<210> SEQ ID NO 352

<400> SEQUENCE: 352

000

<210> SEQ ID NO 353

<400> SEQUENCE: 353

000

<210> SEQ ID NO 354

<400> SEQUENCE: 354

000

<210> SEQ ID NO 355

<400> SEQUENCE: 355

000

<210> SEQ ID NO 356

<400> SEQUENCE: 356

000

<210> SEQ ID NO 357

<400> SEQUENCE: 357

000

<210> SEQ ID NO 358

<400> SEQUENCE: 358

000

<210> SEQ ID NO 359

<400> SEQUENCE: 359

000

<210> SEQ ID NO 360

<400> SEQUENCE: 360

000

<210> SEQ ID NO 361

<400> SEQUENCE: 361

000

<210> SEQ ID NO 362

<400> SEQUENCE: 362

000

<210> SEQ ID NO 363

<400> SEQUENCE: 363

000

<210> SEQ ID NO 364

<400> SEQUENCE: 364

000

<210> SEQ ID NO 365

<400> SEQUENCE: 365

000

<210> SEQ ID NO 366

<400> SEQUENCE: 366

000

<210> SEQ ID NO 367

<400> SEQUENCE: 367

000

<210> SEQ ID NO 368

<400> SEQUENCE: 368

000

<210> SEQ ID NO 369

<400> SEQUENCE: 369

000

<210> SEQ ID NO 370

<400> SEQUENCE: 370

000

<210> SEQ ID NO 371

<400> SEQUENCE: 371

000

<210> SEQ ID NO 372

<400> SEQUENCE: 372

000

<210> SEQ ID NO 373

<400> SEQUENCE: 373

000

<210> SEQ ID NO 374

<400> SEQUENCE: 374

000

<210> SEQ ID NO 375

<400> SEQUENCE: 375

000

<210> SEQ ID NO 376

<400> SEQUENCE: 376

000

<210> SEQ ID NO 377

<400> SEQUENCE: 377

000

<210> SEQ ID NO 378

<400> SEQUENCE: 378

000

<210> SEQ ID NO 379

<400> SEQUENCE: 379

000

<210> SEQ ID NO 380

<400> SEQUENCE: 380

000

<210> SEQ ID NO 381

-continued

<400> SEQUENCE: 381

000

<210> SEQ ID NO 382

<400> SEQUENCE: 382

000

<210> SEQ ID NO 383

<400> SEQUENCE: 383

000

<210> SEQ ID NO 384

<400> SEQUENCE: 384

000

<210> SEQ ID NO 385

<400> SEQUENCE: 385

000

<210> SEQ ID NO 386

<400> SEQUENCE: 386

000

<210> SEQ ID NO 387

<400> SEQUENCE: 387

000

<210> SEQ ID NO 388

<400> SEQUENCE: 388

000

<210> SEQ ID NO 389

<400> SEQUENCE: 389

000

<210> SEQ ID NO 390

<400> SEQUENCE: 390

000

<210> SEQ ID NO 391

<400> SEQUENCE: 391

000

<210> SEQ ID NO 392

<400> SEQUENCE: 392

000

<210> SEQ ID NO 393

<400> SEQUENCE: 393

000

<210> SEQ ID NO 394

<400> SEQUENCE: 394

000

<210> SEQ ID NO 395

<400> SEQUENCE: 395

000

<210> SEQ ID NO 396

<400> SEQUENCE: 396

000

<210> SEQ ID NO 397

<400> SEQUENCE: 397

000

<210> SEQ ID NO 398

<400> SEQUENCE: 398

000

<210> SEQ ID NO 399

<400> SEQUENCE: 399

000

<210> SEQ ID NO 400

<400> SEQUENCE: 400

000

<210> SEQ ID NO 401

<400> SEQUENCE: 401

000

<210> SEQ ID NO 402

<400> SEQUENCE: 402

000

<210> SEQ ID NO 403

<400> SEQUENCE: 403

000

<210> SEQ ID NO 404

<400> SEQUENCE: 404

000

<210> SEQ ID NO 405

<400> SEQUENCE: 405

000

<210> SEQ ID NO 406

<400> SEQUENCE: 406

000

<210> SEQ ID NO 407

<400> SEQUENCE: 407

000

<210> SEQ ID NO 408

<400> SEQUENCE: 408

000

<210> SEQ ID NO 409

<400> SEQUENCE: 409

000

<210> SEQ ID NO 410

<400> SEQUENCE: 410

000

<210> SEQ ID NO 411

<400> SEQUENCE: 411

000

<210> SEQ ID NO 412

<400> SEQUENCE: 412

000

<210> SEQ ID NO 413

<400> SEQUENCE: 413

000

<210> SEQ ID NO 414

<400> SEQUENCE: 414

000

<210> SEQ ID NO 415

<400> SEQUENCE: 415

000

<210> SEQ ID NO 416

<400> SEQUENCE: 416

000

<210> SEQ ID NO 417

<400> SEQUENCE: 417

000

<210> SEQ ID NO 418

<400> SEQUENCE: 418

000

<210> SEQ ID NO 419

<400> SEQUENCE: 419

000

<210> SEQ ID NO 420

<400> SEQUENCE: 420

000

<210> SEQ ID NO 421

<400> SEQUENCE: 421

000

<210> SEQ ID NO 422

<400> SEQUENCE: 422

000

<210> SEQ ID NO 423

<400> SEQUENCE: 423

000

<210> SEQ ID NO 424

<400> SEQUENCE: 424

000

<210> SEQ ID NO 425

<400> SEQUENCE: 425

000

<210> SEQ ID NO 426

<400> SEQUENCE: 426

000

<210> SEQ ID NO 427
<400> SEQUENCE: 427
000

<210> SEQ ID NO 428
<400> SEQUENCE: 428
000

<210> SEQ ID NO 429
<400> SEQUENCE: 429
000

<210> SEQ ID NO 430
<400> SEQUENCE: 430
000

<210> SEQ ID NO 431
<400> SEQUENCE: 431
000

<210> SEQ ID NO 432
<400> SEQUENCE: 432
000

<210> SEQ ID NO 433
<400> SEQUENCE: 433
000

<210> SEQ ID NO 434
<400> SEQUENCE: 434
000

<210> SEQ ID NO 435
<400> SEQUENCE: 435
000

<210> SEQ ID NO 436
<400> SEQUENCE: 436
000

<210> SEQ ID NO 437
<400> SEQUENCE: 437
000

<210> SEQ ID NO 438

<400> SEQUENCE: 438

000

<210> SEQ ID NO 439

<400> SEQUENCE: 439

000

<210> SEQ ID NO 440

<400> SEQUENCE: 440

000

<210> SEQ ID NO 441

<400> SEQUENCE: 441

000

<210> SEQ ID NO 442

<400> SEQUENCE: 442

000

<210> SEQ ID NO 443

<400> SEQUENCE: 443

000

<210> SEQ ID NO 444

<400> SEQUENCE: 444

000

<210> SEQ ID NO 445

<400> SEQUENCE: 445

000

<210> SEQ ID NO 446

<400> SEQUENCE: 446

000

<210> SEQ ID NO 447

<400> SEQUENCE: 447

000

<210> SEQ ID NO 448

<400> SEQUENCE: 448

000

<210> SEQ ID NO 449

<400> SEQUENCE: 449

000

<210> SEQ ID NO 450

<400> SEQUENCE: 450

000

<210> SEQ ID NO 451

<400> SEQUENCE: 451

000

<210> SEQ ID NO 452

<400> SEQUENCE: 452

000

<210> SEQ ID NO 453

<400> SEQUENCE: 453

000

<210> SEQ ID NO 454

<400> SEQUENCE: 454

000

<210> SEQ ID NO 455

<400> SEQUENCE: 455

000

<210> SEQ ID NO 456

<400> SEQUENCE: 456

000

<210> SEQ ID NO 457

<400> SEQUENCE: 457

000

<210> SEQ ID NO 458

<400> SEQUENCE: 458

000

<210> SEQ ID NO 459

<400> SEQUENCE: 459

000

<210> SEQ ID NO 460

<400> SEQUENCE: 460

000

<210> SEQ ID NO 461

<400> SEQUENCE: 461

000

<210> SEQ ID NO 462

<400> SEQUENCE: 462

000

<210> SEQ ID NO 463

<400> SEQUENCE: 463

000

<210> SEQ ID NO 464

<400> SEQUENCE: 464

000

<210> SEQ ID NO 465

<400> SEQUENCE: 465

000

<210> SEQ ID NO 466

<400> SEQUENCE: 466

000

<210> SEQ ID NO 467

<400> SEQUENCE: 467

000

<210> SEQ ID NO 468

<400> SEQUENCE: 468

000

<210> SEQ ID NO 469

<400> SEQUENCE: 469

000

<210> SEQ ID NO 470

<400> SEQUENCE: 470

000

<210> SEQ ID NO 471

<400> SEQUENCE: 471

-continued

000

<210> SEQ ID NO 472

<400> SEQUENCE: 472

000

<210> SEQ ID NO 473

<400> SEQUENCE: 473

000

<210> SEQ ID NO 474

<400> SEQUENCE: 474

000

<210> SEQ ID NO 475

<400> SEQUENCE: 475

000

<210> SEQ ID NO 476

<400> SEQUENCE: 476

000

<210> SEQ ID NO 477

<400> SEQUENCE: 477

000

<210> SEQ ID NO 478

<400> SEQUENCE: 478

000

<210> SEQ ID NO 479

<400> SEQUENCE: 479

000

<210> SEQ ID NO 480

<400> SEQUENCE: 480

000

<210> SEQ ID NO 481

<400> SEQUENCE: 481

000

<210> SEQ ID NO 482

<400> SEQUENCE: 482

000

<210> SEQ ID NO 483

<400> SEQUENCE: 483

000

<210> SEQ ID NO 484

<400> SEQUENCE: 484

000

<210> SEQ ID NO 485

<400> SEQUENCE: 485

000

<210> SEQ ID NO 486

<400> SEQUENCE: 486

000

<210> SEQ ID NO 487

<400> SEQUENCE: 487

000

<210> SEQ ID NO 488

<400> SEQUENCE: 488

000

<210> SEQ ID NO 489

<400> SEQUENCE: 489

000

<210> SEQ ID NO 490

<400> SEQUENCE: 490

000

<210> SEQ ID NO 491

<400> SEQUENCE: 491

000

<210> SEQ ID NO 492

<400> SEQUENCE: 492

000

<210> SEQ ID NO 493

<400> SEQUENCE: 493

000

<210> SEQ ID NO 494

<400> SEQUENCE: 494

000

<210> SEQ ID NO 495

<400> SEQUENCE: 495

000

<210> SEQ ID NO 496

<400> SEQUENCE: 496

000

<210> SEQ ID NO 497

<400> SEQUENCE: 497

000

<210> SEQ ID NO 498

<400> SEQUENCE: 498

000

<210> SEQ ID NO 499

<400> SEQUENCE: 499

000

<210> SEQ ID NO 500

<400> SEQUENCE: 500

000

<210> SEQ ID NO 501

<400> SEQUENCE: 501

000

<210> SEQ ID NO 502

<400> SEQUENCE: 502

000

<210> SEQ ID NO 503

<400> SEQUENCE: 503

000

<210> SEQ ID NO 504

<400> SEQUENCE: 504

000

<210> SEQ ID NO 505

<400> SEQUENCE: 505

000

<210> SEQ ID NO 506

<400> SEQUENCE: 506

000

<210> SEQ ID NO 507

<400> SEQUENCE: 507

000

<210> SEQ ID NO 508

<400> SEQUENCE: 508

000

<210> SEQ ID NO 509

<400> SEQUENCE: 509

000

<210> SEQ ID NO 510

<400> SEQUENCE: 510

000

<210> SEQ ID NO 511

<400> SEQUENCE: 511

000

<210> SEQ ID NO 512

<400> SEQUENCE: 512

000

<210> SEQ ID NO 513

<400> SEQUENCE: 513

000

<210> SEQ ID NO 514

<400> SEQUENCE: 514

000

<210> SEQ ID NO 515

<400> SEQUENCE: 515

000

<210> SEQ ID NO 516

<400> SEQUENCE: 516

000

<210> SEQ ID NO 517

<400> SEQUENCE: 517

000

<210> SEQ ID NO 518

<400> SEQUENCE: 518

000

<210> SEQ ID NO 519

<400> SEQUENCE: 519

000

<210> SEQ ID NO 520

<400> SEQUENCE: 520

000

<210> SEQ ID NO 521

<400> SEQUENCE: 521

000

<210> SEQ ID NO 522

<400> SEQUENCE: 522

000

<210> SEQ ID NO 523

<400> SEQUENCE: 523

000

<210> SEQ ID NO 524

<400> SEQUENCE: 524

000

<210> SEQ ID NO 525

<400> SEQUENCE: 525

000

<210> SEQ ID NO 526

<400> SEQUENCE: 526

000

<210> SEQ ID NO 527

<400> SEQUENCE: 527

000

<210> SEQ ID NO 528

<400> SEQUENCE: 528

000

<210> SEQ ID NO 529

<400> SEQUENCE: 529

000

<210> SEQ ID NO 530

<400> SEQUENCE: 530

000

<210> SEQ ID NO 531

<400> SEQUENCE: 531

000

<210> SEQ ID NO 532

<400> SEQUENCE: 532

000

<210> SEQ ID NO 533

<400> SEQUENCE: 533

000

<210> SEQ ID NO 534

<400> SEQUENCE: 534

000

<210> SEQ ID NO 535

<400> SEQUENCE: 535

000

<210> SEQ ID NO 536

<400> SEQUENCE: 536

000

<210> SEQ ID NO 537

<400> SEQUENCE: 537

000

<210> SEQ ID NO 538

<400> SEQUENCE: 538

000

<210> SEQ ID NO 539

<400> SEQUENCE: 539

000

<210> SEQ ID NO 540

<400> SEQUENCE: 540

000

<210> SEQ ID NO 541

<400> SEQUENCE: 541

000

<210> SEQ ID NO 542

<400> SEQUENCE: 542

000

<210> SEQ ID NO 543

<400> SEQUENCE: 543

000

<210> SEQ ID NO 544

<400> SEQUENCE: 544

000

<210> SEQ ID NO 545

<400> SEQUENCE: 545

000

<210> SEQ ID NO 546

<400> SEQUENCE: 546

000

<210> SEQ ID NO 547

<400> SEQUENCE: 547

000

<210> SEQ ID NO 548

<400> SEQUENCE: 548

000

<210> SEQ ID NO 549

<400> SEQUENCE: 549

000

<210> SEQ ID NO 550

<400> SEQUENCE: 550

000

<210> SEQ ID NO 551

<400> SEQUENCE: 551

000

<210> SEQ ID NO 552

<400> SEQUENCE: 552

000

<210> SEQ ID NO 553

<400> SEQUENCE: 553

000

<210> SEQ ID NO 554

<400> SEQUENCE: 554

000

<210> SEQ ID NO 555

<400> SEQUENCE: 555

000

<210> SEQ ID NO 556

<400> SEQUENCE: 556

000

<210> SEQ ID NO 557

<400> SEQUENCE: 557

000

<210> SEQ ID NO 558

<400> SEQUENCE: 558

000

<210> SEQ ID NO 559

<400> SEQUENCE: 559

000

<210> SEQ ID NO 560

<400> SEQUENCE: 560

000

<210> SEQ ID NO 561

<400> SEQUENCE: 561

000

<210> SEQ ID NO 562

<400> SEQUENCE: 562

000

<210> SEQ ID NO 563

<400> SEQUENCE: 563

000

<210> SEQ ID NO 564

<400> SEQUENCE: 564

000

<210> SEQ ID NO 565

<400> SEQUENCE: 565

000

<210> SEQ ID NO 566

<400> SEQUENCE: 566

000

<210> SEQ ID NO 567

<400> SEQUENCE: 567

000

<210> SEQ ID NO 568

<400> SEQUENCE: 568

000

<210> SEQ ID NO 569

<400> SEQUENCE: 569

000

<210> SEQ ID NO 570

<400> SEQUENCE: 570

000

<210> SEQ ID NO 571

<400> SEQUENCE: 571

000

<210> SEQ ID NO 572

<400> SEQUENCE: 572

000

<210> SEQ ID NO 573

<400> SEQUENCE: 573

000

<210> SEQ ID NO 574

<400> SEQUENCE: 574

000

<210> SEQ ID NO 575

<400> SEQUENCE: 575

000

<210> SEQ ID NO 576

<400> SEQUENCE: 576

000

<210> SEQ ID NO 577

<400> SEQUENCE: 577

000

<210> SEQ ID NO 578

<400> SEQUENCE: 578

000

<210> SEQ ID NO 579

<400> SEQUENCE: 579

000

<210> SEQ ID NO 580

<400> SEQUENCE: 580

000

<210> SEQ ID NO 581

<400> SEQUENCE: 581

000

<210> SEQ ID NO 582

<400> SEQUENCE: 582

000

<210> SEQ ID NO 583

<400> SEQUENCE: 583

000

<210> SEQ ID NO 584

<400> SEQUENCE: 584

000

<210> SEQ ID NO 585

<400> SEQUENCE: 585

000

<210> SEQ ID NO 586

<400> SEQUENCE: 586

000

<210> SEQ ID NO 587

<400> SEQUENCE: 587

000

<210> SEQ ID NO 588

<400> SEQUENCE: 588

000

<210> SEQ ID NO 589

<400> SEQUENCE: 589

000

<210> SEQ ID NO 590

<400> SEQUENCE: 590

000

<210> SEQ ID NO 591

<400> SEQUENCE: 591

000

<210> SEQ ID NO 592

<400> SEQUENCE: 592

000

<210> SEQ ID NO 593

<400> SEQUENCE: 593

000

<210> SEQ ID NO 594

<400> SEQUENCE: 594

000

<210> SEQ ID NO 595

<400> SEQUENCE: 595

000

<210> SEQ ID NO 596

<400> SEQUENCE: 596

000

<210> SEQ ID NO 597

<400> SEQUENCE: 597

000

<210> SEQ ID NO 598

<400> SEQUENCE: 598

000

<210> SEQ ID NO 599

<400> SEQUENCE: 599

000

<210> SEQ ID NO 600

<400> SEQUENCE: 600

000

<210> SEQ ID NO 601

<400> SEQUENCE: 601

000

<210> SEQ ID NO 602

<400> SEQUENCE: 602

000

<210> SEQ ID NO 603

<400> SEQUENCE: 603

000

<210> SEQ ID NO 604

<400> SEQUENCE: 604

000

<210> SEQ ID NO 605

<400> SEQUENCE: 605

000

<210> SEQ ID NO 606
<211> LENGTH: 40
<212> TYPE: PRT
<213> ORGANISM: Artificial Sequence
<220> FEATURE:
<221> NAME/KEY: source
<223> OTHER INFORMATION: /note="Description of Artificial Sequence:

Synthetic polypeptide"
<220> FEATURE:
<221> NAME/KEY: SITE
<222> LOCATION: (1)..(40)
<223> OTHER INFORMATION: /note="This sequence may encompass 1-10 'Gly Gly Gly Ser' repeating units"

<400> SEQUENCE: 606

Gly Gly Gly Ser Gly Gly Gly Ser Gly Gly Gly Ser Gly Gly Gly Ser
1               5                   10                  15

Gly Gly Gly Ser Gly Gly Gly Ser Gly Gly Gly Ser Gly Gly Gly Ser
            20                  25                  30

Gly Gly Gly Ser Gly Gly Gly Ser
        35                  40

<210> SEQ ID NO 607
<211> LENGTH: 105
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 607
acaaaaaaga agtattcatc cagtgtgcac gaccctaacg gtgaatacat gttcatgaga     60
gcagtgaaca cagccaaaaa atccagactc acagatgtga cccta                    105

<210> SEQ ID NO 608
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 608
ggtggcggag gttctggagg tgggggttcc                                     30

<210> SEQ ID NO 609
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: source
<223> OTHER INFORMATION: /note="See specification as filed for detailed description of substitutions and preferred embodiments"

<400> SEQUENCE: 609

Gly Gly Gly Ser
1

<210> SEQ ID NO 610
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 610

Gly Ser Thr Ser Gly Ser Gly Lys Pro Gly Ser Gly Glu Gly Ser Thr
1               5                   10                  15

Lys Gly

<210> SEQ ID NO 611
<211> LENGTH: 233
<212> TYPE: PRT
<213> ORGANISM: Homo sapiens

<400> SEQUENCE: 611

Met Ser Thr Glu Ser Met Ile Arg Asp Val Glu Leu Ala Glu Glu Ala
1               5                   10                  15

Leu Pro Lys Lys Thr Gly Gly Pro Gln Gly Ser Arg Arg Cys Leu Phe
            20                  25                  30

Leu Ser Leu Phe Ser Phe Leu Ile Val Ala Gly Ala Thr Thr Leu Phe
        35                  40                  45

Cys Leu Leu His Phe Gly Val Ile Gly Pro Gln Arg Glu Glu Phe Pro
    50                  55                  60

Arg Asp Leu Ser Leu Ile Ser Pro Leu Ala Gln Ala Val Arg Ser Ser
65                  70                  75                  80

Ser Arg Thr Pro Ser Asp Lys Pro Val Ala His Val Val Ala Asn Pro
                85                  90                  95

Gln Ala Glu Gly Gln Leu Gln Trp Leu Asn Arg Arg Ala Asn Ala Leu
            100                 105                 110

Leu Ala Asn Gly Val Glu Leu Arg Asp Asn Gln Leu Val Val Pro Ser
        115                 120                 125

Glu Gly Leu Tyr Leu Ile Tyr Ser Gln Val Leu Phe Lys Gly Gln Gly
    130                 135                 140

Cys Pro Ser Thr His Val Leu Leu Thr His Thr Ile Ser Arg Ile Ala
145                 150                 155                 160

Val Ser Tyr Gln Thr Lys Val Asn Leu Leu Ser Ala Ile Lys Ser Pro
                165                 170                 175

Cys Gln Arg Glu Thr Pro Glu Gly Ala Glu Ala Lys Pro Trp Tyr Glu
            180                 185                 190

Pro Ile Tyr Leu Gly Gly Val Phe Gln Leu Glu Lys Gly Asp Arg Leu
        195                 200                 205

Ser Ala Glu Ile Asn Arg Pro Asp Tyr Leu Asp Phe Ala Glu Ser Gly
    210                 215                 220

Gln Val Tyr Phe Gly Ile Ile Ala Leu
225                 230

<210> SEQ ID NO 612
<211> LENGTH: 1686
<212> TYPE: DNA
<213> ORGANISM: Homo sapiens

<400> SEQUENCE: 612
cagacgctcc ctcagcaagg acagcagagg accagctaag agggagagaa gcaactacag 60 acccccccctg aaaacaaccc tcagacgcca catcccctga caagctgcca ggcaggttct 120
cttcctctca catactgacc cacggctcca ccctctctcc cctggaaagg acaccatgag 180
cactgaaagc atgatccggg acgtggagct ggccgaggag gcgctcccca agaagacagg 240
ggggccccag ggctccaggc ggtgcttgtt cctcagcctc ttctccttcc tgatcgtggc 300
aggcgccacc acgctcttct gcctgctgca ctttggagtg atcggccccc agagggaaga 360
gttccccagg gacctctctc taatcagccc tctggcccag gcagtcagat catcttctcg 420

```
aaccccgagt gacaagcctg tagcccatgt tgtagcaaac cctcaagctg aggggcagct    480

ccagtggctg aaccgccggg ccaatgccct cctggccaat ggcgtggagc tgagagataa    540

ccagctggtg gtgccatcag agggcctgta cctcatctac tcccaggtcc tcttcaaggg    600

ccaaggctgc cctccaccc atgtgctcct cacccacacc atcagccgca tcgccgtctc    660

ctaccagacc aaggtcaacc tcctctctgc catcaagagc ccctgccaga gggagacccc    720

agagggggct gaggccaagc cctggtatga gcccatctat ctgggagggg tcttccagct    780

ggagaagggt gaccgactca gcgctgagat caatcggccc gactatctcg actttgccga    840

gtctgggcag gtctactttg ggatcattgc cctgtgagga ggacgaacat ccaaccttcc    900

caaacgcctc ccctgcccca atccctttat taccccctcc ttcagacacc ctcaacctct    960

tctggctcaa aaagagaatt gggggcttag ggtcggaacc caagcttaga actttaagca   1020

acaagaccac cacttcgaaa cctgggattc aggaatgtgt ggcctgcaca gtgaagtgct   1080

ggcaaccact aagaattcaa actggggcct ccagaactca ctggggccta cagctttgat   1140

ccctgacatc tggaatctgg agaccaggga gcctttggtt ctggccagaa tgctgcagga   1200

cttgagaaga cctcacctag aaattgacac aagtggacct taggccttcc tctctccaga   1260

tgtttccaga cttccttgag acacggagcc cagccctccc catggagcca gctccctcta   1320

tttatgtttg cacttgtgat tatttattat ttatttatta tttatttatt tacagatgaa   1380

tgtatttatt tgggagaccg gggtatcctg ggggacccaa tgtaggagct gccttggctc   1440

agacatgttt tccgtgaaaa cggagctgaa caataggctg ttcccatgta gcccccctggc   1500

ctctgtgcct tcttttgatt atgtttttta aaatatttat ctgattaagt tgtctaaaca   1560

atgctgattt ggtgaccaac tgtcactcat tgctgagcct ctgctcccca ggggagttgt   1620

gtctgtaatc gccctactat tcagtggcga gaaataaagt ttgcttagaa aagaaaaaaa   1680

aaaaaa                                                               1686
```

```
<210> SEQ ID NO 613
<211> LENGTH: 153
<212> TYPE: PRT
<213> ORGANISM: Homo sapiens

<400> SEQUENCE: 613

Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Asn Asn Tyr Lys Asn Pro Lys Leu Thr Arg Met Leu Thr Phe Lys Phe
    50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
    130                 135                 140
```

Cys Gln Ser Ile Ile Ser Thr Leu Thr
145 150

<210> SEQ ID NO 614
<211> LENGTH: 822
<212> TYPE: DNA
<213> ORGANISM: Homo sapiens

<400> SEQUENCE: 614
agttccctat cactctcttt aatcactact cacagtaacc tcaactcctg ccacaatgta 60
caggatgcaa ctcctgtctt gcattgcact aagtcttgca cttgtcacaa acagtgcacc 120
tacttcaagt tctacaaaga aaacacagct acaactggag catttactgc tggatttaca 180
gatgattttg aatggaatta ataattacaa gaatcccaaa ctcaccagga tgctcacatt 240
taagttttac atgcccaaga aggccacaga actgaaacat cttcagtgtc tagaagaaga 300
actcaaacct ctggaggaag tgctaaattt agctcaaagc aaaaactttc acttaagacc 360
cagggactta atcagcaata tcaacgtaat agttctggaa ctaaagggat ctgaaacaac 420
attcatgtgt gaatatgctg atgagacagc aaccattgta gaatttctga acagatggat 480
taccttttgt caaagcatca tctcaacact gacttgataa ttaagtgctt cccacttaaa 540
acatatcagg ccttctattt atttaaatat ttaaatttta tatttattgt tgaatgtatg 600
gtttgctacc tattgtaact attattctta atcttaaaac tataaatatg gatcttttat 660
gattcttttt gtaagcccta ggggctctaa aatggtttca cttatttatc ccaaaatatt 720
tattattatg ttgaatgtta aatatagtat ctatgtagat tggttagtaa aactatttaa 780
taaatttgat aaatataaaa aaaaaaaaaa aaaaaaaaaa aa 822

<210> SEQ ID NO 615
<211> LENGTH: 521
<212> TYPE: DNA
<213> ORGANISM: Unknown
<220> FEATURE:
<221> NAME/KEY: source
<223> OTHER INFORMATION: /note="Description of Unknown:
PGK promoter sequence"

<400> SEQUENCE: 615
acccctctct ccagccacta agccagttgc tccctcggct gacggctgca cgcgaggcct 60
ccgaacgtct tacgccttgt ggcgcgcccg tccttgtccc gggtgtgatg gcggggtgtg 120
gggcggaggg cgtggcgggg aagggccggc gacgagagcc gcgcgggacg actcgtcggc 180
gataaccggt gtcgggtagc gccagccgcg cgacggtaac gagggaccgc gacaggcaga 240
cgctcccatg atcactctgc acgccgaagg caaatagtgc aggccgtgcg gcgcttggcg 300
ttccttggaa gggctgaatc cccgcctcgt ccttcgcagc ggccccccgg gtgttcccat 360
cgccgcttct aggcccactg cgacgcttgc ctgcacttct tacacgctct gggtcccagc 420
cgcggcgacg caaagggcct tggtgcgggt ctcgtcggcg cagggacgcg tttgggtccc 480
gacggaacct tttccgcgtt ggggttgggg caccataagc t 521

<210> SEQ ID NO 616
<211> LENGTH: 118
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 616
acccctctct ccagccacta agccagttgc tccctcggct gacggctgca cgcgaggcct 60
ccgaacgtct tacgccttgt ggcgcgcccg tccttgtccc gggtgtgatg gcggggtg 118

<210> SEQ ID NO 617
<211> LENGTH: 221
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 617
acccctctct ccagccacta agccagttgc tccctcggct gacggctgca cgcgaggcct 60
ccgaacgtct tacgccttgt ggcgcgcccg tccttgtccc gggtgtgatg gcggggtgtg 120
gggcggaggg cgtggcgggg aagggccggc gacgagagcc gcgcgggacg actcgtcggc 180
gataaccggt gtcgggtagc gccagccgcg cgacggtaac g 221

<210> SEQ ID NO 618
<211> LENGTH: 324
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 618
acccctctct ccagccacta agccagttgc tccctcggct gacggctgca cgcgaggcct 60
ccgaacgtct tacgccttgt ggcgcgcccg tccttgtccc gggtgtgatg gcggggtgtg 120
gggcggaggg cgtggcgggg aagggccggc gacgagagcc gcgcgggacg actcgtcggc 180
gataaccggt gtcgggtagc gccagccgcg cgacggtaac gagggaccgc gacaggcaga 240
cgctcccatg atcactctgc acgccgaagg caaatagtgc aggccgtgcg gcgcttggcg 300
ttccttggaa gggctgaatc cccg 324

<210> SEQ ID NO 619
<211> LENGTH: 422
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 619
acccctctct ccagccacta agccagttgc tccctcggct gacggctgca cgcgaggcct 60
ccgaacgtct tacgccttgt ggcgcgcccg tccttgtccc gggtgtgatg gcggggtgtg 120
gggcggaggg cgtggcgggg aagggccggc gacgagagcc gcgcgggacg actcgtcggc 180
gataaccggt gtcgggtagc gccagccgcg cgacggtaac gagggaccgc gacaggcaga 240
cgctcccatg atcactctgc acgccgaagg caaatagtgc aggccgtgcg gcgcttggcg 300
ttccttggaa gggctgaatc cccgcctcgt ccttcgcagc ggccccccgg gtgttcccat 360
cgccgcttct aggcccactg cgacgcttgc ctgcacttct tacacgctct gggtcccagc 420
cg 422

<210> SEQ ID NO 620
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"
<220> FEATURE:
<221> NAME/KEY: SITE
<222> LOCATION: (1)..(3)
<223> OTHER INFORMATION: /note="This region may or may not be present"

<400> SEQUENCE: 620

Gly Ser Gly Glu Gly Arg Gly Ser Leu Leu Thr Cys Gly Asp Val Glu
1 5 10 15

Glu Asn Pro Gly Pro
20

<210> SEQ ID NO 621
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"
<220> FEATURE:
<221> NAME/KEY: SITE
<222> LOCATION: (1)..(3)
<223> OTHER INFORMATION: /note="This region may or may not be present"

<400> SEQUENCE: 621

Gly Ser Gly Ala Thr Asn Phe Ser Leu Leu Lys Gln Ala Gly Asp Val
1 5 10 15

Glu Glu Asn Pro Gly Pro
20

<210> SEQ ID NO 622
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"
<220> FEATURE:
<221> NAME/KEY: SITE
<222> LOCATION: (1)..(3)
<223> OTHER INFORMATION: /note="This region may or may not be present"

<400> SEQUENCE: 622

Gly Ser Gly Gln Cys Thr Asn Tyr Ala Leu Leu Lys Leu Ala Gly Asp
1 5 10 15

Val Glu Ser Asn Pro Gly Pro
20

<210> SEQ ID NO 623
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"
<220> FEATURE:
<221> NAME/KEY: SITE
<222> LOCATION: (1)..(3)
<223> OTHER INFORMATION: /note="This region may or may not be present"

<400> SEQUENCE: 623

```
Gly Ser Gly Val Lys Gln Thr Leu Asn Phe Asp Leu Leu Lys Leu Ala
1               5                   10                  15

Gly Asp Val Glu Ser Asn Pro Gly Pro
            20                  25
```

<210> SEQ ID NO 624
<211> LENGTH: 486
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: SITE
<222> LOCATION: (1)..(21)
<223> OTHER INFORMATION: /note="This region may or may not be present"
<220> FEATURE:
<221> NAME/KEY: source
<223> OTHER INFORMATION: /note="See specification as filed for detailed description of substitutions and preferred embodiments"

<400> SEQUENCE: 624

```
Met Ala Leu Pro Val Thr Ala Leu Leu Leu Pro Leu Ala Leu Leu Leu
1               5                   10                  15

His Ala Ala Arg Pro Asp Ile Gln Met Thr Gln Thr Thr Ser Ser Leu
            20                  25                  30

Ser Ala Ser Leu Gly Asp Arg Val Thr Ile Ser Cys Arg Ala Ser Gln
        35                  40                  45

Asp Ile Ser Lys Tyr Leu Asn Trp Tyr Gln Gln Lys Pro Asp Gly Thr
    50                  55                  60

Val Lys Leu Leu Ile Tyr His Thr Ser Arg Leu His Ser Gly Val Pro
65                  70                  75                  80

Ser Arg Phe Ser Gly Ser Gly Ser Gly Thr Asp Tyr Ser Leu Thr Ile
                85                  90                  95

Ser Asn Leu Glu Gln Glu Asp Ile Ala Thr Tyr Phe Cys Gln Gln Gly
            100                 105                 110

Asn Thr Leu Pro Tyr Thr Phe Gly Gly Gly Thr Lys Leu Glu Ile Thr
        115                 120                 125

Gly Gly Gly Gly Ser Gly Gly Gly Gly Ser Gly Gly Gly Gly Ser Glu
    130                 135                 140

Val Lys Leu Gln Glu Ser Gly Pro Gly Leu Val Ala Pro Ser Gln Ser
145                 150                 155                 160

Leu Ser Val Thr Cys Thr Val Ser Gly Val Ser Leu Pro Asp Tyr Gly
                165                 170                 175

Val Ser Trp Ile Arg Gln Pro Pro Arg Lys Gly Leu Glu Trp Leu Gly
            180                 185                 190

Val Ile Trp Gly Ser Glu Thr Thr Tyr Tyr Asn Ser Ala Leu Lys Ser
        195                 200                 205

Arg Leu Thr Ile Ile Lys Asp Asn Ser Lys Ser Gln Val Phe Leu Lys
    210                 215                 220

Met Asn Ser Leu Gln Thr Asp Asp Thr Ala Ile Tyr Tyr Cys Ala Lys
225                 230                 235                 240

His Tyr Tyr Tyr Gly Gly Ser Tyr Ala Met Asp Tyr Trp Gly Gln Gly
                245                 250                 255

Thr Ser Val Thr Val Ser Ser Thr Thr Thr Pro Ala Pro Arg Pro Pro
            260                 265                 270
```

Thr Pro Ala Pro Thr Ile Ala Ser Gln Pro Leu Ser Leu Arg Pro Glu
275 280 285

Ala Cys Arg Pro Ala Ala Gly Gly Ala Val His Thr Arg Gly Leu Asp
290 295 300

Phe Ala Cys Asp Ile Tyr Ile Trp Ala Pro Leu Ala Gly Thr Cys Gly
305 310 315 320

Val Leu Leu Leu Ser Leu Val Ile Thr Leu Tyr Cys Lys Arg Gly Arg
325 330 335

Lys Lys Leu Leu Tyr Ile Phe Lys Gln Pro Phe Met Arg Pro Val Gln
340 345 350

Thr Thr Gln Glu Glu Asp Gly Cys Ser Cys Arg Phe Pro Glu Glu Glu
355 360 365

Glu Gly Gly Cys Glu Leu Arg Val Lys Phe Ser Arg Ser Ala Asp Ala
370 375 380

Pro Ala Tyr Lys Gln Gly Gln Asn Gln Leu Tyr Asn Glu Leu Asn Leu
385 390 395 400

Gly Arg Arg Glu Glu Tyr Asp Val Leu Asp Lys Arg Arg Gly Arg Asp
405 410 415

Pro Glu Met Gly Gly Lys Pro Arg Arg Lys Asn Pro Gln Glu Gly Leu
420 425 430

Tyr Asn Glu Leu Gln Lys Asp Lys Met Ala Glu Ala Tyr Ser Glu Ile
435 440 445

Gly Met Lys Gly Glu Arg Arg Arg Gly Lys Gly His Asp Gly Leu Tyr
450 455 460

Gln Gly Leu Ser Thr Ala Thr Lys Asp Thr Tyr Asp Ala Leu His Met
465 470 475 480

Gln Ala Leu Pro Pro Arg
485

<210> SEQ ID NO 625
<211> LENGTH: 465
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 625

Asp Ile Gln Met Thr Gln Thr Thr Ser Ser Leu Ser Ala Ser Leu Gly
1 5 10 15

Asp Arg Val Thr Ile Ser Cys Arg Ala Ser Gln Asp Ile Ser Lys Tyr
20 25 30

Leu Asn Trp Tyr Gln Gln Lys Pro Asp Gly Thr Val Lys Leu Leu Ile
35 40 45

Tyr His Thr Ser Arg Leu His Ser Gly Val Pro Ser Arg Phe Ser Gly
50 55 60

Ser Gly Ser Gly Thr Asp Tyr Ser Leu Thr Ile Ser Asn Leu Glu Gln
65 70 75 80

Glu Asp Ile Ala Thr Tyr Phe Cys Gln Gln Gly Asn Thr Leu Pro Tyr
85 90 95

Thr Phe Gly Gly Gly Thr Lys Leu Glu Ile Thr Gly Gly Gly Gly Ser
100 105 110

Gly Gly Gly Gly Ser Gly Gly Gly Gly Ser Glu Val Lys Leu Gln Glu
115 120 125

```
Ser Gly Pro Gly Leu Val Ala Pro Ser Gln Ser Leu Ser Val Thr Cys
    130                 135                 140
Thr Val Ser Gly Val Ser Leu Pro Asp Tyr Gly Val Ser Trp Ile Arg
145                 150                 155                 160
Gln Pro Pro Arg Lys Gly Leu Glu Trp Leu Gly Val Ile Trp Gly Ser
                165                 170                 175
Glu Thr Thr Tyr Tyr Asn Ser Ala Leu Lys Ser Arg Leu Thr Ile Ile
                180                 185                 190
Lys Asp Asn Ser Lys Ser Gln Val Phe Leu Lys Met Asn Ser Leu Gln
                195                 200                 205
Thr Asp Asp Thr Ala Ile Tyr Tyr Cys Ala Lys His Tyr Tyr Tyr Gly
    210                 215                 220
Gly Ser Tyr Ala Met Asp Tyr Trp Gly Gln Gly Thr Ser Val Thr Val
225                 230                 235                 240
Ser Ser Thr Thr Thr Pro Ala Pro Arg Pro Pro Thr Pro Ala Pro Thr
                245                 250                 255
Ile Ala Ser Gln Pro Leu Ser Leu Arg Pro Glu Ala Cys Arg Pro Ala
                260                 265                 270
Ala Gly Gly Ala Val His Thr Arg Gly Leu Asp Phe Ala Cys Asp Ile
                275                 280                 285
Tyr Ile Trp Ala Pro Leu Ala Gly Thr Cys Gly Val Leu Leu Leu Ser
    290                 295                 300
Leu Val Ile Thr Leu Tyr Cys Lys Arg Gly Arg Lys Lys Leu Leu Tyr
305                 310                 315                 320
Ile Phe Lys Gln Pro Phe Met Arg Pro Val Gln Thr Thr Gln Glu Glu
                325                 330                 335
Asp Gly Cys Ser Cys Arg Phe Pro Glu Glu Glu Glu Gly Gly Cys Glu
                340                 345                 350
Leu Arg Val Lys Phe Ser Arg Ser Ala Asp Ala Pro Ala Tyr Lys Gln
                355                 360                 365
Gly Gln Asn Gln Leu Tyr Asn Glu Leu Asn Leu Gly Arg Arg Glu Glu
    370                 375                 380
Tyr Asp Val Leu Asp Lys Arg Arg Gly Arg Asp Pro Glu Met Gly Gly
385                 390                 395                 400
Lys Pro Arg Arg Lys Asn Pro Gln Glu Gly Leu Tyr Asn Glu Leu Gln
                405                 410                 415
Lys Asp Lys Met Ala Glu Ala Tyr Ser Glu Ile Gly Met Lys Gly Glu
                420                 425                 430
Arg Arg Arg Gly Lys Gly His Asp Gly Leu Tyr Gln Gly Leu Ser Thr
                435                 440                 445
Ala Thr Lys Asp Thr Tyr Asp Ala Leu His Met Gln Ala Leu Pro Pro
    450                 455                 460
Arg
465
```

<210> SEQ ID NO 626
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 626

Arg Gly Asp Ser

-continued

1

```
<210> SEQ ID NO 627
<211> LENGTH: 177
<212> TYPE: PRT
<213> ORGANISM: Homo sapiens

<400> SEQUENCE: 627

Met Phe His Val Ser Phe Arg Tyr Ile Phe Gly Leu Pro Pro Leu Ile
1               5                   10                  15

Leu Val Leu Leu Pro Val Ala Ser Ser Asp Cys Asp Ile Glu Gly Lys
            20                  25                  30

Asp Gly Lys Gln Tyr Glu Ser Val Leu Met Val Ser Ile Asp Gln Leu
        35                  40                  45

Leu Asp Ser Met Lys Glu Ile Gly Ser Asn Cys Leu Asn Asn Glu Phe
    50                  55                  60

Asn Phe Phe Lys Arg His Ile Cys Asp Ala Asn Lys Glu Gly Met Phe
65                  70                  75                  80

Leu Phe Arg Ala Ala Arg Lys Leu Arg Gln Phe Leu Lys Met Asn Ser
                85                  90                  95

Thr Gly Asp Phe Asp Leu His Leu Leu Lys Val Ser Glu Gly Thr Thr
            100                 105                 110

Ile Leu Leu Asn Cys Thr Gly Gln Val Lys Gly Arg Lys Pro Ala Ala
        115                 120                 125

Leu Gly Glu Ala Gln Pro Thr Lys Ser Leu Glu Glu Asn Lys Ser Leu
    130                 135                 140

Lys Glu Gln Lys Lys Leu Asn Asp Leu Cys Phe Leu Lys Arg Leu Leu
145                 150                 155                 160

Gln Glu Ile Lys Thr Cys Trp Asn Lys Ile Leu Met Gly Thr Lys Glu
                165                 170                 175

His

<210> SEQ ID NO 628
<211> LENGTH: 2016
<212> TYPE: DNA
<213> ORGANISM: Homo sapiens

<400> SEQUENCE: 628

acacttgtgg cttccgtgca cacattaaca actcatggtt ctagctccca gtcgccaagc        60

gttgccaagg cgttgagaga tcatctggga agtcttttac ccagaattgc tttgattcag       120

gccagctggt ttttcctgcg gtgattcgga aattcgcgaa ttcctctggt cctcatccag       180

gtgcgcggga agcaggtgcc caggagagag gggataatga agattccatg ctgatgatcc       240

caaagattga acctgcagac caagcgcaaa gtagaaactg aaagtacact gctggcggat       300

cctacggaag ttatggaaaa ggcaaagcgc agagccacgc cgtagtgtgt gccgcccccc       360

ttgggatgga tgaaactgca gtcgcggcgt gggtaagagg aaccagctgc agagatcacc       420

ctgcccaaca cagactcggc aactccgcgg aagaccaggg tcctgggagt gactatgggc       480

ggtgagagct tgctcctgct ccagttgcgg tcatcatgac tacgcccgcc tcccgcagac       540

catgttccat gtttctttta ggtatatctt tggacttcct cccctgatcc ttgttctgtt       600

gccagtagca tcatctgatt gtgatattga aggtaaagat ggcaaacaat atgagagtgt       660

tctaatggtc agcatcgatc aattattgga cagcatgaaa gaaattggta gcaattgcct       720

gaataatgaa tttaactttt ttaaaagaca tatctgtgat gctaataagg aaggtatgtt       780
```

-continued

```
tttattccgt gctgctcgca agttgaggca atttcttaaa atgaatagca ctggtgattt    840
tgatctccac ttattaaaag tttcagaagg cacaacaata ctgttgaact gcactggcca    900
ggttaaagga agaaaaccag ctgccctggg tgaagcccaa ccaacaaaga gtttggaaga    960
aaataaatct ttaaaggaac agaaaaaact gaatgacttg tgtttcctaa agagactatt   1020
acaagagata aaaacttgtt ggaataaaat tttgatgggc actaaagaac actgaaaaat   1080
atggagtggc aatatagaaa cacgaacttt agctgcatcc tccaagaatc tatctgctta   1140
tgcagttttt cagagtggaa tgcttcctag aagttactga atgcaccatg gtcaaaacgg   1200
attagggcat ttgagaaatg catattgtat tactagaaga tgaatacaaa caatggaaac   1260
tgaatgctcc agtcaacaaa ctatttctta tatatgtgaa catttatcaa tcagtataat   1320
tctgtactga tttttgtaag acaatccatg taaggtatca gttgcaataa tacttctcaa   1380
acctgtttaa atatttcaag acattaaatc tatgaagtat ataatggttt caaagattca   1440
aaattgacat tgctttactg tcaaaataat tttatggctc actatgaatc tattatactg   1500
tattaagagt gaaaattgtc ttcttctgtg ctggagatgt tttagagtta acaatgatat   1560
atggataatg ccggtgagaa taagagagtc ataaacctta agtaagcaac agcataacaa   1620
ggtccaagat acctaaaaga gatttcaaga gatttaatta atcatgaatg tgtaacacag   1680
tgccttcaat aaatggtata gcaaatgttt tgacatgaaa aaaggacaat ttcaaaaaaa   1740
taaaataaaa taaaaataaa ttcacctagt ctaaggatgc taaaccttag tactgagtta   1800
cattgtcatt tatatagatt ataacttgtc taaataagtt tgcaatttgg gagatatatt   1860
tttaagataa taatatatgt ttacctttta attaatgaaa tatctgtatt taattttgac   1920
actatatctg tatataaaat attttcatac agcattacaa attgcttact ttggaataca   1980
tttctccttt gataaaataa atgagctatg tattaa                             2016
```